US011919902B2

(12) United States Patent
Lindström et al.

(10) Patent No.: US 11,919,902 B2
(45) Date of Patent: Mar. 5, 2024

(54) ARYL-BIPYRIDINE AMINE DERIVATIVES AS PHOSPHATIDYLINOSITOL PHOSPHATE KINASE INHIBITORS

(71) Applicant: HiberCell, Inc., New York, NY (US)

(72) Inventors: Johan Lindström, Holo (SE); Lars Boukharta Persson, Uppsala (SE); Madeleine Livendahl, Bandhagan (SE); Jenny Viklund, Hägersten (SE); Tobias Ginman, Tullinge (SE); Rickard Forsblom, Tullinge (SE); Fredrik Rahm, Stockholm (SE); Edward A. Kesicki, New York, NY (US); Kannan Karukurichi Ravi, Woodbridge, NJ (US); Eugene R. Hickey, Danbury, CT (US); Markus K. Dahlgren, Shelton, CT (US); Aleksey I. Gerasyuto, Flemington, NJ (US)

(73) Assignee: HiberCell, Inc., New York, NY (US)

( * ) Notice: Subject to any disclaimer, the term of this patent is extended or adjusted under 35 U.S.C. 154(b) by 0 days.

(21) Appl. No.: 16/956,953

(22) PCT Filed: Dec. 21, 2018

(86) PCT No.: PCT/US2018/067267
§ 371 (c)(1),
(2) Date: Jun. 22, 2020

(87) PCT Pub. No.: WO2019/126733
PCT Pub. Date: Jun. 27, 2019

(65) Prior Publication Data
US 2020/0331913 A1    Oct. 22, 2020

Related U.S. Application Data

(60) Provisional application No. 62/609,604, filed on Dec. 22, 2017.

(51) Int. Cl.
| C07D 491/048 | (2006.01) |
| A61K 31/4355 | (2006.01) |
| C07D 401/14 | (2006.01) |
| C07D 471/04 | (2006.01) |
| C07D 471/10 | (2006.01) |
| C07D 471/14 | (2006.01) |
| C07D 487/04 | (2006.01) |
| C07D 491/056 | (2006.01) |
| C07D 495/04 | (2006.01) |
| C07D 513/04 | (2006.01) |

(Continued)

(52) U.S. Cl.
CPC ......... *C07D 471/14* (2013.01); *C07D 401/14* (2013.01); *C07D 471/04* (2013.01); *C07D 471/10* (2013.01); *C07D 487/04* (2013.01); *C07D 491/048* (2013.01); *C07D 491/056* (2013.01); *C07D 495/04* (2013.01); *C07D 513/04* (2013.01); *C07D 519/00* (2013.01); *C07F 5/025* (2013.01)

(58) Field of Classification Search
CPC .............. C07D 491/048; C07D 471/04; C07D 401/14; A61K 31/4355; A61K 31/437; A61K 31/444; A61P 35/00; A61P 25/28; A61P 29/00; C12Q 1/00
USPC ......... 546/115, 113, 256; 514/302, 300, 333
See application file for complete search history.

(56) References Cited

U.S. PATENT DOCUMENTS

| 7,872,031 | B2 * | 1/2011 | Lauffer | ................ | C07D 471/04 |
| | | | | | 514/340 |
| 7,989,458 | B2 * | 8/2011 | Leblanc | ................... | A61P 3/10 |
| | | | | | 544/333 |

(Continued)

FOREIGN PATENT DOCUMENTS

| CN | 106433615 A | 2/2017 |
| CN | 107417605 A | 12/2017 |

(Continued)

OTHER PUBLICATIONS

Wei et al., "Pyridine-Based Electron Transport Materials with High Solubility, Excellent Film-Forming Ability, and Wettability for Inkjet-Printed OLEDs," ACS Applied Materials & Interfaces, 9(44) 38716-38727 (2017).

(Continued)

*Primary Examiner* — Charanjit Aulakh
(74) *Attorney, Agent, or Firm* — Goodwin Procter LLP

(57) ABSTRACT

The invention relates to inhibitors of PI5P4K inhibitors useful in the treatment of cancers, neurodegenerative diseases, inflammatory disorders, and metabolic diseases, having the Formula:

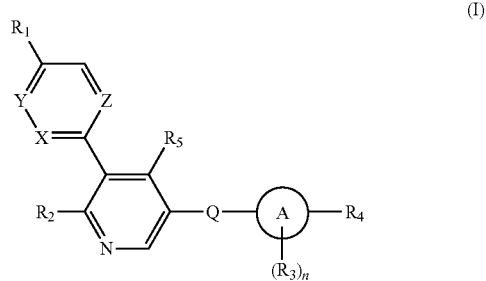

(I)

wherein A, X, Y, Z, Q, $R_1$, $R_2$, $R_3$, $R_4$, $R_5$, and n are described herein.

13 Claims, No Drawings

(51) Int. Cl.
*C07D 519/00* (2006.01)
*C07F 5/02* (2006.01)

(56) References Cited

U.S. PATENT DOCUMENTS

| | | | |
|---|---|---|---|
| 8,153,804 B2* | 4/2012 | Augeri | C07D 401/04 |
| | | | 546/194 |
| 8,173,647 B2 | 5/2012 | Atallah et al. | |
| 8,217,035 B2 | 7/2012 | Burger et al. | |
| 8,431,578 B2 | 4/2013 | Hunt et al. | |
| 8,865,894 B2 | 10/2014 | Caravatti et al. | |
| 9,024,033 B2* | 5/2015 | Witty | C07D 471/04 |
| | | | 546/311 |
| 9,181,272 B2* | 11/2015 | Balestra | A61P 9/00 |
| 9,242,996 B2* | 1/2016 | Bagdanoff | A61K 31/4433 |
| 9,399,638 B2* | 7/2016 | Irlapati | A61P 17/06 |
| 9,493,813 B2 | 11/2016 | Emerling et al. | |
| 11,135,209 B2 | 10/2021 | Cuny et al. | |
| 11,208,423 B2 | 12/2021 | Lindström et al. | |
| 11,219,618 B2 | 1/2022 | Lindström et al. | |
| 2014/0323468 A1 | 10/2014 | Balestra et al. | |
| 2020/0331913 A1 | 10/2020 | Lindstrom et al. | |
| 2020/0392156 A1 | 12/2020 | Kesicki | |
| 2020/0392162 A1 | 12/2020 | Kesicki | |
| 2021/0253600 A1 | 8/2021 | Lindstrom et al. | |
| 2021/0317136 A1 | 10/2021 | Lindstrom et al. | |

FOREIGN PATENT DOCUMENTS

| | | |
|---|---|---|
| EP | 3168219 A1 | 5/2017 |
| WO | WO-2007016674 A2 | 2/2007 |
| WO | WO-2007/095588 A1 | 8/2007 |
| WO | WO-2007147874 A1 | 12/2007 |
| WO | WO-2009013348 A2 | 1/2009 |
| WO | WO-2009087212 A2 | 7/2009 |
| WO | WO-2009087225 A2 | 7/2009 |
| WO | WO-2009115517 A2 | 9/2009 |
| WO | WO-2011024004 A1 | 3/2011 |
| WO | WO-2013124826 A1 | 8/2013 |
| WO | WO-2013/162061 A1 | 10/2013 |
| WO | WO-2013/164769 A1 | 11/2013 |
| WO | WO-2015/066188 A1 | 5/2015 |
| WO | WO-2016109515 A1 | 7/2016 |
| WO | WO-2016210291 A1 | 12/2016 |
| WO | WO-2016210296 A1 | 12/2016 |

OTHER PUBLICATIONS

Jin et al., "An Exceptionally Water Stable Metal-Organic Framework with Amide-Functionalized Cages: Selective $CO_2/CH_4$ Uptake and Removal of Antibiotics and Dyes from Water," Chemistry-A European Journal, 23(53) 13058-13066 (2017).

International Search Report and Written Opinion in PCT/2018/067267, dated Mar. 18, 2019 14 pages.

Hinchliffe et al., "The Type PIPkins (PtdIns5P 4-kinases): enzymes in search of a function?" Biochem. Soc. Trans. 27:657-6661 (1999).

* cited by examiner

ARYL-BIPYRIDINE AMINE DERIVATIVES AS PHOSPHATIDYLINOSITOL PHOSPHATE KINASE INHIBITORS

CROSS-REFERENCE TO RELATED APPLICATIONS

This application is a U.S. National Phase Application, filed under 35 U.S.C. 371, of International Application No. PCT/US2018/067267, filed on Dec. 21, 2018, which claims the benefit of priority of U.S. Provisional Application No. 62/609,604, filed Dec. 22, 2017, which the entire disclosure of each are incorporated herein by reference in their entirety.

FIELD OF INVENTION

The present invention is directed to inhibitors of phosphatidylinositol-5-phosphate-4-kinase (PI5P4K) useful in the treatment of diseases or disorders associated with PI5P4K enzymes. In particular, the invention is concerned with compounds and compositions inhibiting PI5P4K, methods of treating diseases or disorders associated with PI5P4K, and methods of synthesis of these compounds.

BACKGROUND OF THE INVENTION

A minor but ubiquitous component of cells, phosphoinositol lipids are pivotal players in many intracellular signal transduction pathways. Phosphoinositol lipids are formed when phosphatidylinositol (PtdIns) is converted, by the catalytic action of lipid kinases, to polyphosphoinositides. As a prototypic example, the membrane associated phospholipid, phosphatidylinositol-4,5-bisphosphate (PtdIns(4, 5)P2), is formed by two successive phosphorylations of PtdIns by the phosphatidylinositol phosphate kinases (PIP kinases).

PtdIns(4,5)P2 is a substrate for phospholipase C (PLC) and is converted into the second messengers inositol-1,4,5-trisphosphate and diacylglycerol (DAG). Phosphoinositides are involved in regulating a broad spectrum of activities from cytoskeletal assembly and motility to vesicle trafficking and exocytosis to transduction of intracellular signals including stimulating the release of intracellular calcium stores (Hinchliffe et al., Biochem. Soc. Trans., 1999, 27, 657-661).

PIP kinases comprise a unique and promiscuous family of enzymes that catalyze the production of poly-phosphorylated inositol lipids from mono-phosphorylated phosphoinositides. Isolation and purification of several different PIP kinase enzymes able to catalyze phosphorylation of phosphatidylinositol 4-phosphate and produce PtdIns(4,5)P2 led to the further categorization of these enzymes, dubbed the phosphatidylinositol 4-phosphate 5-kinases (PIP5Ks), into two types having different activities. The PIP kinases have no homology to other lipid or protein kinases at the primary sequence level, and are distinguished from each other by their lack of immuno-cross reactivity and by the fact that type I PIP5Ks are stimulated in vitro by phosphatidic acid, whereas the type II PIP5Ks are not. Furthermore, the recent discovery that the type II PTP5Ks are able to phosphorylate multiple lipid substrates in vitro suggests that this family of kinases is potentially able to generate several distinct, often subcellularly compartmentalized, phosphoinositol products for regulation of a variety of physiologically important processes (Hinchliffe et al., Biochem. Soc. Trans., 1999, 27, 657-661).

One particular species of PI, phosphatidylinositol 5-phosphate (PI5P), has been implicated in the regulation of the tumor suppressor ING2 and the oncogene AKT. The phosphatidylinositol 5-phosphate 4-kinase (PI5P4K) family (α, β, γ isoforms) catalyzes the conversion of PI5P to PI4, 5 P2. These enzymes therefore represent one means by which cells can regulate endogenous PI5P levels. Mice deficient for PI5P4Kβ (PI5P4Kβ−/−) have been shown to exhibit enhanced insulin sensitivity and activation of AKT in skeletal muscle.

The pharmacological modulation of PIP5KII-beta activity and/or expression is therefore believed to be an appropriate point of therapeutic intervention in pathological conditions in which cell differentiation, proliferation, and/or motility are compromised, such as cancer or inflammation, and in metabolic disorders.

Currently, there are no known therapeutic agents which effectively inhibit the synthesis of PIP5KII-beta. Inhibition of PI5P4K with small molecule inhibitors, therefore, has the potential to be a treatment for cancers and other disorders. For this reason, there remains a considerable need for novel and potent small molecule inhibitors and agents capable of effectively inhibiting PIP5KII-beta function.

SUMMARY OF THE INVENTION

A first aspect of the invention relates to compounds of Formula (I):

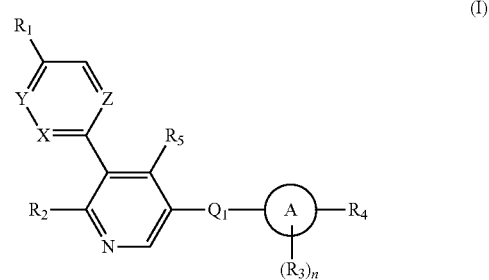

and pharmaceutically acceptable salts, prodrugs, solvates, hydrates, isomers, or tautomers, thereof, wherein:

X, Y, and Z are independently CH, C($C_{1-6}$ alkyl) or N, wherein at least one of X, Y, and Z is CH;

Ring A is aryl, heteroaryl, or heterocyclyl;

$R_1$ is —N($R_6$)C(O)$R_7$, —C(O)N($R_6$)($R_7$), —(CH$_2$)$_t$C(O)N($R_6$)($R_7$), pyrrolidinyl, isoxazolyl, indolinyl, triazolyl, pyridinyl, pyridazinyl, imidazolyl, tetrazolyl, 6,7-dihydro-5H-pyrrolo[2,1-c][1,2,4]triazolyl, 2,8-diazaspiro[4.5]decanyl, or isothiazolidine 1,1-dioxidyl; wherein pyrrolidinyl, isoxazolyl, indolinyl, triazolyl, pyridinyl, pyridazinyl, imidazolyl, tetrazolyl, 6,7-dihydro-5H-pyrrolo[2,1-c][1,2,4]triazolyl, 2,8-diazaspiro[4.5]decanyl, or isothiazolidine 1,1-dioxidyl is optionally substituted with one or more $R_8$;

$R_2$ is —H, —NH$_2$, or $C_{1-6}$ alkyl;

$Q_1$ is a bond;

each $R_3$ is independently, at each occurrence, —H, halogen, oxo, $C_{1-6}$ alkyl, $C_{3-6}$ cycloalkyl, heterocyclyl, —O$R_6$, —N$R_6R_7$, —CN, —C(O)N$R_6R_7$, —N($R_6$)C(O)$R_7$, —C(O)O$R_6$, —S(O)$_2R_6$, —S(O)$_2$N($R_6$)($R_7$), wherein the alkyl, heterocyclyl, or cycloalkyl is optionally substituted with one or more $R_8$; or two $R_3$, when on adjacent atoms, with the atoms they are attached, form a $C_{4-8}$ cycloalkyl, $C_5$-$C_8$ spirocycloalkyl, spiroheterocycloalkyl, or heterocyclyl, wherein the heterocyclyl, spirocycloalkyl, spiroheterocycloalkyl, or cycloalkyl is optionally substituted with one or more $R_8$;

$R_4$ is —H, $C_3$-$C_8$ cycloalkyl, $C_5$-$C_8$ spirocycloalkyl, spiroheterocycloalkyl, aryl, heterocyclyl, heteroaryl, —C(O)N($R_{10}$)—($C_0$-$C_6$ alkylene)-$R_9$, —C(O)N($R_{10}$)—$R_9$, —C(O)—$R_9$, —N($R_{10}$)—($C_0$-$C_6$ alkylene)-$R_9$, —($C_0$-$C_6$ alkylene)-N($R_{10}$)C(O)—($C_0$-$C_6$ alkylene)-$R_9$, —N($R_{10}$)C(O)—($C_0$-$C_6$ alkylene)-$R_9$—N($R_{10}$)C(O)—($C_0$-$C_6$ alkylene)-, —N($R_{10}$)C(O)—$R_9$, —(CH$_2$)$_q$—$R_9$, —(CH$_2$)$_r$—N($R_{10}$)C(O)—(CH$_2$)$_s$—$R_9$, wherein the cycloalkyl, spirocycloalkyl, spiroheterocycloalkyl, heterocyclyl, aryl, or heteroaryl is optionally substituted with one or more $R_9$;

$R_5$ is —H, halogen, —OH, $C_{1-6}$ alkyl, $C_{1-6}$ alkoxy, wherein the alkyl or alkoxy is optionally substituted with $R_{10}$;

$R_6$ is independently, at each occurrence, —H, $C_{1-6}$ alkyl, $C_{2-6}$ alkenyl, $C_{2-6}$ alkynyl, $C_{3-8}$ cycloalkyl, heterocyclyl, aryl, or heteroaryl, wherein the alkyl, alkenyl, alkynyl, cycloalkyl, heterocyclyl, aryl, or heteroaryl is optionally substituted with one or more $R_8$;

$R_7$ is independently, at each occurrence, $C_{1-6}$ alkyl, $C_{2-6}$ alkenyl, $C_{2-6}$ alkynyl, $C_{3-8}$ cycloalkyl, heterocyclyl, aryl, or heteroaryl, wherein the alkyl, alkenyl, alkynyl, cycloalkyl, heterocyclyl, aryl, or heteroaryl is optionally substituted with one or more $R_8$; or $R_6$ and $R_7$ when taken together with the atom to which they are each attached form a $C_3$-$C_8$ cycloalkyl, $C_5$-$C_8$ spirocycloalkyl, spiroheterocycloalkyl, or heterocycle, wherein the cycloalkyl, $C_5$-$C_8$ spirocycloalkyl, spiroheterocycloalkyl, or heterocycle is optionally substituted with one or more $R_8$;

$R_8$ is —CN, halogen, —OH, —NH$_2$, —NO$_2$, —C(O)NH$_2$, —C(O)OH, oxo, $C_{1-6}$ alkyl, $C_{1-6}$ alkoxy, aryl, $C_{3-6}$ cycloalkyl, $C_5$-$C_8$ spirocycloalkyl, spiroheterocycloalkyl, heterocyclyl, or heteroaryl, wherein the alkyl, alkoxy, cycloalkyl, spirocycloalkyl, spiroheterocycloalkyl, aryl, heterocyclyl, or heteroaryl is optionally substituted with one or more $R_9$;

$R_9$ is —H, halogen, $C_{1-6}$ alkyl, $C_{2-6}$ alkenyl, $C_{2-6}$ alkynyl, $C_{3-8}$ cycloalkyl, heterocyclyl, aryl, heteroaryl, —OR$_{11}$, —C(O)O(R$_{11}$), —C(O)N(R$_{11}$)(R$_{12}$), —N(R$_{11}$)(R$_{12}$), —CN, —N(R$_{11}$)C(O)OR$_{12}$, —N(R$_{11}$)C(O)R$_2$, —C(O)—V—N(R$_{11}$)—F, —N(R$_{11}$)C(O)—V—N(R$_{12}$)—F, —C(O)—Ar, or —N(R$_{11}$)C(O)—Ar, wherein the alkyl, alkenyl, alkynyl, cycloalkyl, heterocyclyl, heteroaryl, or aryl is optionally substituted with one or more —OR$_{11}$, —C(O)N(R$_{11}$)(R$_{12}$), —N(R$_{11}$)(R$_{12}$), —CN, —N(R$_{11}$)C(O)OR$_{12}$, —N(R$_{11}$)C(O)R$_2$, —C(O)—V—N(R$_{11}$)—F, —N(R$_{11}$)C(O)—V—N(R$_{12}$)—F, —C(O)—Ar, —N(R$_{11}$)C(O)—V—O(R$_2$), —O-Q$_2$-N(R$_{11}$)C(O)—V—O(R$_{12}$), or —N(R$_{11}$)C(O)—Ar;

Ar is aryl optionally substituted with —NR$_{11}$R$_{12}$, —C(O)-Q$_2$-N(R$_{11}$)—F or —N(R$_{11}$)C(O)-Q$_2$-N(R$_{12}$)—F;

Q$_2$ is —CH═CH(CH$_2$)$_m$, —(CH$_2$)$_m$, or —(CH$_2$CH$_2$O)$_o$—CH$_2$CH$_2$—;

V is —CH═CH(CH$_2$)$_m$, —(CH$_2$)$_m$, or —(CH$_2$CH$_2$O)$_o$—CH$_2$CH$_2$—;

F is —H, $C_{1-6}$ alkyl, or —C(O)-Q$_2$-N(R$_{11}$)(R$_{12}$);

$R_{10}$ is independently —H, halogen, —CN, —OH, —NO$_2$, oxo, $C_{1-6}$ alkyl, $C_{1-6}$ alkoxy, $C_{3-8}$ cycloalkyl, heterocyclyl, heteroaryl, or aryl;

$R_{11}$ and $R_{12}$ are independently —H, $C_{1-6}$ alkyl, $C_{2-6}$ alkenyl, $C_{2-6}$ alkynyl, $C_{3-8}$ cycloalkyl, heterocyclyl, aryl, or heteroaryl, wherein the alkyl, alkenyl, alkynyl, cycloalkyl, heterocyclyl, heteroaryl, or aryl is optionally substituted with one or more —H, halogen, —CN, —OH, —NO$_2$, oxo, $C_{1-6}$ alkyl, $C_{1-6}$ alkoxy, $C_{3-8}$ cycloalkyl, heterocyclyl, heteroaryl, aryl, —N(R$_{13}$)(R$_{14}$), —C(O)R$_{13}$, —N(R$_{13}$)C(O)R$_{14}$, —C(O)N(R$_{13}$)(R$_{14}$), —C(O)OR$_{13}$;

$R_{13}$ and $R_{14}$ are independently, at each occurrence, —H, $C_{1-6}$ alkyl, $C_{1-6}$ alkoxy, $C_{2-6}$ alkenyl, $C_{2-6}$ alkynyl, $C_{3-8}$ cycloalkyl, heterocyclyl, aryl, or heteroaryl, wherein the alkyl, alkenyl, alkynyl, cycloalkyl, heterocyclyl, heteroaryl, or aryl is optionally substituted with one or more H, halogen, —CN, —OH, —NH$_2$, —NO$_2$, oxo, $C_{1-6}$ alkyl, $C_{1-6}$ alkoxy, $C_{3-8}$ cycloalkyl, heterocyclyl, heteroaryl, or aryl;

each m is independently 1-4;

o is 1-3;

n is 1, 2, or 3;

q is 1-4;

r is 0-4;

s is 0-4; and t is 1-6 provided that:

(1) A is not oxadiazolyl, 1,3a-dihydro-4H-pyrazolo[3,4-d]pyrimidin-4-only, or piperidinyl;

(2) when A is phenyl, $R_3$ is not —S(O)$_2$R$_6$;

(3) when $R_1$ is pyrimidinyl and A is pyridinyl both $R_3$ and $R_4$ are not simultaneously H;

(4) when $R_1$ is —N(R$_6$)C(O)R$_7$, $R_6$ is H, and $R_7$ is not methyl;

(5) when $R_1$ is —C(O)N(R$_6$)(R$_7$), $R_6$ is H, and $R_7$ is alkyl, $R_8$ can not independently be both —OH and aryl;

(6) when $R_1$ is —C(O)N(R$_6$)(R$_7$), $R_6$ is H, and $R_7$ is alkyl, $R_8$ is not —OH;

(7) when $R_1$ is —C(O)N(R$_6$)(R$_7$) and $R_6$ is H, $R_7$ is not isopropyl;

(8) when $R_1$ is tetrazolyl, $R_1$ is substituted with $R_8$;

(9) when $R_1$ is imidazolyl and $R_1$ is substituted with $R_8$, $R_8$ is not aryl;

(10) when A is tetrahydropyranyl, thiophenyl, or 1,3,4-oxadiazolyl, both $R_3$ and $R_4$ are not simultaneously H; and

(11) when $R_3$ is —N(R$_6$)(R$_7$) and $R_6$ is H, $R_7$ is not methyl.

Another aspect of the invention relates to a method of treating a disease or disorder associated with modulation of PI5P4K. The method comprises administering to a patient in need of a treatment for diseases or disorders associated with modulation of PI5P4K an effective amount of a compound of Formula (I), or a pharmaceutically acceptable salt, hydrate, solvate, prodrug, stereoisomer, or tautomer thereof.

Another aspect of the invention is directed to a method of inhibiting PI5P4K. The method involves administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating cancer. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating a neurodegenerative disease. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating a viral infection or disease. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating an inflammatory disease or condition. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of inducing cell cycle arrest, apoptosis in tumor cells and/or enhanced tumor-specific T-cell immunity. The method comprises contacting the cells with an effective amount of a compound of Formula (I), or a pharmaceutically acceptable salt, hydrate, solvate, prodrug, stereoisomer, or tautomer thereof.

Another aspect of the invention is directed to pharmaceutical compositions comprising a compound of Formula (I), or a pharmaceutically acceptable salt, hydrate, solvate, prodrug, stereoisomer, or tautomer thereof and a pharmaceutically acceptable carrier. The pharmaceutical acceptable carrier may further include an excipient, diluent, or surfactant.

Another aspect of the present invention relates to a compound of Formula (I), or a pharmaceutically acceptable salt, hydrate, solvate, prodrug, stereoisomer, or tautomer thereof, for use in the manufacture of a medicament for treating a disease associated with inhibiting PI5P4K.

Another aspect of the present invention relates to the use of a compound of Formula (I), or a pharmaceutically acceptable salt, hydrate, solvate, prodrug, stereoisomer, or tautomer thereof, in the treatment of a disease associated with inhibiting PI5P4K.

The present invention further provides methods of treating a disease or disorder associated with modulation of PI5P4K including, cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases, comprising administering to a patient suffering from at least one of said diseases or disorder a compound of Formula (I), or a pharmaceutically acceptable salt, hydrate, solvate, prodrug, stereoisomer, or tautomer thereof.

The present invention provides inhibitors of PI5P4K that are therapeutic agents in the treatment of diseases such as cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases.

The present invention further provides compounds and compositions with an improved efficacy and safety profile relative to known PI5P4K inhibitors. The present disclosure also provides agents with novel mechanisms of action toward PI5P4K enzymes in the treatment of various types of diseases including cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases. Ultimately the present invention provides the medical community with a novel pharmacological strategy for the treatment of diseases and disorders associated with PI5P4K enzymes.

DETAILED DESCRIPTION OF THE INVENTION

The present invention relates to compounds and compositions that are capable of inhibiting the activity PI5P4K. The invention features methods of treating, preventing or ameliorating a disease or disorder in which PI5P4K plays a role by administering to a patient in need thereof a therapeutically effective amount of a compound of Formula (I), or a pharmaceutically acceptable salt, hydrate, solvate, prodrug, stereoisomer, or tautomer thereof. The methods of the present invention can be used in the treatment of a variety of PI5P4K dependent diseases and disorders by inhibiting the activity of PI5P4K enzymes. Inhibition of PI5P4K provides a novel approach to the treatment, prevention, or amelioration of diseases including, but not limited to, cancer and metastasis, neurodegenerative diseases, immunological disorders, osteoporosis, arthritis inflammatory disorders, cardiovascular diseases, ischemic diseases, viral infections and diseases, and bacterial infections and diseases.

In a first aspect of the invention, the compounds of Formula (I) are described:

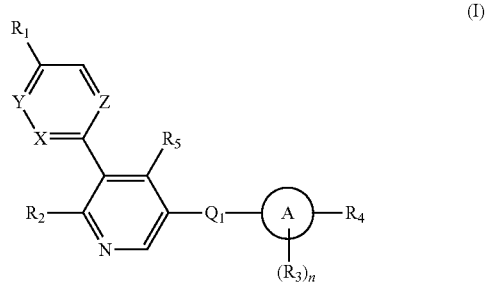

(I)

and pharmaceutically acceptable salts, hydrates, solvates, prodrugs, stereoisomers, and tautomers thereof, wherein A, X, Y, Z, $Q_1$, $R_1$, $R_2$, $R_3$, $R_4$, $R_5$, and n are described herein above.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (i.e., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—(C$_1$-C$_6$)alkyl, (C$_1$-C$_6$)alkyl, (C$_1$-C$_6$)alkoxy, (C$_1$-C$_6$) haloalkyl, (C$_1$-C$_6$)haloalkoxy, —O—(C$_2$-C$_6$)alkenyl, —O—(C$_2$-C$_6$)alkynyl, (C$_2$-C$_6$)alkenyl, (C$_2$-C$_6$)alkynyl, —OH, —OP(O)(OH)$_2$, —OC(O)(C$_1$-C$_6$)alkyl, —C(O)(C$_1$-C$_6$)alkyl, —OC(O)O(C$_1$-C$_6$)alkyl, —NH$_2$, —NH((C$_1$-C$_6$)alkyl), —N((C$_1$-C$_6$)alkyl)$_2$, —NHC(O)(C$_1$-C$_6$)alkyl, —C(O)NH(C$_1$-C$_6$)alkyl, —S(O)$_2$(C$_1$-C$_6$)alkyl, —S(O)NH(C$_1$-C$_6$)alkyl, and S(O)N((C$_1$-C$_6$)alkyl)$_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. The term "aryl" also encompasses polycyclic ring systems in which at least one ring is aromatic and is fused with 1 to 2 saturated or partially unsaturated cycloalkyl or heterocyclyl containing one or more heteroatoms selected from N, O, S, P, or B, and the cycloalkyl or heterocyclyl is optionally substituted with one or more oxo. For example, the term "aryl" may include polycyclic groups such as indanyl, Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, halogen, —O—(C$_1$-C$_6$)alkyl, (C$_1$-C$_6$)alkyl, —O—(C$_2$-C$_6$)alkenyl, —O—(C$_2$-C$_6$)alkynyl, (C$_2$-C$_6$)alkenyl, (C$_2$-C$_6$)alkynyl, —OH, —OP(O)(OH)$_2$, —OC(O)(C$_1$-C$_6$)alkyl, —C(O)(C$_1$-C$_6$)alkyl, —OC(O)O(C$_1$-C$_6$)alkyl, —NH$_2$, NH((C$_1$-C$_6$)alkyl), N((C$_1$-C$_6$)alkyl)$_2$, —S(O)$_2$—(C$_1$-C$_6$)alkyl, —S(O)NH(C$_1$-C$_6$)alkyl, and —S(O)N((C$_1$-C$_6$)alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic or polycyclic aromatic radical of 5 to 24 ring atoms, containing one or more ring heteroatoms selected from N, O, S, P, or B, the remaining ring atoms being C. Heteroaryl as herein defined also means a bicyclic heteroaromatic group wherein the heteroatom is selected from N, O, S, P, or B. Heteroaryl as herein defined also means a tricyclic heteroaromatic group containing one or more ring heteroatoms selected from N, O, S, P, or B. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolinyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl,[1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1λ$^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzoxazolyl, benzisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore, when containing two or more fused rings, the heteroaryl groups defined herein may have one or more saturated or partially unsaturated ring fused with a fully unsaturated ring, e.g., a 5-membered heteroaromatic ring containing 1-3 heteroatoms selected from N, S, or O, or a 6-membered heteroaromatic ring containing 1-3 nitrogens, wherein the saturated or partially unsaturated ring includes 0-4 heteroatoms selected from N, O, S, P, or B, and is optionally substituted with one or more oxo. In heteroaryl ring systems containing more than two fused rings, a saturated or partially unsaturated ring may further be fused with a saturated or partially unsaturated ring described herein. Exemplary ring systems of these heteroaryl groups include, for example, indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuranyl, benzofuranonyl, indolinyl, oxindolyl, indolyl, 1,6-dihydro-7H-pyrazolo[3,4-c]pyridin-7-onyl, 7,8-dihydro-6H-pyrido[3,2-b]pyrrolizinyl, 8H-pyrido[3,2-b]pyrrolizinyl, 1,5,6,7-tetrahydrocyclopenta[b]pyrazolo[4,3-e]pyridinyl, 7,8-dihydro-6H-pyrido[3,2-b]pyrrolizine, pyrazolo[1,5-a]pyrimidin-7(4H)-only, 3,4-dihydropyrazino[1,2-a]indol-1(2H)-onyl, or benzo[c][1,2]oxaborol-1(3H)-olyl. Halogen or "halo" refers to fluorine, chlorine, bromine, or iodine.

Alkyl refers to a straight or branched chain saturated hydrocarbon containing 1-12 carbon atoms. Examples of a (C$_1$-C$_6$)alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain, i.e., —O(alkyl). Examples of alkoxy groups include without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, isobutenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be unsubstituted or substituted.

The term "alkylene" or "alkylenyl" refers to a divalent alkyl radical. Any of the above mentioned monovalent alkyl groups may be an alkylene by abstraction of a second hydrogen atom from the alkyl. As herein defined, alkylene may also be a $C_1$-$C_6$ alkylene. An alkylene may further be a $C_1$-$C_4$ alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

"Cycloalkyl" means monocyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norbornyl, norbornenyl, bicyclo[2.2.2]octanyl, or bicyclo[2.2.2]octenyl.

"Cycloalkylalkyl" means monocyclic saturated carbon rings containing 3-24 carbon atoms further substituted with ($C_1$-$C_6$)alkyl groups. In general cycloalkylalkyl groups herein described display the following formula

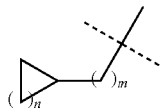

where m is an integer from 1 to 6 and n is an integer from 1 to 16. The cycloalkyl ring or carbocycle may be optionally substituted by one or more substituents, e.g., 1 to 5 substituents, at any point of attachment. The substituents can themselves be optionally substituted. Examples of cycloalkyl groups include, without limitations, cyclopropyl, cyclobutyl, cyclopentyl, cyclohexyl, cycloheptanyl, cyclooctanyl, norbornyl, norbornenyl, bicyclo[2.2.2]octanyl, bicyclo[2.2.2]octenyl, decahydronaphthalenyl, octahydro-1H-indenyl, cyclopentenyl, cyclohexenyl, cyclohexa-1,4-dienyl, cyclohexa-1,3-dienyl, 1,2,3,4-tetrahydronaphthalenyl, octahydropentalenyl, 3a,4,5,6,7,7a-hexahydro-1H-indenyl, 1,2,3,3a-tetrahydropentalenyl, bicyclo[3.1.0]hexanyl, bicyclo[2.1.0]pentanyl, spiro[3.3]heptanyl, bicyclo[2.2.1]heptanyl, bicyclo[2.2.1]hept-2-enyl, bicyclo[2.2.2]octanyl, 6-methylbicyclo[3.1.1]heptanyl, 2,6,6-trimethylbicyclo[3.1.1]heptanyl, and derivatives thereof.

"Heterocyclyl" or "heterocycloalkyl" monocyclic rings containing carbon and heteroatoms taken from containing one or more ring heteroatoms selected from N, O, S, P, or B and wherein there is not delocalized 7 electrons (aromaticity) shared among the ring carbon or heteroatoms. The heterocycloalkyl ring structure may be substituted by one or more substituents. The substituents can themselves be optionally substituted. Examples of heterocyclyl rings include, but are not limited to, oxetanyl, azetidinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl.

The term "hydroxyalkyl" means an alkyl group as defined above, where the alkyl group is substituted with one or more OH groups. Examples of hydroxyalkyl groups include HO—$CH_2$—, HO—$CH_2$—$CH_2$— and $CH_3$—CH(OH)—.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, i.e., C≡N.

The term "amine" as used herein refers to primary (R—$NH_2$, R≠H), secondary ($R_2$—NH, $R_2$≠H) and tertiary ($R_3$—N, $R_3$≠H) amines. A substituted amine is intended to mean an amine where at least one of the hydrogen atoms has been replaced by the substituent.

The term "amino" as used herein means a substituent containing at least one nitrogen atom. Specifically, —$NH_2$, —NH(alkyl) or alkylamino, —N(alkyl)$_2$ or dialkylamino, amide-, carbamide-, urea, and sulfamide substituents are included in the term "amino".

The term "dialkylamino" as used herein refers to an amino or —$NH_2$ group where both of the hydrogens have been replaced with alkyl groups, as defined herein above, i.e., —N(alkyl)$_2$. The alkyl groups on the amino group can be the same or different alkyl groups. Example of alkylamino groups include, but are not limited to, dimethylamino (i.e., —N($CH_3$)$_2$), diethylamino, dipropylamino, diisopropylamino, di-n-butylamino, di-sec-butylamino, di-tert-butylamino, methyl(ethyl)amino, methyl(butylamino), etc.

"Spirocycloalkyl" or "spirocyclyl" means carbogenic bicyclic ring systems with both rings connected through a single atom. The ring can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring. One or more of the carbon atoms in the spirocycle can be substituted with a heteroatom (e.g., O, N, S, or P). A ($C_3$-$C_{12}$) spirocycloalkyl is a spirocycle containing between 3 and 12 carbon atoms. One or more of the carbon atoms can be substituted with a heteroatom.

The term "spiroheterocycloalkyl" or "spiroheterocyclyl" is understood to mean a spirocycle wherein at least one of the rings is a heterocycle (e.g., at least one of the rings is furanyl, morpholinyl, or piperidinyl).

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The present invention also contemplates isotopically-labelled compounds of Formula I (e.g., those labeled with $^2$H and $^{14}$C). Deuterated (i.e., $^2$H or D) and carbon-14 (i.e., $^{14}$C) isotopes are particularly preferred for their ease of preparation and detectability. Further, substitution with heavier isotopes such as deuterium may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples herein below, by substituting an appropriate isotopically labelled reagent for a non-isotopically labelled reagent.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzoate, bicarbonate, bisulfate, bitartrate, borate, bromide, butyrate, calcium, calcium edetate, camsylate, carbonate, chloride, citrate, clavulanate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate, pantothenate, phosphate/diphosphate, picrate, polygalacturonate, propionate, p-toluenesulfonate, salicylate, stearate, subacetate, succinate, sulfate, sulfosalicylate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

The present invention relates to compounds or pharmaceutically acceptable salts, hydrates, solvates, prodrugs, stereoisomers, or tautomers thereof, capable of inhibiting PI5P4K, which are useful for the treatment of diseases and disorders associated with modulation of a PI5P4K enzyme. The invention further relates to compounds, or pharmaceutically acceptable salts, hydrates, solvates, prodrugs, stereoisomers, or tautomers thereof, which are useful for inhibiting PI5P4K.

In one embodiment, the compounds of Formula (I) have the structure of Formula (Ia):

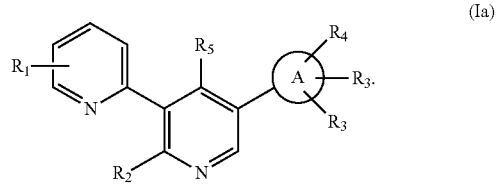

(Ia)

In another embodiment, the compounds of Formula (I) have the structure of Formula (Ib):

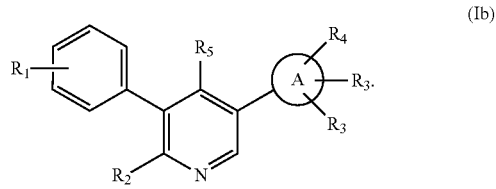

(Ib)

In another embodiment, the compounds of Formula (I) have the structure of Formula (Ic):

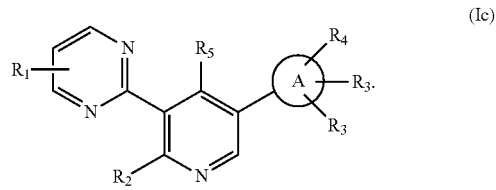

(Ic)

In another embodiment, the compounds of Formula (I) have the structure of Formula (Id):

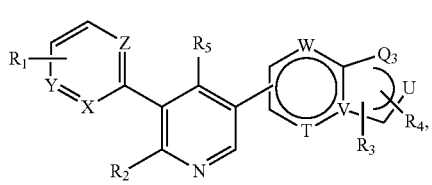

(Id)

wherein U and Q₃ are O, S, NH, or CH, provided that at least one of U or Q₃ is NH, S, or O; T, V, and W is CH or N, provided that only one of W or T is N; ——— is a circle or curve which represents an optional double bond conferring aromaticity to the rings.

In another embodiment, the compounds of Formula (I) have the structure of Formula (Ie):

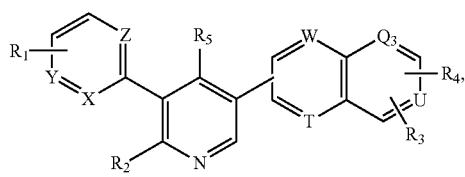

(Ie)

wherein
U and Q₃ are independently N or CH, provided that at least one of U or Q₃ is NH;
T and W are independently CH or N.

In another embodiment, the compounds of Formula (I) have the structure of Formula (If):

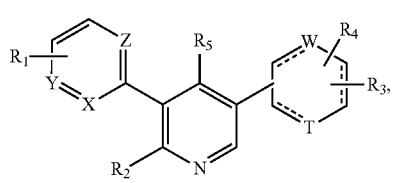

(If)

wherein
T and W are independently CH or N;
- - - - - represents an optional double bond which confers aromaticity or partial or full saturation to the ring.

In another embodiment, the compounds of Formula (I) have the structure of Formula (Ig):

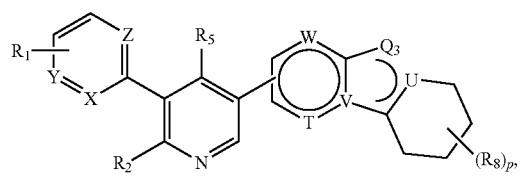

(Ig)

wherein
T and W are independently CH or N;
——— is a circle or curve which represents an optional double bond conferring aromaticity to the rings;
p is an integer from 0 to 3.

In another embodiment, the compounds of Formula (I) have the structure of Formula (Ih):

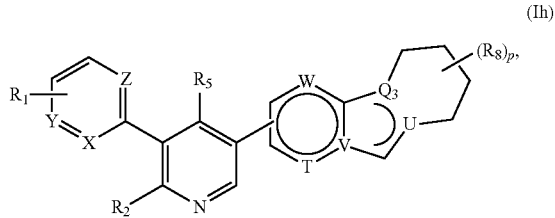

(Ih)

wherein
T and W are independently CH or N;
——— is a circle or curve which represents an optional double bond conferring aromaticity to the rings;
p is an integer from 0 to 3.

In another embodiment, the compounds of Formula (I) have the structure of Formula (Ii):

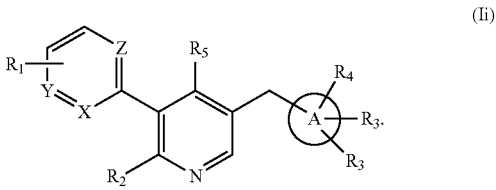

(Ii)

In some embodiments of the compounds of Formula I, $R_1$ is —N($R_6$)C(O)$R_7$, —C(O)N($R_6$)($R_7$), —(CH)$_{1-6}$C(O)N($R_6$)($R_7$), heterocyclyl, or heteroaryl. In another embodiment, $R_1$ is —N($R_6$)C(O)$R_7$. In another embodiment, $R_1$ is —C(O)N($R_6$)($R_7$). In another embodiment, $R_1$ is —(CH)$_{1-6}$C(O)N($R_6$)($R_7$). In another embodiment, $R_1$ is heterocyclyl. In another embodiment, $R_1$ is heteroaryl.

In some embodiments of the compounds of Formula I, $R_1$ is —N($R_6$)C(O)$R_7$, —C(O)N($R_6$)($R_7$), —(CH$_2$)$_t$C(O)N($R_6$)($R_7$), pyrrolidinyl, isoxazolyl, indolinyl, triazolyl, pyridinyl, pyridazinyl, imidazolyl, tetrazolyl, 6,7-dihydro-5H-pyrrolo[2,1-c][1,2,4]triazolyl, 2,8-diazaspiro[4.5]decanyl, or isothiazolidine 1,1-dioxidyl. In another embodiment, $R_1$ is pyrrolidinyl. In another embodiment, $R_1$ is isoxazolyl. In another embodiment, $R_1$ is indolinyl. In another embodiment, $R_1$ is triazolyl. In another embodiment, $R_1$ is pyridinyl. In another embodiment, $R_1$ is pyridazinyl. In another embodiment, $R_1$ is imidazolyl. In another embodiment, $R_1$ is tetrazolyl. In another embodiment, $R_1$ is 6,7-dihydro-5H-pyrrolo[2,1-c][1,2,4]triazolyl. In another embodiment, $R_1$ is 2,8-diazaspiro[4.5]decanyl. In another embodiment, $R_1$ is isothiazolidine 1,1-dioxidyl.

In some embodiments of the compounds of Formula I, $R_1$ is —N($R_6$)C(O)$R_7$, —C(O)N($R_6$)($R_7$), (CH)$_{1-6}$C(O)N($R_6$)($R_7$), pyrrolidinyl, isoxazolyl, indolinyl, triazolyl, pyridinyl, pyridazinyl, imidazolyl, tetrazolyl, 6,7-dihydro-5H-pyrrolo[2,1-c][1,2,4]triazolyl, 2,8-diazaspiro[4.5]decanyl, or isothiazolidine 1,1-dioxidyl; wherein pyrrolidinyl, isoxazolyl, indolinyl, triazolyl, pyridinyl, pyridazinyl, imidazolyl, tetrazolyl, 6,7-dihydro-5H-pyrrolo[2,1-c][1,2,4]triazolyl, 2,8-diazaspiro[4.5]decanyl, or isothiazolidine 1,1-dioxidyl is optionally substituted with one or more $R_8$. In another embodiment, $R_1$ is pyrrolidinyl optionally substituted with one or more $R_8$. In another embodiment, $R_1$ is isoxazolyl optionally substituted with one or more $R_8$. In another embodiment, $R_1$ is indolinyl optionally substituted with one or more $R_8$. In another embodiment, $R_1$ is triazolyl optionally substituted with one or more $R_8$. In another embodiment, $R_1$ is pyridinyl optionally substituted with one or more $R_8$. In another embodiment, $R_1$ is pyridazinyl optionally substituted with one or more $R_8$. In another embodiment, $R_1$ is imidazolyl optionally substituted with one or more $R_8$. In another embodiment, $R_1$ is tetrazolyl optionally substituted with one or more $R_8$. In another embodiment, $R_1$ is 6,7-dihydro-5H-pyrrolo[2,1-c][1,2,4]triazolyl optionally substituted with one or more $R_8$. In another embodiment, $R_1$ is 2,8-diazaspiro[4.5]decanyl optionally substituted with one or more $R_8$. In another embodiment, $R_1$ is isothiazolidine 1,1-dioxidyl optionally substituted with one or more $R_8$.

In some embodiments of the compounds of Formula I, X is CH or N. In another embodiment, X is CH. In another embodiment, X is N.

In some embodiments of the compounds of Formula I, Y is CH or N. In another embodiment, Y is CH. In another embodiment, Y is N.

In some embodiments of the compounds of Formula I, Z is CH or N. In another embodiment, Z is CH. In another embodiment, Z is N.

In some embodiments of the compounds of Formula I, at least one of X, Y, and Z is CH. In another embodiment, at least two of X, Y, and Z are CH. In another embodiment, X, Y, and Z are CH.

In some embodiments of the compounds of Formula I, Ring A is aryl, heteroaryl, or heterocyclyl. In another embodiment, Ring A is aryl or heteroaryl. In another embodiment, Ring A is aryl. In another embodiment, Ring A is heteroaryl. In another embodiment, Ring A is heterocyclyl.

In some embodiments of the compounds of Formula I, $R_2$ is —H, —$NH_2$, or $C_{1-6}$ alkyl. In one embodiment, $R_2$ is —H. In one embodiment, $R_2$ is —$NH_2$. In one embodiment, $R_2$ is $C_{1-6}$ alkyl.

In some embodiments of the compounds of Formula I, $Q_1$ is a bond.

n some embodiments of the compounds of Formula I, $X_2$ is $C(R_5)$ or N. In one embodiment, $X_2$ is $C(R_5)$. In one embodiment, $X_2$ is N.

In some embodiments of the compounds of Formula I, $R_3$ is independently, at each occurrence, —H, halogen, oxo, $C_{1-6}$ alkyl, $C_{3-6}$ cycloalkyl, heterocyclyl, —$OR_6$, —$NR_6R_7$, —CN, —$C(O)NR_6R_7$, —$N(R_6)C(O)R_7$, —$C(O)OR_6$, —$S(O)_2R_6$, or —$S(O)_2N(R_6)(R_7)$. In another embodiment, $R_3$ is —H, halogen, oxo, $C_{1-6}$ alkyl, $C_{3-6}$ cycloalkyl, heterocyclyl, —$OR_6$, —$NR_6R_7$, —CN, —$C(O)NR_6R_7$, —$N(R_6)C(O)R_7$, —$C(O)OR_6$, or —$S(O)_2R_6$. In another embodiment, $R_3$ is —H, halogen, oxo, $C_{1-6}$ alkyl, $C_{3-6}$ cycloalkyl, heterocyclyl, —$OR_6$, —$NR_6R_7$, —CN, —$C(O)NR_6R_7$, —$N(R_6)C(O)R_7$, or —$C(O)OR_6$. In another embodiment, $R_3$ is —H, halogen, oxo, $C_{1-6}$ alkyl, $C_{3-6}$ cycloalkyl, heterocyclyl, —$OR_6$, —$NR_6R_7$, —CN, —$C(O)NR_6R_7$, or —$N(R_6)C(O)R_7$. In another embodiment, $R_3$ is —H, halogen, oxo, $C_{1-6}$ alkyl, $C_{3-6}$ cycloalkyl, heterocyclyl, —$OR_6$, —$NR_6R_7$, —CN, or —$C(O)NR_6R_7$. In another embodiment, $R_3$ is —H, halogen, oxo, $C_{1-6}$ alkyl, $C_{3-6}$ cycloalkyl, heterocyclyl, —$OR_6$, —$NR_6R_7$, or —CN. In another embodiment, $R_3$ is —H, halogen, oxo, $C_{1-6}$ alkyl, $C_{3-6}$ cycloalkyl, heterocyclyl, —$OR_6$, or —$NR_6R_7$. In another embodiment, $R_3$ is —H, halogen, oxo, $C_{1-6}$ alkyl, $C_{3-6}$ cycloalkyl, heterocyclyl, or —$OR_6$. In another embodiment, $R_3$ is —H, halogen, oxo, $C_{1-6}$ alkyl, $C_{3-6}$ cycloalkyl, or heterocyclyl. In another embodiment, $R_3$ is —H, halogen, oxo, $C_{1-6}$ alkyl, or $C_{3-6}$ cycloalkyl. In another embodiment, $R_3$ is —H, halogen, oxo, or $C_{1-6}$ alkyl. In another embodiment, $R_3$ is —H, halogen, or oxo. In another embodiment, $R_3$ is —H or halogen. In another embodiment, $R_3$ is —H. In another embodiment, $R_3$ is halogen. In another embodiment, $R_3$ is oxo. In another embodiment, $R_3$ is $C_{1-6}$ alkyl. In another embodiment, $R_3$ is $C_{3-6}$ cycloalkyl. In another embodiment, $R_3$ is heterocyclyl. In another embodiment, $R_3$ is —$OR_6$. In another embodiment, $R_3$ is —$NR_6R_7$. In another embodiment, $R_3$ is CN. In another embodiment, $R_3$ is —$C(O)NR_6R_7$. In another embodiment, $R_3$ is —$N(R_6)C(O)R_7$. In another embodiment, $R_3$ is —$C(O)OR_6$. In another embodiment, $R_3$ is —$S(O)_2R_6$. In another embodiment, $R_3$ is —$S(O)_2N(R_6)(R_7)$. In another embodiment, $R_3$ is $C_{1-6}$ alkyl optionally substituted with one or more $R_8$. In another embodiment, $R_3$ is $C_{3-6}$ cycloalkyl optionally substituted with one or more $R_8$. In another embodiment, $R_3$ is heterocyclyl optionally substituted with one or more $R_8$.

In some embodiments of the compounds of Formula I, two $R_3$, when on adjacent atoms, with the atoms they are attached, form a $C_{4-8}$ cycloalkyl, $C_5$-$C_8$ spirocycloalkyl, spiroheterocycloalkyl, or heterocyclyl. In another embodiment, two $R_3$, when on adjacent atoms, with the atoms they are attached, form a $C_{4-8}$ cycloalkyl, $C_5$-$C_8$ spirocycloalkyl, or spiroheterocycloalkyl. In another embodiment, two $R_3$, when on adjacent atoms, with the atoms they are attached, form a $C_{4-8}$ cycloalkyl or $C_5$-$C_8$ spirocycloalkyl. In another embodiment, two $R_3$, when on adjacent atoms, with the atoms they are attached, form a $C_{4-8}$ cycloalkyl. In another embodiment, two $R_3$, when on adjacent atoms, with the atoms they are attached, form a $C_5$-$C_8$ spirocycloalkyl. In another embodiment, two $R_3$, when on adjacent atoms, with the atoms they are attached, form a spiroheterocycloalkyl. In another embodiment, two $R_3$, when on adjacent atoms, with the atoms they are attached, form a heterocyclyl. In another embodiment, two $R_3$, when on adjacent atoms, with the atoms they are attached, form a $C_{4-8}$ cycloalkyl optionally substituted with one or more $R_8$. In another embodiment, two $R_3$, when on adjacent atoms, with the atoms they are attached, form a $C_5$-$C_8$ spirocycloalkyl optionally substituted with one or more $R_8$. In another embodiment, two $R_3$, when on adjacent atoms, with the atoms they are attached, form a spiroheterocycloalkyl optionally substituted with one or more $R_8$. In another embodiment, two $R_3$, when on adjacent atoms, with the atoms they are attached, form a heterocyclyl optionally substituted with one or more $R_8$.

In other embodiments of the compounds of Formula I, $R_4$ is H, $C_3$-$C_8$ cycloalkyl, $C_5$-$C_8$ spirocycloalkyl, spiroheterocycloalkyl, aryl, heterocyclyl, heteroaryl, —$C(O)N(R_{10})$—($C_0$-$C_6$ alkylene)-$R_9$, —$C(O)N(R_{10})$— $R_9$, —$C(O)$—$R_9$, —$N(R_{10})$—($C_0$-$C_6$ alkylene)-$R_9$, —($C_0$-$C_6$ alkylene)-$N(R_{10})C(O)$—($C_0$-$C_6$ alkylene)-$R_9$, —$N(R_{10})C(O)$—($C_0$-$C_6$ alkylene)-$R_9$—$N(R_{10})C(O)$—($C_0$-$C_6$ alkylene)-, —$N(R_{10})C(O)$—$R_9$, or —$(CH_2)_q$—$R_9$, —$(CH_2)$—$N(R_{10})C(O)$—$(CH_2)_s$—$R_9$. In another embodiment, $R_4$ is H. In another embodiment, $R_4$ is $C_3$—C cycloalkyl. In another embodiment, $R_4$ is $C_5$-$C_8$ spirocycloalkyl. In another embodiment, $R_4$ is spiroheterocycloalkyl. In another embodiment, $R_4$ is aryl. In another embodiment, $R_4$ is heterocyclyl. In another embodiment, $R_4$ is heteroaryl. In another embodiment, $R_4$ is —$C(O)N(R_{10})$—($C_0$-$C_6$ alkylene)-$R_9$. In another embodiment, $R_4$ is, —$C(O)N(R_{10})$— $R_9$. In another embodiment, $R_4$ is —$N(R_{10})$—($C_0$-$C_6$ alkylene)-$R_9$. In another embodiment, $R_4$ is —($C_0$-$C_6$ alkylene)-$N(R_{10})C(O)$—($C_0$-$C_6$ alkylene)-$R_9$. In another embodiment, $R_4$ is —$N(R_{10})C(O)$—($C_0$-$C_6$ alkylene)-$R_9$—$N(R_{10})C(O)$—($C_0$-$C_6$ alkylene)-. In another embodiment, $R_4$ is —$N(R_{10})C(O)$—

$R_9$. In another embodiment, $R_4$ is —$(CH_2)_qR_9$, —$(CH_2)_r$—$N(R_{10})C(O)$—$(CH_2)_s$—$R_9$. In another embodiment, $R_4$ is $C_3$-$C_8$ cycloalkyl optionally substituted with one or more $R_9$. In another embodiment, $R_4$ is $C_5$-$C_8$ spirocycloalkyl optionally substituted with one or more $R_9$. In another embodiment, $R_4$ is spiroheterocycloalkyl optionally substituted with one or more $R_9$. In another embodiment, $R_4$ is aryl optionally substituted with one or more $R_9$. In another embodiment, $R_4$ is heterocyclyl optionally substituted with one or more $R_9$.

In other embodiments of the compounds of Formula I, $R_5$ is H, halogen, OH, $C_{1-6}$ alkyl, or $C_{1-6}$ alkoxy. In another embodiment, $R_5$ is H, halogen, OH, or $C_{1-6}$ alkyl. In another embodiment, $R_5$ is H, halogen, or OH. In another embodiment, $R_5$ is H or halogen. In another embodiment, $R_5$ is H. In another embodiment, $R_5$ is halogen. In another embodiment, $R_5$ is OH. In another embodiment, $R_5$ is $C_{1-6}$ alkyl. In another embodiment, $R_5$ is $C_{1-6}$ alkoxy. In another embodiment, $R_5$ is $C_{1-6}$ alkyl optionally substituted with $R_{10}$. In another embodiment, $R_5$ is $C_{1-6}$ alkoxy optionally substituted with $R_{10}$.

In other embodiments of the compounds of Formula I, $R_6$ is —H, $C_{1-6}$ alkyl, $C_{2-6}$ alkenyl, $C_{2-6}$ alkynyl, $C_{3-8}$ cycloalkyl, heterocyclyl, aryl, or heteroaryl. In another embodiment, $R_6$ is —H, $C_{1-6}$ alkyl, $C_{2-6}$ alkenyl, $C_{2-6}$ alkynyl, $C_{3-8}$ cycloalkyl, heterocyclyl, or aryl. In another embodiment, $R_6$ is —H, $C_{1-6}$ alkyl, $C_{2-6}$ alkenyl, $C_{2-6}$ alkynyl, $C_{3-8}$ cycloalkyl, or heterocyclyl. In another embodiment, $R_6$ is —H, $C_{1-6}$ alkyl, $C_{2-6}$ alkenyl, $C_{2-6}$ alkynyl, or $C_{3-8}$ cycloalkyl. In another embodiment, $R_6$ is —H, $C_{1-6}$ alkyl, $C_{2-6}$ alkenyl, or $C_{2-6}$ alkynyl. In another embodiment, $R_6$ is —H, $C_{1-6}$ alkyl, or $C_{2-6}$ alkenyl. In another embodiment, $R_6$ is —H or $C_{1-6}$ alkyl. In another embodiment, $R_6$ is H. In another embodiment, $R_6$ is $C_{1-6}$ alkyl. In another embodiment, $R_6$ is $C_{2-6}$ alkenyl. In another embodiment, $R_6$ is $C_{2-6}$ alkynyl. In another embodiment, $R_6$ is $C_{3-8}$ cycloalkyl. In another embodiment, $R_6$ is heterocyclyl. In another embodiment, $R_6$ is aryl. In another embodiment, $R_6$ is heteroaryl. In another embodiment, $R_6$ is $C_{1-6}$ alkyl optionally substituted with one or more $R_8$. In another embodiment, $R_6$ is $C_{2-6}$ alkenyl alkyl optionally substituted with one or more $R_8$. In another embodiment, $R_6$ is $C_{2-6}$ alkynyl alkyl optionally substituted with one or more $R_8$. In another embodiment, $R_6$ is $C_3$—cycloalkyl alkyl optionally substituted with one or more $R_8$. In another embodiment, $R_6$ is heterocyclyl alkyl optionally substituted with one or more $R_8$. In another embodiment, $R_6$ is aryl alkyl optionally substituted with one or more $R_8$. In another embodiment, $R_6$ is heteroaryl alkyl optionally substituted with one or more $R_8$.

In other embodiments of the compounds of Formula I, $R_7$ is $C_{1-6}$ alkyl, $C_{2-6}$ alkenyl, $C_{2-6}$ alkynyl, $C_{3-8}$ cycloalkyl, heterocyclyl, aryl, or heteroaryl. In another embodiment, $R_7$ is $C_{1-6}$ alkyl, $C_{2-6}$ alkenyl, $C_{2-6}$ alkynyl, $C_{3-8}$ cycloalkyl, heterocyclyl, or aryl. In another embodiment, $R_7$ is $C_{1-6}$ alkyl, $C_{2-6}$ alkenyl, $C_{2-6}$ alkynyl, $C_{3-8}$ cycloalkyl, or heterocyclyl. In another embodiment, $R_7$ is $C_{1-6}$ alkyl, $C_{2-6}$ alkenyl, $C_{2-6}$ alkynyl, or $C_{3-8}$ cycloalkyl. In another embodiment, $R_7$ is $C_{1-6}$ alkyl, $C_{2-6}$ alkenyl, or $C_{2-6}$ alkynyl. In another embodiment, $R_7$ is $C_{1-6}$ alkyl, or $C_{2-6}$ alkenyl. In another embodiment, $R_7$ is or $C_{1-6}$ alkyl. In another embodiment, $R_7$ is $C_{1-6}$ alkyl. In another embodiment, $R_7$ is $C_{2-6}$ alkenyl. In another embodiment, $R_7$ is $C_{2-6}$ alkynyl. In another embodiment, $R_7$ is $C_{3-8}$ cycloalkyl. In another embodiment, $R_7$ is heterocyclyl. In another embodiment, $R_7$ is aryl. In another embodiment, $R_7$ is heteroaryl. In another embodiment, $R_7$ is $C_{1-6}$ alkyl optionally substituted with one or more $R_8$. In another embodiment, $R_7$ is $C_{2-6}$ alkenyl alkyl optionally substituted with one or more $R_8$. In another embodiment, $R_7$ is $C_{2-6}$ alkynyl alkyl optionally substituted with one or more $R_8$. In another embodiment, $R_7$ is $C_{3-8}$ cycloalkyl alkyl optionally substituted with one or more $R_8$. In another embodiment, $R_7$ is heterocyclyl alkyl optionally substituted with one or more $R_8$. In another embodiment, $R_6$ is aryl alkyl optionally substituted with one or more $R_8$. In another embodiment, $R_7$ is heteroaryl alkyl optionally substituted with one or more $R_8$.

In some embodiments of the compounds of Formula I, $R_6$ and $R_7$ when taken together with the atom to which they are each attached form a $C_{4-8}$ cycloalkyl, $C_5$-$C_8$ spirocycloalkyl, spiroheterocycloalkyl, or heterocyclyl. In another embodiment, $R_6$ and $R_7$ when taken together with the atom to which they are each attached form a $C_{4-8}$ cycloalkyl, $C_5$-$C_8$ spirocycloalkyl, or spiroheterocycloalkyl. In another embodiment, $R_6$ and $R_7$ when taken together with the atom to which they are each attached form a $C_{4-8}$ cycloalkyl or $C_5$-$C_8$ spirocycloalkyl. In another embodiment, $R_6$ and $R_7$ when taken together with the atom to which they are each attached form a $C_{4-8}$ cycloalkyl. In another embodiment, $R_6$ and $R_7$ when taken together with the atom to which they are each attached form a $C_5$-$C_8$ spirocycloalkyl. In another embodiment, $R_6$ and $R_7$ when taken together with the atom to which they are each attached form a spiroheterocycloalkyl. In another embodiment, $R_6$ and $R_7$ when taken together with the atom to which they are each attached form a heterocyclyl. In another embodiment, $R_6$ and $R_7$ when taken together with the atom to which they are each attached form a $C_{4-8}$ cycloalkyl optionally substituted with one or more $R_8$. In another embodiment, $R_6$ and $R_7$ when taken together with the atom to which they are each attached form a $C_5$-$C_8$ spirocycloalkyl optionally substituted with one or more $R_8$. In another embodiment, $R_6$ and $R_7$ when taken together with the atom to which they are each attached form a spiroheterocycloalkyl optionally substituted with one or more $R_8$. In another embodiment, $R_6$ and $R_7$ when taken together with the atom to which they are each attached form a heterocyclyl optionally substituted with one or more $R_8$.

In other embodiments of the compounds of Formula I, $R_8$ is —CN, halogen, OH, $NH_2$, $NO_2$, oxo, $C_{1-6}$ alkyl, $C_{1-6}$ alkoxy, aryl, $C_{3-8}$ cycloalkyl, $C_5$-$C_8$ spirocycloalkyl, spiroheterocycloalkyl, heterocyclyl, or heteroaryl. In another embodiment, $R_8$ is —CN. In another embodiment, $R_8$ is halogen. In another embodiment, $R_8$ is OH. In another embodiment, $R_8$ is $NH_2$. In another embodiment, $R_8$ is $NO_2$. In another embodiment, $R_8$ is oxo. In another embodiment, $R_8$ is $C_{1-6}$ alkyl. In another embodiment, $R_8$ is $C_{1-6}$ alkoxy. In another embodiment, $R_8$ is aryl. In another embodiment, $R_8$ is $C_{3-8}$ cycloalkyl. In another embodiment, $R_8$ is $C_5$-$C_8$ spirocycloalkyl. In another embodiment, $R_8$ is spiroheterocycloalkyl. In another embodiment, $R_8$ is heterocyclyl. In another embodiment, $R_8$ is heteroaryl. In another embodiment, $R_8$ is $C_{1-6}$ alkyl optionally substituted with one or more $R_9$. In another embodiment, $R_8$ is $C_{1-6}$ alkoxy optionally substituted with one or more $R_9$. In another embodiment, $R_8$ is aryl optionally substituted with one or more $R_9$. In another embodiment, $R_8$ is $C_{3-8}$ cycloalkyl optionally substituted with one or more $R_9$. In another embodiment, $R_8$ is $C_5$-$C_8$ spirocycloalkyl optionally substituted with one or more $R_9$. In another embodiment, $R_8$ is spiroheterocycloalkyl optionally substituted with one or more $R_9$. In another embodiment, $R_8$ is heterocyclyl optionally substituted with one or more $R_9$. In another embodiment, $R_8$ is heteroaryl optionally substituted with one or more $R_9$.

In some embodiments of the compounds of Formula I, $R_9$ is —H, halogen, $C_{1-6}$ alkyl, $C_{2-6}$ alkenyl, $C_{2-6}$ alkynyl, $C_{3-8}$ cycloalkyl, aryl, heteroaryl, heterocyclyl, —$OR_{11}$, —C(O)

$O(R_{11})$, $-C(O)N(R_{11})(R_{12})$, $-N(R_{11})(R_{12})$, $-CN$, $-N(R_{11})C(O)OR_{12}$, $-N(R_{11})C(O)R_{12}$, $-C(O)-V-N(R_{11})-F$, $-N(R_{11})C(O)-V-N(R_{12})-F$, $-C(O)-Ar$, or $-N(R_{11})C(O)-Ar$. In another embodiment, $R_9$ is $-H$. In another embodiment, $R_9$ is halogen. In another embodiment, $R_9$ is $C_{1-6}$ alkyl. In another embodiment, $R_9$ is $C_{2-6}$ alkenyl. In another embodiment, $R_9$ is $C_{2-6}$ alkynyl. In another embodiment, $R_9$ is $C_{3-8}$ cycloalkyl. In another embodiment, $R_9$ is heterocyclyl. In another embodiment, $R_9$ is aryl. In another embodiment, $R_9$ is heteroaryl. In another embodiment, $R_9$ is $-OR_{11}$. In another embodiment, $R_9$ is $-C(O)O(R_{11})$. In another embodiment, $R_9$ is $-C(O)N(R_{11})(R_{12})$. In another embodiment, $R_9$ is $-N(R_{11})(R_{12})$. In another embodiment, $R_9$ is $-CN$. In another embodiment, $R_9$ is $-N(R_{11})C(O)OR_{12}$. In another embodiment, $R_9$ is $-N(R_{11})C(O)R_2$. In another embodiment, $R_9$ is $-C(O)-V-N(R_{11})-F$. In another embodiment, $R_9$ is $-N(R_{11})C(O)-V-N(R_2)-F$. In another embodiment, $R_9$ is $-C(O)-Ar$. In another embodiment, $R_9$ is $-N(R_{11})C(O)-Ar$. In another embodiment, $R_9$ is $C_{1-6}$ alkyl optionally substituted with one or more $-OR_{11}$, $-C(O)N(R_{11})(R_{12})$, $-N(R_{11})(R_{12})$, $-CN$, $-N(R_{11})C(O)OR_{12}$, $-N(R_{11})C(O)R_{12}$, $-C(O)-V-N(R_{11})-F$, $-N(R_{11})C(O)-V-N(R_{12})-F$, $-C(O)-Ar$, $-N(R_{11})C(O)-V-O(R_{12})$, $-O-Q_2-N(R_{11})C(O)-V-O(R_{12})$, or $-N(R_{11})C(O)-Ar$. In another embodiment, $R_9$ is $C_{2-6}$ alkenyl optionally substituted with one or more $-OR_{11}$, $-C(O)N(R_{11})(R_{12})$, $-N(R_{11})(R_{12})$, $-CN$, $-N(R_{11})C(O)OR_{12}$, $-N(R_{11})C(O)R_{12}$, $-C(O)-V-N(R_{11})-F$, $-N(R_{11})C(O)-V-N(R_{12})-F$, $-C(O)-Ar$, $-N(R_{11})C(O)-V-O(R_{12})$, $-O-Q_2-N(R_{11})C(O)-V-O(R_{12})$, or $-N(R_{11})C(O)-Ar$. In another embodiment, $R_9$ is $C_{2-6}$ alkynyl optionally substituted with one or more $-OR_{11}$, $-C(O)N(R_{11})(R_{12})$, $-N(R_{11})(R_{12})$, $-CN$, $-N(R_{11})C(O)OR_{12}$, $-N(R_{11})C(O)R_{12}$, $-C(O)-V-N(R_{11})-F$, $-N(R_{11})C(O)-V-N(R_2)-F$, $-C(O)-Ar$, $-N(R_{11})C(O)-V-O(R_{12})$, $-O-Q_2-N(R_{11})C(O)-V-O(R_2)$, or $-N(R_{11})C(O)-Ar$. In another embodiment, $R_9$ is $C_{3-8}$ cycloalkyl optionally substituted with one or more $-OR_{11}$, $-C(O)N(R_{11})(R_{12})$, $-N(R_{11})(R_{12})$, $-CN$, $-N(R_{11})C(O)OR_{12}$, $-N(R_{11})C(O)R_2$, $-C(O)-V-N(R_{11})-F$, $-N(R_{11})C(O)-V-N(R_{12})-F$, $-C(O)-Ar$, $-N(R_{11})C(O)-V-O(R_2)$, $-O-Q_2-N(R_{11})C(O)-V-O(R_2)$, or $-N(R_{11})C(O)-Ar$. In another embodiment, $R_9$ is heterocyclyl optionally substituted with one or more $-OR_{11}$, $-C(O)N(R_{11})(R_{12})$, $-N(R_{11})(R_{12})$, $-CN$, $-N(R_{11})C(O)OR_{12}$, $-N(R_{11})C(O)R_{12}$, $-C(O)-V-N(R_{11})-F$, $-N(R_{11})C(O)-V-N(R_{12})-F$, $-C(O)-Ar$, $-N(R_{11})C(O)-V-O(R_2)$, $-O-Q_2-N(R_{11})C(O)-V-O(R_{12})$, or $-N(R_{11})C(O)-Ar$. In another embodiment, $R_9$ is aryl optionally substituted with one or more $-OR_{11}$, $-C(O)N(R_{11})(R_{12})$, $-N(R_{11})(R_{12})$, $-CN$, $-N(R_{11})C(O)OR_{12}$, $-N(R_{11})C(O)R_{12}$, $-C(O)-V-N(R_{11})-F$, $-N(R_{11})C(O)-V-N(R_{12})-F$, $-C(O)-Ar$, $-N(R_{11})C(O)-V-O(R_{12})$, $-O-Q_2-N(R_{11})C(O)-V-O(R_{12})$, or $-N(R_{11})C(O)-Ar$. In another embodiment, $R_9$ is heteroaryl optionally substituted with one or more $-OR_{11}$, $-C(O)N(R_{11})(R_{12})$, $-N(R_{11})(R_{12})$, $-CN$, $-N(R_{11})C(O)OR_{12}$, $-N(R_{11})C(O)R_{12}$, $-C(O)-V-N(R_{11})-F$, $-N(R_{11})C(O)-V-N(R_{12})-F$, $-C(O)-Ar$, $-N(R_{11})C(O)-V-O(R_2)$, $-O-Q_2-N(R_{11})C(O)-V-O(R_{12})$, or $-N(R_{11})C(O)-Ar$.

In some embodiments of the compounds of Formula I, $R_{10}$ is independently H, halogen, CN, OH, $NO_2$, oxo, $C_{1-6}$ alkyl, $C_{1-6}$ alkoxy, $C_{3-8}$ cycloalkyl, heterocyclyl, heteroaryl, or aryl. In another embodiment, $R_{10}$ is $-H$. In another embodiment, $R_{10}$ is halogen. In another embodiment, $R_{10}$ is CN. In another embodiment, $R_{10}$ is OH. In another embodiment, $R_{10}$ is $NO_2$. In another embodiment, $R_{10}$ is oxo. In another embodiment, $R_{10}$ is $C_{1-6}$ alkyl. In another embodiment, $R_{10}$ is $C_{2-6}$ alkenyl. In another embodiment, $R_{10}$ is $C_{2-6}$ alkynyl. In another embodiment, $R_{10}$ is $C_{3-8}$ cycloalkyl. In another embodiment, $R_{10}$ is heterocyclyl. In another embodiment, $R_{10}$ is aryl. In another embodiment, $R_{10}$ is heteroaryl.

In some embodiments of the compounds of Formula I, $R_{11}$ is $-H$, $C_{1-6}$ alkyl, $C_{2-6}$ alkenyl, $C_{2-6}$ alkynyl, $C_{3-8}$ cycloalkyl, aryl, heteroaryl, or heterocyclyl. In another embodiment, $R_{11}$ is $-H$. In another embodiment, $R_{11}$ is $C_{1-6}$ alkyl. In another embodiment, $R_{11}$ is $C_{2-6}$ alkenyl. In another embodiment, $R_{11}$ is $C_{2-6}$ alkynyl. In another embodiment, $R_{11}$ is $C_{3-8}$ cycloalkyl. In another embodiment, $R_{11}$ is heterocyclyl. In another embodiment, $R_{11}$ is aryl. In another embodiment, $R_{11}$ is heteroaryl. In another embodiment, $R_{11}$ is $C_{1-6}$ alkyl optionally substituted with one or more H, halogen, CN, OH, $NO_2$, oxo, $C_{1-6}$ alkyl, $C_{1-6}$ alkoxy, $C_{3-8}$ cycloalkyl, heterocyclyl, heteroaryl, aryl, $-N(R_{13})(R_{14})$, $-C(O)R_{13}$, $-N(R_{13})C(O)R_{14}$, $-C(O)N(R_{13})(R_{14})$, $-C(O)OR_{13}$. In another embodiment, $R_{11}$ is $C_{2-6}$ alkenyl optionally substituted with one or more H, halogen, CN, OH, $NO_2$, oxo, $C_{1-6}$ alkyl, $C_{1-6}$ alkoxy, $C_{3-8}$ cycloalkyl, heterocyclyl, heteroaryl, aryl, $-N(R_{13})(R_{14})$, $-C(O)R_{13}$, $-N(R_{13})C(O)R_{14}$, $-C(O)N(R_{13})(R_{14})$, $-C(O)OR_{13}$. In another embodiment, $R_{11}$ is $C_{2-6}$ alkynyl optionally substituted with one or more H, halogen, CN, OH, $NO_2$, oxo, $C_{1-6}$ alkyl, $C_{1-6}$ alkoxy, $C_{3-8}$ cycloalkyl, heterocyclyl, heteroaryl, aryl, $-N(R_{13})(R_{14})$, $-C(O)R_{13}$, $-N(R_{13})C(O)R_{14}$, $-C(O)N(R_{13})(R_{14})$, $-C(O)OR_{13}$. In another embodiment, $R_{11}$ is $C_{3-8}$ cycloalkyl optionally substituted with one or more H, halogen, CN, OH, $NO_2$, oxo, $C_{1-6}$ alkyl, $C_{1-6}$ alkoxy, $C_{3-8}$ cycloalkyl, heterocyclyl, heteroaryl, aryl, $-N(R_{13})(R_{14})$, $-C(O)R_3$, $-N(R_{13})C(O)R_{14}$, $-C(O)N(R_{13})(R_{14})$, $-C(O)OR_{13}$. In another embodiment, $R_{11}$ is heterocyclyl optionally substituted with one or more H, halogen, CN, OH, $NO_2$, oxo, $C_{1-6}$ alkyl, $C_{1-6}$ alkoxy, $C_{3-8}$ cycloalkyl, heterocyclyl, heteroaryl, aryl, $-N(R_{13})(R_{14})$, $-C(O)R_3$, $-N(R_{13})C(O)R_{14}$, $-C(O)N(R_{13})(R_{14})$, $-C(O)OR_{13}$. In another embodiment, $R_{11}$ is aryl optionally substituted with one or more H, halogen, CN, OH, $NO_2$, oxo, $C_{1-6}$ alkyl, $C_{1-6}$ alkoxy, $C_{3-8}$ cycloalkyl, heterocyclyl, heteroaryl, aryl, $-N(R_{13})(R_{14})$, $-C(O)R_3$, $-N(R_{13})C(O)R_{14}$, $-C(O)N(R_{13})(R_{14})$, $-C(O)OR_{13}$. In another embodiment, $R_{11}$ is heteroaryl optionally substituted with one or more H, halogen, CN, OH, $NO_2$, oxo, $C_{1-6}$ alkyl, $C_{1-6}$ alkoxy, $C_{3-8}$ cycloalkyl, heterocyclyl, heteroaryl, aryl, $-N(R_{13})(R_{14})$, $-C(O)R_3$, $-N(R_{13})C(O)R_{14}$, $-C(O)N(R_{13})(R_{14})$, $-C(O)OR_{13}$.

In some embodiments of the compounds of Formula I, $R_{12}$ is $-H$, $C_{1-6}$ alkyl, $C_{2-6}$ alkenyl, $C_{2-6}$ alkynyl, $C_{3-8}$ cycloalkyl, aryl, heteroaryl, or heterocyclyl. In another embodiment, $R_{12}$ is $-H$. In another embodiment, $R_{12}$ is $C_{1-6}$ alkyl. In another embodiment, $R_{12}$ is $C_{2-6}$ alkenyl. In another embodiment, $R_{12}$ is $C_{2-6}$ alkynyl. In another embodiment, $R_{12}$ is $C_{3-8}$ cycloalkyl. In another embodiment, $R_{12}$ is heterocyclyl. In another embodiment, $R_{12}$ is aryl. In another embodiment, $R_{12}$ is heteroaryl. In another embodiment, $R_{12}$ is $C_{1-6}$ alkyl optionally substituted with one or more H, halogen, CN, OH, $NO_2$, oxo, $C_{1-6}$ alkyl, $C_{1-6}$ alkoxy, $C_{3-8}$ cycloalkyl, heterocyclyl, heteroaryl, aryl, $-N(R_{13})(R_{14})$, $-C(O)R_3$, $-N(R_{13})C(O)R_{14}$, $-C(O)N(R_{13})(R_{14})$, $-C(O)OR_{13}$. In another embodiment, $R_{12}$ is $C_{2-6}$ alkenyl optionally substituted with one or more H, halogen, CN, OH, $NO_2$, oxo, $C_{1-6}$ alkyl, $C_{1-6}$ alkoxy, $C_{3-8}$ cycloalkyl, heterocyclyl, heteroaryl, aryl, $-N(R_{13})(R_{14})$, $-C(O)R_3$, $-N(R_{13})C(O)R_{14}$, $-C(O)N(R_{13})(R_{14})$, $-C(O)OR_{13}$. In another embodiment, $R_{12}$ is $C_{2-6}$ alkynyl optionally substituted with one or more H, halogen, CN, OH, $NO_2$, oxo, $C_{1-6}$ alkyl, $C_{1-6}$ alkoxy, $C_{3-8}$ cycloalkyl, heterocyclyl, heteroaryl, aryl, —$N(R_{13})(R_{14})$, —$C(O)R_3$, —$N(R_{13})C(O)R_{14}$, —$C(O)N(R_{13})(R_{14})$, —$C(O)OR_{13}$. In another embodiment, $R_{12}$ is $C_{3-8}$ cycloalkyl optionally substituted with one or more H, halogen, CN, OH, $NO_2$, oxo, $C_{1-6}$ alkyl, $C_{1-6}$ alkoxy, $C_{3-8}$ cycloalkyl, heterocyclyl, heteroaryl, aryl, —$N(R_{13})(R_{14})$, —$C(O)R_3$, —$N(R_{13})C(O)R_{14}$, —$C(O)N(R_{13})(R_{14})$, —$C(O)OR_{13}$. In another embodiment, $R_{12}$ is heterocyclyl optionally substituted with one or more H, halogen, CN, OH, $NO_2$, oxo, $C_{1-6}$ alkyl, $C_{1-6}$ alkoxy, $C_{3-8}$ cycloalkyl, heterocyclyl, heteroaryl, aryl, —$N(R_{13})(R_{14})$, —$C(O)R_3$, —$N(R_{13})C(O)R_{14}$, —$C(O)N(R_{13})(R_{14})$, —$C(O)OR_{13}$. In another embodiment, $R_{12}$ is aryl optionally substituted with one or more H, halogen, CN, OH, $NO_2$, oxo, $C_{1-6}$ alkyl, $C_{1-6}$ alkoxy, $C_{3-8}$ cycloalkyl, heterocyclyl, heteroaryl, aryl, —$N(R_{13})(R_{14})$, —$C(O)R_{13}$, —$N(R_{13})C(O)R_{14}$, —$C(O)N(R_{13})(R_{14})$, —$C(O)OR_{13}$. In another embodiment, $R_{12}$ is heteroaryl optionally substituted with one or more H, halogen, CN, OH, $NO_2$, oxo, $C_{1-6}$ alkyl, $C_{1-6}$ alkoxy, $C_{3-8}$ cycloalkyl, heterocyclyl, heteroaryl, aryl, —$N(R_{13})(R_{14})$, —$C(O)R_{13}$, —$N(R_{13})C(O)R_{14}$, —$C(O)N(R_{13})(R_{14})$, —$C(O)OR_{13}$.

In some embodiments of the compounds of Formula I, Ar is aryl. In another embodiment, Ar is aryl optionally substituted with one or more substituted with —$NR_{11}R_{12}$, —$C(O)$—V—$N(R_{11})$—F or —$N(R_{11})C(O)$—V—$N(R_{12})$—F.

In other embodiments of the compounds of Formula I, V is —CH=CH$(CH_2)_m$—, —$(CH_2)_m$—, —$(CH_2)_m$—Ar—, or —$(CH_2CH_2O)_o$—$CH_2CH_2$—. In another embodiment, V is —CH=CH$(CH_2)_m$—. In another embodiment, V is —$(CH_2)_m$—. In another embodiment, V is —$(CH_2)_m$—Ar—. In another embodiment, V is —$(CH_2CH_2O)_o$—$CH_2CH_2$—.

In other embodiments of the compounds of Formula I, $Q_2$ is —CH=CH$(CH_2)_m$—, —$(CH_2)_m$—, or —$(CH_2CH_2O)_o$—$CH_2CH_2$—. In another embodiment, $Q_2$ is —CH=CH$(CH_2)_m$—. In another embodiment, $Q_2$ is —$(CH_2)_m$—. In another embodiment, $Q_2$ is —$(CH_2CH_2O)_o$—$CH_2CH_2$—.

In other embodiments of the compounds of Formula I, F is H, $C_{1-6}$ alkyl, or —$C(O)$—V—$N(R_{11})(R_{12})$. In another embodiment, F is H. In another embodiment, F is $C_{1-6}$ alkyl. In another embodiment, F is —C(O)-Q-N$(R_{23})(R_{23})$.

In some embodiments of the compounds of Formula I, $R_{13}$ is —H, $C_{1-6}$ alkyl, $C_{1-6}$ alkoxy, $C_{2-6}$ alkenyl, $C_{2-6}$ alkynyl, $C_{3-8}$ cycloalkyl, aryl, heteroaryl, or heterocyclyl. In another embodiment, $R_{13}$ is —H. In another embodiment, $R_{13}$ is $C_{1-6}$ alkyl. In another embodiment, $R_{13}$ is $C_{1-6}$ alkoxy. In another embodiment, $R_{13}$ is $C_{2-6}$ alkenyl. In another embodiment, $R_{13}$ is $C_{2-6}$ alkynyl. In another embodiment, $R_{13}$ is $C_{3-8}$ cycloalkyl. In another embodiment, $R_{13}$ is heterocyclyl. In another embodiment, $R_{13}$ is aryl. In another embodiment, $R_{13}$ is heteroaryl. In another embodiment, $R_{13}$ is $C_{1-6}$ alkyl optionally substituted with one or more H, halogen, CN, OH, $NH_2$, $NO_2$, oxo, $C_{1-6}$ alkyl, $C_{1-6}$ alkoxy, $C_{3-8}$ cycloalkyl, heterocyclyl, heteroaryl, or aryl. In another embodiment, $R_{13}$ is $C_{1-6}$ alkoxy optionally substituted with one or more H, halogen, CN, OH, $NH_2$, $NO_2$, oxo, $C_{1-6}$ alkyl, $C_{1-6}$ alkoxy, $C_{3-8}$ cycloalkyl, heterocyclyl, heteroaryl, or aryl. In another embodiment, $R_{13}$ is $C_{2-6}$ alkenyl optionally substituted with one or more H, halogen, CN, OH, $NH_2$, $NO_2$, oxo, $C_{1-6}$ alkyl, $C_{1-6}$ alkoxy, $C_{3-8}$ cycloalkyl, heterocyclyl, heteroaryl, or aryl. In another embodiment, $R_{13}$ is $C_{2-6}$ alkynyl optionally substituted with one or more H, halogen, CN, OH, $NH_2$, $NO_2$, oxo, $C_{1-6}$ alkyl, $C_{1-6}$ alkoxy, $C_{3-8}$ cycloalkyl, heterocyclyl, heteroaryl, or aryl. In another embodiment, $R_{13}$ is $C_{3-8}$ cycloalkyl optionally substituted with one or more H, halogen, CN, OH, $NH_2$, $NO_2$, oxo, $C_{1-6}$ alkyl, $C_{1-6}$ alkoxy, $C_{3-8}$ cycloalkyl, heterocyclyl, heteroaryl, or aryl. In another embodiment, $R_{13}$ is heterocyclyl optionally substituted with one or more H, halogen, CN, OH, $NH_2$, $NO_2$, oxo, $C_{1-6}$ alkyl, $C_{1-6}$ alkoxy, $C_{3-8}$ cycloalkyl, heterocyclyl, heteroaryl, or aryl. In another embodiment, $R_{13}$ is aryl optionally substituted with one or more H, halogen, CN, OH, $NH_2$, $NO_2$, oxo, $C_{1-6}$ alkyl, $C_{1-6}$ alkoxy, $C_{3-8}$ cycloalkyl, heterocyclyl, heteroaryl, or aryl. In another embodiment, $R_{13}$ is heteroaryl optionally substituted with one or more H, halogen, CN, OH, $NH_2$, $NO_2$, oxo, $C_{1-6}$ alkyl, $C_{1-6}$ alkoxy, $C_{3-8}$ cycloalkyl, heterocyclyl, heteroaryl, or aryl.

In some embodiments of the compounds of Formula I, $R_{14}$ is —H, $C_{1-6}$ alkyl, $C_{1-6}$ alkoxy, $C_{2-6}$ alkenyl, $C_{2-6}$ alkynyl, $C_{3-8}$ cycloalkyl, aryl, heteroaryl, or heterocyclyl. In another embodiment, $R_{13}$ is —H. In another embodiment, $R_{14}$ is $C_{1-6}$ alkyl. In another embodiment, $R_{13}$ is $C_{1-6}$ alkoxy. In another embodiment, $R_{14}$ is $C_{2-6}$ alkenyl. In another embodiment, $R_{14}$ is $C_{2-6}$ alkynyl. In another embodiment, $R_{14}$ is $C_{3-8}$ cycloalkyl. In another embodiment, $R_{14}$ is heterocyclyl. In another embodiment, $R_{14}$ is aryl. In another embodiment, $R_{14}$ is heteroaryl. In another embodiment, $R_{14}$ is $C_{1-6}$ alkyl optionally substituted with one or more H, halogen, CN, OH, $NH_2$, $NO_2$, oxo, $C_{1-6}$ alkyl, $C_{1-6}$ alkoxy, $C_{3-8}$ cycloalkyl, heterocyclyl, heteroaryl, or aryl. In another embodiment, $R_{14}$ is $C_{1-6}$ alkoxy optionally substituted with one or more H, halogen, CN, OH, $NH_2$, $NO_2$, oxo, $C_{1-6}$ alkyl, $C_{1-6}$ alkoxy, $C_{3-8}$ cycloalkyl, heterocyclyl, heteroaryl, or aryl. In another embodiment, $R_{14}$ is $C_{2-6}$ alkenyl optionally substituted with one or more H, halogen, CN, OH, $NH_2$, $NO_2$, oxo, $C_{1-6}$ alkyl, $C_{1-6}$ alkoxy, $C_{3-8}$ cycloalkyl, heterocyclyl, heteroaryl, or aryl. In another embodiment, $R_{14}$ is $C_{2-6}$ alkynyl optionally substituted with one or more H, halogen, CN, OH, $NH_2$, $NO_2$, oxo, $C_{1-6}$ alkyl, $C_{1-6}$ alkoxy, $C_{3-8}$ cycloalkyl, heterocyclyl, heteroaryl, or aryl. In another embodiment, $R_{14}$ is $C_{3-8}$ cycloalkyl optionally substituted with one or more H, halogen, CN, OH, $NH_2$, $NO_2$, oxo, $C_{1-6}$ alkyl, $C_{1-6}$ alkoxy, $C_{3-8}$ cycloalkyl, heterocyclyl, heteroaryl, or aryl. In another embodiment, $R_{14}$ is heterocyclyl optionally substituted with one or more H, halogen, CN, OH, $NH_2$, $NO_2$, oxo, $C_{1-6}$ alkyl, $C_{1-6}$ alkoxy, $C_{3-8}$ cycloalkyl, heterocyclyl, heteroaryl, or aryl. In another embodiment, $R_{14}$ is aryl optionally substituted with one or more H, halogen, CN, OH, $NH_2$, $NO_2$, oxo, $C_{1-6}$ alkyl, $C_{1-6}$ alkoxy, $C_{3-8}$ cycloalkyl, heterocyclyl, heteroaryl, or aryl. In another embodiment, $R_{14}$ is heteroaryl optionally substituted with one or more H, halogen, CN, OH, $NH_2$, $NO_2$, oxo, $C_{1-6}$ alkyl, $C_{1-6}$ alkoxy, $C_{3-8}$ cycloalkyl, heterocyclyl, heteroaryl, or aryl.

In one embodiment, r is 0, 1, 2, 3, or 4. In another embodiment r is 0, 1, 2, or 3. In another embodiment r is 0, 1 or 2. In another embodiment r is 0 or 1. In another embodiment r is 0. In another embodiment r is 1. In another embodiment r is 2. In another embodiment r is 3. In another embodiment r is 4.

In one embodiment, s is 0, 1, 2, 3, or 4. In another embodiment s is 0, 1, 2, or 3. In another embodiment s is 0, 1 or 2. In another embodiment s is 0 or 1. In another embodiment s is 0. In another embodiment s is 1. In another embodiment s is 2. In another embodiment s is 3. In another embodiment s is 4.

In one embodiment, m is 1, 2, 3, or 4. In another embodiment m is 1, 2, or 3. In another embodiment m is 1 or 2. In another embodiment m is 1. In another embodiment m is 2. In another embodiment m is 3. In another embodiment m is 4.

In one embodiment, q is 1, 2, 3, or 4. In another embodiment q is 1, 2, or 3. In another embodiment q is 1 or 2. In another embodiment q is 1. In another embodiment q is 2. In another embodiment q is 3. In another embodiment q is 4.

In one embodiment, n is 1, 2, or 3. In another embodiment n is 1 or 2. In another embodiment n is 1. In another embodiment n is 2. In another embodiment n is 3.

In one embodiment, o is 1, 2, or 3. In another embodiment o is 1 or 2. In another embodiment o is 1. In another embodiment o is 2. In another embodiment o is 3.

In one embodiment of the compounds of Formula I, X is N, Y is CH, Z is CH, $R_1$ is —C(O)N($R_6$)($R_7$), Ring A is heteroaryl, and $R_2$ is $NH_2$.

In one embodiment of the compounds of Formula I, X is N, Y is CH, Z is CH, $R_1$ is —N($R_6$)C(O)$R_7$, Ring A is heteroaryl, and $R_2$ is $NH_2$.

In one embodiment of the compounds of Formula I, X is N, Y is CH, Z is CH, $R_1$ is heteroaryl, Ring A is heteroaryl, and $R_2$ is $NH_2$.

In one embodiment of the compounds of Formula I, X is N, Y is CH, Z is CH, $R_1$ is —C(O)N($R_6$)($R_7$), Ring A is heteroaryl, and $R_2$ is H.

In one embodiment of the compounds of Formula I, X is N, Y is CH, Z is CH, $R_1$ is —N($R_6$)C(O)$R_7$, Ring A is heteroaryl, and $R_2$ is H.

In one embodiment of the compounds of Formula I, X is N, Y is CH, Z is CH, $R_1$ is heteroaryl, Ring A is heteroaryl, and $R_2$ is H.

In one embodiment of the compounds of Formula I, X is N, Y is CH, Z is CH, $R_1$ is —C(O)N($R_6$)($R_7$), Ring A is heteroaryl, and $R_2$ is $C_{1-6}$ alkyl.

In one embodiment of the compounds of Formula I, X is N, Y is CH, Z is CH, $R_1$ is —N($R_6$)C(O)$R_7$, Ring A is heteroaryl, and $R_2$ is $C_{1-6}$ alkyl.

In one embodiment of the compounds of Formula I, X is N, Y is CH, Z is CH, $R_1$ is heteroaryl, Ring A is heteroaryl, and $R_2$ is $C_{1-6}$ alkyl.

In one embodiment of the compounds of Formula I, X is N, Y is CH, Z is CH, $R_1$ is —C(O)N($R_6$)($R_7$), Ring A is aryl, and $R_2$ is $NH_2$.

In one embodiment of the compounds of Formula I, X is N, Y is CH, Z is CH, $R_1$ is —N($R_6$)C(O)$R_7$, Ring A is aryl, and $R_2$ is $NH_2$.

In one embodiment of the compounds of Formula I, X is N, Y is CH, Z is CH, $R_1$ is heteroaryl, Ring A is aryl, and $R_2$ is $NH_2$.

In one embodiment of the compounds of Formula I, X is N, Y is CH, Z is CH, $R_1$ is —C(O)N($R_6$)($R_7$), Ring A is aryl, and $R_2$ is H.

In one embodiment of the compounds of Formula I, X is N, Y is CH, Z is CH, $R_1$ is —N($R_6$)C(O)$R_7$, Ring A is aryl, and $R_2$ is H.

In one embodiment of the compounds of Formula I, X is N, Y is CH, Z is CH, $R_1$ is heteroaryl, Ring A is aryl, and $R_2$ is H.

In one embodiment of the compounds of Formula I, X is N, Y is CH, Z is CH, $R_1$ is —C(O)N($R_6$)($R_7$), Ring A is aryl, and $R_2$ is $C_{1-6}$ alkyl.

In one embodiment of the compounds of Formula I, X is N, Y is CH, Z is CH, $R_1$ is —N($R_6$)C(O)$R_7$, Ring A is aryl, and $R_2$ is $C_{1-6}$ alkyl.

In one embodiment of the compounds of Formula I, X is N, Y is CH, Z is CH, $R_1$ is heteroaryl, Ring A is aryl, and $R_2$ is $C_{1-6}$ alkyl.

In one embodiment of the compounds of Formula I, X is N, Y is CH, Z is CH, $R_1$ is —C(O)N($R_6$)($R_7$), Ring A is heterocyclyl, and $R_2$ is $NH_2$.

In one embodiment of the compounds of Formula I, X is N, Y is CH, Z is CH, $R_1$ is —N($R_6$)C(O)$R_7$, Ring A is heterocyclyl, and $R_2$ is $NH_2$.

In one embodiment of the compounds of Formula I, X is N, Y is CH, Z is CH, $R_1$ is heteroaryl, Ring A is heterocyclyl, and $R_2$ is $NH_2$.

In one embodiment of the compounds of Formula I, X is N, Y is CH, Z is CH, $R_1$ is —C(O)N($R_6$)($R_7$), Ring A is heterocyclyl, and $R_2$ is H.

In one embodiment of the compounds of Formula I, X is N, Y is CH, Z is CH, $R_1$ is —N($R_6$)C(O)$R_7$, Ring A is heterocyclyl, and $R_2$ is H.

In one embodiment of the compounds of Formula I, X is N, Y is CH, Z is CH, $R_1$ is heteroaryl, Ring A is heterocyclyl, and $R_2$ is H.

In one embodiment of the compounds of Formula I, X is N, Y is CH, Z is CH, $R_1$ is —C(O)N($R_6$)($R_7$), Ring A is heterocyclyl, and $R_2$ is $C_{1-6}$ alkyl.

In one embodiment of the compounds of Formula I, X is N, Y is CH, Z is CH, $R_1$ is —N($R_6$)C(O)$R_7$, Ring A is heterocyclyl, and $R_2$ is $C_{1-6}$ alkyl.

In one embodiment of the compounds of Formula I, X is N, Y is CH, Z is CH, $R_1$ is heteroaryl, Ring A is heterocyclyl, and $R_2$ is $C_{1-6}$ alkyl.

In one embodiment of the compounds of Formula I, X is CH, Y is CH, Z is CH, $R_1$ is —C(O)N($R_6$)($R_7$), Ring A is heteroaryl, and $R_2$ is $NH_2$.

In one embodiment of the compounds of Formula I, X is CH, Y is CH, Z is CH, $R_1$ is —N($R_6$)C(O)$R_7$, Ring A is heteroaryl, and $R_2$ is $NH_2$.

In one embodiment of the compounds of Formula I, X is CH, Y is CH, Z is CH, $R_1$ is heteroaryl, Ring A is heteroaryl, and $R_2$ is $NH_2$.

In one embodiment of the compounds of Formula I, X is CH, Y is CH, Z is CH, $R_1$ is —C(O)N($R_6$)($R_7$), Ring A is heteroaryl, and $R_2$ is H.

In one embodiment of the compounds of Formula I, X is CH, Y is CH, Z is CH, $R_1$ is —N($R_6$)C(O)$R_7$, Ring A is heteroaryl, and $R_2$ is H.

In one embodiment of the compounds of Formula I, X is CH, Y is CH, Z is CH, $R_1$ is heteroaryl, Ring A is heteroaryl, and $R_2$ is H.

In one embodiment of the compounds of Formula I, X is CH, Y is CH, Z is CH, $R_1$ is —C(O)N($R_6$)($R_7$), Ring A is heteroaryl, and $R_2$ is $C_{1-6}$ alkyl.

In one embodiment of the compounds of Formula I, X is CH, Y is CH, Z is CH, $R_1$ is —N($R_6$)C(O)$R_7$, Ring A is heteroaryl, and $R_2$ is $C_{1-6}$ alkyl.

In one embodiment of the compounds of Formula I, X is CH, Y is CH, Z is CH, $R_1$ is heteroaryl, Ring A is heteroaryl, and $R_2$ is $C_{1-6}$ alkyl.

In one embodiment of the compounds of Formula I, X is CH, Y is CH, Z is CH, $R_1$ is —C(O)N($R_6$)($R_7$), Ring A is aryl, and $R_2$ is $NH_2$.

In one embodiment of the compounds of Formula I, X is CH, Y is CH, Z is CH, $R_1$ is —N($R_6$)C(O)$R_7$, Ring A is aryl, and $R_2$ is $NH_2$.

In one embodiment of the compounds of Formula I, X is CH, Y is CH, Z is CH, $R_1$ is heteroaryl, Ring A is aryl, and $R_2$ is $NH_2$.

In one embodiment of the compounds of Formula I, X is CH, Y is CH, Z is CH, $R_1$ is —C(O)N($R_6$)($R_7$), Ring A is aryl, and $R_2$ is H.

In one embodiment of the compounds of Formula I, X is CH, Y is CH, Z is CH, $R_1$ is —N($R_6$)C(O)$R_7$, Ring A is aryl, and $R_2$ is H.

In one embodiment of the compounds of Formula I, X is CH, Y is CH, Z is CH, $R_1$ is heteroaryl, Ring A is aryl, and $R_2$ is H.

In one embodiment of the compounds of Formula I, X is CH, Y is CH, Z is CH, $R_1$ is —C(O)N($R_6$)($R_7$), Ring A is aryl, and $R_2$ is $C_{1-6}$ alkyl.

In one embodiment of the compounds of Formula I, X is CH, Y is CH, Z is CH, $R_1$ is —N($R_6$)C(O)$R_7$, Ring A is aryl, and $R_2$ is $C_{1-6}$ alkyl.

In one embodiment of the compounds of Formula I, X is CH, Y is CH, Z is CH, $R_1$ is heteroaryl, Ring A is aryl, and $R_2$ is $C_{1-6}$ alkyl.

In one embodiment of the compounds of Formula I, X is CH, Y is CH, Z is CH, $R_1$ is —C(O)N($R_6$)($R_7$), Ring A is heterocyclyl, and $R_2$ is $NH_2$.

In one embodiment of the compounds of Formula I, X is CH, Y is CH, Z is CH, $R_1$ is —N($R_6$)C(O)$R_7$, Ring A is heterocyclyl, and $R_2$ is $NH_2$.

In one embodiment of the compounds of Formula I, X is CH, Y is CH, Z is CH, $R_1$ is heteroaryl, Ring A is heterocyclyl, and $R_2$ is $NH_2$.

In one embodiment of the compounds of Formula I, X is CH, Y is CH, Z is CH, $R_1$ is —C(O)N($R_6$)($R_7$), Ring A is heterocyclyl, and $R_2$ is H.

In one embodiment of the compounds of Formula I, X is CH, Y is CH, Z is CH, $R_1$ is —N($R_6$)C(O)$R_7$, Ring A is heterocyclyl, and $R_2$ is H.

In one embodiment of the compounds of Formula I, X is CH, Y is CH, Z is CH, $R_1$ is heteroaryl, Ring A is heterocyclyl, and $R_2$ is H.

In one embodiment of the compounds of Formula I, X is CH, Y is CH, Z is CH, $R_1$ is —C(O)N($R_6$)($R_7$), Ring A is heterocyclyl, and $R_2$ is $C_{1-6}$ alkyl.

In one embodiment of the compounds of Formula I, X is CH, Y is CH, Z is CH, $R_1$ is —N($R_6$)C(O)$R_7$, Ring A is heterocyclyl, and $R_2$ is $C_{1-6}$ alkyl.

In one embodiment of the compounds of Formula I, X is CH, Y is CH, Z is CH, $R_1$ is alkyl, Ring A is heterocyclyl, and $R_2$ is $C_{1-6}$ alkyl.

In one embodiment of the compounds of Formula I, X is N, Y is CH, Z is CH, $R_1$ is —C(O)N($R_6$)($R_7$), Ring A is heteroaryl, $R_2$ is $NH_2$, $R_3$ is H, $R_4$ is —C(O)N($R_{10}$)—($C_0$-$C_6$ alkylene)-$R_9$.

In one embodiment of the compounds of Formula I, X is N, Y is CH, Z is CH, $R_1$ is —N($R_6$)C(O)$R_7$, Ring A is heteroaryl, $R_2$ is $NH_2$, $R_3$ is H, $R_4$ is —C(O)N($R_{10}$)—($C_0$-$C_6$ alkylene)-$R_9$.

In one embodiment of the compounds of Formula I, X is N, Y is CH, Z is CH, $R_1$ is heteroaryl, Ring A is heteroaryl, $R_2$ is $NH_2$, $R_3$ is H, $R_4$ is —C(O)N($R_{10}$)—($C_0$-$C_6$ alkylene)-$R_9$.

In one embodiment of the compounds of Formula I, X is N, Y is CH, Z is CH, $R_1$ is —C(O)N($R_6$)($R_7$), Ring A is heteroaryl, $R_2$ is H, $R_3$ is H, $R_4$ is —C(O)N($R_{10}$)—($C_0$-$C_6$ alkylene)-$R_9$.

In one embodiment of the compounds of Formula I, X is N, Y is CH, Z is CH, $R_1$ is —N($R_6$)C(O)$R_7$, Ring A is heteroaryl, $R_2$ is H, $R_3$ is H, $R_4$ is —C(O)N($R_{10}$)—($C_0$-$C_6$ alkylene)-$R_9$.

In one embodiment of the compounds of Formula I, X is N, Y is CH, Z is CH, $R_1$ is heteroaryl, Ring A is heteroaryl, $R_2$ is H, $R_3$ is H, $R_4$ is —C(O)N($R_{10}$)—($C_0$-$C_6$ alkylene)-$R_9$.

In one embodiment of the compounds of Formula I, X is N, Y is CH, Z is CH, $R_1$ is —C(O)N($R_6$)($R_7$), Ring A is heteroaryl, $R_2$ is $C_{1-6}$ alkyl, $R_3$ is H, $R_4$ is —C(O)N($R_{10}$)—($C_0$-$C_6$ alkylene)-$R_9$.

In one embodiment of the compounds of Formula I, X is N, Y is CH, Z is CH, $R_1$ is —N($R_6$)C(O)$R_7$, Ring A is heteroaryl, $R_2$ is $C_{1-6}$ alkyl, $R_3$ is H, $R_4$ is —C(O)N($R_{10}$)—($C_0$-$C_6$ alkylene)-$R_9$.

In one embodiment of the compounds of Formula I, X is N, Y is CH, Z is CH, $R_1$ is heteroaryl, Ring A is heteroaryl, $R_2$ is $C_{1-6}$ alkyl, $R_3$ is H, $R_4$ is —C(O)N($R_{10}$)—($C_0$-$C_6$ alkylene)-$R_9$.

In one embodiment of the compounds of Formula I, X is CH, Y is CH, Z is CH, $R_1$ is —C(O)N($R_6$)($R_7$), Ring A is heteroaryl, $R_2$ is $NH_2$, $R_3$ is H, $R_4$ is —C(O)N($R_{10}$)—($C_0$-$C_6$ alkylene)-$R_9$.

In one embodiment of the compounds of Formula I, X is CH, Y is CH, Z is CH, $R_1$ is —N($R_6$)C(O)$R_7$, Ring A is heteroaryl, $R_2$ is $NH_2$, $R_3$ is H, $R_4$ is —C(O)N($R_{10}$)—($C_0$-$C_6$ alkylene)-$R_9$.

In one embodiment of the compounds of Formula I, X is CH, Y is CH, Z is CH, $R_1$ is heteroaryl, Ring A is heteroaryl, $R_2$ is $NH_2$, $R_3$ is H, $R_4$ is —C(O)N($R_{10}$)—($C_0$-$C_6$ alkylene)-$R_9$.

In one embodiment of the compounds of Formula I, X is CH, Y is CH, Z is CH, $R_1$ is —C(O)N($R_6$)($R_7$), Ring A is heteroaryl, $R_2$ is H, $R_3$ is H, $R_4$ is —C(O)N($R_{10}$)—($C_0$-$C_6$ alkylene)-$R_9$.

In one embodiment of the compounds of Formula I, X is CH, Y is CH, Z is CH, $R_1$ is —N($R_6$)C(O)$R_7$, Ring A is heteroaryl, $R_2$ is H, $R_3$ is H, $R_4$ is —C(O)N($R_{10}$)—($C_0$-$C_6$ alkylene)-$R_9$.

In one embodiment of the compounds of Formula I, X is CH, Y is CH, Z is CH, $R_1$ is heteroaryl, Ring A is heteroaryl, $R_2$ is H, $R_3$ is H, $R_4$ is —C(O)N($R_{10}$)—($C_0$-$C_6$ alkylene)-$R_9$.

In one embodiment of the compounds of Formula I, X is CH, Y is CH, Z is CH, $R_1$ is —C(O)N($R_6$)($R_7$), Ring A is heteroaryl, $R_2$ is $C_{1-6}$ alkyl, $R_3$ is H, $R_4$ is —C(O)N($R_{10}$)—($C_0$-$C_6$ alkylene)-$R_9$.

In one embodiment of the compounds of Formula I, X is CH, Y is CH, Z is CH, $R_1$ is —N($R_6$)C(O)$R_7$, Ring A is heteroaryl, $R_2$ is $C_{1-6}$ alkyl, $R_3$ is H, $R_4$ is —C(O)N($R_{10}$)—($C_0$-$C_6$ alkylene)-$R_9$.

In one embodiment of the compounds of Formula I, X is CH, Y is CH, Z is CH, $R_1$ is heteroaryl, Ring A is heteroaryl, $R_2$ is $C_{1-6}$ alkyl, $R_3$ is H, $R_4$ is —C(O)N($R_{10}$)—($C_0$-$C_6$ alkylene)-$R_9$.

In one embodiment of the compounds of Formula I, X is N, Y is CH, Z is CH, $R_1$ is —C(O)N($R_6$)($R_7$), Ring A is heterocyclyl, $R_2$ is $NH_2$, $R_3$ is H, $R_4$ is —C(O)N($R_{10}$)—($C_0$-$C_6$ alkylene)-$R_9$.

In one embodiment of the compounds of Formula I, X is N, Y is CH, Z is CH, $R_1$ is —N($R_6$)C(O)$R_7$, Ring A is heterocyclyl, $R_2$ is $NH_2$, $R_3$ is H, $R_4$ is —C(O)N($R_{10}$)—($C_0$-$C_6$ alkylene)-$R_9$.

In one embodiment of the compounds of Formula I, X is N, Y is CH, Z is CH, $R_1$ is heteroaryl, Ring A is heterocyclyl, $R_2$ is $NH_2$, $R_3$ is H, $R_4$ is —C(O)N($R_{10}$)—($C_0$-$C_6$ alkylene)-$R_9$.

In one embodiment of the compounds of Formula I, X is N, Y is CH, Z is CH, $R_1$ is —C(O)N($R_6$)($R_7$), Ring A is heterocyclyl, $R_2$ is H, $R_3$ is H, $R_4$ is —C(O)N($R_{10}$)—($C_0$-$C_6$ alkylene)-$R_9$.

In one embodiment of the compounds of Formula I, X is N, Y is CH, Z is CH, $R_1$ is —N($R_6$)C(O)$R_7$, Ring A is heterocyclyl, $R_2$ is H, $R_3$ is H, $R_4$ is —C(O)N($R_{10}$)—($C_0$-$C_6$ alkylene)-$R_9$.

In one embodiment of the compounds of Formula I, X is N, Y is CH, Z is CH, $R_1$ is heteroaryl, Ring A is heterocyclyl, $R_2$ is H, $R_3$ is H, $R_4$ is —C(O)N($R_{10}$)—($C_0$-$C_6$ alkylene)-$R_9$.

In one embodiment of the compounds of Formula I, X is N, Y is CH, Z is CH, $R_1$ is —C(O)N($R_6$)($R_7$), Ring A is heterocyclyl, $R_2$ is $C_{1-6}$ alkyl, $R_3$ is H, $R_4$ is —C(O)N($R_{10}$)—($C_0$-$C_6$ alkylene)-$R_9$.

In one embodiment of the compounds of Formula I, X is N, Y is CH, Z is CH, $R_1$ is —N($R_6$)C(O)$R_7$, Ring A is heterocyclyl, $R_2$ is $C_{1-6}$ alkyl, $R_3$ is H, $R_4$ is —C(O)N($R_{10}$)—($C_0$-$C_6$ alkylene)-$R_9$.

In one embodiment of the compounds of Formula I, X is N, Y is CH, Z is CH, $R_1$ is heteroaryl, Ring A is heterocyclyl, $R_2$ is $C_{1-6}$ alkyl, $R_3$ is H, $R_4$ is —C(O)N($R_{10}$)—($C_0$-$C_6$ alkylene)-$R_9$.

In one embodiment of the compounds of Formula I, X is N, Y is CH, Z is CH, $R_1$ is —N($R_6$)C(O)$R_7$, Ring A is heteroaryl, $R_2$ is $NH_2$, $R_3$ is H, $R_4$ is —C(O)N($R_{10}$)—($C_0$-$C_6$ alkylene)-$R_9$, and $R_6$ and $R_7$ when taken together with the atom to which they are each attached form a $C_3$-$C_8$ cycloalkyl, $C_5$-$C_8$ spirocycloalkyl, spiroheterocycloalkyl, or heterocycle.

In one embodiment of the compounds of Formula I, X is N, Y is CH, Z is CH, $R_1$ is —N($R_6$)C(O)$R_7$, Ring A is heteroaryl, $R_2$ is H, $R_3$ is H, $R_4$ is —C(O)N($R_{10}$)—($C_0$-$C_6$ alkylene)-$R_9$, and $R_6$ and $R_7$ when taken together with the atom to which they are each attached form a $C_3$-$C_8$ cycloalkyl, $C_5$-$C_8$ spirocycloalkyl, spiroheterocycloalkyl, or heterocycle.

In one embodiment of the compounds of Formula I, X is N, Y is CH, Z is CH, $R_1$ is —N($R_6$)C(O)$R_7$, Ring A is heteroaryl, $R_2$ is $C_{1-6}$ alkyl, $R_3$ is H, $R_4$ is —C(O)N($R_{10}$)—($C_0$-$C_6$ alkylene)-$R_9$, and $R_6$ and $R_7$ when taken together with the atom to which they are each attached form a $C_3$-$C_8$ cycloalkyl, $C_5$-$C_8$ spirocycloalkyl, spiroheterocycloalkyl, or heterocycle.

In one embodiment of the compounds of Formula I, X is CH, Y is CH, Z is CH, $R_1$ is —N($R_6$)C(O)$R_7$, Ring A is heteroaryl, $R_2$ is $NH_2$, $R_3$ is H, $R_4$ is —C(O)N($R_{10}$)—($C_0$-$C_6$ alkylene)-$R_9$, and $R_6$ and $R_7$ when taken together with the atom to which they are each attached form a $C_3$-$C_8$ cycloalkyl, $C_5$-$C_8$ spirocycloalkyl, spiroheterocycloalkyl, or heterocycle.

In one embodiment of the compounds of Formula I, X is CH, Y is CH, Z is CH, $R_1$ is —N($R_6$)C(O)$R_7$, Ring A is heteroaryl, $R_2$ is H, $R_3$ is H, $R_4$ is —C(O)N($R_{10}$)—($C_0$-$C_6$ alkylene)-$R_9$, and $R_6$ and $R_7$ when taken together with the atom to which they are each attached form a $C_3$-$C_8$ cycloalkyl, $C_5$-$C_8$ spirocycloalkyl, spiroheterocycloalkyl, or heterocycle.

In one embodiment of the compounds of Formula I, X is CH, Y is CH, Z is CH, $R_1$ is —N($R_6$)C(O)$R_7$, Ring A is heteroaryl, $R_2$ is $C_{1-6}$ alkyl, $R_3$ is H, $R_4$ is —C(O)N($R_{10}$)—($C_0$-$C_6$ alkylene)-$R_9$, and $R_6$ and $R_7$ when taken together with the atom to which they are each attached form a $C_3$-$C_8$ cycloalkyl, $C_5$-$C_8$ spirocycloalkyl, spiroheterocycloalkyl, or heterocycle.

In one embodiment of the compounds of Formula I, X is N, Y is CH, Z is CH, $R_1$ is —N($R_6$)C(O)$R_7$, Ring A is heterocyclyl, $R_2$ is $NH_2$, $R_3$ is H, $R_4$ is —C(O)N($R_{10}$)—($C_0$-$C_6$ alkylene)-$R_9$.

In one embodiment of the compounds of Formula I, X is N, Y is CH, Z is CH, $R_1$ is —N($R_6$)C(O)$R_7$, Ring A is heterocyclyl, $R_2$ is H, $R_3$ is H, $R_4$ is —C(O)N($R_{10}$)—($C_0$-$C_6$ alkylene)-$R_9$, and $R_6$ and $R_7$ when taken together with the atom to which they are each attached form a $C_3$-$C_8$ cycloalkyl, $C_5$-$C_8$ spirocycloalkyl, spiroheterocycloalkyl, or heterocycle.

In one embodiment of the compounds of Formula I, X is N, Y is CH, Z is CH, $R_1$ is —N($R_6$)C(O)$R_7$, Ring A is heterocyclyl, $R_2$ is $C_{1-6}$ alkyl, $R_3$ is H, $R_4$ is —C(O)N($R_{10}$)—($C_0$-$C_6$ alkylene)-$R_9$, and $R_6$ and $R_7$ when taken together with the atom to which they are each attached form a $C_3$-$C_8$ cycloalkyl, $C_5$-$C_8$ spirocycloalkyl, spiroheterocycloalkyl, or heterocycle.

In one embodiment of the compounds of Formula I, X is N, Y is CH, Z is CH, $R_1$ is —C(O)N($R_6$)($R_7$), Ring A is heteroaryl, $R_2$ is $NH_2$, $R_3$ is H, —C(O)N$R_6R_7$, or —C(O)O$R_6$, $R_6$ and $R_7$ are independently, at each occurrence, —H, $C_{1-6}$ alkyl, $C_{3-8}$ cycloalkyl, heterocyclyl, aryl, or heteroaryl, optionally substituted with one or more $R_8$.

In one embodiment of the compounds of Formula I, X is N, Y is CH, Z is CH, $R_1$ is —N($R_6$)C(O)$R_7$, Ring A is heteroaryl, $R_2$ is $NH_2$, $R_3$ is H, —C(O)N$R_6R_7$, or —C(O)O$R_6$, $R_6$ and $R_7$ are independently, at each occurrence, —H, $C_{1-6}$ alkyl, $C_{3-8}$ cycloalkyl, heterocyclyl, aryl, or heteroaryl, optionally substituted with one or more $R_8$.

In one embodiment of the compounds of Formula I, X is N, Y is CH, Z is CH, $R_1$ is heteroaryl, Ring A is heteroaryl, $R_2$ is $NH_2$, $R_3$ is H, —C(O)N$R_6R_7$, or —C(O)O$R_6$, $R_6$ and $R_7$ are independently, at each occurrence, —H, $C_{1-6}$ alkyl, $C_{3-8}$ cycloalkyl, heterocyclyl, aryl, or heteroaryl, optionally substituted with one or more $R_8$.

In one embodiment of the compounds of Formula I, X is N, Y is CH, Z is CH, $R_1$ is —C(O)N($R_6$)($R_7$), Ring A is heteroaryl, $R_2$ is H, $R_3$ is H, —C(O)N$R_6R_7$, or —C(O)O$R_6$, $R_6$ and $R_7$ are independently, at each occurrence, —H, $C_{1-6}$ alkyl, $C_{3-8}$ cycloalkyl, heterocyclyl, aryl, or heteroaryl, optionally substituted with one or more $R_8$.

In one embodiment of the compounds of Formula I, X is N, Y is CH, Z is CH, $R_1$ is —N($R_6$)C(O)$R_7$, Ring A is heteroaryl, $R_2$ is H, $R_3$ is H, —C(O)N$R_6R_7$, or —C(O)O$R_6$, $R_6$ and $R_7$ are independently, at each occurrence, —H, $C_{1-6}$ alkyl, $C_{3-8}$ cycloalkyl, heterocyclyl, aryl, or heteroaryl, optionally substituted with one or more $R_8$.

In one embodiment of the compounds of Formula I, X is N, Y is CH, Z is CH, $R_1$ is heteroaryl, Ring A is heteroaryl, $R_2$ is H, $R_3$ is H, —C(O)N$R_6R_7$, or —C(O)O$R_6$, $R_6$ and $R_7$ are independently, at each occurrence, —H, $C_{1-6}$ alkyl, $C_{3-8}$ cycloalkyl, heterocyclyl, aryl, or heteroaryl, optionally substituted with one or more $R_8$.

In one embodiment of the compounds of Formula I, X is N, Y is CH, Z is CH, $R_1$ is —C(O)N($R_6$)($R_7$), Ring A is heteroaryl, $R_2$ is $C_{1-6}$ alkyl, $R_3$ is H, —C(O)N$R_6R_7$, or —C(O)O$R_6$, $R_6$ and $R_7$ are independently, at each occurrence, —H, $C_{1-6}$ alkyl, $C_{3-8}$ cycloalkyl, heterocyclyl, aryl, or heteroaryl, optionally substituted with one or more $R_8$.

In one embodiment of the compounds of Formula I, X is N, Y is CH, Z is CH, $R_1$ is —N($R_6$)C(O)$R_7$, Ring A is heteroaryl, $R_2$ is $C_{1-6}$ alkyl, $R_3$ is H, —C(O)N$R_6R_7$, or —C(O)O$R_6$, $R_6$ and $R_7$ are independently, at each occurrence, —H, $C_{1-6}$ alkyl, $C_{3-8}$ cycloalkyl, heterocyclyl, aryl, or heteroaryl, optionally substituted with one or more $R_8$.

In one embodiment of the compounds of Formula I, X is CH, Y is CH, Z is CH, $R_1$ is —C(O)N($R_6$)($R_7$), Ring A is heteroaryl, $R_2$ is H, —C(O)N$R_6R_7$, or —C(O)O$R_6$, $R_6$ and $R_7$ are independently, at each occurrence, —H, $C_{1-6}$ alkyl, $C_{3-8}$ cycloalkyl, heterocyclyl, aryl, or heteroaryl, optionally substituted with one or more $R_8$.

In one embodiment of the compounds of Formula I, X is CH, Y is CH, Z is CH, $R_1$ is —N($R_6$)C(O)$R_7$, Ring A is heteroaryl, $R_2$ is $NH_2$, $R_3$ is H, —C(O)N$R_6R_7$, or —C(O)O$R_6$, $R_6$ and $R_7$ are independently, at each occurrence, —H, $C_{1-6}$ alkyl, $C_{3-8}$ cycloalkyl, heterocyclyl, aryl, or heteroaryl, optionally substituted with one or more $R_8$.

In one embodiment of the compounds of Formula I, X is CH, Y is CH, Z is CH, $R_1$ is —C(O)N($R_6$)($R_7$), Ring A is heteroaryl, $R_2$ is H, $R_3$ is H, —C(O)$NR_6R_7$, or —C(O)$OR_6$, $R_6$ and $R_7$ are independently, at each occurrence, —H, $C_{1-6}$ alkyl, $C_{3-8}$ cycloalkyl, heterocyclyl, aryl, or heteroaryl, optionally substituted with one or more $R_8$.

In one embodiment of the compounds of Formula I, X is CH, Y is CH, Z is CH, $R_1$ is —N($R_6$)C(O)$R_7$, Ring A is heteroaryl, $R_2$ is H, $R_3$ is H, —C(O)$NR_6R_7$, or —C(O)$OR_6$, $R_6$ and $R_7$ are independently, at each occurrence, —H, $C_{1-6}$ alkyl, $C_{3-8}$ cycloalkyl, heterocyclyl, aryl, or heteroaryl, optionally substituted with one or more $R_8$.

In one embodiment of the compounds of Formula I, X is N, Y is CH, Z is CH, $R_1$ is —C(O)N($R_6$)($R_7$), Ring A is heterocyclyl, $R_2$ is $NH_2$, $R_3$ is H, —C(O)$NR_6R_7$, or —C(O)$OR_6$, $R_6$ and $R_7$ are independently, at each occurrence, —H, $C_{1-6}$ alkyl, $C_{3-8}$ cycloalkyl, heterocyclyl, aryl, or heteroaryl, optionally substituted with one or more $R_8$.

In one embodiment of the compounds of Formula I, X is N, Y is CH, Z is CH, $R_1$ is —N($R_6$)C(O)$R_7$, Ring A is heterocyclyl, $R_2$ is $NH_2$, $R_3$ is H, —C(O)$NR_6R_7$, or —C(O)$OR_6$, $R_6$ and $R_7$ are independently, at each occurrence, —H, $C_{1-6}$ alkyl, $C_{3-8}$ cycloalkyl, heterocyclyl, aryl, or heteroaryl, optionally substituted with one or more $R_8$.

In one embodiment of the compounds of Formula I, X is N, Y is CH, Z is CH, $R_1$ is —C(O)N($R_6$)($R_7$), Ring A is heterocyclyl, $R_2$ is H, $R_3$ is H, —C(O)$NR_6R_7$, or —C(O)$OR_6$, $R_6$ and $R_7$ are independently, at each occurrence, —H, $C_{1-6}$ alkyl, $C_{3-8}$ cycloalkyl, heterocyclyl, aryl, or heteroaryl, optionally substituted with one or more $R_8$.

In one embodiment of the compounds of Formula I, X is N, Y is CH, Z is CH, $R_1$ is —N($R_6$)C(O)$R_7$, Ring A is heterocyclyl, $R_2$ is H, $R_3$ is H, —C(O)$NR_6R_7$, or —C(O)$OR_6$, $R_6$ and $R_7$ are independently, at each occurrence, —H, $C_{1-6}$ alkyl, $C_{3-8}$ cycloalkyl, heterocyclyl, aryl, or heteroaryl, optionally substituted with one or more $R_8$.

In one embodiment of the compounds of Formula I, X is CH, Y is CH, Z is $CR_{1a}$, $R_{1a}$ and $R_5$ are taken together to form heterocyclyl, $R_1$ is —N($R_6$)C(O)$R_7$, Ring A is heterocyclyl, $R_2$ is H, n is 1-3, each $R_3$ is independently H, $C_{1-6}$ alkyl optionally substituted with $R_5$, —C(O)$NR_6R_7$, or —C(O)$OR_6$, $R_6$ and $R_7$ are independently, at each occurrence, —H, $C_{1-6}$ alkyl, $C_{3-8}$ cycloalkyl, heterocyclyl, aryl, or heteroaryl, optionally substituted with one or more $R_8$, or $R_6$ and $R_7$ are taken together to form heterocyclyl optionally substituted with one or more $R_8$.

In one embodiment of the compounds of Formula I, X is CH, Y is CH, Z is $CR_{1a}$, $R_{1a}$ and $R_5$ are taken together to form heterocyclyl, $R_1$ is —N($R_6$)C(O)$R_7$, Ring A is heteroaryl, $R_2$ is H, n is 1-3, each $R_3$ is independently H, $C_{1-6}$ alkyl optionally substituted with $R_8$, —C(O)$NR_6R_7$, or —C(O)$OR_6$, $R_6$ and $R_7$ are independently, at each occurrence, —H, $C_{1-6}$ alkyl, $C_{3-8}$ cycloalkyl, heterocyclyl, aryl, or heteroaryl, optionally substituted with one or more $R_8$, or $R_6$ and $R_7$ are taken together to form heterocyclyl optionally substituted with one or more $R_8$.

In one embodiment of the compounds of Formula I, X is CH, Y is CH, Z is CH, $R_5$ is H, and $R_2$ is H.

In one embodiment of the compounds of Formula I, X is CH, Y is CH, Z is CH, $R_1$ is —N($R_6$)C(O)$R_7$, $R_5$ is H, $R_2$ is H, Ring A is heteroaryl, and $R_6$ and $R_7$ are independently —H, $C_{1-6}$ alkyl, $C_{3-8}$ cycloalkyl, heterocyclyl, aryl, or heteroaryl, optionally substituted with one or more $R_8$, or $R_6$ and $R_7$ are taken together to form heterocyclyl optionally substituted with one or more $R_8$.

In one embodiment of the compounds of Formula I, X is CH, Y is CH, Z is CH, $R_1$ is —N($R_6$)C(O)$R_7$, $R_5$ is H, and $R_2$ is H, Ring A is heterocyclyl, and $R_6$ and $R_7$ are independently —H, $C_{1-6}$ alkyl, $C_{3-8}$ cycloalkyl, heterocyclyl, aryl, or heteroaryl, optionally substituted with one or more $R_8$, or $R_6$ and $R_7$ are taken together to form heterocyclyl optionally substituted with one or more $R_8$.

In one embodiment of the compounds of Formula I, X is CH, Y is CH, Z is $CR_{1a}$, $R_{1a}$ is $C_{1-6}$ alkyl, $R_5$ is H, $R_2$ is H.

In one embodiment of the compounds of Formula I, X is CH, Y is CH, Z is $CR_{1a}$, $R_{1a}$ is $C_{1-6}$ alkyl, $R_1$ is —N($R_6$)C(O)$R_7$, $R_5$ is H, $R_2$ is H, Ring A is heteroaryl, and $R_6$ and $R_7$ are independently —H, $C_{1-6}$ alkyl, $C_{3-8}$ cycloalkyl, heterocyclyl, aryl, or heteroaryl, optionally substituted with one or more $R_5$, or $R_6$ and $R_7$ are taken together to form heterocyclyl optionally substituted with one or more $R_8$.

In one embodiment of the compounds of Formula I, X is CH, Y is CH, Z is $CR_{1a}$, $R_{1a}$ is $C_{1-6}$ alkyl, $R_1$ is —N($R_6$)C(O)$R_7$, $R_5$ is H, $R_2$ is H, Ring A is heterocyclyl, and $R_6$ and $R_7$ are independently —H, $C_{1-6}$ alkyl, $C_{3-8}$ cycloalkyl, heterocyclyl, aryl, or heteroaryl, optionally substituted with one or more $R_5$, or $R_6$ and $R_7$ are taken together to form heterocyclyl optionally substituted with one or more $R_8$.

In one embodiment of the compounds of Formula I, X is CH, Y is CH, Z is CH, $R_5$ is $C_{1-6}$ alkyl, and $R_2$ is H.

In one embodiment of the compounds of Formula I, X is CH, Y is CH, Z is CH, $R_5$ is $C_{1-6}$ alkyl, $R_2$ is H, $R_1$ is —N($R_6$)C(O)$R_7$, Ring A is heteroaryl, and $R_6$ and $R_7$ are independently —H, $C_{1-6}$ alkyl, $C_{3-8}$ cycloalkyl, heterocyclyl, aryl, or heteroaryl, optionally substituted with one or more $R_5$, or $R_6$ and $R_7$ are taken together to form heterocyclyl optionally substituted with one or more $R_8$.

In one embodiment of the compounds of Formula I, X is CH, Y is CH, Z is CH, $R_5$ is $C_{1-6}$ alkyl, $R_2$ is H, $R_1$ is —N($R_6$)C(O)$R_7$, Ring A is heterocyclyl, and $R_6$ and $R_7$ are independently —H, $C_{1-6}$ alkyl, $C_{3-8}$ cycloalkyl, heterocyclyl, aryl, or heteroaryl, optionally substituted with one or more $R_5$, or $R_6$ and $R_7$ are taken together to form heterocyclyl optionally substituted with one or more $R_8$.

In one embodiment of the compounds of Formula I, X is CH, Y is CH, Z is CH, $R_5$ is H, and $R_2$ is $C_{1-6}$ alkyl.

In one embodiment of the compounds of Formula I, X is CH, Y is CH, Z is CH, $R_5$ is H, $R_2$ is $C_{1-6}$ alkyl, $R_1$ is —N($R_6$)C(O)$R_7$, Ring A is heteroaryl, and $R_6$ and $R_7$ are independently —H, $C_{1-6}$ alkyl, $C_{3-8}$ cycloalkyl, heterocyclyl, aryl, or heteroaryl, optionally substituted with one or more $R_5$, or $R_6$ and $R_7$ are taken together to form heterocyclyl optionally substituted with one or more $R_8$.

In one embodiment of the compounds of Formula I, X is CH, Y is CH, Z is CH, $R_5$ is H, $R_2$ is $C_{1-6}$ alkyl, $R_1$ is —N($R_6$)C(O)$R_7$, Ring A is heterocyclyl, and $R_6$ and $R_7$ are independently —H, $C_{1-6}$ alkyl, $C_{3-8}$ cycloalkyl, heterocyclyl, aryl, or heteroaryl, optionally substituted with one or more $R_5$, or $R_6$ and $R_7$ are taken together to form heterocyclyl optionally substituted with one or more $R_8$.

Non-limiting illustrative compounds of the present disclosure include:

2'-amino-N,N-dimethyl-[2,3':5',4''-terpyridine]-5-carboxamide,
2'-amino-N,N-dimethyl-5'-(quinolin-4-yl)-[2,3'-bipyridine]-5-carboxamide,
2'-amino-N,N-dimethyl-5'-(1H-pyrrolo[2,3-b]pyridin-4-yl)-[2,3'-bipyridine]-5-carboxamide,
4-(5-(4-(dimethylcarbamoyl)phenyl)pyridin-3-yl)-N,1-dimethyl-1H-pyrrolo[2,3-b]pyridine-2-carboxamide,
4-(2'-(2-hydroxypropan-2-yl)-[3,4'-bipyridin]-5-yl)-N,N-dimethylbenzamide,
4-([3,4'-bipyridin]-5-yl)-N,N-dimethylbenzamide,
4-(5-(1,6-naphthyridin-4-yl)pyridin-3-yl)-N,N-dimethylbenzamide,
4-(6-amino-[3,4'-bipyridin]-5-yl)-N,N-dimethylbenzamide, 4-(6-amino-6'-oxo-1',6'-dihydro-[3,3'-bipyridin]-5-yl)-N,N-dimethylbenzamide,
4-(2-amino-5-(3,6-dihydro-2H-pyran-4-yl)pyridin-3-yl)-N,N-dimethylbenzamide,
2'-amino-2"-(2-cyanopropan-2-yl)-N,N-dimethyl-[2,3':5',4"-terpyridine]-5-carboxamide,
2'-amino-2"-(1-cyanocyclopropyl)-N,N-dimethyl-[2,3':5',4"-terpyridine]-5-carboxamide,
2'-amino-N,N-dimethyl-5'-(1-methyl-1H-pyrrolo[2,3-b]pyridin-4-yl)-[2,3'-bipyridine]-5-carboxamide,
2'-amino-2"-(tert-butyl)-N,N-dimethyl-[2,3':5',4"-terpyridine]-5-carboxamide,
2'-amino-2"-cyano-N,N-dimethyl-[2,3':5',4"-terpyridine]-5-carboxamide,
2'-amino-N,N-dimethyl-[2,3':5',3"-terpyridine]-5-carboxamide,
2'-amino-N,N-dimethyl-5'-(2H-pyrazolo[3,4-b]pyridin-4-yl)-[2,3'-bipyridine]-5-carboxamide,
2'-amino-5'-(6-cyanoquinolin-4-yl)-N,N-dimethyl-[2,3'-bipyridine]-5-carboxamide,
2'-amino-N,N-dimethyl-5'-(1,6-naphthyridin-4-yl)-[2,3'-bipyridine]-5-carboxamide,
methyl 4-(2'-amino-5-(dimethylcarbamoyl)-[2,3'-bipyridin]-5'-yl)-1H-pyrrolo[2,3-b]pyridine-2-carboxylate,
2'-amino-N,N-dimethyl-5'-(pyridazin-4-yl)-[2,3'-bipyridine]-5-carboxamide,
2'-amino-5'-(furo[2,3-b]pyridin-4-yl)-N,N-dimethyl-[2,3'-bipyridine]-5-carboxamide,
2'-amino-2"-(2-hydroxypropan-2-yl)-N,N-dimethyl-[2,3':5',4"-terpyridine]-5-carboxamide,
2'-amino-5'-(7-(dimethylamino)quinolin-4-yl)-N,N-dimethyl-[2,3'-bipyridine]-5-carboxamide,
N,N-dimethyl-4-(5-(1-methyl-1H-pyrrolo[2,3-b]pyridin-4-yl)pyridin-3-yl)benzamide,
N,N-dimethyl-4-(5-(1-methyl-1H-pyrrolo[2,3-b]pyridin-5-yl)pyridin-3-yl)benzamide,
4-(5'-(1H-pyrrolo[2,3-b]pyridin-4-yl)-[3,3'-bipyridin]-5-yl)-N,N-dimethylbenzamide,
4-(5-(1H-pyrrolo[2,3-b]pyridin-5-yl)pyridin-3-yl)-N,N-dimethylbenzamide,
4-(5-(1H-pyrrolo[2,3-b]pyridin-4-yl)pyridin-3-yl)-N,N-dimethylbenzamide,
2'-amino-5'-(7-cyanoquinolin-4-yl)-N,N-dimethyl-[2,3'-bipyridine]-5-carboxamide,
2'-amino-N,N-dimethyl-5'-(1,8-naphthyridin-4-yl)-[2,3'-bipyridine]-5-carboxamide,
2'-amino-5'-(5-cyanoquinolin-4-yl)-N,N-dimethyl-[2,3'-bipyridine]-5-carboxamide,
methyl 4-(2'-amino-5-(dimethylcarbamoyl)-[2,3'-bipyridin]-5'-yl)-1H-pyrrolo[2,3-b]pyridine-3-carboxylate,
2'-amino-5'-(1H-imidazo[4,5-b]pyridin-7-yl)-N,N-dimethyl-[2,3'-bipyridine]-5-carboxamide,
tert-butyl (3-(3-(((2'-amino-5-(dimethylcarbamoyl)-[2,3':5',4"-terpyridin]-2"-yl)methyl)amino)-3-oxopropyl)phenyl)carbamate,
2'-amino-2"-((3-(3-aminophenyl)propanamido)methyl)-N,N-dimethyl-[2,3':5',4"-terpyridine]-5-carboxamide,
(E)-2'-amino-2"-((3-(3-(4-(dimethylamino)but-2-enamido)phenyl)propanamido)methyl)-N,N-dimethyl-[2,3':5',4"-terpyridine]-5-carboxamide,
2'-amino-N,N-dimethyl-5'-(2H-pyrazolo[3,4-d]pyrimidin-3-yl)-[2,3'-bipyridine]-5-carboxamide
2',2"-diamino-N,N-dimethyl-[2,3':5',3"-terpyridine]-5-carboxamide,
tert-butyl (3-(((2'-amino-5-(dimethylcarbamoyl)-[2,3':5',4"-terpyridin]-2"-yl)methyl)carbamoyl)phenyl)carbamate,
2'-amino-2"-((3-aminobenzamido)methyl)-N,N-dimethyl-[2,3':5',4"-terpyridine]-5-carboxamide,
(E)-2'-amino-2"-((3-(4-(dimethylamino)but-2-enamido)benzamido)methyl)-N,N-dimethyl-[2,3':5',4"-terpyridine]-5-carboxamide,
tert-butyl (4-(((2'-amino-5-(dimethylcarbamoyl)-[2,3':5',4"-terpyridin]-2"-yl)methyl)carbamoyl)phenyl)carbamate,
2'-amino-2"-((4-aminobenzamido)methyl)-N,N-dimethyl-[2,3':5',4"-terpyridine]-5-carboxamide,
(E)-2'-amino-2"-((4-(4-(dimethylamino)but-2-enamido)benzamido)methyl)-N,N-dimethyl-[2,3':5',4"-terpyridine]-5-carboxamide,
2'-amino-N,N-dimethyl-5'-(1-methyl-3-(pyridin-3-yl)-1H-pyrrolo[2,3-b]pyridin-5-yl)-[2,3'-bipyridine]-5-carboxamide,
2'-amino-N,N-dimethyl-5'-(1-methyl-3-(pyrimidin-5-yl)-1H-pyrrolo[2,3-b]pyridin-5-yl)-[2,3'-bipyridine]-5-carboxamide,
2'-amino-N,N-dimethyl-5'-(2-oxo-2,3-dihydro-1H-imidazo[4,5-b]pyridin-7-yl)-[2,3'-bipyridine]-5-carboxamide,
2'-amino-N,N-dimethyl-5'-(1-methyl-3-(pyridin-3-yl)-1H-pyrazolo[3,4-b]pyridin-5-yl)-[2,3'-bipyridine]-5-carboxamide,
2'-amino-N,N-dimethyl-5'-(1-methyl-3-(pyrimidin-5-yl)-1H-pyrazolo[3,4-b]pyridin-5-yl)-[2,3'-bipyridine]-5-carboxamide,
2'-amino-N,N-dimethyl-5'-(1-methyl-3-(thiazol-5-yl)-1H-pyrrolo[2,3-b]pyridin-5-yl)-[2,3'-bipyridine]-5-carboxamide,
1-(2'-amino-5'-(imidazo[1,2-a]pyridin-5-yl)-[2,3'-bipyridin]-5-yl)pyrrolidin-2-one,
1-(2'-amino-5'-(benzo[d]thiazol-7-yl)-[2,3'-bipyridin]-5-yl)pyrrolidin-2-one,
1-(2'-amino-5'-(thieno[2,3-b]pyridin-3-yl)-[2,3'-bipyridin]-5-yl)pyrrolidin-2-one,
4-(5-(4-(dimethylcarbamoyl)phenyl)pyridin-3-yl)-N-methylfuro[2,3-b]pyridine-2-carboxamide,
1-(4-(5-(5-chloro-1H-pyrrolo[2,3-b]pyridin-3-yl)pyridin-3-yl)phenyl)pyrrolidin-2-one,
4-(5-(5-chloro-1H-pyrrolo[2,3-b]pyridin-3-yl)pyridin-3-yl)-N,N-dimethylbenzamide,
1-(4-(5-(1H-pyrrolo[2,3-b]pyridin-3-yl)pyridin-3-yl)phenyl)pyrrolidin-2-one,
1-(2'-amino-5'-(5-chloro-1H-pyrrolo[2,3-b]pyridin-3-yl)-[2,3'-bipyridin]-5-yl)pyrrolidin-2-one,
5-(4-(dimethylcarbamoyl)phenyl)-N,N-dimethyl-[3,4'-bipyridine]-2'-carboxamide,
1-(4-(5-(2H-pyrazolo[3,4-b]pyridin-4-yl)pyridin-3-yl)phenyl)pyrrolidin-2-one,
4-(5-(1H-pyrrolo[2,3-b]pyridin-3-yl)pyridin-3-yl)-N,N-dimethylbenzamide,
4-(2'-amino-5-(dimethylcarbamoyl)-[2,3'-bipyridin]-5'-yl)-N,N-dimethyl-H-pyrrolo[2,3-b]pyridine-2-carboxamide,
2'-amino-5'-(6-((3-aminophenyl)amino)pyrimidin-4-yl)-N,N-dimethyl-[2,3'-bipyridine]-5-carboxamide,
2'-amino-5'-(6-aminopyrimidin-4-yl)-N,N-dimethyl-[2,3'-bipyridine]-5-carboxamide,
4-(5-(4-(2-oxopyrrolidin-1-yl)phenyl)pyridin-3-yl)-8,9-dihydropyrido[3',2':4,5]pyrrolo[1,2-a]pyrazin-6(7H)-one,
1-(4-(5-(1-methyl-1H-pyrazolo[3,4-b]pyridin-4-yl)pyridin-3-yl)phenyl)pyrrolidin-2-one,
1-(4-(5-(1-(2-hydroxyethyl)-1H-pyrazolo[3,4-b]pyridin-4-yl)pyridin-3-yl)phenyl)pyrrolidin-2-one,
1-(4-(5-(5-methyl-1H-pyrrolo[2,3-b]pyridin-3-yl)pyridin-3-yl)phenyl)pyrrolidin-2-one,
1-(4-(5-(7H-pyrrolo[2,3-d]pyrimidin-5-yl)pyridin-3-yl)phenyl)pyrrolidin-2-one, 4-(5-(5-(1-hydroxyethyl)-1H-pyrrolo[2,3-b]pyridin-3-yl)pyridin-3-yl)-N,N-dimethylbenzamide,
N,N-dimethyl-4-(5-(2-methyl-1H-pyrrolo[2,3-b]pyridin-3-yl)pyridin-3-yl)benzamide,
2'-amino-5'-(2-(3-hydroxyazetidine-1-carbonyl)-1H-pyrrolo[2,3-b]pyridin-4-yl)-N,N-dimethyl-[2,3'-bipyridine]-5-carboxamide,
2'-amino-5'-(2-(3-carbamoylazetidine-1-carbonyl)-1H-pyrrolo[2,3-b]pyridin-4-yl)-N,N-dimethyl-[2,3'-bipyridine]-5-carboxamide,
2'-amino-5'-(6-((3-(3-aminobenzamido)phenyl)amino)pyrimidin-4-yl)-N,N-dimethyl-[2,3'-bipyridine]-5-carboxamide,
1-(4-(5-(2H-pyrazolo[4,3-b]pyridin-7-yl)pyridin-3-yl)phenyl)pyrrolidin-2-one,
1-(4-(5-(5-(1-hydroxyethyl)-1H-pyrrolo[2,3-b]pyridin-3-yl)pyridin-3-yl)phenyl)pyrrolidin-2-one,
N-methyl-4-(5-(4-(2-oxopyrrolidin-1-yl)phenyl)pyridin-3-yl)furo[2,3-b]pyridine-2-carboxamide,
N,N-dimethyl-4-(5-(4-(2-oxopyrrolidin-1-yl)phenyl)pyridin-3-yl)furo[2,3-b]pyridine-2-carboxamide,
1'-methyl-5-(4-(2-oxopyrrolidin-1-yl)phenyl)-[3,4'-bipyridin]-2'(1'H)-one,
1-(4-(5-(5-methoxy-TH-pyrrolo[2,3-b]pyridin-4-yl)pyridin-3-yl)phenyl)pyrrolidin-2-one,
1-(4-(5-(5-methyl-TH-pyrrolo[2,3-b]pyridin-4-yl)pyridin-3-yl)phenyl)pyrrolidin-2-one,
5'-(4-(2-oxopyrrolidin-1-yl)phenyl)-[3,3'-bipyridin]-6(1H)-one,
1-methyl-5'-(4-(2-oxopyrrolidin-1-yl)phenyl)-[3,3'-bipyridin]-6(1H)-one,
7-methyl-4-(5-(4-(2-oxopyrrolidin-1-yl)phenyl)pyridin-3-yl)-8,9-dihydropyrido[3',2':4,5]pyrrolo[1,2-a]pyrazin-6(7H)-one,
7-(cyclopropylmethyl)-4-(5-(4-(2-oxopyrrolidin-1-yl)phenyl)pyridin-3-yl)-8,9-dihydropyrido[3',2':4,5]pyrrolo[1,2-a]pyrazin-6(7H)-one,
2'-amino-N,N-dimethyl-5'-(2-(morpholine-4-carbonyl)-1H-pyrrolo[2,3-b]pyridin-4-yl)-[2,3'-bipyridine]-5-carboxamide,
4-(2'-amino-5-(dimethylcarbamoyl)-[2,3'-bipyridin]-5'-yl)-N-benzyl-1H-pyrrolo[2,3-b]pyridine-2-carboxamide,
4-(2'-amino-5-(benzylcarbamoyl)-[2,3'-bipyridin]-5'-yl)-N-benzyl-1H-pyrrolo[2,3-b]pyridine-2-carboxamide,
4-(2'-amino-5-((2,2,2-trifluoroethyl)carbamoyl)-[2,3'-bipyridin]-5'-yl)-N-(2,2,2-trifluoroethyl)-1H-pyrrolo[2,3-b]pyridine-2-carboxamide,
4-(2'-amino-5-(dimethylcarbamoyl)-[2,3'-bipyridin]-5'-yl)-N-isobutyl-1H-pyrrolo[2,3-b]pyridine-2-carboxamide,
4-(2'-amino-5-(dimethylcarbamoyl)-[2,3'-bipyridin]-5'-yl)-N-(2-methoxyethyl)-1H-pyrrolo[2,3-b]pyridine-2-carboxamide,
4-(2'-amino-5-(dimethylcarbamoyl)-[2,3'-bipyridin]-5'-yl)-N-(pyridin-4-ylmethyl)-1H-pyrrolo[2,3-b]pyridine-2-carboxamide,
4-(2'-amino-5-(dimethylcarbamoyl)-[2,3'-bipyridin]-5'-yl)-N-(pyridin-3-ylmethyl)-1H-pyrrolo[2,3-b]pyridine-2-carboxamide,
4-(2'-amino-5-(dimethylcarbamoyl)-[2,3'-bipyridin]-5'-yl)-N-(2,2,2-trifluoroethyl)-1H-pyrrolo[2,3-b]pyridine-2-carboxamide,
2'-amino-N,N-dimethyl-5'-(2-(piperazine-1-carbonyl)-1H-pyrrolo[2,3-b]pyridin-4-yl)-[2,3'-bipyridine]-5-carboxamide,
4-(2'-amino-5-(dimethylcarbamoyl)-[2,3'-bipyridin]-5'-yl)-N-(2-aminoethyl)-1H-pyrrolo[2,3-b]pyridine-2-carboxamide,
4-(2'-amino-5-(dimethylcarbamoyl)-[2,3'-bipyridin]-5'-yl)-N-(tetrahydro-2H-pyran-4-yl)-1H-pyrrolo[2,3-b]pyridine-2-carboxamide,
2'-amino-N,N-dimethyl-5'-(2-(pyrrolidine-1-carbonyl)-1H-pyrrolo[2,3-b]pyridin-4-yl)-[2,3'-bipyridine]-5-carboxamide,
2'-amino-5'-(2-(1,1-dioxidothiomorpholine-4-carbonyl)-1H-pyrrolo[2,3-b]pyridin-4-yl)-N,N-dimethyl-[2,3'-bipyridine]-5-carboxamide,
2'-amino-5'-(6-((4-aminopyridin-2-yl)amino)pyrimidin-4-yl)-N,N-dimethyl-[2,3'-bipyridine]-5-carboxamide,
3-(5-(4-(2-oxopyrrolidin-1-yl)phenyl)pyridin-3-yl)-1H-pyrrolo[2,3-b]pyridine-2-carbonitrile,
1-(4-(5-(2H-pyrazolo[3,4-d]pyrimidin-4-yl)pyridin-3-yl)phenyl)pyrrolidin-2-one
1-(4-([3,4'-bipyridin]-5-yl)phenyl)pyrrolidin-2-one,
1-(4-(5-(6-chloro-2H-pyrazolo[3,4-b]pyridin-4-yl)pyridin-3-yl)phenyl)pyrrolidin-2-one,
1-(4-(5-(6-methyl-2H-pyrazolo[3,4-d]pyrimidin-4-yl)pyridin-3-yl)phenyl)pyrrolidin-2-one,
N-methyl-N-(5-(4-(2-oxopyrrolidin-1-yl)phenyl)-[3,4'-bipyridin]-2'-yl)acetamide,
4-(5-(4-(2-oxopyrrolidin-1-yl)phenyl)pyridin-3-yl)-1,3-dihydro-2H-pyrrolo[2,3-b]pyridin-2-one,
1-(4-(5-(1-methyl-5-(piperazin-1-yl)-1H-pyrrolo[2,3-b]pyridin-3-yl)pyridin-3-yl)phenyl)pyrrolidin-2-one,
6-methyl-4-(5-(4-(2-oxopyrrolidin-1-yl)phenyl)pyridin-3-yl)-1,6-dihydro-7H-pyrazolo[3,4-c]pyridin-7-one,
N-(2-amino-2-oxoethyl)-4-(2'-amino-5-(dimethylcarbamoyl)-[2,3'-bipyridin]-5'-yl)-1H-pyrrolo[2,3-b]pyridine-2-carboxamide,
(4-(2'-amino-5-(dimethylcarbamoyl)-[2,3'-bipyridin]-5'-yl)-1H-pyrrolo[2,3-b]pyridine-2-carbonyl)glycine,
4-(2'-amino-5-(dimethylcarbamoyl)-[2,3'-bipyridin]-5'-yl)-N-(2-oxopyrrolidin-3-yl)-1H-pyrrolo[2,3-b]pyridine-2-carboxamide,
4-(2'-amino-5-(dimethylcarbamoyl)-[2,3'-bipyridin]-5'-yl)-H-pyrrolo[2,3-b]pyridine-2-carboxamide,
4-(2'-amino-5-(dimethylcarbamoyl)-[2,3'-bipyridin]-5'-yl)-N-((3R,4S)-4-aminotetrahydrofuran-3-yl)-1H-pyrrolo[2,3-b]pyridine-2-carboxamide,
N-(2-(1H-imidazol-2-yl)ethyl)-4-(2'-amino-5-(dimethylcarbamoyl)-[2,3'-bipyridin]-5'-yl)-1H-pyrrolo[2,3-b]pyridine-2-carboxamide,
4-(2'-amino-5-(dimethylcarbamoyl)-[2,3'-bipyridin]-5'-yl)-N-(oxetan-3-yl)-1H-pyrrolo[2,3-b]pyridine-2-carboxamide,
5'-(2-(2-oxa-6-azaspiro[3.3]heptane-6-carbonyl)-1H-pyrrolo[2,3-b]pyridin-4-yl)-2'-amino-N,N-dimethyl-[2,3'-bipyridine]-5-carboxamide,
methyl 4-(5-(4-(2-oxopyrrolidin-1-yl)phenyl)pyridin-3-yl)-1H-pyrrolo[2,3-b]pyridine-2-carboxylate,
N,N-dimethyl-3-(5-(4-(2-oxopyrrolidin-1-yl)phenyl)pyridin-3-yl)-2H-pyrazolo[3,4-b]pyridine-5-carboxamide,
N-(2-methoxyethyl)-4-(5-(4-(2-oxopyrrolidin-1-yl)phenyl)pyridin-3-yl)-1H-pyrrolo[2,3-b]pyridine-2-carboxamide,
1-(4-(5-(2-(morpholine-4-carbonyl)-1H-pyrrolo[2,3-b]pyridin-4-yl)pyridin-3-yl)phenyl)pyrrolidin-2-one,
N,N,1-trimethyl-3-(5-(4-(2-oxopyrrolidin-1-yl)phenyl)pyridin-3-yl)-1H-pyrazolo[3,4-b]pyridine-5-carboxamide,
N-benzyl-4-(5-(4-(2-oxopyrrolidin-1-yl)phenyl)pyridin-3-yl)-1H-pyrrolo[2,3-b]pyridine-2-carboxamide,
4-(5-(4-(2-oxopyrrolidin-1-yl)phenyl)pyridin-3-yl)-N-(pyridin-4-ylmethyl)-1H-pyrrolo[2,3-b]pyridine-2-carboxamide,
N-isobutyl-4-(5-(4-(2-oxopyrrolidin-1-yl)phenyl)pyridin-3-yl)-1H-pyrrolo[2,3-b]pyridine-2-carboxamide, 1-(4-(5-(2-(pyrrolidine-1-carbonyl)-1H-pyrrolo[2,3-b]pyridin-4-yl)pyridin-3-yl)phenyl)pyrrolidin-2-one,
4-(5-(4-(2-oxopyrrolidin-1-yl)phenyl)pyridin-3-yl)-N-phenethyl-1H-pyrrolo[2,3-b]pyridine-2-carboxamide,
4-(5-(4-(2-oxopyrrolidin-1-yl)phenyl)pyridin-3-yl)-N-(2-(pyridin-3-yl)ethyl)-1H-pyrrolo[2,3-b]pyridine-2-carboxamide,
4-(5-(4-(2-oxopyrrolidin-1-yl)phenyl)pyridin-3-yl)-N-(pyridin-3-ylmethyl)-1H-pyrrolo[2,3-b]pyridine-2-carboxamide,
4-(5-(4-(2-oxopyrrolidin-1-yl)phenyl)pyridin-3-yl)-N-(pyridin-2-ylmethyl)-1H-pyrrolo[2,3-b]pyridine-2-carboxamide,
N-methyl-4-(5-(4-(2-oxopyrrolidin-1-yl)phenyl)pyridin-3-yl)-1H-pyrrolo[2,3-b]pyridine-2-carboxamide,
N,N-dimethyl-4-(5-(4-(2-oxopyrrolidin-1-yl)phenyl)pyridin-3-yl)-1H-pyrrolo[2,3-b]pyridine-2-carboxamide,
N-cyclopropyl-4-(5-(4-(2-oxopyrrolidin-1-yl)phenyl)pyridin-3-yl)-1H-pyrrolo[2,3-b]pyridine-2-carboxamide,
1,6-dimethyl-3-(5-(4-(2-oxopyrrolidin-1-yl)phenyl)pyridin-3-yl)-1,6-dihydro-7H-pyrrolo[2,3-c]pyridin-7-one,
N-(2-(1H-imidazol-2-yl)ethyl)-4-(5-(4-(pyrrolidin-1-yl)phenyl)pyridin-3-yl)-1H-pyrrolo[2,3-b]pyridine-2-carboxamide,
N-(benzo[d]oxazol-2-ylmethyl)-4-(5-(4-(2-oxopyrrolidin-1-yl)phenyl)pyridin-3-yl)-1H-pyrrolo[2,3-b]pyridine-2-carboxamide,
2-isopropyl-N,N-dimethyl-3-(5-(4-(2-oxopyrrolidin-1-yl)phenyl)pyridin-3-yl)-1H-pyrrolo[2,3-b]pyridine-5-carboxamide,
2-isopropyl-N,N,1-trimethyl-3-(5-(4-(2-oxopyrrolidin-1-yl)phenyl)pyridin-3-yl)-1H-pyrrolo[2,3-b]pyridine-5-carboxamide,
4-(5-(4-(2-oxopyrrolidin-1-yl)phenyl)pyridin-3-yl)-N-(2-(pyridin-2-yl)ethyl)-H-pyrrolo[2,3-b]pyridine-2-carboxamide,
4-(5-(4-(2-oxopyrrolidin-1-yl)phenyl)pyridin-3-yl)-N-(2-(pyridin-4-yl)ethyl)-H-pyrrolo[2,3-b]pyridine-2-carboxamide,
methyl 4-(5-(2-oxopyrrolidin-1-yl)-[2,3'-bipyridin]-5'-yl)-1H-pyrrolo[2,3-b]pyridine-2-carboxylate,
N,N,1,2-tetramethyl-3-(5-(4-(2-oxopyrrolidin-1-yl)phenyl)pyridin-3-yl)-1H-pyrrolo[2,3-b]pyridine-5-carboxamide,
N,N,2-trimethyl-3-(5-(4-(2-oxopyrrolidin-1-yl)phenyl)pyridin-3-yl)-1H-pyrrolo[2,3-b]pyridine-5-carboxamide,
N-(2-(2H-tetrazol-5-yl)ethyl)-4-(5-(4-(2-oxopyrrolidin-1-yl)phenyl)pyridin-3-yl)-1H-pyrrolo[2,3-b]pyridine-2-carboxamide,
2-cyclopropyl-N,N-dimethyl-3-(5-(4-(2-oxopyrrolidin-1-yl)phenyl)pyridin-3-yl)-1H-pyrrolo[2,3-b]pyridine-5-carboxamide,
1-(4-(5-(1H-pyrrolo[3,2-b]pyridin-1-yl)pyridin-3-yl)phenyl)pyrrolidin-2-one,
N,N-dimethyl-1-(5-(4-(2-oxopyrrolidin-1-yl)phenyl)pyridin-3-yl)-1H-pyrrolo[3,2-b]pyridine-6-carboxamide,
4-(5-(4-(2-oxopyrrolidin-1-yl)phenyl)pyridin-3-yl)-N-(2-(pyrazin-2-yl)ethyl)-1H-pyrrolo[2,3-b]pyridine-2-carboxamide,
4-(5-(4-(2-oxopyrrolidin-1-yl)phenyl)pyridin-3-yl)-N-(2-(thiazol-2-yl)ethyl)-1H-pyrrolo[2,3-b]pyridine-2-carboxamide,
1-(4-(6-amino-[3,4'-bipyridin]-5-yl)phenyl)pyrrolidin-2-one,
N-(cyclopropylmethyl)-4-(5-(4-(2-oxopyrrolidin-1-yl)phenyl)pyridin-3-yl)furo[2,3-b]pyridine-2-carboxamide,
4-(6-amino-5-(4-(2-oxopyrrolidin-1-yl)phenyl)pyridin-3-yl)-7-(cyclopropylmethyl)-8,9-dihydropyrido[3',2':4,5]pyrrolo[1,2-a]pyrazin-6(7H)-one,
1-methyl-4-(5-(4-(2-oxopyrrolidin-1-yl)phenyl)pyridin-3-yl)-1,3-dihydro-2H-pyrrolo[2,3-b]pyridin-2-one,
1-(1-methyl-3-(5-(4-(2-oxopyrrolidin-1-yl)phenyl)pyridin-3-yl)-1H-pyrrolo[2,3-b]pyridin-5-yl)pyrrolidin-2-one,
1-(4-(2-amino-5-(1-methyl-1H-pyrrolo[2,3-b]pyridin-3-yl)pyridin-3-yl)phenyl)pyrrolidin-2-one,
4-(5-(4-(2-oxopyrrolidin-1-yl)phenyl)pyridin-3-yl)-6-((tetrahydro-2H-pyran-4-yl)methyl)-1,6-dihydro-7H-pyrazolo[3,4-c]pyridin-7-one,
4-(6-amino-5-(4-(2-oxopyrrolidin-1-yl)phenyl)pyridin-3-yl)-N-(2-methoxyethyl)furo[2,3-b]pyridine-2-carboxamide,
6-isobutyl-4-(5-(4-(2-oxopyrrolidin-1-yl)phenyl)pyridin-3-yl)-1,6-dihydro-7H-pyrazolo[3,4-c]pyridin-7-one,
1-(4-(5-(6-methoxy-2H-pyrazolo[3,4-b]pyridin-4-yl)pyridin-3-yl)phenyl)pyrrolidin-2-one,
4-(6-amino-5-(4-(2-oxopyrrolidin-1-yl)phenyl)pyridin-3-yl)-N-methylfuro[2,3-b]pyridine-2-carboxamide,
4-(6-amino-5-(4-(2-oxopyrrolidin-1-yl)phenyl)pyridin-3-yl)-N-(cyclopropylmethyl)furo[2,3-b]pyridine-2-carboxamide,
4-(5-(4-(2-oxopyrrolidin-1-yl)phenyl)pyridin-3-yl)-5,6-dihydro-7H-pyrrolo[3,4-b]pyridin-7-one,
N-(2-methoxyethyl)-4-(5-(4-(2-oxopyrrolidin-1-yl)phenyl)pyridin-3-yl)furo[2,3-b]pyridine-2-carboxamide,
1-(4-(2-amino-5-(1-methyl-5-(2-oxopyrrolidin-1-yl)-1H-pyrrolo[2,3-b]pyridin-3-yl)pyridin-3-yl)phenyl)pyrrolidin-2-one,
1-(4-(2-amino-5-(7-methoxy-2H-pyrazolo[3,4-c]pyridin-4-yl)pyridin-3-yl)phenyl)pyrrolidin-2-one,
1-methyl-4-(5-(4-(2-oxopyrrolidin-1-yl)phenyl)pyridin-3-yl)-6-((tetrahydro-2H-pyran-4-yl)methyl)-1,6-dihydro-7H-pyrazolo[3,4-c]pyridin-7-one,
4-(6-amino-5-(4-(2-oxopyrrolidin-1-yl)phenyl)pyridin-3-yl)-1-methyl-6-((tetrahydro-2H-pyran-4-yl)methyl)-1,6-dihydro-7H-pyrazolo[3,4-c]pyridin-7-one,
N,1,6-trimethyl-7-oxo-3-(5-(4-(2-oxopyrrolidin-1-yl)phenyl)pyridin-3-yl)-6,7-dihydro-1H-pyrrolo[2,3-c]pyridine-5-carboxamide,
N,N,1,6-tetramethyl-7-oxo-3-(5-(4-(2-oxopyrrolidin-1-yl)phenyl)pyridin-3-yl)-6,7-dihydro-1H-pyrrolo[2,3-c]pyridine-5-carboxamide,
N-(2-(1H-pyrrol-2-yl)ethyl)-4-(5-(4-(2-oxopyrrolidin-1-yl)phenyl)pyridin-3-yl)-1H-pyrrolo[2,3-b]pyridine-2-carboxamide,
2-cyclopropyl-N,N,1-trimethyl-3-(5-(4-(2-oxopyrrolidin-1-yl)phenyl)pyridin-3-yl)-1H-pyrrolo[2,3-b]pyridine-5-carboxamide,
1,6-dimethyl-7-oxo-3-(5-(4-(2-oxopyrrolidin-1-yl)phenyl)pyridin-3-yl)-6,7-dihydro-1H-pyrrolo[2,3-c]pyridine-5-carboxamide,
4-(5-(4-(2-oxopyrrolidin-1-yl)phenyl)pyridin-3-yl)-N-(2-phenylcyclopropyl)-1H-pyrrolo[2,3-b]pyridine-2-carboxamide,
N,N,1-trimethyl-3-(5-(4-(2-oxopyrrolidin-1-yl)phenyl)pyridin-3-yl)-1H-pyrrolo[2,3-b]pyridine-5-sulfonamide,
1-(4-(5-(1-methyl-1H-pyrrolo[2,3-b]pyridin-3-yl)pyridin-3-yl)phenyl)pyrrolidin-2-one,
1-(4-(5-(1H-pyrrolo[2,3-b]pyridin-4-yl)pyridin-3-yl)phenyl)pyrrolidin-2-one,
1-(4-(5-(2,3-dihydro-[1,4]dioxino[2,3-b]pyridin-8-yl)pyridin-3-yl)phenyl)pyrrolidin-2-one,
1,6-dimethyl-4-(5-(4-(2-oxopyrrolidin-1-yl)phenyl)pyridin-3-yl)-1,6-dihydro-7H-pyrazolo[3,4-c]pyridin-7-one, N,N,1-trimethyl-3-(5-(4-(2-oxopyrrolidin-1-yl)phenyl)pyridin-3-yl)-1H-pyrrolo[2,3-b]pyridine-5-carboxamide,
N-methyl-3-(5-(4-(2-oxopyrrolidin-1-yl)phenyl)pyridin-3-yl)-1H-pyrrolo[2,3-b]pyridine-5-carboxamide,
methyl 4-(5-(4-(2-oxopyrrolidin-1-yl)phenyl)pyridin-3-yl)-5,7-dihydro-6H-pyrrolo[3,4-b]pyridine-6-carboxylate,
1-(4-(5-(6-cyclopropyl-2H-pyrazolo[3,4-b]pyridin-4-yl)pyridin-3-yl)phenyl)pyrrolidin-2-one,
1-(4-(5-(5-((tetrahydro-2H-pyran-4-yl)oxy)-1H-pyrrolo[2,3-b]pyridin-4-yl)pyridin-3-yl)phenyl)pyrrolidin-2-one,
1-(4-(4-(methoxymethyl)-[3,4'-bipyridin]-5-yl)phenyl)pyrrolidin-2-one,
1-(4-(5-(5-(1-hydroxyethyl)-1-methyl-1H-pyrrolo[2,3-b]pyridin-3-yl)pyridin-3-yl)phenyl)pyrrolidin-2-one,
N,1-dimethyl-3-(5-(4-(2-oxopyrrolidin-1-yl)phenyl)pyridin-3-yl)-1H-pyrrolo[2,3-b]pyridine-5-carboxamide,
N,N-dimethyl-3-(5-(4-(2-oxopyrrolidin-1-yl)phenyl)pyridin-3-yl)-1H-pyrrolo[2,3-b]pyridine-5-carboxamide,
1-(4-(5-(5-(piperidin-3-yloxy)-1H-pyrrolo[2,3-b]pyridin-4-yl)pyridin-3-yl)phenyl)pyrrolidin-2-one,
1-(4-(5-(6-(methylsulfonyl)-6,7-dihydro-5H-pyrrolo[3,4-b]pyridin-4-yl)pyridin-3-yl)phenyl)pyrrolidin-2-one,
1-(4-(5-(5-ethoxy-1H-pyrrolo[2,3-b]pyridin-4-yl)pyridin-3-yl)phenyl)pyrrolidin-2-one,
6-benzyl-4-(5-(4-(2-oxopyrrolidin-1-yl)phenyl)pyridin-3-yl)-1,6-dihydro-7H-pyrazolo[3,4-c]pyridin-7-one,
1-(4-(5-(7-methoxy-2H-pyrazolo[3,4-c]pyridin-4-yl)pyridin-3-yl)phenyl)pyrrolidin-2-one,
4-(5-(4-(2-oxopyrrolidin-1-yl)phenyl)pyridin-3-yl)-1,6-dihydro-7H-pyrazolo[3,4-c]pyridin-7-one,
4-(6-amino-5-(4-(2-oxopyrrolidin-1-yl)phenyl)pyridin-3-yl)-5,6-dihydro-7H-pyrrolo[3,4-b]pyridin-7-one,
methyl 4-(6-amino-5-(4-(2-oxopyrrolidin-1-yl)phenyl)pyridin-3-yl)-1H-pyrrolo[2,3-b]pyridine-2-carboxylate,
4-(6-amino-5-(4-(2-oxopyrrolidin-1-yl)phenyl)pyridin-3-yl)-1,6-dihydro-7H-pyrazolo[3,4-c]pyridin-7-one,
4-(6-amino-5-(4-(2-oxopyrrolidin-1-yl)phenyl)pyridin-3-yl)-1,6-dimethyl-1,6-dihydro-7H-pyrazolo[3,4-c]pyridin-7-one,
1-(4-(4-methyl-[3,4'-bipyridin]-5-yl)phenyl)pyrrolidin-2-one,
1-(4-(2-amino-5-(5-(1-hydroxyethyl)-1-methyl-TH-pyrrolo[2,3-b]pyridin-3-yl)pyridin-3-yl)phenyl)pyrrolidin-2-one,
4-(6-amino-5-(4-(2-oxopyrrolidin-1-yl)phenyl)pyridin-3-yl)-N-(oxetan-3-yl)furo[2,3-b]pyridine-2-carboxamide,
4-(6-amino-5-(4-(2-oxopyrrolidin-1-yl)phenyl)pyridin-3-yl)-6-isobutyl-1-methyl-1,6-dihydro-7H-pyrazolo[3,4-c]pyridin-7-one,
1-(4-([3,4'-bipyridin]-5-yl)-3-methylphenyl)pyrrolidin-2-one,
1-(4-(5-(7-methyl-7H-pyrrolo[2,3-d]pyrimidin-5-yl)pyridin-3-yl)phenyl)pyrrolidin-2-one,
1-(4-(6-methyl-[3,4'-bipyridin]-5-yl)phenyl)pyrrolidin-2-one,
1-[4-[5-(7-Methylpyrrolo[2,3-d]pyrimidin-5-yl)-3-pyridyl]phenyl]pyrrolidin-2-one,
1-(4-(5-(5-(2-hydroxypropan-2-yl)-1-methyl-TH-pyrrolo[2,3-b]pyridin-3-yl)pyridin-3-yl)phenyl)pyrrolidin-2-one,
1-(4-(5-(5-(2-methoxypropan-2-yl)-1-methyl-1H-pyrrolo[2,3-b]pyridin-3-yl)pyridin-3-yl)phenyl)pyrrolidin-2-one,
1-(4-(5-(7-methoxy-1-methyl-1H-pyrazolo[3,4-c]pyridin-4-yl)pyridin-3-yl)phenyl)pyrrolidin-2-one,
2-Methyl-8-[5-(4-pyridyl)-3-pyridyl]-2,8-diazaspiro[4.5]decan-1-one,
trans-N-[(4-aminocyclohexyl)methyl]-N-methyl-4-[5-(4-pyridyl)-3-pyridyl]benzamide,
1-[4-[5-(3-Bromo-7,8-dihydro-6H-pyrido[3,2-b]pyrrolizin-5-yl)-3-pyridyl]phenyl]pyrrolidin-2-one,
1-[4-[5-[3-(1-Hydroxyethyl)-7,8-dihydro-6H-pyrido[3,2-b]pyrrolizin-5-yl]-3-pyridyl]phenyl]pyrrolidin-2-one,
1-[4-[5-(7,8-dihydro-6H-pyrimido[5,4-b]pyrrolizin-5-yl)-3-pyridyl]phenyl]pyrrolidin-2-one,
1-(4-(5-(imidazo[1,2-a]pyrimidin-6-yl)pyridin-3-yl)phenyl)pyrrolidin-2-one,
N-((1-hydroxy-1,3-dihydrobenzo[c][1,2]oxaborol-5-yl)methyl)-4-(5-(4-(2-oxopyrrolidin-1-yl)phenyl)pyridin-3-yl)-1H-pyrrolo[2,3-b]pyridine-2-carboxamide,
5-ethyl-6-methyl-3-(5-(4-(2-oxopyrrolidin-1-yl)phenyl)pyridin-3-yl)pyrazolo[1,5-a]pyrimidin-7(4H)-one,
1-(4-(5-(5-(2-oxopyrrolidin-1-yl)furo[2,3-b]pyridin-3-yl)pyridin-3-yl)phenyl)pyrrolidin-2-one,
1-(4-(5-(5-(1-hydroxyethyl)furo[2,3-b]pyridin-3-yl)pyridin-3-yl)phenyl)pyrrolidin-2-one,
N-((1-hydroxy-1,3-dihydrobenzo[c][1,2]oxaborol-6-yl)methyl)-4-(5-(4-(2-oxopyrrolidin-1-yl)phenyl)pyridin-3-yl)-1H-pyrrolo[2,3-b]pyridine-2-carboxamide,
5-isopropyl-3-(5-(4-(2-oxopyrrolidin-1-yl)phenyl)pyridin-3-yl)pyrazolo[1,5-a]pyrimidin-7(4H)-one,
N,N-dimethyl-3-(5-(4-(2-oxopyrrolidin-1-yl)phenyl)pyridin-3-yl)furo[2,3-b]pyridine-5-carboxamide,
N-(3-(1H-1,2,3-triazol-1-yl)phenyl)-4-(5-(1H-pyrazolo[3,4-b]pyridin-4-yl)pyridin-3-yl)-N-methylbenzamide,
7-methyl-4-(5-(4-(2-oxoindolin-1-yl)phenyl)pyridin-3-yl)-8,9-dihydropyrido[3',2':4,5]pyrrolo[1,2-a]pyrazin-6(7H)-one,
1-(4-(5-(5-cyclopropyl-1H-pyrazolo[3,4-b]pyridin-3-yl)pyridin-3-yl)phenyl)pyrrolidin-2-one,
6-(2-hydroxyethyl)-2,5-dimethyl-3-(5-(4-(2-oxopyrrolidin-1-yl)phenyl)pyridin-3-yl)pyrazolo[1,5-a]pyrimidin-7(4H)-one,
(S)-7-methyl-4-(5-(4-(4-methyl-2-oxopyrrolidin-1-yl)phenyl)pyridin-3-yl)-8,9-dihydropyrido[3',2':4,5]pyrrolo[1,2-a]pyrazin-6(7H)-one,
(R)-7-methyl-4-(5-(4-(4-methyl-2-oxopyrrolidin-1-yl)phenyl)pyridin-3-yl)-8,9-dihydropyrido[3',2':4,5]pyrrolo[1,2-a]pyrazin-6(7H)-one,
1-(4-(5-(5-(methoxymethyl)-2-methylpyrazolo[1,5-a]pyrimidin-7-yl)pyridin-3-yl)phenyl)pyrrolidin-2-one,
N-(4-(5-(4-(2-oxopyrrolidin-1-yl)phenyl)pyridin-3-yl)pyrimidin-2-yl)cyclobutanecarboxamide,
6-ethyl-5-methyl-3-(5-(4-(2-oxopyrrolidin-1-yl)phenyl)pyridin-3-yl)pyrazolo[1,5-a]pyrimidin-7(4H)-one,
N-(4-(5-(1H-pyrazolo[3,4-b]pyridin-4-yl)pyridin-3-yl)phenyl)-2-(2-azabicyclo[2.2.1]heptan-2-yl)-2-oxoacetamide,
7-methyl-4-(5-(4-(6-oxo-5-azaspiro[2.4]heptan-5-yl)phenyl)pyridin-3-yl)-8,9-dihydropyrido[3',2':4,5]pyrrolo[1,2-a]pyrazin-6(7H)-one,
4-(5-(4-(6-ethyl-2-oxoindolin-1-yl)phenyl)pyridin-3-yl)-7-methyl-8,9-dihydropyrido[3',2':4,5]pyrrolo[1,2-a]pyrazin-6(7H)-one,
4-(5-(4-(4-ethyl-2-oxoindolin-1-yl)phenyl)pyridin-3-yl)-7-methyl-8,9-dihydropyrido[3',2':4,5]pyrrolo[1,2-a]pyrazin-6(7H)-one,
7-methyl-4-(5-(4-(4-methyl-2-oxoindolin-1-yl)phenyl)pyridin-3-yl)-8,9-dihydropyrido[3',2':4,5]pyrrolo[1,2-a]pyrazin-6(7H)-one,
1-(4-(5-(8-cyclobutyl-7H-purin-6-yl)pyridin-3-yl)phenyl)pyrrolidin-2-one,
4-(5-(4-(2-oxopyrrolidin-1-yl)phenyl)pyridin-3-yl)-7-(pyridin-2-yl)-8,9-dihydropyrido[3',2':4,5]pyrrolo[1,2-a]pyrazin-6(7H)-one,
N-(4-(5-(1H-pyrazolo[3,4-b]pyridin-4-yl)pyridin-3-yl)phenyl)-5-cyclobutylisoxazole-3-carboxamide, N-(4-(5-(1H-pyrazolo[3,4-b]pyridin-4-yl)pyridin-3-yl)phenyl)-2-(7-azabicyclo[2.2.1]heptan-7-yl)-2-oxoacetamide,
4-(5-(4-(4,4-dimethyl-2-oxopyrrolidin-1-yl)phenyl)pyridin-3-yl)-7-methyl-8,9-dihydropyrido[3',2':4,5]pyrrolo[1,2-a]pyrazin-6(7H)-one,
methyl 5-methyl-4-(5-(4-(2-oxopyrrolidin-1-yl)phenyl)pyridin-3-yl)-1H-pyrrolo[2,3-b]pyridine-2-carboxylate,
(S)-1-(4-(5-(5-(1-hydroxyethyl)-1-methyl-TH-pyrrolo[2,3-b]pyridin-3-yl)pyridin-3-yl)-3-methylphenyl)pyrrolidin-2-one,
(R)-1-(4-(5-(5-(1-hydroxyethyl)-1-methyl-1H-pyrrolo[2,3-b]pyridin-3-yl)pyridin-3-yl)-3-methylphenyl)pyrrolidin-2-one,
1-(4-(5-(5-(1-hydroxyethyl)-1-methyl-1H-pyrrolo[2,3-b]pyridin-3-yl)pyridin-3-yl)-3-methylphenyl)pyrrolidin-2-one,
1-(4-(5-(2-cyclopropyl-5-(1-hydroxyethyl)-1H-pyrrolo[2,3-b]pyridin-3-yl)pyridin-3-yl)phenyl)pyrrolidin-2-one,
(S)-1-(4-(5-(5-(1-hydroxyethyl)-1-methyl-1H-pyrrolo[2,3-b]pyridin-3-yl)-4-methylpyridin-3-yl)phenyl)pyrrolidin-2-one,
(R)-1-(4-(5-(5-(1-hydroxyethyl)-1-methyl-1H-pyrrolo[2,3-b]pyridin-3-yl)-4-methylpyridin-3-yl)phenyl)pyrrolidin-2-one,
1-(4-(5-(5-(1-hydroxyethyl)-1-methyl-1H-pyrrolo[2,3-b]pyridin-3-yl)-4-methylpyridin-3-yl)phenyl)pyrrolidin-2-one,
1-(4-(5-(thieno[2,3-b]pyridin-3-yl)pyridin-3-yl)phenyl)pyrrolidin-2-one,
(R)-1-(4-(5-(5-(1-hydroxyethyl)-1-methyl-1H-pyrrolo[2,3-b]pyridin-3-yl)pyridin-3-yl)phenyl)pyrrolidin-2-one,
(S)-1-(4-(5-(5-(1-hydroxyethyl)-1-methyl-1H-pyrrolo[2,3-b]pyridin-3-yl)pyridin-3-yl)phenyl)pyrrolidin-2-one,
N-methyl-4-(4-methyl-5-(4-(2-oxopyrrolidin-1-yl)phenyl)pyridin-3-yl)furo[2,3-b]pyridine-2-carboxamide,
N,N-dimethyl-3-(5-(4-(2-oxopyrrolidin-1-yl)phenyl)pyridin-3-yl)-1H-pyrrolo[2,3-b]pyridine-5-sulfonamide,
methyl 5-chloro-4-(5-(4-(2-oxopyrrolidin-1-yl)phenyl)pyridin-3-yl)-1H-pyrrolo[2,3-b]pyridine-2-carboxylate,
4-(5-(4-(2-oxopyrrolidin-1-yl)phenyl)pyridin-3-yl)-N-((1r,3r)-3-phenylcyclobutyl)-1H-pyrrolo[2,3-b]pyridine-2-carboxamide,
N-(oxetan-3-yl)-4-(5-(4-(2-oxopyrrolidin-1-yl)phenyl)pyridin-3-yl)furo[2,3-b]pyridine-2-carboxamide,
N,N-dimethyl-4-(4-methyl-5-(4-(2-oxopyrrolidin-1-yl)phenyl)pyridin-3-yl)-1H-pyrrolo[2,3-b]pyridine-2-carboxamide,
1-(4-(5-(5-(2-hydroxypropan-2-yl)-1-methyl-TH-pyrrolo[2,3-b]pyridin-3-yl)-4-methylpyridin-3-yl)phenyl)pyrrolidin-2-one,
N,N-dimethyl-4-(5-(2-methyl-4-(2-oxopyrrolidin-1-yl)phenyl)pyridin-3-yl)-1H-pyrrolo[2,3-b]pyridine-2-carboxamide,
1-(4-(5-(5-(2-hydroxypropan-2-yl)-1-methyl-TH-pyrrolo[2,3-b]pyridin-3-yl)pyridin-3-yl)-3-methylphenyl)pyrrolidin-2-one,
methyl 4-(5-(4-(2-oxopyrrolidin-1-yl)phenyl)pyridin-3-yl)furo[2,3-b]pyridine-2-carboxylate,
4-(5-(4-(2-oxopyrrolidin-1-yl)phenyl)pyridin-3-yl)-N-(2-(thiazol-5-yl)ethyl)-1H-pyrrolo[2,3-b]pyridine-2-carboxamide,
1-(4-(5-(7,8-dihydro-6H-pyrido[3,2-b]pyrrolizin-5-yl)pyridin-3-yl)phenyl)pyrrolidin-2-one,
1-(4-(5-(1-methyl-1,5,6,7-tetrahydrocyclopenta[b]pyrazolo[4,3-e]pyridin-4-yl)pyridin-3-yl)phenyl)pyrrolidin-2-one,
4-([3,4'-bipyridin]-5-yl)-N-methyl-N-(piperidin-4-ylmethyl)benzamide,
methyl 4-(4-methyl-5-(4-(2-oxopyrrolidin-1-yl)phenyl)pyridin-3-yl)-1H-pyrrolo[2,3-b]pyridine-2-carboxylate,
2-(1-methyl-7-oxo-4-(5-(4-(2-oxopyrrolidin-1-yl)phenyl)pyridin-3-yl)-1,7-dihydro-6H-pyrazolo[3,4-c]pyridin-6-yl)acetonitrile,
methyl 4-(5-(2-methyl-4-(2-oxopyrrolidin-1-yl)phenyl)pyridin-3-yl)-1H-pyrrolo[2,3-b]pyridine-2-carboxylate,
4-([3,4'-bipyridin]-5-yl)-N-(((1r,4r)-4-aminocyclohexyl)methyl)-N-methylbenzamide,
isopropyl 4-(5-(4-(2-oxopyrrolidin-1-yl)phenyl)pyridin-3-yl)furo[2,3-b]pyridine-2-carboxylate,
1-(4-(5-(1-methyl-3-(pyrimidin-5-yl)-1H-pyrrolo[2,3-b]pyridin-5-yl)pyridin-3-yl)phenyl)pyrrolidin-2-one,
4-([3,4'-bipyridin]-5-yl)-N-methyl-N-(piperidin-3-ylmethyl)benzamide,
1-(4-(5-(1H-benzo[d]imidazol-1-yl)pyridin-3-yl)phenyl)pyrrolidin-2-one,
N-methyl-4-(5-(2-methyl-4-(2-oxopyrrolidin-1-yl)phenyl)pyridin-3-yl)furo[2,3-b]pyridine-2-carboxamide,
1-(4-(5-(7-methoxy-2-methyl-2H-pyrazolo[3,4-c]pyridin-4-yl)pyridin-3-yl)phenyl)pyrrolidin-2-one,
ethyl 4-(5-(4-(2-oxopyrrolidin-1-yl)phenyl)pyridin-3-yl)-1H-pyrrolo[2,3-b]pyridine-2-carboxylate,
2-methyl-4-(5-(4-(2-oxopyrrolidin-1-yl)phenyl)pyridin-3-yl)-2,6-dihydro-7H-pyrazolo[3,4-c]pyridin-7-one,
4-(5-(4-(2-oxopyrrolidin-1-yl)phenyl)pyridin-3-yl)-1H-pyrrolo[2,3-b]pyridine-2-carboxylic acid,
isopropyl 4-(5-(4-(2-oxopyrrolidin-1-yl)phenyl)pyridin-3-yl)-1H-pyrrolo[2,3-b]pyridine-2-carboxylate,
1-methyl-4-(5-(4-(2-oxopyrrolidin-1-yl)phenyl)pyridin-3-yl)-1,6-dihydro-7H-pyrazolo[3,4-c]pyridin-7-one,
1-(4-(5-(1-methyl-3-(2-methylpyrimidin-5-yl)-1H-pyrrolo[2,3-b]pyridin-5-yl)pyridin-3-yl)phenyl)pyrrolidin-2-one,
1-(4-(5-(5-methyl-2-(piperidin-1-yl)thiazolo[4,5-d]pyrimidin-7-yl)pyridin-3-yl)phenyl)pyrrolidin-2-one,
1-(4-(5-(1H-pyrazolo[3,4-b]pyridin-4-yl)pyridin-3-yl)phenyl)pyrrolidin-2-one,
1-(4-(5-(1H-pyrazolo[4,3-b]pyridin-7-yl)pyridin-3-yl)phenyl)pyrrolidin-2-one,
1-(4-(5-(6-methyl-TH-pyrazolo[3,4-d]pyrimidin-4-yl)pyridin-3-yl)phenyl)pyrrolidin-2-one,
1-[4-[5-(2,3-Dihydro-[1,4]dioxino[2,3-b]pyridin-8-yl)-3-pyridyl]phenyl]pyrrolidin-2-one,
1-[4-[5-(4-Pyridyl)-3-pyridyl]phenyl]pyrrolidin-2-one,
1-(4-(5-(2-methyl-2H-pyrazolo[3,4-b]pyridin-4-yl)pyridin-3-yl)phenyl)pyrrolidin-2-one,
1-(4-(5-(1H-pyrazolo[3,4-d]pyrimidin-4-yl)pyridin-3-yl)phenyl)pyrrolidin-2-one,
1-(4-(5-(6-chloro-1H-pyrazolo[3,4-b]pyridin-4-yl)pyridin-3-yl)phenyl)pyrrolidin-2-one,
1-(4-(5-(6-cyclopropyl-1H-pyrazolo[3,4-b]pyridin-4-yl)pyridin-3-yl)phenyl)pyrrolidin-2-one,
1-(4-(5-(7-methoxy-1H-pyrazolo[3,4-c]pyridin-4-yl)pyridin-3-yl)phenyl)pyrrolidin-2-one,
1-(4-(5-(6-methoxy-TH-pyrazolo[3,4-b]pyridin-4-yl)pyridin-3-yl)phenyl)pyrrolidin-2-one,
4-[5-[4-(2-Oxopyrrolidin-1-yl)phenyl]-3-pyridyl]-5,6-dihydropyrrolo[3,4-b]pyridin-7-one,
1-(4-(2-amino-5-(7-methoxy-TH-pyrazolo[3,4-c]pyridin-4-yl)pyridin-3-yl)phenyl)pyrrolidin-2-one,
2'-amino-N,N-dimethyl-5'-(1H-pyrazolo[3,4-b]pyridin-4-yl)-[2,3'-bipyridine]-5-carboxamide,
2'-amino-5'-(3H-imidazo[4,5-b]pyridin-7-yl)-N,N-dimethyl-[2,3'-bipyridine]-5-carboxamide,
2'-amino-N,N-dimethyl-5'-(1H-pyrazolo[3,4-d]pyrimidin-3-yl)-[2,3'-bipyridine]-5-carboxamide, 4-(2'-amino-5-(dimethylcarbamoyl)-[2,3'-bipyridin]-5'-yl)-N-((3S,4R)-4-aminotetrahydrofuran-3-yl)-1H-pyrrolo[2,3-b]pyridine-2-carboxamide,
1-[4-[5-(7-methoxy-2-methyl-pyrazolo[3,4-c]pyridin-4-yl)-3-pyridyl]phenyl]pyrrolidin-2-one,
8-([3,4'-bipyridin]-5-yl)-2-methyl-2,8-diazaspiro[4.5]decan-1-one,
1-[4-[5-(7,8-Dihydro-6H-pyrido[3,2-b]pyrrolizin-5-yl)-3-pyridyl]phenyl]pyrrolidin-2-one,
1-[4-[5-(4-Methyl-2,4,5-triazatricyclo[7.3.0.03,7]dodeca-1,3(7),5,8-tetraen-8-yl)-3-pyridyl]phenyl]pyrrolidin-2-one,
(R)-7-methyl-4-(5-(4-(2-methyl-5-oxopyrrolidin-1-yl)phenyl)pyridin-3-yl)-8,9-dihydropyrido[3',2':4,5]pyrrolo[1,2-a]pyrazin-6(7H)-one,
1-(4-(5-(3-methylisoxazolo[5,4-b]pyridin-4-yl)pyridin-3-yl)phenyl)pyrrolidin-2-one,
7-(2,3-dihydro-[1,4]dioxino[2,3-b]pyridin-6-yl)-4-(5-(4-(2-oxopyrrolidin-1-yl)phenyl)pyridin-3-yl)-8,9-dihydropyrido[3',2':4,5]pyrrolo[1,2-a]pyrazin-6(7H)-one,
1-(4-(2-amino-5-(3-methyl-1H-pyrrolo[2,3-b]pyridin-4-yl)pyridin-3-yl)phenyl)pyrrolidin-2-one,
N-methyl-4-(5-(4-(2-oxopyrrolidin-1-yl)phenyl)pyridin-3-yl)-N-(pyridin-3-yl)-H-pyrrolo[2,3-b]pyridine-2-carboxamide,
N-methyl-4-(5-(4-(2-oxopyrrolidin-1-yl)phenyl)pyridin-3-yl)-N-phenyl-H-pyrrolo[2,3-b]pyridine-2-carboxamide,
4-(5-(4-(2-oxopyrrolidin-1-yl)phenyl)pyridin-3-yl)-N-(pyridin-2-yl)-1H-pyrrolo[2,3-b]pyridine-2-carboxamide,
N,3-dimethyl-4-(5-(4-(2-oxopyrrolidin-1-yl)phenyl)pyridin-3-yl)-1H-pyrrolo[2,3-b]pyridine-2-carboxamide,
4-(5-(4-(2-oxopyrrolidin-1-yl)phenyl)pyridin-3-yl)-N-(pyridin-4-yl)-1H-pyrrolo[2,3-b]pyridine-2-carboxamide,
N-((5,6-dimethyl-1H-benzo[d]imidazol-2-yl)methyl)-4-(5-(4-(2-oxopyrrolidin-1-yl)phenyl)pyridin-3-yl)-1H-pyrrolo[2,3-b]pyridine-2-carboxamide,
1-(4-(6-amino-5-(3-methyl-1H-pyrrolo[2,3-b]pyridin-4-yl)pyridin-3-yl)phenyl)pyrrolidin-2-one,
N-((4-methyl-1H-benzo[d]imidazol-2-yl)methyl)-4-(5-(4-(2-oxopyrrolidin-1-yl)phenyl)pyridin-3-yl)-1H-pyrrolo[2,3-b]pyridine-2-carboxamide,
1-(4-(5-(3-methyl-2H-pyrazolo[3,4-b]pyridin-4-yl)pyridin-3-yl)phenyl)pyrrolidin-2-one,
N-(benzo[d]thiazol-2-ylmethyl)-4-(5-(4-(2-oxopyrrolidin-1-yl)phenyl)pyridin-3-yl)-1H-pyrrolo[2,3-b]pyridine-2-carboxamide,
N-((6-methyl-1H-benzo[d]imidazol-2-yl)methyl)-4-(5-(4-(2-oxopyrrolidin-1-yl)phenyl)pyridin-3-yl)-1H-pyrrolo[2,3-b]pyridine-2-carboxamide,
N-((1-methyl-1H-benzo[d]imidazol-2-yl)methyl)-4-(5-(4-(2-oxopyrrolidin-1-yl)phenyl)pyridin-3-yl)-1H-pyrrolo[2,3-b]pyridine-2-carboxamide,
N-((1H-benzo[d]imidazol-2-yl)methyl)-4-(5-(4-(2-oxopyrrolidin-1-yl)phenyl)pyridin-3-yl)-1H-pyrrolo[2,3-b]pyridine-2-carboxamide,
1-(4-(5-(3-methyl-1H-pyrrolo[2,3-b]pyridin-4-yl)pyridin-3-yl)phenyl)pyrrolidin-2-one,
N-ethyl-N-methyl-4-(5-(7-methyl-6-oxo-6,7,8,9-tetrahydropyrido[3',2':4,5]pyrrolo[1,2-a]pyrazin-4-yl)pyridin-3-yl)benzamide,
1-(4-(5-(2-(6-methyl-3,4-dihydro-2H-benzo[b][1,4]oxazine-4-carbonyl)-1H-pyrrolo[2,3-b]pyridin-4-yl)pyridin-3-yl)phenyl)pyrrolidin-2-one,
4-(5-(4-(5,5-dimethyl-2-oxopiperidin-1-yl)phenyl)pyridin-3-yl)-7-methyl-8,9-dihydropyrido[3',2':4,5]pyrrolo[1,2-a]pyrazin-6(7H)-one,
7-methyl-4-(5-(4-(morpholine-4-carbonyl)phenyl)pyridin-3-yl)-8,9-dihydropyrido[3',2':4,5]pyrrolo[1,2-a]pyrazin-6(7H)-one,
4-(5-(4-(2-oxopyrrolidin-1-yl)phenyl)pyridin-3-yl)-N-(pyridin-3-yl)-1H-pyrrolo[2,3-b]pyridine-2-carboxamide,
4-(5-(4-(2-oxopyrrolidin-1-yl)phenyl)pyridin-3-yl)-N-phenyl-1H-pyrrolo[2,3-b]pyridine-2-carboxamide,
N-(oxazol-2-ylmethyl)-4-(5-(4-(2-oxopyrrolidin-1-yl)phenyl)pyridin-3-yl)-1H-pyrrolo[2,3-b]pyridine-2-carboxamide,
7-(1,5-dimethyl-1H-pyrazol-3-yl)-4-(5-(4-(2-oxopyrrolidin-1-yl)phenyl)pyridin-3-yl)-8,9-dihydropyrido[3',2':4,5]pyrrolo[1,2-a]pyrazin-6(7H)-one,
1-(4-(5-(2-(1-oxa-7-azaspiro[4.5]decane-7-carbonyl)-1H-pyrrolo[2,3-b]pyridin-4-yl)pyridin-3-yl)phenyl)pyrrolidin-2-one,
1-(4-(5-(7-cyclopropyl-[1,2,4]triazolo[4,3-a]pyrimidin-5-yl)pyridin-3-yl)phenyl)pyrrolidin-2-one,
1-(4-(5-(3-(2-aminopyrimidin-5-yl)imidazo[1,2-a]pyrimidin-6-yl)pyridin-3-yl)phenyl)pyrrolidin-2-one,
4-(5-(4-(4,4-dimethylpiperidine-1-carbonyl)phenyl)pyridin-3-yl)-7-methyl-8,9-dihydropyrido[3',2':4,5]pyrrolo[1,2-a]pyrazin-6(7H)-one,
1-(4-(5-(7-methyl-[1,2,4]triazolo[4,3-a]pyrimidin-5-yl)pyridin-3-yl)phenyl)pyrrolidin-2-one,
1-(4-(5-(3-(6-aminopyridin-3-yl)imidazo[1,2-a]pyrimidin-6-yl)pyridin-3-yl)phenyl)pyrrolidin-2-one,
1-(4-(5-(2-cyclopropyl-5-(2-hydroxypropan-2-yl)-1H-pyrrolo[2,3-b]pyridin-3-yl)pyridin-3-yl)phenyl)pyrrolidin-2-one,
1-(4-(5-(2-(7-methyl-3,4-dihydro-2H-benzo[b][1,4]oxazine-4-carbonyl)-1H-pyrrolo[2,3-b]pyridin-4-yl)pyridin-3-yl)phenyl)pyrrolidin-2-one,
1-(4-(5-([1,2,4]triazolo[4,3-a]pyrimidin-5-yl)pyridin-3-yl)phenyl)pyrrolidin-2-one,
1-(4-(5-(3-(pyrimidin-5-yl)imidazo[1,2-a]pyrimidin-6-yl)pyridin-3-yl)phenyl)pyrrolidin-2-one,
4-(5-(4-(4,4-dimethyl-2-oxopiperidin-1-yl)phenyl)pyridin-3-yl)-7-methyl-8,9-dihydropyrido[3',2':4,5]pyrrolo[1,2-a]pyrazin-6(7H)-one,
N-(5-(1-methyl-5-(5-(4-(2-oxopyrrolidin-1-yl)phenyl)pyridin-3-yl)-1H-pyrrolo[2,3-b]pyridin-3-yl)pyridin-2-yl)acetamide,
1-(4-(5-(3-(pyridin-3-yl)imidazo[1,2-a]pyrimidin-6-yl)pyridin-3-yl)phenyl)pyrrolidin-2-one,
7-methyl-4-(5-(4-(2-oxoazepan-1-yl)phenyl)pyridin-3-yl)-8,9-dihydropyrido[3',2':4,5]pyrrolo[1,2-a]pyrazin-6(7H)-one,
7-methyl-4-(5-(4-(2-oxopiperidin-1-yl)phenyl)pyridin-3-yl)-8,9-dihydropyrido[3',2':4,5]pyrrolo[1,2-a]pyrazin-6(7H)-one,
1-(4-(5-(3-(6-aminopyridin-3-yl)-1-methyl-1H-pyrrolo[2,3-b]pyridin-5-yl)pyridin-3-yl)phenyl)pyrrolidin-2-one,
4-(5-(4-(6,7-dihydro-5H-pyrrolo[2,1-c][1,2,4]triazol-3-yl)phenyl)pyridin-3-yl)-7-methyl-8,9-dihydropyrido[3',2':4,5]pyrrolo[1,2-a]pyrazin-6(7H)-one,
7-methyl-4-(5-(4-(pyrrolidine-1-carbonyl)phenyl)pyridin-3-yl)-8,9-dihydropyrido[3',2':4,5]pyrrolo[1,2-a]pyrazin-6(7H)-one,
N-(5-(1-methyl-5-(5-(4-(2-oxopyrrolidin-1-yl)phenyl)pyridin-3-yl)-1H-pyrrolo[2,3-b]pyridin-3-yl)pyrimidin-2-yl)acetamide,
1-(4-(5-(3-(1-hydroxyethyl)-7,8-dihydro-6H-pyrido[3,2-b]pyrrolizin-5-yl)pyridin-3-yl)phenyl)pyrrolidin-2-one,
1-(4-(5-(7,8-dihydro-6H-pyrimido[5,4-b]pyrrolizin-5-yl)pyridin-3-yl)phenyl)pyrrolidin-2-one, 1-(4-(5-(3-bromo-7,8-dihydro-6H-pyrido[3,2-b]pyrrolizin-5-yl)pyridin-3-yl)phenyl)pyrrolidin-2-one, 7-methyl-4-(5-(4-(piperidine-1-carbonyl)phenyl)pyridin-3-yl)-8,9-dihydropyrido[3',2':4,5]pyrrolo[1,2-a]pyrazin-6(7H)-one, 1-(4-(5-(3-(2-aminopyrimidin-5-yl)-1-methyl-TH-pyrrolo[2,3-b]pyridin-5-yl)pyridin-3-yl)phenyl)pyrrolidin-2-one, 4-(5-(4-(4-cyclobutyl-4H-1,2,4-triazol-3-yl)phenyl)pyridin-3-yl)-5-methyl-7-(pyridin-2-yl)-8,9-dihydropyrido[3',2':4,5]pyrrolo[1,2-a]pyrazin-6(7H)-one, 4-(5-(4-(5-isopropyl-TH-1,2,3-triazol-1-yl)phenyl)pyridin-3-yl)-7-(pyridin-2-yl)-8,9-dihydropyrido[3',2':4,5]pyrrolo[1,2-a]pyrazin-6(7H)-one, 4-(5-(4-(4-ethyl-4H-1,2,4-triazol-3-yl)phenyl)pyridin-3-yl)-7-methyl-8,9-dihydropyrido[3',2':4,5]pyrrolo[1,2-a]pyrazin-6(7H)-one, 4-(5-(4-(1-isopropyl-1H-imidazol-5-yl)phenyl)pyridin-3-yl)-7-methyl-8,9-dihydropyrido[3',2':4,5]pyrrolo[1,2-a]pyrazin-6(7H)-one, (S)-4-(5-(4-(4-(sec-butyl)-4H-1,2,4-triazol-3-yl)phenyl)pyridin-3-yl)-7-methyl-8,9-dihydropyrido[3',2':4,5]pyrrolo[1,2-a]pyrazin-6(7H)-one, (R)-4-(5-(4-(4-(sec-butyl)-4H-1,2,4-triazol-3-yl)phenyl)pyridin-3-yl)-7-methyl-8,9-dihydropyrido[3',2':4,5]pyrrolo[1,2-a]pyrazin-6(7H)-one, 4-(6-amino-5-(4-(4-isopropyl-4H-1,2,4-triazol-3-yl)phenyl)pyridin-3-yl)-N-methylfuro[2,3-b]pyridine-2-carboxamide, 4-(5-(4-(4-isopropylisoxazol-5-yl)phenyl)pyridin-3-yl)-7-methyl-8,9-dihydropyrido[3',2':4,5]pyrrolo[1,2-a]pyrazin-6(7H)-one, 4-(5-(4-(1-isopropyl-1H-imidazol-2-yl)phenyl)pyridin-3-yl)-7-methyl-8,9-dihydropyrido[3',2':4,5]pyrrolo[1,2-a]pyrazin-6(7H)-one, 4-(5-(4-(4-cyclobutyl-4H-1,2,4-triazol-3-yl)phenyl)pyridin-3-yl)-7-methyl-8,9-dihydropyrido[3',2':4,5]pyrrolo[1,2-a]pyrazin-6(7H)-one, 4-(6-amino-5-(4-(4-isobutyl-4H-1,2,4-triazol-3-yl)phenyl)pyridin-3-yl)-N-methylfuro[2,3-b]pyridine-2-carboxamide, 4-(5-(4-(4-isobutyl-4H-1,2,4-triazol-3-yl)phenyl)pyridin-3-yl)-7-(pyridin-2-yl)-8,9-dihydropyrido[3',2':4,5]pyrrolo[1,2-a]pyrazin-6(7H)-one, 4-(5-(4-(5-isopropyl-TH-1,2,3-triazol-1-yl)phenyl)pyridin-3-yl)-7-methyl-8,9-dihydropyrido[3',2':4,5]pyrrolo[1,2-a]pyrazin-6(7H)-one, 4-(5-(4-(4-(2-cyclopropylethyl)-4H-1,2,4-triazol-3-yl)phenyl)pyridin-3-yl)-7-methyl-8,9-dihydropyrido[3',2':4,5]pyrrolo[1,2-a]pyrazin-6(7H)-one, 7-methyl-4-(5-(4-(4-methylpyridazin-3-yl)phenyl)pyridin-3-yl)-8,9-dihydropyrido[3',2':4,5]pyrrolo[1,2-a]pyrazin-6(7H)-one, 4-(5-(4-(4-isopropyl-4H-1,2,4-triazol-3-yl)phenyl)pyridin-3-yl)-N-(2-(pyridin-4-yl)ethyl)-1H-pyrrolo[2,3-b]pyridine-2-carboxamide, N-benzyl-4-(5-(4-(4-isobutyl-4H-1,2,4-triazol-3-yl)phenyl)pyridin-3-yl)-1H-pyrrolo[2,3-b]pyridine-2-carboxamide, N-benzyl-4-(5-(4-(4-isopropyl-4H-1,2,4-triazol-3-yl)phenyl)pyridin-3-yl)-1H-pyrrolo[2,3-b]pyridine-2-carboxamide, 4-(6-amino-5-(4-(4-isopropyl-4H-1,2,4-triazol-3-yl)phenyl)pyridin-3-yl)-7-(cyclopropylmethyl)-8,9-dihydropyrido[3',2':4,5]pyrrolo[1,2-a]pyrazin-6(7H)-one, 4-(5-(4-(4-isopropylisoxazol-3-yl)phenyl)pyridin-3-yl)-7-methyl-8,9-dihydropyrido[3',2':4,5]pyrrolo[1,2-a]pyrazin-6(7H)-one, 4-(5-(4-(4-(cyclopropylmethyl)-4H-1,2,4-triazol-3-yl)phenyl)pyridin-3-yl)-7-methyl-8,9-dihydropyrido[3',2':4,5]pyrrolo[1,2-a]pyrazin-6(7H)-one, 4-(5-(4-(4-(tert-butyl)-4H-1,2,4-triazol-3-yl)phenyl)pyridin-3-yl)-7-methyl-8,9-dihydropyrido[3',2':4,5]pyrrolo[1,2-a]pyrazin-6(7H)-one, 4-(5-(4-(4-isopropyl-4H-1,2,4-triazol-3-yl)phenyl)pyridin-3-yl)-N-(pyridin-3-ylmethyl)-1H-pyrrolo[2,3-b]pyridine-2-carboxamide, N-((1-hydroxy-1,3-dihydrobenzo[c][1,2]oxaborol-7-yl)methyl)-4-(5-(4-(2-oxopyrrolidin-1-yl)phenyl)pyridin-3-yl)-1H-pyrrolo[2,3-b]pyridine-2-carboxamide, 4-(5-(4-(5-isopropylpyridin-3-yl)phenyl)pyridin-3-yl)-7-methyl-8,9-dihydropyrido[3',2':4,5]pyrrolo[1,2-a]pyrazin-6(7H)-one, 4-(5-(4-(3,3-dimethylazetidine-1-carbonyl)phenyl)pyridin-3-yl)-7-methyl-8,9-dihydropyrido[3',2':4,5]pyrrolo[1,2-a]pyrazin-6(7H)-one, 4-(5-(4-(7-azabicyclo[2.2.1]heptane-7-carbonyl)phenyl)pyridin-3-yl)-7-methyl-8,9-dihydropyrido[3',2':4,5]pyrrolo[1,2-a]pyrazin-6(7H)-one, 4-(5-(4-(4-isobutyl-4H-1,2,4-triazol-3-yl)phenyl)pyridin-3-yl)-7-methyl-8,9-dihydropyrido[3',2':4,5]pyrrolo[1,2-a]pyrazin-6(7H)-one, 4-(5-(4-(4-isopropyl-4H-1,2,4-triazol-3-yl)phenyl)pyridin-3-yl)-7-methyl-8,9-dihydropyrido[3',2':4,5]pyrrolo[1,2-a]pyrazin-6(7H)-one, 4-(5-(4-(4-isopropyl-4H-1,2,4-triazol-3-yl)phenyl)pyridin-3-yl)-7-(pyridin-4-ylmethyl)-8,9-dihydropyrido[3',2':4,5]pyrrolo[1,2-a]pyrazin-6(7H)-one, 4-(5-(4-(1-isopropyl-1H-tetrazol-5-yl)phenyl)pyridin-3-yl)-7-methyl-8,9-dihydropyrido[3',2':4,5]pyrrolo[1,2-a]pyrazin-6(7H)-one, N-(8-(2-((2-(2,6-dioxopiperidin-3-yl)-1,3-dioxoisoindolin-4-yl)oxy)acetamido)octyl)-4-(5-(4-(4-isopropyl-4H-1,2,4-triazol-3-yl)phenyl)pyridin-3-yl)-1H-pyrrolo[2,3-b]pyridine-2-carboxamide, N-(1-((2-(2,6-dioxopiperidin-3-yl)-1,3-dioxoisoindolin-4-yl)oxy)-2-oxo-6,9,12-trioxa-3-azatetradecan-14-yl)-4-(5-(4-(4-isopropyl-4H-1,2,4-triazol-3-yl)phenyl)pyridin-3-yl)-1H-pyrrolo[2,3-b]pyridine-2-carboxamide, N-((4,5-dimethyloxazol-2-yl)methyl)-4-(5-(4-(2-oxopyrrolidin-1-yl)phenyl)pyridin-3-yl)-1H-pyrrolo[2,3-b]pyridine-2-carboxamide, 4-(6-amino-5-(4-(4-isobutyl-4H-1,2,4-triazol-3-yl)phenyl)pyridin-3-yl)-7-(cyclopropylmethyl)-8,9-dihydropyrido[3',2':4,5]pyrrolo[1,2-a]pyrazin-6(7H)-one, 4-(6-amino-5-(4-(4-isopropyl-4H-1,2,4-triazol-3-yl)phenyl)pyridin-3-yl)-N-(cyclopropylmethyl)furo[2,3-b]pyridine-2-carboxamide, N-(1-((2-(2,6-dioxopiperidin-3-yl)-1,3-dioxoisoindolin-4-yl)oxy)-2-oxo-6,9,12-trioxa-3-azatetradecan-14-yl)-4-(5-(4-(2-oxopyrrolidin-1-yl)phenyl)pyridin-3-yl)-1H-pyrrolo[2,3-b]pyridine-2-carboxamide, 4-(5-(4-(4-(3,3-difluorocyclobutyl)-4H-1,2,4-triazol-3-yl)phenyl)pyridin-3-yl)-7-methyl-8,9-dihydropyrido[3',2':4,5]pyrrolo[1,2-a]pyrazin-6(7H)-one, N-(8-(2-((2-(2,6-dioxopiperidin-3-yl)-1,3-dioxoisoindolin-4-yl)oxy)acetamido)octyl)-4-(5-(4-(2-oxopyrrolidin-1-yl)phenyl)pyridin-3-yl)-1H-pyrrolo[2,3-b]pyridine-2-carboxamide, 4-(5-(4-(4-isobutyl-4H-1,2,4-triazol-3-yl)phenyl)pyridin-3-yl)-N-(2-(pyridin-4-yl)ethyl)-1H-pyrrolo[2,3-b]pyridine-2-carboxamide, 1-(4-(5-(2-((2S,4R)-2-(2-hydroxypropan-2-yl)-4-methylpyrrolidine-1-carbonyl)-1H-pyrrolo[2,3-b]pyridin-4-yl)pyridin-3-yl)phenyl)pyrrolidin-2-one, 1-(4-(5-(2-(3-cyclopropyl-3-hydroxypiperidine-1-carbonyl)-1H-pyrrolo[2,3-b]pyridin-4-yl)pyridin-3-yl)phenyl)pyrrolidin-2-one,
methyl 4-(5-(4-(4-isopropyl-4H-1,2,4-triazol-3-yl)phenyl)pyridin-3-yl)-1H-pyrrolo[2,3-b]pyridine-2-carboxylate,
N-((1-hydroxy-1,3-dihydrobenzo[c][1,2]oxaborol-4-yl)methyl)-4-(5-(4-(2-oxopyrrolidin-1-yl)phenyl)pyridin-3-yl)-1H-pyrrolo[2,3-b]pyridine-2-carboxamide,
4-(5-(4-(5-azaspiro[2.4]heptane-5-carbonyl)phenyl)pyridin-3-yl)-7-methyl-8,9-dihydropyrido[3',2':4,5]pyrrolo[1,2-a]pyrazin-6(7H)-one, and
4-(5-(4-(1,1-dioxidoisothiazolidin-2-yl)phenyl)pyridin-3-yl)-7-methyl-8,9-dihydropyrido[3',2':4,5]pyrrolo[1,2-a]pyrazin-6(7H)-one.

It should be understood that all isomeric forms are included within the present invention, including mixtures thereof. If the compound contains a double bond, the substituent may be in the E or Z configuration. If the compound contains a di-substituted cycloalkyl, the cycloalkyl substituent may have a cis- or trans configuration. All tautomeric forms are also intended to be included.

Compounds of the invention, and pharmaceutically acceptable salts, hydrates, solvates, stereoisomers and prodrugs thereof may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of a chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula I may form salts which are also within the scope of this invention. Reference to a compound of the Formula herein is understood to include reference to salts thereof, unless otherwise indicated.

The present invention relates to compounds which are modulators of PI5P4K. In one embodiment, the compounds of the present invention are inhibitors of PI5P4K.

The invention is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Method of Synthesizing the Compounds

The compounds of the present invention may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their Those skilled in the art will recognize if a stereocenter exists in the compounds of Formula (I). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Compounds of the present invention can be synthesized by following the steps outlined in General Scheme 1 which comprise different sequences of assembling intermediates or compounds (II) Starting materials are either commercially available or made by known procedures in the reported literature or as illustrated below.

A compound of formula (I) may be obtained (Scheme 1) by starting from, for example, a compound of formula (II), wherein T represents a coupling metal including, but not limited to, boronic acid (B(OH)$_2$) or a boronic ester (B(OR)$_2$) or a potassium trifluoroborate (BF$_3$K) or a MIDA boronate or a stannane and reacting said compound (II) with a compound of formula LG-A, wherein LG represents a leaving group including, but not limited to, halogen (such as chlorine, bromine or iodine), or an alkyl-, aryl- or haloalkyl-sulfonate (such as triflate), under the influence of a transition metal catalyst as described in for example *Metal-Catalyzed Cross-Coupling Reactions, 2$^{nd}$, Completely Revised and Enlarged Edition* by A. de Meijere and F. Diederich, Wiley VCH, 2004. The compound of formula (II) may be generated from the corresponding LG-(II), wherein LG represents a leaving group such as, but not limited to, halogen (such as chlorine, bromine or iodine), or an alkyl-, aryl- or haloalkyl-sulfonate (such as triflate), by known methods as described in for example *Advanced Organic Chemistry, Part A and B* by F. A. Carey and R. J. Sundberg, 5$^{th}$ edition, Springer Science, 2007.

Scheme 1

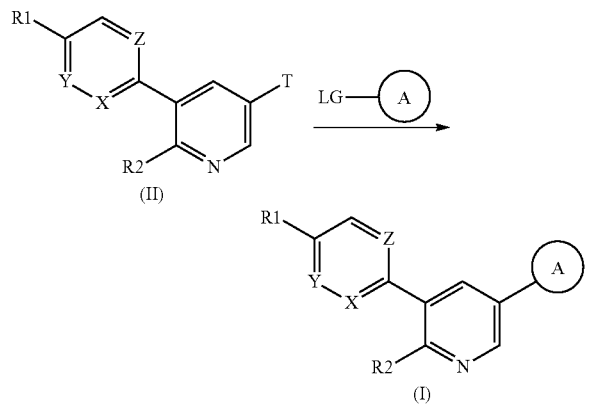

The reaction may be carried out by coupling of a compound of formula LG-A, with an appropriate aryl or heteroaryl boronic acid or boronic ester or stannane of formula (II). The reaction may also be carried out using a suitable metal catalyst including, but not limited to, palladium catalyst (e.g., bis (di-tert-butylphosphino)ferrocene palladium (II) dichloride, tetrakis(triphenylphosphine)palladium (0), palladium (diphenylphosphino)ferrocene dichloride, palladium(II) acetate or bis(dibenzylideneacetone) palladium (0)). Optionally a suitable ligand, for example, triphenylphosphine, tri-tert-butylphosphine or 2-(dicyclohexylphosphino)biphenyl or 2-dicyclohexylphosphino-2',4',6'-triisopropylbiphenylis employed. Suitable bases, including an alkyl amine base, (e.g., triethylamine), an alkali metal or alkaline earth metal carbonate or hydroxide, or phosphate base, (e.g., potassium carbonate, sodium carbonate, cesium carbonate, sodium hydroxide, or potassium phosphate), may be used in the reaction. Said reaction may be performed at a temperature range between +20° C. and +160° C., in suitable solvents, including, without limitation, toluene, tetrahydrofuran, 2-methyl-tetrahydrofuran, 1,4-dioxane, 1,2-dimethoxyethane, acetonitrile, water, ethanol, N,N-dimethylacetamide or N,N-dimethylformamide, or mixtures thereof. If enantiomerically pure or enriched compound (II) is used in this reaction, an enantiomerically pure or enantiomerically enriched compound (I) is obtained.

Compounds of formula (II) and LG-A are commercially available compounds, or are known in the literature, or they are prepared by standard processes known in the art. A compound of formula (I), (II) or LG-A may be separated into its enantiomers by standard processes known in the art by for example chromatography on a chiral stationary phase.

Methods of Using the Disclosed Compounds

Another aspect of the invention relates to a method of treating a disease or disorder associated with modulation of PI5P4K. The method comprises administering to a patient in need of a treatment for diseases or disorders associated with modulation of PI5P4K an effective amount the compositions and compounds of Formula (I).

In another aspect, the present invention is directed to a method of inhibiting PI5P4K. The method involves administering to a patient in need thereof an effective amount of a compound of Formula (I).

Another aspect of the present invention relates to a method of treating, preventing, inhibiting or eliminating a disease or disorder in a patient associated with the inhibition of PI5P4K, the method comprising administering to a patient in need thereof an effective amount of a compound of Formula (I). In one embodiment, the disease may be, but not limited to, cancer or cell proliferative disorder, a metabolic disorder, neurodegenerative disease, and an inflammatory disease.

The present invention also relates to the use of an inhibitor of PI5P4K for the preparation of a medicament used in the treatment, prevention, inhibition or elimination of a disease or condition mediated by PI5P4K, wherein the medicament comprises a compound of Formula (I).

In another aspect, the present invention relates to a method for the manufacture of a medicament for treating, preventing, inhibiting, or eliminating a disease or condition mediated by PI5P4K, wherein the medicament comprises a compound of Formula (I).

Another aspect of the present invention relates to a compound of Formula (I) for use in the manufacture of a medicament for treating a disease associated with inhibiting PI5P4K.

In another aspect, the present invention relates to the use of a compound of Formula (I) in the treatment of a disease associated with inhibiting PI5P4K.

Another aspect of the invention relates to a method of treating cancer. The method comprises administering to a patient in need thereof an effective amount of a compound of Formula (I).

In another aspect of the invention, the method relates to treating a cell proliferative disease. The method comprises administering to a patient in need thereof an effective amount of a compound of Formula (I).

In yet another aspect, the present invention relates to a method of treating a neurodegenerative disease. The method comprises administering to a patient in need thereof an effective amount of a compound of Formula (I).

In another aspect, the present invention relates to a method of treating an inflammatory disease or condition. The method comprises administering to a patient in need thereof an effective amount of a compound of Formula (I).

Another aspect of the invention relates to a method of inducing cell cycle arrest, apoptosis in tumor cells, and/or enhanced tumor-specific T cell immunity. The method comprises contacting the cells with an effective amount of a compound of Formula (I).

In one embodiment, the present invention relates to the use of an inhibitor of PI5P4K for the preparation of a medicament used in treatment, prevention, inhibition or elimination of a disease or disorder associated with cancer or cell proliferative disorder, a metabolic disorder, neurodegenerative disease, and an inflammatory disease.

In another embodiment, the present invention relates to a compound of Formula (I) or a pharmaceutical composition comprising a compound of the present invention and a pharmaceutically acceptable carrier used for the treatment of cancers or cell proliferative disorders including, but not limited to, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendothelio sarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

In another embodiment, the present invention relates to a compound of Formula (I) or a pharmaceutical composition comprising a compound of the present invention and a pharmaceutically acceptable carrier used for the treatment of neurodegenerative diseases including, but not limited to, brain trauma, spinal cord trauma, trauma to the peripheral nervous system, Alzheimer's disease, Pick's disease, diffuse Lewy body disease, progressive supranuclear palsy (Steel-Richardson syndrome), multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffman disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, and prion diseases (including Creutzfeldt-Jakob, Gerstmann-Straussler-Scheinker disease, Kuru and fatal familial insomnia, age-related dementia, vascular dementia, diffuse white matter disease (Binswanger's disease), dementia of endocrine or metabolic origin, dementia of head trauma and diffuse brain damage, dementia pugilistica or frontal lobe dementia, neurodegenerative disorders resulting from cerebral ischemia or infaction including embolic occlusion and thrombotic occlusion as well as intracranial hemorrhage of any type, intracranial and intravertebral lesions, hereditary cerebral angiopathy, normeuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis arthropathy, and Finnish and Iowa amyloidosis.

In another embodiment, the present invention relates to a compound of Formula (I) or a pharmaceutical composition comprising a compound of the present invention and a pharmaceutically acceptable carrier used for the treatment of inflammatory disease. In some embodiments, the inflammatory disease is associated with a metabolic disorder. In some embodiments the treated inflammation is associated with, but not limited to, Type II diabetes, insulin resistance cardiovascular disease, arrhythmia, atherosclerosis, coronary artery disease, hypertriglyceridemia, dyslipidemia, retinopathy, nephropathy, neuropathy, obesity, and macular edema.

In yet another embodiment, the present invention relates to a compound of Formula (I) or a pharmaceutical composition comprising a compound of the present invention and a pharmaceutically acceptable carrier used for the treatment of a metabolic disease including, but not limited, Type II diabetes, insulin resistance cardiovascular disease, arrhythmia, atherosclerosis, coronary artery disease, hypertriglyceridemia, dyslipidemia, retinopathy, nephropathy, neuropathy, obesity, and macular edema.

In another embodiment, the present invention relates to a compound of Formula (I) or a pharmaceutical composition comprising a compound of the present invention and a pharmaceutically acceptable carrier used for the treatment of inflammatory disease associated with inflammatory disease. In some embodiments the treated inflammation is associated with, but not limited to, ileitis, ulcerative colitis, Barrett's syndrome, or Crohn's disease.

In some embodiments, the patient is selected for treatment based on gene amplification and/or elevated tumor expression of PI5P4K. In other embodiments, the patient is selected for treatment based on gene amplification and/or elevated tumor expression of PI5P4Kα gene, PI5P4Kβ gene, or PI5P4Kγ gene. In other embodiments, the patient is selected for the treatment based on tumor expression of p53 mutations.

In some embodiments, administration of a compound of Formula (I) or a pharmaceutical composition comprising a compound of the present invention and a pharmaceutically acceptable carrier induces a change in the cell cycle or cell viability.

Another aspect of the invention is directed to pharmaceutical compositions comprising a compound of Formula (I) and a pharmaceutically acceptable carrier. The pharmaceutical acceptable carrier may further include an excipient, diluent, or surfactant.

In one embodiment, are provided methods of treating a disease or disorder associated with modulation of PI5P4K including, cancer or cell proliferative disorder, a metabolic disorder, neurodegenerative disease, and an inflammatory disease, comprising administering to a patient suffering from at least one of said diseases or disorder a compound of Formula (I).

One therapeutic use of the compounds or compositions of the present invention which inhibit PI5P4K is to provide treatment to patients or subjects suffering from c cancer or cell proliferative disorder, a metabolic disorder, neurodegenerative disease, and an inflammatorydisease.

The disclosed compounds of the invention can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, poly(hydroxypropyl) methacrylamide-phenol, poly(hydroxyethyl)-aspanamide phenol, or poly(ethyleneoxide)-polylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention is directed to pharmaceutical compositions comprising a compound of Formula (I) and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Analytical Methods, Materials, and Instrumentation

Unless otherwise noted, reagents and solvents were used as received from commercial suppliers. All solvents used were of analytical grade and commercially available anhydrous solvents were routinely used for reactions. Starting materials were available from commercial sources, or prepared according to literature procedures. Room temperature refers to +20-25° C. Solvent mixture compositions are given as volume percentages or volume ratios.

Microwave heating was performed in a Biotage Initiator microwave cavity producing continuous irradiation at 2.45 GHz. It is understood that microwaves may be used for the heating of reaction mixtures.

Straight phase chromatography was manually performed on Merck Silica gel 60 (0.040-0.063 mm), or automatically using an ISCO Combiflash® Companion™ system using SiliaSep™ normal-phase flash columns using the solvent system indicated.

NMR spectra were recorded on a 400 MHz (or higher field) NMR spectrometer fitted with a probe of suitable configuration. Spectra were recorded at ambient temperature unless otherwise stated. Chemical shifts are given in ppm down- and upfield from TMS (0.00 ppm). The following reference signals were used: the residual solvent signal of DMSO-d6 δ 2.5, CDCl3 δ 7.26 or Methanol-d4 δ 3.31. Resonance multiplicities are denoted s, d, t, q, m and br for singlet, doublet, triplet, quartet, multiplet and broad, respectively.

High pressure liquid chromatography (HPLC) was performed on a reverse phase column. A linear gradient was applied using for example mobile phase A (aqueous 0.1% $NH_3$ or aqueous 0.1% acetic acid or aqueous 0.1% formic acid) and B (acetonitrile or methanol). Mass spectrometer (MS) analyses were performed in positive ion mode using electrospray ionization (ES+).

Preparative chromatography was run on a Gilson-PREP GX271 or GX281 with Trilution 1c as software on a reverse phase column. A linear gradient was applied using for example mobile phase A (aqueous 0.1% $NH_3$ or aqueous 0.1% acetic acid or aqueous 0.1% formic acid) and B (acetonitrile or methanol).

Preparative chiral chromatography for separation of enantiomers was run on a Thar SFC using supercritical fluid chromatography on a chiral stationary phase. A linear gradient was applied using mobile phase A (carbon dioxide) and B (acetonitrile or methanol or ethanol or 2-propanol or any mixtures thereof). Additives (such as diethyl amine or isopropyl amine or ammonia or formic acid or TFA) may be used.

Abbreviations used in the following examples and elsewhere herein are:

AcOH acetic acid
$AlMe_3$ trimethylaluminum
Amphos bis(4-(N,N-Dimethylamino)phenyl)di-tert-butyl phosphine
anh. anhydrous
atm atmosphere
aq. aqueous
br broad
$B_2Pin_2$ bis(pinacolato)diboron
BINAP (±)-2,2'-bis(diphenylphosphino)-1,1'-binaphthalene
Boc tert-butyloxycarbonyl
BrettPhos 2-(dicyclohexylphosphino)3,6-dimethoxy-2',4',6'-triisopropyl-1,1'-biphenyl
BrettPhos Pd G3 [(2-dicyclohexylphosphino-3,6-dimethoxy-2',4',6'-triisopropyl-1,1'-biphenyl)-2-(2'-amino-1,1'-biphenyl)]palladium(II) methanesulfonate
brine saturated aqueous sodium chloride
n-BuLi n-butyllithium
n-BuOH n-butanol
Calc'd calculated
cataCXium A-Pd-G2 chloro[(di(1-adamantyl)-N-butylphosphine)-2-(2-aminobiphenyl)]palladium(II)
$CDCl_3$ deuterated chloroform
CDI carbonyldiimidazole
Chloroform-d deuterated chloroform
d doublet
dd doublet of doublets
dt doublet of triplets
DCE dichloroethane
DCM dichloromethane
DIAD diisopropyl azodicarboxylate
DIPEA N,N-diisopropylethylamine
DMAc N,N-dimethyl acetamide
DMAP N,N-dimethylpyridin-4-amine
DME 1,2-dimethoxyethane
DMEDA N,N'-dimethylethylenediamine
DMF N,N-dimethylformamide
DMSO dimethyl sulfoxide
DMSO-$d_6$ deuterated dimethyl sulfoxide
Dowtherm® A eutectic mixture of 26.5% diphenyl and 73.5% diphenyl oxide
EDA ethylenediamine
EDC 1-ethyl-3-(3-dimethylaminopropyl)carbodiimide
$Et_2O$ diethyl ether
EtOAc ethyl acetate
EtOH ethanol
ESI electrosprayionization
g gram
h hour(s)
H hydrogen
$^1H$ NMR nuclear magnetic resonance (proton nucleus)
HATU [bis(dimethylamino)methylene]-1H-1,2,3-triazolo[4,5-b]pyridinium 3-oxide hexafluorophosphate
HBTU 3-[bis(dimethylamino)methylene]-3H-benzotriazol-1-oxide hexafluorophosphate Hoveyda Grubbs dichloro[1,3-bis(2,4,6-trimethylphenyl)-2-imidazolidinylidene](2-cat. $2^{nd}$ gen. isopropoxyphenylmethylene)ruthenium(II)
HOBt hydroxybenzotriazole
HPLC high pressure (or performance) liquid chromatography
Hz hertz
J coupling constant
KHMDS potassium hexamethyldisilazide
KOAc potassium acetate
LCMS liquid chromatography mass spectrometry
LHMDS lithium hexamethyldisilazide
[#] M molar concentration
m multiplet
[M+H]+ molecular ion plus hydrogen
[M-tBu+H]+ molecular ion minus tert-butyl plus hydrogen
mCPBA meta-chloroperoxybenzoic acid
Me$_2$NH dimethylamine
Me$_4$NBr tetramethylammonium bromide
MeCN acetonitrile
Meldrum's acid 2,2-dimethyl-1,3-dioxane-4,6-dione
MeNH$_2$ methylamine
MeOH methanol
Methanol-d4 deuterated methanol
2-MeTHF 2-methyl tetrahydrofuran
mg milligram
MHz megahertz
min min
mmol millimole
mL milliliter
MS mass spectrometry
MS ES mass spectrometry electrospray
Ms$_2$O methanesulfonic anhydride
MTBE methyl tert-butyl ether
MW microwave
m/z mass-to-charge ratio
μL microliter
N$_2$ nitrogen
NIS N-iodosuccinimide
NMP N-methyl-2-pyrrolidone
NMR nuclear magnetic resonance
PEPPSI-iPr [1,3-bis(2,6-diisopropylphenyl)imidazol-2-ylidene](3-chloropyridyl)palladium(II) dichloride
PdCl$_2$(Amphos) bis(di-tert-butyl(4-dimethylaminophenyl)phosphine) dichloropalladium(II)
Pd$_2$(dba)$_3$ tris(dibenzylideneacetone)dipalladium(O)
Pd(OAc)$_2$ palladium(II) acetate
PdCl$_2$(dppf) [1,1'-bis(diphenylphosphino)ferrocene]dichloropalladium(II)
PdCl$_2$(MeCN)$_2$ bis(acetonitrile)dichloropalladium(II)
PdCl$_2$(PPh$_3$)$_2$ bis(triphenylphosphinepalladium(II) dichloride
Pd(P(Cy)$_3$)$_2$Cl$_2$ dichlorobis(tricyclohexylphosphine)palladium(II)
Pd(PPh$_3$)$_4$ tetrakis(triphenylphosphine)palladium(O)
Pd(t-Bu$_3$P)$_2$ bis(tri-tert-butylphosphine)palladium(O)
pH potential of hydrogen
PMB 4-methoxybenzyl
PMBCl 4-methoxybenzyl chloride
ppm parts per million
prep preparative
py pyridine
q quartet
qd quartet of doublets
quant. quantitative
quin. quintuplet
quind quintuplet of doublets
Rt retention time
rt room temperature
s singlet
sat. saturated
sat. aq. saturated aqueous
SEMCl 2-(trimethylsilyl)ethoxymethyl chloride
t triplet
t-BuLi tert-butyllithium
td triplet of doublets
TMS trimethylsilyl
TMSCl trimethylsilyl chloride
tt triplet of triplets
T3P polyphosphonic anhydride
TBAB tetrabutylammonium bromide
TEA triethylamine
TFA trifluoroacetic acid
TFAA trifluoroacetic anhydride
THF tetrahydrofuran
TLC thin layer chromatography
TPPO triphenylphosphine oxide
XantPhos 4,5-bis(diphenylphosphino)-9,9-dimethylxanthene
XPhos 2-dicyclohexylphosphino-2',4',6'-triisopropylbiphenyl Example 1: 4-([3,4'-bipyridin]-5-yl)-N,N-dimethylbenzamide

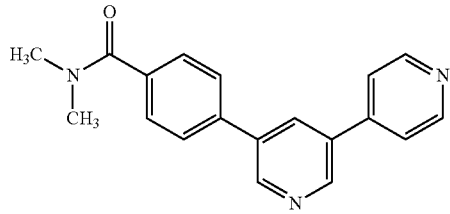 [SMILES: CN(C)C(=O)c1ccc(-c2cncc(-c3ccncc3)c2)cc1]

To a mixture of 3,5-dibromopyridine (200 mg, 0.84 mmol), 4-pyridylboronic acid (52 mg, 0.42 mmol) and K$_2$CO$_3$ (0.47 g, 3.38 mmol) in 1,4-dioxane (3 ml) and water (0.75 ml) under N$_2$ was added Pd(PPh$_3$)$_4$ (49 mg, 0.04 mmol). The resulting mixture was stirred at 70° C. for 3 h, then [4-(dimethylcarbamoyl)phenyl]boronic acid (81 mg, 0.42 mmol) was added and the mixture was stirred at 90° C. for 2 h. More [4-(dimethylcarbamoyl)phenyl]boronic acid (81 mg, 0.42 mmol) and PdCl$_2$(Amphos) (15 mg, 0.02 mmol) were added and stirring continued at 90° C. overnight. When cooled to rt water and EtOAc were added, the organic layer separated and the aqueous layer was extracted with EtOAc. The combined organics were washed with brine, dried over Na$_2$SO$_4$, filtered, concentrated and purified by preparative HPLC to give the product as a solid (18 mg, 7%). $^1$H NMR (500 MHz, CHLOROFORM-d) δ ppm 3.05 (br s, 3H), 3.15 (br s, 3H), 7.59 (br d, J=7.10 Hz, 2H), 7.64-7.74 (m, 4H), 8.06-8.19 (m, 1H), 8.80 (br s, 2H), 8.92 (br s, 1H), 8.96 (s, 1H). MS ES+m/z 304 [M+H]⁺.

Example 2: 4-(5-(1H-pyrrolo[2,3-b]pyridin-4-yl)pyridin-3-yl)-N,N-dimethylbenzamide

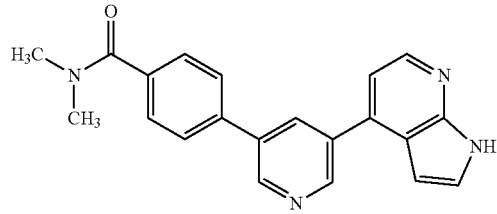 [SMILES: CN(C)C(=O)c1ccc(-c2cncc(-c3ccnc4[nH]ccc34)c2)cc1]

Example 3: 4-(5'-(H-pyrrolo[2,3-b]pyridin-4-yl)-[3,3'-bipyridin]-5-yl)-N,N-dimethylbenzamide

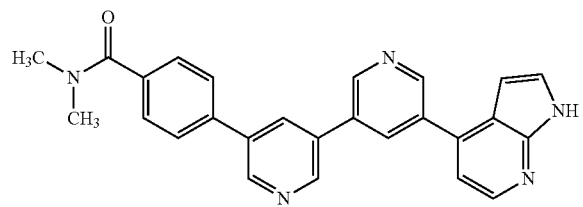 [SMILES: CN(C)C(=O)c1ccc(-c2cncc(-c3cncc(-c4ccnc5[nH]ccc45)c3)c2)cc1]

A mixture of (5-chloro-3-pyridyl)boronic acid (227 mg, 1.44 mmol), 4-chloro-1H-pyrrolo[2,3-b]pyridine (200 mg, 1.31 mmol), K$_2$CO$_3$ (453 mg, 3.28 mmol) and PdCl$_2$(Amphos) (46 mg, 0.07 mmol) in 1,4-dioxane (5 ml) and water (2 ml) was heated in a microwave reactor at 125° C. for 40 min. EtOAc and water were added and the organic layer separated. The aqueous layer was extracted with EtOAc. The combined organics were washed with brine, dried over Na$_2$SO$_4$, filtered, concentrated and recrystallized from 2-propanol to give a mixture of intermediates as a solid (130 mg). The solid was taken up in 1,4-dioxane (5 ml) and water (2 ml), together with [4-(dimethylcarbamoyl)phenyl]boronic acid (120 mg, 0.62 mmol), K$_2$CO$_3$ (196 mg, 1.42 mmol) and PdCl$_2$(Amphos) (20 mg, 0.03 mmol). The resulting mixture was stirred at 95° C. for 2 h. When cooled to rt EtOAc and water were added and the organic layer separated. The aqueous layer was extracted with EtOAc. The combined organics were washed with brine, dried over Na$_2$SO$_4$, filtered, concentrated and purified by preparative HPLC to give the two products as solids.

Example 2, (9 mg, 5%). ¹H NMR (500 MHz, METHANOL-d$_4$) δ ppm 3.00-3.15 (m, 6H), 6.61-6.70 (m, 1H), 7.18-7.29 (m, 1H), 7.42-7.48 (m, 1H), 7.53-7.59 (m, 2H), 7.70-7.80 (m, 2H), 8.32 (s, 2H), 8.80-8.88 (m, 1H), 8.89-8.93 (m, 1H). MS ES+m/z 343 [M+H]⁺.

Example 3, (3 mg, 1%). ¹H NMR (500 MHz, METHANOL-d$_4$) δ ppm 3.01-3.18 (m, 6H), 6.60-6.72 (m, 1H), 7.21-7.32 (m, 1H), 7.43-7.50 (m, 1H), 7.55-7.59 (m, 2H), 7.72-7.82 (m, 2H), 8.27-8.30 (m, 1H), 8.31-8.34 (m, 1H), 8.40 (d, J=1.58 Hz, 1H), 8.83-8.91 (m, 2H), 8.94 (s, 1H), 9.00 (d, J=0.95 Hz, 1H). MS ES+m/z 420 [M+H]⁺.

Example 4: 4-(5-(1H-pyrrolo[2,3-b]pyridin-5-yl)pyridin-3-yl)-N,N-dimethylbenzamide

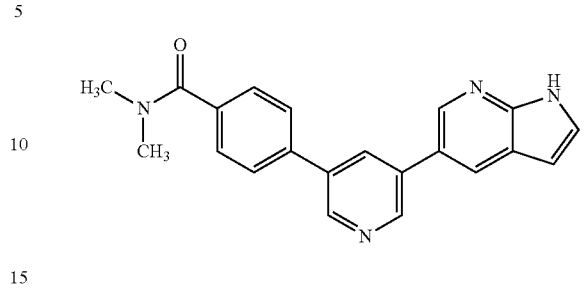

A mixture of (5-chloro-3-pyridyl)boronic acid (264 mg, 1.67 mmol), 5-bromo-1H-pyrrolo[2,3-b]pyridine (300 mg, 1.52 mmol), K$_2$CO$_3$ (526 mg, 3.81 mmol) and PdCl$_2$(Amphos) (54 mg, 0.08 mmol) in 1,4-dioxane (5 ml) and water (2 ml) was stirred at 95° C. for 1 h. [4-(dimethylcarbamoyl)phenyl]boronic acid (294 mg, 1.52 mmol) was added and stirring continued at 95° C. for 1 h. When cooled to rt water and EtOAc were added and the organic layer separated. The aqueous layer was extracted with EtOAc. The combined organics were washed with brine, dried over Na$_2$SO$_4$, filtered and concentrated. Recrystallization from EtOH gave the product as a solid (380 mg, 69%). ¹H NMR (500 MHz, DMSO-d$_6$) δ ppm 3.01 (br d, J=18.92 Hz, 6H), 6.55 (dd, J=3.15, 1.89 Hz, 1H), 7.51-7.60 (m, 3H), 7.96 (d, J=7.58 Hz, 2H), 8.43 (s, 1H), 8.45 (s, 1H), 8.70 (d, J=2.21 Hz, 1H), 8.92 (d, J=1.89 Hz, 1H), 8.98 (d, J=2.21 Hz, 1H), 11.81 (br s, 1H). MS ES+m/z 343 [M+H]⁺.

Example 5: N,N-dimethyl-4-(5-(1-methyl-1H-pyrrolo[2,3-b]pyridin-4-yl)pyridin-3-yl)benzamide

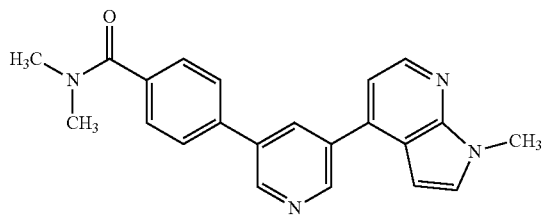

NaH (60% in mineral oil, 18 mg, 0.44 mmol) was added to a solution of N,N-dimethyl-4-[5-(1H-pyrrolo[2,3-b]pyridin-4-yl)-3-pyridyl]benzamide (50 mg, 0.15 mmol) in DCM at 0° C. The mixture was stirred for 20 min then iodomethane (11 μl, 0.18 mmol) was added and the mixture was stirred at rt overnight. Sat. aq. NH$_4$Cl and DCM were added and the organic layer was separated, filtered, concentrated and purified by preparative HPLC to give the product as a solid (5 mg, 9%). ¹H NMR (500 MHz, CHLOROFORM-d) δ ppm 2.90-3.32 (m, 6H), 4.00 (s, 3H), 6.68 (d, J=3.47 Hz, 1H), 7.25 (d, J=4.73 Hz, 1H), 7.34 (d, J=3.47 Hz, 1H), 7.58-7.63 (m, 2H), 7.69-7.76 (m, 2H), 8.26 (t, J=2.05 Hz, 1H), 8.49 (d, J=5.04 Hz, 1H), 8.92-8.98 (m, 1H), 9.00-9.04 (m, 1H). MS ES+m/z 357 [M+H]⁺.

Example 6: N,N-dimethyl-4-(5-(1-methyl-1H-pyrrolo[2,3-b]pyridin-5-yl)pyridin-3-yl)benzamide

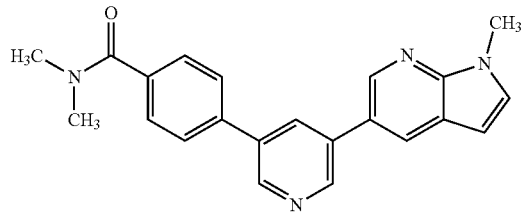 [SMILES: CN(C)C(=O)c1ccc(-c2cncc(-c3cnc4c(ccn4C)c3)c2)cc1]

The title compound was prepared as described for Example 5, replacing N,N-dimethyl-4-[5-(1H-pyrrolo[2,3-b]pyridin-4-yl)-3-pyridyl]benzamide for N,N-dimethyl-4-[5-(1H-pyrrolo[2,3-b]pyridin-5-yl)-3-pyridyl]benzamide, to give the product as a solid (4 mg, 7%). $^1$H NMR (500 MHz, DMSO-$d_6$) δ ppm 3.01 (br d, J=18.92 Hz, 6H), 3.89 (s, 3H), 6.57 (d, J=3.47 Hz, 1H), 7.56-7.59 (m, 2H), 7.62 (d, J=3.47 Hz, 1H), 7.94-7.97 (m, 2H), 8.44 (s, 1H), 8.46 (d, J=2.46 Hz, 1H), 8.75 (d, J=2.21 Hz, 1H), 8.93 (d, J=2.21 Hz, 1H), 8.98 (d, J=2.21 Hz, 1H). MS ES+m/z 357 [M+H]$^+$.

Example 7: 4-(5-(1,6-naphthyridin-4-yl)pyridin-3-yl)-N,N-dimethylbenzamide

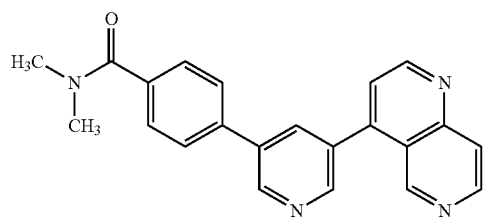 [SMILES: CN(C)C(=O)c1ccc(-c2cncc(-c3ccnc4ccncc34)c2)cc1]

Step 1: Intermediate 1—4-(5-Bromo-3-pyridyl)-N,N-dimethyl-benzamide

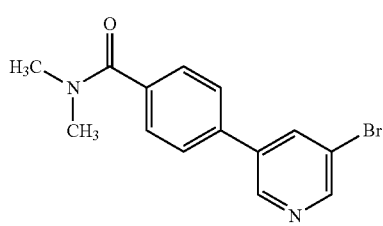 [SMILES: CN(C)C(=O)c1ccc(-c2cncc(Br)c2)cc1]

A mixture of 4-iodo-N,N-dimethyl-benzamide (1.04 g, 3.78 mmol), (5-bromo-3-pyridyl)boronic acid (763 mg, 3.78 mmol), Pd(PPh$_3$)$_4$ (218 mg, 0.19 mmol) and K$_2$CO$_3$ (1.3 g, 9.41 mmol) in n-BuOH (12 ml) and H$_2$O (3 ml) was stirred at 90° C. for 2.5 h. The reaction mixture was filtered through celite and rinsed with EtOAc. The organic phase was washed with brine, dried over MgSO$_4$, filtered, concentrated and purified on a silica gel column eluted with 0-100% EtOAc in heptane to give the product as a solid (900 mg, 78%). MS ES+m/z 305 [M+H]$^+$.

Step 2: Intermediate 2—N,N-dimethyl-4-[5-(4,4,5,5-tetramethyl-1,3,2-dioxaborolan-2-yl)-3-pyridyl]benzamide

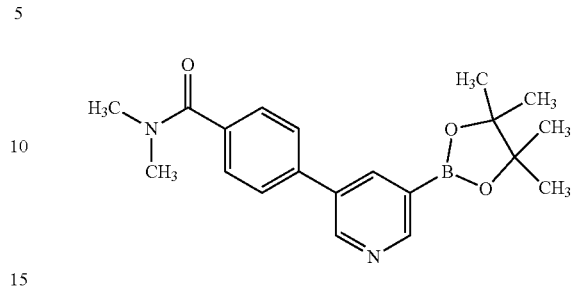

4-(5-Bromo-3-pyridyl)-N,N-dimethyl-benzamide (490 mg, 1.61 mmol), 4,4,5,5-tetramethyl-2-(4,4,5,5-tetramethyl-1,3,2-dioxaborolan-2-yl)-1,3,2-dioxaborolane (570 mg, 2.24 mmol), PdCl$_2$(dppf) (60 mg, 0.08 mmol) and KOAc (280 mg, 2.85 mmol) were taken up in 1,4-dioxane (10 ml) and the resulting mixture was stirred at 90° C. for 4 h. When cooled to rt the mixture was filtered through celite and the filter cake rinsed with EtOAc. The filtrate was concentrated and purified on a silica gel column eluted with 0-100% EtOAc in heptane to give the product as a solid (184 mg, 33%). MS ES+m/z 353 [M+H]$^+$.

Step 3: 4-(5-(1,6-naphthyridin-4-yl)pyridin-3-yl)-N,N-dimethylbenzamide

N,N-dimethyl-4-[5-(4,4,5,5-tetramethyl-1,3,2-dioxaborolan-2-yl)-3-pyridyl]benzamide (70 mg, 0.2 mmol), 4-chloro-1,6-naphthyridine (36 mg, 0.22 mmol), Pd(PPh$_3$)$_4$ (12 mg, 0.01 mmol) and K$_2$CO$_3$ (69 mg, 0.5 mmol) were taken up in 1,4-dioxane (1 ml) and water (0.25 ml) and the resulting mixture was stirred at 90° C. for 1 h. When cooled to rt the mixture was filtered through celite and the filter cake rinsed with EtOAc. The filtrate was concentrated and purified by preparative HPLC to give the product as a solid (18 mg, 26%). $^1$H NMR (500 MHz, METHANOL-$d_4$) δ ppm 3.08 (s, 3H), 3.16 (s, 3H), 7.63 (m, J=8.20 Hz, 2H), 7.81 (d, J=4.41 Hz, 1H), 7.92 (m, J=8.20 Hz, 2H), 8.10 (d, J=5.99 Hz, 1H), 8.45 (t, J=1.89 Hz, 1H), 8.82 (d, J=6.12 Hz, 1H), 8.85 (s, 1H), 9.11 (d, J=2.21 Hz, 1H), 9.24 (d, J=4.73 Hz, 1H), 9.33 (s, 1H). MS ES+m/z 355 [M+H]$^+$.

Example 8: 4-(2'-(2-hydroxypropan-2-yl)-[3,4'-bipyridin]-5-yl)-N,N-dimethylbenzamide

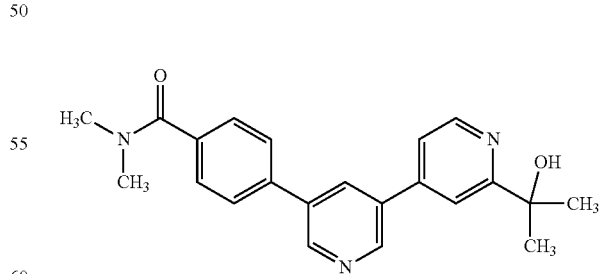

The title compound was prepared as described for Example 7, replacing 4-chloro-1,6-naphthyridine for 2-(4-bromo-2-pyridyl)propan-2-ol, to give the product as a solid (2 mg, 2%). $^1$H NMR (500 MHz, Methanol-$d_4$) δ 1.66 (s, 6H), 3.11 (s, 3H), 3.19 (s, 3H), 7.62-7.69 (m, 2H), 7.73 (dd, J=5.2, 1.9 Hz, 1H), 7.90-7.96 (m, 2H), 8.12 (d, J=1.7 Hz, 1H), 8.50 (t, J=2.2 Hz, 1H), 8.67 (d, J=5.2 Hz, 1H), 8.99 (dd, J=3.5, 2.2 Hz, 2H). MS ES+m/z 362 [M+H]⁺.

Example 9: 5-(4-(dimethylcarbamoyl)phenyl)-N,N-dimethyl-[3,4'-bipyridine]-2'-carboxamide

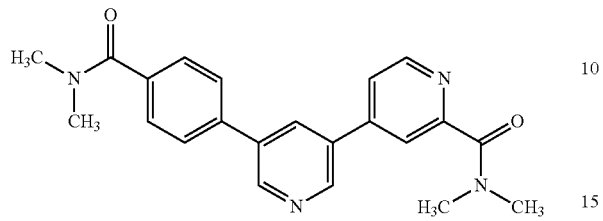

The title compound was prepared as described for Example 7, replacing 4-chloro-1,6-naphthyridine for 4-bromo-N,N-dimethyl-pyridine-2-carboxamide and using PdCl₂(dppf) instead of Pd(PPh₃)₄, in n-BuOH, to give the product as a solid (acetate salt (2 eq), 7 mg, 6%). ¹H NMR (500 MHz, DMSO-d₆) δ ppm 1.84 (s, 6H), 2.96 (s, 6H), 2.97-3.02 (m, 3H), 3.05 (s, 3H), 7.54-7.57 (m, 2H), 7.95-7.98 (m, 2H), 8.01 (dd, J=5.04, 1.89 Hz, 1H), 8.09 (dd, J=1.73, 0.79 Hz, 1H), 8.56 (t, J=2.21 Hz, 1H), 8.71 (dd, J=5.36, 0.63 Hz, 1H), 9.04 (d, J=2.21 Hz, 1H), 9.07 (d, J=2.21 Hz, 1H). MS ES+m/z 375 [M+H]⁺.

Example 10: 4-(5-(1H-pyrrolo[2,3-b]pyridin-3-yl)pyridin-3-yl)-N,N-dimethylbenzamide

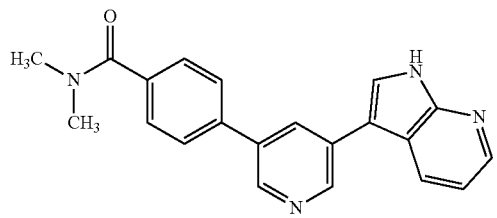 [SMILES: CN(C)C(=O)c1ccc(-c2cncc(-c3c[nH]c4ncccc34)c2)cc1]

The title compound was prepared as described for Example 7, replacing 4-chloro-1,6-naphthyridine for 3-bromo-1H-pyrrolo[2,3-b]pyridine and using PdCl₂(Amphos) instead of Pd(PPh₃)₄, to give the product as a solid (10 mg, 7%). ¹H NMR (500 MHz, DMSO-d₆) δ ppm 2.93-2.99 (m, 3H), 3.01 (br s, 3H), 7.20 (dd, J=8.04, 4.57 Hz, 1H), 7.54-7.57 (m, 2H), 7.91 (d, J=8.20 Hz, 2H), 8.14 (s, 1H), 8.31 (dd, J=4.73, 1.58 Hz, 1H), 8.35 (t, J=2.21 Hz, 1H), 8.39 (dd, J=8.04, 1.42 Hz, 1H), 8.79 (d, J=2.21 Hz, 1H), 8.98 (d, J=2.21 Hz, 1H). MS ES+m/z 343 [M+H]⁺.

Example 11: N,N-dimethyl-4-(5-(2-methyl-1H-pyrrolo[2,3-b]pyridin-3-yl)pyridin-3-yl)benzamide

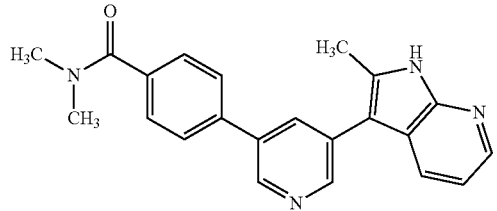 [SMILES: Cc1[nH]c2ncccc2c1-c1cncc(-c2ccc(C(=O)N(C)C)cc2)c1]

The title compound was prepared as described for Example 7, replacing 4-chloro-1,6-naphthyridine for 3-bromo-2-methyl-1H-pyrrolo[2,3-b]pyridine and using PdCl₂(dppf) instead of Pd(PPh₃)₄, to give the product as a solid (6 mg, 4%). ¹H NMR (500 MHz, DMSO-d₆) δ ppm 2.57 (s, 3H), 2.99 (br d, J=18.29 Hz, 6H), 7.10 (dd, J=7.88, 4.73 Hz, 1H), 7.52-7.56 (m, 2H), 7.85-7.89 (m, 2H), 8.01 (dd, J=7.88, 1.58 Hz, 1H), 8.14 (t, J=2.21 Hz, 1H), 8.20 (dd, J=4.57, 1.42 Hz, 1H), 8.74 (d, J=1.89 Hz, 1H), 8.84 (d, J=2.21 Hz, 1H), 11.90 (s, 1H). MS ES+m/z 357 [M+H]⁺.

Example 12: 4-(5-(5-chloro-1H-pyrrolo[2,3-b]pyridin-3-yl)pyridin-3-yl)-N,N-dimethylbenzamide

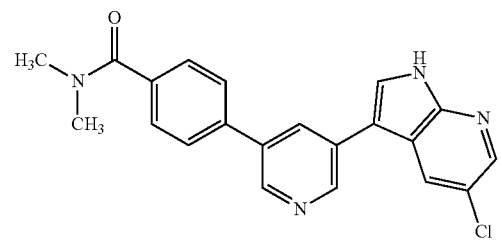 [SMILES: CN(C)C(=O)c1ccc(-c2cncc(-c3c[nH]c4ncc(Cl)cc34)c2)cc1]

The title compound was prepared as described for Example 7, replacing 4-chloro-1,6-naphthyridine for 3-bromo-5-chloro-1H-pyrrolo[2,3-b]pyridine and using PdCl₂(Amphos) instead of Pd(PPh₃)₄, to give the product as a solid (15 mg, 9%). ¹H NMR (500 MHz, DMSO-d₆) δ ppm 2.98 (br s, 3H), 3.00-3.05 (m, 3H), 7.54-7.59 (m, 2H), 7.59-7.65 (m, 1H), 7.91-7.99 (m, 2H), 8.27 (s, 1H), 8.32 (d, J=2.52 Hz, 1H), 8.37 (t, J=2.21 Hz, 1H), 8.49 (d, J=2.21 Hz, 1H), 8.82 (d, J=2.21 Hz, 1H), 9.00 (d, J=2.21 Hz, 1H). MS ES+m/z 377 [M+H]⁺.

Example 13: 4-(5-(4-(dimethylcarbamoyl)phenyl)pyridin-3-yl)-N,1-dimethyl-1H-pyrrolo[2,3-b]pyridine-2-carboxamide

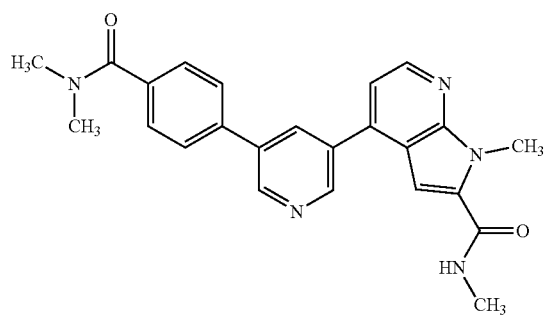 [SMILES: CNC(=O)c1cc2c(-c3cncc(-c4ccc(C(=O)N(C)C)cc4)c3)ccnc2n1C]

Step 1: Intermediate 3—4-Chloro-1-methyl-pyrrolo[2,3-b]pyridine-2-carboxylic acid

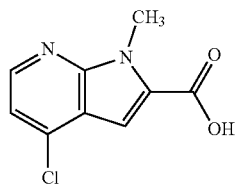

K$_2$CO$_3$ (105 mg, 0.76 mmol) and iodomethane (60 µl, 0.96 mmol) were added to a solution of methyl 4-chloro-H-pyrrolo[2,3-b]pyridine-2-carboxylate(160 mg, 0.76 mmol) in THF (5 ml) and the resulting mixture was stirred at 50° C. for 2 h. More iodomethane (60 µl, 0.96 mmol) and TEA (250 µl, 1.8 mmol) were added and stirring continued at 50° C. overnight. LiOH H$_2$O (159 mg, 3.8 mmol), MeOH (2 ml) and water (2 ml) were added and stirring continued at 50° C. for 4 h. The mixture was concentrated and the resulting residue was taken up in water (5 ml) and EtOAc (5 ml). The aqueous layer was separated and the organic layer extracted with 1M aq. NaOH (5 ml). The pH of the combined aqueous layer was adjusted to ~3 using conc. HCl and the milky suspension was kept in refrigerator for 1 h. The formed precipitate was filtered off and dried to give the product as a solid (110 mg, 69%). MS ES+m/z 211 [M+H]$^+$.

Step 2: Intermediate 4—4-Chloro-N,1-dimethyl-pyrrolo[2,3-b]pyridine-2-carboxamide

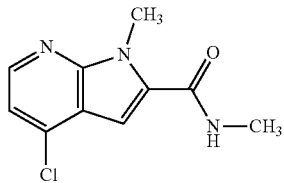

4-Chloro-1-methyl-pyrrolo[2,3-b]pyridine-2-carboxylic acid (110 mg, 0.52 mmol), DIPEA (130 µl, 0.75 mmol) and methylamine (33% in EtOH, 90 µl, 0.72 mmol) were taken up in EtOAc (2 ml). DMF (1 ml) was added to give a clear solution. Propylphosphonic anhydride (50% in EtOAc, 350 µl, 0.59 mmol) was added and the resulting mixture was stirred at rt overnight. The mixture was concentrated and the product was purified on a silica gel column eluted with 0-50% EtOAc in Heptane to give the product as a solid (60 mg, 51%). MS ES+m/z 224 [M+H]$^+$.

Step 3: 4-(5-(4-(dimethylcarbamoyl)phenyl)pyridin-3-yl)-N,1-dimethyl-1H-pyrrolo[2,3-b]pyridine-2-carboxamide The title compound was prepared as described for Example 7, replacing 4-chloro-1,6-naphthyridine for 4-chloro-N,1-dimethyl-pyrrolo[2,3-b]pyridine-2-carboxamide and using PdCl$_2$(PPh$_3$)$_2$ instead of Pd(PPh$_3$)$_4$, in n-BuOH, to give the product as a solid (26 mg, 23%). $^1$H NMR (500 MHz, DMSO-d$_6$) δ ppm 2.77-2.82 (m, 3H), 3.00 (br d, J=18.60 Hz, 6H), 4.11 (s, 3H), 7.37-7.41 (m, 1H), 7.53 (d, J=4.73 Hz, 1H), 7.58 (d, J=8.20 Hz, 2H), 7.95 (d, J=8.20 Hz, 2H), 8.45 (t, J=2.05 Hz, 1H), 8.51-8.57 (m, 1H), 8.58-8.65 (m, 1H), 9.03 (d, J=2.21 Hz, 1H), 9.07 (d, J=1.89 Hz, 1H). MS ES+m/z 414 [M+H]$^+$.

Example 14: 4-(5-(4-(dimethylcarbamoyl)phenyl)pyridin-3-yl)-N-methylfuro[2,3-b]pyridine-2-carboxamide

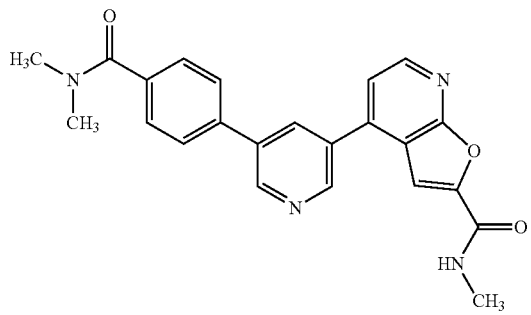 [SMILES: CNC(=O)c1cc2c(-c3cncc(-c4ccc(C(=O)N(C)C)cc4)c3)ccnc2o1]

Step 1: Intermediate 5—Methyl 5-[(2,2-dimethyl-4,6-dioxo-1,3-dioxan-5-ylidene)methylamino]furan-2-carboxylate

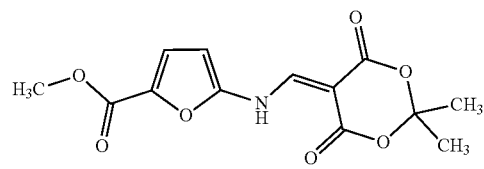

Ethyl 5-aminofuran-2-carboxylate (2 g, 12.9 mmol) was added to a mixture of triethyl orthoformate (10 ml, 60.1 mmol) and 2-propanol (10 ml) at rt. Meldrum's acid (2.25 g, 15.6 mmol) was added and the resulting mixture was stirred at 100° C. for 1.5 h. When cooled to rt the precipitate was filtered off, washed sequentially with 2-propanol (2×3 ml), Pentane (4 ml) and dried to give the product as a solid (2.8 g, 67%). $^1$H NMR (500 MHz, CHLOROFORM-d) δ ppm 1.77 (s, 6H), 3.91 (s, 3H), 6.08 (d, J=3.78 Hz, 1H), 7.22 (d, J=3.47 Hz, 1H), 8.64 (d, J=13.56 Hz, 1H), 11.51 (br d, J=12.61 Hz, 1H). MS ES+m/z 238 [M+H]+(NH$_3$ mobile phase).

Step 2: Intermediate 6—Methyl 4-hydroxyfuro[2,3-b]pyridine-2-carboxylate

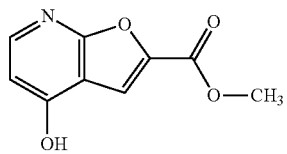

Methyl 5-[(2,2-dimethyl-4,6-dioxo-1,3-dioxan-5-ylidene)methylamino]furan-2-carboxylate (2.8 g, 9.48 mmol) was taken up in Dowtherm® A (20 ml) and the resulting mixture was stirred at 200° C. for 1 h, followed by 220° C. for 15 min. When cooled to rt Et$_2$O (10 ml) was added and the precipitate was filtered off, washed with Et₂O (2×5 ml) and dried to give the product as a solid (1.53 g, 84%). MS ES+m/z 194 [M+H]⁺.

Step 3: Intermediate 7—4-Chloro-N-methyl-furo[2,3-b]pyridine-2-carboxamide

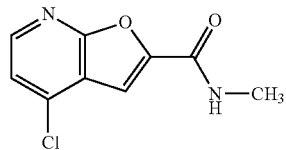

Methyl 4-hydroxyfuro[2,3-b]pyridine-2-carboxylate (250 mg, 1.29 mmol) and LiOH H₂O (163 mg, 3.88 mmol) were taken up in THF (5 ml), MeOH (1 ml) and water (0.5 ml) and the resulting mixture was stirred at 50° C. overnight. The mixture was concentrated and the residue was taken up in SOCl₂ (5 ml, 68.5 mmol) and 2-MeTHF (5 ml). DMF (3 drops) was added and the mixture refluxed for 1 h. When cooled to rt the mixture was concentrated and the resulting residue was suspended in THF (5 ml) and added slowly to a solution of 40% aq. methylamine (1 ml, 11.6 mmol) in THF (5 ml) at 0° C. The resulting mixture was stirred at 0° C. for 30 min. Sat. aq. NH₄Cl (5 ml) and EtOAc (5 ml) were added and the organic layer separated. The aqueous layer was diluted with water to give a clear solution and extracted with EtOAc (2×5 ml). The combined organics were washed with brine, dried over Na₂SO₄, filtered and concentrated. The resulting residue was triturated with Et₂O to give the product as a solid (225 mg, 83%). MS ES+m/z 211 [M+H]⁺.

Step 4: 4-(5-(4-(dimethylcarbamoyl)phenyl)pyridin-3-yl)-N-methylfuro[2,3-b]pyridine-2-carboxamide The title compound was prepared as described for Example 7, replacing 4-chloro-1,6-naphthyridine for 4-chloro-N-methyl-furo[2,3-b]pyridine-2-carboxamide and using PdCl₂(dppf) instead of Pd(PPh₃)₄, in n-BuOH, to give the product as a solid (3 mg, 2%). ¹H NMR (500 MHz, DMSO-d₆) δ ppm 2.82-2.86 (m, 3H), 2.98-3.03 (m, 6H), 7.56-7.63 (m, 2H), 7.83-7.85 (m, 2H), 7.96-8.00 (m, 2H), 8.51 (t, J=2.05 Hz, 1H), 8.60 (d, J=5.36 Hz, 1H), 8.87 (q, J=4.41 Hz, 1H), 9.03 (d, J=2.21 Hz, 1H), 9.11 (d, J=1.89 Hz, 1H). MS ES+m/z 401 [M+H]⁺.

Example 15: 4-(5-(5-(1-hydroxyethyl)-1H-pyrrolo[2,3-b]pyridin-3-yl)pyridin-3-yl)-N,N-dimethylbenzamide

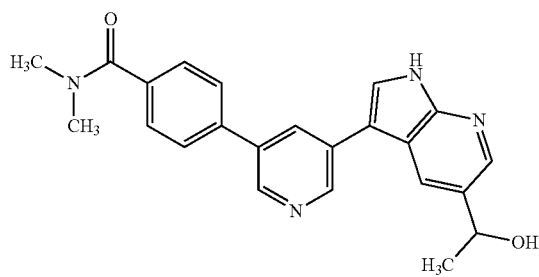 [SMILES: CC(O)c1cnc2[nH]cc(-c3cncc(-c4ccc(C(=O)N(C)C)cc4)c3)c2c1]

Step 1: Intermediate 8—1-(3-Bromo-1H-pyrrolo[2,3-b]pyridin-5-yl)ethenone

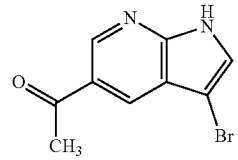

N-bromosuccinimide (863 mg, 4.85 mmol) was added to a solution of 1-(1H-pyrrolo[2,3-b]pyridin-5-yl)ethanone (518 mg, 3.23 mmol) in DCM (3 mL) at 0° C. and the resulting mixture was stirred for 40 min. Sat. aq. Na₂S₂O₃ was added and the mixture extracted with EtOAc. The combined organics were dried over MgSO₄, filtered, concentrated and purified on a silica gel column eluted with 0-100% EtOAc in heptane to give the product as a solid (697 mg, 90%). ¹H NMR (500 MHz, METHANOL-d₄) δ ppm 2.66-2.80 (m, 3H), 7.61 (s, 1H), 8.51 (d, J=1.89 Hz, 1H), 8.92-8.96 (m, 1H). MS ES+m/z 239 [M+H]⁺.

Step 2: Intermediate 9—1-(3-Bromo-1H-pyrrolo[2,3-b]pyridin-5-yl)ethanol

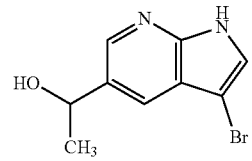

NaBH₄ (130 mg, 3.44 mmol) was added portion wise to a solution of 1-(3-bromo-1H-pyrrolo[2,3-b]pyridin-5-yl)ethanone (411 mg, 1.72 mmol) in methanol (5 ml) at 0° C. and the resulting mixture was stirred at rt for 1 h. The mixture was concentrated and the resulting residue was dissolved in DCM and water. The organic layer was separated and the aqueous layer was extracted with DCM. The combined organics were dried over MgSO₄, filtered and concentrated to give the product as a solid (361 mg, 87%). MS ES+m/z 241 [M+H]⁺.

Step 3: 4-(5-(5-(1-hydroxyethyl)-1H-pyrrolo[2,3-b]pyridin-3-yl)pyridin-3-yl)-N,N-dimethylbenzamide The title compound was prepared as described for Example 7, replacing 4-chloro-1,6-naphthyridine for 1-(3-bromo-1H-pyrrolo[2,3-b]pyridin-5-yl)ethanol and using PdCl₂(Amphos) instead of Pd(PPh₃)₄, to give the product as a solid (8 mg, 11%). ¹H NMR (500 MHz, DMSO-d₆) δ ppm 1.44 (d, J=6.62 Hz, 3H), 3.00 (br d, J=17.02 Hz, 6H), 4.92-4.97 (m, 1H), 5.23 (d, J=4.41 Hz, 1H), 7.54-7.60 (m, 2H), 7.89-7.93 (m, 2H), 8.14 (s, 1H), 8.29-8.32 (m, 2H), 8.35 (t, J=2.05 Hz, 1H), 8.80 (d, J=2.21 Hz, 1H), 9.00 (d, J=1.89 Hz, 1H), 12.02 (br s, 1H). MS ES+m/z 387 [M+H]⁺.

Example 16: 4-(6-amino-[3,4'-bipyridin]-5-yl)-N,N-dimethylbenzamide

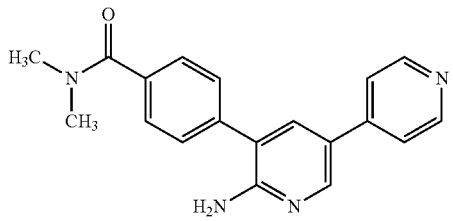 [SMILES: CN(C)C(=O)c1ccc(-c2cc(-c3ccncc3)cnc2N)cc1]

Step 1: Intermediate 10—3-Bromo-5-(4-pyridyl)pyridin-2-amine

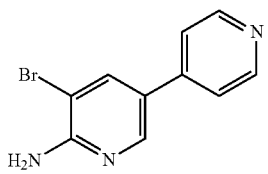 [SMILES: Nc1ncc(-c2ccncc2)cc1Br]

5-(4-Pyridyl)pyridin-2-amine (780 mg, 4.56 mmol) and NBS (811 mg, 4.56 mmol) were taken up in DMF (5 ml) and the resulting mixture was stirred at rt overnight. Water (30 ml) and DCM (25 ml) were added and the mixture filtered. The organic layer was separated and the aqueous layer extracted with DCM (2×20 ml). The mixture was filtered every time before separation of the layers. The combined organics were washed with water, brine, dried over $Na_2SO_4$, filtered and concentrated. The resulting residue was taken up in DCM (3 ml) and stirred at rt for 10 min. The precipitate was filtered off, washed with DCM and dried to give the product as a solid (130 mg, 11%). MS ES+m/z 250 [M+H]+.

Step 2: 4-[2-Amino-5-(4-pyridyl)-3-pyridyl]-N,N-dimethyl-benzamide

3-Bromo-5-(4-pyridyl)pyridin-2-amine (50 mg, 0.2 mmol), [4-(dimethylcarbamoyl)phenyl]boronic acid (42 mg, 0.22 mmol), $PdCl_2$(Amphos) (7 mg, 0.01 mmol) and $K_2CO_3$ (69 mg, 0.5 mmol) were taken up in DMF (1.5 ml) and water (0.5 ml). The resulting mixture was heated in a microwave reactor at 150° C. for 1 h. When cooled to rt the mixture was poured into water (10 ml) and extracted with EtOAc (3×5 ml). The combined organics were washed with water, brine, dried over $Na_2SO_4$, filtered, concentrated and purified by preparative HPLC to give the product as a solid. 1H NMR (500 MHz, DMSO-$d_6$) δ=8.54 (d, J=5.7 Hz, 2H), 8.50 (d, J=2.2 Hz, 1H), 7.81 (d, J=1.9 Hz, 1H), 7.72 (d, J=5.7 Hz, 2H), 7.58 (d, J=7.9 Hz, 2H), 7.50 (d, J=8.2 Hz, 2H), 6.14 (s, 2H), 3.00 (br s, 6H). MS ES+m/z 319 [M+H]+.

Example 17: 4-(6-amino-6'-oxo-1',6'-dihydro-[3,3'-bipyridin]-5-yl)-N,N-dimethylbenzamide

Step 1: Intermediate 11—4-(2-Amino-5-bromo-3-pyridyl)-N,N-dimethyl-benzamide

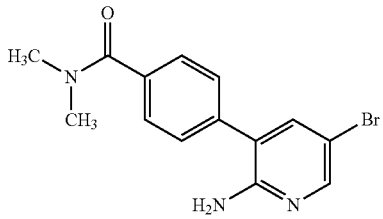

The title compound was prepared as described in Example 16, starting from 5-bromo-3-iodo-pyridin-2-amine and [4-(dimethylcarbamoyl)phenyl]boronic acid, in 1,4-dioxane, water, EtOH (6:3:1) and heating in a microwave reactor at 130° C. for 1 h, to give the product as a solid (412 mg, 77%). MS ES+m/z 320 [M+H]+.

Step 2: 4-(6-amino-6'-oxo-1',6'-dihydro-[3,3'-bipyridin]-5-yl)-N,N-dimethylbenzamide 4-(2-Amino-5-bromo-3-pyridyl)-N,N-dimethyl-benzamide (260 mg, 0.81 mmol), (6-methoxy-3-pyridyl)boronic acid (149 mg, 0.97 mmol), $PdCl_2$(Amphos) (29 mg, 0.04 mmol) and $K_2CO_3$ (337 mg, 2.44 mmol) were taken up in 1,4-dioxane:$H_2O$:EtOH (6:3:1, 2 ml) and the resulting mixture was heated in a microwave reactor at 130° C. for 1 h. When cooled to rt the mixture was diluted with EtOAc (20 ml) and water (10 ml). The organic layer was separated and the aqueous layer extracted with EtOAc (2×20 ml). The combined organics were washed with water and brine, dried over $Na_2SO_4$, filtered and concentrated. The resulting residue was dissolved in DCM (4 ml), $BBr_3$ (1.25 ml, 12.96 mmol) was added and the mixture stirred at rt overnight. Aq. 2M HCl (5 mL) was added and the mixture heated in a microwave reactor at 100° C. for 30 min. Water (20 ml) and DCM (20 ml) were added and the pH of the aqueous phase was adjusted to 8 with aq. 6M KOH. The organic layer was separated and the aqueous layer extracted with DCM (3×15 ml), the combined organics were washed with brine, dried over $MgSO_4$, filtered, concentrated and purified by preparative HPLC to give the product as a solid (0.8 mg, 0.3%). 1H NMR (500 MHz, METHANOL-$d_4$) δ ppm 3.06-3.13 (m, 3H), 3.16 (s, 3H), 6.63 (d, J=9.46 Hz, 1H), 7.56-7.61 (m, 2H), 7.61-7.66 (m, 3H), 7.75 (d, J=2.52 Hz, 1H), 7.88 (dd, J=9.30, 2.68 Hz, 1H), 8.16 (d, J=2.52 Hz, 1H). MS ES+m/z 335 [M+H]+.

Example 18: 4-(2-amino-5-(3,6-dihydro-2H-pyran-4-yl)pyridin-3-yl)-N,N-dimethylbenzamide

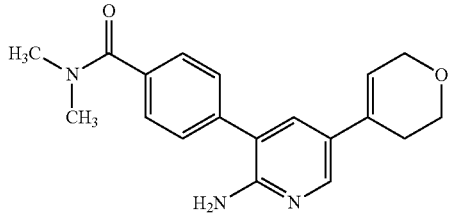 [SMILES: CN(C)C(=O)c1ccc(-c2cc(C3=CCOCC3)cnc2N)cc1]

The title compound was prepared as described in Example 16, starting from 4-(2-amino-5-bromo-3-pyridyl)-N,N-dimethyl-benzamide and 3,6-dihydro-2H-pyran-4-ylboronic acid, in 1,4-dioxane, water, EtOH (6:3:1) and heating in a microwave reactor at 130° C. for 1 h, to give the product as a solid (9 mg, 13%). $^1$H NMR (500 MHz, METHANOL-d$_4$) δ ppm 2.00 (s, 1H), 2.51 (br dd, J=4.41, 2.52 Hz, 2H), 3.06-3.12 (m, 3H), 3.12-3.24 (m, 3H), 3.93 (t, J=5.52 Hz, 2H), 4.30 (q, J=2.73 Hz, 2H), 6.13 (br s, 1H), 7.51-7.62 (m, 5H), 8.05 (br s, 1H). MS ES+m/z 324 [M+H]$^+$.

Example 19: 2'-amino-N,N-dimethyl-[2,3':5',4"-terpyridine]-5-carboxamide

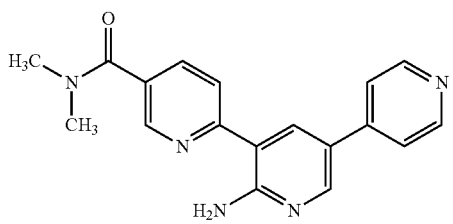 [SMILES: CN(C)C(=O)c1ccc(-c2cc(-c3ccncc3)cnc2N)nc1]

Step 1: Intermediate 12—6-(2-Amino-3-pyridyl)-N,N-dimethyl-pyridine-3-carboxamide

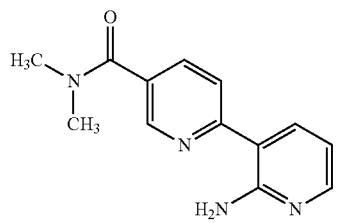 [SMILES: CN(C)C(=O)c1ccc(-c2cccnc2N)nc1]

6-Bromo-N,N-dimethyl-pyridine-3-carboxamde (394 mg, 1.72 mmol), (2-amino-3-pyridyl)boronic acid (220 mg, 1 mmol), PdCl$_2$ (Amphos) (122 mg, 0.17 mmol) and K$_2$CO$_3$ (536 mg, 3.88 mmol) was taken up in n-BuOH (3 ml) and water (0.75 ml) and the resulting mixture was stirred at 90° C. for 5 h. When cooled to rt EtOAc (20 ml) and water (15 ml) were added and the organic layer separated. The aqueous layer was extracted with EtOAc (2×15 ml) and the combined organics were concentrated and purified on a silica gel column eluted with 0-100% EtOAc in heptane to give the product as an oil (135 mg, 560%). MS ES+m/z 243 [M+H]$^+$.

Step 2: Intermediate 13—6-(2-Amino-5-bromo-3-pyridyl)-N,N-dimethyl-pyridine-3-carboxamide

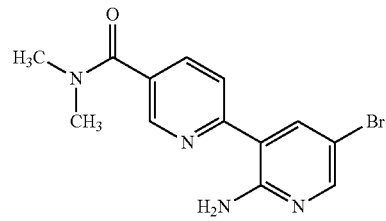 [SMILES: CN(C)C(=O)c1ccc(-c2cc(Br)cnc2N)nc1]

A solution of Br$_2$ (58 μl, 1.14 mmol) in AcOH (0.58 ml) was added dropwise to a solution of 6-(2-amino-3-pyridyl)-N,N-dimethyl-pyridine-3-carboxamde (250 mg, 1.0 mmol) in AcOH (3 ml) at rt and the resulting mixture was stirred for 4 h. Sat. aq. Na$_2$S$_2$O$_3$ (5 ml) was added followed by water (10 ml) and EtOAc (20 ml). The aqueous layer was separated, the pH adjusted to ~9 using aq. 2 M NaOH followed by extraction with EtOAc (2×30 ml). The combined organics were washed with brine, dried over MgSO$_4$, filtered and concentrated to give the product as a solid (228 mg, 69%). MS ES+m/z 321 [M+H]$^+$.

Step 3: 2'-amino-N,N-dimethyl-[2,3':5',4"-terpyridine]-5-carboxamide

The title compound was prepared as described in Example 16, starting from 6-(2-amino-5-bromo-3-pyridyl)-N,N-dimethyl-pyridine-3-carboxamide and 4-pyridylboronic acid, in 1,4-dioxane, water, EtOH (6:3:1) and heating in a microwave reactor at 130° C. for 1 h, to give the product as a solid (8 mg, 18%). $^1$H NMR (500 MHz, DMSO-d$_6$) δ ppm 3.03 (br d, J=11.98 Hz, 6H), 7.76-7.92 (m, 4H), 8.01 (dd, J=8.20, 1.58 Hz, 1H), 8.29 (d, J=8.51 Hz, 1H), 8.46-8.54 (m, 1H), 8.55-8.64 (m, 3H), 8.74 (s, 1H). MS ES+m/z 320 [M+H]$^+$.

Example 20: 2'-amino-N,N-dimethyl-5'-(quinolin-4-yl)-[2,3'-bipyridine]-5-carboxamide

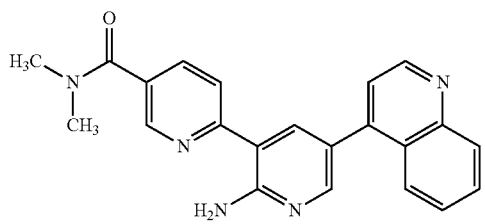 [SMILES: CN(C)C(=O)c1ccc(-c2cc(-c3ccnc4ccccc34)cnc2N)nc1]

The title compound was prepared as described in Example 16, starting from 6-(2-amino-5-bromo-3-pyridyl)-N,N-dimethyl-pyridine-3-carboxamide and quinoline-4-boronic acid, in DME and water, and heating in a microwave reactor at 130° C. for 1.5 h, to give the product as a solid (8 mg, 7%). $^1$H NMR (500 MHz, METHANOL-d$_4$) δ ppm 3.09 (s, 3H), 3.14 (s, 3H), 7.54 (d, J=4.41 Hz, 1H), 7.63 (m, J=7.60, 7.60 Hz, 1H), 7.81 (m, J=7.70, 7.70 Hz, 1H), 7.93-7.98 (m, 1H), 8.00-8.12 (m, 3H), 8.24-8.25 (m, 1H), 8.27-8.28 (m, 1H), 8.76 (d, J=1.58 Hz, 1H), 8.88 (d, J=4.41 Hz, 1H). MS ES+m/z 370 [M+H]$^+$.

Example 21: 2'-amino-N,N-dimethyl-5'-(1H-pyrrolo[2,3-b]pyridin-4-yl)-[2,3'-bipyridine]-5-carboxamide

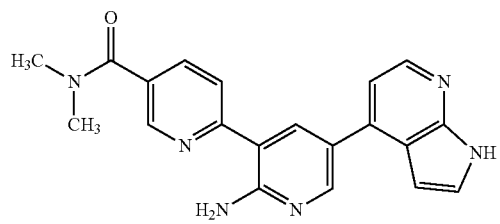 [SMILES: CN(C)C(=O)c1ccc(-c2cc(-c3ccnc4[nH]ccc34)cnc2N)nc1]

Step 1: Intermediate 14—2'-amino-N,N-dimethyl-5'-(1-(phenylsulfonyl)-1H-pyrrolo[2,3-b]pyridin-4-yl)-[2,3'-bipyridine]-5-carboxamide

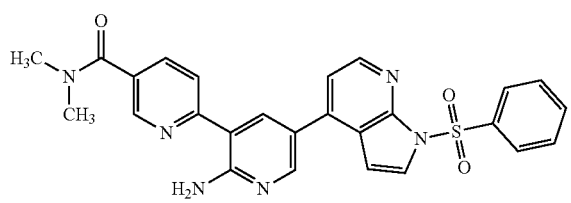 [SMILES: CN(C)C(=O)c1ccc(-c2cc(-c3ccnc4c3ccn4S(=O)(=O)c3ccccc3)cnc2N)nc1]

The title compound was prepared as described in Intermediate 12, starting from 6-(2-amino-5-bromo-3-pyridyl)-N,N-dimethyl-pyridine-3-carboxamide and 1-(benzenesulfonyl)-4-(4,4,5,5-tetramethyl-1,3,2-dioxaborolan-2-yl)pyrrolo[2,3-b]pyridine, to give the product as an oil (40 mg, 32%). MS ES+m/z 499 [M+H]+.

Step 2: 2'-amino-N,N-dimethyl-5'-(1H-pyrrolo[2,3-b]pyridin-4-yl)-[2,3'-bipyridine]-5-carboxamide A mixture of 6-[2-amino-5-[1-(benzenesulfonyl)pyrrolo[2,3-b]pyridin-4-yl]-3-pyridyl]-N,N-dimethyl-pyridine-3-carboxamide (40 mg, 0.08 mmol) and 5.6 M dimethyl amine EtOH (2 ml) was heated in a microwave reactor at 120° C. for 15 min. Water (1 ml) and LiOH monohydrate (10 mg, 0.24 mmol) was added and the mixture was stirred at 50° C. for 1 h. EtOAc (10 ml) and water (10 ml) were added and the organic layer separated. The aqueous layer was extracted with EtOAc (10 ml) and the combined organics were washed with brine, dried over MgSO4, filtered, concentrated and purified by preparative HPLC to give the product as a solid (5 mg, 17%). $^1$H NMR (500 MHz, METHANOL-d$_4$) δ ppm 3.10 (s, 3H), 3.15 (s, 3H), 6.71 (d, J=3.47 Hz, 1H), 7.26 (d, J=5.04 Hz, 1H), 7.46 (d, J=3.47 Hz, 1H), 7.99 (dd, J=8.20, 2.21 Hz, 1H), 8.07 (d, J=8.20 Hz, 1H), 8.24 (d, J=5.04 Hz, 1H), 8.45 (d, J=1.89 Hz, 1H), 8.50 (d, J=2.21 Hz, 1H), 8.76 (d, J=1.58 Hz, 1H). MS ES+m/z 359 [M+H]+.

Example 22: 1-(2'-amino-5'-bromo-[2,3'-bipyridin]-5-yl)pyrrolidin-2-one

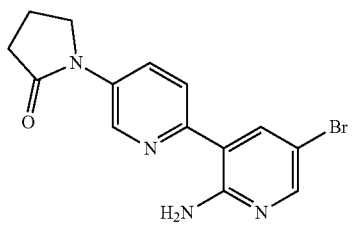 [SMILES: Nc1ncc(Br)cc1-c1ccc(N2CCCC2=O)cn1]

1-(6-Chloro-3-pyridyl)pyrrolidin-2-one (2.47 g, 12.5 mmol), 3-(4,4,5,5-tetramethyl-1,3,2-dioxaborolan-2-yl)pyridin-2-amine (3.87 g, 17.6 mmol), K$_2$CO$_3$ (3.47 g, 25.1 mmol) and Pd(dppf)Cl$_2$ (918 mg, 1.25 mmol) were taken up in n-BuOH (36 ml) and water (12 ml) and the mixture was stirred at 90° C. overnight. When cooled to rt the mixture was filtered through celite and washed with DCM. The filtrate was concentrated and the resulting residue was dissolved in DCM, washed with brine, dried over MgSO$_4$, filtered and concentrated. The resulting residue was dissolved in DCM (200 ml), cooled to 0° C. and a solution of Br$_2$ (645 uL, 12.5 mmol) was added slowly. The reaction mixture was stirred for 1 h and then basified to pH 9 using aq. 1M NaOH. Sat. aq. NaHCO$_3$(10 mL) and sat. aq. Na$_2$S$_2$O$_3$ (1 mL) were added and the organic layer separated, washed with brine, dried over MgSO$_4$, filtered concentrated and crystallized from DCM:pentane to give the product as a solid (1.29 g). The mother liquor was concentrated and purified on a silica gel column to give additional product (670 mg). The crops were combined to give the product as a solid (1.96 g, 47%). $^1$H NMR (500 MHz, DMSO-d$_6$) δ ppm 2.13 (quin, J=7.57 Hz, 2H), 2.53-2.57 (m, 2H), 3.93 (t, J=7.09 Hz, 2H), 7.59 (br s, 2H), 8.04-8.08 (m, 2H), 8.17 (d, J=2.21 Hz, 1H), 8.27 (dd, J=8.83, 2.84 Hz, 1H), 8.94 (d, J=2.52 Hz, 1H). MS ES+m/z 333 [M+H]+.

Example 23: 1-(2'-amino-5'-(thieno[2,3-b]pyridin-3-yl)-[2,3'-bipyridin]-5-yl)pyrrolidin-2-one

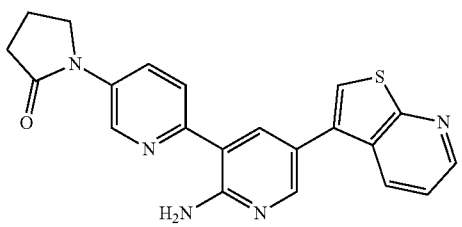 [SMILES: Nc1ncc(-c2csc3ncccc23)cc1-c1ccc(N2CCCC2=O)cn1]

Step 1: Intermediate 15—1-[6-[2-amino-5-(4,4,5,5-tetramethyl-1,3,2-dioxaborolan-2-yl)-3-pyridyl]-3-pyridyl]pyrrolidin-2-one

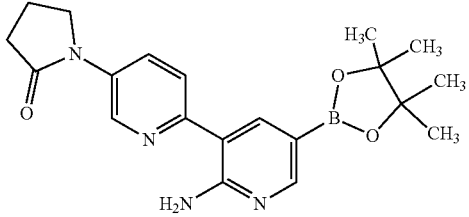 [SMILES: CC1(C)OB(c2cnc(N)c(-c3ccc(N4CCCC4=O)cn3)c2)OC1(C)C]

The title compound was prepared as described in Intermediate 2, starting from 1-[6-(2-amino-5-bromo-3-pyridyl)-3-pyridyl]pyrrolidin-2-one, replacing 1,4-dioxane for toluene and stirring the mixture at 110° C. overnight. Crystallization from 2-propanol/heptane gave the product as a solid (744 mg, 55%). MS ES+m/z 381 [M+H]+.

Step 2: 1-(2'-amino-5'-(thieno[2,3-b]pyridin-3-yl)-[2,3'-bipyridin]-5-yl)pyrrolidin-2-one 1-[6-[2-Amino-5-(4,4,5,5-tetramethyl-1,3,2-dioxaborolan-2-yl)-3-pyridyl]-3-pyridyl]pyrrolidin-2-one (146 mg, 0.38 mmol), 3-bromothieno[2,3-b]pyridine (82 mg, 0.38 mmol), $K_2CO_3$ (106 mg, 0.77 mmol) and $PdCl_2(dppf)$ (28 mg, 0.04 mmol) were taken up in n-BuOH (2 ml) and water (0.5 ml) and stirred at 90° C. for 1 h. When cooled to rt the mixture was filtered through celite and washed with DCM. The filtrate was evaporated and purified by preparative HPLC to give the product as a solid (9 mg, 6%). $^1$H NMR (500 MHz, DMSO-$d_6$) δ ppm 2.10-2.16 (m, 2H), 2.53-2.56 (m, 2H), 3.92 (q, J=7.25 Hz, 2H), 7.45-7.55 (m, 1H), 7.59 (br s, 2H), 7.98 (s, 1H), 8.12 (d, J=8.83 Hz, 1H), 8.21-8.24 (m, 1H), 8.24-8.28 (m, 1H), 8.28-8.37 (m, 2H), 8.63 (dd, J=4.57, 1.42 Hz, 1H), 8.95-8.96 (m, 1H). MS ES+m/z 388 [M+H]+.

Example 24: 1-(2'-amino-5'-(benzo[d]thiazol-7-yl)-[2,3'-bipyridin]-5-yl)pyrrolidin-2-one

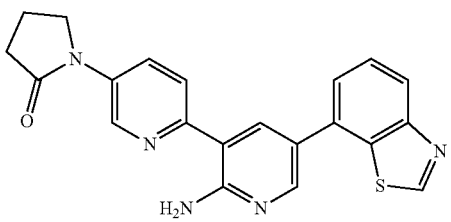 [SMILES: Nc1ncc(-c2cccc3ncsc23)cc1-c1ccc(N2CCCC2=O)cn1]

The title compound was prepared as described in Example 23, replacing 3-bromothieno[2,3-b]pyridine for 7-bromo-1,3-benzothiazole, to give the product as a solid (13 mg, 9%). $^1$H NMR (500 MHz, DMSO-$d_6$) δ ppm 2.07-2.16 (m, 2H), 2.52-2.59 (m, 2H), 3.89-3.98 (m, 2H), 7.56-7.76 (m, 2H), 8.03-8.12 (m, 2H), 8.23-8.29 (m, 1H), 8.32 (d, J=2.21 Hz, 1H), 8.40 (d, J=2.21 Hz, 1H), 8.92-8.99 (m, 1H), 9.45 (s, 1H). MS ES+m/z 388 [M+H]+.

Example 25:1-(2'-amino-5'-(imidazo[1,2-a]pyridin-5-yl)-[2,3'-bipyridin]-5-yl)pyrrolidin-2-one

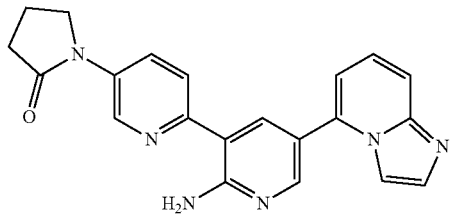 [SMILES: Nc1ncc(-c2cccc3nccn23)cc1-c1ccc(N2CCCC2=O)cn1]

The title compound was prepared as described in Example 23, replacing 3-bromothieno[2,3-b]pyridine for 5-bromo-imidazo[1,2-a]pyridine, to give the product as a solid (11 mg, 8%). $^1$H NMR (500 MHz, DMSO-$d_6$) δ ppm 2.12 (quin, J=7.57 Hz, 2H), 2.52-2.56 (m, 2H), 3.90-3.95 (m, 2H), 6.95 (dd, J=6.94, 0.95 Hz, 1H), 7.33 (dd, J=9.14, 6.94 Hz, 1H), 7.58 (d, J=8.94 Hz, 1H), 7.60 (s, 1H), 7.78-7.99 (m, 1H), 8.10 (d, J=8.83 Hz, 1H), 8.24 (dd, J=8.83, 2.84 Hz, 1H), 8.33-8.34 (m, 2H), 8.97 (d, J=2.21 Hz, 1H). MS ES+m/z 371 [M+H]+.

Example 26: 1-(2'-amino-5'-(5-chloro-1H-pyrrolo[2,3-b]pyridin-3-yl)-[2,3'-bipyridin]-5-yl)pyrrolidin-2-one

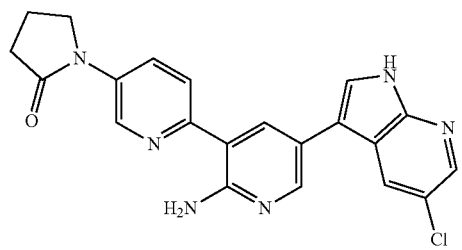 [SMILES: Nc1ncc(-c2c[nH]c3ncc(Cl)cc23)cc1-c1ccc(N2CCCC2=O)cn1]

The title compound was prepared as described in Example 23, replacing 3-bromothieno[2,3-b]pyridine for 3-bromo-5-chloro-1H-pyrrolo[2,3-b]pyridine and 1,4-dioxane instead of n-BuOH, to give the product as a solid (2 mg, 2%). $^1$H NMR (500 MHz, DMSO-$d_6$) δ ppm 2.13 (quin, J=7.57 Hz, 2H), 2.52-2.57 (m, 2H), 3.94 (t, J=7.09 Hz, 2H), 7.35 (br s, 2H), 7.96 (s, 1H), 8.15 (d, J=8.83 Hz, 1H), 8.21-8.31 (m, 4H), 8.38 (d, J=2.21 Hz, 1H), 8.94-8.96 (m, 1H), 12.08 (br s, 1H). MS ES+m/z 405 [M+H]+.

Example 27:1-(4-(5-(5-chloro-1H-pyrrolo[2,3-b]pyridin-3-yl)pyridin-3-yl)phenyl)pyrrolidin-2-one

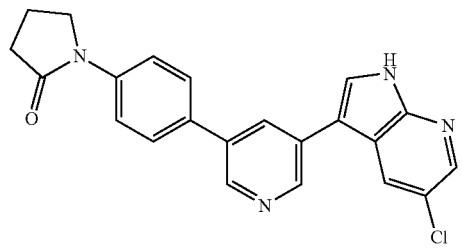 [SMILES: O=C1CCCN1c1ccc(-c2cncc(-c3c[nH]c4ncc(Cl)cc34)c2)cc1]

Step 1. Intermediate 16—1-[4-(5-Bromo-3-pyridyl)phenyl]pyrrolidin-2-one

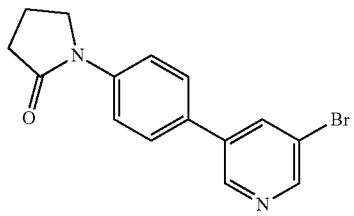 [SMILES: O=C1CCCN1c1ccc(-c2cncc(Br)c2)cc1]

A mixture of 1-[4-(4,4,5,5-tetramethyl-1,3,2-dioxaborolan-2-yl)phenyl]pyrrolidin-2-one (9.4 g, 32.7 mmol), 3,5-dibromopyridine (7.04 g, 29.7 mmol) and K$_2$CO$_3$ (10.7 g, 77.2 mmol) in n-BuOH (20 mL) and water (5 mL) was degassed with nitrogen for 5 min. PdCl$_2$(PPh$_3$)$_2$ (555 mg, 0.76 mmol) was added and the resulting mixture was stirred at 70° C. for 1 h. When cooled to rt the precipitate was filtered off and washed sequentially with water, 2-propanol and pentane and dried to give the product as a solid (9.96 g, quant.). MS ES+m/z 317 [M+H]$^+$.

Step 2: Intermediate 17—1-[4-[5-(4,4,5,5-Tetramethyl-1,3,2-dioxaborolan-2-yl)-3-pyridyl]phenyl]pyrrolidin-2-one

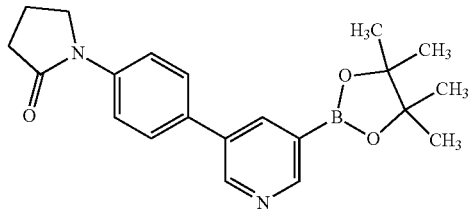 [SMILES: CC1(C)OB(c2cncc(-c3ccc(N4CCCC4=O)cc3)c2)OC1(C)C]

A mixture of 1-[4-(5-bromo-3-pyridyl)phenyl]pyrrolidin-2-one (9.42 g, 29.7 mmol), bis(pinacolato)diboron (9.05 g, 35.6 mmol) and KOAc (8.74 g, 89.1 mmol) were taken up in toluene (200 ml) and degassed with nitrogen for 10 min. PdCl$_2$(dppf) (1.09 g, 1.48 mmol) was added and the resulting mixture was stirred at 90° C. for 1 h. When cooled to rt EtOAc (25 ml) and celite (3 spoons) were added and the mixture filtered through celite. The celite was rinsed with EtOAc (2×10 ml) and the filtrate was washed with water (25 mL), sat. aq. NaHCO$_3$ (25 mL), brine, stirred with MgSO$_4$ and active charcoal (2 g), filtered through celite and concentrated. The residue was suspended in Et$_2$O (15 ml) and pentane (10 ml) was added. The resulting mixture was stirred at rt for 2 h and the precipitate was filtered off, washed sequentially with Et$_2$O/Pentane (1:1, 20 ml), pentane (10 ml) and dried to give the product as a solid (5.77 g, 53% yield). MS ES+m/z 365 [M+H]$^+$.

Step 3: 1-(4-(5-(5-chloro-1H-pyrrolo[2,3-b]pyridin-3-yl)pyridin-3-yl)phenyl)pyrrolidin-2-one The title compound was prepared as described in Example 23, replacing 3-bromothieno[2,3-b]pyridine for 3-bromo-5-chloro-1H-pyrrolo[2,3-b]pyridine, to give the product as a solid (2 mg, 2%). $^1$H NMR (500 MHz, DMSO-d$_6$) δ ppm 2.05-2.15 (m, 2H), 2.52-2.57 (m, 2H), 3.92 (t, J=7.09 Hz, 2H), 7.81-7.86 (m, 2H), 7.86-7.93 (m, 2H), 8.25 (s, 1H), 8.28-8.36 (m, 2H), 8.46 (d, J=2.21 Hz, 1H), 8.80 (d, J=2.21 Hz, 1H), 8.94 (d, J=1.89 Hz, 1H), 12.40 (br s, 1H). MS ES+m/z 389 [M+H]$^+$.

Example 28: 1-(4-(5-(1H-pyrrolo[2,3-b]pyridin-3-yl)pyridin-3-yl)phenyl)pyrrolidin-2-one

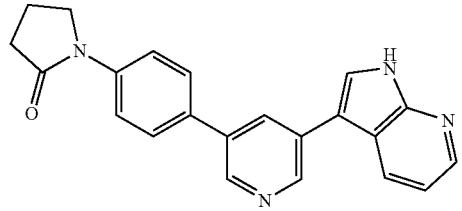 [SMILES: O=C1CCCN1c1ccc(-c2cncc(-c3c[nH]c4ncccc34)c2)cc1]

The title compound was prepared as described in Example 23, replacing 3-bromothieno[2,3-b]pyridine for 3-bromo-1H-pyrrolo[2,3-b]pyridine, to give the product as a solid (4 mg, 4%). $^1$H NMR (500 MHz, DMSO-d$_6$) δ ppm 2.08-2.13 (m, 2H), 2.51-2.56 (m, 2H), 3.90 (t, J=7.09 Hz, 2H), 7.20 (dd, J=8.04, 4.57 Hz, 1H), 7.80-7.84 (m, 2H), 7.84-7.89 (m, 2H), 8.14 (s, 1H), 8.29-8.33 (m, 2H), 8.39 (dd, J=8.04, 1.42 Hz, 1H), 8.77 (d, J=2.21 Hz, 1H), 8.94 (d, J=2.21 Hz, 1H), 12.11 (br s, 1H). MS ES+m/z 355 [M+H]$^+$.

Example 29: 1-(4-(5-(1H-pyrazolo[3,4-b]pyridin-4-yl)pyridin-3-yl)phenyl)pyrrolidin-2-one

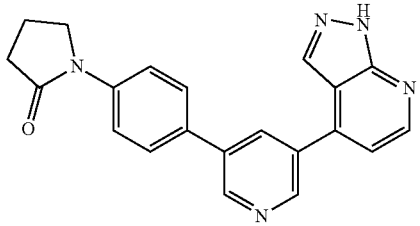 [SMILES: O=C1CCCN1c1ccc(-c2cncc(-c3ccnc4[nH]ncc34)c2)cc1]

The title compound was prepared as described in Example 23, replacing 3-bromothieno[2,3-b]pyridine for 4-chloro-1H-pyrazolo[3,4-b]pyridine, to give the product as a solid (3 mg, 2%). $^1$H NMR (500 MHz, DMSO-d$_6$) δ ppm 2.06-2.15 (m, 2H), 2.53-2.57 (m, 2H), 3.91 (t, J=7.09 Hz, 2H), 7.58 (d, J=4.73 Hz, 1H), 7.81-7.87 (m, 2H), 7.92-7.95 (m, 2H), 8.44 (s, 1H), 8.48 (t, J=2.21 Hz, 1H), 8.66 (d, J=4.73 Hz, 1H), 9.04 (d, J=2.21 Hz, 1H), 9.07 (d, J=2.21 Hz, 1H), 13.91 (br s, 1H). MS ES+m/z 356 [M+H]$^+$.

Example 30: 1-(4-(5-(7H-pyrrolo[2,3-d]pyrimidin-5-yl)pyridin-3-yl)phenyl)pyrrolidin-2-one

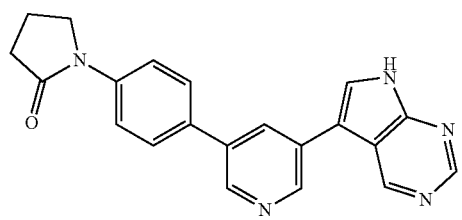 [SMILES: O=C1CCCN1c1ccc(-c2cncc(-c3c[nH]c4ncncc34)c2)cc1]

A mixture of 1-[4-[5-(4,4,5,5-tetramethyl-1,3,2-dioxaborolan-2-yl)-3-pyridyl]phenyl]pyrrolidin-2-one (150 mg, 0.41 mmol), 5-bromo-7H-pyrrolo[2,3-d]pyrimidine (90 mg, 0.45 mmol), K₂CO₃ (114 mg, 0.82 mmol) and PdCl₂(Amphos) (15 mg, 0.02 mmol) in 1,4-dioxane (1 ml) and water (0.3 ml) was stirred at 100° C. for 1 h. When cooled to rt the mixture was filtered through celite and rinsed with EtOAc. The filtrate was washed with brine, concentrated and purified by preparative HPLC to give the product as a solid (15 mg, 10%). ¹H NMR (500 MHz, DMSO-d₆) δ ppm 2.10 (quin, J=7.49 Hz, 2H), 2.51-2.56 (m, 2H), 3.90 (t, J=7.09 Hz, 2H), 7.80-7.85 (m, 2H), 7.87-7.91 (m, 2H), 8.25 (s, 1H), 8.39 (t, J=2.21 Hz, 1H), 8.81 (d, J=2.21 Hz, 1H), 8.85 (s, 1H), 9.00 (d, J=2.21 Hz, 1H), 9.45 (s, 1H). MS ES+m/z 356 [M+H]⁺.

Example 31: 1-(4-(5-(5-methyl-1H-pyrrolo[2,3-b]pyridin-3-yl)pyridin-3-yl)phenyl)pyrrolidin-2-one

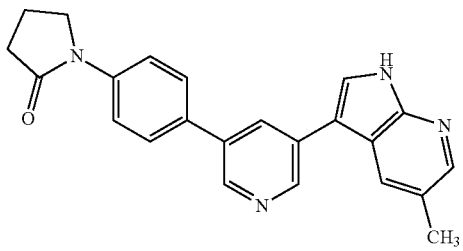 [SMILES: Cc1cnc2[nH]cc(-c3cncc(-c4ccc(N5CCCC5=O)cc4)c3)c2c1]

The title compound was prepared as described in Example 30, replacing 5-bromo-7H-pyrrolo[2,3-d]pyrimidine for 3-bromo-5-methyl-1H-pyrrolo[2,3-b]pyridine, to give the product as a solid (16 mg, 11%). ¹H NMR (500 MHz, DMSO-d₆) δ ppm 2.05-2.14 (m, 2H), 2.44 (s, 3H), 2.51-2.56 (m, 2H), 3.90 (t, J=7.09 Hz, 2H), 7.80-7.86 (m, 2H), 7.86-7.88 (m, 2H), 8.08 (s, 1H), 8.15 (d, J=1.58 Hz, 1H), 8.18 (s, 1H), 8.29 (t, J=2.21 Hz, 1H), 8.75 (d, J=2.21 Hz, 1H), 8.93 (d, J=2.21 Hz, 1H). MS ES+m/z 369 [M+H]⁺.

Example 32: 1-(4-(5-(1H-pyrazolo[4,3-b]pyridin-7-yl)pyridin-3-yl)phenyl)pyrrolidin-2-one

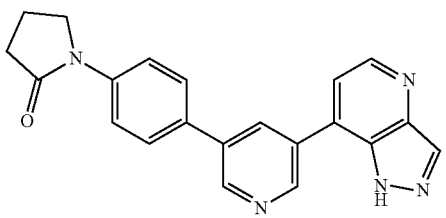 [SMILES: O=C1CCCN1c1ccc(-c2cncc(-c3ccnc4cn[nH]c34)c2)cc1]

The title compound was prepared as described in Example 30, replacing 5-bromo-7H-pyrrolo[2,3-d]pyrimidine for 7-bromo-1H-pyrazolo[4,3-b]pyridine, to give the product as a solid (19 mg, 13%). ¹H NMR (500 MHz, DMSO-d₆) δ ppm 2.10 (quin, J=7.57 Hz, 2H), 2.52-2.58 (m, 2H), 3.91 (t, J=7.09 Hz, 2H), 7.66 (d, J=4.41 Hz, 1H), 7.82-7.86 (m, 2H), 7.93-7.97 (m, 2H), 8.46 (s, 1H), 8.48 (br s, 1H), 8.65 (d, J=4.41 Hz, 1H), 8.99 (s, 1H), 9.06 (d, J=2.21 Hz, 1H). MS ES+m/z 356 [M+H]⁺.

Example 33: 1'-methyl-5-(4-(2-oxopyrrolidin-1-yl)phenyl)-[3,4'-bipyridin]-2'(1'H)-one

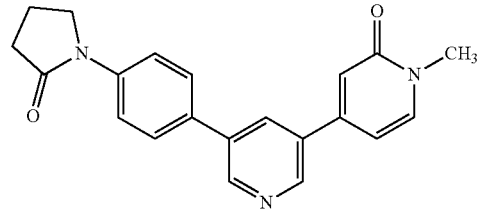 [SMILES: Cn1ccc(-c2cncc(-c3ccc(N4CCCC4=O)cc3)c2)cc1=O]

The title compound was prepared as described in Example 30, replacing 5-bromo-7H-pyrrolo[2,3-d]pyrimidine for 4-chloro-1-methyl-pyridin-2-one, to give the product as a solid (64 mg, 45%). ¹H NMR (500 MHz, DMSO-d₆) δ ppm 2.09 (quin, J=7.57 Hz, 2H), 2.51-2.55 (m, 2H), 3.45-3.52 (m, 3H), 3.89 (t, J=7.09 Hz, 2H), 6.76 (dd, J=6.94, 2.21 Hz, 1H), 6.91 (d, J=1.89 Hz, 1H), 7.79-7.84 (m, 3H), 7.87-7.90 (m, 2H), 8.33-8.34 (m, 1H), 8.87 (d, J=2.21 Hz, 1H), 8.96 (d, J=2.21 Hz, 1H). MS ES+m/z 346 [M+H]⁺.

Example 34: 1-(4-(5-(5-methoxy-1H-pyrrolo[2,3-b]pyridin-4-yl)pyridin-3-yl)phenyl)pyrrolidin-2-one

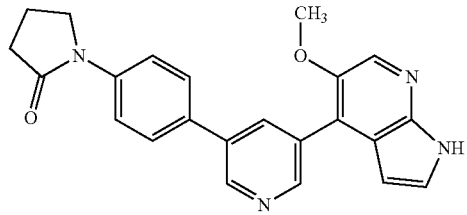 [SMILES: COc1cnc2[nH]ccc2c1-c1cncc(-c2ccc(N3CCCC3=O)cc2)c1]

The title compound was prepared as described in Example 30, replacing 5-bromo-7H-pyrrolo[2,3-d]pyrimidine for 4-chloro-5-methoxy-1H-pyrrolo[2,3-b]pyridine, to give the product as a solid (28 mg, 17%). ¹H NMR (500 MHz, CHLOROFORM-d) δ ppm 2.22 (s, 2H), 2.67 (t, J=8.20 Hz, 2H), 3.90-3.95 (m, 5H), 6.47 (dd, J=3.47, 2.21 Hz, 1H), 7.37-7.39 (m, 1H), 7.68 (m, J=8.83 Hz, 2H), 7.78 (m, J=8.83 Hz, 2H), 8.19 (t, J=2.05 Hz, 1H), 8.25 (s, 1H), 8.88 (d, J=2.21 Hz, 3H). MS ES+m/z 385 [M+H]⁺.

Example 35: 1-(4-(5-(5-methyl-1H-pyrrolo[2,3-b]pyridin-4-yl)pyridin-3-yl)phenyl)pyrrolidin-2-one

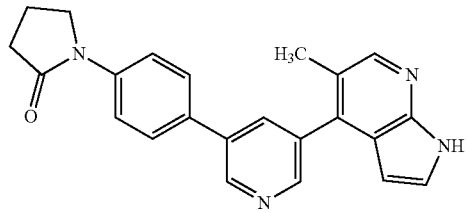 [SMILES: Cc1cnc2[nH]ccc2c1-c1cncc(-c2ccc(N3CCCC3=O)cc2)c1]

The title compound was prepared as described in Example 30, replacing 5-bromo-7H-pyrrolo[2,3-d]pyrimidine for 4-chloro-5-methyl-1H-pyrrolo[2,3-b]pyridine, to give the product as a solid (6 mg, 4%). ¹H NMR (500 MHz, CHLOROFORM-d) δ ppm 2.22 (t, J=7.57 Hz, 2H), 2.39 (s, 3H), 2.67 (t, J=8.20 Hz, 2H), 3.94 (t, J=6.94 Hz, 2H), 6.30 (d, J=3.47 Hz, 1H), 7.27-7.32 (m, 1H), 7.61-7.71 (m, 2H), 7.77-7.81 (m, 2H), 7.96 (t, J=2.21 Hz, 1H), 8.31 (s, 1H), 8.68 (d, J=1.89 Hz, 1H), 8.92 (d, J=2.21 Hz, 2H). MS ES+m/z 369 [M+H]+.

Example 36: 5'-(4-(2-oxopyrrolidin-1-yl)phenyl)-[3, 3'-bipyridin]-6(1H)-one

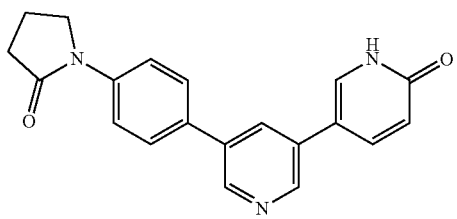 [SMILES: O=C1CCCN1c1ccc(-c2cncc(-c3ccc(=O)[nH]c3)c2)cc1]

The title compound was prepared as described in Example 30, replacing 5-bromo-7H-pyrrolo[2,3-d]pyrimidine for 5-bromo-1H-pyridin-2-one, to give the product as a solid (6 mg, 2%). $^1$H NMR (500 MHz, DMSO-d$_6$) δ ppm 2.03-2.16 (m, 2H), 2.51-2.55 (m, 2H), 3.17 (s, 1H), 3.89 (t, J=7.09 Hz, 2H), 6.47 (d, J=9.46 Hz, 1H), 7.68-7.83 (m, 2H), 7.83-7.89 (m, 2H), 7.92-8.06 (m, 2H), 8.22 (t, J=2.21 Hz, 1H), 8.76 (d, J=1.89 Hz, 1H), 8.80 (d, J=2.21 Hz, 1H). MS ES+m/z 332 [M+H]+.

Example 37: 1-methyl-5'-(4-(2-oxopyrrolidin-1-yl)phenyl)-[3,3'-bipyridin]-6(1H)-one

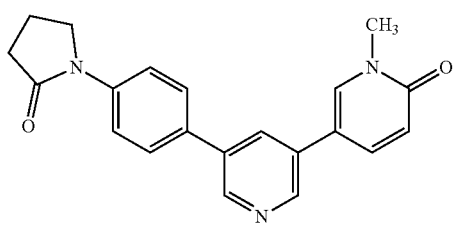 [SMILES: Cn1cc(-c2cncc(-c3ccc(N4CCCC4=O)cc3)c2)ccc1=O]

The title compound was prepared as described in Example 30, replacing 5-bromo-7H-pyrrolo[2,3-d]pyrimidine for 5-bromo-1-methyl-pyridin-2-one, to give the product as a solid (48 mg, 51%). $^1$H NMR (500 MHz, DMSO-d$_6$) δ ppm 2.09 (quin, J=7.57 Hz, 2H), 2.51-2.56 (m, 2H), 3.53 (s, 3H), 3.89 (t, J=7.09 Hz, 2H), 6.53 (d, J=9.46 Hz, 1H), 7.79-7.82 (m, 2H), 7.82-7.86 (m, 2H), 8.01 (dd, J=9.46, 2.84 Hz, 1H), 8.23 (t, J=2.21 Hz, 1H), 8.35 (d, J=2.52 Hz, 1H), 8.77 (d, J=2.21 Hz, 1H), 8.81 (d, J=2.21 Hz, 1H). MS ES+m/z 346 [M+H]+.

Example 38: 1-(4-(5-(6-methyl-1H-pyrazolo[3,4-d]pyrimidin-4-yl)pyridin-3-yl)phenyl)pyrrolidin-2-one

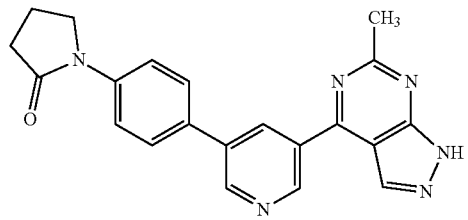 [SMILES: Cc1nc(-c2cncc(-c3ccc(N4CCCC4=O)cc3)c2)c2cn[nH]c2n1]

The title compound was prepared as described in Example 30, replacing 5-bromo-7H-pyrrolo[2,3-d]pyrimidine for 4-chloro-6-methyl-1H-pyrazolo[3,4-d]pyrimidine, to give the product as a solid (7 mg, 7%). $^1$H NMR (500 MHz, DMSO-d$_6$) δ ppm 2.06-2.15 (m, 2H), 2.51-2.57 (m, 2H), 2.80 (s, 3H), 3.91 (t, J=6.94 Hz, 2H), 7.84-7.87 (m, 2H), 7.89-7.92 (m, 2H), 8.72 (s, 1H), 8.74 (t, J=2.21 Hz, 1H), 9.13 (d, J=2.21 Hz, 1H), 9.36 (d, J=2.21 Hz, 1H). MS ES+m/z 371 [M+H]+.

Example 39: 1-(4-(5-(1-methyl-1H-pyrrolo[2,3-b]pyridin-3-yl)pyridin-3-yl)phenyl)pyrrolidin-2-one

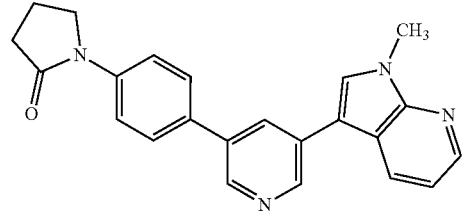 [SMILES: Cn1cc(-c2cncc(-c3ccc(N4CCCC4=O)cc3)c2)c2cccnc21]

The title compound was prepared as described in Example 30, replacing 5-bromo-7H-pyrrolo[2,3-d]pyrimidine for 3-bromo-1-methyl-pyrrolo[2,3-b]pyridine, to give the product as a solid (40 mg, 46%). $^1$H NMR (500 MHz, CHLOROFORM-d) δ ppm 2.16-2.30 (m, 2H), 2.67 (s, 2H), 3.95 (s, 2H), 4.01 (s, 3H), 7.16-7.23 (m, 1H), 7.52 (s, 1H), 7.66-7.70 (m, 2H), 7.78-7.81 (m, 2H), 8.08 (s, 1H), 8.18-8.27 (m, 1H), 8.41-8.47 (m, 1H), 8.75 (d, J=2.21 Hz, 1H), 8.87 (d, J=2.21 Hz, 1H). MS ES+m/z 369 [M+H]+.

Example 40: 1-[4-[5-(2,3-Dihydro-[1,4]dioxino[2,3-b]pyridin-8-yl)-3-pyridyl]phenyl]pyrrolidin-2-one

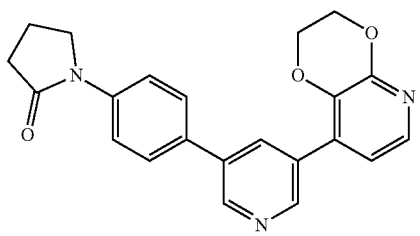 [SMILES: O=C1CCCN1c1ccc(-c2cncc(-c3ccnc4c3OCCO4)c2)cc1]

The title compound was prepared as described in Example 30, replacing 5-bromo-7H-pyrrolo[2,3-d]pyrimidine for 8-iodo-2,3-dihydro-[1,4]dioxino[2,3-b]pyridine, to give the product as a solid (59 mg, 58%). $^{1}$H NMR (500 MHz, DMSO-d$_{6}$) δ ppm 2.10 (quin, J=7.65 Hz, 2H), 2.52-2.58 (m, 2H), 3.89 (t, J=6.94 Hz, 2H), 4.31 (dd, J=4.89, 2.99 Hz, 2H), 4.40-4.54 (m, 2H), 7.21 (d, J=5.04 Hz, 1H), 7.82 (s, 4H), 7.85 (d, J=5.04 Hz, 1H), 8.25 (t, J=2.21 Hz, 1H), 8.77 (d, J=1.89 Hz, 1H), 8.92 (d, J=2.21 Hz, 1H). MS ES+m/z 374 [M+H]$^{+}$.

Example 41: 1-[4-[5-(4-Pyridyl)-3-pyridyl]phenyl]pyrrolidin-2-one

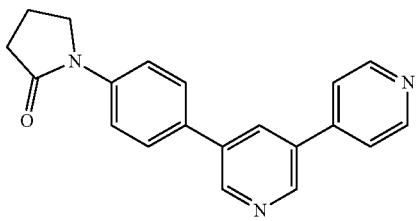 [SMILES: O=C1CCCN1c1ccc(-c2cncc(-c3ccncc3)c2)cc1]

The title compound was prepared as described in Example 30, replacing 5-bromo-7H-pyrrolo[2,3-d]pyrimidine for 4-bromopyridine hydrochloride, to give the product as a solid (30 mg, 34%). $^{1}$H NMR (500 MHz, DMSO-d$_{6}$) δ ppm 2.10 (quin, J=7.57 Hz, 2H), 2.51-2.58 (m, 2H), 3.91 (t, J=6.94 Hz, 2H), 7.81-7.84 (m, 2H), 7.89-7.93 (m, 4H), 8.45 (t, J=2.21 Hz, 1H), 8.69-8.72 (m, 2H), 8.99 (dd, J=8.83, 2.21 Hz, 2H). MS ES+m/z 316 [M+H]$^{+}$.

Example 42: 4-(5-(4-(2-oxopyrrolidin-1-yl)phenyl)pyridin-3-yl)-1,3-dihydro-2H-pyrrolo[2,3-b]pyridin-2-one

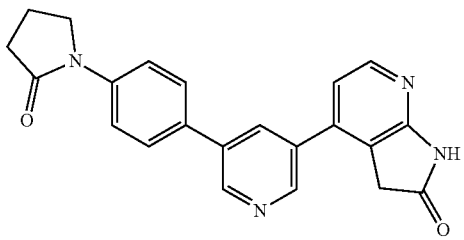 [SMILES: O=C1Cc2c(-c3cncc(-c4ccc(N5CCCC5=O)cc4)c3)ccnc2N1]

The title compound was prepared as described in Example 30, replacing 5-bromo-7H-pyrrolo[2,3-d]pyrimidine for 4-bromo-1,3-dihydropyrrolo[2,3-b]pyridin-2-one, to give the product as a solid (12 mg, 12%). $^{1}$H NMR (500 MHz, DMSO-d$_{6}$) δ ppm 2.10 (quin, J=7.49 Hz, 2H) 2.52-2.59 (m, 2H) 3.82-3.96 (m, 4H) 7.27 (d, J=5.67 Hz, 1H) 7.80-7.97 (m, 4H) 8.19 (d, J=5.67 Hz, 1H) 8.32 (s, 1H) 8.85 (s, 1H) 8.98-9.05 (m, 1H) 11.14 (s, 1H). MS ES+m/z 371 [M+H]$^{+}$.

Example 43: 1-(4-(5-(2-methyl-2H-pyrazolo[3,4-b]pyridin-4-yl)pyridin-3-yl)phenyl)pyrrolidin-2-one

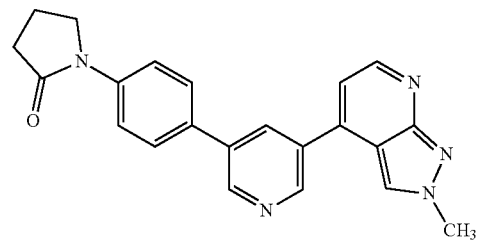 [SMILES: Cn1cc2c(-c3cncc(-c4ccc(N5CCCC5=O)cc4)c3)ccnc2n1]

The title compound was prepared as described in Example 30, replacing 5-bromo-7H-pyrrolo[2,3-d]pyrimidine for 4-chloro-2-methyl-pyrazolo[3,4-b]pyridine, to give the product as a solid (38 mg, 38%). $^{1}$H NMR (500 MHz, DMSO-d$_{6}$) δ ppm 2.08-2.14 (m, 2H), 2.53-2.59 (m, 2H), 3.91 (t, J=7.09 Hz, 2H), 4.14 (s, 3H), 7.62 (d, J=4.73 Hz, 1H), 7.83-7.86 (m, 2H), 7.91-7.95 (m, 2H), 8.45 (s, 1H), 8.47 (t, J=2.21 Hz, 1H), 8.70 (d, J=4.73 Hz, 1H), 9.04 (d, J=2.21 Hz, 1H), 9.06-9.09 (m, 1H). MS ES+m/z 370 [M+H]$^{+}$.

Example 44: 1-(4-(5-(1-(2-hydroxyethyl)-1H-pyrazolo[3,4-b]pyridin-4-yl)pyridin-3-yl)phenyl)pyrrolidin-2-one

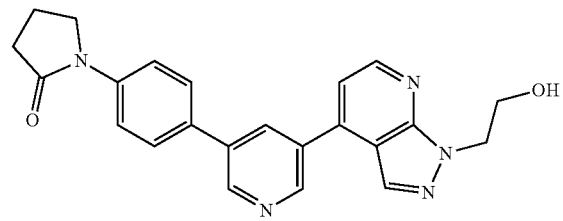 [SMILES: O=C1CCCN1c1ccc(-c2cncc(-c3ccnc4c3cnn4CCO)c2)cc1]

Step 1: Intermediate 18—2-(4-Chloropyrazolo[3,4-b]pyridin-1-yl)ethanol

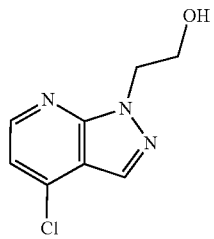 [SMILES: OCCn1ncc2c(Cl)ccnc21]

4-Chloro-1H-pyrazolo[3,4-b]pyridine (500 mg, 3.26 mmol), 2-bromoethan-1-ol (462 μl, 6.51 mmol) and K$_{2}$CO$_{3}$ (1.35 g, 9.77 mmol) were taken up in DMF (5 ml) and the resulting mixture was stirred at 80° C. for 2 h. When cooled to rt water (20 ml) and EtOAc (5 ml) were added and the organic layer separated. The aqueous layer was extracted with EtOAc (2×5 ml) and the combined organics were washed with brine, dried over Na$_{2}$SO$_{4}$, filtered and concentrated to give the product as a solid (540 mg, 84%). MS ES+m/z 198 [M+H]$^{+}$.

Step 2: 1-(4-(5-(1-(2-hydroxyethyl)-1H-pyrazolo[3,4-b]pyridin-4-yl)pyridin-3-yl)phenyl)pyrrolidin-2-one The title compound was prepared as described in Example 30, replacing 5-bromo-7H-pyrrolo[2,3-d]pyrimidine for 2-(4-chloropyrazolo[3,4-b]pyridin-1-yl)ethanol, to give the product as a solid (49 mg, 45%). $^1$H NMR (500 MHz, DMSO-$d_6$) δ ppm 2.06-2.13 (m, 2H), 2.51-2.56 (m, 2H), 3.87-3.93 (m, 4H), 4.58 (t, J=5.99 Hz, 2H), 4.89 (br s, 1H), 7.60 (d, J=4.73 Hz, 1H), 7.80-7.86 (m, 2H), 7.90-7.94 (m, 2H), 8.43-8.46 (m, 1H), 8.46-8.47 (m, 1H), 8.67 (d, J=4.73 Hz, 1H), 9.03 (d, J=2.21 Hz, 1H), 9.06 (d, J=2.21 Hz, 1H). MS ES+m/z 400 [M+H]$^+$.

Example 45: 4-(5-(4-(2-oxopyrrolidin-1-yl)phenyl)pyridin-3-yl)-8,9-dihydropyrido[3',2':4,5]pyrrolo[1,2-a]pyrazin-6(7H)-one

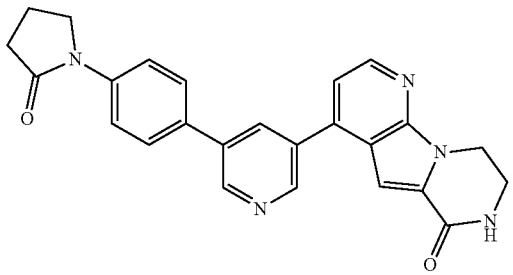 [SMILES: O=C1NCCn2c1cc1c(-c3cncc(-c4ccc(N5CCCC5=O)cc4)c3)ccnc12]

Step 1: Intermediate 19—Methyl 1-[2-(tert-butoxycarbonylamino)ethyl]-4-chloro-pyrrolo[2,3-b]pyridine-2-carboxylate

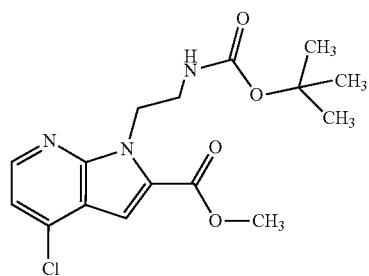 [SMILES: COC(=O)c1cc2c(Cl)ccnc2n1CCNC(=O)OC(C)(C)C]

Methyl 4-chloro-1H-pyrrolo[2,3-b]pyridine-2-carboxylate (2 g, 9.50 mmol) was taken up in DMF (30 ml), cooled to 0° C. and KOtBu (1.1 g, 9.80 mmol) was added. After 30 min tert-butyl 2,2-dioxooxathiazolidine-3-carboxylate (2.3 g, 10.3 mmol) was added, the cooling bath removed, and the mixture stirred at rt for 1.5 h. Aq. 10% citric acid (50 ml) and EtOAc (30 ml) were added and the organic layer separated. The aqueous layer was extracted with EtOAc (3×15 ml) and the combined organics were washed with water (3×20 ml), brine (20 ml), dried over Na$_2$SO$_4$, filtered and concentrated to give the product as a gum, which solidified upon standing (2.9 g, 86%). MS ES+m/z 354 [M+H]$^+$.

Step 2: Intermediate 20—4-Chloro-8,9-dihydro-7H-pyrido[3,4]pyrrolo[3,5-b]pyrazin-6-one

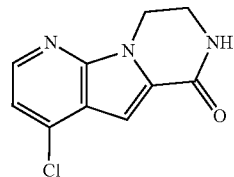 [SMILES: O=C1NCCn2c1cc1c(Cl)ccnc12]

TFA (6 ml, 80.8 mmol) was added to a solution of methyl 1-[2-(tert-butoxycarbonylamino)ethyl]-4-chloro-pyrrolo[2,3-b]pyridine-2-carboxylate (2.9 g, 8.20 mmol) in DCM (20 ml) at rt and the mixture was stirred at rt overnight. The mixture was concentrated and the resulting residue was taken up in MeOH (20 ml). K$_2$CO$_3$ (4.5 g, 32.6 mmol) was added portion wise and the mixture was stirred at rt for 3 h. Water (20 ml) and EtOAc (30 ml) were added and the organic layer separated. The aqueous layer was extracted with EtOAc (2×10 ml) and the combined organics were washed with brine, dried over Na$_2$SO$_4$, filtered and concentrated. Recrystallization from 2-propanol (10 ml) and water (5 ml) gave the product as a solid (1.05 g, 58%). MS ES+m/z 222 [M+H]$^+$.

Step 3: 4-(5-(4-(2-oxopyrrolidin-1-yl)phenyl)pyridin-3-yl)-8,9-dihydropyrido[3',2':4,5]pyrrolo[1,2-a]pyrazin-6(7H)-one The title compound was prepared as described in Example 30, replacing 5-bromo-7H-pyrrolo[2,3-d]pyrimidine for 4-chloro-8,9-dihydro-7H-pyrido[3,4]pyrrolo[3,5-b]pyrazin-6-one, to give the product as a solid (19 mg, 11%). $^1$H NMR (500 MHz, DMSO-$d_6$) δ ppm 2.06-2.13 (m, 2H), 2.51-2.58 (m, 2H), 3.66-3.73 (m, 2H), 3.87-3.93 (m, 2H), 4.39-4.45 (m, 2H), 7.16 (s, 1H), 7.53 (d, J=4.73 Hz, 1H), 7.81-7.86 (m, 2H), 7.86-7.91 (m, 2H), 8.33 (br s, 1H), 8.39 (t, J=2.05 Hz, 1H), 8.56 (d, J=4.73 Hz, 1H), 8.94 (d, J=1.89 Hz, 1H), 9.03 (d, J=2.21 Hz, 1H). MS ES+m/z 424 [M+H]$^+$.

Example 46: 7-methyl-4-(5-(4-(2-oxopyrrolidin-1-yl)phenyl)pyridin-3-yl)-8,9-dihydropyrido[3',2':4,5]pyrrolo[1,2-a]pyrazin-6(7H)-one

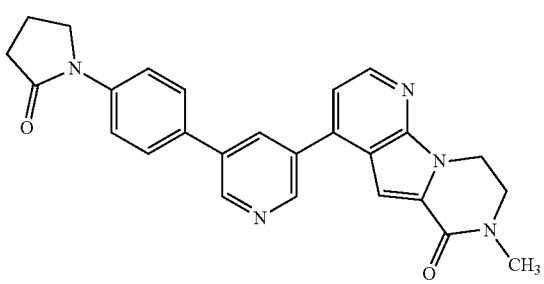 [SMILES: CN1CCn2c(cc3c(-c4cncc(-c5ccc(N6CCCC6=O)cc5)c4)ccnc32)C1=O]

Step 1: Intermediate 21—4-Chloro-7-methyl-8,9-dihydropyrido[3,4]pyrrolo[3,5-b]pyrazin-6-one

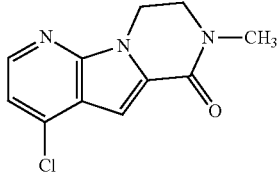 [SMILES: CN1CCn2c(cc3c(Cl)ccnc32)C1=O]

60% NaH in mineral oil (69 mg, 1.8 mmol) was added to a solution of 4-chloro-8,9-dihydro-7H-pyrido[3,4]pyrrolo[3,5-b]pyrazin-6-one (100 mg, 0.45 mmol) in THF (2 ml) at rt. After 10 min, iodomethane (31 µl, 0.5 mmol) was added and the resulting mixture was stirred at rt overnight. Sat. aq. NH$_4$Cl was added and the mixture extracted with EtOAc. The combined organics were dried over MgSO$_4$, filtered and concentrated to give the product as a solid (108 mg, quant.). MS ES+m/z 236 [M+H]$^+$.

Step 2: 7-methyl-4-(5-(4-(2-oxopyrrolidin-1-yl)phenyl)pyridin-3-yl)-8,9-dihydropyrido[3',2':4,5]pyrrolo[1,2-a]pyrazin-6(7H)-one The title compound was prepared as described in Example 30, replacing 5-bromo-7H-pyrrolo[2,3-d]pyrimidine for 4-chloro-7-methyl-8,9-dihydropyrido[3,4]pyrrolo[3,5-b]pyrazin-6-one, to give the product as a solid (52 mg, 29%). $^1$H NMR (500 MHz, DMSO-d$_6$) δ ppm 2.05-2.13 (m, 2H), 2.51-2.56 (m, 2H), 3.07-3.11 (m, 3H), 3.83-3.93 (m, 4H), 4.42-4.51 (m, 2H), 7.14 (s, 1H), 7.52 (d, J=4.73 Hz, 1H), 7.78-7.86 (m, 2H), 7.86-7.93 (m, 2H), 8.36-8.40 (m, 1H), 8.55 (d, J=5.04 Hz, 1H), 8.94 (d, J=2.21 Hz, 1H), 8.95-9.11 (m, 1H). MS ES+m/z 438 [M+H]$^+$.

Example 47: 7-(cyclopropylmethyl)-4-(5-(4-(2-oxopyrrolidin-1-yl)phenyl)pyridin-3-yl)-8,9-dihydropyrido[3',2':4,5]pyrrolo[1,2-a]pyrazin-6(7H)-one

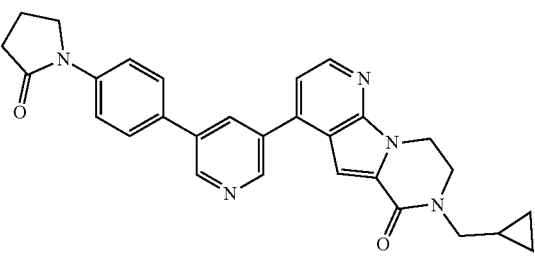 [SMILES: O=C1c2cc3c(-c4cncc(-c5ccc(N6CCCC6=O)cc5)c4)ccnc3n2CCN1CC1CC1]

Step 1: Intermediate 22—4-Chloro-7-(cyclopropylmethyl)-8,9-dihydropyrido[3,4]pyrrolo[3,5-b]pyrazin-6-one

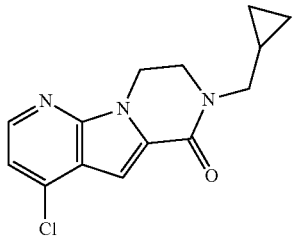 [SMILES: O=C1c2cc3c(Cl)ccnc3n2CCN1CC1CC1]

The title compound was prepared as described for Intermediate 21, replacing iodomethane for bromomethyl cyclopropane, using 4 eq. of NaH and refluxing the mixture over weekend, to give the product (138 mg, quant.). MS ES+m/z 276 [M+H]$^+$.

Step 2: 7-(cyclopropylmethyl)-4-(5-(4-(2-oxopyrrolidin-1-yl)phenyl)pyridin-3-yl)-8,9-dihydropyrido[3',2':4,5]pyrrolo[1,2-a]pyrazin-6(7H)-one The title compound was prepared as described in Example 30, replacing 5-bromo-7H-pyrrolo[2,3-d]pyrimidine for 4-chloro-7-(cyclopropylmethyl)-8,9-dihydropyrido[3,4]pyrrolo[3,5-b]pyrazin-6-one, to give the product as a solid (18 mg, 14%). $^1$H NMR (500 MHz, DMSO-d$_6$) δ ppm 0.30-0.36 (m, 2H), 0.47-0.54 (m, 2H), 1.05-1.16 (m, 1H), 2.07-2.13 (m, 2H), 2.51-2.58 (m, 2H), 3.44 (d, J=6.94 Hz, 2H), 3.90 (t, J=7.09 Hz, 2H), 3.93-3.98 (m, 2H), 4.46-4.54 (m, 2H), 7.16 (s, 1H), 7.54 (d, J=4.73 Hz, 1H), 7.82-7.87 (m, 2H), 7.87-7.92 (m, 2H), 8.40 (t, J=2.21 Hz, 1H), 8.56 (d, J=4.73 Hz, 1H), 8.95 (d, J=2.21 Hz, 1H), 9.04 (d, J=2.21 Hz, 1H). MS ES+m/z 478 [M+H]$^+$.

Example 48: 1-(4-(5-(5-(1-hydroxyethyl)-1H-pyrrolo[2,3-b]pyridin-3-yl)pyridin-3-yl)phenyl)pyrrolidin-2-one

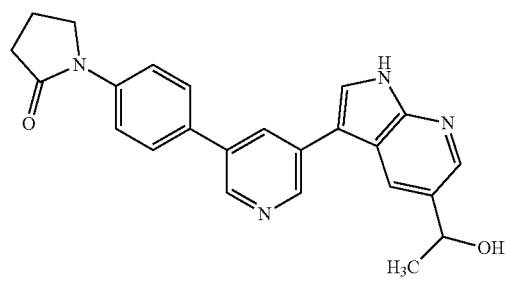 [SMILES: CC(O)c1cnc2[nH]cc(-c3cncc(-c4ccc(N5CCCC5=O)cc4)c3)c2c1]

The title compound was prepared as described in Example 30, replacing 5-bromo-7H-pyrrolo[2,3-d]pyrimidine for 1-(3-bromo-1H-pyrrolo[2,3-b]pyridin-5-yl)ethanol, to give the product as a solid (9 mg, 6%). $^1$H NMR (500 MHz, DMSO-d$_6$) δ ppm 1.44 (d, J=6.31 Hz, 3H), 2.06-2.14 (m, 2H), 2.52-2.58 (m, 2H), 3.91 (t, J=7.09 Hz, 2H), 4.91-4.97 (m, 1H), 5.22 (d, J=4.41 Hz, 1H), 7.81-7.84 (m, 2H), 7.84-7.88 (m, 2H), 8.12 (s, 1H), 8.27-8.30 (m, 2H), 8.30-8.32 (m, 1H), 8.77 (d, J=2.21 Hz, 1H), 8.94 (d, J=2.21 Hz, 1H), 12.01 (br s, 1H). MS ES+m/z 399 [M+H]$^+$.

Example 49: N-methyl-4-(5-(4-(2-oxopyrrolidin-1-yl)phenyl)pyridin-3-yl)furo[2,3-b]pyridine-2-carboxamide

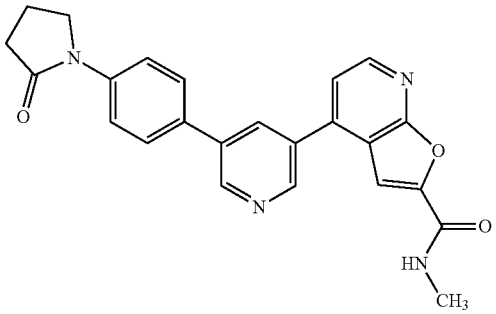

The title compound was prepared as described in Example 30, replacing 5-bromo-7H-pyrrolo[2,3-d]pyrimidine for 4-chloro-N-methyl-furo[2,3-b]pyridine-2-carboxamide, to give the product as a solid (4 mg, 5%). $^1$H NMR (500 MHz, CHLOROFORM-d) δ ppm 2.23 (t, J=7.57 Hz, 2H), 2.64-2.69 (m, 2H), 3.08 (d, J=5.04 Hz, 3H), 3.94 (t, J=7.09 Hz, 2H), 6.71-6.83 (m, 1H), 7.48 (d, J=5.04 Hz, 1H), 7.65-7.68 (m, 3H), 7.80-7.83 (m, 2H), 8.12 (t, J=2.21 Hz, 1H), 8.55 (d, J=5.04 Hz, 1H), 8.89 (d, J=2.21 Hz, 1H), 8.96 (d, J=2.21 Hz, 1H). MS ES+m/z 413 [M+H]$^+$.

Example 50: N,N-dimethyl-4-(5-(4-(2-oxopyrrolidin-1-yl)phenyl)pyridin-3-yl)furo[2,3-b]pyridine-2-carboxamide

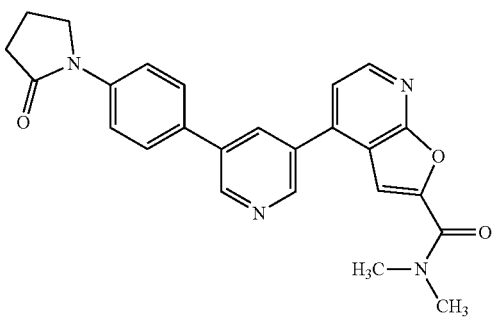 [SMILES: CN(C)C(=O)c1cc2c(-c3cncc(-c4ccc(N5CCCC5=O)cc4)c3)ccnc2o1]

Step 1: Intermediate 23—4-Chloro-N,N-dimethyl-furo[2,3-b]pyridine-2-carboxamide

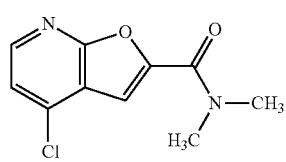

The title compound was prepared as described in Intermediate 7, replacing methylamine for dimethylamine HCl and TEA, to give the product as a solid (200 mg, 64%). MS ES+m/z 225 [M+H]$^+$.

Step 2: N,N-dimethyl-4-(5-(4-(2-oxopyrrolidin-1-yl)phenyl)pyridin-3-yl)furo[2,3-b]pyridine-2-carboxamide The title compound was prepared as described in Example 30, replacing 5-bromo-7H-pyrrolo[2,3-d]pyrimidine for 4-chloro-N,N-dimethyl-furo[2,3-b]pyridine-2-carboxamide, to give the product as a solid (68 mg, 36%). $^1$H NMR (500 MHz, CHLOROFORM-d) δ ppm 2.23 (t, J=7.57 Hz, 2H), 2.67 (t, J=8.04 Hz, 2H), 3.18 (br s, 3H), 3.44 (br s, 3H), 3.95 (t, J=7.09 Hz, 2H), 7.48 (d, J=5.04 Hz, 1H), 7.60 (s, 1H), 7.65-7.69 (m, 2H), 7.79-7.83 (m, 2H), 8.14 (t, J=2.21 Hz, 1H), 8.55 (d, J=5.04 Hz, 1H), 8.90 (d, J=2.21 Hz, 1H), 8.96 (d, J=2.21 Hz, 1H). MS ES+m/z 427 [M+H]$^+$.

Example 51: 3-(5-(4-(2-oxopyrrolidin-1-yl)phenyl)pyridin-3-yl)-1H-pyrrolo[2,3-b]pyridine-2-carbonitrile

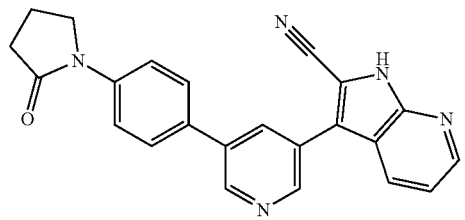 [SMILES: N#Cc1[nH]c2ncccc2c1-c1cncc(-c2ccc(N3CCCC3=O)cc2)c1]

Step 1: Intermediate 24—3-Bromo-1H-pyrrolo[2,3-b]pyridine-2-carbonitrile

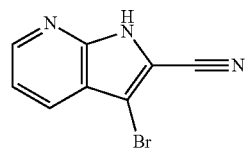

A mixture of 1H-pyrrolo[2,3-b]pyridine-2-carbonitrile (653 mg, 4.56 mmol) and NBS (1.22 g, 6.84 mmol) in DCM (20 ml) was stirred at 0° C. for 40 min. The mixture was concentrated onto silica gel and purified on a silica gel column, eluted with 0-20% MeOH in DCM to give the product as a solid (195 mg, 19%). MS ES+m/z 222 [M+H]$^+$.

Step 2: 3-(5-(4-(2-oxopyrrolidin-1-yl)phenyl)pyridin-3-yl)-1H-pyrrolo[2,3-b]pyridine-2-carbonitrile The title compound was prepared as described in Example 30, replacing 5-bromo-7H-pyrrolo[2,3-d]pyrimidine for 3-bromo-1H-pyrrolo[2,3-b]pyridine-2-carbonitrile, to give the product as a solid (9 mg, 9%). $^1$H NMR (500 MHz, DMSO-d$_6$) δ ppm 2.06-2.13 (m, 2H), 2.52-2.56 (m, 2H), 3.90 (t, J=7.09 Hz, 2H), 7.16 (dd, J=8.04, 4.57 Hz, 1H), 7.81-7.86 (m, 4H), 8.26 (d, J=8.20 Hz, 1H), 8.30 (t, J=2.21 Hz, 1H), 8.45 (d, J=4.41 Hz, 1H), 8.86 (d, J=1.89 Hz, 1H), 8.88 (d, J=1.89 Hz, 1H). MS ES+m/z 380 [M+H]$^+$.

Example 52: 1-(4-(5-(1H-pyrazolo[3,4-d]pyrimidin-4-yl)pyridin-3-yl)phenyl)pyrrolidin-2-one

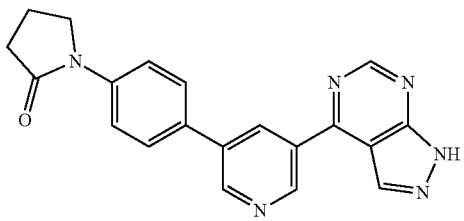 [SMILES: O=C1CCCN1c1ccc(-c2cncc(-c3ncnc4[nH]ncc34)c2)cc1]

Step 1: Intermediate 25—1-(Benzenesulfonyl)-4-chloro-pyrazolo[3,4-d]pyrimidine

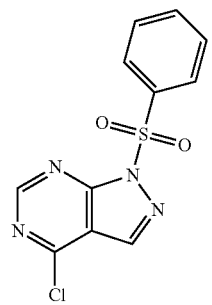 [SMILES: O=S(=O)(c1ccccc1)n1ncc2c(Cl)ncnc21]

Benzenesulfonyl chloride (873 µl, 6.81 mmol) was added to a solution of 4-chloro-1H-pyrazolo[3,4-d]pyrimidine (877 mg, 5.67 mmol) and TEA (791 µl, 5.67 mmol) in NMP (5 ml) and the resulting mixture was stirred at rt over weekend. EtOAc and water were added, and the organic layer was separated, washed with brine, dried over $Na_2SO_4$, filtered, concentrated and purified on a silica gel column eluted with 0-100% EtOAc in isohexane to give the product as a solid (544 mg, 33%). MS ES+m/z 295 $[M+H]^+$.

Step 2: Intermediate 26—1-[4-[5-[1-(Benzenesulfonyl)pyrazolo[3,4-d]pyrimidin-4-yl]-3-pyridyl]phenyl]pyrrolidin-2-one

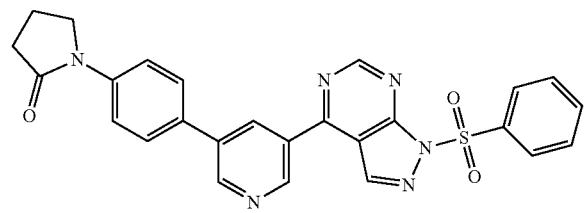 [SMILES: O=C1CCCN1c1ccc(-c2cncc(-c3ncnc4c3cnn4S(=O)(=O)c3ccccc3)c2)cc1]

The title compound was prepared as described in Example 30, replacing 5-bromo-7H-pyrrolo[2,3-d]pyrimidine for 1-(benzenesulfonyl)-4-chloro-pyrazolo[3,4-d]pyrimidine, to give the product as a solid (27 mg, 8%). MS ES+m/z 497 $[M+H]^+$.

Step 3: 1-(4-(5-(1H-pyrazolo[3,4-d]pyrimidin-4-yl)pyridin-3-yl)phenyl)pyrrolidin-2-one 1-[4-[5-[1-(Benzenesulfonyl)pyrazolo[3,4-d]pyrimidin-4-yl]-3-pyridyl]phenyl]pyrrolidin-2-one (27 mg, 0.05 mmol) and pyrrolidine (5 µl, 0.07 mmol) was dissolved in 2-propanol (0.5 ml) and the resulting mixture was heated in a microwave reactor at 100° C. for 1.5 h. The mixture was purified by preparative HPLC to give the product as a solid (1.4 mg, 7%). $^1$H NMR (500 MHz, DMSO-$d_6$) δ ppm 2.11 (quin, J=7.57 Hz, 2H), 2.52-2.58 (m, 2H), 3.91 (t, J=7.09 Hz, 2H), 7.82-7.88 (m, 2H), 7.89-7.94 (m, 2H), 8.77-8.81 (m, 2H), 9.08 (s, 1H), 9.14 (d, J=2.21 Hz, 1H), 9.39 (d, J=2.21 Hz, 1H). MS ES+m/z 357 $[M+H]^+$.

Example 53: 1-(4-(5-(6-chloro-1H-pyrazolo[3,4-b]pyridin-4-yl)pyridin-3-yl)phenyl)pyrrolidin-2-one

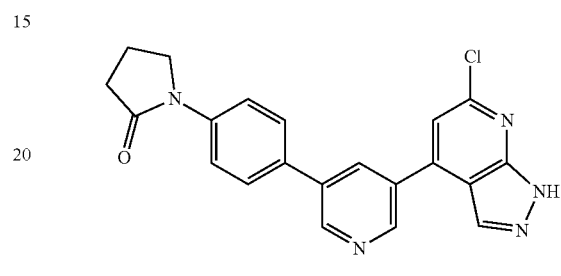

Step 1: Intermediate 27—4-Iodo-7-oxido-1H-pyrazolo[3,4-b]pyridin-7-ium

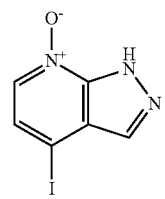 [SMILES: [O-][n+]1ccc(I)c2cn[nH]c21]

4-Iodo-1H-pyrazolo[3,4-b]pyridine (1 g, 4.08 mmol) was dissolved in NMP (5 ml) at rt and then cooled to 0° C. mCPBA (1.2 g, 5.22 mmol) was added portion wise and the resulting mixture was stirred at rt overnight. More mCPBA (200 mg, 0.87 mmol) was added and the mixture stirred at rt for 1 h. MTBE (10 ml) was added and the mixture stirred vigorously for 30 min. The formed precipitate was filtered off, washed with pentane and dried to give the product as a solid (820 mg, 77%). MS ES+m/z 262 $[M+H]^+$.

Step 2: Intermediate 28—6-Chloro-4-iodo-1H-pyrazolo[3,4-b]pyridine

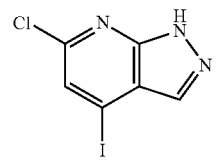 [SMILES: Clc1cc(I)c2cn[nH]c2n1]

POCl$_3$ (1 ml, 10.7 mmol) was added slowly to a suspension of 4-iodo-7-oxido-1H-pyrazolo[3,4-b]pyridin-7-ium (600 mg, 2.3 mmol) in MeCN (5 ml) and the resulting mixture was stirred at rt for 2 h. 20% aq. NaOH (5 ml) was added slowly, followed by sat. aq. NaHCO$_3$ until pH 7. The formed precipitate was filtered off, washed with water and dried to give the product as a solid (1.1 g, quant.). MS ES+m/z 280 [M+H]+.

Step 3: 1-(4-(5-(6-chloro-1H-pyrazolo[3,4-b]pyridin-4-yl)pyridin-3-yl)phenyl)pyrrolidin-2-one The title compound was prepared as described in Example 30, replacing 5-bromo-7H-pyrrolo[2,3-d]pyrimidine for 6-chloro-4-iodo-1H-pyrazolo[3,4-b]pyridine, to give the product as a solid (73 mg, 34%). $^1$H NMR (500 MHz, DMSO-$d_6$) δ ppm 2.07-2.14 (m, 2H), 2.52-2.58 (m, 2H), 3.91 (t, J=6.94 Hz, 2H), 7.72 (s, 1H), 7.81-7.86 (m, 2H), 7.91-7.98 (m, 2H), 8.47 (d, J=1.26 Hz, 1H), 8.51 (t, J=2.21 Hz, 1H), 9.05 (d, J=2.21 Hz, 1H), 9.09 (d, J=2.21 Hz, 1H), 14.05 (s, 1H). MS ES+m/z 390 [M+H]+.

Example 54: 6-methyl-4-(5-(4-(2-oxopyrrolidin-1-yl)phenyl)pyridin-3-yl)-1,6-dihydro-7H-pyrazolo[3,4-c]pyridin-7-one

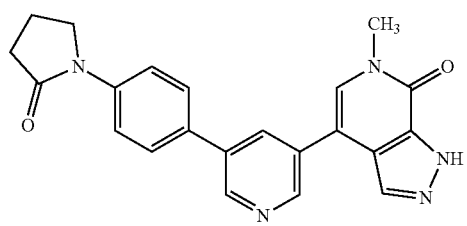 [SMILES: Cn1cc(-c2cncc(-c3ccc(N4CCCC4=O)cc3)c2)c2cn[nH]c2c1=O]

Step 1: Intermediate 29—3-Amino-5-bromo-1,4-dimethyl-pyridin-2-one

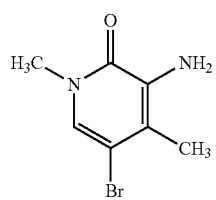

5-Bromo-1,4-dimethyl-3-nitro-pyridin-2-one (1.67 g, 6.76 mmol), Fe (1.89 g, 33.8 mmol) and ammonium chloride (723 mg, 13.5 mmol) were taken up in EtOH (25 ml), THF (25 ml), water (8 ml) and the resulting mixture was refluxed for 1.5 h. When slightly cooled the mixture was filtered through celite, rinsed with MeOH and the filtrate was concentrated. The resulting residue was dissolved in EtOAc, washed with sat. aq. NaHCO₃, brine, dried over Na₂SO₄, filtered and concentrated to give the product as a solid (1.19 g, 81%). MS ES+m/z 217 [M+H]+.

Step 2: Intermediate 30—4-Bromo-6-methyl-1H-pyrazolo[3,4-c]pyridin-7-one

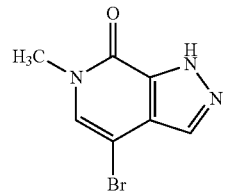

3-Amino-5-bromo-1,4-dimethyl-pyridin-2-one (1.19 g, 5.48 mmol) was dissolved in toluene (30 ml). Acetic anhydride (1.55 ml, 16.4 mmol) was added followed by KOAc (646 mg, 6.58 mmol) and the reaction mixture was stirred at 50° C. for 4 h. Isoamyl nitrite (1.1 ml, 8.22 mmol) was added and the reaction mixture was stirred at 80° C. for 48 h. Additional isoamyl nitrite (1.1 ml, 8.22 mmol) was added and the mixture was stirred at 90° C. for 8 h. When cooled to rt the mixture was washed with water, brine, dried over MgSO₄, filtered, concentrated and purified on a silica gel column eluted with 0-100% EtOAc in isohexane to give the product as a solid (323 mg, 26%). MS ES+m/z 228 [M+H]+.

Step 3: 6-methyl-4-(5-(4-(2-oxopyrrolidin-1-yl)phenyl)pyridin-3-yl)-1,6-dihydro-7H-pyrazolo[3,4-c]pyridin-7-one The title compound was prepared as described in Example 30, replacing 5-bromo-7H-pyrrolo[2,3-d]pyrimidine for 4-bromo-6-methyl-TH-pyrazolo[3,4-c]pyridin-7-one, to give the product as a solid (5 mg, 3%). $^1$H NMR (500 MHz, DMSO-$d_6$) δ ppm 2.06-2.14 (m, 2H), 2.52-2.57 (m, 2H), 3.64 (s, 3H), 3.91 (t, J=6.94 Hz, 2H), 7.83-7.89 (m, 3H), 7.93-7.98 (m, 2H), 8.27-8.34 (m, 1H), 8.56-8.61 (m, 1H), 8.96 (d, J=1.89 Hz, 1H), 9.03 (d, J=2.21 Hz, 1H). MS ES+m/z 386 [M+H]+.

Example 55: 1,6-dimethyl-4-(5-(4-(2-oxopyrrolidin-1-yl)phenyl)pyridin-3-yl)-1,6-dihydro-7H-pyrazolo[3,4-c]pyridin-7-one

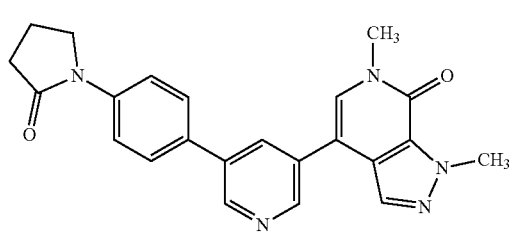 [SMILES: Cn1cc(-c2cncc(-c3ccc(N4CCCC4=O)cc3)c2)c2cnn(C)c2c1=O]

Step 1: Intermediate 31—4-Bromo-1,6-dimethyl-pyrazolo[3,4-c]pyridin-7-one


1M LHMDS (526 µl, 0.53 mmol) was added to a solution of 4-bromo-6-methyl-1H-pyrazolo[3,4-c]pyridin-7-one (100 mg, 0.44 mmol) in THF (1 mL) at rt. After 5 min iodomethane (33 µl, 0.53 mmol) was added and the resulting mixture was stirred at rt overnight. EtOAc and water were added, the organic layer was separated, dried over MgSO$_4$, filtered and concentrated to give the product as a solid (96 mg, 90%). MS ES+m/z 242 [M+H]$^+$.

Step 2: 1,6-dimethyl-4-(5-(4-(2-oxopyrrolidin-1-yl)phenyl)pyridin-3-yl)-1,6-dihydro-7H-pyrazolo[3,4-c]pyridin-7-one The title compound was prepared as described in Example 30, replacing 5-bromo-7H-pyrrolo[2,3-d]pyrimidine for 4-bromo-1,6-dimethyl-pyrazolo[3,4-c]pyridin-7-one, to give the product as a solid (12 mg, 9%). $^1$H NMR (500 MHz, DMSO-d$_6$) δ ppm 2.07-2.15 (m, 2H), 2.52-2.58 (m, 2H), 3.52-3.59 (m, 3H), 3.86-3.94 (m, 2H), 4.09-4.15 (m, 3H), 7.61-7.67 (m, 1H), 7.77-7.85 (m, 2H), 7.85-7.91 (m, 2H), 8.16-8.24 (m, 1H), 8.49-8.53 (m, 1H), 8.77-8.82 (m, 1H), 8.84-8.90 (m, 1H). MS ES+m/z 400 [M+H]$^+$.

Example 56: 1-(4-(5-(1-methyl-5-(piperazin-1-yl)-1H-pyrrolo[2,3-b]pyridin-3-yl)pyridin-3-yl)phenyl)pyrrolidin-2-one

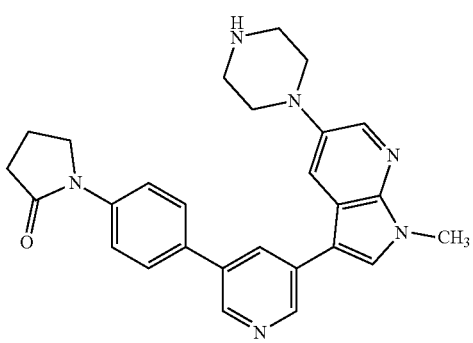 [SMILES: Cn1cc(-c2cncc(-c3ccc(N4CCCC4=O)cc3)c2)c2cc(N3CCNCC3)cnc21]

Step 1: Intermediate 32—tert-Butyl 4-(1-methylpyrrolo[2,3-b]pyridin-5-yl)piperazine-1-carboxylate

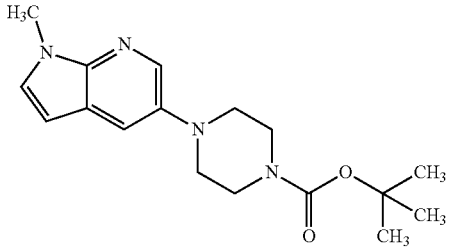 [SMILES: Cn1ccc2cc(N3CCN(C(=O)OC(C)(C)C)CC3)cnc21]

A mixture of 5-chloro-1H-pyrrolo[2,3-b]pyridine (200 mg, 1.2 mmol), tert-butyl piperazine-1-carboxylate (313 mg, 1.68 mmol), KOtBu (337 mg, 3 mmol) and PEPPSI-IPr (82 mg, 0.12 mmol) in 1,4-dioxane (1.5 ml) was heated in a microwave reactor at 150° C. for 3 h. The mixture was filtered through celite and rinsed with EtOAc and MeOH. The filtrate was concentrated, and the resulting residue was dissolved in EtOAc and washed with water and brine. The organic layer was dried over MgSO$_4$, filtered, concentrated and purified on a silica gel column eluted with 0-20% MeOH in DCM to give the product as a solid (113 mg, 30%). MS ES+m/z 317 [M+H]$^+$.

Step 2: Intermediate 33—tert-Butyl 4-(3-bromo-1-methyl-pyrrolo[2,3-b]pyridin-5-yl)piperazine-1-carboxylate

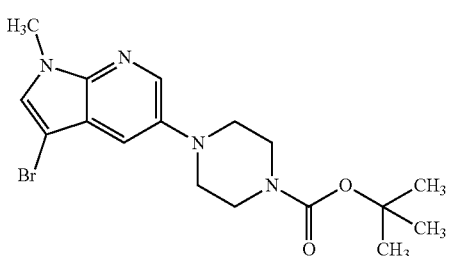

tert-Butyl 4-(1-methylpyrrolo[2,3-b]pyridin-5-yl)piperazine-1-carboxylate (113 mg, 0.36 mmol) was dissolved in DCM (1.5 ml) and cooled down to 0° C. before NBS (76 mg, 0.43 mmol) was added. The reaction mixture was stirred at 0° C. for 15 min. DCM (3 ml) was added and the mixture washed with sat. aq. Na$_2$S$_2$O$_3$, sat. aq. NaHCO$_3$, dried over Na$_2$SO$_4$, filtered and concentrated to give the product as a solid (142 mg, quant.). MS ES+m/z 395 [M+H]$^+$.

Step 3: Intermediate 34—tert-Butyl 4-[1-methyl-3-[5-[4-(2-oxopyrrolidin-1-yl)phenyl]-3-pyridyl]pyrrolo[2,3-b]pyridin-5-yl]piperazine-1-carboxylate

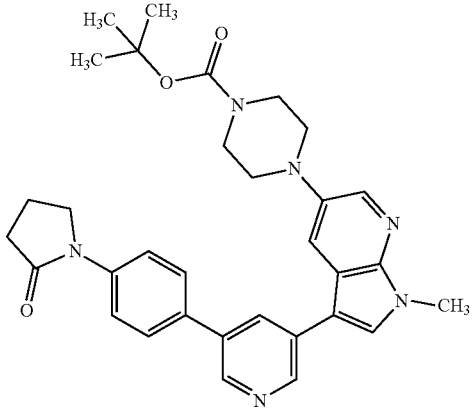 [SMILES: Cn1cc(-c2cncc(-c3ccc(N4CCCC4=O)cc3)c2)c2cc(N3CCN(C(=O)OC(C)(C)C)CC3)cnc21]

The title compound was prepared as described in Example 30, replacing 5-bromo-7H-pyrrolo[2,3-d]pyrimidine for tert-butyl 4-(3-bromo-1-methyl-pyrrolo[2,3-b]pyridin-5-yl)piperazine-1-carboxylate, to give the product as a solid (43 mg, 22%). MS ES+m/z 553 [M+H]+.

Step 4: 1-(4-(5-(1-methyl-5-(piperazin-1-yl)-1H-pyrrolo[2,3-b]pyridin-3-yl)pyridin-3-yl)phenyl)pyrrolidin-2-one TFA (12 μl, 0.16 mmol) was added to a solution of tert-butyl 4-[1-methyl-3-[5-[4-(2-oxopyrrolidin-1-yl)phenyl]-3-pyridyl]pyrrolo[2,3-b]pyridin-5-yl]piperazine-1-carboxylate (43 mg, 0.08 mmol) in DCM (0.5 ml) at 0° C. The resulting mixture was stirred at rt overnight. Sat. aq. NaHCO₃ was added and the organic layer separated. The aqueous layer was extracted with DCM and the combined organics were dried over Na₂SO₄, filtered and concentrated to give the product as a solid (32 mg, 91%). ¹H NMR (500 MHz, DMSO-d₆) δ ppm 2.06-2.14 (m, 2H), 2.51-2.57 (m, 2H), 2.86-2.92 (m, 4H), 3.03-3.11 (m, 4H), 3.82-3.87 (m, 3H), 3.88-3.93 (m, 2H), 7.73-7.77 (m, 1H), 7.79-7.89 (m, 4H), 8.08 (s, 1H), 8.20 (d, J=2.52 Hz, 1H), 8.24 (s, 1H), 8.76 (d, J=2.21 Hz, 1H), 8.86-8.91 (m, 1H). MS ES+m/z 453 [M+H]+.

Example 57: N-methyl-N-(5-(4-(2-oxopyrrolidin-1-yl)phenyl)-[3,4'-bipyridin]-2'-yl)acetamide

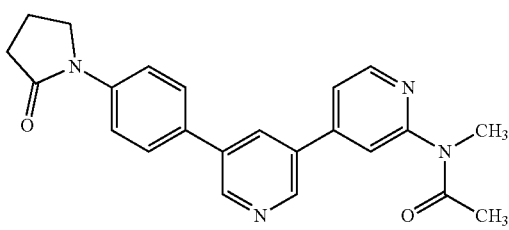 [SMILES: CC(=O)N(C)c1cc(-c2cncc(-c3ccc(N4CCCC4=O)cc3)c2)ccn1]

Step 1: Intermediate 35—N-(4-bromo-2-pyridyl)-N-methyl-acetamide

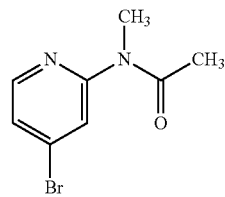

NaH (43 mg, 1.88 mmol) was added to a solution of N-(4-bromo-2-pyridyl)acetamide (337 mg, 1.57 mmol) in THF (3 mL) at 0° C. Iodomethane (98 μl, 1.57 mmol) was added and the resulting mixture was stirred at rt overnight. EtOAc was added and the mixture was washed with water, dried over MgSO₄, filtered, concentrated and purified on a silica gel column eluted with 0-100% EtOAc in heptane to give the product as a solid (208 mg, 58%). MS ES+m/z 229 [M+H]+.

Step 2: N-methyl-N-(5-(4-(2-oxopyrrolidin-1-yl)phenyl)-[3,4'-bipyridin]-2'-yl)acetamide The title compound was prepared as described in Example 30, replacing 5-bromo-7H-pyrrolo[2,3-d]pyrimidine for N-(4-bromo-2-pyridyl)-N-methyl-acetamide, to give the product as a solid (28 mg, 26%). ¹H NMR (500 MHz, DMSO-d₆) δ ppm 2.07 (s, 3H), 2.09-2.13 (m, 2H), 2.51-2.56 (m, 2H), 3.32 (s, 3H), 3.90 (t, J=6.94 Hz, 2H), 7.79-7.86 (m, 3H), 7.88-7.94 (m, 2H), 8.02 (d, J=0.95 Hz, 1H), 8.48 (t, J=2.21 Hz, 1H), 8.60 (dd, J=5.36, 0.63 Hz, 1H), 8.99-9.02 (m, 2H). MS ES+m/z 387 [M+H]+.

Example 58: 1-(4-(5-(1H-pyrrolo[2,3-b]pyridin-4-yl)pyridin-3-yl)phenyl)pyrrolidin-2-one

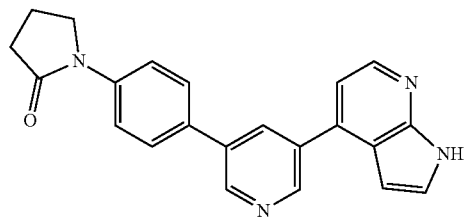 [SMILES: O=C1CCCN1c1ccc(-c2cncc(-c3ccnc4[nH]ccc34)c2)cc1]

Step 1: Intermediate 36—1-[4-[5-[1-(Benzenesulfonyl)pyrrolo[2,3-b]pyridin-4-yl]-3-pyridyl]phenyl]pyrrolidin-2-one

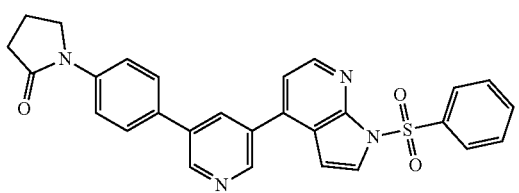 [SMILES: O=C1CCCN1c1ccc(-c2cncc(-c3ccnc4c3ccn4S(=O)(=O)c3ccccc3)c2)cc1]

The title compound was prepared as described in Example 30, replacing 5-bromo-7H-pyrrolo[2,3-d]pyrimidine for 1-(benzenesulfonyl)-4-chloro-pyrrolo[2,3-b]pyridine, to give the product as a solid (32 mg, 16%). MS ES+m/z 495 [M+H]+.

Step 2: 1-(4-(5-(1H-pyrrolo[2,3-b]pyridin-4-yl)pyridin-3-yl)phenyl)pyrrolidin-2-one A mixture of 1-[4-[5-[1-(benzenesulfonyl)pyrrolo[2,3-b]pyridin-4-yl]-3-pyridyl]phenyl]pyrrolidin-2-one (32 mg, 0.06 mmol), pyrrolidine (30 μl, 0.36 mmol) and KOH (4 mg, 0.06 mmol) in 2-propanol (0.5 ml), MeCN (0.5 ml) and NMP (1 ml) was heated in a microwave reactor at 140° C. for 30 min. EtOAc and water were added and the organic layer separated. The aqueous layer was extracted with EtOAc and the combined organics were dried over Na₂SO₄, filtered and concentrated. The resulting residue was dissolved in a minimal amount of DCM and MeOH was added. The formed precipitate was filtered off and dried to give the product as a solid (5 mg, 23%). $^1$H NMR (500 MHz, DMSO-d₆) δ ppm 2.10 (t, J=7.57 Hz, 2H), 2.51-2.57 (m, 2H), 3.86-3.93 (m, 2H), 6.64-6.70 (m, 1H), 7.33-7.40 (m, 1H), 7.58-7.63 (m, 1H), 7.79-7.85 (m, 2H), 7.86-7.91 (m, 2H), 8.33-8.37 (m, 2H), 8.94 (d, J=1.89 Hz, 1H), 8.99 (d, J=2.21 Hz, 1H), 11.83-11.95 (m, 1H). MS ES+m/z 355 [M+H]+.

Example 59: 1-(4-(5-(5-ethoxy-1H-pyrrolo[2,3-b]pyridin-4-yl)pyridin-3-yl)phenyl)pyrrolidin-2-one

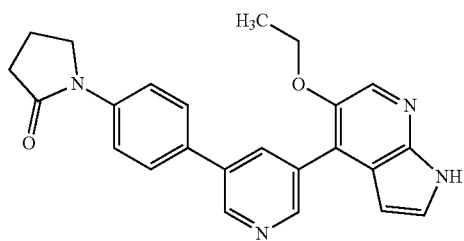 [SMILES: CCOc1cnc2[nH]ccc2c1-c1cncc(-c2ccc(N3CCCC3=O)cc2)c1]

Step 1: Intermediate 37—(4-Chloro-5-ethoxy-pyrrolo[2,3-b]pyridin-1-yl)-triisopropyl-silane

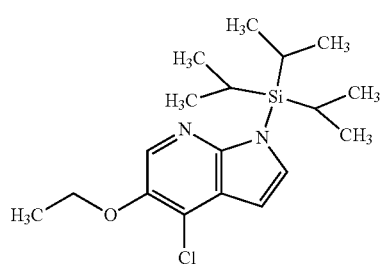 [SMILES: CCOc1cnc2c(ccn2[Si](C(C)C)(C(C)C)C(C)C)c1Cl]

A mixture of 4-chloro-1-triisopropylsilyl-pyrrolo[2,3-b]pyridin-5-ol (300 mg, 0.92 mmol), K₂CO₃ (319 mg, 2.31 mmol) and ethyl iodide (89 μl, 1.11 mmol) in MeCN (5 ml) was stirred at rt until all starting material was consumed. EtOAc and water were added, the organic layer separated, dried over Na₂SO₄, filtered and concentrated to give the product (292 mg, 90%). MS ES+m/z 353 [M+H]+.

Step 2: Intermediate 38—1-[4-[5-(5-Ethoxy-1-triisopropylsilyl-pyrrolo[2,3-b]pyridin-4-yl)-3-pyridyl]phenyl]pyrrolidin-2-one

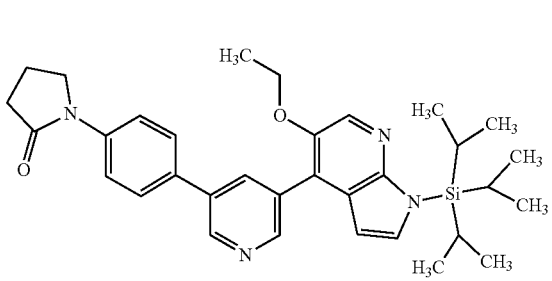 [SMILES: CCOc1cnc2c(ccn2[Si](C(C)C)(C(C)C)C(C)C)c1-c1cncc(-c2ccc(N3CCCC3=O)cc2)c1]

The title compound was prepared as described in Example 30, replacing 5-bromo-7H-pyrrolo[2,3-d]pyrimidine for (4-chloro-5-ethoxy-pyrrolo[2,3-b]pyridin-1-yl)-triisopropyl-silane, to give the product as a solid (93 mg, 23%). MS ES+m/z 555 [M+H]+.

Step 3: 1-(4-(5-(5-ethoxy-1H-pyrrolo[2,3-b]pyridin-4-yl)pyridin-3-yl)phenyl)pyrrolidin-2-one TBAF in THF (1M, 168 μl, 0.17 mmol) was added to a solution of 1-[4-[5-(5-ethoxy-1-triisopropylsilyl-pyrrolo[2,3-b]pyridin-4-yl)-3-pyridyl]phenyl]pyrrolidin-2-one (93 mg, 0.17 mmol) THF (1 ml) and the resulting mixture was stirred at rt for 2 h. 1,2-Dichloroethane and sat. aq. NaHCO₃ solution were added and the organic layer separated. The aqueous layer was extracted with 1,2-dichloroethane and the combined organics were washed with brine, dried over Na₂SO₄, filtered, concentrated and purified by preparative HPLC to give the product as a solid (16 mg, 24%). $^1$H NMR (500 MHz, DMSO-d₆) δ ppm 1.19-1.25 (m, 3H), 2.07-2.13 (m, 2H), 2.51-2.56 (m, 2H), 3.86-3.92 (m, 2H), 4.04-4.12 (m, 2H), 6.29-6.37 (m, 1H), 7.50-7.55 (m, 1H), 7.78-7.85 (m, 4H), 8.21-8.25 (m, 1H), 8.25-8.28 (m, 1H), 8.71-8.79 (m, 1H), 8.87-8.98 (m, 1H), 11.62-11.73 (m, 1H). MS ES+m/z 399 [M+H]+.

Example 60: N,1-dimethyl-3-(5-(4-(2-oxopyrrolidin-1-yl)phenyl)pyridin-3-yl)-1H-pyrrolo[2,3-b]pyridine-5-carboxamide

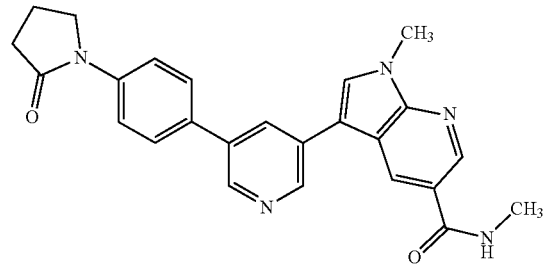 [SMILES: CNC(=O)c1cnc2c(c1)c(-c1cncc(-c3ccc(N4CCCC4=O)cc3)c1)cn2C]

Step 1: Intermediate 39—Methyl 3-bromo-1H-methyl-pyrrolo[2,3-b]pyridine-5-carboxylate

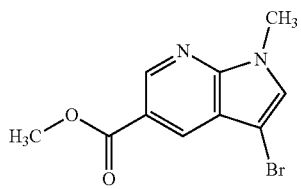

A mixture of methyl 3-bromo-H-pyrrolo[2,3-b]pyridine-5-carboxylate (2.2 g 8.63 mmol) and Cs$_2$CO$_3$ (5.62 g, 17.3 mmol) in DMF (25 ml) was stirred at rt for 1 h. Iodomethane (0.67 ml, 10.8 mmol) was added and the mixture stirred at rt overnight. Water (150 ml) was added and the mixture extracted with EtOAc. The combined organics were washed with brine, dried over Na$_2$SO$_4$, filtered and concentrated to give the product as a solid (2.2 g, 95%). MS ES+m/z 269 [M+H]$^+$.

Step 2: Intermediate 40—3-Bromo-1-methyl-pyrrolo[2,3-b]pyridine-5-carboxylic acid

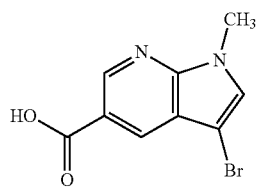

A mixture of methyl 3-bromo-1-methyl-pyrrolo[2,3-b]pyridine-5-carboxylate (2.4 g, 8.92 mmol) and LiOH (235 mg, 9.81 mmol) in MeOH (20 ml), THF (20 ml) and water (5 ml) was stirred at rt over weekend. Water (30 ml) was added and the organic solvents were removed in vacuo. The aqueous residue was acidified with 2M aq. HCl to pH 5 and the mixture was kept at rt overnight. The formed precipitate was filtered off and washed with pentane to give the product as a solid (2.17 g, 87%). MS ES+m/z 255 [M+H]$^+$.

Step 3: Intermediate 41—3-Bromo-N,1-dimethyl-pyrrolo[2,3-b]pyridine-5-carboxamide

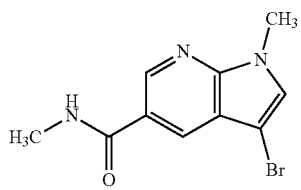

Oxalyl chloride (1.09 ml, 12.9 mmol) was added to a mixture of 3-bromo-1-methyl-pyrrolo[2,3-b]pyridine-5-carboxylic acid (1.1 g, 4.31 mmol) and DMF (5 drops) in DCM (50 ml) at 0° C. The resulting mixture was stirred at rt for 3 h. The mixture was concentrated and the resulting residue was suspended in THF (20 ml) and added to 40% aq. methylamine (19 ml, 216 mmol) at 0° C. After 1 h at rt the volatiles were removed in vacuo. The resulting aqueous residue was kept at rt for 2 h and the formed precipitate was filtered off, washed with water and dried. The solid was suspended in Et$_2$O and EtOAc, stirred at rt for 1 h, filtered and dried to give the product as a solid (0.75 g, 59%). MS ES+m/z 268 [M+H]$^+$.

Step 4: N,1-dimethyl-3-(5-(4-(2-oxopyrrolidin-1-yl)phenyl)pyridin-3-yl)-1H-pyrrolo[2,3-b]pyridine-5-carboxamide The title compound was prepared as described in Example 30, replacing 5-bromo-7H-pyrrolo[2,3-d]pyrimidine for 3-bromo-N,1-dimethyl-pyrrolo[2,3-b]pyridine-5-carboxamide, to give the product as a solid (55 mg, 39%). $^1$H NMR (500 MHz, DMSO-d$_6$) δ ppm 2.06-2.14 (m, 2H), 2.52-2.56 (m, 2H), 2.82-2.86 (m, 3H), 3.89-3.93 (m, 2H), 3.93-3.95 (m, 3H), 7.81-7.86 (m, 2H), 7.86-7.90 (m, 2H), 8.27-8.30 (m, 1H), 8.31-8.34 (m, 1H), 8.64-8.70 (m, 1H), 8.80-8.82 (m, 1H), 8.82-8.83 (m, 1H), 8.86 (d, J=1.89 Hz, 1H), 9.01 (d, J=2.21 Hz, 1H). MS ES+m/z 426 [M+H]$^+$.

Example 61: N,N,1-trimethyl-3-(5-(4-(2-oxopyrrolidin-1-yl)phenyl)pyridin-3-yl)-1H-pyrrolo[2,3-b]pyridine-5-carboxamide

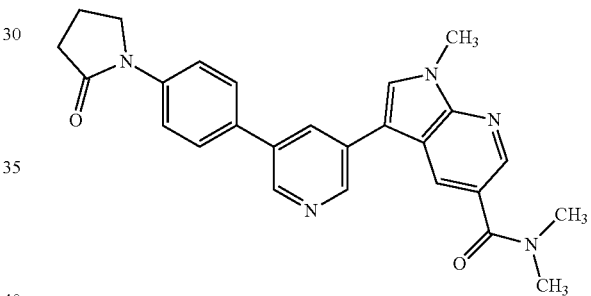

Step 1: Intermediate 42—3-Bromo-N,N,1-trimethyl-pyrrolo[2,3-b]pyridine-5-carboxamide

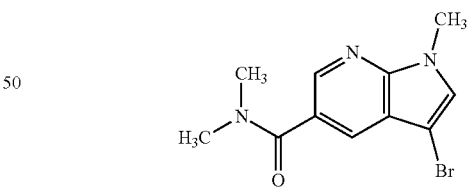

The title compound was prepared as described in Intermediate 41, replacing methylamine for dimethylamine (1M in THF). Purification on a silica gel column eluted with 0-20% MeOH in DCM gave the product as a solid (1.02 g, 84%). MS ES+m/z 282 [M+H]$^+$.

Step 2: N,N,1-trimethyl-3-(5-(4-(2-oxopyrrolidin-1-yl)phenyl)pyridin-3-yl)-1H-pyrrolo[2,3-b]pyridine-5-carboxamide The title compound was prepared as described in Example 30, replacing 5-bromo-7H-pyrrolo[2,3-d]pyrimidine for 3-bromo-N,N,1-trimethyl-pyrrolo[2,3-b]pyridine-5-carboxamide, to give the product as a solid (46 mg, 23%). $^1$H NMR (500 MHz, DMSO-d$_6$) δ ppm 2.06-2.14 (m, 2H), 2.52-2.56 (m, 2H), 2.99-3.07 (m, 6H), 3.88-3.93 (m, 2H), 3.93-3.95 (m, 3H), 7.81-7.84 (m, 2H), 7.85-7.88 (m, 2H), 8.27-8.29 (m, 1H), 8.29-8.30 (m, 1H), 8.40-8.42 (m, 1H), 8.42-8.43 (m, 1H), 8.79-8.81 (m, 1H), 8.90-8.93 (m, 1H). MS ES+m/z 440 [M+H]$^+$.

Example 62: 1-(4-(5-(5-(1-hydroxyethyl)-1-methyl-1H-pyrrolo[2,3-b]pyridin-3-yl)pyridin-3-yl)phenyl)pyrrolidin-2-one

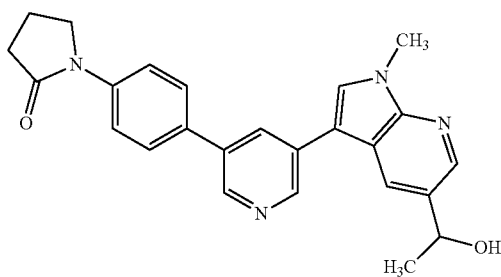 [SMILES: CC(O)c1cnc2c(c1)c(-c1cncc(-c3ccc(N4CCCC4=O)cc3)c1)cn2C]

Step 1: Intermediate 43—1-(3-Bromo-1H-pyrrolo[2,3-b]pyridin-5-yl)ethenone

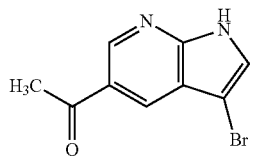

A mixture of 1-(1H-pyrrolo[2,3-b]pyridin-5-yl)ethanone (400 mg, 2.5 mmol) and NBS (668 mg, 3.25 mmol) in DCM (2.5 ml) was stirred at 0° C. for 40 min. Sat. aq. Na$_2$S$_2$O$_3$ was added and the reaction mixture was extracted DCM (4×). The combined organics were washed with brine, dried over Na$_2$SO$_4$, filtered, concentrated and purified on a silica gel column eluted with 0-100% EtOAc in Heptane to give the product as a solid (650 mg, quant.). MS ES+m/z 239 [M+H]$^+$.

Step 2: Intermediate 44—1-(3-Bromo-1-methyl-pyrrolo[2,3-b]pyridin-5-yl)ethanone

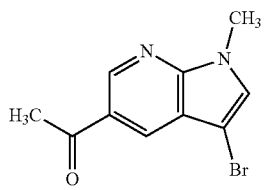

The title compound was prepared as described in Intermediate 39, replacing methyl 3-bromo-1H-pyrrolo[2,3-b]pyridine-5-carboxylate for 1-(3-bromo-1H-pyrrolo[2,3-b]pyridin-5-yl)ethenone, to give the product as a solid (380 mg, 56%). MS ES+m/z 253 [M+H]$^+$.

Step 3: Intermediate 45—1-(3-Bromo-1-methyl-pyrrolo[2,3-b]pyridin-5-yl)ethanol

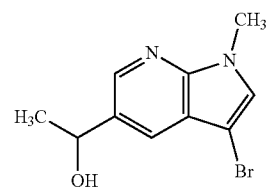

NaBH$_4$ (114 mg, 3 mmol) was added to a solution of 1-(3-bromo-1-methyl-pyrrolo[2,3-b]pyridin-5-yl)ethanone (380 mg, 1.5 mmol) in MeOH (5 ml) and THF (2 ml) at 0° C. and the resulting mixture was stirred at 0° C. for 1 h. Aq. 50% AcOH was added, the mixture concentrated and purified on a silica gel column eluted with 0-10% MeOH in DCM to give the product as a solid (260 mg, 68%). MS ES+m/z 255 [M+H]$^+$.

Step 4: 1-(4-(5-(5-(1-hydroxyethyl)-1-methyl-1H-pyrrolo[2,3-b]pyridin-3-yl)pyridin-3-yl)phenyl)pyrrolidin-2-one The title compound was prepared as described in Example 30, replacing 5-bromo-7H-pyrrolo[2,3-d]pyrimidine for 1-(3-bromo-1-methyl-pyrrolo[2,3-b]pyridin-5-yl)ethanol, to give the product as a solid (59 mg, 43%). $^1$H NMR (500 MHz, DMSO-d$_6$) δ ppm 1.44 (d, J=6.31 Hz, 2H), 2.10 (quin, J=7.57 Hz, 2H), 2.52-2.58 (m, 2H), 3.89-3.95 (m, 5H), 4.93-5.11 (m, 1H), 5.26 (d, J=4.73 Hz, 1H), 7.77-7.91 (m, 4H), 8.18 (s, 1H), 8.27 (t, J=2.21 Hz, 1H), 8.30 (d, J=1.89 Hz, 1H), 8.36 (d, J=1.89 Hz, 1H), 8.78 (d, J=2.21 Hz, 1H), 8.92 (d, J=1.89 Hz, 1H). MS ES+m/z 413 [M+H]$^+$.

Example 63: 1-(4-(5-(6-cyclopropyl-1H-pyrazolo[3,4-b]pyridin-4-yl)pyridin-3-yl)phenyl)pyrrolidin-2-one

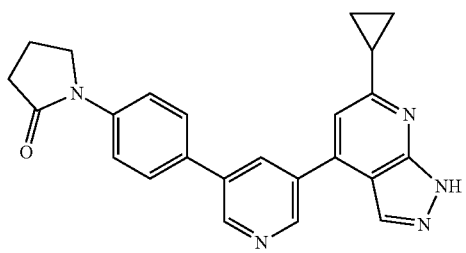 [SMILES: O=C1CCCN1c1ccc(-c2cncc(-c3cc(C4CC4)nc4[nH]ncc34)c2)cc1]

Step 1: Intermediate 46—6-Chloro-1-[(4-methoxyphenyl)methyl]pyrazolo[3,4-b]pyridine

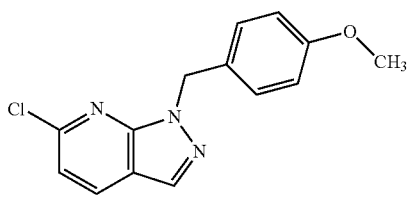 [SMILES: COc1ccc(Cn2ncc3ccc(Cl)nc32)cc1]

6-Chloro-1H-pyrazolo[3,4-b]pyridine (1.05 g, 6.82 mmol) was dissolved in MeCN (25 ml) at rt. 4-Methoxybenzylchloride (1.69 ml, 11.6 mmol) was added followed by $K_2CO_3$ (2.83 g, 20.5 mmol) and the resulting mixture was stirred at 60° C. for 1 h. Sat. aq. $NaHCO_3$ (30 ml) was added and the mixture extracted with DCM (3×30 ml). The combined organics were dried over $Na_2SO_4$, filtered, concentrated and purified on a silica gel column eluted with 0-100% EtOAc in Heptane to give the product as a solid (1.9 g, quant.). MS ES+m/z 274 [M+H]+.

Step 2: Intermediate 47—6-Cyclopropyl-1-[(4-methoxyphenyl)methyl]pyrazolo[3,4-b]pyridine

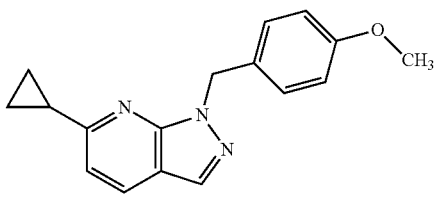 [SMILES: COc1ccc(Cn2ncc3ccc(C4CC4)nc32)cc1]

6-Chloro-1-[(4-methoxyphenyl)methyl]pyrazolo[3,4-b]pyridine (1 g, 3.65 mmol), cyclopropyl boronic acid (628 mg, 7.31 mmol), $K_2CO_3$ (1.01 g, 7.31 mmol) and $PdCl_2(PPh_3)_2$ (133 mg, 0.18 mmol) were taken up in 1,4-dioxane (3 ml) and water (0.7 ml) and the mixture was heated in a microwave reactor at 130° C. for 1 h. The mixture was dried over $Na_2SO_4$, filtered through celite, concentrated and purified on a silica gel column eluted with 0-100% EtOAc in Heptane to give the product as a solid (874 mg, 86%). MS ES+m/z 280 [M+H]+.

Step 3: Intermediate 48—6-Cyclopropyl-1H-pyrazolo[3,4-b]pyridine

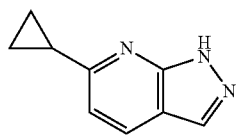 [SMILES: c1cc2cn[nH]c2nc1C1CC1]

6-Cyclopropyl-1-[(4-methoxyphenyl)methyl]pyrazolo[3,4-b]pyridine (874 mg, 3.13 mmol) was dissolved in TFA (5 ml, 21.5 mmol) and stirred at 75° C. for 2 h. The mixture was concentrated and purified on a silica gel column eluted with 0-10% MeOH in DCM to give the product as a solid (330 mg, 66%). 1H NMR (500 MHz, DMSO-$d_6$) δ ppm 0.98-1.04 (m, 4H), 2.22 (tt, J=7.88, 4.89 Hz, 1H), 7.12 (d, J=8.20 Hz, 1H), 8.01 (s, 1H), 8.05 (d, J=8.20 Hz, 1H). MS ES+m/z 160 [M+H]+.

Step 4: Intermediate 49—6-Cyclopropyl-7-oxido-1H-pyrazolo[3,4-b]pyridin-7-ium

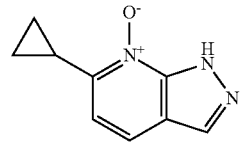 [SMILES: [O-][n+]1c(C2CC2)ccc2cn[nH]c21]

m-CPBA (954 mg, 4.15 mmol) was added portion wise to a solution of 6-cyclopropyl-1H-pyrazolo[3,4-b]pyridine (330 mg, 3.36 mmol) in DME (5 ml) at rt and the resulting mixture was stirred at rt for 3 h. The reaction mixture was washed with sat. aq. $NaHCO_3$, dried over $Na_2SO_4$, filtered and concentrated to give the product as a solid (374 mg, quant.). MS ES+m/z 176 [M+H]+.

Step 5: Intermediate 50—4-Chloro-6-cyclopropyl-1H-pyrazolo[3,4-b]pyridine

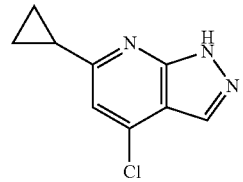 [SMILES: Clc1cc(C2CC2)nc2[nH]ncc12]

Oxalyl chloride (351 μL, 4.14 mmol) was added dropwise to a suspension of 6-cyclopropyl-7-oxido-1H-pyrazolo[3,4-b]pyridin-7-ium (363 mg, 2.07 mmol) in DMF (2 ml) at 0° C. and the resulting mixture was stirred at rt overnight. Water was added and the mixture extracted with DCM. The combined organics were dried over $Na_2SO_4$, filtered, concentrated and purified on a silica gel column eluted with 0-20% MeOH in DCM to give the product as a solid (80 mg, 20%). MS ES+m/z 194 [M+H]+.

Step 6: 1-(4-(5-(6-cyclopropyl-1H-pyrazolo[3,4-b]pyridin-4-yl)pyridin-3-yl)phenyl)pyrrolidin-2-one The title compound was prepared as described in Example 30, replacing 5-bromo-7H-pyrrolo[2,3-d]pyrimidine for 4-chloro-6-cyclopropyl-1H-pyrazolo[3,4-b]pyridine, to give the product as a solid (6 mg, 4%). 1H NMR (500 MHz, DMSO-$d_6$) δ ppm 1.03-1.14 (m, 4H), 2.10 (quin, J=7.57 Hz, 2H), 2.31-2.39 (m, 1H), 2.52-2.58 (m, 2H), 3.91 (t, J=7.09 Hz, 2H), 7.52 (s, 1H), 7.82-7.85 (m, 2H), 7.91-7.95 (m, 2H), 8.28 (s, 1H), 8.46 (t, J=2.05 Hz, 1H), 9.02 (d, J=2.21 Hz, 1H), 9.03-9.06 (m, 1H), 13.43-13.68 (m, 1H). MS ES+m/z 396 [M+H]+.

Example 64: 1-(4-(5-(6-(methylsulfonyl)-6,7-di-
hydro-5H-pyrrolo[3,4-b]pyridin-4-yl)pyridin-3-yl)
phenyl)pyrrolidin-2-one

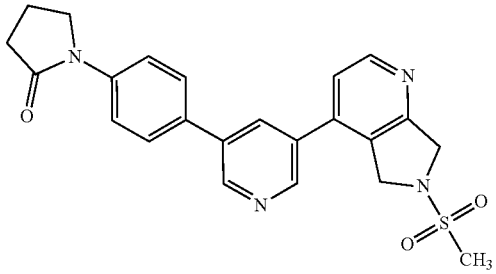 [SMILES: CS(=O)(=O)N1Cc2nccc(-c3cncc(-c4ccc(N5CCCC5=O)cc4)c3)c2C1]

Step 1: Intermediate 51—6-Methylsulfonyl-5,7-
dihydropyrrolo[3,4-b]pyridine

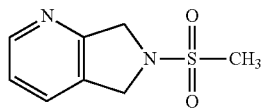

Methanesulfonyl chloride (479 μl, 6.18 mmol) was added dropwise to a solution of DIPEA (2.69 ml, 15.5 mmol) and 6,7-dihydro-5H-pyrrolo[3,4-b]pyridine×2 HCl (995 mg, 5.15 mmol) in DCM (10 ml) at −10° C. and the resulting mixture was stirred at rt overnight. Additional DCM was added and the mixture washed with sat. aq. NaHCO₃, dried over Na₂SO₄, filtered and concentrated to give the product as a solid (1.02 g, quant.). MS ES+m/z 199 [M+H]⁺.

Step 2: Intermediate 52—6-Methylsulfonyl-1-
oxido-5,7-dihydropyrrolo[3,4-b]pyridin-1-ium

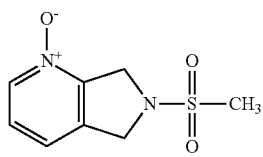

The title compound was prepared as described in Intermediate 49, replacing 6-cyclopropyl-1H-pyrazolo[3,4-b] pyridine for 6-methylsulfonyl-5,7-dihydropyrrolo[3,4-b] pyridine. Et₂O was added to the reaction mixture and the formed precipitate was filtered off and dried to give the product as a solid (751 mg, 68%). MS ES+m/z 215 [M+H]⁺.

Step 3: Intermediate 53—4-Chloro-6-methylsulfo-
nyl-5,7-dihydropyrrolo[3,4-b]pyridine

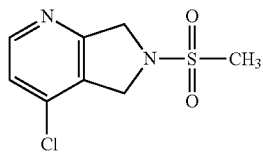

The title compound was prepared as described in Intermediate 50, replacing 6-cyclopropyl-7-oxido-1H-pyrazolo [3,4-b]pyridin-7-ium for 6-methylsulfonyl-1-oxido-5,7-dihydropyrrolo[3,4-b]pyridin-1-ium, to give the product as a solid (80 mg, 10%). MS ES+m/z 233 [M+H]⁺.

Step 4: 1-(4-(5-(6-(methylsulfonyl)-6,7-dihydro-5H-
pyrrolo[3,4-b]pyridin-4-yl)pyridin-3-yl)phenyl)pyr-
rolidin-2-one The title compound was prepared as described in Example 30, replacing 5-bromo-7H-pyrrolo[2,3-d]pyrimidine for 4-chloro-6-methylsulfonyl-5,7-dihydropyrrolo[3,4-b]pyridine, to give the product as a solid (53 mg, 38%). ¹H NMR (500 MHz, DMSO-d₆) δ ppm 2.08-2.14 (m, 2H), 2.53-2.58 (m, 2H), 3.06-3.12 (m, 3H), 3.89-3.95 (m, 2H), 4.71-4.77 (m, 2H), 4.92-4.98 (m, 2H), 7.64-7.67 (m, 1H), 7.82-7.87 (m, 2H), 7.87-7.92 (m, 2H), 8.30-8.34 (m, 1H), 8.63-8.68 (m, 1H), 8.81-8.85 (m, 1H), 9.02-9.06 (m, 1H). MS ES+m/z 435 [M+H]⁺.

Example 65: methyl 4-(5-(4-(2-oxopyrrolidin-1-yl)
phenyl)pyridin-3-yl)-5,7-dihydro-6H-pyrrolo[3,4-b]
pyridine-6-carboxylate

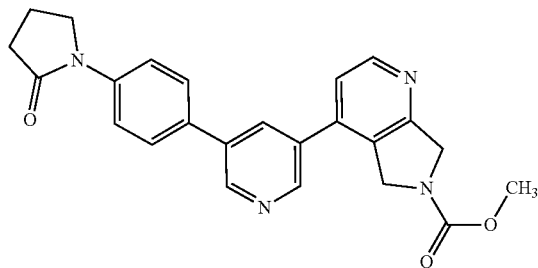 [SMILES: COC(=O)N1Cc2nccc(-c3cncc(-c4ccc(N5CCCC5=O)cc4)c3)c2C1]

Step 1: Intermediate 54—Methyl 5,7-dihydropyr-
rolo[3,4-b]pyridine-6-carboxylate

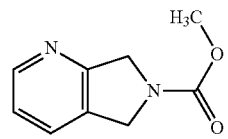

The title compound was prepared as described in Intermediate 51, replacing methanesulfonyl chloride for methyl chloroformate, to give the product as a solid (1.3 g, 97%). MS ES+m/z 179 [M+H]⁺.

Step 2: Intermediate 55—Methyl 1-oxido-5,7-dihy-
dropyrrolo[3,4-b]pyridin-1-ium-6-carboxylate

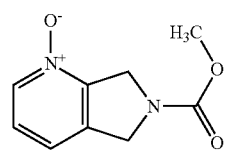

The title compound was prepared as described in Intermediate 49, replacing 6-cyclopropyl-1H-pyrazolo[3,4-b]pyridine for methyl 5,7-dihydropyrrolo[3,4-b]pyridine-6-carboxylate, to give the product as a solid (950 mg, 67%). MS ES+m/z 195 [M+H]+.

Step 3: Intermediate 56—Methyl 4-chloro-5,7-dihydropyrrolo[3,4-b]pyridine-6-carboxylate

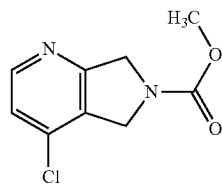

The title compound was prepared as described in Intermediate 50, replacing 6-cyclopropyl-7-oxido-1H-pyrazolo[3,4-b]pyridin-7-ium for methyl 1-oxido-5,7-dihydropyrrolo[3,4-b]pyridin-1-ium-6-carboxylate, to give the product as a solid (115 mg, 23%). MS ES+m/z 213 [M+H]+.

Step 4: methyl 4-(5-(4-(2-oxopyrrolidin-1-yl)phenyl)pyridin-3-yl)-5,7-dihydro-6H-pyrrolo[3,4-b]pyridine-6-carboxylate The title compound was prepared as described in Example 30, replacing 5-bromo-7H-pyrrolo[2,3-d]pyrimidine for methyl 4-chloro-5,7-dihydropyrrolo[3,4-b]pyridine-6-carboxylate, to give the product as a solid (59 mg, 43%). 1H NMR (500 MHz, DMSO-d6) 2.11 (quin, J=7.49 Hz, 2H), 2.53-2.57 (m, 2H), 3.64-3.74 (m, 3H), 3.91 (t, J=7.09 Hz, 2H), 4.72 (br d, J=15.13 Hz, 2H), 4.92 (br d, J=12.30 Hz, 2H), 7.61 (t, J=5.36 Hz, 1H), 7.80-7.90 (m, 4H), 8.31 (br s, 1H), 8.63 (d, J=5.04 Hz, 1H), 8.79 (br d, J=9.46 Hz, 1H), 9.03 (br s, 1H). MS ES+m/z 415 [M+H]+.

Example 66: 1-(4-(5-(5-(piperidin-3-yloxy)-1H-pyrrolo[2,3-b]pyridin-4-yl)pyridin-3-yl)phenyl)pyrrolidin-2-one

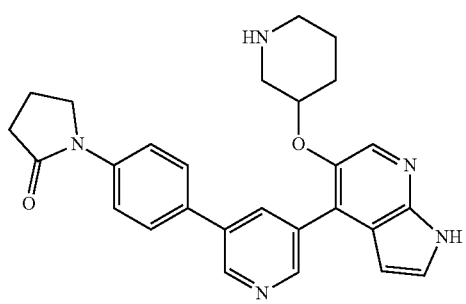 [SMILES: O=C1CCCN1c1ccc(-c2cncc(-c3c(OC4CCCNC4)cnc4[nH]ccc34)c2)cc1]

Step 1: Intermediate 57—tert-Butyl 3-(4-chloro-1-triisopropylsilyl-pyrrolo[2,3-b]pyridin-5-yl)oxypiperidine-1-carboxylate

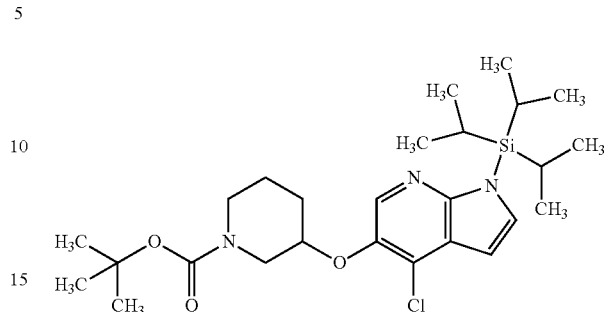

DIAD (197 μl, 1 mmol) was added dropwise to a solution of 4-chloro-1-triisopropylsilyl-pyrrolo[2,3-b]pyridin-5-ol (250 mg, 0.77 mmol), tert-butyl 3-hydroxypiperidine-1-carboxylate (201 mg, 1 mmol) and PPh3 (262 mg, 1 mmol) in toluene (2.5 ml) at rt and the resulting mixture was stirred at rt overnight. EtOAc and water were added and the organic layer was separated, concentrated and purified on a silica gel column eluted with 0-100% EtOAc in heptane to give the product as a solid (283 mg, 72%). MS ES+m/z 508 [M+H]+.

Step 2: Intermediate 58—tert-Butyl 3-[4-[5-[4-(2-oxopyrrolidin-1-yl)phenyl]-3-pyridyl]-1-triisopropylsilyl-pyrrolo[2,3-b]pyridin-5-yl]oxypiperidine-1-carboxylate

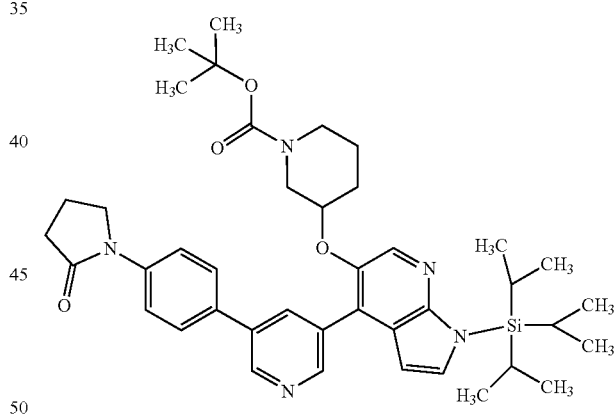

The title compound was prepared as described in Example 30, replacing 5-bromo-7H-pyrrolo[2,3-d]pyrimidine for tert-butyl 3-(4-chloro-1-triisopropylsilyl-pyrrolo[2,3-b]pyridin-5-yl)oxypiperidine-1-carboxylate. Extraction of the reaction mixture, using 1,2-dichloroethane and concentration of the organic layer gave a solid (252 mg), which was used in the next step. MS ES+m/z 710 [M+H]+.

Step 3: 1-(4-(5-(5-(piperidin-3-yloxy)-1H-pyrrolo[2,3-b]pyridin-4-yl)pyridin-3-yl)phenyl)pyrrolidin-2-one tert-Butyl 3-[4-[5-[4-(2-oxopyrrolidin-1-yl)phenyl]-3-pyridyl]-1-triisopropylsilyl-pyrrolo[2,3-b]pyridin-5-yl]oxypiperidine-1-carboxylate (crude from previous step, 252 mg) was dissolved in MeOH (2 mL) at rt, a few drops of conc. HCl was added and the mixture was stirred at rt for 2 h. 1,2-dichloroethane and sat. aq. NaHCO$_3$ were added and the organic layer separated. The aqueous layer was extracted with 1,2-dichloroethane and the combined organics were washed with brine, dried over Na$_2$SO$_4$, filtered and concentrated. The resulting residue was dissolved in DCM, a few drops of TFA was added and the mixture was stirred at rt until all Boc-groups had been deprotected. Sat. aq. NaHCO$_3$ was added and the mixture extracted with DCM. The combined organics were dried over Na$_2$SO$_4$, filtered, concentrated and purified by preparative HPLC to give the product as a solid (8 mg, 5%). $^1$H NMR (500 MHz, METHANOL-d$_4$) δ ppm 1.55-1.72 (m, 2H), 1.73-1.82 (m, 1H), 1.86-1.92 (m, 1H), 2.15-2.27 (m, 2H), 2.63 (t, J=8.04 Hz, 2H), 2.95-3.22 (m, 4H), 3.92-4.05 (m, 2H), 4.10-4.23 (m, 1H), 6.43 (d, J=3.47 Hz, 1H), 7.44-7.56 (m, 1H), 7.74-7.84 (m, 4H), 8.19-8.29 (m, 1H), 8.33-8.41 (m, 1H), 8.77-8.85 (m, 1H), 8.92 (d, J=2.21 Hz, 1H). MS ES+m/z 454 [M+H]$^+$.

Example 67: 6-benzyl-4-(5-(4-(2-oxopyrrolidin-1-yl)phenyl)pyridin-3-yl)-1,6-dihydro-7H-pyrazolo[3,4-c]pyridin-7-one

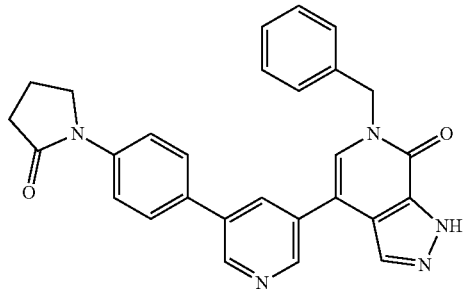 [SMILES: O=C1CCCN1c1ccc(-c2cncc(-c3cn(Cc4ccccc4)c(=O)c4[nH]ncc34)c2)cc1]

Step 1: Intermediate 61—1-Benzyl-5-bromo-4-methyl-3-nitro-pyridin-2-one

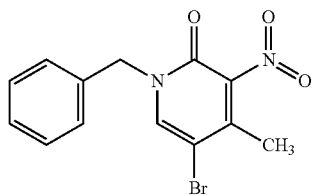 [SMILES: Cc1c(Br)cn(Cc2ccccc2)c(=O)c1[N+](=O)[O-]]

NaH (60% in mineral oil, 395 mg, 10.3 mmol) was added to a solution of 5-bromo-4-methyl-3-nitro-1H-pyridin-2-one (2 g, 8.58 mmol) in DMF (30 ml). After 15 min benzyl bromide (1.02 ml, 8.58 mmol) was added and the resulting mixture was stirred at rt overnight. The mixture was poured into ice/water and stirred for 15 min. The formed precipitate was filtered off washed with water and dried to give the product as a solid (2.57 g, 93%). MS ES+m/z 323 [M+H]$^+$.

Step 2: Intermediate 62—3-Amino-1-benzyl-5-bromo-4-methyl-pyridin-2-one

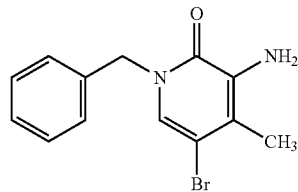 [SMILES: Cc1c(Br)cn(Cc2ccccc2)c(=O)c1N]

The title compound was prepared as described in Intermediate 29, replacing 5-bromo-1,4-dimethyl-3-nitro-pyridin-2-one for 1-benzyl-5-bromo-4-methyl-3-nitro-pyridin-2-one, to give the product as solid (2.3 g, quant). MS ES+m/z 293 [M+H]$^+$.

Step 3: Intermediate 63—N-(1-benzyl-5-bromo-4-methyl-2-oxo-3-pyridyl)acetamide

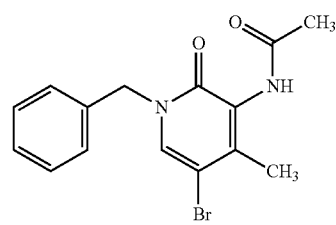 [SMILES: CC(=O)Nc1c(C)c(Br)cn(Cc2ccccc2)c1=O]

Acetic anhydride (4.3 ml, 45.5 mmol) and KOAc (937 mg, 9.55 mmol) were added to a solution of 3-amino-1-benzyl-5-bromo-4-methyl-pyridin-2-one (2.3 g, 7.95 mmol) in toluene (30 ml) and the resulting mixture was stirred at 50° C. overnight. EtOAc and brine were added and the organic layer was separated, dried over Na$_2$SO$_4$, filtered, concentrated and purified on a silica gel column eluted with 0-100% EtOAc in heptane to give the product as a solid (1.22 g, 46%). MS ES+m/z 335 [M+H]$^+$.

Step 4: Intermediate 64—6-Benzyl-4-bromo-1H-pyrazolo[3,4-c]pyridin-7-one

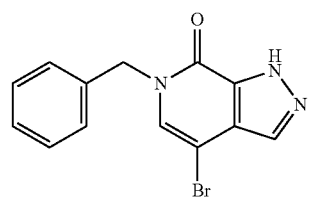 [SMILES: O=c1c2[nH]ncc2c(Br)cn1Cc1ccccc1]

N-(1-benzyl-5-bromo-4-methyl-2-oxo-3-pyridyl)acetamide (803 mg, 2.4 mmol) was dissolved in toluene (15 mL) and KOAc (282 mg, 2.87 mmol) was added followed by isoamyl nitrite (641 μl, 4.79 mmol) and acetic anhydride (450 μl, 4.79 mmol). The resulting mixture was stirred at 110° C. for 2 h. Water was added and the mixture extracted with EtOAc. The combined organics were dried over Na$_2$SO$_4$, filtered, concentrated and purified on a silica gel column eluted with 0-10% MeOH in DCM to give the product as a solid (131 mg, 18%). MS ES+m/z 304 [M+H]+.

Step 5: 6-benzyl-4-(5-(4-(2-oxopyrrolidin-1-yl)phenyl)pyridin-3-yl)-1,6-dihydro-7H-pyrazolo[3,4-c]pyridin-7-one The title compound was prepared as described in Example 30, replacing 5-bromo-7H-pyrrolo[2,3-d]pyrimidine for 6-benzyl-4-bromo-1H-pyrazolo[3,4-c]pyridin-7-one, to give the product as a solid (8 mg, 4%). $^1$H NMR (500 MHz, DMSO-$d_6$) δ ppm 2.04-2.13 (m, 2H), 2.51-2.57 (m, 2H), 3.86-3.92 (m, 2H), 5.24-5.35 (m, 2H), 7.24-7.41 (m, 6H), 7.79-7.91 (m, 4H), 8.16-8.26 (m, 2H), 8.75-8.94 (m, 2H), 14.20-14.43 (m, 1H). MS ES+m/z 462 [M+H]+.

Example 68: 6-isobutyl-4-(5-(4-(2-oxopyrrolidin-1-yl)phenyl)pyridin-3-yl)-1,6-dihydro-7H-pyrazolo[3,4-c]pyridin-7-one

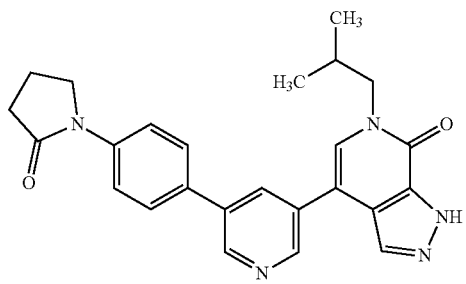 [SMILES: CC(C)Cn1cc(-c2cncc(-c3ccc(N4CCCC4=O)cc3)c2)c2cn[nH]c2c1=O]

Step 1: Intermediate 65—5-Bromo-1-isobutyl-4-methyl-3-nitro-pyridin-2-one

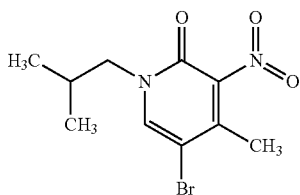 [SMILES: Cc1c(Br)cn(CC(C)C)c(=O)c1[N+](=O)[O-]]

The title compound was prepared as described in Intermediate 61, replacing benzyl bromide for 1-iodo-2-methylpropane, to give the product as solid (790 mg, 42%). MS ES+m/z 289 [M+H]+.

Step 2: Intermediate 66—3-Amino-5-bromo-1-isobutyl-4-methyl-pyridin-2-one

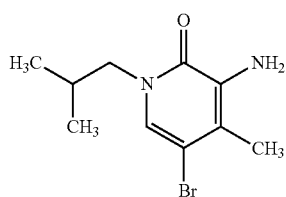

The title compound was prepared as described in Intermediate 29, replacing 5-bromo-1,4-dimethyl-3-nitro-pyridin-2-one for 5-bromo-1-isobutyl-4-methyl-3-nitro-pyridin-2-one, to give the product as solid (640 mg, 92%). MS ES+m/z 259 [M+H]+.

Step 3: Intermediate 67—N-(5-bromo-1-isobutyl-4-methyl-2-oxo-3-pyridyl)acetamide

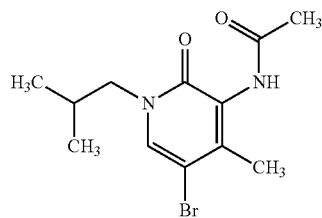 [SMILES: CC(=O)Nc1c(C)c(Br)cn(CC(C)C)c1=O]

The title compound was prepared as described in Intermediate 63, to give the product as solid (970 mg, 77%). MS ES+m/z 301 [M+H]+.

Step 4 Intermediate 68—4-Bromo-6-isobutyl-1H-pyrazolo[3,4-c]pyridin-7-one

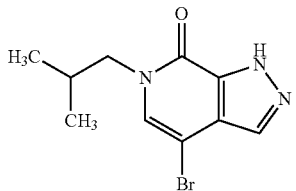

The title compound was prepared as described in Intermediate 64, to give the product as solid (238 mg, 59%). MS ES+m/z 270 [M+H]+.

Step 5: 6-isobutyl-4-(5-(4-(2-oxopyrrolidin-1-yl)phenyl)pyridin-3-yl)-1,6-dihydro-7H-pyrazolo[3,4-c]pyridin-7-one The title compound was prepared as described in Example 30, replacing 5-bromo-7H-pyrrolo[2,3-d]pyrimidine for 4-bromo-6-isobutyl-1H-pyrazolo[3,4-c]pyridin-7-one, to give the product as a solid (10 mg, 7%). $^1$H NMR (500 MHz, DMSO-$d_6$) δ ppm 0.93 (d, J=6.62 Hz, 6H), 2.07-2.25 (m, 3H), 2.53-2.59 (m, 2H), 3.87-3.99 (m, 4H), 7.65-7.73 (m, 1H), 7.77-7.96 (m, 4H), 8.21-8.29 (m, 2H), 8.85 (s, 1H), 8.89 (s, 1H), 14.29 (br s, 1H). MS ES+m/z 428 [M+H]+.

113

Example 69: 4-(5-(4-(2-oxopyrrolidin-1-yl)phenyl)pyridin-3-yl)-6-((tetrahydro-2H-pyran-4-yl)methyl)-1,6-dihydro-7H-pyrazolo[3,4-c]pyridin-7-one

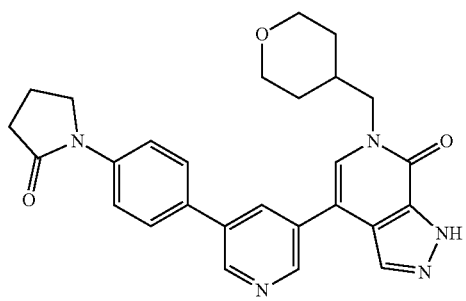 [SMILES: O=C1CCCN1c1ccc(-c2cncc(-c3cn(CC4CCOCC4)c(=O)c4[nH]ncc34)c2)cc1]

Step 1: Intermediate 69—5-Bromo-4-methyl-3-nitro-1-(tetrahydropyran-4-ylmethyl)pyridin-2-one

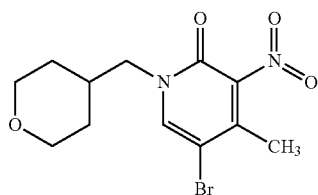 [SMILES: Cc1c(Br)cn(CC2CCOCC2)c(=O)c1[N+](=O)[O-]]

The title compound was prepared as described in Intermediate 61, replacing benzyl bromide for 4-bromomethyl tetrahydropyran, to give the product as solid (2 g, 49%). MS ES+m/z 331 [M+H]$^+$.

Step 2: Intermediate 70—3-Amino-5-bromo-4-methyl-1-(tetrahydropyran-4-ylmethyl)pyridin-2-one

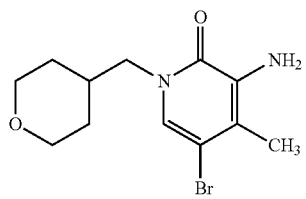 [SMILES: Cc1c(Br)cn(CC2CCOCC2)c(=O)c1N]

The title compound was prepared as described in Intermediate 29, replacing 5-bromo-1,4-dimethyl-3-nitro-pyridin-2-one for 5-bromo-4-methyl-3-nitro-1-(tetrahydropyran-4-ylmethyl)pyridin-2-one, to give the product as solid (1.6 g, 88%). MS ES+m/z 301 [M+H]$^+$.

114

Step 3: Intermediate 71—N-[5-bromo-4-methyl-2-oxo-1-(tetrahydropyran-4-ylmethyl)-3-pyridyl]acetamide

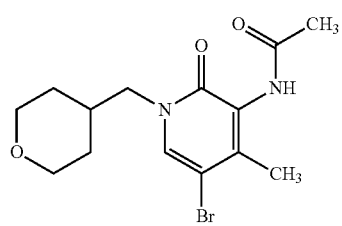 [SMILES: CC(=O)Nc1c(C)c(Br)cn(CC2CCOCC2)c1=O]

The title compound was prepared as described in Intermediate 63, to give the product as solid (1.39 g, 76%). MS ES+m/z 343 [M+H]$^+$.

Step 4: Intermediate 72—4-Bromo-6-(tetrahydropyran-4-ylmethyl)-1H-pyrazolo[3,4-c]pyridin-7-one

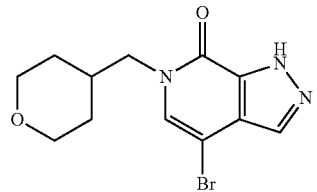 [SMILES: O=c1c2[nH]ncc2c(Br)cn1CC1CCOCC1]

The title compound was prepared as described in Intermediate 64, to give the product as solid (970 mg, 78%). MS ES+m/z 312 [M+H]$^+$.

Step 5: 4-(5-(4-(2-oxopyrrolidin-1-yl)phenyl)pyridin-3-yl)-6-((tetrahydro-2H-pyran-4-yl)methyl)-1,6-dihydro-7H-pyrazolo[3,4-c]pyridin-7-one The title compound was prepared as described in Example 30, replacing 5-bromo-7H-pyrrolo[2,3-d]pyrimidine for 4-bromo-6-(tetrahydropyran-4-ylmethyl)-1H-pyrazolo[3,4-c]pyridin-7-one, to give the product as a solid (30 mg, 19%). $^1$H NMR (500 MHz, DMSO-d$_6$) δ ppm 1.35 (qd, J=12.09, 4.41 Hz, 2H), 1.50 (br d, J=11.35 Hz, 2H), 2.06-2.19 (m, 3H), 2.53-2.59 (m, 2H), 3.22-3.30 (m, 2H), 3.75-3.96 (m, 4H), 3.98-4.08 (m, 2H), 7.72 (s, 1H), 7.76-7.91 (m, 4H), 8.19-8.27 (m, 2H), 8.83-8.92 (m, 2H), 14.25-14.34 (m, 1H). MS ES+m/z 470 [M+H]$^+$.

Example 70: 1-methyl-4-(5-(4-(2-oxopyrrolidin-1-yl)phenyl)pyridin-3-yl)-6-((tetrahydro-2H-pyran-4-yl)methyl)-1,6-dihydro-7H-pyrazolo[3,4-c]pyridin-7-one

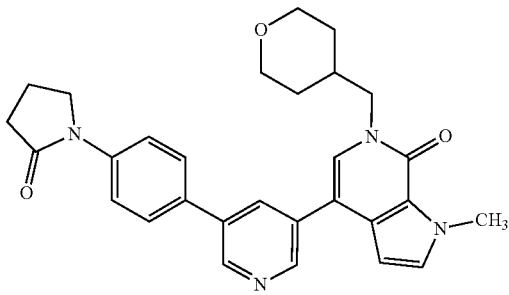 [SMILES: Cn1ccc2c(-c3cncc(-c4ccc(N5CCCC5=O)cc4)c3)cn(CC3CCOCC3)c(=O)c21]

Step 1: Intermediate 73—4-Bromo-1-methyl-6-(tetrahydropyran-4-ylmethyl)pyrazolo[3,4-c]pyridin-7-one

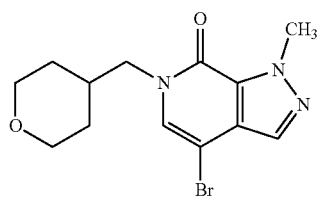 [SMILES: Cn1ncc2c(Br)cn(CC3CCOCC3)c(=O)c21]

1M LHMDS in THF (1.92 ml, 1.92 mmol) was added to a solution of 4-bromo-6-(tetrahydropyran-4-ylmethyl)-1H-pyrazolo[3,4-c]pyridin-7-one (500 mg, 1.6 mmol) in THF (4.5 ml) at rt. After 15 min iodomethane (0.12 ml, 1.92 mmol) was added and the resulting mixture was stirred at rt overnight. Water was added and the mixture extracted with EtOAc. The combined organics were dried over $Na_2SO_4$, filtered, concentrated and purified on a silica gel column eluted with 0-12% MeOH in DCM to give the product as a solid (280 mg, 45%). MS ES+m/z 326 $[M+H]^+$.

Step 2: 1-methyl-4-(5-(4-(2-oxopyrrolidin-1-yl)phenyl)pyridin-3-yl)-6-((tetrahydro-2H-pyran-4-yl)methyl)-1,6-dihydro-7H-pyrazolo[3,4-c]pyridin-7-one The title compound was prepared as described in Example 30, replacing 5-bromo-7H-pyrrolo[2,3-d]pyrimidine for 4-bromo-1-methyl-6-(tetrahydropyran-4-ylmethyl)pyrazolo[3,4-c]pyridin-7-one, to give the product as a solid (50 mg, 34%). $^1$H NMR (500 MHz, DMSO-$d_6$) δ ppm, 1.33 (qd, J=12.14, 4.26 Hz, 2H), 1.49 (br d, J=12.30 Hz, 2H), 2.11 (quin, J=7.57 Hz, 3H), 2.53-2.58 (m, 2H), 3.21-3.30 (m, 2H), 3.85 (br d, J=8.83 Hz, 2H), 3.88-3.97 (m, 4H), 4.13 (s, 3H), 7.62 (s, 1H), 7.81-7.91 (m, 4H), 8.21 (t, J=2.05 Hz, 1H), 8.52 (s, 1H), 8.81 (d, J=1.89 Hz, 1H), 8.87 (d, J=1.89 Hz, 1H). MS ES+m/z 484 $[M+H]^+$.

Example 71: N-methyl-3-(5-(4-(2-oxopyrrolidin-1-yl)phenyl)pyridin-3-yl)-1H-pyrrolo[2,3-b]pyridine-5-carboxamide

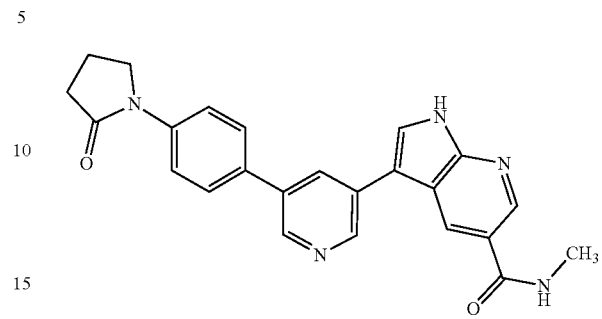

Step 1: Intermediate 74—3-Bromo-N-methyl-1H-pyrrolo[2,3-b]pyridine-5-carboxamide

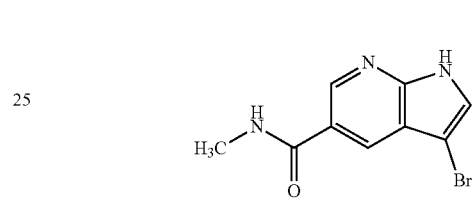

The title compound was prepared as described in Intermediate 41, replacing 3-bromo-1-methyl-pyrrolo[2,3-b]pyridine-5-carboxylic acid for 3-bromo-1H-pyrrolo[2,3-b]pyridine-5-carboxylic acid, to give the product as a solid (1.02 g, 81%). MS ES+m/z 254 $[M+H]^+$.

Step 2: N-methyl-3-(5-(4-(2-oxopyrrolidin-1-yl)phenyl)pyridin-3-yl)-1H-pyrrolo[2,3-b]pyridine-5-carboxamide The title compound was prepared as described in Example 30, replacing 5-bromo-7H-pyrrolo[2,3-d]pyrimidine for 3-bromo-N-methyl-1H-pyrrolo[2,3-b]pyridine-5-carboxamide, to give the product as a solid (8 mg, 6%). $^1$H NMR (500 MHz, DMSO-$d_6$) δ ppm 2.11 (quin, J=7.57 Hz, 2H), 2.52-2.57 (m, 2H), 2.85 (d, J=4.41 Hz, 3H), 3.92 (t, J=7.09 Hz, 2H), 7.83-7.91 (m, 4H), 8.25 (s, 1H), 8.37 (t, J=2.05 Hz, 1H), 8.62-8.68 (m, 1H), 8.79-8.84 (m, 3H), 9.03 (d, J=2.21 Hz, 1H), 12.36 (br s, 1H). MS ES+m/z 412 $[M+H]^+$.

Example 72: N,N-dimethyl-3-(5-(4-(2-oxopyrrolidin-1-yl)phenyl)pyridin-3-yl)-1H-pyrrolo[2,3-b]pyridine-5-carboxamide

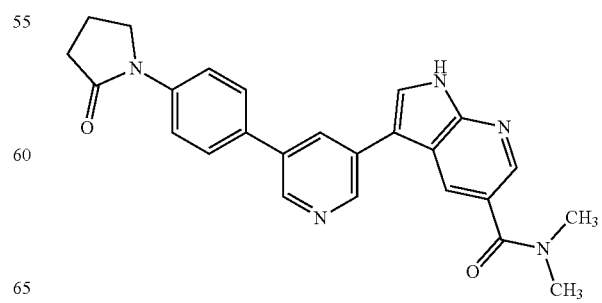

Step 1: Intermediate 75—3-Bromo-N,N-dimethyl-1H-pyrrolo[2,3-b]pyridine-5-carboxamide

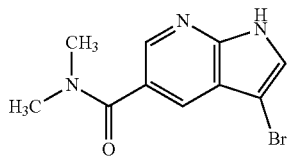

The title compound was prepared as described in Intermediate 41, replacing methylamine for dimethylamine (aq. 40%), to give the product as a solid (840 mg, 63%). MS ES+m/z 268 [M+H]+.

Step 2: N,N-dimethyl-3-(5-(4-(2-oxopyrrolidin-1-yl)phenyl)pyridin-3-yl)-1H-pyrrolo[2,3-b]pyridine-5-carboxamide The title compound was prepared as described in Example 30, replacing 5-bromo-7H-pyrrolo[2,3-d]pyrimidine for 3-bromo-N,N-dimethyl-1H-pyrrolo[2,3-b]pyridine-5-carboxamide, to give the product as a solid (18 mg, 13%). $^1$H NMR (500 MHz, DMSO-$d_6$) δ ppm 2.11 (quin, J=7.57 Hz, 2H), 2.52-2.57 (m, 2H), 3.04 (s, 6H), 3.92 (t, J=7.09 Hz, 2H), 7.81-7.90 (m, 4H), 8.23 (s, 1H), 8.33 (t, J=2.21 Hz, 1H), 8.39 (d, J=7.75 Hz, 2H), 8.80 (d, J=2.21 Hz, 1H), 8.94 (d, J=2.21 Hz, 1H), 12.33 (br s, 1H). MS ES+m/z 426 [M+H]+.

Example 73: 1-(4-(5-(7-methoxy-1H-pyrazolo[3,4-c]pyridin-4-yl)pyridin-3-yl)phenyl)pyrrolidin-2-one

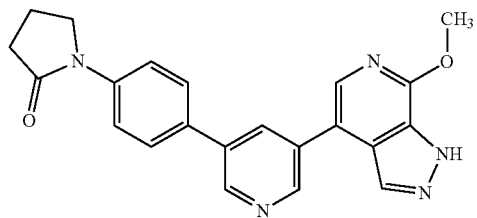 [SMILES: COc1ncc(-c2cncc(-c3ccc(N4CCCC4=O)cc3)c2)c2cn[nH]c12]

Step 1: Intermediate 75—4-Bromo-7-methoxy-1H-pyrazolo[3,4-c]pyridine

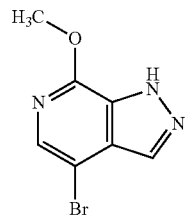

The title compound was prepared as described in Intermediate 30, replacing 3-amino-5-bromo-1,4-dimethyl-pyridin-2-one for 5-bromo-2-methoxy-4-methyl-pyridin-3-amine, to give the product as a solid (430 mg, 82%). MS ES+m/z 228 [M+H]+.

Step 2: 1-(4-(5-(7-methoxy-1H-pyrazolo[3,4-c]pyridin-4-yl)pyridin-3-yl)phenyl)pyrrolidin-2-one The title compound was prepared as described in Example 30, replacing 5-bromo-7H-pyrrolo[2,3-d]pyrimidine for 4-bromo-7-methoxy-1H-pyrazolo[3,4-c]pyridine, to give the product as a solid (75 mg, 50%). $^1$H NMR (500 MHz, DMSO-$d_6$) δ ppm 2.06-2.14 (m, 2H), 2.51-2.56 (m, 2H), 3.90 (t, J=7.09 Hz, 2H), 4.14 (s, 3H), 7.80-7.85 (m, 2H), 7.88-7.93 (m, 2H), 8.05 (s, 1H), 8.30-8.35 (m, 1H), 8.38 (d, J=1.58 Hz, 1H), 8.90 (d, J=2.21 Hz, 1H), 8.94 (d, J=2.21 Hz, 1H), 14.01-14.20 (m, 1H). MS ES+m/z 386 [M+H]+.

Example 74: 4-(5-(4-(2-oxopyrrolidin-1-yl)phenyl)pyridin-3-yl)-1,6-dihydro-7H-pyrazolo[3,4-c]pyridin-7-one

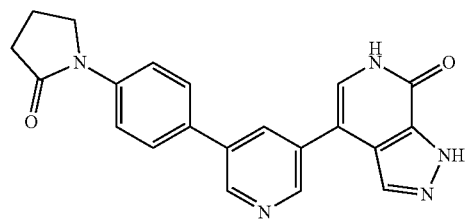 [SMILES: O=C1CCCN1c1ccc(-c2cncc(-c3c[nH]c(=O)c4[nH]ncc34)c2)cc1]

NaI (19 mg, 0.13 mmol) and TMSCl (17 μl, 0.14 mmol) were added to a solution of 1-(4-(5-(7-methoxy-1H-pyrazolo[3,4-c]pyridin-4-yl)pyridin-3-yl)phenyl)pyrrolidin-2-one (50 mg, 0.13 mmol) in MeCN (3 ml) and the resulting mixture was stirred at 60° C. overnight. The formed precipitate was filtered off, washed sequentially with EtOAc, DCM, MeOH, 2-propanol and dried to give the product as a solid (19 mg, 39%). $^1$H NMR (500 MHz, DMSO-$d_6$) δ ppm 2.07-2.13 (m, 2H), 2.52-2.56 (m, 2H), 3.88-3.92 (m, 2H), 7.33-7.39 (m, 1H), 7.79-7.83 (m, 2H), 7.86-7.90 (m, 2H), 8.12-8.27 (m, 2H), 8.77-8.91 (m, 2H), 11.60-11.79 (m, 1H), 14.16-14.33 (m, 1H). MS ES+m/z 372 [M+H]+.

Example 75: 1-(4-(5-(6-methoxy-1H-pyrazolo[3,4-b]pyridin-4-yl)pyridin-3-yl)phenyl)pyrrolidin-2-one

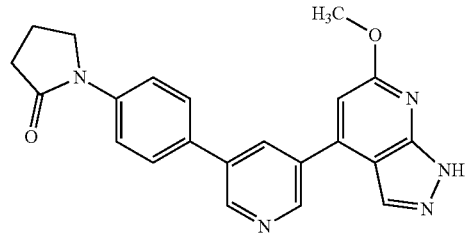 [SMILES: COc1cc(-c2cncc(-c3ccc(N4CCCC4=O)cc3)c2)c2cn[nH]c2n1]

Step 1 Intermediate 76—6-Methoxy-7-oxido-1H-pyrazolo[3,4-b]pyridin-7-ium

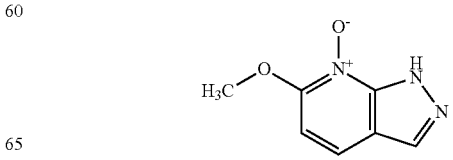

The title compound was prepared as described in Intermediate 49, replacing 6-cyclopropyl-1H-pyrazolo[3,4-b]pyridine for 6-methoxy-1H-pyrazolo[3,4-b]pyridine, to give the product as a solid (286 mg, quant.). MS ES+m/z 166 [M+H]⁺.

Step 2: Intermediate 77—4-Chloro-6-methoxy-1H-pyrazolo[3,4-b]pyridine

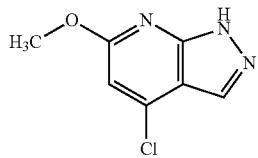

The title compound was prepared as described in Intermediate 50, replacing 6-cyclopropyl-7-oxido-1H-pyrazolo[3,4-b]pyridin-7-ium for 6-methoxy-7-oxido-1H-pyrazolo[3,4-b]pyridin-7-ium, to give the product as a solid (23 mg, 10%). MS ES+m/z 184 [M+H]⁺.

Step 3: 1-(4-(5-(6-methoxy-1H-pyrazolo[3,4-b]pyridin-4-yl)pyridin-3-yl)phenyl)pyrrolidin-2-one The title compound was prepared as described in Example 30, replacing 5-bromo-7H-pyrrolo[2,3-d]pyrimidine for 4-chloro-6-methoxy-1H-pyrazolo[3,4-b]pyridine, to give the product as a solid (2 mg, 3%). ¹H NMR (500 MHz, DMSO-d₆) δ ppm 2.09 (quin, J=7.57 Hz, 2H), 2.51-2.55 (m, 2H), 3.87-3.93 (m, 2H), 3.98 (s, 3H), 7.77-7.84 (m, 4H), 8.05 (s, 1H), 8.20 (t, J=2.21 Hz, 1H), 8.30 (s, 1H), 8.71 (d, J=2.21 Hz, 1H), 8.87 (d, J=2.21 Hz, 1H), 13.49 (s, 1H). MS ES+m/z 386 [M+H]⁺.

Example 76: 1-methyl-4-(5-(4-(2-oxopyrrolidin-1-yl)phenyl)pyridin-3-yl)-1,3-dihydro-2H-pyrrolo[2,3-b]pyridin-2-one

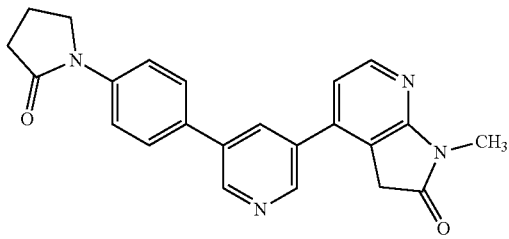 [SMILES: CN1C(=O)Cc2c(-c3cncc(-c4ccc(N5CCCC5=O)cc4)c3)ccnc21]

Step 1: Intermediate 78—3,3-Dibromo-4-chloro-1-methyl-pyrrolo[2,3-b]pyridin-2-one

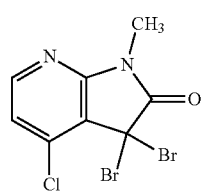

Pyridinium perbromide (7.08 g, 22.1 mmol) was added portion wise over 30 min to a solution of 4-chloro-1-methyl-pyrrolo[2,3-b]pyridine (1.23 g, 7.38 mmol) in t-BuOH (60 ml) at rt and the resulting mixture was stirred at rt for 1.5 h. EtOAc (150 ml) was added and the mixture was washed with water, brine, dried over Na₂SO₄, filtered and concentrated to give the product as a solid (2.4 g, 96%). MS ES+m/z 339 [M+H]⁺.

Step 2: Intermediate 79—4-Chloro-1-methyl-3H-pyrrolo[2,3-b]pyridin-2-one

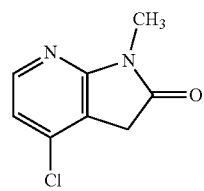

Zinc (4.61 g, 70.5 mmol) was added in portions over 10 min to a solution of 3,3-dibromo-4-chloro-1-methyl-pyrrolo[2,3-b]pyridin-2-one (2.4 g, 7.05 mmol) in MeCN (30 ml) and AcOH (20 ml) at 0° C. The resulting mixture was stirred at 0° C. for 1 h. The mixture was filtered through celite and the filtrate concentrated. The resulting residue was dissolved in EtOAc and washed with sat. aq. NaHCO₃ (3×), dried over Na₂SO₄, filtered and concentrated. Recrystallization from Et₂O gave the product as a solid (815 mg, 63%). MS ES+m/z 183 [M+H]⁺.

Step 3: 1-methyl-4-(5-(4-(2-oxopyrrolidin-1-yl)phenyl)pyridin-3-yl)-1,3-dihydro-2H-pyrrolo[2,3-b]pyridin-2-one The title compound was prepared as described in Example 30, replacing 5-bromo-7H-pyrrolo[2,3-d]pyrimidine for 4-chloro-1-methyl-3H-pyrrolo[2,3-b]pyridin-2-one, to give the product as a solid (68 mg, 52%). ¹H NMR (500 MHz, DMSO-d₆) δ ppm 2.11 (quin, J=7.57 Hz, 2H), 2.52-2.57 (m, 2H), 3.17-3.22 (m, 3H), 3.91 (t, J=6.94 Hz, 2H), 3.97 (s, 2H), 7.36 (d, J=5.36 Hz, 1H), 7.81-7.90 (m, 4H), 8.31 (d, J=5.55 Hz, 1H), 8.34 (s, 1H), 8.87 (d, J=2.21 Hz, 1H), 9.01 (d, J=2.21 Hz, 1H). MS ES+m/z 385 [M+H]⁺.

Example 77: 1-(1-methyl-3-(5-(4-(2-oxopyrrolidin-1-yl)phenyl)pyridin-3-yl)-1H-pyrrolo[2,3-b]pyridin-5-yl)pyrrolidin-2-one

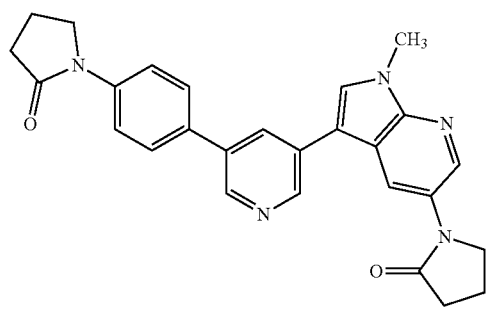 [SMILES: Cn1cc(-c2cncc(-c3ccc(N4CCCC4=O)cc3)c2)c2cc(N3CCCC3=O)cnc21]

Step 1: Intermediate 80—3-Iodo-1-methyl-pyrrolo[2,3-b]pyridin-5-amine

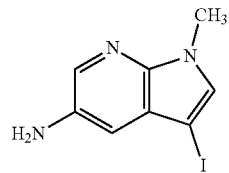

The title compound was prepared as described in Intermediate 29, replacing 5-bromo-1,4-dimethyl-3-nitro-pyridin-2-one for 3-iodo-1-methyl-5-nitro-2,3-dihydropyrrolo[2,3-b]pyridine, to give the product as solid (1.29 g, 95%). MS ES+m/z 274 [M+H]+.

Step 2: Intermediate 81—4-Chloro-N-(3-iodo-1-methyl-pyrrolo[2,3-b]pyridin-5-yl)butanamide

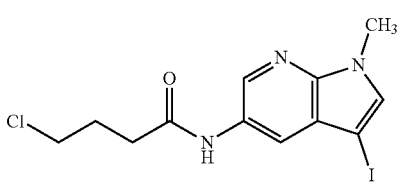 [SMILES: Cn1cc(I)c2cc(NC(=O)CCCCl)cnc21]

4-Chlorobutyryl chloride (0.78 ml, 6.98 mmol) was added drop wise to a solution of 3-iodo-1-methyl-pyrrolo[2,3-b]pyridin-5-amine (1.29 g, 5.59 mmol) and TEA (1.17 ml, 8.38 mmol) in DCM (25 ml) at 0° C. and the resulting mixture was stirred for 1 h. EtOAc and brine were added, the organic layer was separated and washed with sat. aq. NaHCO3, dried over Na2SO4, filtered and concentrated to give the product as a solid (2 g, 95%). MS ES+m/z 378 [M+H]+.

Step 3: Intermediate 82—1-(3-Iodo-1-methyl-pyrrolo[2,3-b]pyridin-5-yl)pyrrolidin-2-one

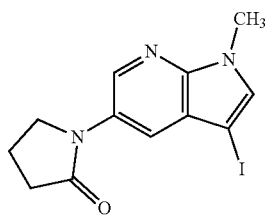 [SMILES: Cn1cc(I)c2cc(N3CCCC3=O)cnc21]

KOtBu (743 mg, 6.62 mmol) was added to a solution of 4-chloro-N-(3-iodo-1-methyl-pyrrolo[2,3-b]pyridin-5-yl)butanamide (2 g, 5.30 mmol) in THF (25 ml) at 0° C. and the resulting mixture was stirred for 1 h. Water was added, the mixture neutralized using aq. 5% citric acid and extracted with EtOAc (3×). The combined organics were washed with brine, dried over Na2SO4, filtered and concentrated. Recrystallization from EtOAc gave the product as a solid (720 mg, 40%). MS ES+m/z 342 [M+H]+.

Step 4: 1-(1-methyl-3-(5-(4-(2-oxopyrrolidin-1-yl)phenyl)pyridin-3-yl)-1H-pyrrolo[2,3-b]pyridin-5-yl)pyrrolidin-2-one The title compound was prepared as described in Example 30, replacing 5-bromo-7H-pyrrolo[2,3-d]pyrimidine for 1-(3-iodo-1-methyl-pyrrolo[2,3-b]pyridin-5-yl)pyrrolidin-2-one, to give the product as a solid (59 mg, 38%). 1H NMR (500 MHz, DMSO-d6) δ ppm 2.12 (dquin, J=12.00, 7.56, 7.56, 7.56, 7.56 Hz, 4H), 2.52-2.57 (m, 4H), 3.89-4.06 (m, 7H), 7.80-7.90 (m, 4H), 8.22 (s, 1H), 8.28 (t, J=2.21 Hz, 1H), 8.58 (d, J=2.21 Hz, 1H), 8.60 (d, J=2.21 Hz, 1H), 8.80 (d, J=2.21 Hz, 1H), 8.90 (d, J=2.21 Hz, 1H). MS ES+m/z 452 [M+H]+.

Example 78: 4-[5-[4-(2-Oxopyrrolidin-1-yl)phenyl]-3-pyridyl]-5,6-dihydropyrrolo[3,4-b]pyridin-7-one

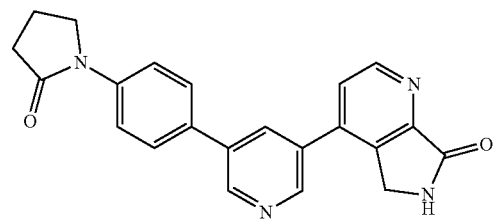 [SMILES: O=C1NCc2c(-c3cncc(-c4ccc(N5CCCC5=O)cc4)c3)ccnc21]

Step 1: Intermediate 83—4-Chloro-5,6-dihydropyrrolo[3,4-b]pyridin-7-one

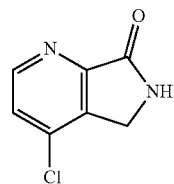 [SMILES: O=C1NCc2c(Cl)ccnc21]

Aq. 25% NH3 (0.5 ml) was added to a solution of methyl 3-(bromomethyl)-4-chloro-2,3-dihydropyridine-2-carboxylate (660 mg, 2.47 mmol) in THF (5 ml) and the resulting mixture was stirred at 70° C. for 2 h. Additional aq. 25% NH3 (2 ml) was added and the reaction was stirred for 2 h at 70° C. The mixture was concentrated and the resulting residue was purified on a silica gel column eluted with 0-10% MeOH in DCM to give the product as a solid (370 mg, 89%). MS ES+m/z 169 [M+H]+.

Step 2: 4-[5-[4-(2-Oxopyrrolidin-1-yl)phenyl]-3-pyridyl]-5,6-dihydropyrrolo[3,4-b]pyridin-7-one The title compound was prepared as described in Example 30, replacing 5-bromo-7H-pyrrolo[2,3-d]pyrimidine for 4-chloro-5,6-dihydropyrrolo[3,4-b]pyridin-7-one, to give the product as a solid (60 mg, 47%). 1H NMR (500 MHz, DMSO-d6) δ ppm 2.11 (quin, J=7.57 Hz, 2H), 2.53-2.57 (m, 2H), 3.91 (t, J=7.09 Hz, 2H), 4.72 (s, 2H), 7.81-7.87 (m, 2H), 7.87-7.93 (m, 3H), 8.41 (t, J=2.05 Hz, 1H), 8.87 (d, J=5.52 Hz, 1H), 8.91 (s, 1H), 9.05 (d, J=1.89 Hz, 1H), 9.14 (s, 1H). MS ES+m/z 371 [M+H]+.

Example 79: N-(cyclopropylmethyl)-4-(5-(4-(2-oxopyrrolidin-1-yl)phenyl)pyridin-3-yl)furo[2,3-b]pyridine-2-carboxamide

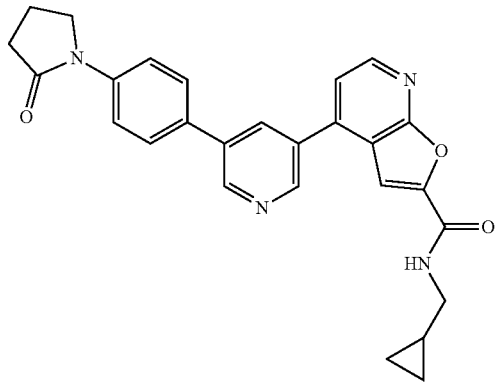 [SMILES: O=C(NCC1CC1)c1cc2c(-c3cncc(-c4ccc(N5CCCC5=O)cc4)c3)ccnc2o1]

Step 1: Intermediate 84—4-Chloro-N-(cyclopropylmethyl)furo[2,3-b]pyridine-2-carboxamide

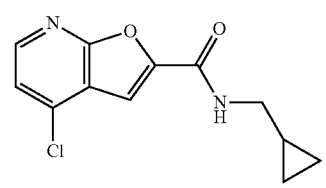 [SMILES: O=C(NCC1CC1)c1cc2c(Cl)ccnc2o1]

The title compound was prepared as described in Intermediate 7, replacing methylamine for aminomethyl cyclopropane, to give the product as a solid (102 mg, quant.). MS ES+m/z 251 [M+H]$^+$.

Step 2: N-(cyclopropylmethyl)-4-(5-(4-(2-oxopyrrolidin-1-yl)phenyl)pyridin-3-yl)furo[2,3-b]pyridine-2-carboxamide The title compound was prepared as described in Example 30, replacing 5-bromo-7H-pyrrolo[2,3-d]pyrimidine for 4-chloro-N-(cyclopropylmethyl)furo[2,3-b]pyridine-2-carboxamide, to give the product as a solid (32 mg, 39%). $^1$H NMR (500 MHz, DMSO-d$_6$) δ ppm 0.24-0.28 (m, 2H), 0.43-0.47 (m, 2H), 1.02-1.10 (m, 1H), 2.10 (dt, J=14.90, 7.53 Hz, 2H), 2.51-2.58 (m, 2H), 3.17 (t, J=6.31 Hz, 2H), 3.91 (t, J=7.09 Hz, 2H), 7.81-7.84 (m, 2H), 7.84-7.86 (m, 2H), 7.91-7.94 (m, 2H), 8.46 (t, J=2.21 Hz, 1H), 8.59 (d, J=5.04 Hz, 1H), 8.96-9.01 (m, 2H), 9.08 (d, J=2.21 Hz, 1H). MS ES+m/z 453 [M+H]$^+$.

Example 80: N-(2-methoxyethyl)-4-(5-(4-(2-oxopyrrolidin-1-yl)phenyl)pyridin-3-yl)furo[2,3-b]pyridine-2-carboxamide

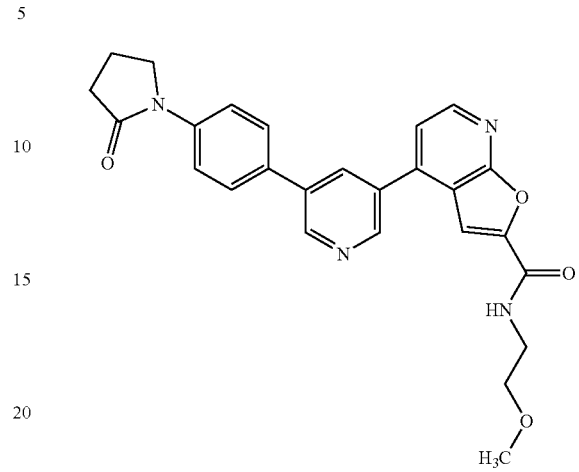

Step 1: Intermediate 85—4-Chloro-N-(2-methoxyethyl)furo[2,3-b]pyridine-2-carboxamide

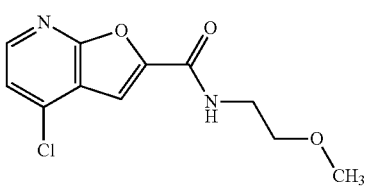

The title compound was prepared as described in Intermediate 7, replacing methylamine for 2-methoxyethylamine, to give the product as a solid (103 mg, quant.). MS ES+m/z 255 [M+H]$^+$.

Step 2: N-(2-methoxyethyl)-4-(5-(4-(2-oxopyrrolidin-1-yl)phenyl)pyridin-3-yl)furo[2,3-b]pyridine-2-carboxamide The title compound was prepared as described in Example 30, replacing 5-bromo-7H-pyrrolo[2,3-d]pyrimidine for 4-chloro-N-(2-methoxyethyl)furo[2,3-b]pyridine-2-carboxamide, to give the product as a solid (20 mg, 25%). $^1$H NMR (500 MHz, DMSO-d$_6$) δ ppm 2.05-2.14 (m, 2H), 2.54 (t, J=8.04 Hz, 2H), 3.27-3.29 (s, 3H), 3.44-3.50 (m, 4H), 3.90 (t, J=7.09 Hz, 2H), 7.80-7.83 (m, 2H), 7.83-7.85 (m, 1H), 7.87 (s, 1H), 7.89-7.93 (m, 2H), 8.44 (t, J=2.05 Hz, 1H), 8.58 (d, J=5.04 Hz, 1H), 8.92 (t, J=5.36 Hz, 1H), 8.97 (d, J=2.21 Hz, 1H), 9.07 (d, J=1.89 Hz, 1H). MS ES+m/z 457 [M+H]$^+$.

Example 81: 1-(4-([3,4'-bipyridin]-5-yl)-3-methylphenyl)pyrrolidin-2-one

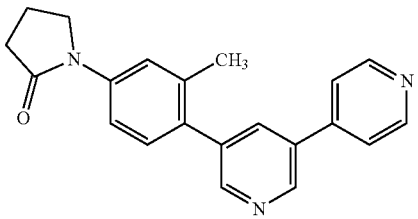 [SMILES: Cc1cc(N2CCCC2=O)ccc1-c1cncc(-c2ccncc2)c1]

Step 1: Intermediate 86—1-[3-Methyl-4-(4,4,5,5-tetramethyl-1,3,2-dioxaborolan-2-yl)phenyl]pyrrolidin-2-one

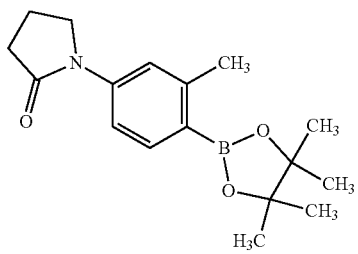 [SMILES: Cc1cc(N2CCCC2=O)ccc1B1OC(C)(C)C(C)(C)O1]

1-(4-Bromo-3-methyl-phenyl)pyrrolidin-2-one (1.36 g, 5.35 mmol), 4,4,5,5-tetramethyl-2-(4,4,5,5-tetramethyl-1,3,2-dioxaborolan-2-yl)-1,3,2-dioxaborolane (1.49 g, 5.89 mmol) and KOAc (1.57 g, 16 mmol) were taken up in toluene (15 ml) and degassed with nitrogen for 5 min. PdCl$_2$(dppf) (116 mg, 0.16 mmol) was added and the resulting mixture was stirred at 110° C. for 2 h. When cooled to rt 1,2-dichloroethane and water were added, the organic layer separated and the aqueous layer extracted with 1,2-dichloroethane. The combined organics were dried over Na$_2$SO$_4$, filtered and concentrated. The resulting residue was dissolved in a small amount of 1,2-dichloroethane and filtered through celite. To the filtrate was added Et$_2$O and the formed precipitate was filtered off and dried to give the product as a solid (330 mg, 21%). MS ES+m/z 302 [M+H]$^+$.

Step 2: 1-(4-([3,4'-bipyridin]-5-yl)-3-methylphenyl)pyrrolidin-2-one

1-[3-Methyl-4-(4,4,5,5-tetramethyl-1,3,2-dioxaborolan-2-yl)phenyl]pyrrolidin-2-one (150 mg, 0.5 mmol) and 3,5-dibromopyridine (121 mg, 0.51 mmol) were dissolved in 1,4-dioxane (1 ml) and water (0.1 ml) and degassed with nitrogen. PdCl$_2$(PPh$_3$)$_2$ (18 mg, 0.02 mmol) and K$_2$CO$_3$ (138 mg, 1 mmol) were added and the mixture was stirred at 100° C. for 2 h. When cooled to rt 1,2-dichloroethane and water were added, the organic layer separated and the aqueous layer extracted with 1,2-dichloroethane. The combined organics were dried over Na$_2$SO$_4$, filtered and concentrated. The resulting residue was taken up in 1,4-dioxane (1 ml) and water (0.1 ml). 4-Pyridylboronic acid (61 mg, 0.5 mmol) was added followed by PdCl$_2$(Amphos) (18 mg, 0.02 mmol) and K$_2$CO$_3$ (138 mg, 1 mmol) and the resulting mixture was stirred at 100° C. for 2 h. When cooled to rt 1,2-dichloroethane and water were added, the organic layer separated and the aqueous layer extracted with 1,2-dichloroethane. The combined organics were dried over Na$_2$SO$_4$, filtered, concentrated and purified by preparative HPLC to give the product as a solid (14 mg, 9%). $^1$H NMR (500 MHz, METHANOL-d$_4$) δ ppm 2.16-2.23 (m, 2H), 2.31-2.35 (m, 3H), 2.59-2.65 (m, 2H), 3.93-3.99 (m, 2H), 7.28-7.34 (m, 1H), 7.55-7.60 (m, 1H), 7.61-7.65 (m, 1H), 7.80-7.86 (m, 2H), 8.17 (t, J=2.21 Hz, 1H), 8.60 (d, J=2.21 Hz, 1H), 8.63-8.69 (m, 2H), 8.92 (d, J=2.21 Hz, 1H). MS ES+m/z 330 [M+H]$^+$.

Example 82: 1-(4-(4-methyl-[3,4'-bipyridin]-5-yl)phenyl)pyrrolidin-2-one

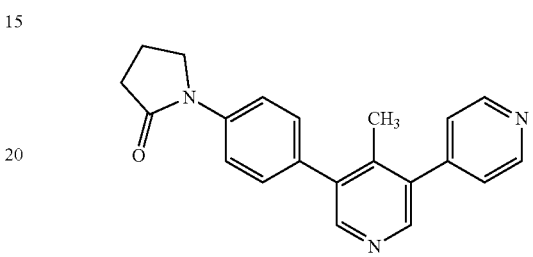

The title compound was prepared as described in Example 81, replacing 1-[3-Methyl-4-(4,4,5,5-tetramethyl-1,3,2-dioxaborolan-2-yl)phenyl]pyrrolidin-2-one for 1-[4-(4,4,5,5-tetramethyl-1,3,2-dioxaborolan-2-yl)phenyl]pyrrolidin-2-one and 3,5-dibromopyridine for 3,5-dibromo-4-methylpyridine, to give the product as a solid (82 mg, 20%). $^1$H NMR (500 MHz, DMSO-d$_6$) δ ppm 2.04-2.13 (m, 2H), 2.14-2.18 (m, 3H), 2.51-2.56 (m, 2H), 3.84-3.94 (m, 2H), 7.42-7.49 (m, 2H), 7.50-7.54 (m, 2H), 7.76-7.83 (m, 2H), 8.41 (s, 1H), 8.42-8.47 (m, 1H), 8.66-8.74 (m, 2H). MS ES+m/z 330 [M+H]$^+$.

Example 83: 1-(4-(4-(methoxymethyl)-[3,4'-bipyridin]-5-yl)phenyl)pyrrolidin-2-one

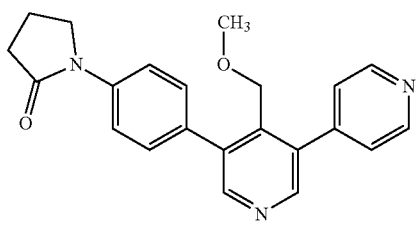 [SMILES: COCc1c(-c2ccncc2)cncc1-c1ccc(N2CCCC2=O)cc1]

Step 1: Intermediate 87—3-Bromo-5-chloro-4-(methoxymethyl)pyridine

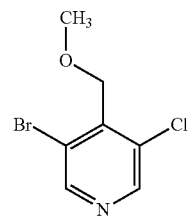

NaBH₄ (86 mg, 2.27 mmol) was added to a solution of 3-bromo-5-chloro-pyridine-4-carbaldehyde (250 mg, 1.13 mmol) in MeOH (10 mL) at 0° C. and the resulting mixture was stirred for 2 h. The mixture was concentrated and the resulting residue was dissolved in EtOAc, washed with brine, dried over Na₂SO₄, filtered and concentrated. The residue was dissolved in THF (3 ml) and NaH (60% in mineral oil, 87 mg, 2.27 mmol) was added at rt. After 10 min iodomethane (141 μl, 2.27 mmol) was added and the reaction mixture was stirred at rt overnight. Water was added, the organic layer separated, dried over Na₂SO₄, filtered and concentrated to give the product (213 mg, 79%). MS ES+m/z 236 [M+H]⁺.

Step 2: Intermediate 88—1-[4-[5-Chloro-4-(methoxymethyl)-3-pyridyl]phenyl]pyrrolidin-2-one

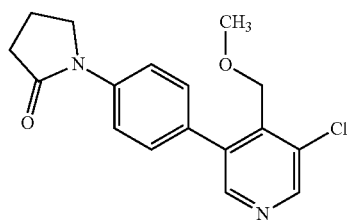 [SMILES: COCc1c(Cl)cncc1-c1ccc(N2CCCC2=O)cc1]

1-[4-(4,4,5,5-Tetramethyl-1,3,2-dioxaborolan-2-yl)phenyl]pyrrolidin-2-one (128 mg, 0.45 mmol) and 3-bromo-5-chloro-4-(methoxymethyl)pyridine (158 mg, 0.67 mmol) were dissolved in 1,4-dioxane (6 ml) and water (1.6 ml) and degassed with nitrogen. PdCl₂(PPh₃)₂ (16 mg, 0.02 mmol) and K₂CO₃ (62 mg, 0.45 mmol) were added and the mixture was stirred at 50° C. for 2 h. DCM and brine were added, the organic layer separated and the aqueous layer extracted with DCM. The combined organics were dried over Na₂SO₄, filtered, concentrated and purified on a silica gel column eluted with 0-10% MeOH in DCM to give the product as a solid (73 mg, 52%). MS ES+m/z 317 [M+H]⁺.

Step 3: 1-(4-(4-(methoxymethyl)-[3,4'-bipyridin]-5-yl)phenyl)pyrrolidin-2-one

The title compound was prepared as described in Example 30, replacing 5-bromo-7H-pyrrolo[2,3-d]pyrimidine for 1-[4-[5-chloro-4-(methoxymethyl)-3-pyridyl]phenyl]pyrrolidin-2-one and 1-[4-[5-(4,4,5,5-tetramethyl-1,3,2-dioxaborolan-2-yl)-3-pyridyl]phenyl]pyrrolidin-2-one for 4-(4,4,5,5-tetramethyl-1,3,2-dioxaborolan-2-yl)pyridine, to give the product as a solid (12 mg, 17%). ¹H NMR (500 MHz, METHANOL-d₄) δ ppm 2.16-2.26 (m, 2H), 2.59-2.66 (m, 2H), 3.15-3.20 (m, 3H), 3.95-3.97 (m, 1H), 3.97-4.01 (m, 1H), 4.05-4.09 (m, 2H), 7.53-7.59 (m, 2H), 7.63-7.67 (m, 2H), 7.77-7.81 (m, 2H), 8.49-8.54 (m, 1H), 8.55-8.60 (m, 1H), 8.64-8.70 (m, 2H). MS ES+m/z 360 [M+H]⁺.

Example 84: 1-(4-(6-amino-[3,4'-bipyridin]-5-yl)phenyl)pyrrolidin-2-one

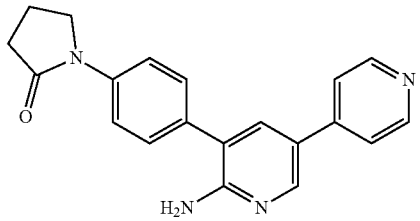 [SMILES: Nc1ncc(-c2ccncc2)cc1-c1ccc(N2CCCC2=O)cc1]

The title compound was prepared as described in Example 81, replacing 1-[3-Methyl-4-(4,4,5,5-tetramethyl-1,3,2-dioxaborolan-2-yl)phenyl]pyrrolidin-2-one for 1-[4-(4,4,5,5-tetramethyl-1,3,2-dioxaborolan-2-yl)phenyl]pyrrolidin-2-one and 3,5-dibromopyridine for 5-bromo-3-iodo-pyridin-2-amine, to give the product as a solid (9 mg, 2%). ¹H NMR (500 MHz, DMSO-d₆) δ ppm 2.05-2.13 (m, 2H), 2.51-2.56 (m, 2H), 3.84-3.91 (m, 2H), 5.99-6.03 (m, 8.49 (m, 1H), 8.51-8.56 (m, 2H). MS ES+m/z 331 [M+H]⁺.

Example 85: 4-(6-amino-5-(4-(2-oxopyrrolidin-1-yl)phenyl)pyridin-3-yl)-N-methylfuro[2,3-b]pyridine-2-carboxamide

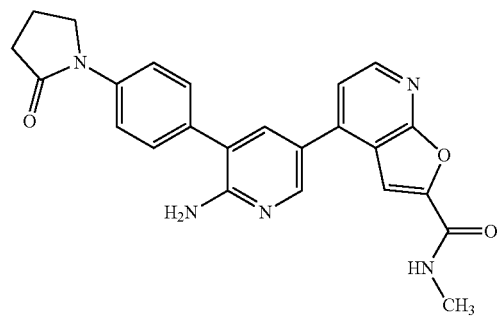 [SMILES: CNC(=O)c1cc2c(-c3cnc(N)c(-c4ccc(N5CCCC5=O)cc4)c3)ccnc2o1]

Step 1: Intermediate 89—1-[4-(2-Amino-5-bromo-3-pyridyl)phenyl]pyrrolidin-2-one

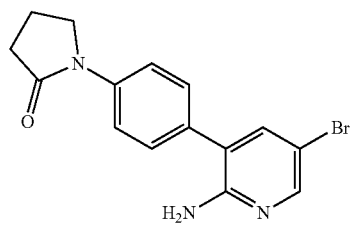 [SMILES: Nc1ncc(Br)cc1-c1ccc(N2CCCC2=O)cc1]

1-[4-(4,4,5,5-Tetramethyl-1,3,2-dioxaborolan-2-yl)phenyl]pyrrolidin-2-one (456 mg, 1.59 mmol) and 5-bromo-3-iodo-pyridin-2-amine (500 mg, 1.67 mmol) were dissolved in n-BuOH (8 ml) and water (1 ml). The solution was degassed with nitrogen, PdCl₂(PPh₃)₂ (59 mg, 0.08 mol) and K₂CO₃ (277 mg, 2 mmol) were added and the resulting mixture was stirred at 100° C. for 5 h. When cooled to rt the mixture was diluted with DCM and water. The organic layer was separated and the aqueous layer extracted with DCM. The combined organics were dried over Na$_2$SO$_4$, filtered, concentrated and purified on a silica gel column eluted with 0-10% MeOH in DCM to give the product as a solid (420 mg, 76%). MS ES+m/z 332 [M+H]$^+$.

Step 2: Intermediate 90—1-[4-[2-Amino-5-(4,4,5,5-tetramethyl-1,3,2-dioxaborolan-2-yl)-3-pyridyl]phenyl]pyrrolidin-2-one

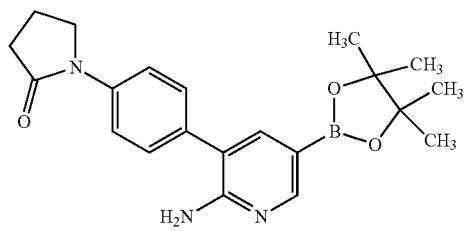 [SMILES: CC1(C)OB(c2cnc(N)c(-c3ccc(N4CCCC4=O)cc3)c2)OC1(C)C]

A mixture of 1-[4-(2-amino-5-bromo-3-pyridyl)phenyl]pyrrolidin-2-one (1.5 g, 4.52 mmol), 4,4,5,5-tetramethyl-2-(4,4,5,5-tetramethyl-1,3,2-dioxaborolan-2-yl)-1,3,2-dioxaborolane (1.72 g, 6.77 mmol), KOAc (1.33 g, 13.5 mmol) and PdCl$_2$(dppf) (330 mg, 0.45 mmol) in DMSO (21 ml) was stirred at 100° C. for 2 h. When cooled to rt water and 1,2-dichloroethane were added, the organic layer was separated and the aqueous layer extracted with 1,2-dichloroethane. The combined organics were dried over Na$_2$SO$_4$, filtered through celite and concentrated. The resulting residue was triturated with cold Et$_2$O to give the product as a solid (680 mg, 40%). MS ES+m/z 380 [M+H]$^+$.

Step 3: 4-(6-amino-5-(4-(2-oxopyrrolidin-1-yl)phenyl)pyridin-3-yl)-N-methylfuro[2,3-b]pyridine-2-carboxamide 1-[4-[2-Amino-5-(4,4,5,5-tetramethyl-1,3,2-dioxaborolan-2-yl)-3-pyridyl]phenyl]pyrrolidin-2-one (100 mg, 0.26 mmol), 4-chloro-N-methyl-furo[2,3-b]pyridine-2-carboxamide (58 mg, 0.28 mmol), K$_2$CO$_3$ (73 mg, 0.53 mmol) and PdCl$_2$(Amphos) (10 mg, 0.014 mmol) were taken up in 1,4-dioxane (1 ml) and distilled water (0.3 ml) and the mixture was stirred at 90° C. for 30 min. When cooled to rt the mixture was filtered, concentrated and purified by preparative HPLC to give the product as a solid (49 mg, 43%). $^1$H NMR (500 MHz, DMSO-d$_6$) δ ppm 2.10 (t, J=7.57 Hz, 2H), 2.52-2.55 (m, 2H), 2.81 (d, J=4.41 Hz, 3H), 3.89 (t, J=7.09 Hz, 2H), 6.17 (s, 2H), 7.57-7.60 (m, 2H), 7.61 (d, J=5.36 Hz, 1H), 7.72 (s, 1H), 7.75 (d, J=2.52 Hz, 1H), 7.78-7.81 (m, 2H), 8.42 (d, J=5.36 Hz, 1H), 8.46 (d, J=2.21 Hz, 1H), 8.80 (d, J=4.73 Hz, 1H). MS ES+m/z 428 [M+H]$^+$.

Example 86: 1-(4-(2-amino-5-(7-methoxy-1H-pyrazolo[3,4-c]pyridin-4-yl)pyridin-3-yl)phenyl)pyrrolidin-2-one

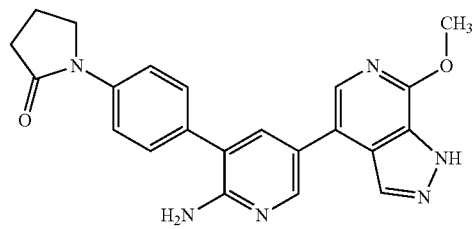 [SMILES: COc1ncc(-c2cnc(N)c(-c3ccc(N4CCCC4=O)cc3)c2)c2cn[nH]c12]

The title compound was prepared as described in Example 85, replacing 4-chloro-N-methyl-furo[2,3-b]pyridine-2-carboxamide for 4-bromo-7-methoxy-1H-pyrazolo[3,4-c]pyridine, to give the product as a solid (2 mg, 3%). $^1$H NMR (500 MHz, DMSO-d$_6$) δ ppm 2.05-2.14 (m, 2H), 2.51-2.55 (m, 2H), 3.86-3.91 (m, 2H), 4.06-4.11 (m, 3H), 5.75-5.82 (m, 2H), 7.57-7.61 (m, 2H), 7.62-7.64 (m, 1H), 7.75-7.80 (m, 2H), 7.81 (s, 1H), 8.29 (s, 1H), 8.30-8.33 (m, 1H), 13.57-14.26 (bs, 1H). MS ES+m/z 401 [M+H]$^+$.

Example 87: 1-(4-(2-amino-5-(1-methyl-1H-pyrrolo[2,3-b]pyridin-3-yl)pyridin-3-yl)phenyl)pyrrolidin-2-one

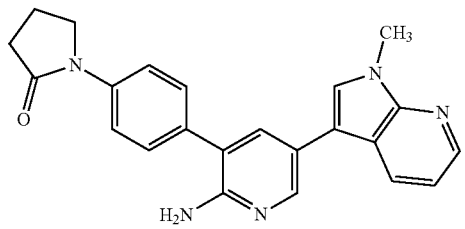 [SMILES: Cn1cc(-c2cnc(N)c(-c3ccc(N4CCCC4=O)cc3)c2)c2cccnc21]

The title compound was prepared as described in Example 85, replacing 4-chloro-N-methyl-furo[2,3-b]pyridine-2-carboxamide for 3-bromo-1-methyl-pyrrolo[2,3-b]pyridine and 1,4-dioxane for DMSO, to give the product as a solid (7 mg, 14%). $^1$H NMR (500 MHz, DMSO-d$_6$) δ ppm 2.05-2.13 (m, 2H), 2.51-2.57 (m, 2H), 3.83-3.86 (m, 3H), 3.86-3.90 (m, 2H), 5.59 (s, 2H), 7.12-7.18 (m, 1H), 7.54-7.59 (m, 2H), 7.59-7.62 (m, 1H), 7.75-7.80 (m, 2H), 7.82-7.88 (m, 1H), 8.19-8.23 (m, 1H), 8.31 (br d, J=2.52 Hz, 2H). MS ES+m/z 384 [M+H]$^+$.

Example 88: 4-(6-amino-5-(4-(2-oxopyrrolidin-1-yl)phenyl)pyridin-3-yl)-7-(cyclopropylmethyl)-8,9-dihydropyrido[3',2':4,5]pyrrolo[1,2-a]pyrazin-6(7H)-one

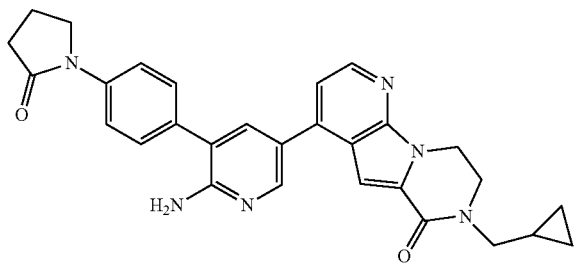 [SMILES: Nc1ncc(-c2ccnc3c2cc2n3CCN(CC3CC3)C2=O)cc1-c1ccc(N2CCCC2=O)cc1]

The title compound was prepared as described in Example 85, replacing 4-chloro-N-methyl-furo[2,3-b]pyridine-2-carboxamide for 4-chloro-7-(cyclopropylmethyl)-8,9-dihydropyrido[3,4]pyrrolo[3,5-b]pyrazin-6-one, to give the product as a solid (18 mg, 23%). $^1$H NMR (500 MHz, DMSO-$d_6$) δ ppm 0.20-0.32 (m, J=4.73 Hz, 2H), 0.48-0.52 (m, J=4.73 Hz, 2H), 1.06-1.09 (m, 1H), 2.10 (m, 2H), 2.52-2.57 (m, 2H), 3.43 (d, J=6.94 Hz, 2H), 3.89 (t, J=6.94 Hz, 2H), 3.92-3.94 (m, 2H), 4.43-4.45 (m, 2H), 6.06 (s, 2H), 7.12 (s, 1H), 7.35 (d, J=5.04 Hz, 1H), 7.57 (d, J=8.83 Hz, 2H), 7.73 (d, J=2.52 Hz, 1H), 7.80 (d, J=8.83 Hz, 2H), 8.42 (d, J=5.04 Hz, 1H), 8.44 (d, J=2.52 Hz, 1H). MS ES+m/z 493 [M+H]$^+$.

Example 89: 4-(6-amino-5-(4-(2-oxopyrrolidin-1-yl)phenyl)pyridin-3-yl)-N-(cyclopropylmethyl)furo[2,3-b]pyridine-2-carboxamide

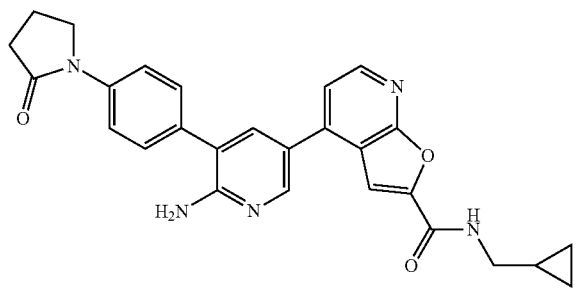 [SMILES: Nc1ncc(-c2ccnc3oc(C(=O)NCC4CC4)cc23)cc1-c1ccc(N2CCCC2=O)cc1]

The title compound was prepared as described in Example 85, replacing 4-chloro-N-methyl-furo[2,3-b]pyridine-2-carboxamide for 4-chloro-N-(cyclopropylmethyl)furo[2,3-b]pyridine-2-carboxamide, to give the product as a solid (21 mg, 25%). $^1$H NMR (500 MHz, DMSO-$d_6$) δ ppm 0.25 (dd, J=4.73, 1.58 Hz, 2H), 0.45 (dd, J=8.04, 1.73 Hz, 2H), 1.01-1.08 (m, 1H), 2.10 (t, J=7.72 Hz, 2H), 2.52-2.56 (m, 2H), 3.16 (t, J=6.31 Hz, 2H), 3.89 (t, J=6.94 Hz, 2H), 6.16 (s, 2H), 7.54-7.60 (m, 2H), 7.61 (d, J=5.36 Hz, 1H), 7.76 (d, J=2.52 Hz, 1H), 7.77 (s, 1H), 7.78-7.81 (m, 2H), 8.42 (d, J=5.36 Hz, 1H), 8.47 (d, J=2.21 Hz, 1H), 8.94 (s, 1H). MS ES+m/z 468 [M+H]$^+$.

Example 90: 4-(6-amino-5-(4-(2-oxopyrrolidin-1-yl)phenyl)pyridin-3-yl)-N-(2-methoxyethyl)furo[2,3-b]pyridine-2-carboxamide

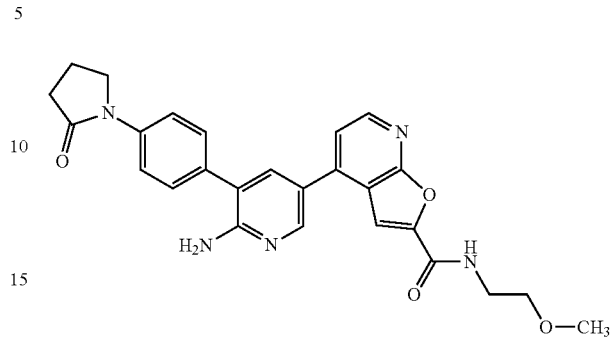

The title compound was prepared as described in Example 85, replacing 4-chloro-N-methyl-furo[2,3-b]pyridine-2-carboxamide for 4-chloro-N-(2-methoxyethyl)furo[2,3-b]pyridine-2-carboxamide, to give the product as a solid (30 mg, 36%). $^1$H NMR (500 MHz, DMSO-$d_6$) δ ppm 2.09 (d, J=7.57 Hz, 2H), 2.52-2.55 (m, 2H), 3.27 (s, 3H), 3.41-3.50 (m, 4H), 3.89 (t, J=6.94 Hz, 2H), 6.17 (s, 2H), 7.58 (d, J=8.83 Hz, 2H), 7.61 (d, J=5.04 Hz, 1H), 7.75 (d, J=2.21 Hz, 1H), 7.77-7.82 (m, 3H), 8.42 (d, J=5.36 Hz, 1H), 8.47 (d, J=2.52 Hz, 1H), 8.85-8.88 (m, 1H). MS ES+m/z 472 [M+H]$^+$.

Example 91: 1-(4-(2-amino-5-(1-methyl-5-(2-oxopyrrolidin-1-yl)-1H-pyrrolo[2,3-b]pyridin-3-yl)pyridin-3-yl)phenyl)pyrrolidin-2-one

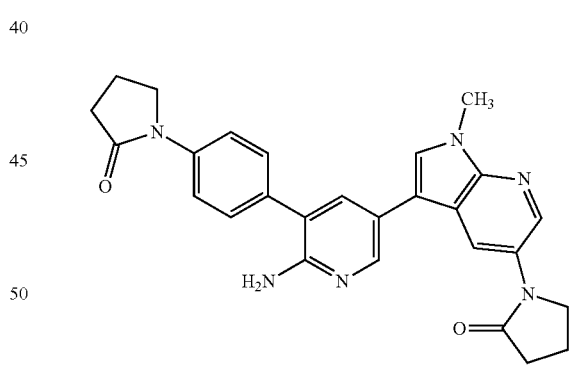

The title compound was prepared as described in Example 85, replacing 4-chloro-N-methyl-furo[2,3-b]pyridine-2-carboxamide for 1-(3-iodo-1-methyl-pyrrolo[2,3-b]pyridin-5-yl)pyrrolidin-2-one, to give the product as a solid (40 mg, 33%). $^1$H NMR (500 MHz, DMSO-$d_6$) δ ppm 2.11 (quind, J=7.49, 7.49, 7.49, 7.49, 4.10 Hz, 4H), 2.48-2.49 (m, 1H), 2.52-2.56 (m, 3H), 3.84-3.96 (m, 7H), 5.60 (s, 2H), 7.54-7.60 (m, 3H), 7.79 (d, J=7.80 Hz, 2H), 7.87 (s, 1H), 8.29 (d, J=2.21 Hz, 1H), 8.43 (d, J=2.21 Hz, 1H), 8.50 (d, J=2.21 Hz, 1H). MS ES+m/z 467 [M+H]$^+$.

Example 92: 4-(6-amino-5-(4-(2-oxopyrrolidin-1-yl)phenyl)pyridin-3-yl)-1-methyl-6-((tetrahydro-2H-pyran-4-yl)methyl)-1,6-dihydro-7H-pyrazolo[3,4-c]pyridin-7-one

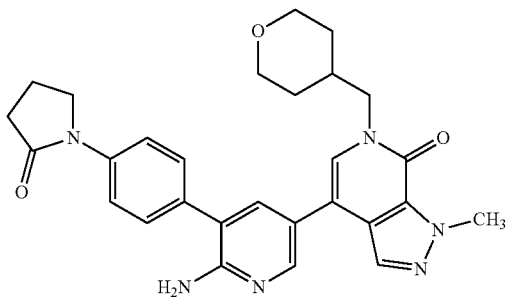 [SMILES: Cn1ncc2c(-c3cnc(N)c(-c4ccc(N5CCCC5=O)cc4)c3)cn(CC3CCOCC3)c(=O)c21]

The title compound was prepared as described in Example 85, replacing 4-chloro-N-methyl-furo[2,3-b]pyridine-2-carboxamide for 4-bromo-1-methyl-6-(tetrahydropyran-4-ylmethyl)pyrazolo[3,4-c]pyridin-7-one, to give the product as a solid (30 mg, 30%). $^1$H NMR (500 MHz, DMSO-$d_6$) δ ppm 1.23-1.37 (m, 2H), 1.46 (br d, J=11.03 Hz, 2H), 2.04-2.15 (m, 3H), 2.52-2.56 (m, 2H), 3.17-3.29 (m, 2H), 3.81-3.93 (m, 6H), 4.10 (s, 3H), 5.72 (s, 2H), 7.30 (s, 1H), 7.53-7.59 (m, 3H), 7.78 (d, J=7.75 Hz, 2H), 8.21 (d, J=2.52 Hz, 1H), 8.36 (s, 1H). MS ES+m/z 499 [M+H]$^+$.

Example 93: 4-(6-amino-5-(4-(2-oxopyrrolidin-1-yl)phenyl)pyridin-3-yl)-N-(oxetan-3-yl)furo[2,3-b]pyridine-2-carboxamide

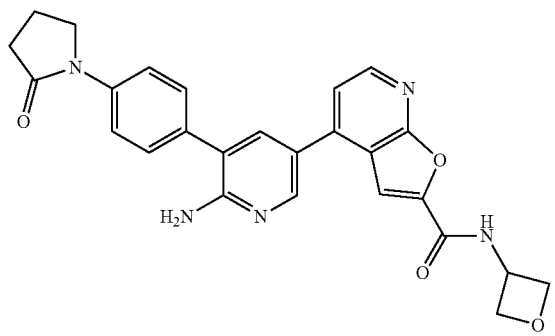 [SMILES: Nc1ncc(-c2ccnc3oc(C(=O)NC4COC4)cc23)cc1-c1ccc(N2CCCC2=O)cc1]

The title compound was prepared as described in Example 85, replacing 4-chloro-N-methyl-furo[2,3-b]pyridine-2-carboxamide for 4-chloro-N-(oxetan-3-yl)furo[2,3-b]pyridine-2-carboxamide, to give the product as a solid (1 mg, 3%). $^1$H NMR (500 MHz, DMSO-$d_6$) δ ppm 2.10 (t, J=7.57 Hz, 2H), 2.51-2.55 (m, 2H), 3.89 (t, J=7.09 Hz, 2H), 4.64 (t, J=6.46 Hz, 2H), 4.77 (dd, J=7.25, 6.62 Hz, 2H), 5.04 (m, 1H), 6.18 (s, 2H), 7.57-7.61 (m, 2H), 7.62 (d, J=5.36 Hz, 1H), 7.76 (d, J=2.52 Hz, 1H), 7.80 (d, J=8.83 Hz, 2H), 7.85 (s, 1H), 8.44 (d, J=5.36 Hz, 1H), 8.47 (d, J=2.52 Hz, 1H), 9.52 (d, J=6.62 Hz, 1H). MS ES+m/z 470 [M+H]$^+$.

Example 94: methyl 4-(6-amino-5-(4-(2-oxopyrrolidin-1-yl)phenyl)pyridin-3-yl)-1H-pyrrolo[2,3-b]pyridine-2-carboxylate

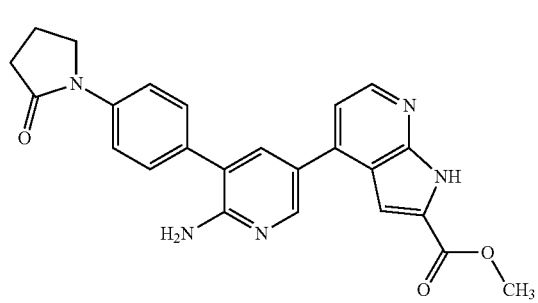 [SMILES: COC(=O)c1cc2c(-c3cnc(N)c(-c4ccc(N5CCCC5=O)cc4)c3)ccnc2[nH]1]

The title compound was prepared as described in Example 85, replacing 4-chloro-N-methyl-furo[2,3-b]pyridine-2-carboxamide for methyl 4-chloro-1H-pyrrolo[2,3-b]pyridine-2-carboxylate, to give the product as a solid (3 mg, 3%). $^1$H NMR (500 MHz, DMSO-$d_6$) δ ppm 2.10 (quin, J=7.49 Hz, 2H), 2.51-2.56 (m, 2H), 3.87 (s, 3H), 3.87-3.92 (m, 2H), 6.04 (s, 2H), 7.24 (s, 1H), 7.30 (d, J=5.04 Hz, 1H), 7.53-7.61 (m, 2H), 7.71 (d, J=2.21 Hz, 1H), 7.77-7.82 (m, 2H), 8.41 (d, J=4.73 Hz, 1H), 8.43 (d, J=2.52 Hz, 1H). MS ES+m/z 428 [M+H]$^+$.

Example 95: 4-(6-amino-5-(4-(2-oxopyrrolidin-1-yl)phenyl)pyridin-3-yl)-5,6-dihydro-7H-pyrrolo[3,4-b]pyridin-7-one

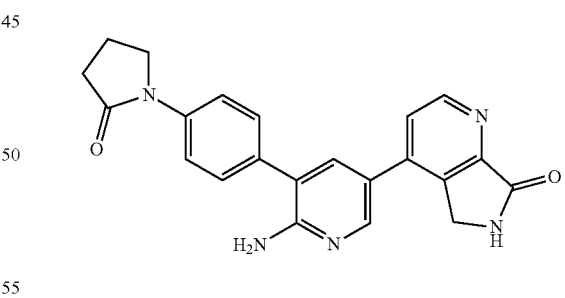

The title compound was prepared as described in Example 85, replacing 4-chloro-N-methyl-furo[2,3-b]pyridine-2-carboxamide for 4-chloro-5,6-dihydropyrrolo[3,4-b]pyridin-7-one, to give the product as a solid (2 mg, 2%). $^1$H NMR (500 MHz, DMSO-$d_6$) δ ppm 2.05-2.13 (m, 2H), 2.52-2.57 (m, 2H), 3.84-3.92 (m, 2H), 4.62-4.68 (m, 2H), 6.08-6.13 (m, 2H), 7.51-7.58 (m, 2H), 7.68-7.72 (m, 1H), 7.72-7.76 (m, 1H), 7.76-7.81 (m, 2H), 8.36-8.39 (m, 1H), 8.66-8.71 (m, 1H), 9.00-9.04 (m, 1H). MS ES+m/z 386 [M+H]$^+$.

Example 96: 4-(6-amino-5-(4-(2-oxopyrrolidin-1-yl)phenyl)pyridin-3-yl)-1,6-dimethyl-1,6-dihydro-7H-pyrazolo[3,4-c]pyridin-7-one

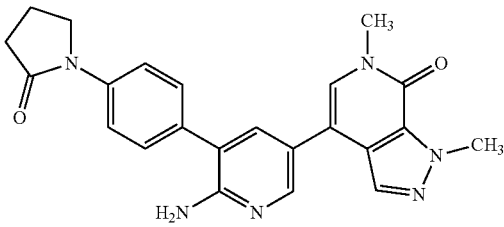 [SMILES: Cn1cc(-c2cnc(N)c(-c3ccc(N4CCCC4=O)cc3)c2)c2cnn(C)c2c1=O]

The title compound was prepared as described in Example 85, replacing 4-chloro-N-methyl-furo[2,3-b]pyridine-2-carboxamide for 4-bromo-1,6-dimethyl-pyrazolo[3,4-c]pyridin-7-one, to give the product as a solid (29 mg, 13%). $^1$H NMR (500 MHz, DMSO-d$_6$) δ ppm 2.06-2.13 (m, 2H), 2.51-2.55 (m, 2H), 3.49-3.51 (m, 3H), 3.86-3.91 (m, 2H), 4.08-4.11 (m, 3H), 5.69-5.73 (m, 2H), 7.31-7.33 ((m, 1H), 7.52-7.54 (m, 1H), 7.54-7.58 (m, 2H), 7.74-7.80 (m, 2H), 8.18-8.22 (m, 1H), 8.35 (s, 1H). MS ES+m/z 415 [M+H]$^+$.

Example 97: 4-(6-amino-5-(4-(2-oxopyrrolidin-1-yl)phenyl)pyridin-3-yl)-6-isobutyl-1-methyl-1,6-dihydro-7H-pyrazolo[3,4-c]pyridin-7-one

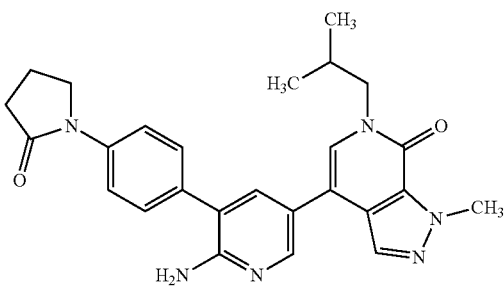 [SMILES: CC(C)Cn1cc(-c2cnc(N)c(-c3ccc(N4CCCC4=O)cc3)c2)c2cnn(C)c2c1=O]

The title compound was prepared as described in Example 85, replacing 4-chloro-N-methyl-furo[2,3-b]pyridine-2-carboxamide for 4-bromo-6-isobutyl-1-methyl-pyrazolo[3,4-c]pyridin-7-one, to give the product as a solid (14 mg, 12%). $^1$H NMR (500 MHz, DMSO-d$_6$) δ ppm 0.89 (d, J=6.62 Hz, 6H), 2.05-2.18 (m, 3H), 2.52-2.56 (m, 2H), 3.80 (d, J=7.25 Hz, 2H), 3.89 (t, J=7.09 Hz, 2H), 4.10 (s, 3H), 5.72 (s, 2H), 7.28 (s, 1H), 7.53-7.60 (m, 3H), 7.78 (d, J=7.86 Hz, 2H), 8.21 (d, J=2.52 Hz, 1H), 8.36 (s, 1H). MS ES+m/z 457 [M+H]$^+$.

Example 98: 1-(4-(2-amino-5-(5-(1-hydroxyethyl)-1-methyl-1H-pyrrolo[2,3-b]pyridin-3-yl)pyridin-3-yl)phenyl)pyrrolidin-2-one

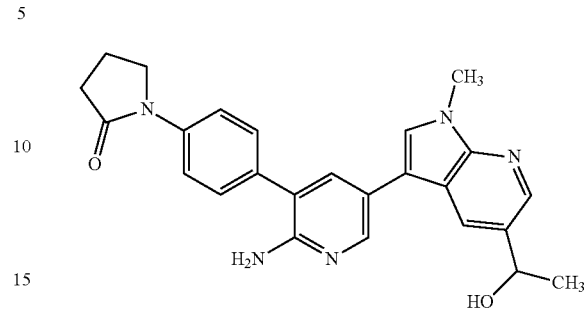

The title compound was prepared as described in Example 85, replacing 4-chloro-N-methyl-furo[2,3-b]pyridine-2-carboxamide for 1-(3-bromo-1-methyl-pyrrolo[2,3-b]pyridin-5-yl)ethanol, to give the product as a solid (12 mg, 11%). $^1$H NMR (500 MHz, DMSO-d$_6$) δ ppm 1.42 (d, J=6.31 Hz, 3H), 2.11 (quin, J=7.57 Hz, 2H), 2.52-2.56 (m, 2H), 3.84 (s, 3H), 3.90 (t, J=7.09 Hz, 2H), 4.92 (br dd, J=6.31, 3.47 Hz, 1H), 5.21 (d, J=3.78 Hz, 1H), 5.58 (s, 2H), 7.54-7.61 (m, 3H), 7.78-7.83 (m, 3H), 8.13 (d, J=1.89 Hz, 1H), 8.31 (dd, J=9.30, 2.05 Hz, 2H). MS ES+m/z 428 [M+H]$^+$.

Example 99: 4-(6-amino-5-(4-(2-oxopyrrolidin-1-yl)phenyl)pyridin-3-yl)-1,6-dihydro-7H-pyrazolo[3,4-c]pyridin-7-one

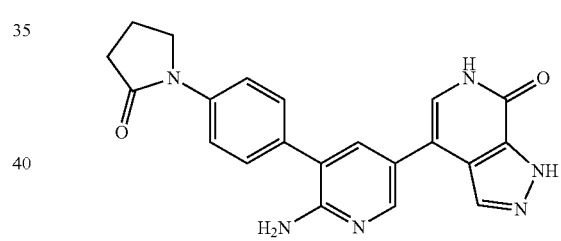

A mixture of 1-[4-[2-amino-5-(4,4,5,5-tetramethyl-1,3,2-dioxaborolan-2-yl)-3-pyridyl]phenyl]pyrrolidin-2-one (95 mg, 0.25 mmol) and 4-bromo-7-methoxy-1H-pyrazolo[3,4-c]pyridine (57 mg, 0.25 mmol) in 1,4-dioxane (1 ml) and water (0.1 ml) was degassed with nitrogen. PdCl$_2$(Amphos) (9 mg, 0.013 mmol) and K$_2$CO$_3$ (69 mg, 0.5 mmol) were added and the resulting mixture was stirred at 100° C. for 2 h. When cooled to rt water and 1,2-dichloroethane were added, the organic layer was separated and the aqueous layer extracted with 1,2-dichloroethane. The combined organics were dried over Na$_2$SO$_4$, filtered and concentrated. The resulting residue was dissolved in MeCN (3 ml), NaI (38 mg, 0.25 mmol) and TMSCl (33 µl, 0.26 mmol) were added and the mixture was stirred at 60° C. for 1 h. When cooled to rt water and 1,2-dichloroethane were added, the aqueous layer was separated, concentrated and purified by preparative HPLC to give the product as a solid (3 mg, 3%). $^1$H NMR (500 MHz, DMSO-d$_6$) δ ppm 2.05-2.14 (m, 2H), 2.51-2.55 (m, 2H), 3.86-3.90 (m, 2H), 5.64-5.74 (m, 2H), 7.00-7.08 (m, 1H), 7.49-7.54 (m, 1H), 7.54-7.60 (m, 2H), 7.73-7.80 (m, 2H), 8.02-8.13 (m, 1H), 8.18-8.24 (m, 1H), 11.29-11.51 (m, 1H), 13.30-14.75 (m, 1H). MS ES+m/z 387 [M+H]$^+$.

Example 100: 2'-Amino-5'-(6-cyanoquinolin-4-yl)-N,N-dimethyl-[2,3'-bipyridine]-5-carboxamide

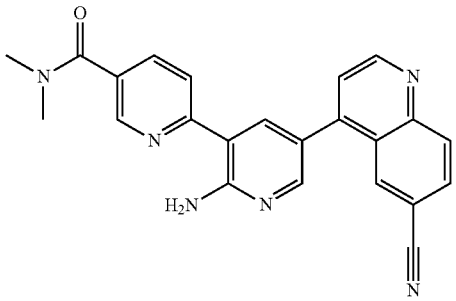 [SMILES: CN(C)C(=O)c1ccc(-c2cc(-c3ccnc4ccc(C#N)cc34)cnc2N)nc1]

Step 1: Preparation of 3-(4,4,5,5-tetramethyl-1,3,2-dioxaborolan-2-yl)pyridin-2-amine

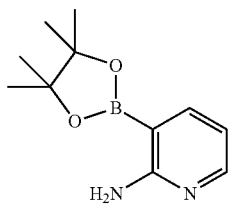 [SMILES: CC1(C)OB(c2cccnc2N)OC1(C)C]

A mixture of 3-bromopyridin-2-amine (14.0 g, 80.9 mmol), B₂Pin₂ (41.1 g, 162 mmol), KOAc (23.8 g, 243 mmol) and Pd(dppf)Cl₂ (2.37 g, 3.24 mmol, 4 mol %) in dioxane (200 mL) was stirred at 110° C. for 3 hour under N₂ atmosphere. The red suspension turned to black. Crude LCMS showed the purity of product is 11% (Rt=0.775 min; MS Calc'd: 220.1; MS Found: 221.1 [M+H]⁺). The reaction mixture was diluted with EtOAc (80 mL), filtered and concentrated to give crude compound 3-(4,4,5,5-tetramethyl-1,3,2-dioxaborolan-2-yl)pyridin-2-amine (60.0 g) as black oil and directly used to next step.

Step 2: Preparation of 6-bromonicotinic acid

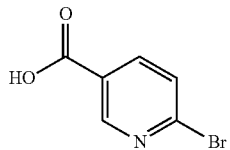

To a mixture of methyl 6-bromopyridine-3-carboxylate (15.0 g, 69.4 mmol) in THF (75 mL) and H₂O (15 mL) was added NaOH (11.1 g, 278 mmol) in one portion at 25° C. Then the mixture was stirred for 16 h. TLC showed the reaction was completed. The mixture was poured into water (100 mL) and washed with EtOAc (150 mL×2). The aqueous phase was acidified with HCl aq. (1N) to pH=3 and extracted with EtOAc (150 mL×3). The combined organic phase was washed with brine (100 mL), dried over Na₂SO₄, filtered and concentrated in vacuum to afford 6-bromonicotinic acid (13.0 g, yield: 93%) as a white solid. ¹H NMR (400 MHz, DMSO-d₆) δ 7.80 (1H, d, J=8.8 Hz), 8.16 (1H, dd, J=8.4, 2.4 Hz), 8.48 (1H, d, J=2.4 Hz).

Step 3: Preparation of 6-bromo-N,N-dimethylnicotinamide

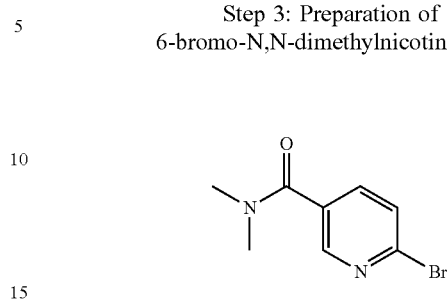

A mixture of 6-bromonicotinic acid (13.0 g, 64.3 mmol) in SOCl₂ (150 mL) was heated at 80° C. for 2 h under N₂ atmosphere. After cooling, the reaction mixture was concentrated under reduced pressure. Then to the mixture was added DCM (240 mL), Me₂NH (7.00 g, 85.8 mmol) and TEA (60 mL), the mixture was stirred at 25° C. for 16 h under N₂. TLC showed the reaction was completed. The residue was poured into water (100 mL) and extracted with DCM (100 mL×3). The combined organic layer was washed with water (100 mL), dried over Na₂SO₄, filtered and concentrated in vacuum. The residue was purified by Combi Flash (50% EtOAc in pentane) to afford 6-bromo-N,N-dimethylnicotinamide (12.2 g, yield: 83%) as a white solid. ¹H NMR (400 MHz, DMSO-d₆) δ 2.92 (3H, s), 2.99 (3H, s), 7.59 (1H, dd, J=8.4, 0.8 Hz), 7.92 (1H, dd, J=8.4, 2.4 Hz), 8.47 (1H, dd, J=2.4, 0.8 Hz).

Step 4: Preparation of 2'-amino-N,N-dimethyl-[2,3'-bipyridine]-5-carboxamide

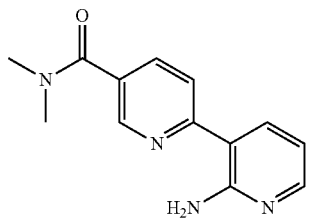 [SMILES: CN(C)C(=O)c1ccc(-c2cccnc2N)nc1]

A mixture of 6-bromo-N,N-dimethylnicotinamide (11.0 g, 48.0 mmol), 3-(4,4,5,5-tetramethyl-1,3,2-dioxaborolan-2-yl)pyridin-2-amine (17.8 g, 80.9 mmol), Na₂CO₃ (2 M in water, 120 mL) and Pd(dppf)Cl₂ (2.11 g, 2.88 mmol, 6 mol %) in DME (240 mL) was stirred at 110° C. for 16 h under N₂ atmosphere. Crude LCMS showed the purity of product is 38% (Rt=0.286 min; MS Calc'd: 242.1; MS Found: 242.8 [M+H]⁺). The reaction mixture was diluted with ethyl acetate (300 mL), washed with water (80 mL×3), dried over Na₂SO₄, filtered and concentrated. The residue was purified by Combi Flash (85% EtOAc in pentane) to afford 2'-amino-N,N-dimethyl-[2,3'-bipyridine]-5-carboxamide (11.3 g, yield: 97%) as an off-white solid. ¹H NMR (400 MHz, DMSO-d₆) δ 3.01 (3H, s), 3.03 (3H, s), 6.69 (1H, dd, J=7.6, 4.8 Hz), 7.44 (2H, s), 7.95 (1H, dd, J=8.4, 2.4 Hz), 8.01 (1H, dd, J=8.4, 0.8 Hz), 8.06 (1H, s), 8.08 (1H, dd, J=4.4, 1.6 Hz), 8.70 (1H, dd, J=2.4, 1.2 Hz).

Step 5: Preparation of 2'-amino-5'-bromo-N,N-dimethyl-[2,3'-bipyridine]-5-carboxamide

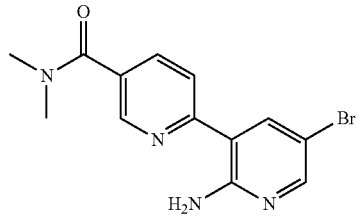 [SMILES: CN(C)C(=O)c1ccc(-c2cc(Br)cnc2N)nc1]

To a mixture of 2'-amino-N,N-dimethyl-[2,3'-bipyridine]-5-carboxamide (11.3 g, 46.6 mmol) in MeCN (120 mL) was added NBS (8.50 g, 48.0 mmol) in one portion at 0° C. The mixture was stirred at 25° C. for 16 hour. The color of the mixture was form light to deep yellow. TLC showed the reaction was completed. The residue was quenched with sat. aq. $Na_2S_2O_3$ (100 mL) and $NaHCO_3$ (100 mL) and stirred for 30 min. The reaction mixture was extracted with EtOAc (100 mL×3). The combined organic layer was washed with sat. $NaHCO_3$ (100 mL), dried over $Na_2SO_4$, filtered and concentrated in vacuum. The residue was purified by Combi Flash (50% EtOAc in pentane) to afford 2'-amino-5'-bromo-N,N-dimethyl-[2,3'-bipyridine]-5-carboxamide (14.3 g, yield: 95%) as a yellow solid. $^1$H NMR (400 MHz, DMSO-$d_6$) δ 2.99 (3H, s), 3.02 (3H, s), 7.62 (2H, br s), 7.95 (1H, dd, J=8.4, 2.4 Hz), 8.08 (1H, dd, J=8.4, 0.8 Hz), 8.12 (1H, d, J=2.0 Hz), 8.23 (1H, d, J=2.4 Hz), 8.70 (1H, dd, J=2.0, 0.8 Hz).

Step 6: Preparation of 2'-amino-N,N-dimethyl-5'-(4,4,5,5-tetramethyl-1,3,2-dioxaborolan-2-yl)-[2,3'-bipyridine]-5-carboxamide

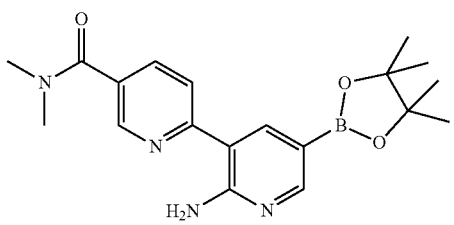

A mixture of 2'-amino-5'-bromo-N,N-dimethyl-[2,3'-bipyridine]-5-carboxamide (250 mg, 0.778 mmol), $B_2Pin_2$ (237 mg, 0.934 mmol), Pd(dppf)Cl$_2$ (57 mg, 0.078 mmol, 10 mol %) and KOAc (229 mg, 2.34 mmol) in dioxane (3 mL) was stirred at 100° C. for 5 h under N$_2$ atmosphere. A black suspension was formed. Crude LCMS showed the purity of product is 5% (Rt=0.559 min; MS Calc'd: 368.2; MS Found: 368.8 [M+H]$^+$). The mixture was filtered and concentrated in vacuum to afford 2'-amino-N,N-dimethyl-5'-(4,4,5,5-tetramethyl-1,3,2-dioxaborolan-2-yl)-[2,3'-bipyridine]-5-carboxamide (300 mg, crude) as a red solid and immediately used to next step.

Step 7: Preparation of 2'-amino-5'-(6-cyanoquinolin-4-yl)-N,N-dimethyl-[2,3'-bipyridine]-5-carboxamide

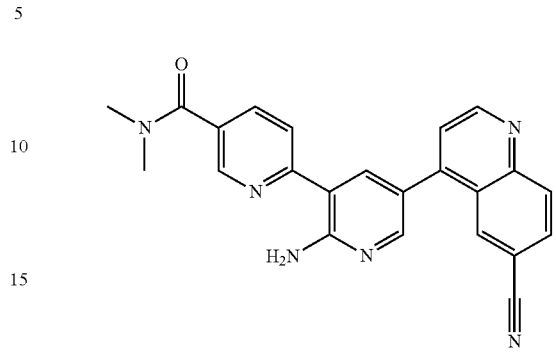

A mixture of 2'-amino-N,N-dimethyl-5'-(4,4,5,5-tetramethyl-1,3,2-dioxaborolan-2-yl)-[2,3'-bipyridine]-5-carboxamide (292 mg, 0.795 mmol, crude), 4-chloroquinoline-6-carbonitrile (100 mg, 0.530 mmol), Cs$_2$CO$_3$ (1 M in water, 1.1 mL) and CataCXium A-Pd-G2 (35 mg, 0.053 mmol, 10 mol %) in dioxane (5 mL) was stirred at 100° C. for 17 h under N$_2$ atmosphere. A black suspension was formed. Crude LCMS showed the purity of product is 15% (Rt=0.631 min; MS Calc'd: 394.2; MS Found: 395.1 [M+H]$^+$). The reaction mixture was diluted with ethyl acetate (10 mL), dried over Na$_2$SO$_4$, filtered and concentrated. The residue was purified by Combi Flash (90% EtOAc in pentane), then the impure product was purified by prep-HPLC (0.05% NH$_3$·H$_2$O as additive) and lyophilized to afford 2'-amino-5'-(6-cyanoquinolin-4-yl)-N,N-dimethyl-[2,3'-bipyridine]-5-carboxamide (17.4 mg, yield: 8%) as a light yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 99.88%, Rt=1.050 min; MS Calc'd.: 394.2; MS Found: 395.1 [M+H]$^+$. $^1$H NMR (400 MHz, CDCl$_3$) δ 3.10 (3H, s), 3.17 (3H, s), 7.15 (2H, br s), 7.50 (1H, d, J=4.4 Hz), 7.78 (1H, d, J=8.8 Hz), 7.89 (1H, dd, J=4.0, 1.6 Hz), 7.91 (1H, dd, J=3.6, 2.4 Hz), 8.01 (1H, d, J=2.0 Hz), 8.27 (1H, d, J=8.8 Hz), 8.30 (1H, d, J=2.4 Hz), 8.41 (1H, d, J=1.2 Hz), 8.78 (1H, dd, J=2.4, 0.8 Hz), 9.08 (1H, d, J=4.0 Hz).

Example 101: 2'-Amino-2''-(2-hydroxypropan-2-yl)-N,N-dimethyl-[2,3':5',4''-terpyridine]-5-carboxamide

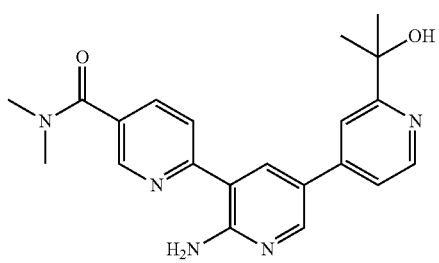 [SMILES: CN(C)C(=O)c1ccc(-c2cc(-c3ccnc(C(C)(C)O)c3)cnc2N)nc1]

Step 1: Preparation of 2-(4-bromopyridin-2-yl)-2-methylpropanenitrile

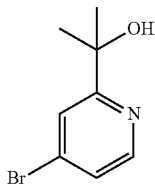

To a solution of Methyl 4-bromopyridine-2-carboxylate 9a (300 mg, 1.39 mmol) in THF (10 mL) was added MeMgBr (3 M in THF, 2.3 mL) at 0° C. The reaction was warmed to 25° C. and stirred for 0.5 h. The colourless reaction mixture turned to yellow. TLC showed the reaction was completed. After quenching with saturated NaHCO$_3$ (5 mL), diluting with DCM (40 mL), the resulting mixture was stirred vigorously for 30 min to break up the resulting solid. The organic layer was washed with NaHCO$_3$ (20 mL), dried over Na$_2$SO$_4$ and concentrated under reduced pressure. This residue were purified by Combi Flash (7% EtOAc in PE) to give compound 9 (170 mg, yield: 57%) as yellow oil. 1H NMR (400 MHz, CDCl$_3$) δ 1.54 (3H, s), 1.56 (3H, s), 4.50 (1H, s), 7.37 (1H, dd, J=5.6, 2.0 Hz), 7.58 (1H, s), 8.34 (1H, d, J=5.2 Hz)

Step 2: Preparation of 2'-amino-2"-(2-hydroxypropan-2-yl)-N,N-dimethyl-[2,3':5',4"-terpyridine]-5-carboxamide

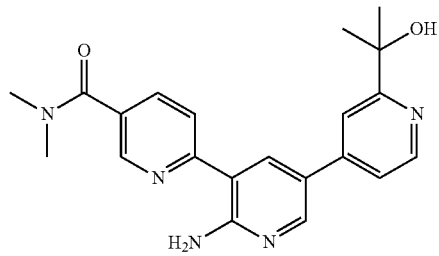 [SMILES: CN(C)C(=O)c1ccc(-c2cc(-c3ccnc(C(C)(C)O)c3)cnc2N)nc1]

A mixture of 2'-amino-N,N-dimethyl-5'-(4,4,5,5-tetramethyl-1,3,2-dioxaborolan-2-yl)-[2,3'-bipyridine]-5-carboxamide (300 mg, crude), 2-(4-bromo-2-pyridyl)propan-2-ol (100 mg, 0.463 mmol), Cs$_2$CO$_3$ (452 mg, 1.39 mmol) and Pd(t-Bu$_3$P)$_2$ (24 mg, 0.046 mmol, 10 mol %) in dioxane (1 mL) and H$_2$O (0.1 mL) was stirred at 100° C. for 16 h under N$_2$ atmosphere. A black suspension was formed. Crude LCMS showed the purity of product is 37% (Rt=0.540 min; MS Calc'd: 377.2; MS Found: 378.0 [M+H]$^+$). The mixture was concentrated under reduced pressure. The residue was purified by Combi Flash (10% MeOH in EtOH) to give an impure product which was purified by re-crystallization from MeCN (1 mL) to give the pure 2'-amino-2"-(2-hydroxypropan-2-yl)-N,N-dimethyl-[2,3':5',4"-terpyridine]-5-carboxamide (16 mg, yield: 9%) as a yellow solid. LCMS (Shimadzu LCMS 2010, mobile phase: from 100% [water+ 0.05% NH$_3$·H$_2$O] and 0% [MeCN] to 5% [water+0.05% NH$_3$·H$_2$O] and 95% [MeCN] in 5.8 min, then under this condition for 1.1 min, finally changed to 100% [water+ 0.05% NH$_3$·H$_2$O] and 0% [MeCN] and under this condition for 0.09 min.) purity is 99.29%, Rt=2.260 min; MS Calc'd.: 377.2, MS Found: 378.2 [M+H]$^+$. $^1$H NMR (400 MHz, CDCl$_3$) δ 1.61 (6H, s), 3.10 (3H, s), 3.17 (3H, m), 4.90 (1H, s), 7.03 (2H, br s), 7.35-7.45 (1H, m), 7.55 (1H, s), 7.87 (1H, d, J=8.0 Hz), 7.92 (1H, d, J=2.4 Hz), 8.13 (1H, d, J=2.8 Hz), 8.47 (1H, d, J=2.0 Hz), 8.56 (1H, d, J=4.8 Hz), 8.75 (1H, d, J=2.0 Hz).

Example 102: 2'-Amino-2"-(2-cyanopropan-2-yl)-N,N-dimethyl-[2,3':5',4"-terpyridine]-5-carboxamide

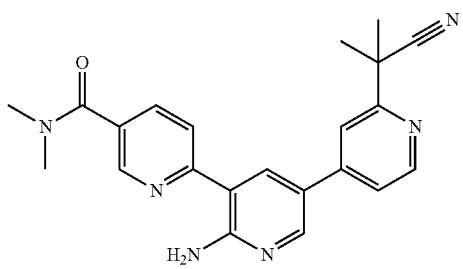 [SMILES: CN(C)C(=O)c1ccc(-c2cc(-c3ccnc(C(C)(C)C#N)c3)cnc2N)nc1]

Step 1: Preparation of 2-(4-bromopyridin-2-yl)-2-methylpropanenitrile

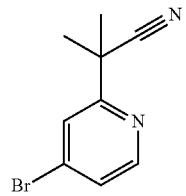

To a mixture of 4-bromo-2-fluoropyridine (500 mg, 2.84 mmol) and isobutyronitrile (216 mg, 3.12 mmol) in toluene (10 mL) was added LHMDS (1 M in hexane, 4.3 mL) at −5° C. and the mixture was stirred at 25° C. for 16 hour. TLC showed the reaction was completed. The mixture was poured into water (50 mL) and extracted with EtOAc (50 mL×3). The combined organic layer was washed with brine (50 mL), dried over Na$_2$SO$_4$, filtered and concentrated in vacuum. The residue was purified by Combi Flash (5% EtOAc in pentane) to 2-(4-bromopyridin-2-yl)-2-methylpropanenitrile (590 mg, yield: 92%) as a white solid. $^1$H NMR (400 MHz, DMSO-d$_6$) δ 1.71 (6H, s), 7.69 (1H, dd, J=5.6, 2.0 Hz), 7.84 (1H, s), 8.50 (1H, d, J=5.2 Hz).

Step 2: Preparation of 2'-amino-2"-(2-cyanopropan-2-yl)-N,N-dimethyl-[2,3':5',4"-terpyridine]-5-carboxamide

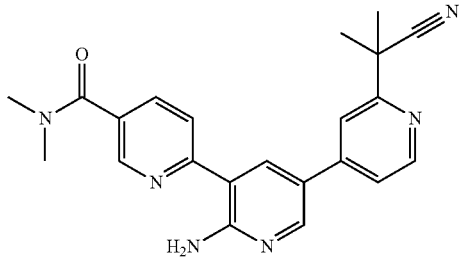

A mixture of 2'-amino-N,N-dimethyl-5'-(4,4,5,5-tetramethyl-1,3,2-dioxaborolan-2-yl)-[2,3'-bipyridine]-5-carboxamide (150 mg, 0.407 mmol, crude), 2-(4-bromopyridin-2-yl)-2-methylpropanenitrile (46 mg, 0.204 mmol), Na$_2$CO$_3$ (2 M in water, 0.51 mL) and Pd(dppf)Cl$_2$ (15 mg, 0.020 mmol, 10 mol %) in DME (2 mL) was stirred at 110° C. for 16 hour under N$_2$ atmosphere. Crude LCMS showed the purity of product is 31% (Rt=0.865 min; MS Calc'd: 386.2; MS Found: 387.2 [M+H]$^+$). The reaction mixture was diluted with ethyl acetate (10 mL), dried over Na$_2$SO$_4$, filtered and concentrated. The residue was purified by Combi Flash (90% EtOAc in pentanepentane), then the impure product was purified by prep-HPLC (0.1% TFA as additive) and lyophilized to afford 2'-amino-2"-(2-cyanopropan-2-yl)-N,N-dimethyl-[2,3':5',4"-terpyridine]-5-carboxamide (39.0 mg, yield: 49%) as a light yellow solid. LCMS (Shimadzu LCMS 2010, mobile phase: from 100% [water+0.05% NH$_3$·H$_2$O] and 0% [MeCN] to 5% [water+0.05% NH$_3$·H$_2$O] and 95% [MeCN] in 5.8 min, then under this condition for 1.1 min, finally changed to 100% [water+0.05% NH$_3$·H$_2$O] and 0% [MeCN] and under this condition for 0.09 min.) purity is 99.79%, Rt=2.590 min; MS Calc'd.: 386.2, MS Found: 387.2 [M+H]$^+$. $^1$H NMR (400 MHz, DMSO-d$_6$) δ 1.77 (6H, s) 2.98 (3H, s), 3.02 (3H, s), 7.82 (1H, dd, J=5.2, 1.6 Hz), 7.91 (1H, d, J=1.2 Hz), 8.06 (1H, dd, J=8.4, 2.0 Hz), 8.31 (1H, d, J=7.8 Hz), 8.63 (1H, d, J=2.4 Hz), 8.64 (1H, s), 8.71 (1H, d, J=2.4 Hz), 8.73 (1H, dd, J=2.4, 0.8 Hz).

Example 103: 2'-amino-2"-(1-cyanocyclopropyl)-N,N-dimethyl-[2,3':5',4"-terpyridine]-5-carboxamide

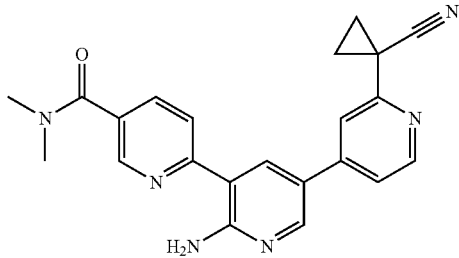 [SMILES: CN(C)C(=O)c1ccc(-c2cc(-c3ccnc(C4(C#N)CC4)c3)cnc2N)nc1]

Step 1: Preparation of 1-(4-bromopyridin-2-yl)cyclopropane-1-carbonitrile

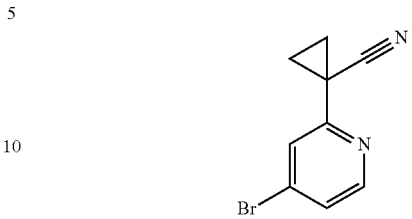

To a mixture of 4-bromo-2-fluoro-pyridine (500 mg, 2.84 mmol) and cyclopropanecarbonitrile (572 mg, 8.52 mmol) in toluene (10 mL) was added LHMDS (1 M in hexane, 10.0 mL) at −5° C. and the mixture was stirred at 25° C. for 16 h. TLC showed the reaction was completed. The mixture was poured into water (50 mL) and extracted with EtOAc (50 mL×3). The combined organic layer was washed with brine (50 mL), dried over Na$_2$SO$_4$, filtered and concentrated in vacuum. The residue was purified by Combi Flash (5% EtOAc in pentane) to afford 1-(4-bromopyridin-2-yl)cyclopropane-1-carbonitrile (300 mg, yield: 47%) as a white solid. $^1$H NMR (400 MHz, DMSO-d$_6$) δ 1.64-1.77 (2H, m), 1.77-1.94 (2H, m), 7.53-7.70 (1H, m), 7.67 (1H, s), 8.40 (1H, d, J=5.2 Hz).

Step 2: Preparation of 2'-amino-2"-(1-cyanocyclopropyl)-N,N-dimethyl-[2,3':5',4"-terpyridine]-5-carboxamide

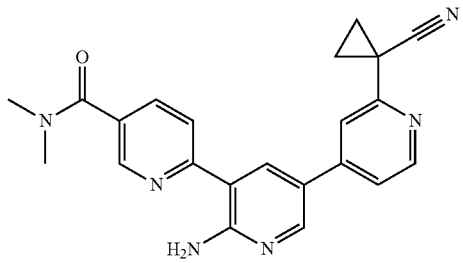 [SMILES: CN(C)C(=O)c1ccc(-c2cc(-c3ccnc(C4(C#N)CC4)c3)cnc2N)nc1]

A mixture of 2'-amino-N,N-dimethyl-5'-(4,4,5,5-tetramethyl-1,3,2-dioxaborolan-2-yl)-[2,3'-bipyridine]-5-carboxamide (196 mg, 0.534 mmol, crude), 1-(4-bromopyridin-2-yl)cyclopropane-1-carbonitrile (80 mg, 0.36 mmol), Na$_2$CO$_3$ (2 M in water, 0.9 mL) and Pd(dppf)Cl$_2$ (26 mg, 0.036 mmol) in DME (4 mL) was stirred at 100° C. for 16 hour under N$_2$ atmosphere. A black suspension was formed. Crude LCMS showed the purity of product is 38% (Rt=0.538 min; MS Calc'd: 384.2; MS Found: 384.8 [M+H]$^+$). The reaction mixture was diluted with ethyl acetate (10 mL), dried over Na$_2$SO$_4$, filtered and concentrated. The residue was purified by Combi Flash (85% EtOAc in pentane), then the impure product was washed with MTBE (3 mL×3) to afford 2'-amino-2"-(1-cyanocyclopropyl)-N,N-dimethyl-[2,3':5',4"-terpyridine]-5-carboxamide as an off-white solid. At last, the product was purified by prep-HPLC (0.05% NH$_3$·H$_2$O as additive) and lyophilized to afford 2'-amino-2"-(1-cyanocyclopropyl)-N,N-dimethyl-[2,3':5',4"-terpyridine]-5-carboxamide (27.8 mg yield: 20%) as a light yellow solid.

LCMS (Shimadzu LCMS 2010, mobile phase: from 100% [water+0.05% $NH_3 \cdot H_2O$] and 0% [MeCN] to 5% [water+0.05% $NH_3 \cdot H_2O$] and 95% [MeCN] in 5.8 min, then under this condition for 1.1 min, finally changed to 100% [water+0.05% $NH_3 \cdot H_2O$] and 0% [MeCN] and under this condition for 0.09 min.) purity is 99.83%, Rt=2.586 min; MS Calc'd.: 384.2, MS Found: 385.2 [M+H]$^+$. $^1$H NMR (400 MHz, CDCl$_3$) δ 1.75 (2H, q, J=3.6 Hz), 1.89 (2H, q, J=4.0 Hz), 3.10 (3H, s), 3.17 (3H, s), 7.06 (2H, br s), 7.36 (1H, dd, J=5.2, 2.0 Hz), 7.90-7.85 (2H, m), 7.92 (1H, dd, J=8.4, 2.0 Hz), 8.16 (1H, d, J=3.2 Hz), 8.47 (1H, dd, J=5.6, 0.8 Hz), 8.49 (1H, d, J=2.4 Hz), 8.75 (1H, dd, J=2.4, 0.4 Hz).

Example 104: 2'-amino-5'-(furo[2,3-b]pyridin-4-yl)-N,N-dimethyl-[2,3'-bipyridine]-5-carboxamide

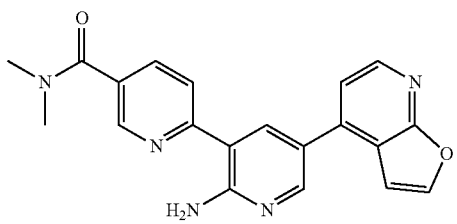 [SMILES: CN(C)C(=O)c1ccc(-c2cc(-c3ccnc4occc34)cnc2N)nc1]

Step 1: Preparation of 4-bromofuro[2,3-b]pyridine

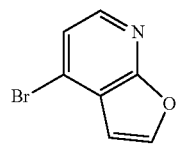

A mixture of furo[2,3-b]pyridine 7-oxide (170 mg, 1.26 mmol) in CHCl$_3$ (10 mL) was added POBr$_3$ (361 mg, 1.26 mmol) and the mixture was stirred at 70° C. for 18 h. The colourless solution produced yellow precipitate. TLC showed the reaction was completed. The mixture was poured into ice-water (20 mL) and stirred at 25° C. for 30 min. The aqueous phase was extracted with DCM (20 mL×3). The combined organic phase was washed with brine (50 mL), dried over Na$_2$SO$_4$, filtered and concentrated in vacuum. The residue was purified by Combi Flash (5% EtOAc in pentane) to give 4-bromofuro[2,3-b]pyridine (90 mg, yield: 36%) as yellow oil. $^1$H NMR (400 MHz, CDCl$_3$) δ 6.83 (1H, d, J=2.4 Hz), 7.42 (1H, d, J=5.2 Hz), 7.76 (1H, d, J=2.4 Hz), 8.16 (1H, d, J=5.2 Hz).

Step 2: Preparation of 2'-amino-5'-(furo[2,3-b]pyridin-4-yl)-N,N-dimethyl-[2,3'-bipyridine]-5-carboxamide

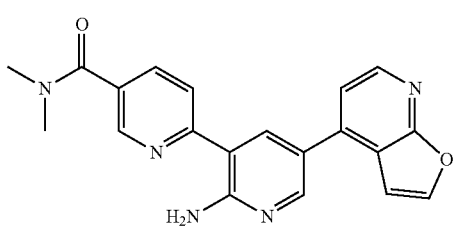 [SMILES: CN(C)C(=O)c1ccc(-c2cc(-c3ccnc4occc34)cnc2N)nc1]

A mixture of 4-bromofuro[2,3-b]pyridine (80 mg, 0.40 mmol), 2'-amino-N,N-dimethyl-5'-(4,4,5,5-tetramethyl-1,3,2-dioxaborolan-2-yl)-[2,3'-bipyridine]-5-carboxamide (229 mg, 0.622 mmol), Pd(t-Bu$_3$P)$_2$ (21 mg, 0.040 mmol, 10 mol %) and Cs$_2$CO$_3$ (1 M in water, 1 mL) in dioxane (4 mL) was stirred at 100° C. for 16 h under N$_2$ atmosphere. A black suspension was formed. Crude LCMS showed the purity of product is 36%. (Rt=0.610 min; MS Calc'd: 359.1; MS Found: 360.0 [M+H]$^+$). The reaction mixture was diluted with EtOAc (10 mL), dried over Na$_2$SO$_4$, filtered and concentrated. The residue was purified by Combi Flash (85% EtOAc in pentane) then the impure product was purified by prep-HPLC (0.05% $NH_3 \cdot H_2O$ as additive) and lyophilized to give 2'-amino-5'-(furo[2,3-b]pyridin-4-yl)-N,N-dimethyl-[2,3'-bipyridine]-5-carboxamide (5.6 mg, yield: 4%) as a yellow solid. LCMS (Shimadzu LCMS 2010, mobile phase: from 100% [water+0.05% $NH_3 \cdot H_2O$] and 0% [MeCN] to 5% [water+0.05% $NH_3 \cdot H_2O$] and 95% [MeCN] in 5.8 min, then under this condition for 1.1 min, finally changed to 100% [water+0.05% $NH_3 \cdot H_2O$] and 0% [MeCN] and under this condition for 0.09 min.) purity is 98.36%, Rt=2.359 min; MS Calc'd.: 359.1, MS Found: 360.1 [M+H]$^+$.

$^1$H NMR (400 MHz, CDCl$_3$) δ 3.11 (3H, s), 3.17 (3H, s), 6.99 (1H, d, J=2.4 Hz), 7.08 (2H, br s), 7.33 (1H, d, J=5.2 Hz), 7.78 (1H, d, J=2.4 Hz), 7.85 (1H, dd, J=8.4, 0.4 Hz), 7.93 (1H, dd, J=4.4, 2.4 Hz), 8.20 (1H, d, J=2.0 Hz), 8.39 (1H, d, J=4.8 Hz), 8.53 (1H, d, J=2.0 Hz), 8.76 (1H, dd, J=2.0, 0.8 Hz).

Example 105: 2'-amino-N,N-dimethyl-5'-(1-methyl-1H-pyrrolo[2,3-b]pyridin-4-yl)-[2,3'-bipyridine]-5-carboxamide

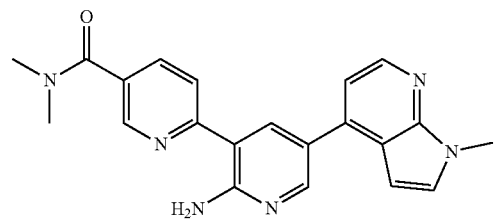

Step 1: Preparation of 4-bromo-1-methyl-H-pyrrolo[2,3-b]pyridine

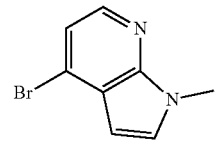

To a solution of 4-bromo-1H-pyrrolo[2,3-b]pyridine (200 mg, 1.02 mmol) in DMF (3 mL) was added NaH (49 mg, 2.0 mmol, 60% in mineral oil) at 0° C. Then to the mixture was stirred at 0° C. for 30 min. And then MeI (290 mg, 2.04 mmol) was added to the above mixture at 0° C., then the mixture was stirred at 25° C. for 15.5 h. TLC showed the reaction was completed. The resulting mixture was concentrated under reduced pressure. The residue was poured into water (50 mL) and stirred at 0° C. for 30 min. The aqueous phase was extracted with EtOAc (50 mL×3). The combined organic phase was washed with brine (50 mL), dried over Na₂SO₄, filtered and concentrated in vacuum. The residue was purified by Combi Flash (10% EtOAc in pentane) to give 4-bromo-1-methyl-H-pyrrolo[2,3-b]pyridine (180 mg, yield: 84%) as yellow oil. ¹H NMR (400 MHz, CDCl₃) δ 3.89 (3H, s), 6.49 (1H, d, J=3.6 Hz), 7.20-7.25 (1H, m), 7.26 (1H, d, J=2.4 Hz), 8.13 (1H, d, J=5.2 Hz).

Step 2: Preparation of 2'-amino-N,N-dimethyl-5'-(1-methyl-1H-pyrrolo[2,3-b]pyridin-4-yl)-[2,3'-bipyridine]-5-carboxamide

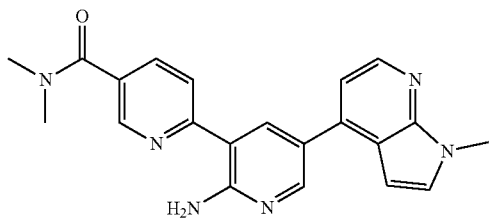

A mixture of 2'-amino-N,N-dimethyl-5'-(4,4,5,5-tetramethyl-1,3,2-dioxaborolan-2-yl)-[2,3'-bipyridine]-5-carboxamide (360 mg, crude), 4-bromo-1-methyl-pyrrolo[2,3-b]pyridine (103 mg, 0.489 mmol), Na₂CO₃ (2 M in water, 1 mL) and Pd(dppf)Cl₂ (36 mg, 0.049 mmol, 10 mol %) in DME (5 mL) was stirred at 100° C. for 16 h under N₂ atmosphere. A black suspension was formed. Crude LCMS showed the purity of product is 13% (Rt=0.513 min; MS Calc'd: 372.1; MS Found: 372.8 [M+H]⁺). The reaction mixture was diluted with ethyl acetate (10 mL), dried over Na₂SO₄, filtered and concentrated. The residue was purified by Combi Flash (90% EtOAc in pentane), then the impure product was purified by prep-HPLC (0.1% TFA as additive) and lyophilized to afford 2'-amino-N,N-dimethyl-5'-(1-methyl-1H-pyrrolo[2,3-b]pyridin-4-yl)-[2,3'-bipyridine]-5-carboxamide (15.8 mg, yield: 9%) as a light yellow solid. LCMS (Shimadzu LCMS 2010, mobile phase: from 100% [water+0.05% NH₃·H₂O] and 0% [MeCN] to 5% [water+0.05% NH₃·H₂O] and 95% [MeCN] in 5.8 min, then under this condition for 1.1 min, finally changed to 100% [water+0.05% NH₃·H₂O] and 0% [MeCN] and under this condition for 0.09 min.) purity is 97.33%, Rt=2.472 min; MS Calc'd.: 372.1, MS Found: 373.2 [M+H]⁺. ¹H NMR (400 MHz, CDCl₃) δ 3.11 (3H, s, overlapped with H₂O signal), 3.19 (3H, s, overlapped with H₂O signal), 4.05 (3H, s), 6.72 (1H, d, J=3.6 Hz), 7.29 (1H, d, J=5.2 Hz), 7.40 (1H, d, J=3.6 Hz), 7.98 (1H, d, J=8.4 Hz), 8.04 (1H, dd, J=8.0, 1.6 Hz), 8.37 (1H, s), 8.60 (1H, d, J=6.4 Hz), 8.61 (1H, s), 8.80 (1H, d, J=1.6 Hz). 10.27 (2H, br s).

Example 106: 2'-amino-2"-(tert-butyl)-N,N-dimethyl-[2,3':5',4"-terpyridine]-5-carboxamide

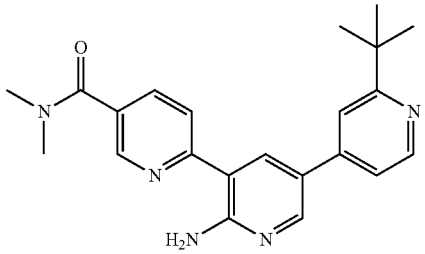 [SMILES: CN(C)C(=O)c1ccc(-c2cc(-c3ccnc(C(C)(C)C)c3)cnc2N)nc1]

A mixture of 2'-amino-N,N-dimethyl-5'-(4,4,5,5-tetramethyl-1,3,2-dioxaborolan-2-yl)-[2,3'-bipyridine]-5-carboxamide (360 mg, crude), 4-bromo-2-(tert-butyl)pyridine (109 mg, 0.510 mmol), Na₂CO₃ (2 M in water, 1 mL) and Pd(dppf)Cl₂ (37 mg, 0.051 mmol, 10 mol %) in DME (5 mL) was stirred at 100° C. for 16 hour under N₂ atmosphere. Crude LCMS showed the purity of product is 14% (Rt=0.505 min; MS Calc'd: 375.2; MS Found: 375.9 [M+H]⁺). The reaction mixture was diluted with ethyl acetate (10 mL), dried over Na₂SO₄, filtered and concentrated. The residue was purified by Combi Flash (90% EtOAc in pentane), then the impure product was purified by prep-HPLC (0.1% TFA as additive) and lyophilized to afford 2'-amino-2"-(tert-butyl)-N,N-dimethyl-[2,3':5',4"-terpyridine]-5-carboxamide (14.0 mg, yield: 7%) as a light yellow solid. LCMS (Shimadzu LCMS 2010, mobile phase: from 100% [water+0.05% NH₃·H₂O] and 0% [MeCN] to 5% [water+0.05% NH₃·H₂O] and 95% [MeCN] in 5.8 min, then under this condition for 1.1 min, finally changed to 100% [water+0.05% NH₃·H₂O] and 0% [MeCN] and under this condition for 0.09 min.) purity is 100.00%, Rt=2.935 min; MS Calc'd.: 375.2, MS Found: 376.2 [M+H]⁺. ¹H NMR (400 MHz, CDCl₃) δ 1.53 (9H, s), 3.10 (3H, s), 3.15 (3H, s), 7.55-7.59 (1H, m), 7.65 (1H, s), 7.99 (1H, d, J=8.8 Hz), 8.05 (1H, dd, J=8.0, 1.6 Hz), 8.31 (1H, d, J=1.6 Hz), 8.46 (1H, d, J=1.6 Hz), 8.79 (1H, d, J=1.6 Hz), 9.01 (1H, dd, J=4.8, 0.8 Hz), 10.13 (2H, br s).

Example 107: 2'-amino-2"-cyano-N,N-dimethyl-[2,3':5',4"-terpyridine]-5-carboxamide

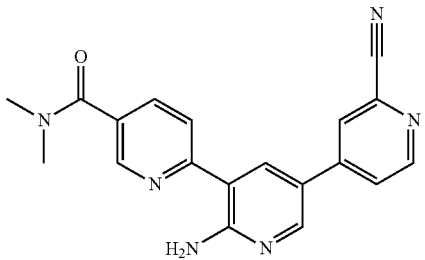 [SMILES: CN(C)C(=O)c1ccc(-c2cc(-c3ccnc(C#N)c3)cnc2N)nc1]

A mixture of 2'-amino-N,N-dimethyl-5'-(4,4,5,5-tetramethyl-1,3,2-dioxaborolan-2-yl)-[2,3'-bipyridine]-5-carboxamide (906 mg, crude), 4-bromopyridine-2-carbonitrile (300 mg, 1.64 mmol), Na₂CO₃ (2 M in water, 4 mL) and Pd(dppf)Cl₂ (120 mg, 0.164 mmol, 10 mol %) in DME (10 mL) was stirred at 100° C. for 16 hour under N₂ atmosphere. A black suspension was formed. Crude LCMS showed the purity of product is 12% (Rt=0.608 min; MS Calc'd: 344.1; MS Found: 345.0 [M+H]⁺). The reaction mixture was diluted with ethyl acetate (10 mL), dried over Na$_2$SO$_4$, filtered and concentrated. The residue was purified by Combi Flash (EtOAc), then the impure product was purified by prep-HPLC (0.05% NH$_3$·H$_2$O as additive) and lyophilized to afford 2'-amino-2"-cyano-N,N-dimethyl-[2,3':5',4"-terpyridine]-5-carboxamide (14.0 mg, yield: 7%) as a light yellow solid. LCMS (Shimadzu LCMS 2010, mobile phase: from 100% [water+0.05% NH$_3$·H$_2$O] and 0% [MeCN] to 5% [water+0.05% NH$_3$·H$_2$O] and 95% [MeCN] in 5.8 min, then under this condition for 1.1 min, finally changed to 100% [water+0.05% NH$_3$·H$_2$O] and 0% [MeCN] and under this condition for 0.09 min.) purity is 98.42%, Rt=2.306 min; MS Calc'd.: 344.1, MS Found: 345.2 [M+H]⁺. ¹H NMR (400 MHz, CDCl$_3$) δ 3.10 (3H, s), 3.17 (3H, s), 7.20 (2H, br s), 7.70 (1H, dd, J=5.2, 1.6 Hz), 7.90-7.86 (2H, m), 7.95 (1H, dd, J=8.4, 2.4 Hz), 8.14 (1H, d, J=2.4 Hz), 8.48 (1H, d, J=2.4 Hz), 8.72 (1H, d, J=5.2 Hz), 8.75 (1H, dd, J=2.4, 1.6 Hz).

Example 108: 2'-amino-N,N-dimethyl-5'-(pyridazin-4-yl)-[2,3'-bipyridine]-5-carboxamide

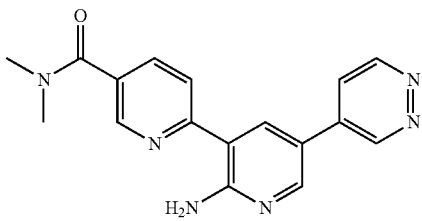 [SMILES: CN(C)C(=O)c1ccc(-c2cc(-c3ccnnc3)cnc2N)nc1]

A mixture of 2'-amino-N,N-dimethyl-5'-(4,4,5,5-tetramethyl-1,3,2-dioxaborolan-2-yl)-[2,3'-bipyridine]-5-carboxamide (243 mg, crude), 4-bromopyridazine (100 mg, 0.440 mmol), Cs$_2$CO$_3$ (1 M in water, 0.4 mL) and Pd(t-Bu$_3$P)$_2$ (23 mg, 0.044 mmol) in dioxane (3 mL) was stirred at 100° C. for 16 h under N$_2$ atmosphere. A black suspension was formed. Crude LCMS showed the purity of product is 30% (Rt=0.504 min; MS Calc'd: 320.1; MS Found: 321.0 [M+H]⁺). The reaction mixture was diluted with ethyl acetate (20 mL), dried over Na$_2$SO$_4$, filtered and concentrated. The residue was purified by Combi Flash (EtOAc), then the impure product was purified by prep-HPLC (0.05% NH$_3$·H$_2$O as an additive) and lyophilized to afford 2'-amino-N,N-dimethyl-5'-(pyridazin-4-yl)-[2,3'-bipyridine]-5-carboxamide (10.0 mg, yield: 7%) as a light yellow solid. LCMS (Shimadzu LCMS 2010, mobile phase: from 100% [water+0.05% NH$_3$·H$_2$O] and 0% [MeCN] to 5% [water+0.05% NH$_3$·H$_2$O] and 95% [MeCN] in 5.8 min, then under this condition for 1.1 min, finally changed to 100% [water+0.05% NH$_3$·H$_2$O] and 0% [MeCN] and under this condition for 0.09 min.) purity is 99.84%, Rt=1.822 min; MS Calc'd.: 320.1, MS Found: 321.2 [M+H]⁺. ¹H NMR (400 MHz, CDCl$_3$) δ 3.09 (3H, s), 3.17 (3H, s), 7.15 (2H, br s, overlapped with CDCl$_3$), 7.64 (1H, d, J=2.4 Hz), 7.86 (1H, d, J=8.0 Hz), 7.95 (1H, d, J=8.0 Hz), 8.18 (1H, s), 8.51 (1H, s), 8.75 (1H, s), 9.19 (1H, d, J=4.8 Hz), 9.47 (1H, s).

Example 109: 2'-amino-5'-(7-cyanoquinolin-4-yl)-N,N-dimethyl-[2,3'-bipyridine]-5-carboxamide

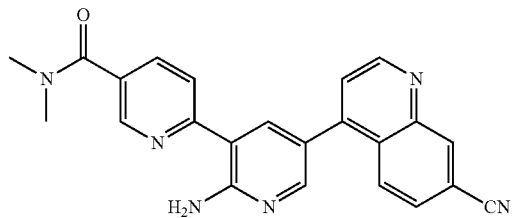 [SMILES: CN(C)C(=O)c1ccc(-c2cc(-c3ccnc4cc(C#N)ccc34)cnc2N)nc1]

A mixture of 2'-amino-N,N-dimethyl-5'-(4,4,5,5-tetramethyl-1,3,2-dioxaborolan-2-yl)-[2,3'-bipyridine]-5-carboxamide (287 mg, crude), 4-chloroquinoline-7-carbonitrile (100 mg, 0.530 mmol), Cs$_2$CO$_3$ (1 M in water, 1 mL) and Pd(t-Bu$_3$P)$_2$ (27 mg, 0.053 mmol) in dioxane (5 mL) was stirred at 100° C. for 16 h under N$_2$ atmosphere. The color of the mixture was black still. Crude LCMS s'howed the starting material was consumed completely and the purity of the desired product is 27% (Rt=0.620 min; MS Calc'd: 394.2; MS Found: 395.2 [M+H]⁺). The reaction mixture was diluted with EtOAc (15 mL), dried over Na$_2$SO$_4$, filtered and concentrated. The residue was purified by Combi Flash (EtOAc), then the impure product (80 mg) was purified by prep-HPLC (0.225% FA as an additive) and lyophilized to afford2'-amino-5'-(7-cyanoquinolin-4-yl)-N,N-dimethyl-[2,3'-bipyridine]-5-carboxamide (27.1 mg, yield: 13%) as a yellow solid. LCMS (Shimadzu LCMS 2010, mobile phase: from 100% [water+0.05% NH$_3$·H$_2$O] and 0% [MeCN] to 5% [water+0.05% NH$_3$·H$_2$O] and 95% [MeCN] in 5.8 min, then under this condition for 1.1 min, finally changed to 100% [water+0.05% NH$_3$·H$_2$O] and 0% [MeCN] and under this condition for 0.09 min.) purity is 99.89%, Rt=2.541 min; MS Calc'd.: 394.2, MS Found: 395.2 [M+H]⁺. ¹H NMR (400 MHz, CDCl$_3$) δ 3.09 (3H, s), 3.17 (3H, s), 7.20 (2H, br s), 7.51 (1H, d, J=4.4 Hz), 7.70 (1H, dd, J=8.8, 1.6 Hz), 7.79 (1H, dd, J=8.4, 0.8 Hz), 7.89 (1H, dd, J=8.4, 2.4 Hz), 8.03 (1H, d, J=2.0 Hz), 8.12 (1H, d, J=8.4 Hz), 8.30 (1H, d, J=2.0 Hz), 8.56 (1H, d, J=1.2 Hz), 8.76 (1H, dd, J=2.4, 0.8 Hz), 9.07 (1H, d, J=4.4 Hz).

Example 110: 2'-amino-5'-(7-(dimethylamino)quinolin-4-yl)-N,N-dimethyl-[2,3'-bipyridine]-5-carboxamide

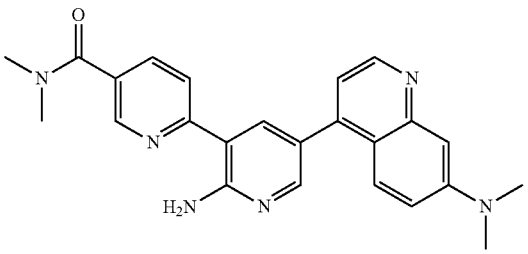

A mixture of 2'-amino-N,N-dimethyl-5'-(4,4,5,5-tetramethyl-1,3,2-dioxaborolan-2-yl)-[2,3'-bipyridine]-5-carboxamide (300 mg, crude),4-chloro-N,N-dimethylquinolin-7-amine (120 mg, 0.581 mmol), Cs$_2$CO$_3$ (568 mg, 1.74 mmol) and Pd(t-Bu$_3$P)$_2$ (30 mg, 0.058 mmol) in dioxane (1 mL) and H₂O (0.1 mL) was stirred at 100° C. for 16 h under N₂ atmosphere. A black suspension was formed. Crude LCMS showed the purity of product is 82% (Rt=0.593 min; MS Calc'd: 412.2; MS Found: 413.1 [M+H]⁺). The mixture was concentrated under reduced pressure. The residue was purified by Combi Flash (10% MeOH in EtOAc) to give an impure product. Then the impure product was purified by re-crystallization from MeCN (2 mL) to give 2'-amino-5'-(7-(dimethylamino)quinolin-4-yl)-N,N-dimethyl-[2,3'-bipyridine]-5-carboxamide (55 mg, yield: 23%) as a yellow solid. LCMS (Shimadzu LCMS 2010, mobile phase: from 100% [water+0.05% NH₃·H₂O] and 0% [MeCN] to 5% [water+0.05% NH₃·H₂O] and 95% [MeCN] in 5.8 min, then under this condition for 1.1 min, finally changed to 100% [water+0.05% NH₃·H₂O] and 0% [MeCN] and under this condition for 0.09 min.) purity is 100%, Rt=2.731 min; MS Calc'd.: 412.2, MS Found: 413.2 [M+H]⁺. ¹H NMR (400 MHz, CDCl₃) δ 3.00-3.20 (12H, m), 6.95-7.08 (3H, m), 7.16 (1H, d, J=10.0 Hz), 7.25 (1H, s), 7.70-7.90 (3H, m), 8.05 (1H, d, J=2.0 Hz), 8.32 (1H, d, J=2.0 Hz), 8.72-8.79 (2H, m).

Example 111: 2'-amino-N,N-dimethyl-5'-(1,8-naphthyridin-4-yl)-[2,3'-bipyridine]-5-carboxamide

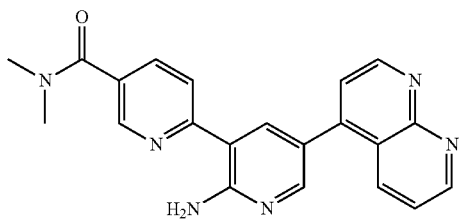 [SMILES: CN(C)C(=O)c1ccc(-c2cc(-c3ccnc4ncccc34)cnc2N)nc1]

A mixture of 2'-amino-N,N-dimethyl-5'-(4,4,5,5-tetramethyl-1,3,2-dioxaborolan-2-yl)-[2,3'-bipyridine]-5-carboxamide (287 mg, crude), 4-bromo-1,8-naphthyridine (110 mg, 0.526 mmol), Cs₂CO₃ (1 M in water, 1 mL) and Pd(t-Bu₃P)₂ (27 mg, 0.053 mmol) in dioxane (5 mL) was stirred at 100° C. for 16 h under N₂ atmosphere. The color of the mixture was black still. Crude LCMS showed the starting material was consumed completely and the purity of the desired product is 34% (Rt=0.538 min; MS Calc'd: 370.2; MS Found: 392.9 [M+Na]⁺). The reaction mixture was diluted with ethyl acetate (20 mL), dried over Na₂SO₄, filtered and concentrated. The residue was purified by Combi Flash (10% MeOH in EtOAc), the impure product (65 mg) was purified by prep-HPLC (0.05% NH₃·H₂O as an additive) and lyophilized to afford 2'-amino-N,N-dimethyl-5'-(1,8-naphthyridin-4-yl)-[2,3'-bipyridine]-5-carboxamide (27.2 mg, yield: 14%) as a light yellow solid. LCMS (Shimadzu LCMS 2010, mobile phase: from 100% [water+0.05% NH₃·H₂O] and 0% [MeCN] to 5% [water+0.05% NH₃·H₂O] and 95% [MeCN] in 5.8 min, then under this condition for 1.1 min, finally changed to 100% [water+0.05% NH₃·H₂O] and 0% [MeCN] and under this condition for 0.09 min.) purity is 98.93%, Rt=2.003 min; MS Calc'd.: 370.2, MS Found: 371.2 [M+H]⁺. ¹H NMR (400 MHz, CDCl₃) δ 3.09 (3H, s), 3.16 (3H, s), 7.11 (2H, br s), 7.48-7.52 (2H, m), 7.80 (1H, d, J=8.0 Hz), 7.89 (1H, dd, J=8.4, 2.0 Hz), 8.03 (1H, d, J=2.0 Hz), 8.31 (1H, d, J=2.0 Hz), 8.40 (1H, dd, J=8.4, 2.0 Hz), 8.76 (1H, dd, J=2.4, 0.8 Hz), 9.15-9.19 (2H, m).

Example 112: 2'-amino-N,N-dimethyl-5'-(1,6-naphthyridin-4-yl)-[2,3'-bipyridine]-5-carboxamide

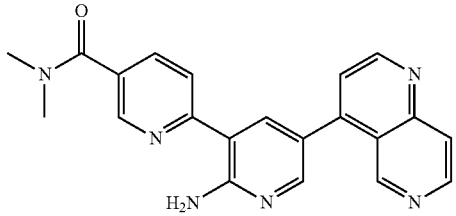 [SMILES: CN(C)C(=O)c1ccc(-c2cc(-c3ccnc4ccncc34)cnc2N)nc1]

A mixture of 2'-amino-N,N-dimethyl-5'-(4,4,5,5-tetramethyl-1,3,2-dioxaborolan-2-yl)-[2,3'-bipyridine]-5-carboxamide (235 mg, crude), 4-bromo-1,6-naphthyridine (70 mg, 0.425 mmol), Cs₂CO₃ (1 M in water, 0.9 mL) and Pd(t-Bu₃P)₂ (22 mg, 0.042 mmol) in dioxane (4 mL) was stirred at 100° C. for 16 h under N₂ atmosphere. The color of the mixture was black still. Crude LCMS showed the starting material was consumed completely and the purity of the desired product is 24% (Rt=0.623 min; MS Calc'd: 370.2; MS Found: 371.1 [M+H]⁺). The reaction mixture was diluted with EtOAc (20 mL), dried over Na₂SO₄, filtered and concentrated. The residue was purified by Combi Flash (EtOAc), then the impure product (90 mg) was purified by prep-HPLC (0.05% NH₃·H₂O as an additive) and lyophilized to afford 2'-amino-N,N-dimethyl-5'-(1,6-naphthyridin-4-yl)-[2,3'-bipyridine]-5-carboxamide (11.8 mg, yield: 7%) as a light yellow solid. LCMS (Shimadzu LCMS 2010, mobile phase: from 100% [water+0.05% NH₃·H₂O] and 0% [MeCN] to 5% [water+0.05% NH₃·H₂O] and 95% [MeCN] in 5.8 min, then under this condition for 1.1 min, finally changed to 100% [water+0.05% NH₃·H₂O] and 0% [MeCN] and under this condition for 0.09 min.) purity is 99.32%, Rt=2.091 min; MS Calc'd.: 370.2, MS Found: 371.1 [M+H]⁺. ¹H NMR (400 MHz, CDCl₃) δ 3.10 (3H, s), 3.16 (3H, s), 7.15 (2H, br s), 7.49 (1H, d, J=4.0 Hz), 7.81 (1H, d, J=8.4 Hz), 7.89 (1H, dd, J=8.0, 2.0 Hz), 8.00 (1H, d, J=6.0 Hz), 8.12 (1H, d, J=2.0 Hz), 8.39 (1H, d, J=2.4 Hz), 8.77 (1H, d, J=2.8 Hz), 8.81 (1H, d, J=6.0 Hz), 9.12 (1H, d, J=4.4 Hz), 9.49 (1H, s).

Example 113: 2'-amino-N,N-dimethyl-5'-(2-oxo-2,3-dihydro-1H-imidazo[4,5-b]pyridin-7-yl)-[2,3'-bipyridine]-5-carboxamide

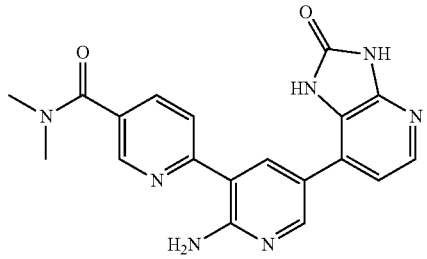 [SMILES: CN(C)C(=O)c1ccc(-c2cc(-c3ccnc4[nH]c(=O)[nH]c34)cnc2N)nc1]

Step 1: Preparation of 7-bromo-1,3-dihydro-2H-imidazo[4,5-b]pyridin-2-one

To a mixture of 4-bromopyridine-2,3-diamine (1.00 g, 5.32 mmol) in THF (30 mL) was added CDI (1.73 g, 10.6 mmol). The mixture was stirred at 80° C. for 8 h under $N_2$. A deep yellow solution was formed. TLC showed the starting material was consumed completely. The reaction mixture was filtered and concentrated. The residue was washed with DCM (30 mL) to give 7-bromo-1,3-dihydro-2H-imidazo[4,5-b]pyridin-2-one (1.01 g, yield: 89%) as a yellow solid. $^1$H NMR (400 MHz, DMSO-$d_6$) δ 7.15 (1H, d, J=5.6 Hz), 7.72 (1H, d, J=5.6 Hz), 11.48 (2H, br s).

Step 2: Preparation of 7-bromo-1,3-bis((2-(trimethylsilyl)ethoxy)methyl)-1,3-dihydro-2H-imidazo[4,5-b]pyridin-2-one

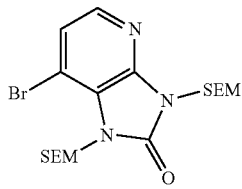 [SMILES: C[Si](C)(C)CCOCn1c(=O)n(COCC[Si](C)(C)C)c2c(Br)ccnc21]

To a solution of 7-bromo-1,3-dihydro-2H-imidazo[4,5-b]pyridin-2-one (1.01 g, 4.72 mmol) was added NaH (472 mg, 11.8 mmol, 60% purity in mineral oil) in DMF (15 mL). The reaction mixture was cooled to 0° C. for 0.5 h, and then added SEMCl (2.1 mL, 11.80 mmol) dropwise. The reaction mixture was warmed to 20° C., stirred at 20° C. for 16 h under $N_2$ atmosphere. The yellow solution turned to dark red gradually. LCMS showed the purity of the desired product (Rt=0.963 min; MS Calc'd: 473.1; MS Found: 476.1 [M+H]$^+$). The reaction mixture was quenched with MeOH (2 mL), then DMF was removed under reduced pressure. The residue was purified by Combi Flash (2% EA in pentane) to afford 7-bromo-1,3-bis((2-(trimethylsilyl)ethoxy)methyl)-1,3-dihydro-2H-imidazo[4,5-b]pyridin-2-one (1.65 g, yield: 74%) as a yellow solid. $^1$H NMR (400 MHz, CDCl$_3$) δ 0.01 (18H, s), 0.92-0.99 (4H, m), 3.60-3.72 (4H, m), 5.42 (2H, s), 5.58 (2H, s), 7.18 (1H, d, J=5.6 Hz), 7.89 (1H, d, J=5.2 Hz).

Step 3: Preparation of 2'-amino-N,N-dimethyl-5'-(2-oxo-1,3-bis((2-(trimethylsilyl)ethoxy)methyl)-2,3-dihydro-1H-imidazo[4,5-b]pyridin-7-yl)-[2,3'-bipyridine]-5-carboxamide

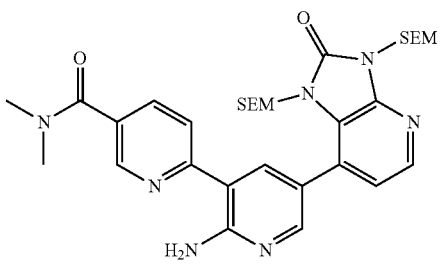 [SMILES: CN(C)C(=O)c1ccc(-c2cc(-c3ccnc4c3n(COCC[Si](C)(C)C)c(=O)n4COCC[Si](C)(C)C)cnc2N)nc1]

A mixture of 2'-amino-N,N-dimethyl-5'-(4,4,5,5-tetramethyl-1,3,2-dioxaborolan-2-yl)-[2,3'-bipyridine]-5-carboxamide (170 mg, crude), 7-bromo-1,3-bis((2-(trimethylsilyl)ethoxy)methyl)-1,3-dihydro-2H-imidazo[4,5-b]pyridin-2-one (169 mg, 0.355 mmol), Cs$_2$CO$_3$ (1 M in water, 0.1 mL) and Pd(t-Bu$_3$P)$_2$ (18 mg, 0.036 mmol) in dioxane (5 mL) was stirred at 100° C. for 16 h under $N_2$ atmosphere. A black suspension was formed. Crude LCMS showed the purity of product is 55% (Rt=0.732 min; MS Calc'd: 635.3; MS Found: 636.3 [M+H]$^+$). The reaction mixture was diluted with EtOAc (10 mL), dried over Na$_2$SO$_4$, filtered and concentrated. The residue was purified by prep-HPLC to afford 2'-amino-N,N-dimethyl-5'-(2-oxo-1,3-bis((2-(trimethylsilyl)methyl)-2,3-dihydro-1H-imidazo[4,5-b]pyridin-7-yl)-[2,3'-bipyridine]-5-carboxamide (35.0 mg, yield: 16%) as yellow oil.

Step 4: Preparation of 2'-amino-N,N-dimethyl-5'-(2-oxo-2,3-dihydro-1H-imidazo[4,5-b]pyridin-7-yl)-[2,3'-bipyridine]-5-carboxamide

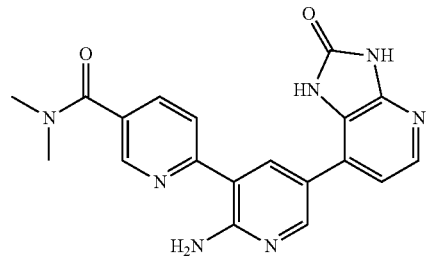 [SMILES: CN(C)C(=O)c1ccc(-c2cc(-c3ccnc4[nH]c(=O)[nH]c34)cnc2N)nc1]

To a solution of 2'-amino-N,N-dimethyl-5'-(2-oxo-1,3-bis((2-(trimethylsilyl)ethoxy)methyl)-2,3-dihydro-1H-imidazo[4,5-b]pyridin-7-yl)-[2,3'-bipyridine]-5-carboxamide (35 mg, 0.55 mmol) in DCM (1 mL) was added TFA (1 mL) at 20° C., and it was stirred at 20° C. for 1 hour. Then the mixture was concentrated under reduced pressure and the residue was diluted with MeOH (1 mL) and then EDA (0.1 mL) was added at 20° C. The residue was stirred at 20° C. for 16 h under $N_2$ atmosphere. Crude LCMS showed the purity of product (Rt=0.459 min, MS Calc'd: 375.1; MS Found: 376.0 [M+H]$^+$). The mixture was concentrated under reduced pressure. The residue was purified by prep-HPLC (0.1% TFA as an additive) and lyophilized to give 2'-amino-N,N-dimethyl-5'-(2-oxo-2,3-dihydro-1H-imidazo[4,5-b]pyridin-7-yl)-[2,3'-bipyridine]-5-carboxamide (6.0 mg, yield: 29%) as a light yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 99.37%, Rt=1.284 min; MS Calc'd.: 375.1; MS Found: 376.0 [M+H]+.

$^1$H NMR (400 MHz, DMSO) δ 3.00 (3H, s), 3.03 (3H, s), 7.14 (1H, d, J=4.8 Hz), 7.77 (2H, br s), 7.91 (1H, d, J=5.6 Hz), 8.00 (1H, dd, J=8.4, 2.4 Hz), 8.26-8.18 (2H, m), 8.35 (1H, d, J=2.4 Hz), 8.35 (1H, d, J=1.2 Hz), 11.16 (H, br s), 11.39 (H, br s).

Example 114: methyl 4-(2'-amino-5-(dimethylcarbamoyl)-[2,3'-bipyridin]-5'-yl)-1H-pyrrolo[2,3-b]pyridine-3-carboxylate

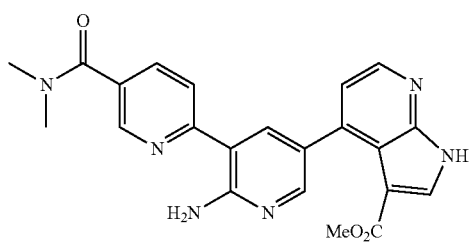 [SMILES: COC(=O)c1c[nH]c2nccc(-c3cnc(N)c(-c4ccc(C(=O)N(C)C)cn4)c3)c12]

A mixture of 2'-amino-N,N-dimethyl-5'-(4,4,5,5-tetramethyl-1,3,2-dioxaborolan-2-yl)-[2,3'-bipyridine]-5-carboxamide (404 mg, crude), methyl 4-bromo-1H-pyrrolo[2,3-b]pyridine-3-carboxylate (200 mg, 0.784 mmol), Cs$_2$CO$_3$ (1 M in water, 0.8 mL) and Pd(t-Bu$_3$P)$_2$ (40 mg, 0.078 mmol) in dioxane (5 mL) was stirred at 100° C. for 16 h under N$_2$ atmosphere. A black suspension was formed. Crude LCMS showed the purity of product is 14% (Rt=0.593 min; MS Calc'd: 416.2; MS Found: 417.3 [M+H]+). The reaction mixture was diluted with EtOAc (10 mL), dried over Na$_2$SO$_4$, filtered and concentrated. The residue was purified by Combi Flash (10% MeOH in EtOAc), then the impure product was purified by prep-HPLC (0.05% NH$_3$·H$_2$O as an additive) and lyophilized to afford methyl 4-(2'-amino-5-(dimethylcarbamoyl)-[2,3'-bipyridin]-5'-yl)-1H-pyrrolo[2,3-b]pyridine-3-carboxylate (3.5 mg, yield: 1%) as a yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 95.10%, Rt=1.451 min; MS Calc'd.: 416.2; MS Found: 417.0 [M+H]+. $^1$H NMR (400 MHz, CDCl$_3$) δ 3.08 (3H, s), 3.17 (3H, s), 3.55 (3H, s), 7.20 (1H, d, J=4.8 Hz), 7.80 (1H, d, J=8.4 Hz), 7.88 (1H, dd, J=8.4, 2.4 Hz), 8.01 (1H, d, J=1.6 Hz), 8.14 (1H, s), 8.25 (1H, d, J=1.6 Hz), 8.42 (1H, d, J=4.8 Hz), 8.73 (1H, d, J=2.0 Hz), 9.78 (1H, br s).

Example 115: 2'-amino-N,N-dimethyl-5'-(1H-pyrazolo[3,4-b]pyridin-4-yl)-[2,3'-bipyridine]-5-carboxamide

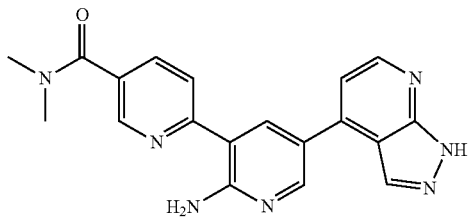 [SMILES: CN(C)C(=O)c1ccc(-c2cc(-c3ccnc4[nH]ncc34)cnc2N)nc1]

A mixture of 2'-amino-N,N-dimethyl-5'-(4,4,5,5-tetramethyl-1,3,2-dioxaborolan-2-yl)-[2,3'-bipyridine]-5-carboxamide (279 mg, crude), 4-bromo-1H-pyrazolo[3,4-b]pyridine (100 mg, 0.505 mmol), Na$_2$CO$_3$ (161 mg, 1.52 mmol) in water (1 ml) and Pd(dppf)Cl$_2$ (37 mg, 0.051 mmol) in DME (5 mL) was stirred at 100° C. for 16 h under N$_2$ atmosphere. A black suspension was formed. Crude LCMS showed the purity of product is 11% (Rt=0.480 min; MS Calc'd: 359.2; MS Found: 359.8 [M+H]+). The reaction mixture was diluted with EtOAc (10 mL), dried over Na$_2$SO$_4$, filtered and concentrated. The residue was purified by Combi Flash (EtOAc), then the impure product was purified by prep-HPLC (0.1% TFA as an additive) and lyophilized to afford 2'-amino-N,N-dimethyl-5'-(1H-pyrazolo[3,4-b]pyridin-4-yl)-[2,3'-bipyridine]-5-carboxamide (21.0 mg, yield: 12%) as a light yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 98.02%, Rt=1.333 min; MS Calc'd.: 359.2; MS Found: 360.0 [M+H]+. $^1$H NMR (400 MHz, CDCl$_3$) δ 3.11 (3H, s), 3.19 (3H, s), 7.31 (1H, d, J=4.8 Hz), 7.98 (1H, d, J=8.4 Hz), 8.05 (1H, dd, J=8.4, 2.4 Hz), 8.28 (1H, s), 8.39 (1H, d, J=2.0 Hz), 8.66-8.61 (2H, m), 8.81 (1H, d, J=1.6 Hz), 10.32 (2H, br s).

Example 116: 2'-amino-5'-(3H-imidazo[4,5-b]pyridin-7-yl)-N,N-dimethyl-[2,3'-bipyridine]-5-carboxamide

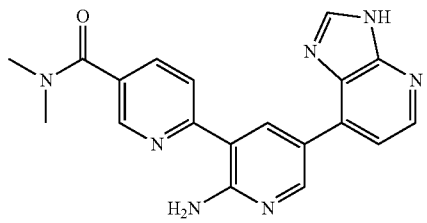 [SMILES: CN(C)C(=O)c1ccc(-c2cc(-c3ccnc4[nH]cnc34)cnc2N)nc1]

Step 1: Preparation of 7-bromo-3-((2-(trimethylsilyl)ethoxy)methyl)-3H-imidazo[4,5-b]pyridine

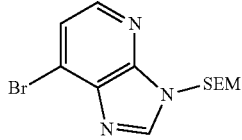 [SMILES: C[Si](C)(C)CCOCn1cnc2c(Br)ccnc21]

To a solution of 7-bromo-3H-imidazo[4,5-b]pyridine (100 mg, 0.505 mmol) in anhydrous DMF (2.5 mL) was added NaH (31 mg, 1.27 mmol, 60% in mineral oil) at 0° C. The mixture was stirred at 0° C. for 0.5 h under $N_2$ atmosphere. To the mixture was added SEM-C$_1$ (126 mg, 0.758 mmol) at 0° C., and stirred for another 16 h at 25° C. The light solution turned to deep yellow. Crude LCMS indicated that the purity of product is 37% (Rt=0.736 min; MS Calc'd.: 327.0; MS Found: 327.6 [M+H]$^+$ with bromine isotope). The mixture was quenched with $H_2O$ (15 mL) and then extracted with EtOAc (20 mL×2). The combined organic layer was washed with brine (25 mL), dried over $Na_2SO_4$ and concentrated under reduced pressure. The residue was purified by Combi Flash (20-25% EtOAc in pentane) to give 7-bromo-3-((2-(trimethylsilyl)ethoxy)methyl)-3H-imidazo[4,5-b]pyridine (93.0 mg, yield: 56%) as yellow oil.

Step 2: Preparation of 2'-amino-N,N-dimethyl-5'-(3-((2-(trimethylsilyl)ethoxy)methyl)-3H-imidazo[4,5-b]pyridin-7-yl)-[2,3'-bipyridine]-5-carboxamide

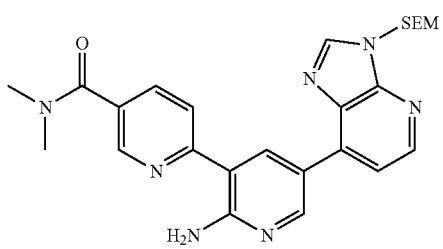 [SMILES: CN(C)C(=O)c1ccc(-c2cc(-c3ccnc4c3ncn4COCC[Si](C)(C)C)cnc2N)nc1]

A mixture of 2'-amino-N,N-dimethyl-5'-(4,4,5,5-tetramethyl-1,3,2-dioxaborolan-2-yl)-[2,3'-bipyridine]-5-carboxamide (156 mg, crude), 7-bromo-3-((2-(trimethylsilyl)ethoxy)methyl)-3H-imidazo[4,5-b]pyridine (93 mg, 0.28 mmol), $Cs_2CO_3$ (1 M in water, 0.3 mL) and Pd(t-Bu$_3$P)$_2$ (15 mg, 0.028 mmol) in dioxane (3 mL) was stirred at 100° C. for 16 h under $N_2$ atmosphere. A black suspension was formed. Crude LCMS showed the purity of product is 33% (Rt=0.642 min; MS Calc'd: 489.2; MS Found: 490.0 [M+H]$^+$). The reaction mixture was diluted with EtOAc (10 mL), dried over $Na_2SO_4$, filtered and concentrated. The residue was purified by Combi Flash (10% MeOH in EtOAc) to afford 2'-amino-N,N-dimethyl-5'-(3-((2-(trimethylsilyl)ethoxy)methyl)-3H-imidazo[4,5-b]pyridin-7-yl)-[2,3'-bipyridine]-5-carboxamide (70 mg, crude) as black oil.

Step 3: Preparation of 2'-amino-5'-(3H-imidazo[4,5-b]pyridin-7-yl)-N,N-dimethyl-[2,3'-bipyridine]-5-carboxamide

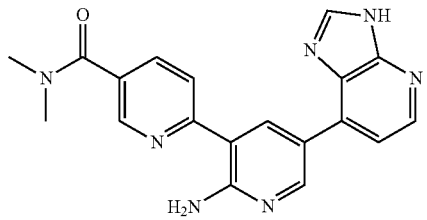 [SMILES: CN(C)C(=O)c1ccc(-c2cc(-c3ccnc4[nH]cnc34)cnc2N)nc1]

To a solution of 2'-amino-N,N-dimethyl-5'-(3-((2-(trimethylsilyl)ethoxy)methyl)-3H-imidazo[4,5-b]pyridin-7-yl)-[2,3'-bipyridine]-5-carboxamide (30 mg, crude) in DCM (1.5 mL) was added TFA (1.5 mL) at 25° C., and it was stirred at 25° C. for 1 hour. Then the mixture was concentrated under reduced pressure and the residue was diluted with MeOH (1.5 mL) and then EDA (1.5 mL) was added at 25° C. The residue was stirred at 25° C. for 16 h under $N_2$ atmosphere. Crude LCMS showed the purity of product was 42% (Rt=0.565 min, MS Calc'd.: 359.2; MS Found: 360.2 [M+H]$^+$). The mixture was concentrated under reduced pressure. The residue was purified by prep-HPLC (0.1% TFA as an additive) and lyophilized to give 2'-amino-5'-(3H-imidazo[4,5-b]pyridin-7-yl)-N,N-dimethyl-[2,3'-bipyridine]-5-carboxamide (7.6 mg, two steps yield: 8%) as a light yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 98.42%, Rt=1.378 min; MS Calc'd.: 359.2; MS Found: 360.0 [M+H]$^+$. $^1$H NMR (400 MHz, DMSO-d$_6$) δ 3.01 (3H, s), 3.05 (3H, s), 7.80 (1H, d, J=5.2 Hz), 8.10 (1H, dd, J=8.4, 2.0 Hz), 8.28 (1H, d, J=8.4 Hz), 8.44 (1H, d, J=5.2 Hz), 8.61 (1H, d, J=0.8 Hz), 8.77 (1H, d, J=2.0 Hz), 9.23-9.16 (2H, m). $^1$H NMR (400 MHz, DMSO-d$_6$+-D$_{20}$) δ 2.98 (3H, s), 3.02 (3H, s), 7.74 (1H, d, J=5.6 Hz), 8.06 (1H, dd, J=8.0, 1.6 Hz), 8.24 (1H, d, J=8.0 Hz), 8.45 (1H, d, J=5.2 Hz), 8.56 (1H, s), 8.74 (1H, d, J=2.4 Hz), 9.05 (1H, s), 9.12 (1H, s).

Example 117: 2'-amino-N,N-dimethyl-5'-(1H-pyrazolo[3,4-d]pyrimidin-3-yl)-[2,3'-bipyridine]-5-carboxamide

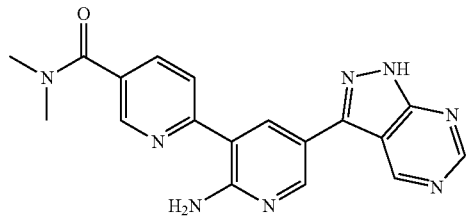 [SMILES: CN(C)C(=O)c1ccc(-c2cc(-c3n[nH]c4ncncc34)cnc2N)nc1]

Step 1: Preparation of 3-bromo-1-((2-(trimethylsilyl)ethoxy)methyl)-1H-pyrazolo[3,4-d]pyrimidine

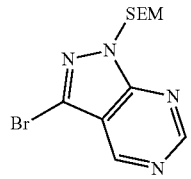 [SMILES: C[Si](C)(C)CCOCn1nc(Br)c2cncnc21]

To a solution of 3-bromo-H-pyrazolo[3,4-d]pyrimidine (100 mg, 0.502 mmol) in anhydrous DMF (4 mL) was added NaH (18 mg, 0.75 mmol, 60% in mineral oil) at 0° C. The mixture was stirred at 0° C. for 0.5 h under $N_2$ atmosphere. The mixture was added SEM-C$_1$ (168 mg, 1.00 mmol) at 0° C., and stirred for another 16 h at 25° C. The light solution turned to deep yellow. TLC showed the starting material was consumed. The mixture was quenched with $H_2O$ (15 mL) and then extracted with EtOAc (20 mL×2). The combined organic layer was washed with brine (25 mL), dried over $Na_2SO_4$ and concentrated under reduced pressure. The residue was purified by Combi Flash (20-25% EtOAc in pentane) to give 3-bromo-1-((2-(trimethylsilyl)ethoxy)methyl)-1H-pyrazolo[3,4-d]pyrimidine (100 mg, yield: 60%) as yellow oil.

Step 2: Preparation of 2'-amino-N,N-dimethyl-5'-(1-((2-(trimethylsilyl)ethoxy)methyl)-1H-pyrazolo[3,4-d]pyrimidin-3-yl)-[2,3'-bipyridine]-5-carboxamide

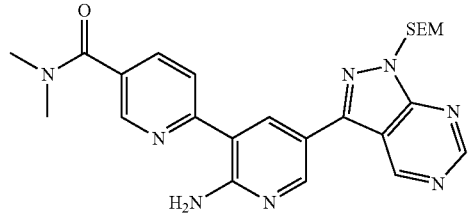 [SMILES: CN(C)C(=O)c1ccc(-c2cc(-c3nn(COCC[Si](C)(C)C)c4ncncc34)cnc2N)nc1]

A mixture of 2'-amino-N,N-dimethyl-5'-(4,4,5,5-tetramethyl-1,3,2-dioxaborolan-2-yl)-[2,3'-bipyridine]-5-carboxamide (168 mg, crude), 3-bromo-1-((2-(trimethylsilyl)ethoxy)methyl)-1H-pyrazolo[3,4-d]pyrimidine (100 mg, 0.30 mmol), $Cs_2CO_3$ (1 M in water, 0.3 mL) and Pd(t-Bu$_3$P)$_2$ (16 mg, 0.030 mmol) in dioxane (4 mL) was stirred at 100° C. for 16 h under $N_2$ atmosphere. A black suspension was formed. Crude LCMS showed the purity of product is 31% (Rt=0.636 min; MS Calc'd: 490.2; MS Found: 490.9 [M+H]$^+$). The reaction mixture was diluted with EtOAc (10 mL), dried over $Na_2SO_4$, filtered and concentrated. The residue was purified by Combi Flash (10% MeOH in EtOAc) to afford 2'-amino-N,N-dimethyl-5'-(1-((2-(trimethylsilyl)ethoxy)methyl)-1H-pyrazolo[3,4-d]pyrimidin-3-yl)-[2,3'-bipyridine]-5-carboxamide (100 mg, crude) as black oil.

Step 3: Preparation of 2'-amino-N,N-dimethyl-5'-(1H-pyrazolo[3,4-d]pyrimidin-3-yl)-[2,3'-bipyridine]-5-carboxamide

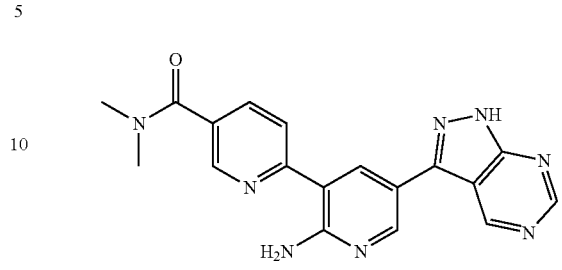

To a solution of 2'-amino-N,N-dimethyl-5'-(1-((2-(trimethylsilyl)ethoxy)methyl)-1H-pyrazolo[3,4-d]pyrimidin-3-yl)-[2,3'-bipyridine]-5-carboxamide (100 mg, crude) in DCM (5 mL) was added TFA (7 mL) and stirred at 20° C. for 1 hour. Then the mixture was concentrated under reduced pressure and the residue was diluted with MeOH (5 mL) and then EDA (1 mL) was added at 20° C. The residue was stirred at 20° C. for 16 h under $N_2$ atmosphere. Crude LCMS showed the purity of product (Rt=0.465 min, MS Calc'd.: 360.1; MS Found: 360.7 [M+H]$^+$). The mixture was concentrated under reduced pressure. The residue was purified by prep-TLC (10% MeOH in DCM) to give 2'-amino-N,N-dimethyl-5'-(1H-pyrazolo[3,4-d]pyrimidin-3-yl)-[2,3'-bipyridine]-5-carboxamide (3.6 mg, two steps yield: 4%) as a yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 95.22%, Rt=1.443 min; MS Calc'd.: 360.1; MS Found: 361.0 [M+H]$^+$. $^1$H NMR (400 MHz, DMSO-d$_6$) δ 3.02 (3H, s), 3.04 (3H, s), 7.95 (2H, br s), 8.02 (1H, dd, J=8.0, 1.6 Hz), 8.24 (1H, dd, J=8.0, 0.4 Hz), 8.67 (1H, s), 8.75 (1H, d, J=1.6 Hz), 8.80 (1H, d, J=2.0 Hz), 9.03 (1H, s), 9.73 (1H, s), 14.16 (1H, s).

Example 118: 2'-amino-5'-(5-cyanoquinolin-4-yl)-N,N-dimethyl-[2,3'-bipyridine]-5-carboxamide

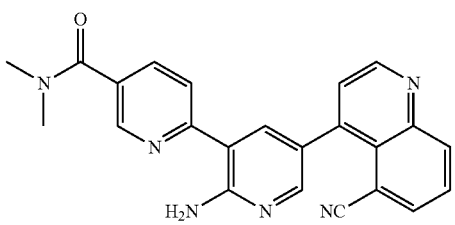 [SMILES: CN(C)C(=O)c1ccc(-c2cc(-c3ccnc4cccc(C#N)c34)cnc2N)nc1]

A mixture of 2'-amino-N,N-dimethyl-5'-(4,4,5,5-tetramethyl-1,3,2-dioxaborolan-2-yl)-[2,3'-bipyridine]-5-carboxamide (284 mg, crude), 4-bromoquinoline-5-carbonitrile (120 mg, 0.515 mmol), $Cs_2CO_3$ (1 M in water, 1 mL) and Pd(t-Bu$_3$P)$_2$ (26 mg, 0.051 mmol) in dioxane (6 mL) was stirred at 100° C. for 16 h under $N_2$ atmosphere. The color of the mixture was black still. TLC showed the reaction was completed. The reaction mixture was diluted with EtOAc (20 mL), dried over $Na_2SO_4$, filtered and concentrated. The residue was purified by Combi Flash (EtOAc), then the impure product (70 mg) was purified by prep-HPLC (0.05% NH₃·H₂O as an additive) and lyophilized to afford 2'-amino-5'-(5-cyanoquinolin-4-yl)-N,N-dimethyl-[2,3'-bipyridine]-5-carboxamide (4.8 mg, yield: 2%) as a light yellow solid. LCMS (Shimadzu LCMS 2010, mobile phase: from 100% [water+0.05% NH₃·H₂O] and 0% [MeCN] to 5% [water+0.05% NH₃·H₂O] and 95% [MeCN] in 5.8 min, then under this condition for 1.1 min, finally changed to 100% [water+0.05% NH₃·H₂O] and 0% [MeCN] and under this condition for 0.09 min.) purity is 99.80%, Rt=2.317 min; MS Calc'd.: 394.2, MS Found: 395.2 [M+H]⁺. ¹H NMR (400 MHz, CDCl₃) δ 3.07 (3H, s), 3.14 (3H, s), 7.11 (2H, br s), 7.47 (1H, d, J=4.4 Hz), 7.78-7.83 (2H, m), 7.85 (1H, dd, J=8.4, 2.4 Hz), 7.94 (1H, d, J=2.0 Hz), 8.03 (1H, dd, J=8.4, 1.6 Hz), 8.20 (1H, d, J=2.0 Hz), 8.44 (1H, dd, J=8.8, 1.2 Hz), 8.72 (1H, dd, J=2.4, 1.2 Hz), 9.03 (1H, d, J=4.0 Hz).

Example 119:2'-amino-N,N-dimethyl-[2,3':5',3"-terpyridine]-5-carboxamide

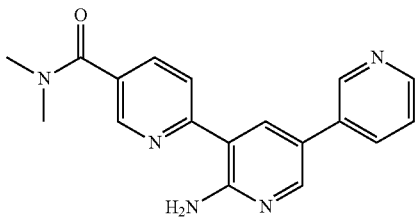 [SMILES: CN(C)C(=O)c1ccc(-c2cc(-c3cccnc3)cnc2N)nc1]

Step 1: Preparation of 3-(4,4,5,5-tetramethyl-1,3,2-dioxaborolan-2-yl)pyridine

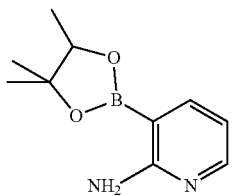

A mixture of 3-bromopyridin-2-amine (470 mg, 2.72 mmol), B₂Pin₂ (1.38 g, 5.44 mmol), KOAc (800 mg, 8.16 mmol) and Pd(dppf)Cl₂ (199 mg, 0.272 mmol) in dioxane (7 mL) was stirred at 110° C. for 3 h under N₂ atmosphere. The red mixture turned to black. Crude LCMS showed the purity of product is 10%. (Rt=0.782 min; MS Calc'd: 220.1; MS Found: 221.1 [M+H]⁺). The mixture was diluted with EtOAc (20 mL), filtered and concentrated under reduced pressure to give 3-(4,4,5,5-tetramethyl-1,3,2-dioxaborolan-2-yl)pyridin-2-amine (crude) as a black solid and directly used to next step.

Step 2: Preparation of 2'-amino-N,N-dimethyl-[2,3'-bipyridine]-5-carboxamide

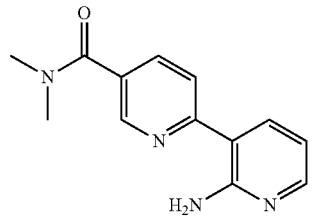 [SMILES: CN(C)C(=O)c1ccc(-c2cccnc2N)nc1]

A mixture of 3-(4,4,5,5-tetramethyl-1,3,2-dioxaborolan-2-yl)pyridin-2-amine (883 mg, 4.02 mmol), 6-bromo-N,N-dimethylnicotinamide (460 mg, 2.01 mmol), Na₂CO₃ (2 M in water, 5 mL) and Pd(dppf)Cl₂ (147 mg, 0.201 mmol, 10 mol %) in DME (13 mL) was stirred at 110° C. for 16 h under N₂ atmosphere. The colour of the mixture was black still. Crude LCMS showed the purity of product is 54%. (Rt=0.791 min; MS Calc'd: 242.1; MS Found: 243.1 [M+H]⁺). The reaction mixture was diluted with EtOAc (50 mL), washed with water (15 mL×3), dried over Na₂SO₄, filtered and concentrated. The reaction mixture was purified by Combi Flash (75% EtOAc in pentane), then the crude product was purified by prep-TLC (DCM:MeOH=10:1) to give 2'-amino-N,N-dimethyl-[2,3'-bipyridine]-5-carboxamide (12.0 mg, yield: 2%) as a white solid. LCMS (Shimadzu LCMS 2010, mobile phase: from 100% [water+0.05% NH₃·H₂O] and 0% [MeCN] to 5% [water+0.05% NH₃·H₂O] and 95% [MeCN] in 5.8 min, then under this condition for 1.1 min, finally changed to 100% [water+0.05% NH₃—H₂O] and 0% [MeCN] and under this condition for 0.09 min.) purity is 97.69%, Rt=1.875 min; MS Calc'd.: 242.1, MS Found: 243.1 [M+H]⁺. ¹H NMR (400 MHz, CDCl₃) δ 3.09 (3H, s), 3.15 (3H, s), 6.73 (1H, dd, J=7.6, 4.8 Hz), 6.77 (2H, br s), 7.75 (1H, dd, J=8.4, 0.8 Hz), 7.86 (1H, dd, J=4.4, 2.4 Hz), 7.88 (1H, dd, J=4.0, 1.6 Hz), 8.14 (1H, dd, J=4.8, 1.6 Hz), 8.70 (1H, dd, J=2.0, 0.4 Hz).

Step 3: Preparation of 2'-amino-5'-bromo-N,N-dimethyl-[2,3'-bipyridine]-5-carboxamide

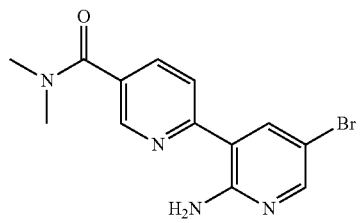 [SMILES: CN(C)C(=O)c1ccc(-c2cc(Br)cnc2N)nc1]

To a mixture of 2'-amino-N,N-dimethyl-[2,3'-bipyridine]-5-carboxamide (11.3 g, 46.6 mmol) in MeCN (120 mL) was added NBS (8.50 g, 48.0 mmol) in one portion at 0° C. The mixture was stirred at 25° C. for 16 h. The color of the mixture was form light to deep yellow. TLC showed the reaction was completed. The residue was quenched with sat.Na₂S₂O₃ (100 mL) and NaHCO₃ (100 mL). The mixture was stirred for 30 min, extracted with EtOAc (100 mL×3). The combined organic layer was washed with sat.NaHCO₃ (100 mL), dried over Na₂SO₄, filtered and concentrated in vacuum. The residue was purified by Combi Flash (50%

EtOAc in pentane) to afford 2'-amino-5'-bromo-N,N-dimethyl-[2,3'-bipyridine]-5-carboxamide (14.3 g, yield: 95%) as a yellow solid. ¹H NMR (400 MHz, DMSO-d₆) δ 2.99 (3H, s), 3.02 (3H, s), 7.62 (2H, br s), 7.95 (1H, dd, J=8.4, 2.4 Hz), 8.08 (1H, dd, J=8.4, 0.8 Hz), 8.12 (1H, d, J=2.0 Hz), 8.23 (1H, d, J=2.4 Hz), 8.70 (1H, dd, J=2.0, 0.8 Hz).

Step 4: Preparation of 3-(4,4,5,5-tetramethyl-1,3,2-dioxaborolan-2-yl)pyridine

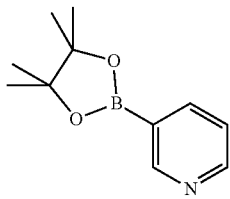

A mixture of 3-bromopyridine (150 mg, 0.949 mmol), B₂Pin₂ (362 mg, 1.42 mmol), KOAc (280 mg, 2.85 mmol) and Pd(dppf)Cl₂ (70 mg, 0.095 mmol) in dioxane (5 mL) was stirred at 110° C. for 3 h under N₂ atmosphere. The red suspension turned to black. TLC showed the reaction was completed. The reaction mixture was diluted with EtOAc (10 mL), filtered and concentrated to give crude 3-(4,4,5,5-tetramethyl-1,3,2-dioxaborolan-2-yl)pyridine (crude) as black oil and directly used to next step.

Step 5: Preparation of 2'-amino-N,N-dimethyl-[2,3':5',3''-terpyridine]-5-carboxamide

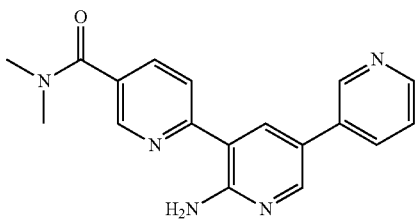

A mixture of 2'-amino-5'-bromo-N,N-dimethyl-[2,3'-bipyridine]-5-carboxamide (188 mg, 0.585 mmol), 3-(4,4,5,5-tetramethyl-1,3,2-dioxaborolan-2-yl)pyridine (180 mg, crude), Na₂CO₃ (2 M in water, 1 mL) and Pd(dppf)Cl₂ (43 mg, 0.059 mmol) in DME (5 mL) was stirred at 100° C. for 16 h under N₂ atmosphere. A black suspension was formed. Crude LCMS showed the purity of product is 11% (Rt=0.306 min; MS Calc'd: 319.1; MS Found: 319.8 [M+H]⁺). The reaction mixture was diluted with ethyl acetate (20 mL), dried over Na₂SO₄, filtered and concentrated. The residue was purified by Combi Flash (EtOAc), then the impure product was purified by prep-HPLC (0.05% NH₃·H₂O as an additive) and lyophilized to afford reparation of 2'-amino-N,N-dimethyl-[2,3':5',3''-terpyridine]-5-carboxamide (107 mg, yield: 57%) as alight yellow solid. LCMS (Shimadzu LCMS 2010, mobile phase: from 100% [water+0.05% NH₃·H₂O] and 0% [MeCN] to 5% [water+0.05% NH₃·H₂O] and 95% [MeCN] in 5.8 min, then under this condition for 1.1 min, finally changed to 100% [water+0.05% NH₃·H₂O] and 0% [MeCN] and under this condition for 0.09 min.) purity is 97.98%, Rt=2.079 min; MS Calc'd.: 319.1, MS Found: 320.2 [M+H]⁺. ¹H NMR (400 MHz, CDCl₃) δ 3.10 (3H, s), 3.17 (3H, s), 6.95 (2H, br s), 7.36-7.42 (1H, m), 7.86 (1H, d, J=4.0 Hz), 7.88 (1H, d, J=6.4 Hz), 7.93 (1H, dd, J=8.4, 2.4 Hz), 8.09 (1H, d, J=2.0 Hz), 8.40 (1H, d, J=2.4 Hz), 8.60 (1H, dd, J=4.8, 1.6 Hz), 8.75 (1H, d, J=1.2 Hz), 8.84 (1H, d, J=2.0 Hz).

Example 120: 2',2''-diamino-N,N-dimethyl-[2,3':5',3''-terpyridine]-5-carboxamide

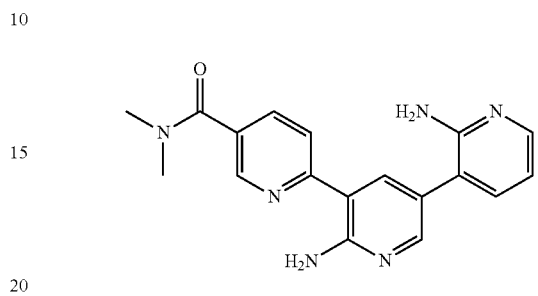

A mixture of 3-(4,4,5,5-tetramethyl-1,3,2-dioxaborolan-2-yl)pyridin-2-amine (250 mg, crude), 2'-amino-5'-bromo-N,N-dimethyl-[2,3'-bipyridine]-5-carboxamide (244 mg, 0.760 mmol), Na₂CO₃ (2 M in water, 1 mL) and Pd(t-Bu₃P)₂ (56 mg, 0.076 mmol, 10 mol %) in DME (4 mL) was stirred at 100° C. for 16 h under N₂ atmosphere. A black suspension was formed. Crude LCMS showed the purity of product is 7% (Rt=0.262 min; MS Calc'd: 334.1; MS Found: 335.2 [M+H]⁺). The reaction mixture was diluted with EtOAc (20 mL), dried over Na₂SO₄, filtered and concentrated. The residue was purified by Combi Flash (EtOAc), then the impure product was purified by prep-HPLC (0.05% NH₃·H₂O as an additive) and lyophilized to afford 2',2''-diamino-N,N-dimethyl-[2,3':5',3''-terpyridine]-5-carboxamide (14.2 mg, two steps yield: 6%) as a light yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 99.23%, Rt=1.294 min; MS Calc'd.: 334.1; MS Found: 334.9 [M+H]⁺. ¹H NMR (400 MHz, CDCl₃) δ 3.08 (3H, s), 3.16 (3H, s), 4.55 (2H, br s), 6.77 (1H, dd, J=7.2, 4.8 Hz), 6.93 (2H, br s), 7.38 (1H, dd, J=7.2, 1.6 Hz), 7.78 (1H, d, J=8.0 Hz), 7.88 (1H, dd, J=8.0, 2.0 Hz), 8.01 (1H, d, J=2.4 Hz), 8.09 (1H, dd, J=5.2, 2.0 Hz), 8.21 (1H, d, J=2.0 Hz), 8.73 (1H, dd, J=2.4, 0.8 Hz).

Example 121: 2'-amino-N,N-dimethyl-5'-(1-methyl-3-(pyridin-3-yl)-1H-pyrrolo[2,3-b]pyridin-5-yl)-[2,3'-bipyridine]-5-carboxamide

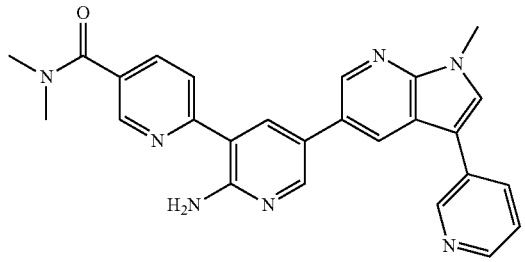 [SMILES: CN(C)C(=O)c1ccc(-c2cc(-c3cnc4c(c3)c(-c3cccnc3)cn4C)cnc2N)nc1]

Step 1: Preparation of 5-chloro-1-methyl-1H-pyrrolo[2,3-b]pyridine

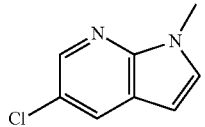

To a solution of 5-chloro-1H-pyrrolo[2,3-b]pyridine (3.00 g, 19.7 mmol) in anhydrous DMF (40 mL) was added NaH (1.18 g, 29.5 mmol, 60% in mineral oil) at 0° C. The mixture was stirred at 0° C. for 1 h under $N_2$ atmosphere. To the mixture was added MeI (6.02 g, 42.4 mmol) at 0° C., and stirred for another 5 h at 20° C. The solution turned to light yellow. TLC showed the reaction was completed. The mixture was quenched with MeOH (30 mL) concentrated under reduced pressure. The residue was purified by Combi Flash (pentane) to give 5-chloro-1-methyl-1H-pyrrolo[2,3-b]pyridine (3.14 g, yield: 96%) as a yellow solid. $^1$H NMR (400 MHz, CDCl$_3$) δ 3.87 (3H, s), 6.40 (1H, d, J=3.2 Hz), 7.21 (1H, d, J=3.6 Hz), 7.86 (1H, d, J=2.0 Hz), 8.26 (1H, d, J=2.0 Hz).

Step 2: Preparation of 3-bromo-5-chloro-1-methyl-H-pyrrolo[2,3-b]pyridine

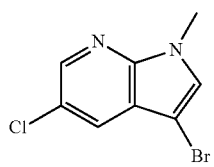

To a mixture of 5-chloro-1-methyl-1H-pyrrolo[2,3-b]pyridine (3.14 g, 18.9 mmol) in DCM (60 mL) was added NBS (3.52 g, 19.8 mmol) in one portion at 0° C. Then the mixture was stirred at 20° C. for 16 h. Crude LCMS showed the purity of product is 81% (Rt=0.754 min; MS Calc'd: 245.9; MS Found: 246.5 [M+H]$^+$). The reaction was quenched with sat.Na$_2$S$_2$O$_3$ (30 ml) and NaHCO$_3$ (30 ml) and stirred for 30 min. The mixture was extracted with EtOAc (15 mL×3). The combined organic phase was washed with NaHCO$_3$ (50 mL), dried over Na$_2$SO$_4$, filtered and concentrated in vacuum. The residue was purified by Combi Flash (5% EtOAc in pentane) to afford 3-bromo-5-chloro-1-methyl-H-pyrrolo[2,3-b]pyridine (4.40 g, yield: 95%) as a white solid. $^1$H NMR (400 MHz, CDCl$_3$) δ 3.86 (3H, s), 7.24 (1H, s), 7.83 (1H, d, J=2.0 Hz), 8.29 (1H, d, J=2.4 Hz).

Step 3: Preparation of 5-chloro-1-methyl-3-(pyridin-3-yl)-1H-pyrrolo[2,3-b]pyridine

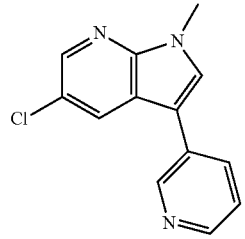 [SMILES: Cn1cc(-c2cccnc2)c2cc(Cl)cnc21]

A mixture of 3-(4,4,5,5-tetramethyl-1,3,2-dioxaborolan-2-yl)pyridine (1.51 g, 7.34 mmol), 3-bromo-5-chloro-1-methyl-1H-pyrrolo[2,3-b]pyridine (900 mg, 3.67 mmol), Cs$_2$CO$_3$ (1 M in water, 7 mL) and Pd(t-Bu$_3$P)$_2$ (188 mg, 0.367 mmol) in dioxane (15 mL) was stirred at 100° C. for 15 h under N$_2$ atmosphere. The color of the mixture was black. Crude LCMS showed the starting material was consumed completely and the purity of the desired product is 73% (Rt=0.502 min; MS Calc'd: 243.1; MS Found: 243.6 [M+H]$^+$). The reaction mixture was diluted with ethyl acetate (10 mL), dried over Na$_2$SO$_4$, filtered and concentrated. The residue was purified by Combi Flash (35% EtOAc in pentane) to afford 5-chloro-1-methyl-3-(pyridin-3-yl)-1H-pyrrolo[2,3-b]pyridine (850 mg, yield: 95%) as a white solid. $^1$H NMR (400 MHz, CDCl$_3$) δ 3.95 (3H, s), 7.35-7.40 (1H, m), 7.47 (1H, s), 7.85-7.89 (1H, m), 8.13 (1H, d, J=2.0 Hz), 8.34 (1H, d, J=2.0 Hz), 8.54 (1H, dd, J=4.8, 1.6 Hz), 8.85 (1H, s).

Step 4: Preparation of 2'-amino-N,N-dimethyl-5'-(1-methyl-3-(pyridin-3-yl)-1H-pyrrolo[2,3-b]pyridin-5-yl)-[2,3'-bipyridine]-5-carboxamide

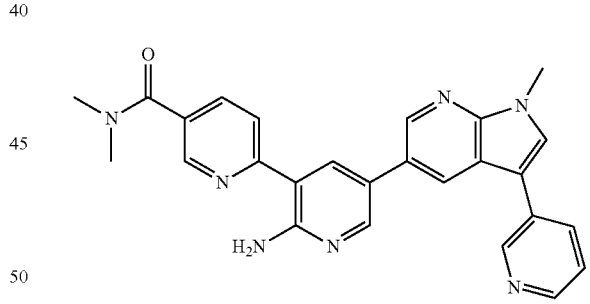

A mixture of 2'-amino-N,N-dimethyl-5'-(4,4,5,5-tetramethyl-1,3,2-dioxaborolan-2-yl)-[2,3'-bipyridine]-5-carboxamide (260 mg, crude), 5-chloro-1-methyl-3-(pyridin-3-yl)-1H-pyrrolo[2,3-b]pyridine (101 mg, 0.415 mmol), K$_3$PO$_4$ (1 M in water, 0.1 mL) and Pd(t-Bu$_3$P)$_2$ (21 mg, 0.042 mmol) in dioxane (4 mL) was stirred at 100° C. for 14 h under N$_2$ atmosphere. A black suspension was formed. Crude LCMS showed the purity of product is 30% (Rt=0.501 min; MS Calc'd: 449.2; MS Found: 449.8 [M+H]$^+$). The reaction mixture was diluted with ethyl acetate (20 mL), dried over Na$_2$SO$_4$, filtered and concentrated. The residue was purified by Combi Flash (10% MeOH in EtOAc), then the impure product was purified by prep-HPLC (0.05% NH$_3$·H$_2$O as an additive) and lyophilized to afford 2'-amino-N,N-dimethyl-5'-(1-methyl-3-(pyridin-3-yl)-1H-pyrrolo[2,3-b]pyridin-5- yl)-[2,3'-bipyridine]-5-carboxamide (30.5 mg, yield: 16%) as a light yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 96.57%, Rt=1.349 min; MS Calc'd.: 449.2; MS Found: 450.1 [M+H]+. $^1$H NMR (400 MHz, CDCl$_3$) δ 3.10 (3H, s), 3.17 (3H, s), 4.01 (3H, s), 7.06 (2H, br s), 7.40 (1H, dd, J=8.0, 4.8 Hz), 7.50 (1H, s), 7.85-7.96 (3H, m), 8.13 (1H, d, J=2.0 Hz), 8.28 (1H, d, J=2.0 Hz), 8.40 (1H, d, J=2.4 Hz), 8.55 (1H, dd, J=4.8, 1.2 Hz), 8.60 (1H, d, J=2.4 Hz), 8.75 (1H, d, J=1.6 Hz), 8.96 (1H, d, J=1.6 Hz).

Example 122: 2'-amino-N,N-dimethyl-5'-(1-methyl-3-(pyrimidin-5-yl)-1H-pyrrolo[2,3-b]pyridin-5-yl)-[2,3'-bipyridine]-5-carboxamide

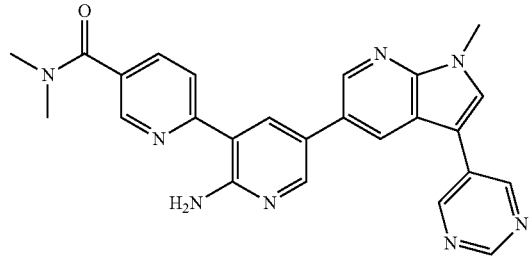 [SMILES: CN(C)C(=O)c1ccc(-c2cc(-c3cnc4c(c3)c(-c3cncnc3)cn4C)cnc2N)nc1]

Step 1: Preparation of 5-chloro-1-methyl-3-(pyrimidin-5-yl)-1H-pyrrolo[2,3-b]pyridine

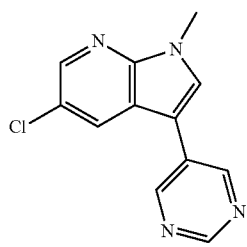 [SMILES: Cn1cc(-c2cncnc2)c2cc(Cl)cnc21]

A mixture of pyrimidin-5-ylboronic acid (909 mg, 7.33 mmol), 3-bromo-5-chloro-1-methyl-1H-pyrrolo[2,3-b]pyridine (600 mg, 2.44 mmol), Cs$_2$CO$_3$ (1 M in water, 5 mL) and Pd(t-Bu$_3$P)$_2$ (125 mg, 0.367 mmol) in dioxane (10 mL) was stirred at 100° C. for 15 h under N$_2$ atmosphere. The color of the mixture was black. Crude LCMS showed the starting material was consumed completely and the purity of the desired product is 64% (Rt=0.768 min; MS Calc'd: 244.0; MS Found: 244.8 [M+H]+). The reaction mixture was diluted with ethyl acetate (10 mL), dried over Na$_2$SO$_4$, filtered and concentrated. The residue was purified by Combi Flash (40% EtOAc in pentane) to afford 5-chloro-1-methyl-3-(pyrimidin-5-yl)-1H-pyrrolo[2,3-b]pyridine (400 mg, yield: 67%) as a white solid. $^1$H NMR (400 MHz, CDCl$_3$) δ 3.97 (3H, s), 7.54 (1H, s), 8.11 (1H, d, J=1.6 Hz), 8.37 (1H, d, J=2.4 Hz), 8.97 (2H, s), 9.15 (1H, s).

Step 2: Preparation of 2'-amino-N,N-dimethyl-5'-(1-methyl-3-(pyrimidin-5-yl)-1H-pyrrolo[2,3-b]pyridin-5-yl)-[2,3'-bipyridine]-5-carboxamide

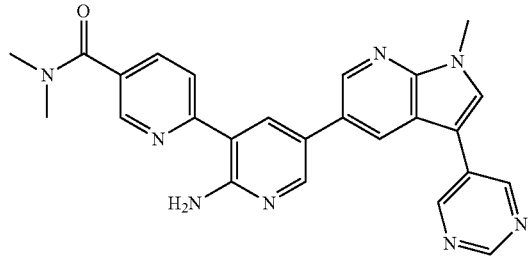 [SMILES: CN(C)C(=O)c1ccc(-c2cc(-c3cnc4c(c3)c(-c3cncnc3)cn4C)cnc2N)nc1]

A mixture of 2'-amino-N,N-dimethyl-5'-(4,4,5,5-tetramethyl-1,3,2-dioxaborolan-2-yl)-[2,3'-bipyridine]-5-carboxamide (260 mg, crude), 5-chloro-1-methyl-3-(pyrimidin-5-yl)-1H-pyrrolo[2,3-b]pyridine (102 mg, 0.415 mmol), K$_3$PO$_4$ (1 M in water, 0.1 mL) and Pd(t-Bu$_3$P)$_2$ (21 mg, 0.042 mmol) in dioxane (4 mL) was stirred at 100° C. for 14 h under N$_2$ atmosphere. A black suspension was formed. Crude LCMS showed the purity of product is 26% (Rt=0.502 min; MS Calc'd: 450.2; MS Found: 450.8 [M+H]+). The reaction mixture was diluted with ethyl acetate (20 mL), dried over Na$_2$SO$_4$, filtered and concentrated. The residue was purified by Combi Flash (10% MeOH in EtOAc), then the impure product was purified by prep-HPLC (0.05% NH$_3$·H$_2$O as an additive) and lyophilized to afford 2'-amino-N,N-dimethyl-5'-(1-methyl-3-(pyrimidin-5-yl)-1H-pyrrolo[2,3-b]pyridin-5-yl)-[2,3'-bipyridine]-5-carboxamide (27.4 mg, yield: 15%) as a light yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 95.07%, Rt=1.467 min; MS Calc'd.: 450.2; MS Found: 451.1 [M+H]+. $^1$H NMR (400 MHz, CDCl$_3$) δ 3.10 (3H, s), 3.17 (3H, s), 4.03 (3H, s), 6.90 (2H, br s), 7.57 (1H, s), 7.87 (1H, dd, J=8.4, 0.4 Hz), 7.92 (1H, dd, J=8.4, 2.0 Hz), 8.09 (1H, d, J=2.4 Hz), 8.25 (1H, d, J=2.0 Hz), 8.42 (1H, d, J=2.4 Hz), 8.64 (1H, d, J=2.0 Hz), 8.75 (1H, dd, J=2.4, 0.8 Hz), 9.06 (2H, s), 9.15 (1H, s).

Example 123: 2'-amino-N,N-dimethyl-5'-(1-methyl-3-(pyridin-3-yl)-1H-pyrazolo[3,4-b]pyridin-5-yl)-[2,3'-bipyridine]-5-carboxamide

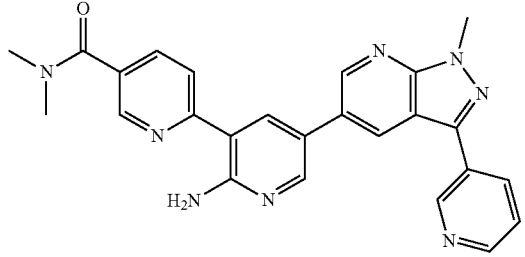 [SMILES: CN(C)C(=O)c1ccc(-c2cc(-c3cnc4c(c3)c(-c3cccnc3)nn4C)cnc2N)nc1]

Step 1: Preparation of 5-chloro-1H-pyrazolo[3,4-b]pyridine

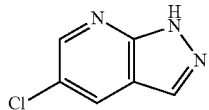

To a solution of 5-chloro-2-fluoronicotinaldehyde (3.00 g, 18.8 mmol) in EtOH (10 mL) was added $NH_2NH_2 \cdot H_2O$ (2.82 g, 56.4 mmol) at 15° C. The mixture stirred 16 h at 80° C. The solution turned to light yellow. TLC showed the reaction was completed. The mixture was concentrated under reduced pressure. The residue was purified by Combi Flash (20% EtOAc in pentane) to give 5-chloro-1H-pyrazolo [3,4-b]pyridine (2.80 g, yield: 97%) as an off-white solid. $^1$H NMR (400 MHz, $CDCl_3$) δ 8.05 (1H, s), 8.09 (1H, d, J=2.0 Hz), 8.52 (1H, d, J=2.4 Hz).

Step 2: Preparation of 5-chloro-1-methyl-1H-pyraolo[3,4-b]pyridine

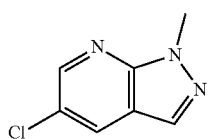

To a solution of 5-chloro-H-pyrazolo[3,4-b]pyridine (2.50 g, 16.3 mmol) in anhydrous DMF (25 mL) was added NaH (977 mg, 24.4 mmol, 60% in mineral oil) at 0° C. The mixture was stirred at 0° C. for 1 h under $N_2$ atmosphere. To the mixture was added MeI (4.62 g, 32.6 mmol) at 0° C., and stirred for another 4 h at 20° C. The solution turned to light yellow. TLC showed the reaction was completed. The mixture was quenched with MeOH (30 mL) concentrated under reduced pressure. The residue was purified by Combi Flash (pentane) to give 5-chloro-1-methyl-1H-pyrazolo[3,4-b]pyridine (1.90 g, yield: 70%) as a white solid. 1H NMR (400 MHz, $CDCl_3$) δ 4.14 (3H, s), 7.95 (1H, s), 8.01 (1H, d, J=2.4 Hz), 8.47 (1H, d, J=2.0 Hz).

Step 3: Preparation of 3-bromo-5-chloro-1-methyl-H-pyrazolo[3,4-b]pyridine

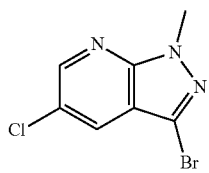

To a mixture of 5-chloro-1-methyl-H-pyrazolo[3,4-b]pyridine (1.50 g, 8.95 mmol) in $CHCl_3$ (18 mL) was added $Br_2$ (2.86 g, 17.9 mmol) in one portion at 0° C. Then the mixture was stirred at 18° C. for 16 h. The solution turned to red. TLC showed the reaction was almost completed. The mixture was quenched with sat.$Na_2S_2O_3$ (30 ml) and $NaHCO_3$ (30 ml) and stirred for 30 min. The reaction mixture was extracted with DCM (20 mL×3). The combined organic phase was washed with $NaHCO_3$ (50 mL), dried over $Na_2SO_4$, filtered and concentrated in vacuum. The residue was purified by Combi Flash (10% EtOAc in pentane) to afford 3-bromo-5-chloro-1-methyl-1H-pyrazolo[3,4-b]pyridine (1.40 g, yield: 63%) as an off-white solid. $^1$H NMR (400 MHz, $CDCl_3$) δ 4.12 (3H, s), 7.93 (1H, d, J=2.0 Hz), 8.50 (1H, d, J=2.0 Hz).

Step 4: Preparation of 5-chloro-1-methyl-3-(pyridin-3-yl)-1H-pyrazolo[3,4-b]pyridine

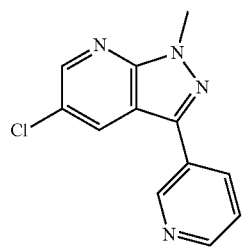 [SMILES: Cn1nc(-c2cccnc2)c2cc(Cl)cnc21]

A mixture of 3-(4,4,5,5-tetramethyl-1,3,2-dioxaborolan-2-yl)pyridine (599 mg, 2.92 mmol), 3-bromo-5-chloro-1-methyl-1H-pyrazolo[3,4-b]pyridine (400 mg, 1.62 mmol), $Cs_2CO_3$ (1 M in water, 3 mL) and $Pd(t-Bu_3P)_2$ (83 mg, 0.162 mmol) in dioxane (15 mL) was stirred at 100° C. for 15 h under $N_2$ atmosphere. The red solution turned to black. Crude LCMS showed the starting material was consumed completely and the purity of the desired product is 70% (Rt=0.530 min; MS Calc'd: 244.0; MS Found: 244.9 [M+H]$^+$). The reaction mixture was diluted with ethyl acetate (10 mL), dried over $Na_2SO_4$, filtered and concentrated. The residue was purified by Combi Flash (15% EtOAc in pentane) to afford 5-chloro-1-methyl-3-(pyridin-3-yl)-1H-pyrazolo[3,4-b]pyridine 490 mg, yield: 99%) as a white solid. $^1$H NMR (400 MHz, $CDCl_3$) δ 4.21 (3H, s), 7.45 (1H, dd, J=8.0, 4.8 Hz), 8.22 (1H, d, J=8.0 Hz), 8.29 (1H, d, J=0.8 Hz), 8.53 (1H, d, J=2.0 Hz), 8.66 (1H, d, J=3.6 Hz), 9.16 (1H, s).

Step 5: Preparation of 1-methyl-3-(pyridin-3-yl)-5-(4,4,5,5-tetramethyl-1,3,2-dioxaborolan-2-yl)-1H-pyrazolo[3,4-b]pyridine

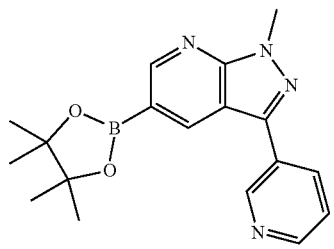 [SMILES: Cn1nc(-c2cccnc2)c2cc(B3OC(C)(C)C(C)(C)O3)cnc21]

A mixture of 5-chloro-1-methyl-3-(pyridin-3-yl)-1H-pyrazolo[3,4-b]pyridine (190 mg, 0.777 mmol), $B_2Pin_2$ (296 mg, 0.116 mmol), $Pd(dppf)Cl_2$ (57 mg, 0.078 mmol) and KOAc (229 mg, 2.34 mmol) in dioxane (5 mL) was stirred at 100° C. for 5 h under $N_2$ atmosphere. A black suspension was formed. Crude LCMS showed the purity of product is 8% (Rt=0.610 min; MS Calc'd: 336.1; MS Found: 337.0

[M+H]⁺). The mixture was filtered and concentrated in vacuum to afford 1-methyl-3-(pyridin-3-yl)-5-(4,4,5,5-tetramethyl-1,3,2-dioxaborolan-2-yl)-1H-pyrazolo[3,4-b]pyridine (400 mg, crude) as a black gum and immediately used to next step.

Step 6: Preparation of 2'-amino-N,N-dimethyl-5'-(1-methyl-3-(pyridin-3-yl)-1H-pyrazolo[3,4-b]pyridin-5-yl)-[2,3'-bipyridine]-5-carboxamide

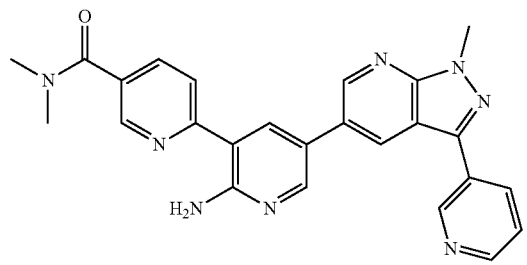 [SMILES: CN(C)C(=O)c1ccc(-c2cc(-c3cnc4c(c3)c(-c3cccnc3)nn4C)cnc2N)nc1]

A mixture of 2'-amino-5'-bromo-N,N-dimethyl-[2,3'-bipyridine]-5-carboxamide (207 mg, 0.644 mmol),1-methyl-3-(pyridin-3-yl)-5-(4,4,5,5-tetramethyl-1,3,2-dioxaborolan-2-yl)-1H-pyrazolo[3,4-b]pyridine (260 mg, crude), K₃PO₄ (1 M in water, 0.2 mL) and Pd(t-Bu₃P)₂ (33 mg, 0.064 mmol) in dioxane (5 mL) was stirred at 100° C. for 16 h under N₂ atmosphere. A black suspension was formed. Crude LCMS showed the purity of product is 49% (Rt=0.526 min; MS Calc'd: 450.2; MS Found: 451.3 [M+H]⁺). The reaction mixture was diluted with ethyl acetate (20 mL), dried over Na₂SO₄, filtered and concentrated. The residue was purified by Combi Flash (10% MeOH in EtOAc), then the impure product was purified by prep-HPLC (0.05% NH₃·H₂O as an additive) and lyophilized to afford 2'-amino-N,N-dimethyl-5'-(1-methyl-3-(pyridin-3-yl)-1H-pyrazolo[3,4-b]pyridin-5-yl)-[2,3'-bipyridine]-5-carboxamide (23.0 mg, yield: 8%) as a light yellow solid. LCMS (Shimadzu LCMS 2010, mobile phase: from 100% [water+0.05% NH₃·H₂O] and 0% [MeCN] to 5% [water+0.05% NH₃·H₂O] and 95% [MeCN] in 5.8 min, then under this condition for 1.1 min, finally changed to 100% [water+0.05% NH₃·H₂O] and 0% [MeCN] and under this condition for 0.09 min.) purity is 96.22%, Rt=2.592 min; MS Calc'd.: 450.2, MS Found: 451.2 [M+H]⁺. ¹H NMR (400 MHz, CDCl₃) δ 3.10 (3H, s), 3.17 (3H, s), 4.27 (3H, s), 7.00 (2H, br s), 7.47 (1H, dd, J=7.6, 4.8 Hz), 7.90 (1H, d, J=8.4 Hz), 7.94 (1H, dd, J=8.0, 2.0 Hz), 8.12 (1H, d, J=2.0 Hz), 8.28-8.33 (1H, m), 8.40-8.44 (2H, m), 8.67 (1H, d, J=4.0 Hz), 8.76 (1H, d, J=1.2 Hz), 8.81 (1H, d, J=2.0 Hz), 9.27 (1H, s).

Example 124:2'-amino-N,N-dimethyl-5'-(1-methyl-3-(pyrimidin-5-yl)-1H-pyrazolo[3,4-b]pyridin-5-yl)-[2,3'-bipyridine]-5-carboxamide

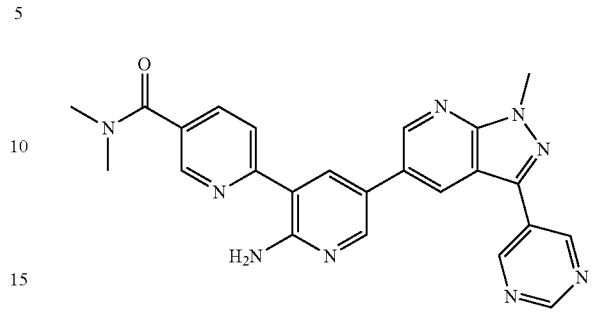

Step 1: Preparation of 5-chloro-1-methyl-3-(pyrimidin-5-yl)-1H-pyrazolo[3,4-b]pyridine

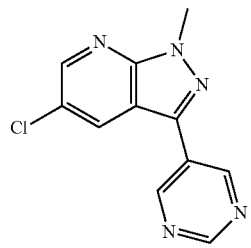 [SMILES: Cn1nc(-c2cncnc2)c2cc(Cl)cnc21]

A mixture of pyrimidin-5-ylboronic acid (502 mg, 4.06 mmol), 3-bromo-5-chloro-1-methyl-1H-pyrazolo[3,4-b]pyridine (500 mg, 2.03 mmol), Cs₂CO₃ (1 M in water, 4 mL) and Pd(t-Bu₃P)₂ (104 mg, 0.203 mmol) in dioxane (15 mL) was stirred at 100° C. for 15 h under N₂ atmosphere. The red solution turned to black. Crude LCMS showed the starting material was consumed completely and the purity of the desired product is 70% (Rt=0.591 min; MS Calc'd: 245.0; MS Found: 246.0 [M+H]⁺). The reaction mixture was diluted with ethyl acetate (10 mL), dried over Na₂SO₄, filtered and concentrated. The residue was purified by Combi Flash (EtOAc) to afford 5-chloro-1-methyl-3-(pyrimidin-5-yl)-1H-pyrazolo[3,4-b]pyridine (490 mg, yield: 98%) as a white solid. ¹H NMR (400 MHz, CDCl₃) δ 4.24 (3H, s), 8.27 (1H, s), 8.57 (1H, d, J=2.0 Hz), 9.26 (1H, s), 9.28 (2H, s).

Step 2: Preparation of 2'-amino-N,N-dimethyl-5'-(4,4,5,5-tetramethyl-1,3,2-dioxaborolan-2-yl)-[2,3'-bipyridine]-5-carboxamide

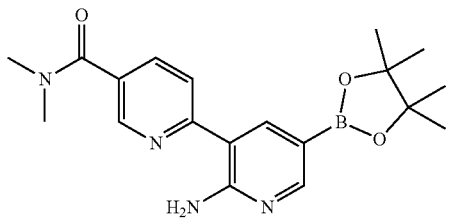

A mixture of 2'-amino-5'-bromo-N,N-dimethyl-[2,3'-bipyridine]-5-carboxamide (250 mg, 0.778 mmol), B₂Pin₂ (297 mg, 0.117 mmol), Pd(dppf)Cl₂ (57 mg, 0.078 mmol) and KOAc (229 mg, 2.34 mmol) in dioxane (5 mL) was stirred at 100° C. for 5 h under N₂ atmosphere. A black suspension was formed. Crude LCMS showed the purity of product is 47% (Rt=0.496 min; MS Calc'd: 286.1; MS Found: 286.9 [M+H]⁺). The mixture was filtered and concentrated in vacuum to afford 2'-amino-N,N-dimethyl-5'-(4,4,5,5-tetramethyl-1,3,2-dioxaborolan-2-yl)-[2,3'-bipyridine]-5-carboxamide (300 mg, crude) as a black gum and immediately used to next step.

Step 3: Preparation of 2'-amino-N,N-dimethyl-5'-(1-methyl-3-(pyrimidin-5-yl)-1H-pyrazolo[3,4-b]pyridin-5-yl)-[2,3'-bipyridine]-5-carboxamide

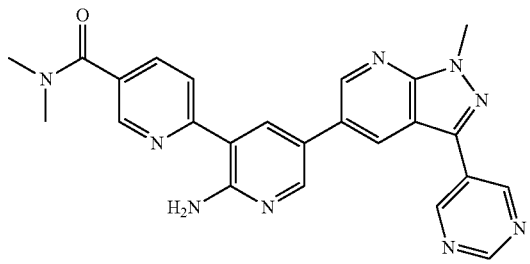 [SMILES: CN(C)C(=O)c1ccc(-c2cc(-c3cnc4c(c3)c(-c3cncnc3)nn4C)cnc2N)nc1]

A mixture of 2'-amino-N,N-dimethyl-5'-(4,4,5,5-tetramethyl-1,3,2-dioxaborolan-2-yl)-[2,3'-bipyridine]-5-carboxamide (170 mg, crude), 5-chloro-1-methyl-3-(pyrimidin-5-yl)-1H-pyrazolo[3,4-b]pyridine (95 mg, 0.385 mmol), K₃PO₄ (1 M in water, 0.1 mL) and Pd(t-Bu₃P)₂ (20 mg, 0.038 mmol) in dioxane (4 mL) was stirred at 100° C. for 14 h under N₂ atmosphere. A black suspension was formed. Crude LCMS showed the purity of product is 32% (Rt=0.534 min; MS Calc'd: 451.2; MS Found: 452.1 [M+H]⁺). The reaction mixture was diluted with ethyl acetate (20 mL), dried over Na₂SO₄, filtered and concentrated. The residue was purified by Combi Flash (10% MeOH in EtOAc), then the impure product was purified by prep-HPLC (0.05% NH₃·H₂O as an additive) and lyophilized to afford 2'-amino-N,N-dimethyl-5'-(1-methyl-3-(pyrimidin-5-yl)-1H-pyrazolo[3,4-b]pyridin-5-yl)-[2,3'-bipyridine]-5-carboxamide (31.6 mg, yield: 18%) as a light yellow solid. LCMS (Shimadzu LCMS 2010, mobile phase: from 100% [water+0.05% NH₃·H₂O] and 0% [MeCN] to 5% [water+0.05% NH₃·H₂O] and 95% [MeCN] in 5.8 min, then under this condition for 1.1 min, finally changed to 100% [water+0.05% NH₃·H₂O] and 0% [MeCN] and under this condition for 0.09 min.) purity is 100.00%, Rt=2.445 min; MS Calc'd.: 451.2, MS Found: 452.2 [M+H]⁺. ¹H NMR (400 MHz, CDCl₃) δ 3.10 (3H, s), 3.17 (3H, s), 4.29 (3H, s), 6.95 (2H, br s), 7.89 (1H, d, J=8.8 Hz), 7.94 (1H, dd, J=8.8, 2.4 Hz), 8.10 (1H, d, J=2.0 Hz), 8.37 (1H, d, J=2.0 Hz), 8.43 (1H, d, J=2.4 Hz), 8.76 (1H, dd, J=2.0, 0.8 Hz), 8.84 (1H, d, J=2.0 Hz), 9.26 (1H, s), 9.38 (2H, s).

Example 125:2'-amino-N,N-dimethyl-5'-(1-methyl-3-(thiazol-5-yl)-1H-pyrrolo[2,3-b]pyridin-5-yl)-[2,3'-bipyridine]-5-carboxamide

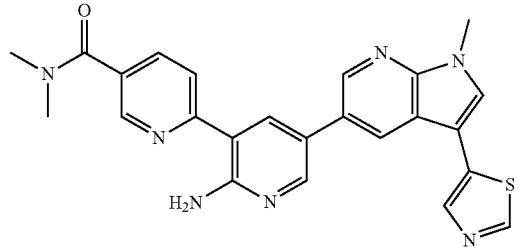 [SMILES: CN(C)C(=O)c1ccc(-c2cc(-c3cnc4c(c3)c(-c3cncs3)cn4C)cnc2N)nc1]

Step 1: Preparation of 5-(5-chloro-1-methyl-H-pyrrolo[2,3-b]pyridin-3-yl)thiazole

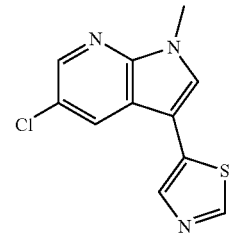 [SMILES: Cn1cc(-c2cncs2)c2cc(Cl)cnc21]

A mixture of 5-(4,4,5,5-tetramethyl-1,3,2-dioxaborolan-2-yl)thiazole (604 mg, 3.03 mmol), 3-bromo-5-chloro-1-methyl-1H-pyrrolo[2,3-b]pyridine (372 mg, 1.52 mmol), Cs₂CO₃ (0.8 M in water, 6 mL) and Pd(t-Bu₃P)₂ (77 mg, 0.152 mmol) in dioxane (8 mL) was stirred at 100° C. for 15 h under N₂ atmosphere. The color of the mixture was black. Crude LCMS showed the starting material was consumed completely and the purity of the desired product is 10% (Rt=0.695 min; MS Calc'd: 249.0; MS Found: 249.9 [M+H]⁺). The reaction mixture was diluted with ethyl acetate (20 mL), dried over Na₂SO₄, filtered and concentrated. The residue was purified by Combi Flash (50% EtOAc in pentane) to afford 5-(5-chloro-1-methyl-1H-pyrrolo[2,3-b]pyridin-3-yl)thiazole (35.0 mg, yield: 9%) as a yellow solid. 1H NMR (400 MHz, CDCl₃) δ 3.94 (3H, s), 7.24 (1H, d, J=3.2 Hz), 7.81-7.84 (2H, m), 8.34 (1H, d, J=2.0 Hz), 8.56 (1H, d, J=2.0 Hz).

Step 2: Preparation of 2'-amino-N,N-dimethyl-5'-(1-methyl-3-(thiazol-5-yl)-1H-pyrrolo[2,3-b]pyridin-5-yl)-[2,3'-bipyridine]-5-carboxamide

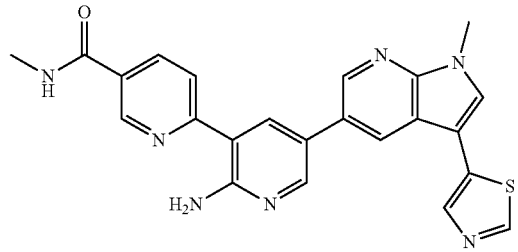 [SMILES: CNC(=O)c1ccc(-c2cc(-c3cnc4c(c3)c(-c3cncs3)cn4C)cnc2N)nc1]

A mixture of 2'-amino-N,N-dimethyl-5'-(4,4,5,5-tetramethyl-1,3,2-dioxaborolan-2-yl)-[2,3'-bipyridine]-5-carboxamide (77 mg, crude), 5-(5-chloro-1-methyl-1H-pyrrolo[2,3-b]pyridin-3-yl)thiazole (35 mg, 0.14 mmol), K$_3$PO$_4$ (1 M in water, 0.4 mL) and Pd(t-Bu$_3$P)$_2$ (7 mg, 0.014 mmol) in dioxane (4 mL) was stirred at 100° C. for 14 h under N$_2$ atmosphere. A black suspension was formed. Crude LCMS showed the purity of product is 19% (Rt=0.573 min; MS Calc'd: 455.2; MS Found: 456.1 [M+H]$^+$). The reaction mixture was diluted with ethyl acetate (20 mL), dried over Na$_2$SO$_4$, filtered and concentrated. The residue was purified by Combi Flash (5% MeOH in EtOAc), then the impure product was purified by prep-HPLC (0.05% NH$_3$·H$_2$O as an additive) and lyophilized to afford 2'-amino-N,N-dimethyl-5'-(1-methyl-3-(thiazol-5-yl)-1H-pyrrolo[2,3-b]pyridin-5-yl)-[2,3'-bipyridine]-5-carboxamide (4.0 mg, yield: 6%) as a light yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 96.12%, Rt=1.543 min; MS Calc'd.: 455.2; MS Found: 456.0 [M+H]$^+$. $^1$H NMR (400 MHz, CDCl$_3$) δ 3.10 (3H, s), 3.16 (3H, s), 3.99 (3H, s), 6.89 (2H, br s), 7.24 (1H, d, J=3.6 Hz), 7.84 (1H, d, J=3.2 Hz), 7.85 (1H, s), 7.90 (1H, s), 7.91 (1H, d, J=2.0 Hz), 8.16 (1H, d, J=2.0 Hz), 8.46 (1H, d, J=2.0 Hz), 8.60 (1H, d, J=2.0 Hz), 8.69 (1H, d, J=2.0 Hz), 8.75 (1H, s).

Example 126: methyl 4-(2'-amino-5-(dimethylcarbamoyl)-[2,3'-bipyridin]-5'-yl)-1H-pyrrolo[2,3-b]pyridine-2-carboxylate

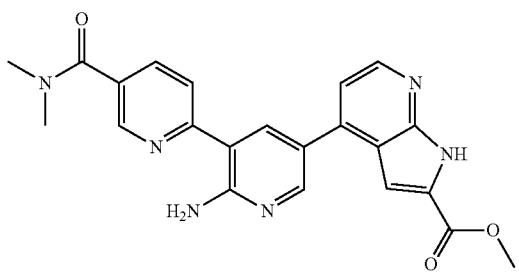

Step 1: Preparation of 1H-pyrrolo[2,3-b]pyridine-2-carboxylic acid

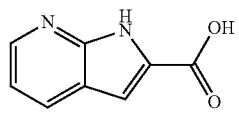 [SMILES: O=C(O)c1cc2cccnc2[nH]1]

To a mixture of 1H-pyrrolo[2,3-b]pyridine (20.0 g, 169 mmol) in anhydrous THF (100 mL) was added drop wise n-BuLi (2.0 M, 93.1 mL) in hexane at −70° C. for 30 min. After stirring for 30 min at −70° C., the mixture was bubbled with CO$_2$ for 30 min. The mixture is then allowed to return to 25° C., and concentrated under reduced pressure. A white solid was obtained, which was dissolved in THF (400 mL). This solution was cooled to −70° C. and t-BuLi (1.3 M, 143.25 mL) in hexane was then added drop wise for 30 min. After stirring for 30 min at −70° C., the mixture was bubbled with CO$_2$ for 30 min. A yellow suspension was formed. TLC showed the starting material was consumed completely. The mixture was then allowed to return to 25° C., and this reaction mixture was then poured into 200 mL of distilled water cooled to 0° C. The THF was evaporated off under reduced pressure. The residual aqueous solution was diluted with 500 mL of distilled water, washed twice with DCM (500 mL), acidified to pH=1 by adding aqueous 5 N hydrochloric acid solution, and then concentrated under reduced pressure. 20 g of a pasty solid are obtained, which is recrystallized from MeOH (50 mL) to give 1H-pyrrolo[2,3-b]pyridine-2-carboxylic acid (15.0 g, impure) as a yellow solid. $^1$H NMR (400 MHz, DMSO-d$_6$) δ 7.19 (1H, dd, J=8.0, 4.8 Hz), 7.30-7.40 (1H, m), 8.17 (1H, dd, J=8.0, 1.6 Hz), 8.36-8.46 (1H, m), 8.46-8.59 (1H, br s), 12.48 (1H, br s).

Step 2: Preparation of methyl 1H-pyrrolo[2,3-b]pyridine-2-carboxylate

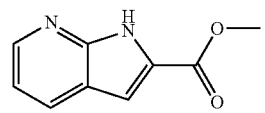

To a solution of 1H-pyrrolo[2,3-b]pyridine-2-carboxylic acid (20.0 g, 92.5 mmol) in MeOH (100 mL) are added SOCl$_2$ (49.2 g, 414 mmol) at 25° C. The reaction mixture is then stirred for 40 h at 25° C. A yellow suspension was formed. LCMS showed the purity of product is 25% (Rt=0.631 min; MS Calc'd: 176.1; MS Found: 176.9 [M+H]$^+$) and TLC showed most of the starting material was consumed. The mixture was concentrated under reduced pressure and purified by Combi Flash (DCM) to give methyl 1H-pyrrolo[2,3-b]pyridine-2-carboxylate (8.00 g, yield for 2 steps: 20%) as a white solid. $^1$H NMR (400 MHz, DMSO-d$_6$) δ 3.88 (3H, s), 7.10-7.21 (2H, m), 8.11 (1H, d, J=7.2 Hz), 8.41 (1H, dd, J=4.8, 1.6 Hz), 12.51 (1H, br s).

Step 3: Preparation of 2-(methoxycarbonyl)-1H-pyrrolo[2,3-b]pyridine 7-oxide

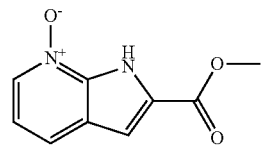

To a solution of methyl 1H-pyrrolo[2,3-b]pyridine-2-carboxylate (5.00 g, 28.4 mmol) in DCM (50 mL) was added m-CPBA (10.5 g, 42.6 mmol, 70% purity). And the mixture was stirred 25° C. for 16 h. TLC showed the reaction was completed. LCMS showed the purity of product is 87% (Rt=0.763 min; MS Calc'd: 192.1; MS Found: 192.8 [M+H]$^+$). A white suspension was formed. The resulting mixture was concentrated under reduced pressure and purified by Combi Flash (10% MeOH in DCM) to give 2-(methoxycarbonyl)-1H-pyrrolo[2,3-b]pyridine 7-oxide (5.00 g, crude) as a yellow solid.

Step 4: Preparation of methyl 4-bromo-1H-pyrrolo
[2,3-b]pyridine-2-carboxylate

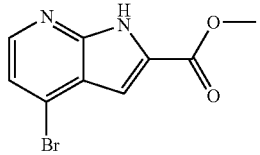

To a stirred solution of 2-(methoxycarbonyl)-1H-pyrrolo
[2,3-b]pyridine 7-oxide (5.00 g, 26.0 mmol) and Me$_4$NBr
(6.01 g, 39.0 mmol) in CHCl$_3$ (50 mL) at 0° C. was added
portion wise over 5 min Ms$_2$O (9.06 g, 52.0 mmol). The
reaction was allowed to warm to 25° C. and stirred for 16 h.
A white suspension was formed. LCMS showed the purity
of product is 86% (Rt=0.796 min; MS Calc'd: 254.0; MS
Found: 254.8 [M+H]$^+$). The reaction was evaporated to
dryness under vacuum, neutralized with cold 0.5 N aq
NaHCO$_3$ (100 mL), filtered, rinsed with cold water, and
concentrated under vacuum to give methyl 4-bromo-1H-
pyrrolo[2,3-b]pyridine-2-carboxylate (5.00 g, yield for 2
steps: 69%) as a white solid. $^1$H NMR (400 MHz, DMSO-
d$_6$) δ 3.90 (3H, s), 7.06 (1H, d, J=2.4 Hz), 7.47 (1H, d, J=5.2
Hz), 8.28 (1H, d, J=4.8 Hz), 12.98 (1H, br s).

Step 5: Preparation of methyl 4-(2'-amino-5-(dim-
ethylcarbamoyl)-[2,3'-bipyridin]-5'-yl)-1H-pyrrolo
[2,3-b]pyridine-2-carboxylate

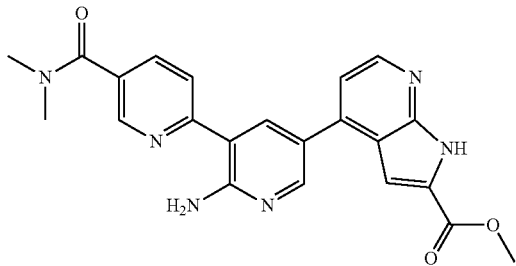

A mixture of 2'-amino-N,N-dimethyl-5'-(4,4,5,5-tetram-
ethyl-1,3,2-dioxaborolan-2-yl)-[2,3'-bipyridine]-5-carbox-
amide (7.22 g, crude), methyl 4-bromo-1H-pyrrolo[2,3-b]
pyridine-2-carboxylate (2.50 g, 9.80 mmol), Cs$_2$CO$_3$ (9.58
g, 29.4 mmol) and Pd(t-Bu$_3$P)$_2$ (5.01 g, 9.80 mmol) in
dioxane (150 mL) and H$_2$O (15 mL) was stirred at 90-100°
C. for 16 h under N$_2$ atmosphere. The color of the mixture
was black still. LCMS showed the purity of product is 40%
(Rt=0.642 min; MS Calc'd: 416.2; MS Found: 416.9
[M+H]$^+$) and TLC showed the starting material was con-
sumed completely. The mixture was concentrated under
reduced pressure. The residue was purified by Combi Flash
(5% MeOH in DCM) to give methyl 4-(2'-amino-5-(dim-
ethylcarbamoyl)-[2,3'-bipyridin]-5'-yl)-1H-pyrrolo[2,3-b]
pyridine-2-carboxylate (1.20 g, yield: 29%) as a yellow
solid. $^1$H NMR (400 MHz, CDCl$_3$) δ 3.12 (3H, s), 3.18 (3H,
s), 4.01 (3H, s), 7.12 (2H, br s), 7.25 (1H, s), 7.42 (1H, s),
7.88 (1H, d, J=8.0 Hz), 7.94 (1H, d, J=8.4 Hz), 8.28 (1H, d,
J=2.0 Hz), 8.56-8.65 (2H, m), 8.78 (1H, d, J=1.6 Hz), 11.09
(1H, br s).

Example 127: 4-(2'-amino-5-(dimethylcarbamoyl)-
[2,3'-bipyridin]-5'-yl)-N,N-dimethyl-1H-pyrrolo[2,3-
b]pyridine-2-carboxamide

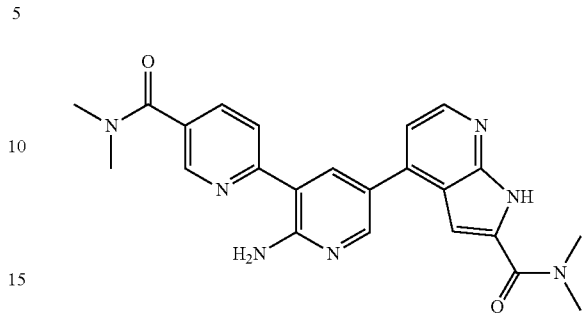

Step 1: Preparation of 4-(2'-amino-5-(dimethylcar-
bamoyl)-[2,3'-bipyridin]-5'-yl)-1H-pyrrolo[2,3-b]
pyridine-2-carboxylicacid

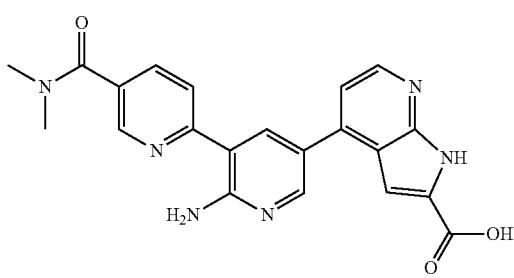 [SMILES: CN(C)C(=O)c1ccc(-c2cc(-c3ccnc4[nH]c(C(=O)O)cc34)cnc2N)nc1]

A mixture of methyl 4-(2'-amino-5-(dimethylcarbamoyl)-
[2,3'-bipyridin]-5'-yl)-1H-pyrrolo[2,3-b]pyridine-2-car-
boxylate (1.00 g, 2.40 mmol) and KOH (269 mg, 4.80
mmol) in acetone (2 mL) and H$_2$O (20 mL) was stirred at
25° C. for 16 h. A yellow solution was formed. LCMS
showed the purity of product is 98% (Rt=0.643 min; MS
Calc'd: 402.1; MS Found: 403.0 [M+H]$^+$). The reaction
mixture was concentrated under reduced pressure. Then the
residue was lyophilized to give 4-(2'-amino-5-(dimethylcar-
bamoyl)-[2,3'-bipyridin]-5'-yl)-1H-pyrrolo[2,3-b]pyridine-
2-carboxylic acid (1.10 g, crude) as a yellow solid.

Step 2: Preparation of 4-(2'-amino-5-(dimethylcar-
bamoyl)-[2,3'-bipyridin]-5'-yl)-N,N-dimethyl-1H-
pyrrolo[2,3-b]pyridine-2-carboxamide

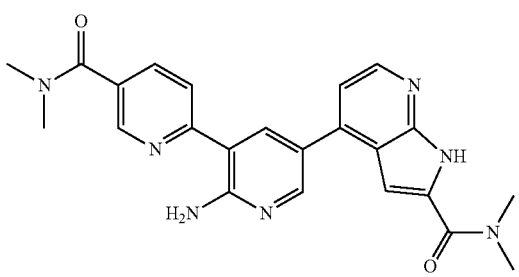

To a solution of 4-(2'-amino-5-(dimethylcarbamoyl)-[2,
3'-bipyridin]-5'-yl)-1H-pyrrolo[2,3-b]pyridine-2-carboxylic acid (50 mg, 0.12 mmol) and Me₂NH·HCl (11 mg, 0.25 mmol) in pyridine (1 mL) was added EDC•HCl (48 mg, 0.25 mmol) under N₂ atmosphere. The mixture was stirred at 18-20° C. for 16 h under N₂ atmosphere. A red solution was formed. LCMS showed the purity of product is 75% (Rt=0.609 min; MS Calc'd: 429.2; MS Found: 430.0 [M+H]⁺). The mixture was concentrated under reduced pressure. The residue was purified by prep-HPLC (0.05% NH₃·H₂O as an additive) and lyophilized to give 4-(2'-amino-5-(dimethylcarbamoyl)-[2,3'-bipyridin]-5'-yl)-N,N-dimethyl-1H-pyrrolo[2,3-b]pyridine-2-carboxamide (14.8 mg, yield: 28%) as a yellow solid. ¹H NMR (400 MHz, DMSO-d₆) δ 3.02 (3H, s), 3.04 (3H, s), 3.10-3.30 (6H, m, overlapped with H₂O signal), 6.98 (1H, d, J=0.8 Hz), 7.34 (1H, d, J=5.2 Hz), 7.78 (2H, br s), 7.99 (1H, d, J=6.4 Hz), 8.18 (1H, d, J=8.4 Hz), 8.36 (1H, d, J=4.8 Hz), 8.42 (1H, d, J=2.0 Hz), 8.56 (1H, d, J=2.0 Hz), 8.75 (1H, d, J=2.0 Hz), 12.19 (1H, br s).

Example 128: 2'-amino-N,N-dimethyl-5'-(2-(morpholine-4-carbonyl)-1H-pyrrolo[2,3-b]pyridin-4-yl)-[2,3'-bipyridine]-5-carboxamide

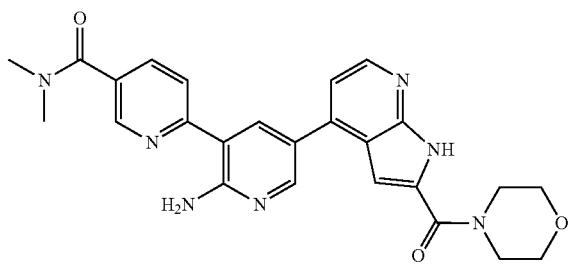 [SMILES: CN(C)C(=O)c1ccc(-c2cc(-c3ccnc4[nH]c(C(=O)N5CCOCC5)cc34)cnc2N)nc1]

Step 1: Preparation of 4-(2'-amino-5-(dimethylcarbamoyl)-[2,3'-bipyridin]-5'-yl)-1H-pyrrolo[2,3-b]pyridine-2-carboxylic acid

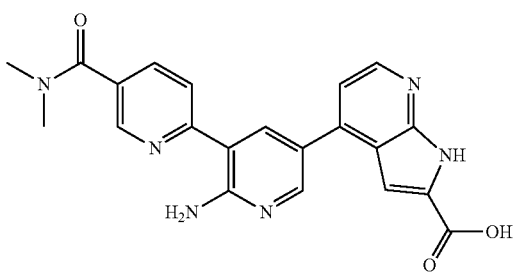 [SMILES: CN(C)C(=O)c1ccc(-c2cc(-c3ccnc4[nH]c(C(=O)O)cc34)cnc2N)nc1]

A mixture of methyl 4-(2'-amino-5-(dimethylcarbamoyl)-[2,3'-bipyridin]-5'-yl)-1H-pyrrolo[2,3-b]pyridine-2-carboxylate (1.00 g, 2.40 mmol) and KOH (269 mg, 4.80 mmol) in acetone (2 mL) and H₂O (20 mL) was stirred at 25° C. for 16 hours. A yellow solution was formed. LCMS showed the purity of product is 98% (Rt=0.643 min; MS Calcd: 402.1; MS Found: 403.0 [M+H]⁺). The reaction mixture was concentrated under reduced pressure. Then the residue was lyophilized to give 4-(2'-amino-5-(dimethylcarbamoyl)-[2,3'-bipyridin]-5'-yl)-1H-pyrrolo[2,3-b]pyridine-2-carboxylic acid (1.10 g, crude) as a yellow solid Step 2: Preparation of 2'-amino-N,N-dimethyl-5'-(2-(morpholine-4-carbonyl)-1H-pyrrolo[2,3-b]pyridin-4-yl)-[2,3'-bipyridine]-5-carboxamide

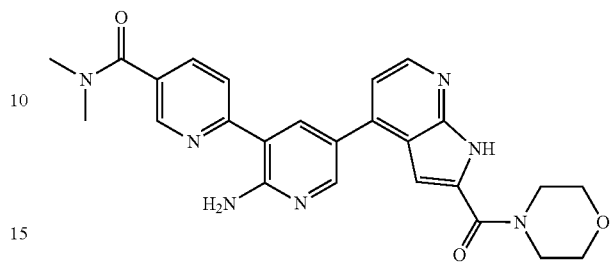

To a solution of 4-(2'-amino-5-(dimethylcarbamoyl)-[2,3'-bipyridin]-5'-yl)-1H-pyrrolo[2,3-b]pyridine-2-carboxylic acid (50 mg, 0.12 mmol) and morpholine hydrochloride (31 mg, 0.25 mmol) in pyridine (1 mL) was added EDC·HCl (48 mg, 0.25 mmol) under N₂ atmosphere. The mixture was stirred at 18-20° C. for 16 hours under N₂ atmosphere. A red solution was formed. LCMS showed the purity of product is 75% (Rt=0.609 min; MS Calcd: 429.2; MS Found: 430.0 [M+H]⁺). The mixture was concentrated under reduced pressure. The residue was further purified by prep-HPLC (0.05% NH₃·H₂O as an additive) and lyophilized to give 2'-amino-N,N-dimethyl-5'-(2-(morpholine-4-carbonyl)-1H-pyrrolo[2,3-b]pyridin-4-yl)-[2,3'-bipyridine]-5-carboxamide (13.6 mg, purity: 100%) as a yellow solid. ¹H NMR (400 MHz, DMSO-d₆) δ 2.98-3.07 (4H, m), 3.60-3.88 (10H, m), 6.94 (1H, s), 7.35 (1H, d, J=4.8 Hz), 7.78 (2H, br s), 7.99 (1H, dd, J=8.4, 2.0 Hz), 8.19 (1H, dd, J=8.4, 3.6 Hz), 8.36 (1H, d, J=4.8 Hz), 8.41 (1H, d, J=2.0 Hz), 8.55 (1H, d, J=2.0 Hz), 8.74 (1H, d, J=2.0 Hz), 12.26 (1H, br s).

Example 129: 2'-amino-5'-(2-(3-hydroxyazetidine-1-carbonyl)-1H-pyrrolo[2,3-b]pyridin-4-yl)-N,N-dimethyl-[2,3'-bipyridine]-5-carboxamide

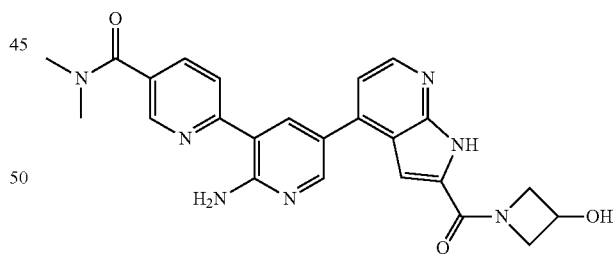

To a solution of azetidin-3-ol (33 mg, 0.30 mmol, HCl salt) and 4-(2'-amino-5-(dimethylcarbamoyl)-[2,3'-bipyridin]-5'-yl)-1H-pyrrolo[2,3-b]pyridine-2-carboxylic acid (100 mg, 0.249 mmol) in pyridine (1 mL) was added EDC•HCl (95 mg, 0.50 mmol) under N₂ atmosphere. The mixture was stirred at 25° C. for 16 h under N₂ atmosphere. A red solution was formed. LCMS showed the purity of product is 68% (Rt=0.605 min; MS Calc'd: 457.2; MS Found: 458.0 [M+H]⁺). The mixture was concentrated under reduced pressure. The residue was purified by prep-HPLC (0.05% HCl as an additive), prep-HPLC (0.05% NH₃H₂O as an additive) and lyophilized to give 2'-amino-5'-(2-(3-hydroxyazetidine-1-carbonyl)-1H-pyrrolo[2,3-b]pyridin-4- yl)-N,N-dimethyl-[2,3'-bipyridine]-5-carboxamide (7.9 mg, yield: 7%) as a yellow solid. $^1$H NMR (400 MHz, DMSO-d$_6$) δ 3.01 (3H, s), 3.03 (3H, s), 3.75-4.00 (1H, m, overlapped with H$_2$O signal), 4.20-4.40 (2H, m), 4.50-4.63 (1H, m), 4.67-4.79 (1H, m), 5.84 (1H, d, J=6.0 Hz), 6.95 (1H, s), 7.35 (1H, d, J=4.8 Hz), 7.78 (2H, br s), 7.98 (1H, dd, J=8.4, 1.6 Hz), 8.18 (1H, d, J=8.8 Hz), 8.38 (1H, d, J=4.8 Hz), 8.42 (1H, s), 8.56 (1H, s), 8.74 (1H, s), 12.22 (1H, br s).

Example 130: 2'-amino-5'-(2-(3-carbamoylazetidine-1-carbonyl)-1H-pyrrolo[2,3-b]pyridin-4-yl)-N,N-dimethyl-[2,3'-bipyridine]-5-carboxamide

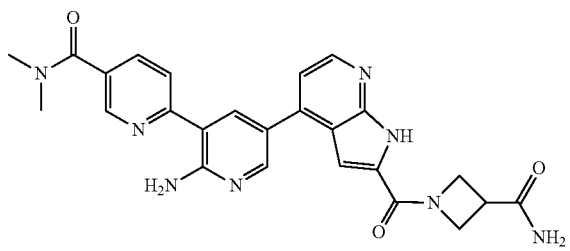 [SMILES: CN(C)C(=O)c1ccc(-c2cc(-c3ccnc4[nH]c(C(=O)N5CC(C(N)=O)C5)cc34)cnc2N)nc1]

To a solution of azetidine-3-carboxamide (50 mg, 0.36 mmol, HCl salt) and 4-(2'-amino-5-(dimethylcarbamoyl)-[2,3'-bipyridin]-5'-yl)-1H-pyrrolo[2,3-b]pyridine-2-carboxylic acid (100 mg, 0.249 mmol) in pyridine (1 mL) was added EDC•HCl (95 mg, 0.50 mmol) under N$_2$ atmosphere. The mixture was stirred at 25° C. for 16 h under N$_2$ atmosphere. A red solution was formed. LCMS showed the purity of product (Rt=0.595 min; MS Calc'd: 484.2; MS Found: 485.1 [M+H]$^+$). The mixture was concentrated under reduced pressure. The residue was purified by prep-HPLC (0.05% HCl as an additive), prep-HPLC (0.05% NH$_3$·H$_2$O as an additive) and lyophilized to give 2'-amino-5'-(2-(3-carbamoylazetidine-1-carbonyl)-1H-pyrrolo[2,3-b]pyridin-4-yl)-N,N-dimethyl-[2,3'-bipyridine]-5-carboxamide (4.1 mg, yield: 3%) as a yellow solid. $^1$H NMR (400 MHz, DMSO-d$_6$) δ 3.01 (3H, s), 3.03 (3H, s), 4.00-4.25 (2H, m, overlapped with H$_2$O signal), 4.49-4.59 (2H, m), 4.64-4.75 (1H, m), 6.97 (1H, s), 7.11 (1H, s), 7.35 (1H, d, J=4.8 Hz), 7.54 (1H, s), 7.77 (2H, br s), 7.99 (1H, d, J=2.0 Hz), 8.18 (1H, d, J=8.4 Hz), 8.38 (1H, d, J=5.2 Hz), 8.42 (1H, d, J=2.0 Hz), 8.56 (1H, d, J=2.0 Hz), 8.74 (1H, d, J=2.0 Hz), 12.24 (1H, br s).

Example 131: 4-(2'-amino-5-(dimethylcarbamoyl)-[2,3'-bipyridin]-5'-yl)-N-isobutyl-1H-pyrrolo[2,3-b]pyridine-2-carboxamide

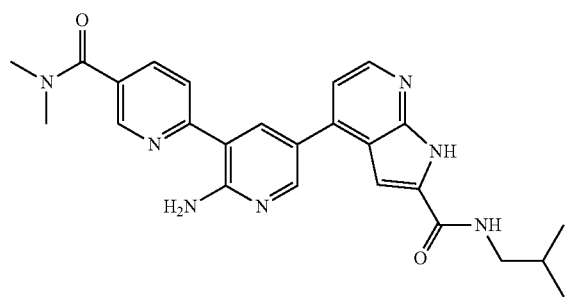 [SMILES: CC(C)CNC(=O)c1cc2c(-c3cnc(N)c(-c4ccc(C(=O)N(C)C)cn4)c3)ccnc2[nH]1]

To a mixture of methyl 4-(2'-amino-5-(dimethylcarbamoyl)-[2,3'-bipyridin]-5'-yl)-1H-pyrrolo[2,3-b]pyridine-2-carboxylate (40 mg, 0.096 mmol), 2-methylpropan-1-amine (28 mg, 0.38 mmol) in toluene (5 mL) was added AlMe$_3$ (2 M in toluene, 0.19 mL) at 0° C., then warmed to 25° C. and stirred for 0.5 hour, then heated to 50° C. and stirred for another 7.5 h to give a yellow suspension. LCMS the purity of product is 14% (Rt=0.650 min; MS Calc'd: 457.2; MS Found: 480.1 [M+Na]+). The mixture was quenched with a saturated aqueous solution of sodium potassium tartrate (10 mL) and then filtered. The filter cake was washed with EtOAc (5 mL×2). The filtrate was extracted with EtOAc (20 mL×2). The combined extracts was washed with brine (25 mL×2), dried over Na$_2$SO$_4$, filtered and concentrated under reduced pressure to give a residue. The residue was purified by prep-HPLC (0.05% NH$_3$·H$_2$O as an additive) and lyophilized to give 4-(2'-amino-5-(dimethylcarbamoyl)-[2,3'-bipyridin]-5'-yl)-N-isobutyl-1H-pyrrolo[2,3-b]pyridine-2-carboxamide (20.3 mg, purity: 99.37%, yield: 46%) as a yellow solid. $^1$H NMR (400 MHz, DMSO-d$_6$) δ 0.90 (6H, d, J=6.8 Hz), 1.74-1.90 (1H, m), 3.02 (3H, s), 3.03 (3H, s), 3.11 (2H, t, J=6.4 Hz), 7.35 (1H, d, J=5.2 Hz), 7.47 (1H, d, J=1.6 Hz), 7.79 (2H, br s), 7.99 (1H, dd, J=8.4, 2.4 Hz), 8.21 (1H, d, J=8.4 Hz), 8.35 (1H, d, J=4.8 Hz), 8.41 (1H, d, J=2.0 Hz), 8.54 (1H, br s), 8.58 (1H, d, J=2.4 Hz), 8.75 (1H, d, J=1.6 Hz), 12.16 (1H, br s).

Example 132: 4-(2'-amino-5-(dimethylcarbamoyl)-[2,3'-bipyridin]-5'-yl)-N-(2-methoxyethyl)-1H-pyrrolo[2,3-b]pyridine-2-carboxamide

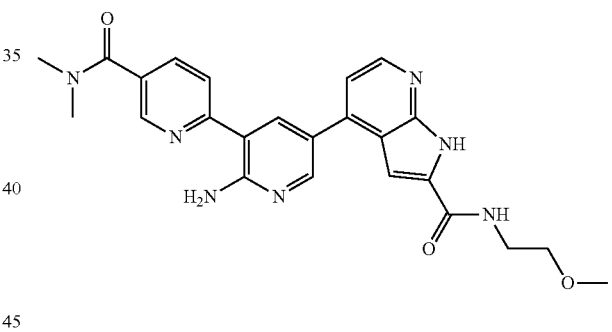

To a mixture of methyl 4-(2'-amino-5-(dimethylcarbamoyl)-[2,3'-bipyridin]-5'-yl)-1H-pyrrolo[2,3-b]pyridine-2-carboxylate (40 mg, 0.096 mmol), 2-methoxyethanamine (29 mg, 0.38 mmol) in toluene (5 mL) was added AlMe$_3$ (2 M in toluene, 0.19 mL) at 0° C., then warmed to 25° C. and stirred for 0.5 hour, then heated to 50° C. and stirred for another 7.5 h to give a yellow suspension. LCMS showed the purity of product is 35% (Rt=0.610 min; MS Calc'd: 459.2; MS Found: 460.1 [M+H]$^+$). The mixture was quenched with a saturated aqueous solution of sodium potassium tartrate (10 mL) and then filtered. The filter cake was washed with EtOAc (5 mL×2). The filtrate was extracted with EtOAc (20 mL×2). The combined extracts was washed with brine (25 mL×2), dried over Na$_2$SO$_4$, filtered and concentrated under reduced pressure to give a residue. The residue was purified by prep-HPLC (0.05% NH$_3$·H$_2$O as an additive) and lyophilized to give 4-(2'-amino-5-(dimethylcarbamoyl)-[2,3'-bipyridin]-5'-yl)-N-(2-methoxyethyl)-1H-pyrrolo[2,3-b]pyridine-2-carboxamide (6.1 mg, purity: 100%, yield: 14%) as a yellow solid. $^1$H NMR (400 MHz, DMSO-d$_6$) δ 2.50-2.55 (2H, m), 3.02 (3H, s), 3.03 (3H, s), 3.27 (3H, s), 3.43-3.50 (2H, m), 7.35 (1H, d, J=4.8 Hz), 7.48 (1H, s), 7.79 (2H, br s), 8.00 (1H, dd, J=8.0, 2.0 Hz), 8.20 (1H, d, J=8.0 Hz), 8.36 (1H, d, J=5.2 Hz), 8.41 (1H, d, J=2.0 Hz), 8.57 (1H, d, J=2.0 Hz), 8.65 (1H, br s), 8.75 (1H, d, J=2.0 Hz), 12.18 (1H, br s).

Example 133: 4-(2'-amino-5-(dimethylcarbamoyl)-[2,3'-bipyridin]-5'-yl)-N-(2-aminoethyl)-1H-pyrrolo[2,3-b]pyridine-2-carboxamide

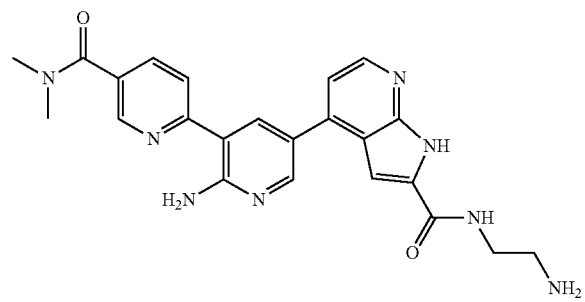 [SMILES: CN(C)C(=O)c1ccc(-c2cc(-c3ccnc4[nH]c(C(=O)NCCN)cc34)cnc2N)nc1]

Step 1

To a mixture of methyl 4-(2'-amino-5-(dimethylcarbamoyl)-[2,3'-bipyridin]-5'-yl)-1H-pyrrolo[2,3-b]pyridine-2-carboxylate (80 mg, 0.19 mmol), tert-butyl N-(2-aminoethyl)carbamate (123 mg, 0.768 mmol) in toluene (5 mL) was added AlMe$_3$ (2 M in toluene, 0.38 mL) at 0° C., then warmed to 25° C. and stirred for 0.5 hour, then heated to 50° C. and stirred for another 1.5 h to give a yellow suspension. LCMS showed the purity of product is 71% (Rt=0.660 min; MS Calc'd: 544.3; MS Found: 545.3 [M+H]$^+$). The mixture was quenched with a saturated aqueous solution of sodium potassium tartrate (20 mL) and then filtered. The filter cake was washed with EtOAc (10 mL×2). The filtrate was extracted with EtOAc (30 mL×2). The combined extracts was washed with brine (30 mL×2), dried over Na$_2$SO$_4$, filtered and concentrated under reduced pressure to give an intermediate (0.1 g, crude) as a yellow solid.

Step 2

To a mixture of the intermediate (100 mg, 0.184 mmol) in DCM (5 mL) was added TFA (1 mL), the reaction mixture was stirred at 25° C. for 2 h to give a yellow solution. TLC (DCM:MeOH=10:1) showed the reaction was completed. The mixture was concentrated under reduced pressure to give a residue. The residue was dissolved in MeOH (5 mL), then adjust to pH=7-8 with NaHCO$_3$ solid. DCM (20 mL) was added into it and filtered. The filtrate was concentrated under reduced pressure to give a residue. The residue was purified by prep-HPLC (0.05% NH$_3$·H$_2$O as an additive) and lyophilized to give an impure product (25 mg). The impure product was further purified by prep-HPLC (0.225% FA as an additive) and lyophilized to give 4-(2'-amino-5-(dimethylcarbamoyl)-[2,3'-bipyridin]-5'-yl)-N-(2-aminoethyl)-1H-pyrrolo[2,3-b]pyridine-2-carboxamide (24.3 mg, purity: 98.21%, yield: 27%, FA salt) as a pale yellow solid. $^1$H NMR (400 MHz, DMSO-d$_6$) δ 2.95-3.10 (8H, m), 3.52 (2H, q, J=5.6 Hz), 7.38-7.44 (2H, m), 7.81 (3H, br s), 8.03 (1H, dd, J=8.0, 2.0 Hz), 8.23 (1H, d, J=8.4 Hz), 8.40 (1H, d, J=4.8 Hz), 8.51 (1H, d, J=2.0 Hz), 8.57 (1H, d, J=2.4 Hz), 8.72 (1H, br s), 8.76 (1H, d, J=2.0 Hz), 12.31 (1H, br s).

Example 134: 4-(2'-amino-5-(dimethylcarbamoyl)-[2,3'-bipyridin]-5'-yl)-N-benzyl-1H-pyrrolo[2,3-b]pyridine-2-carboxamide

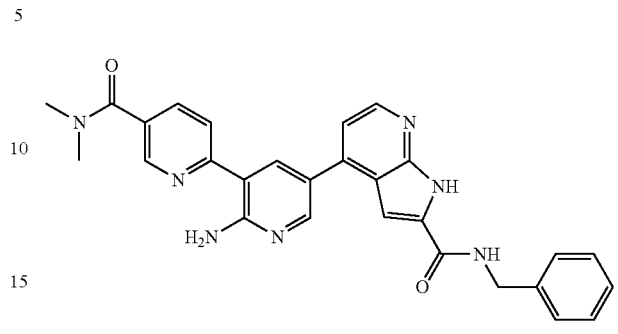

Step 1: The First Batch

To a mixture of methyl 4-(2'-amino-5-(dimethylcarbamoyl)-[2,3'-bipyridin]-5'-yl)-1H-pyrrolo[2,3-b]pyridine-2-carboxylate (20 mg, 0.048 mmol), benzylamine (10 mg, 0.096 mmol) in toluene (5 mL) was added AlMe$_3$ (2 M in toluene, 0.048 mL) at 0° C., then warmed to 25° C. and stirred for 0.5 h, then stirred at 60° C. for 2 h to give a yellow solution. LCMS showed the purity of the desired product is 36% (Rt=0.668 min; MS Calc'd: 491.2; MS Found: 492.1 [M+H]$^+$). The mixture was quenched with a saturated aqueous solution of sodium potassium tartrate (15 mL) and then filtered. The filter cake was washed with EtOAc (10 mL×2). The filtrate was extracted with EtOAc (20 mL×2). The combined extracts was washed with brine (20 mL×2), dried over Na$_2$SO$_4$, filtered and concentrated under reduced pressure to give a residue (20 mg, crude) as a yellow solid.

Step 2: The Second Batch

To a mixture of methyl 4-(2'-amino-5-(dimethylcarbamoyl)-[2,3'-bipyridin]-5'-yl)-1H-pyrrolo[2,3-b]pyridine-2-carboxylate (20 mg, 0.048 mmol) in MeOH (5 mL) was added benzylamine (20 mg, 0.19 mmol), the reaction mixture was stirred at 65° C. for 4 h to give a yellow suspension. TLC (DCM:MeOH=10:1) showed no reaction. The mixture was concentrated under reduced pressure to give a residue. The residue in toluene (5 mL) was added AlMe$_3$ (2 M in toluene, 0.096 mL) at 0° C., then warmed to 25° C. and stirred for 0.5 hour, then heated to 65° C. and stirred for another 2.5 h to give a yellow solution. TLC (DCM:MeOH=10:1) and LCMS showed the reaction was completed. A byproduct (4-(2'-amino-5-(benzylcarbamoyl)-[2,3'-bipyridin]-5'-yl)-N-benzyl-1H-pyrrolo[2,3-b]pyridine-2-carboxamide, amide was hydrolyzed to acid) was found by LCMS. The mixture was quenched with a saturated aqueous solution of sodium potassium tartrate (15 mL) and then filtered. The filter cake was washed with EtOAc (10 mL×2). The filtrate was extracted with EtOAc (20 mL×2). The combined extracts was washed with brine (20 mL×2), dried over Na$_2$SO$_4$, filtered and concentrated under reduced pressure to give a residue. The residue and the first batch were combined and purified by washing with MeCN (12 mL) to give an impure product (38 mg). The impure product was further purified by prep-HPLC (0.05% NH$_3$·H$_2$O as an additive) and lyophilized to give 4-(2'-amino-5-(dimethylcarbamoyl)-[2,3'-bipyridin]-5'-yl)-N-benzyl-1H-pyrrolo[2,3-b]pyridine-2-carboxamide (9.2 mg, purity: 99.93%, average yield: 19%) as a yellow solid and 4-(2'-amino-5-(benzylcarbamoyl)-[2,3'-bipyridin]-5'-yl)-N-benzyl-1H-pyrrolo[2,3-b]pyridine-2-carboxamide (4.2 mg, purity: 98.31%, average yield: 8%) as a yellow solid. $^1$H NMR (400 MHz, DMSO-d$_6$) δ 3.01 (3H, s), 3.03 (3H, s), 4.51 (2H, d, J=6.0 Hz), 7.20-7.28 (1H, m), 7.30-7.39 (5H, m), 7.53 (1H, s), 7.79 (2H, br s), 7.99 (1H, dd, J=8.4, 2.4 Hz), 8.20 (1H, d, J=8.4 Hz), 8.37 (1H, d, J=4.8 Hz), 8.42 (1H, d, J=2.0 Hz), 8.57 (1H, d, J=2.0 Hz), 8.74 (1H, d, J=1.2 Hz), 9.12 (1H, br s), 12.24 (1H, br s). $^1$H NMR (400 MHz, DMSO-d$_6$) δ 4.48-4.56 (4H, m), 7.20-7.28 (2H, m), 7.31-7.39 (9H, m), 7.53 (1H, s), 7.85 (2H, br s), 8.27 (1H, d, J=8.4 Hz), 8.35-8.40 (2H, m), 8.45 (1H, d, J=2.0 Hz), 8.59 (1H, d, J=2.0 Hz), 9.12 (1H, br s), 9.16 (1H, d, J=2.0 Hz), 9.31 (1H, br s), 12.24 (1H, br s).

Example 135: 4-(2'-amino-5-(dimethylcarbamoyl)-[2,3'-bipyridin]-5'-yl)-N-(pyridin-4-ylmethyl)-1H-pyrrolo[2,3-b]pyridine-2-carboxamide

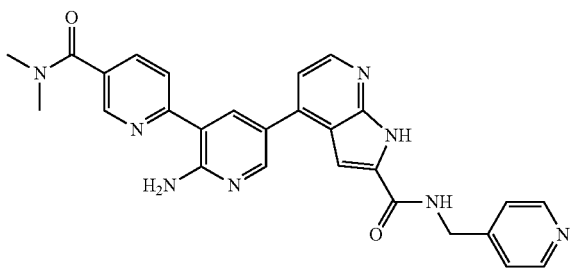 [SMILES: CN(C)C(=O)c1ccc(-c2cc(-c3ccnc4[nH]c(C(=O)NCc5ccncc5)cc34)cnc2N)nc1]

To a mixture of methyl 4-(2'-amino-5-(dimethylcarbamoyl)-[2,3'-bipyridin]-5'-yl)-1H-pyrrolo[2,3-b]pyridine-2-carboxylate (40 mg, 0.096 mmol), 4-pyridylmethanamine (42 mg, 0.38 mmol) in toluene (5 mL) was added AlMe$_3$ (2 M in toluene, 0.19 mL) at 0° C., then warmed to 25° C. and stirred for 0.5 hour, then heated to 50° C. and stirred for another 7.5 h to give a yellow suspension. TLC (DCM:MeOH=10:1) showed the reaction was completed. The mixture was quenched with a saturated aqueous solution of sodium potassium tartrate (10 mL) and then filtered. The filter cake was washed with EtOAc (5 mL×2). The filtrate was extracted with EtOAc (20 mL×2). The combined extracts was washed with brine (20 mL×2), dried over Na$_2$SO$_4$, filtered and concentrated under reduced pressure to give a residue. The residue was purified by prep-HPLC (0.05% NH$_3$·H$_2$O as an additive) and lyophilized to give 4-(2'-amino-5-(dimethylcarbamoyl)-[2,3'-bipyridin]-5'-yl)-N-(pyridin-4-ylmethyl)-1H-pyrrolo[2,3-b]pyridine-2-carboxamide (9.0 mg, purity: 100%, yield: 19%) as a yellow solid. $^1$H NMR (400 MHz, DMSO-d$_6$) δ 3.01 (3H, s), 3.03 (3H, s), 4.53 (2H, d, J=6.0 Hz), 7.33 (2H, d, J=6.0 Hz), 7.37 (1H, d, J=5.2 Hz), 7.56 (1H, s), 7.80 (2H, br s), 8.00 (1H, dd, J=8.4, 2.4 Hz), 8.21 (1H, d, J=8.4 Hz), 8.38 (1H, d, J=4.8 Hz), 8.43 (1H, d, J=2.0 Hz), 8.51 (2H, d, J=6.0 Hz), 8.59 (1H, d, J=2.0 Hz), 8.74 (1H, d, J=2.0 Hz), 9.22 (1H, br s), 12.29 (1H, br s).

Example 136: 4-(2'-amino-5-(dimethylcarbamoyl)-[2,3'-bipyridin]-5'-yl)-N-(pyridin-3-ylmethyl)-1H-pyrrolo[2,3-b]pyridine-2-carboxamide

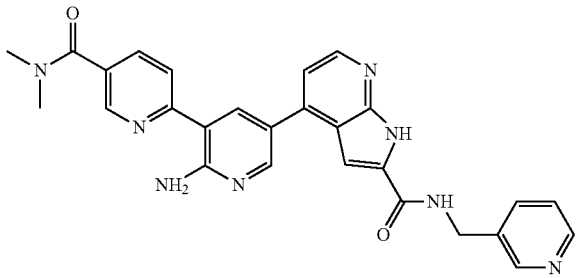 [SMILES: CN(C)C(=O)c1ccc(-c2cc(-c3ccnc4[nH]c(C(=O)NCc5cccnc5)cc34)cnc2N)nc1]

To a mixture of methyl 4-(2'-amino-5-(dimethylcarbamoyl)-[2,3'-bipyridin]-5'-yl)-1H-pyrrolo[2,3-b]pyridine-2-carboxylate (40 mg, 0.096 mmol), 3-pyridylmethanamine (42 mg, 0.38 mmol) in toluene (5 mL) was added AlMe$_3$ (2 M in toluene, 0.19 mL) at 0° C., then warmed to 25° C. and stirred for 0.5 hour, then heated to 50° C. and stirred for another 7.5 h to give a yellow suspension. LCMS showed the purity of product is 86% (Rt=0.587 min; MS Calc'd: 492.2; MS Found: 493.1 [M+H]$^+$). The mixture was quenched with a saturated aqueous solution of sodium potassium tartrate (10 mL) and then filtered. The filter cake was washed with EtOAc (5 mL×2). The filtrate was extracted with EtOAc (20 mL×2). The combined extracts was washed with brine (25 mL×2), dried over Na$_2$SO$_4$, filtered and concentrated under reduced pressure to give a residue. The residue was purified prep-HPLC (0.05% NH$_3$·H$_2$O as an additive) and lyophilized to give 4-(2'-amino-5-(dimethylcarbamoyl)-[2,3'-bipyridin]-5'-yl)-N-(pyridin-3-ylmethyl)-1H-pyrrolo[2,3-b]pyridine-2-carboxamide (11.8 mg, purity: 96.48%, yield: 24%) as a yellow solid. $^1$H NMR (400 MHz, DMSO-d$_6$) δ 3.01 (3H, s), 3.03 (3H, s), 4.53 (2H, d, J=6.0 Hz), 7.33-7.39 (2H, m), 7.51 (1H, s), 7.70-7.85 (3H, m), 7.99 (1H, dd, J=8.4, 2.4 Hz), 8.20 (1H, d, J=8.0 Hz), 8.37 (1H, d, J=4.8 Hz), 8.42 (1H, d, J=2.0 Hz), 8.47 (1H, dd, J=4.4, 1.6 Hz), 8.55-8.61 (2H, m), 8.74 (1H, d, J=1.6 Hz), 9.17 (1H, br s), 12.27 (1H, br s).

Example 137: 4-(2'-amino-5-(dimethylcarbamoyl)-[2,3'-bipyridin]-5'-yl)-N-(tetrahydro-2H-pyran-4-yl)-1H-pyrrolo[2,3-b]pyridine-2-carboxamide

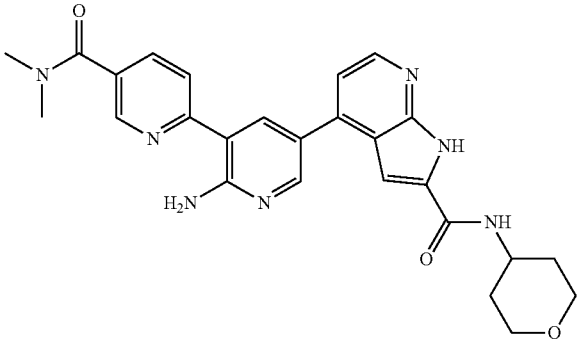 [SMILES: CN(C)C(=O)c1ccc(-c2cc(-c3ccnc4[nH]c(C(=O)NC5CCOCC5)cc34)cnc2N)nc1]

To a mixture of methyl 4-(2'-amino-5-(dimethylcarbamoyl)-[2,3'-bipyridin]-5'-yl)-1H-pyrrolo[2,3-b]pyridine-2- carboxylate (40 mg, 0.096 mmol), tetrahydropyran-4-amine (39 mg, 0.38 mmol) in toluene (5 mL) was added AlMe₃ (2 M in toluene, 0.19 mL) at 0° C., then warmed to 25° C. and stirred for 0.5 hour, then heated to 50° C. and stirred for another 7.5 h to give a yellow suspension. LCMS showed the purity of product is 88% (Rt=0.620 min; MS Calc'd: 485.2; MS Found: 486.2 [M+H]⁺). The mixture was quenched with a saturated aqueous solution of sodium potassium tartrate (15 mL) and then filtered. The filter cake was washed with EtOAc (10 mL×2). The filtrate was extracted with EtOAc (20 mL×2). The combined extracts was washed with brine (30 mL×2), dried over Na₂SO₄, filtered and concentrated under reduced pressure to give a residue. The residue was purified by prep-HPLC (0.05% NH₃·H₂O as an additive) and lyophilized to give 4-(2'-amino-5-(dimethylcarbamoyl)-[2,3'-bipyridin]-5'-yl)-N-(tetrahydro-2H-pyran-4-yl)-1H-pyrrolo[2,3-b]pyridine-2-carboxamide (6.4 mg, purity: 99.32%, yield: 14%) as a yellow solid. ¹H NMR (400 MHz, DMSO-d₆) δ 1.51-1.60 (2H, m), 1.72-1.88 (2H, m), 3.02 (3H, s), 3.03 (3H, s), 3.45-3.50 (2H, m), 3.83-3.95 (2H, m), 3.96-4.10 (1H, m), 7.35 (1H, d, J=4.4 Hz), 7.48 (1H, s), 7.78 (2H, br s), 8.00 (1H, dd, J=8.8, 2.4 Hz), 8.21 (1H, d, J=8.0 Hz), 8.32-8.44 (3H, m), 8.59 (1H, d, J=2.0 Hz), 8.75 (1H, br s), 12.17 (1H, br s).

Example 138: 4-(2'-amino-5-(dimethylcarbamoyl)-[2,3'-bipyridin]-5'-yl)-N-(2,2,2-trifluoroethyl)-1H-pyrrolo[2,3-b]pyridine-2-carboxamide

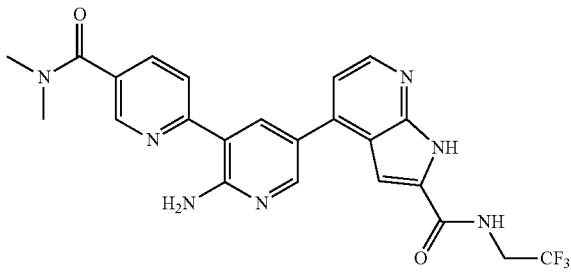 [SMILES: CN(C)C(=O)c1ccc(-c2cc(-c3ccnc4[nH]c(C(=O)NCC(F)(F)F)cc34)cnc2N)nc1]

To a mixture of methyl 4-(2'-amino-5-(dimethylcarbamoyl)-[2,3'-bipyridin]-5'-yl)-1H-pyrrolo[2,3-b]pyridine-2-carboxylate (40 mg, 0.096 mmol), 2,2,2-trifluoroethanamine (38 mg, 0.38 mmol) in toluene (5 mL) was added AlMe₃ (2 M in toluene, 0.19 mL) at 0° C., then warmed to 25° C. and stirred for 0.5 h, then heated to 50° C. and stirred for another 7.5 h to give a yellow suspension. LCMS showed the purity of product is 47% (Rt=0.652 min; MS Calc'd: 483.2; MS Found: 484.2 [M+H]⁺). The mixture was quenched with a saturated aqueous solution of sodium potassium tartrate (15 mL) and then filtered. The filter cake was washed with EtOAc (10 mL×2). The filtrate was extracted with EtOAc (20 mL×2). The combined extracts was washed with brine (30 mL×2), dried over Na₂SO₄, filtered and concentrated under reduced pressure to give a residue. The residue was purified by prep-HPLC (0.05% NH₃·H₂O as an additive) and lyophilized to give 4-(2'-amino-5-(dimethylcarbamoyl)-[2,3'-bipyridin]-5'-yl)-N-(2,2,2-trifluoroethyl)-1H-pyrrolo[2,3-b]pyridine-2-carboxamide (5.5 mg, purity 99.12%, yield: 12%) as a yellow solid. ¹H NMR (400 MHz, DMSO-d₆) δ 3.02 (3H, s), 3.03 (3H, s), 4.10-4.21 (2H, m), 7.38 (1H, d, J=5.2 Hz), 7.62 (1H, d, J=2.0 Hz), 7.81 (2H, br s), 8.00 (1H, dd, J=8.8, 2.4 Hz), 8.21 (1H, d, J=8.4 Hz), 8.39 (1H, d, J=4.8 Hz), 8.43 (1H, d, J=2.4 Hz), 8.58 (1H, d, J=2.0 Hz), 8.75 (1H, d, J=1.6 Hz), 9.16 (1H, br s), 12.35 (1H, br s).

Example 139: 4-(2'-amino-5-((2,2,2-trifluoroethyl) carbamoyl)-[2,3'-bipyridin]-5'-yl)-N-(2,2,2-trifluoroethyl)-1H-pyrrolo[2,3-b]pyridine-2-carboxamide

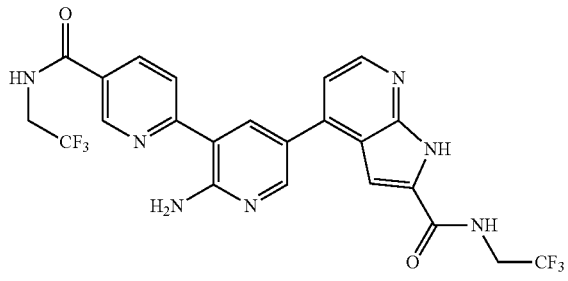 [SMILES: Nc1ncc(-c2ccnc3[nH]c(C(=O)NCC(F)(F)F)cc23)cc1-c1ccc(C(=O)NCC(F)(F)F)cn1]

To a mixture of 4-(2'-amino-5-carboxy-[2,3'-bipyridin]-5'-yl)-1H-pyrrolo[2,3-b]pyridine-2-carboxylic acid (50 mg, 0.12 mmol) in DMF (5 mL) was added EDC•HCl (71 mg, 0.37 mmol) and hydroxybenzotriazole (HOBt) (50 mg, 0.37 mmol), TEA (38 mg, 0.37 mmol), the reaction mixture was stirred at 25° C. for 0.5 hour to give a yellow suspension. 2,2,2-trifluoroethanamine (49 mg, 0.50 mmol) was added into the resulting mixture and stirred at 25° C. for another 15.5 h to give a yellow suspension. LCMS showed the reaction was completed. The mixture was diluted with water (15 mL), then extracted with EtOAc (20 mL×2), the combined extracts was washed with brine (30 mL×2), dried over Na₂SO₄, filtered and concentrated under reduced pressure to give a residue. The residue was purified by prep-HPLC (0.05% NH₃·H₂O as an additive) and lyophilized to give 4-(2'-amino-5-((2,2,2-trifluoroethyl)carbamoyl)-[2,3'-bipyridin]-5'-yl)-N-(2,2,2-trifluoroethyl)-1H-pyrrolo[2,3-b]pyridine-2-carboxamide (6.0 mg, yield: 9%) as a yellow solid. ¹H NMR (400 MHz, DMSO-d₆) δ 4.05-4.23 (4H, m), 7.39 (1H, d, J=4.8 Hz), 7.62 (1H, s), 7.87 (2H, br s), 8.31 (1H, d, J=8.4 Hz), 8.35-8.43 (2H, m), 8.47 (1H, d, J=2.0 Hz), 8.61 (1H, d, J=2.4 Hz), 9.10-9.16 (2H, m), 9.38 (1H, br s), 12.35 (1H, br s).

Example 140: 2'-amino-N,N-dimethyl-5'-(2-(piperazine-1-carbonyl)-1H-pyrrolo[2,3-b]pyridin-4-yl)-[2,3'-bipyridine]-5-carboxamide

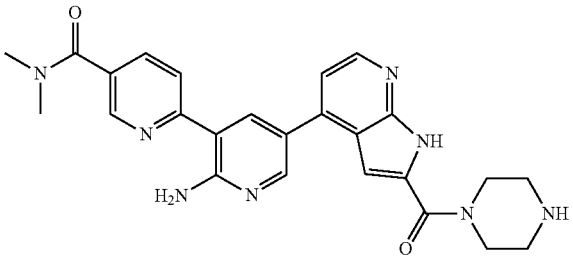 [SMILES: CN(C)C(=O)c1ccc(-c2cc(-c3ccnc4[nH]c(C(=O)N5CCNCC5)cc34)cnc2N)nc1]

To a mixture of methyl 4-(2'-amino-5-(dimethylcarbamoyl)-[2,3'-bipyridin]-5'-yl)-1H-pyrrolo[2,3-b]pyridine-2-carboxylate (40 mg, 0.096 mmol), piperazine (66 mg, 0.77 mmol) in toluene (5 mL) was added AlMe₃ (2 M in toluene, 0.19 mL) at 0° C., then warmed to 25° C. and stirred for 0.5 hour, then heated to 50° C. and stirred for another 7.5 h to give a yellow suspension. LCMS showed the purity of product is 64% (Rt=0.561 min; MS Calc'd: 470.2; MS Found: 471.1 [M+H]⁺). The mixture was quenched with a saturated aqueous solution of sodium potassium tartrate (15 mL) and then filtered. The filter cake was washed with DCM (10 mL×2). The filtrate was extracted with DCM/MeOH (20 mL/2 mL×2). The combined extracts was washed with brine (20 mL×2), dried over $Na_2SO_4$, filtered and concentrated under reduced pressure to give a residue. The residue was purified by prep-HPLC (0.05% $NH_3·H_2O$ as an additive) and lyophilized to give 2'-amino-N,N-dimethyl-5'-(2-(piperazine-1-carbonyl)-1H-pyrrolo[2,3-b]pyridin-4-yl)-[2,3'-bipyridine]-5-carboxamide (20.0 mg, purity: 99.66%, yield: 44%) as a yellow solid.

¹H NMR (400 MHz, DMSO-d₆) δ 2.69-2.78 (4H, m), 3.02 (3H, s), 3.03 (3H, s), 3.54-3.68 (4H, m), 6.88 (1H, s), 7.34 (1H, d, J=4.8 Hz), 7.77 (2H, br s), 7.99 (1H, dd, J=8.0, 2.0 Hz), 8.17 (1H, d, J=8.4 Hz), 8.34 (1H, d, J=4.8 Hz), 8.42 (1H, d, J=2.0 Hz), 8.55 (1H, d, J=2.0 Hz), 8.74 (1H, d, J=1.6 Hz), 12.21 (1H, br s).

Example 141: 2'-amino-N,N-dimethyl-5'-(2-(pyrrolidine-1-carbonyl)-1H-pyrrolo[2,3-b]pyridin-4-yl)-[2,3'-bipyridine]-5-carboxamide

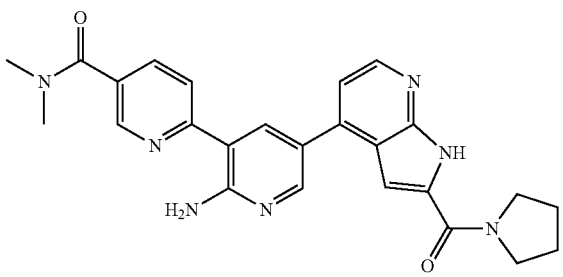 [SMILES: CN(C)C(=O)c1ccc(-c2cc(-c3ccnc4[nH]c(C(=O)N5CCCC5)cc34)cnc2N)nc1]

To a mixture of methyl 4-(2'-amino-5-(dimethylcarbamoyl)-[2,3'-bipyridin]-5'-yl)-1H-pyrrolo[2,3-b]pyridine-2-carboxylate (40 mg, 0.096 mmol), pyrrolidine (27 mg, 0.38 mmol) in toluene (5 mL) was added $AlMe_3$ (2 M in toluene, 0.19 mL) at 0° C., then warmed to 25° C. and stirred for 0.5 hour, then heated to 50° C. and stirred for another 2.5 h to give a yellow suspension. LCMS showed the purity of product (Rt=0.623 min; MS Calc'd: 455.2; MS Found: 456.1 [M+H]⁺). The mixture was quenched with a saturated aqueous solution of sodium potassium tartrate (15 mL) and then filtered. The filter cake was washed with DCM (10 mL×2). The filtrate was extracted with DCM/MeOH (20 mL/2 mL×2). The combined extracts was washed with brine (20 mL×2), dried over $Na_2SO_4$, filtered and concentrated under reduced pressure to give a residue. The residue was purified by prep-HPLC (0.05% $NH_3·H_2O$ as an additive) and lyophilized to give 2'-amino-N,N-dimethyl-5'-(2-(pyrrolidine-1-carbonyl)-1H-pyrrolo[2,3-b]pyridin-4-yl)-[2,3'-bipyridine]-5-carboxamide (8.2 mg, purity: 100%, yield: 19%) as a yellow solid. ¹H NMR (400 MHz, DMSO-d₆) δ 1.75-2.04 (4H, m), 3.02 (3H, s), 3.03 (3H, s), 3.55 (2H, t, J=6.8 Hz), 3.83 (2H, t, J=6.8 Hz), 7.08 (1H, s), 7.34 (1H, d, J=4.8 Hz), 7.77 (2H, br s), 7.98 (1H, dd, J=8.4, 2.4 Hz), 8.18 (1H, d, J=8.4 Hz), 8.37 (1H, d, J=5.2 Hz), 8.42 (1H, d, J=2.0 Hz), 8.57 (1H, d, J=2.0 Hz), 8.74 (1H, d, J=2.0 Hz), 12.16 (1H, br s).

Example 142: 2'-amino-5'-(2-(1,1-dioxidothiomorpholine-4-carbonyl)-1H-pyrrolo[2,3-b]pyridin-4-yl)-N,N-dimethyl-[2,3'-bipyridine]-5-carboxamide

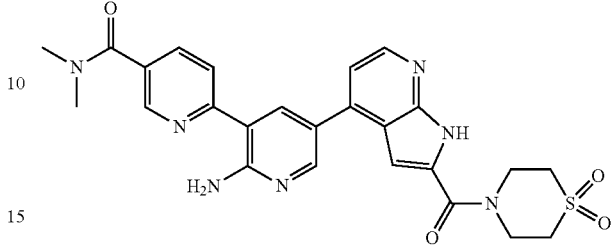

To a mixture of methyl 4-(2'-amino-5-(dimethylcarbamoyl)-[2,3'-bipyridin]-5'-yl)-1H-pyrrolo[2,3-b]pyridine-2-carboxylate (40 mg, 0.096 mmol), 1,4-thiazinane 1,1-dioxide (66 mg, 0.38 mmol, HCl salt) in toluene (5 mL) was added $AlMe_3$ (2 M in toluene, 0.19 mL) at 0° C., then warmed to 25° C. and stirred for 0.5 h, then heated to 50° C. and stirred for another 7.5 h to give a yellow suspension. LCMS showed the purity of product (Rt=0.594 min; MS Calc'd: 519.2; MS Found: 520.1 [M+H]⁺). The mixture was quenched with a saturated aqueous solution of sodium potassium tartrate (10 mL) and then filtered. The filter cake was washed with EtOAc (10 mL×2). The filtrate was extracted with EtOAc (20 mL/2 mL×2). The combined extracts was washed with brine (30 mL×2), dried over $Na_2SO_4$, filtered and concentrated under reduced pressure to give a residue. The residue was purified by prep-HPLC (0.05% $NH_3·H_2O$ as an additive) and lyophilized to give 2'-amino-5'-(2-(1,1-dioxidothiomorpholine-4-carbonyl)-1H-pyrrolo[2,3-b]pyridin-4-yl)-N,N-dimethyl-[2,3'-bipyridine]-5-carboxamide (15.8 mg, purity: 99.60%, yield: 32%) as a yellow solid. ¹H NMR (400 MHz, DMSO-d₆) δ 2.92-3.10 (8H, m), 3.25-3.30 (2H, m), 4.03-4.12 (4H, m), 7.08 (1H, s), 7.38 (1H, d, J=5.2 Hz), 7.78 (2H, br s), 8.00 (1H, dd, J=8.4, 2.0 Hz), 8.19 (1H, d, J=8.8 Hz), 8.37 (1H, d, J=4.8 Hz), 8.45 (1H, d, J=2.4 Hz), 8.58 (1H, d, J=2.0 Hz), 8.74 (1H, d, J=2.0 Hz), 12.26 (1H, br s).

Example 143: 4-(2'-amino-5-(dimethylcarbamoyl)-[2,3'-bipyridin]-5'-yl)-1H-pyrrolo[2,3-b]pyridine-2-carboxamide

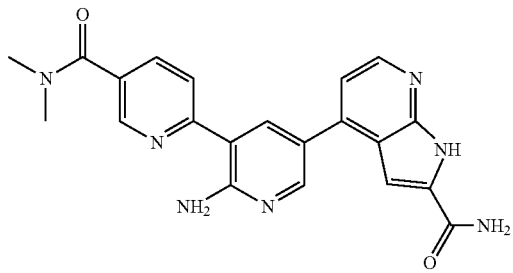 [SMILES: CN(C)C(=O)c1ccc(-c2cc(-c3ccnc4[nH]c(C(N)=O)cc34)cnc2N)nc1]

Step 1: Preparation of 2'-(bis(4-methoxybenzyl)amino)-5'-bromo-N,N-dimethyl-[2,3'-bipyridine]-5-carboxamide

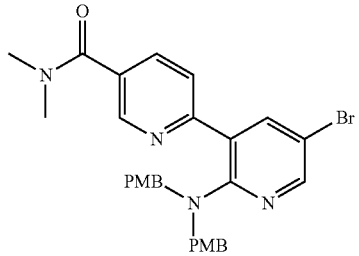

To a solution of 2'-amino-5'-bromo-N,N-dimethyl-[2,3'-bipyridine]-5-carboxamide (2.00 g, 6.23 mmol) in DMF (10 mL) was added NaH (0.997 g, 24.9 mmol, 60% in mineral oil) at 0° C. PMBCl (3.90 g, 24.9 mmol) was added dropwise at 0° C. The mixture was warmed to 25° C. and stirred for another 1 hour. The red suspension turned to yellow. TLC (pentane/EtOAc=1:1, by UV) showed that starting material was consumed and a less polar spot was formed. The reaction was added sat.NH$_4$Cl (50 mL), extracted with EtOAc (50 mL×3), the combined organic layer was washed with brine (50 mL), dried over Na$_2$SO$_4$ and concentrated. The residue was purified by Combi Flash (EA in PE from 0 to 50%) to give 2'-(bis(4-methoxybenzyl)amino)-5'-bromo-N,N-dimethyl-[2,3'-bipyridine]-5-carboxamide (4.00 g, 92% yield) as a yellow gum. $^1$H NMR (400 MHz, CDCl$_3$) δ 3.03 (3H, s), 3.16 (3H, s), 3.80 (6H, s), 4.15 (4H, s), 6.81 (4H, d, J=8.8 Hz), 7.00 (4H, d, J=8.8 Hz), 7.79-7.80 (2H, m), 8.00 (1H, d, J=2.4 Hz), 8.33 (1H, d, J=2.4 Hz), 8.75 (1H, t, J=1.6 Hz).

Step 2: Preparation of 2'-(bis(4-methoxybenzyl)amino)-N,N-dimethyl-5'-(4,4,5,5-tetramethyl-1,3,2-dioxaborolan-2-yl)-[2,3'-bipyridine]-5-carboxamide

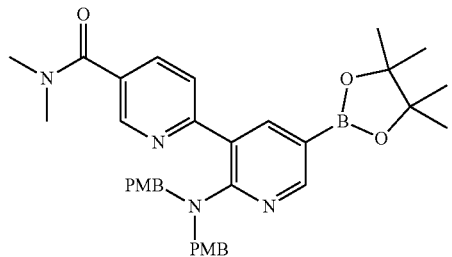

To a solution of 2'-(bis(4-methoxybenzyl)amino)-5'-bromo-N,N-dimethyl-[2,3'-bipyridine]-5-carboxamide (4.00 g, 7.12 mmol) in dioxane (20 mL) was added B$_2$Pin$_2$ (2.71 g, 10.7 mmol), KOAc (2.10 g, 21.4 mmol,) and Pd(dppf)Cl$_2$ (0.521 g, 0.712 mmol). The reaction mixture was stirred at 90° C. under N$_2$ atmosphere for 4 h to give a brown suspension. LCMS showed starting material was consumed and the purity of boronic acid (Rt=0.704 min; MS Calc'd: 526.1; MS Found: 527.1 [M+H]$^+$) The mixture was filtered to give 2'-(bis(4-methoxybenzyl)amino)-N,N-dimethyl-5'-(4,4,5,5-tetramethyl-1,3,2-dioxaborolan-2-yl)-[2,3'-bipyridine]-5-carboxamide in dioxane as black solution, which was used to next step directly.

Step 3: Preparation of methyl 4-(2'-(bis(4-methoxybenzyl)amino)-5-(dimethylcarbamoyl)-[2,3'-bipyridin]-5'-yl)-1H-pyrrolo[2,3-b]pyridine-2-carboxylate

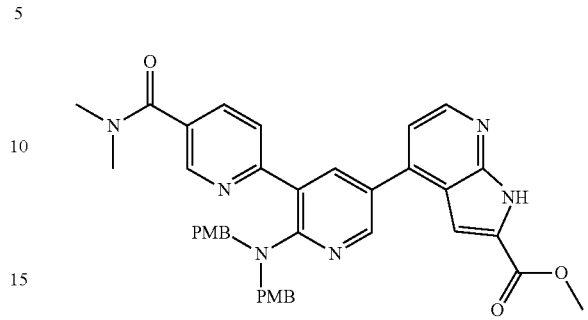

To a mixture of 2'-(bis(4-methoxybenzyl)amino)-N,N-dimethyl-5'-(4,4,5,5-tetramethyl-1,3,2-dioxaborolan-2-yl)-[2,3'-bipyridine]-5-carboxamide (310 mg, 0.510 mmol, crude solution) in dioxane (5 mL) and H$_2$O (0.5 mL) was added methyl 4-bromo-1H-pyrrolo[2,3-b]pyridine-2-carboxylate (100 mg, 0.392 mmol), Na$_2$CO$_3$ (125 mg, 1.18 mmol) and Pd(dppf)Cl$_2$ (29 mg, 0.039 mmol), the resulting mixture was stirred at 90° C. for 12 h to give a brown suspension. LCMS showed the reaction was completed. The mixture was diluted with water (15 mL), then extracted with EtOAc (20 mL×2), the combined extracts was washed with brine (25 mL×2), dried over Na$_2$SO$_4$, filtered and concentrated under reduced pressure to give a residue. The residue was purified by Combi Flash (EtOAc:MeOH=100:0 to 95:5 to 10:1) (TLC:DCM:MeOH=10:1) to give methyl 4-(2'-(bis(4-methoxybenzyl)amino)-5-(dimethylcarbamoyl)-[2,3'-bipyridin]-5'-yl)-1H-pyrrolo[2,3-b]pyridine-2-carboxylate (180 mg, yield: 70%) as a brown solid. $^1$H NMR (400 MHz, DMSO-d$_6$) δ 2.92 (3H, s), 3.02 (3H, s), 3.72 (6H, s), 3.89 (3H, s), 4.25 (4H, s), 6.85 (4H, d, J=8.4 Hz), 7.09 (4H, d, J=8.4 Hz), 7.29 (1H, d, J=2.0 Hz), 7.39 (1H, d, J=4.8 Hz), 7.87 (1H, d, J=8.0 Hz), 7.94 (1H, dd, J=8.0, 2.4 Hz), 8.16 (1H, d, J=2.8 Hz), 8.46 (1H, d, J=5.2 Hz), 8.70 (1H, d, J=2.4 Hz), 8.75 (1H, d, J=1.2 Hz), 12.73 (1H, br s).

Step 4: Preparation of 4-(2'-(bis(4-methoxybenzyl)amino)-5-(dimethylcarbamoyl)-[2,3'-bipyridin]-5'-yl)-1H-pyrrolo[2,3-b]pyridine-2-carboxamide

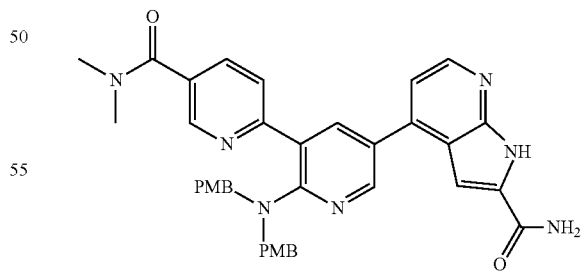

To a mixture of methyl 4-(2'-(bis(4-methoxybenzyl)amino)-5-(dimethylcarbamoyl)-[2,3'-bipyridin]-5'-yl)-1H-pyrrolo[2,3-b]pyridine-2-carboxylate (90 mg, 0.137 mmol) in MeOH (1 mL) was added NH$_3$ (liquid, 10 mL), the reaction mixture was stirred at 120° C. for 16 h in a sealed tube to give a white suspension. LCMS showed the purity of the desired product (Rt=1.84 min; MS Calc'd: 641.3; MS Found: 642.1 [M+H]⁺). The mixture was concentrated under reduced pressure to give 4-(2'-(bis(4-methoxybenzyl)amino)-5-(dimethylcarbamoyl)-[2,3'-bipyridin]-5'-yl)-1H-pyrrolo[2,3-b]pyridine-2-carboxamide (60 mg, yield: 68%) as a white solid.

Step 5: Preparation of 4-(2'-amino-5-(dimethylcarbamoyl)-[2,3'-bipyridin]-5'-yl)-1H-pyrrolo[2,3-b]pyridine-2-carboxamide

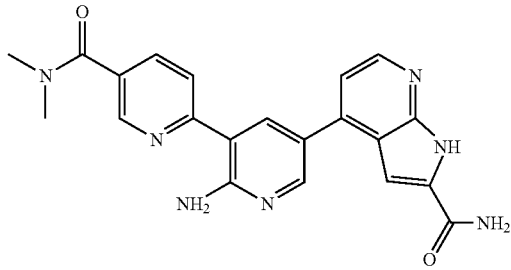 [SMILES: CN(C)C(=O)c1ccc(-c2cc(-c3ccnc4[nH]c(C(N)=O)cc34)cnc2N)nc1]

A mixture of 4-(2'-(bis(4-methoxybenzyl)amino)-5-(dimethylcarbamoyl)-[2,3'-bipyridin]-5'-yl)-1H-pyrrolo[2,3-b]pyridine-2-carboxamide (60 mg, 0.093 mmol) in DCM (1 mL) was added TFA (3 mL), the reaction mixture was stirred at 50° C. for 4 h to give a brown solution. LCMS showed the purity of the desired product (Rt=0.578 min; MS Calc'd: 401.2; MS Found: 402.2 [M+H]⁺). The mixture and concentrated under reduced pressure to give a residue. The residue was purified by prep-HPLC (0.1% TFA as an additive) and lyophilized to give 4-(2'-amino-5-(dimethylcarbamoyl)-[2,3'-bipyridin]-5'-yl)-1H-pyrrolo[2,3-b]pyridine-2-carboxamide (15.6 mg, purity: 100%, yield: 42%) as a white solid. ¹H NMR (400 MHz, DMSO-d₆) δ 3.01 (3H, s), 3.04 (3H, s), 7.38-7.47 (2H, m), 7.53 (1H, br s), 8.04 (1H, br s), 8.08 (1H, dd, J=8.8, 2.4 Hz), 8.32 (1H, d, J=8.8 Hz), 8.43 (1H, d, J=4.8 Hz), 8.58 (1H, d, J=2.0 Hz), 8.73 (1H, d, J=2.0 Hz), 8.78 (1H, d, J=1.2 Hz), 12.33 (1H, br s).

Example 144: N-(2-amino-2-oxoethyl)-4-(2'-amino-5-(dimethylcarbamoyl)-[2,3'-bipyridin]-5'-yl)-1H-pyrrolo[2,3-b]pyridine-2-carboxamide

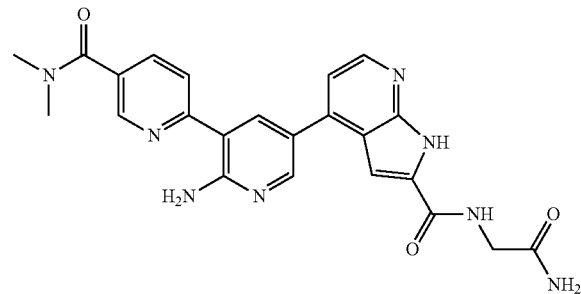 [SMILES: CN(C)C(=O)c1ccc(-c2cc(-c3ccnc4[nH]c(C(=O)NCC(N)=O)cc34)cnc2N)nc1]

Step 1: Preparation of 2-(ethoxycarbonyl)-1H-pyrrolo[2,3-b]pyridine 7-oxide

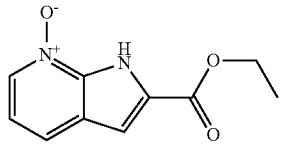

To a mixture of ethyl 1H-pyrrolo[2,3-b]pyridine-2-carboxylate (3.5 g, 18.4 mmol) in DCM (50 mL) was added m-CPBA (5.95 g, 27.6 mmol, 80% purity), the reaction mixture was stirred at 25° C. for 16 h to give a brown suspension. TLC (pentane:EtOAc=2:1) showed the reaction was completed. The mixture was concentrated under reduced pressure to give a residue. The residue was washed with MTBE (50 mL×2) and filtered. The filter cake was concentrated under reduced pressure to give an impure product. The impure product was further washed with MTBE (30 mL) and then filtered. The filter cake was concentrated under reduced pressure to give 2-(ethoxycarbonyl)-1H-pyrrolo[2,3-b]pyridine 7-oxide (3.5 g, yield: 92%) as an off-white solid. ¹H NMR (400 MHz, DMSO-d₆) δ 1.34 (3H, t, J=7.2 Hz), 4.33 (2H, q, J=7.2 Hz), 7.17 (1H, dd, J=8.0, 6.4 Hz), 7.29 (1H, s), 7.76 (1H, d, J=8.0 Hz), 8.32 (1H, d, J=6.0 Hz).

Step 2: Preparation of ethyl 4-bromo-1H-pyrrolo[2,3-b]pyridine-2-carboxylate

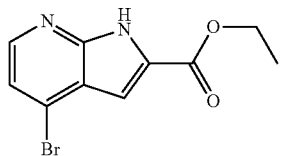

Step 3: First Batch

To a stirred solution of 2-(ethoxycarbonyl)-1H-pyrrolo[2,3-b]pyridine 7-oxide (500 mg, 2.42 mmol) and Me₄NBr (560 mg, 3.64 mmol) in CHCl₃ (15 mL) at 0° C. was added Ms₂O (845 mg, 4.85 mmol) in portions. The reaction mixture was allowed to warm to 25° C. and stir for 16 h. A pale yellow suspension was formed. LCMS showed the reaction was completed. The mixture was concentrated under reduced pressure to give a residue of ethyl 4-bromo-1H-pyrrolo[2,3-b]pyridine-2-carboxylate (0.8 g, crude) as an off-white solid.

Step 4: Second Batch

To a stirred solution of 2-(ethoxycarbonyl)-1H-pyrrolo[2,3-b]pyridine 7-oxide (3.50 g, 17.0 mmol) and Me₄NBr (3.92 g, 25.5 mmol) in CHCl₃ (40 mL) at 0° C. was added Ms₂O (5.91 g, 34.0 mmol) in portions. The reaction mixture was allowed to warm to 25° C. and stir for 16 h. A pale yellow suspension was formed. LCMS showed the reaction was completed. The mixture was concentrated under reduced pressure to give a residue. The residue and the above batch were combined and neutralized with cold 0.5 N aq NaHCO₃

(80 mL) and stirred for 0.5 hour and then filtered. The filter cake was further purified by washing with EtOAc/pentane (15 mL/30 mL) to give ethyl 4-bromo-1H-pyrrolo[2,3-b]pyridine-2-carboxylate (3.2 g, average yield: 61%) as an off-white solid. $^1$H NMR (400 MHz, DMSO-d$_6$) δ 1.36 (3H, t, J=7.2 Hz), 4.37 (2H, q, J=7.2 Hz), 7.06 (1H, s), 7.48 (1H, d, J=5.2 Hz), 8.29 (1H, d, J=4.8 Hz), 12.96 (1H, br s).

Step 5: Preparation of 4-bromo-1H-pyrrolo[2,3-b]pyridine-2-carboxylic acid

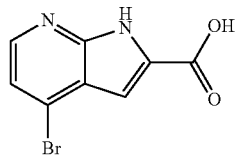 [SMILES: O=C(O)c1cc2c(Br)ccnc2[nH]1]

A mixture of ethyl 4-bromo-1H-pyrrolo[2,3-b]pyridine-2-carboxylate (1.50 g, 5.57 mmol) in MeOH (20 mL) was added NaOH (446 mg, 11.2 mmol) in H$_2$O (2 mL), the reaction mixture was stirred at 50° C. for 6 h to give a yellow suspension. LCMS showed the reaction was completed. The mixture was filtered. The filter cake was washed with MeCN (10 mL×2) to give 4-bromo-1H-pyrrolo[2,3-b]pyridine-2-carboxylic acid (1.2 g, yield: 89%) as an off-white solid. $^1$H NMR (400 MHz, DMSO-d$_6$) δ 6.51 (1H, s), 7.27 (1H, d, J=5.2 Hz), 8.06 (1H, d, J=5.2 Hz).

Step 6: Preparation of N-(2-amino-2-oxoethyl)-4-bromo-1H-pyrrolo[2,3-b]pyridine-2-carboxamide

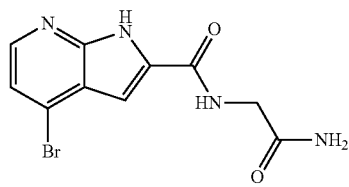 [SMILES: NC(=O)CNC(=O)c1cc2c(Br)ccnc2[nH]1]

A mixture of 4-bromo-1H-pyrrolo[2,3-b]pyridine-2-carboxylic acid (250 mg, 1.04 mmol) in DMF (15 mL) was added hydroxybenzotriazole (HOBt) (280 mg, 2.07 mmol), EDC•HCl (398 mg, 2.07 mmol), TEA (315 mg, 3.11 mmol), the reaction mixture was stirred at 50° C. for 0.5 hour and then added 2-aminoacetamide (230 mg, 3.11 mmol). The mixture was stirred for another 5.5 h to give a pale yellow suspension. LCMS showed the reaction was completed. The mixture was diluted with water (15 mL). Some white solid was precipitate out. The white suspension was filtered. The filter cake was washed with MeCN (10 mL) to give N-(2-amino-2-oxoethyl)-4-bromo-1H-pyrrolo[2,3-b]pyridine-2-carboxamide (250 mg, yield: 81%) as a white solid. $^1$H NMR (400 MHz, DMSO-d$_6$) δ 3.86 (2H, d, J=6.0 Hz), 7.10 (1H, br s), 7.22 (1H, s), 7.36-7.48 (2H, m), 8.20 (1H, d, 5.2 Hz), 8.92 (1H, br s), 12.51 (1H, br s).

Step 7: Preparation of N-(2-amino-2-oxoethyl)-4-(2'-(bis(4-methoxybenzyl)amino)-5-(dimethylcarbamoyl)-[2,3'-bipyridin]-5'-yl)-1H-pyrrolo[2,3-b]pyridine-2-carboxamide

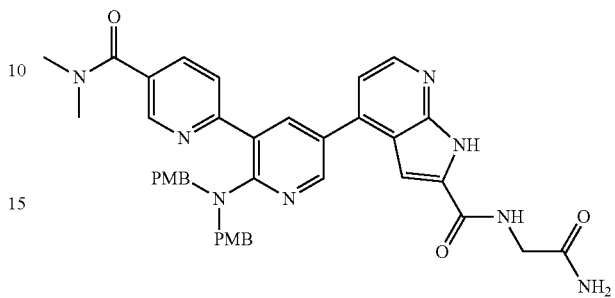

To a mixture of 2'-(bis(4-methoxybenzyl)amino)-N,N-dimethyl-5'-(4,4,5,5-tetramethyl-1,3,2-dioxaborolan-2-yl)-[2,3'-bipyridine]-5-carboxamide (246 mg, 0.404 mmol, crude) in dioxane (5 mL) and H$_2$O (0.5 mL) was added N-(2-amino-2-oxoethyl)-4-bromo-H-pyrrolo[2,3-b]pyridine-2-carboxamide (100 mg, 0.337 mmol), Na$_2$CO$_3$ (107 mg, 1.01 mmol) and Pd(dppf)Cl$_2$ (25 mg, 0.034 mmol), the resulting mixture was stirred at 90° C. for 12 h to give a brown suspension. LCMS showed the purity of desired product (Rt=0.757 min; MS Calc'd: 698.3; MS Found: 699.3 [M+H]$^+$). The mixture was diluted with water (15 mL), then extracted with EtOAc (20 mL×2), the combined extracts was washed with brine (30 mL×2), dried over Na$_2$SO$_4$, filtered and concentrated under reduced pressure to give a residue. The residue was purified by Combi Flash (EtOAc:MeOH=100:0 to 95:5 to 10:1) (TLC:DCM:MeOH=10:1) to give N-(2-amino-2-oxoethyl)-4-(2'-(bis(4-methoxybenzyl)amino)-5-(dimethylcarbamoyl)-[2,3'-bipyridin]-5'-yl)-1H-pyrrolo[2,3-b]pyridine-2-carboxamide (190 mg, yield: 81%) as a brown solid. $^1$H NMR (400 MHz, DMSO-d$_6$) δ 2.92 (3H, s), 3.02 (3H, s), 3.72 (6H, s), 3.86 (2H, d, J=6.0 Hz), 4.26 (4H, s), 6.85 (4H, d, J=8.8 Hz), 7.01-7.11 (5H, m), 7.35 (1H, d, J=6.0 Hz), 7.44 (1H, br s), 7.51 (1H, d, J=2.4 Hz), 7.88 (1H, dd, J=8.0, 0.8 Hz), 7.94 (1H, dd, J=8.0, 2.0 Hz), 8.17 (1H, d, J=2.4 Hz), 8.38 (1H, d, J=6.0 Hz), 8.72-8.79 (2H, m), 8.88 (1H, br s), 12.29 (1H, br s).

Step 8: Preparation of N-(2-amino-2-oxoethyl)-4-(2'-amino-5-(dimethylcarbamoyl)-[2,3'-bipyridin]-5'-yl)-1H-pyrrolo[2,3-b]pyridine-2-carboxamide

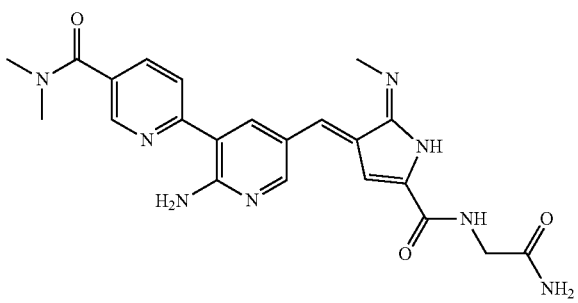 [SMILES: C/N=C1/NC(C(=O)NCC(N)=O)=C/C1=C\c1cnc(N)c(-c2ccc(C(=O)N(C)C)cn2)c1]

A mixture of N-(2-amino-2-oxoethyl)-4-(2'-(bis(4-methoxybenzyl)amino)-5-(dimethylcarbamoyl)-[2,3'-bipyridin]-5'-yl)-1H-pyrrolo[2,3-b]pyridine-2-carboxamide (100 mg, 0.143 mmol) in DCM (1 mL) was added TFA (2 mL), the reaction mixture was stirred at 50° C. for 3 h to give a brown solution. LCMS showed the purity of the desired product (Rt=0.568 min; MS Calc'd: 458.2; MS Found: 459.2 [M+H]$^+$). The mixture and concentrated under reduced pressure, then dissolved in MeOH (15 mL). The mixture was adjust to pH=8 with NaHCO$_3$ solid. DCM (20 mL) was added. The mixture was filtered. The filtrate was concentrated under reduced pressure to give a residue. The residue was purified by prep-HPLC (0.05% NH$_3$·H$_2$O as an additive) and lyophilized to give N-(2-amino-2-oxoethyl)-4-(2'-amino-5-(dimethylcarbamoyl)-[2,3'-bipyridin]-5'-yl)-1H-pyrrolo[2,3-b]pyridine-2-carboxamide (4.3 mg, purity: 99.60%, yield: 7%) as a yellow solid. $^1$H NMR (400 MHz, DMSO-d$_6$) δ 3.02 (3H, s), 3.03 (3H, s), 3.85 (2H, d, J=6.0 Hz), 7.07 (1H, br s), 7.36 (1H, d, 6.0 Hz), 7.42 (1H, br s), 7.51 (1H, s), 7.79 (2H, br s), 8.01 (1H, dd, J=8.0, 2.4 Hz), 8.20 (1H, d, J=8.4 Hz), 8.37 (1H, d, J=4.8 Hz), 8.42 (1H, d, J=1.6 Hz), 8.58 (1H, d, J=1.6 Hz), 8.75 (1H, d, J=2.0 Hz), 8.82 (1H, br s), 12.22 (1H, br s).

Example 145: (4-(2'-amino-5-(dimethylcarbamoyl)-[2,3'-bipyridin]-5'-yl)-1H-pyrrolo[2,3-b]pyridine-2-carbonyl)glycine

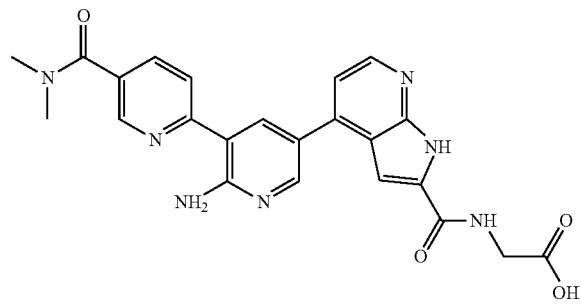 [SMILES: CN(C)C(=O)c1ccc(-c2cc(-c3ccnc4[nH]c(C(=O)NCC(=O)O)cc34)cnc2N)nc1]

Step 1: Preparation of tert-butyl (4-bromo-1H-pyrrolo[2,3-b]pyridine-2-carbonyl)glycinate

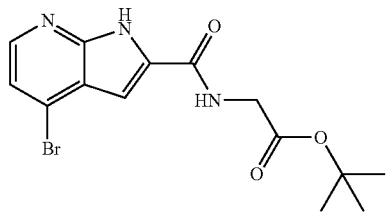 [SMILES: CC(C)(C)OC(=O)CNC(=O)c1cc2c(Br)ccnc2[nH]1]

A mixture of 4-bromo-1H-pyrrolo[2,3-b]pyridine-2-carboxylic acid (300 mg, 1.24 mmol) in DMF (15 mL) was added hydroxybenzotriazole (HOBt) (335 mg, 2.48 mmol), EDC·HCl (475 mg, 2.48 mmol) and TEA (376 mg, 3.72 mmol), the reaction mixture was stirred at 50° C. for 0.5 hour, then added tert-butyl 2-aminoacetate (325 mg, 2.48 mmol) and stirred for another 5.5 h to give a pale yellow suspension. LCMS showed the reaction was completed. The mixture was diluted with water (15 mL). Some white solid was precipitated out. The white suspension was filtered. The filter cake was washed with MeCN (10 mL) to give tert-butyl (4-bromo-1H-pyrrolo[2,3-b]pyridine-2-carbonyl)glycinate (300 mg, yield: 68%) as an off-white solid. $^1$H NMR (400 MHz, DMSO-d$_6$) δ 1.44 (9H, s), 3.95 (2H, d, J=6.0 Hz), 7.22 (1H, s), 7.43 (1H, d, J=5.2 Hz), 8.21 (1H, d, J=5.2 Hz), 9.09 (1H, br s), 12.62 (1H, br s).

Step 2: Preparation of tert-butyl (4-(2'-(bis(4-methoxybenzyl)amino)-5-(dimethylcarbamoyl)-[2,3'-bipyridin]-5'-yl)-1H-pyrrolo[2,3-b]pyridine-2-carbonyl)glycinate

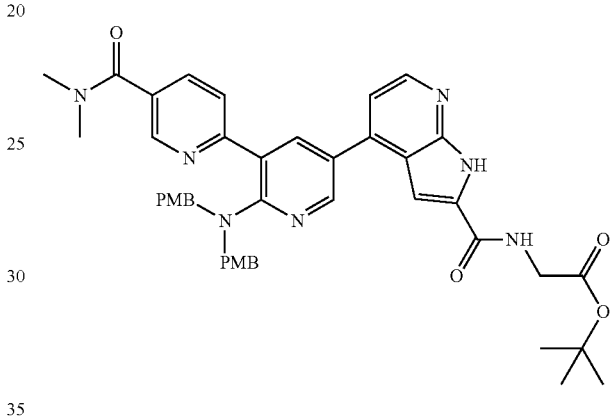

To a mixture of 2'-(bis(4-methoxybenzyl)amino)-N,N-dimethyl-5'-(4,4,5,5-tetramethyl-1,3,2-dioxaborolan-2-yl)-[2,3'-bipyridine]-5-carboxamide (200 mg, 0.329 mmol, crude) in dioxane (5 mL) and H$_2$O (0.5 mL) was added tert-butyl (4-bromo-1H-pyrrolo[2,3-b]pyridine-2-carbonyl)glycinate (97 mg, 0.274 mmol), Na$_2$CO$_3$ (87 mg, 0.82 mmol) and Pd(dppf)Cl$_2$ (20 mg, 0.027 mmol), the resulting mixture was stirred at 90° C. under N$_2$ atmosphere for 12 h to give a brown suspension. LCMS showed the reaction was completed. The mixture was diluted with water (15 mL), then extracted with EtOAc (20 mL×2), the combined extracts was washed with brine (30 mL×2), dried over Na$_2$SO$_4$, filtered and concentrated under reduced pressure to give a residue. The residue was purified by Combi Flash (EtOAc:MeOH=100:0 to 95:5 to 10:1) (TLC:DCM:MeOH=10:1) to give tert-butyl (4-(2'-(bis(4-methoxybenzyl)amino)-5-(dimethylcarbamoyl)-[2,3'-bipyridin]-5'-yl)-1H-pyrrolo[2,3-b]pyridine-2-carbonyl)glycinate (160 mg, yield: 77%) as a brown solid. $^1$H NMR (400 MHz, DMSO-d$_6$) δ 1.44 (9H, s), 2.92 (3H, s), 3.02 (3H, s), 3.72 (6H, s), 3.94 (2H, d, J=6.0 Hz), 4.26 (4H, s), 6.86 (4H, d, J=8.4 Hz), 7.10 (4H, d, J=8.8 Hz), 7.35 (1H, d, J=5.2 Hz), 7.51 (1H, d, J=2.0 Hz), 7.88 (1H, d, J=8.8 Hz), 7.94 (1H, dd, J=8.0, 2.4 Hz), 8.17 (1H, d, J=2.8 Hz), 8.39 (1H, d, J=6.0 Hz), 8.75 (2H, d, J=2.4 Hz), 9.03 (1H, br s), 12.34 (1H, br s).

Step 3: Preparation of (4-(2'-amino-5-(dimethylcarbamoyl)-[2,3'-bipyridin]-5'-yl)-1H-pyrrolo[2,3-b]pyridine-2-carbonyl)glycine

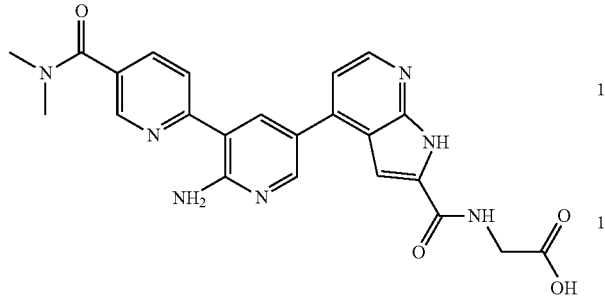

A mixture of tert-butyl (4-(2'-(bis(4-methoxybenzyl)amino)-5-(dimethylcarbamoyl)-[2,3'-bipyridin]-5'-yl)-1H-pyrrolo[2,3-b]pyridine-2-carbonyl)glycinate 80 mg, 0.11 mmol) in DCM (2 mL) as added TFA (2 mL), the reaction mixture was stirred at 50° C. for 6 h to give a brown solution. The reaction was repeated once. LCMS (first batch) showed the purity of the desired product is 81% (Rt=0.587 min; MS Calc'd: 459.2; MS Found: 460.3 [M+H]$^+$). LCMS (second batch) showed the purity of the desired product is 83% (Rt=0.582 min; MS Calc'd: 459.2; MS Found: 460.2 [M+H]$^+$). The two batches were combined and concentrated under reduced pressure, then dissolved with MeOH (15 mL). The mixture was adjust to pH=8 with NaHCO$_3$ solid. DCM (20 mL) was added. The mixture was filtered. The filtrate was concentrated under reduced pressure to give a residue. The residue was purified by prep-HPLC (0.05% NH$_3$·H$_2$O as an additive) and lyophilized to give (4-(2'-amino-5-(dimethylcarbamoyl)-[2,3'-bipyridin]-5'-yl)-1H-pyrrolo[2,3-b]pyridine-2-carbonyl)glycine (19.1 mg, purity: 100%, yield: 20%) as a yellow solid. $^1$H NMR (400 MHz, DMSO-d$_6$) δ 3.02 (6H, s), 3.90 (2H, d, J=6.0 Hz), 7.36 (1H, d, J=4.8 Hz), 7.49 (1H, s), 7.79 (2H, br s), 8.00 (1H, dd, J=8.4, 2.4 Hz), 8.20 (1H, d, J=8.4 Hz), 8.37 (1H, d, J=4.8 Hz), 8.42 (1H, d, J=2.4 Hz), 8.58 (1H, d, J=2.0 Hz), 8.75 (1H, d, J=1.6 Hz), 8.84 (1H, br s), 12.27 (1H, br s).

Example 146: 4-(2'-amino-5-(dimethylcarbamoyl)-[2,3'-bipyridin]-5'-yl)-N-(oxetan-3-yl)-1H-pyrrolo[2,3-b]pyridine-2-carboxamide

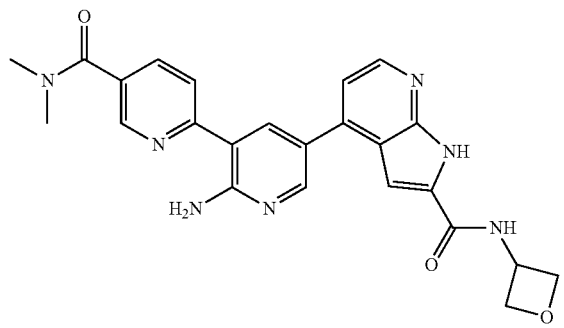 [SMILES: CN(C)C(=O)c1ccc(-c2cc(-c3ccnc4[nH]c(C(=O)NC5COC5)cc34)cnc2N)nc1]

Step 1: Preparation of ethyl 4-(2'-(bis(4-methoxybenzyl)amino)-5-(dimethylcarbamoyl)-[2,3'-bipyridin]-5'-yl)-1H-pyrrolo[2,3-b]pyridine-2-carboxylate

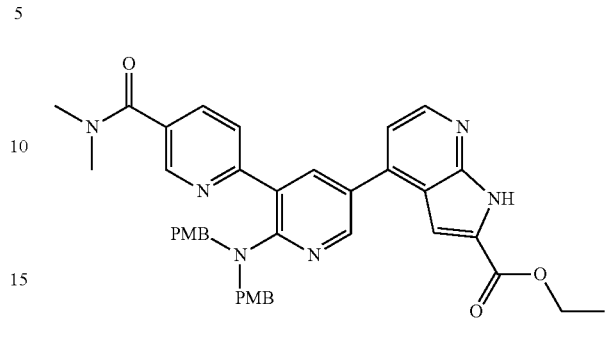

A solution of 2'-(bis(4-methoxybenzyl)amino)-N,N-dimethyl-5'-(4,4,5,5-tetramethyl-1,3,2-dioxaborolan-2-yl)-[2,3'-bipyridine]-5-carboxamide (3.00 g, 4.93 mmol) in dioxane (15 mL) and H$_2$O (5 mL) was added ethyl 4-bromo-1H-pyrrolo[2,3-b]pyridine-2-carboxylate (1.00 g, 3.72 mmol), Pd(dppf)Cl$_2$ (0.271 g, 0.371 mmol) and Na$_2$CO$_3$ (1.18 g, 11.2 mmol). The mixture was stirred at 90° C. under N$_2$ atmosphere for 16 h. A black suspension was formed. LCMS showed the purity of desired product (Rt=0.709 min; MS Calc'd: 670.8; MS Found: 671.3 [M+H]$^+$). The mixture was added sat.NH$_4$Cl (40 mL), extracted with EtOAc (40 mL×3). The combined layer was washed with brine (30 mL), dried over Na$_2$SO$_4$ and concentrate. The residue was purified by Combi Flash (EtOAc in PE from 0 to 100%) to give ethyl 4-(2'-(bis(4-methoxybenzyl)amino)-5-(dimethylcarbamoyl)-[2,3'-bipyridin]-5'-yl)-1H-pyrrolo[2,3-b]pyridine-2-carboxylate (0.9 g, yield: 36.1%) as a brown solid. $^1$H NMR (400 MHz, CDCl$_3$) δ 1.44 (3H, t, J=7.2 Hz), 3.03 (3H, s), 3.15 (3H, s), 3.80 (6H, s), 4.15 (4H, s), 4.46 (2H, q, J=7.2 Hz), 6.83 (4H, d, J=8.4 Hz), 7.06 (4H, d, J=8.4 Hz), 7.28 (1H, d, J=4.8 Hz), 7.47 (1H, s), 7.75-7.81 (2H, m), 8.21 (1H, d, J=2.4 Hz), 8.55 (1H, d, J=4.8 Hz), 8.75-8.78 (2H, m), 10.13 (1H, br s).

Step 2: Preparation of ethyl 4-(2'-amino-5-(dimethylcarbamoyl)-[2,3'-bipyridin]-5'-yl)-1H-pyrrolo[2,3-b]pyridine-2-carboxylate

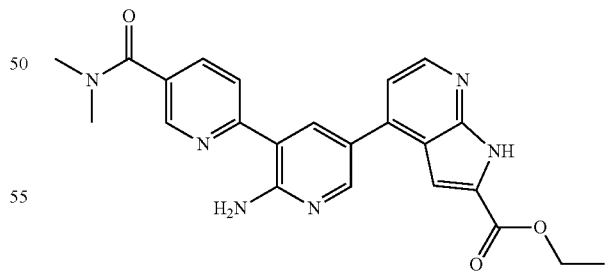

To a solution of ethyl 4-(2'-amino-5-(dimethylcarbamoyl)-[2,3'-bipyridin]-5'-yl)-1H-pyrrolo[2,3-b]pyridine-2-carboxylate (0.900 g, 1.34 mmol) in DCM (10 mL) was added TFA (10 mL). The mixture was stirred at 50° C. for 5 h. LCMS showed the purity of desired product (Rt=0.651 min; MS Calc'd: 430.5; MS Found: 431.2 [M+H]$^+$). The mixture was added sat.Na$_2$CO$_3$ (20 mL), extracted with EtOAc (30 mL×3) and DCM (20 mL×2), dried over Na$_2$SO$_4$ and concentrated. The residue was purified by Combi Flash (MeOH in DCM from 0 to 8%) to give ethyl 4-(2'-amino-5-(dimethylcarbamoyl)-[2,3'-bipyridin]-5'-yl)-1H-pyrrolo[2,3-b]pyridine-2-carboxylate (0.7 g, crude) as a yellow solid. $^1$H NMR (400 MHz, CDCl$_3$) δ 1.45 (3H, t, J=7.2 Hz), 3.15 (3H, s), 3.17 (3H, s), 4.46 (2H, q, J=6.8 Hz), 7.26 (1H, d, J=5.2 Hz), 7.42 (1H, s), 7.89 (1H, d, J=8.4 Hz), 7.95 (1H, dd, J=8.4, 2.4 Hz), 8.29 (1H, s), 8.60-8.61 (2H, m), 8.79 (1H, dd, J=2.0, 0.8 Hz), 12.44 (1H, br s).

Step 3: Preparation of 4-(2'-amino-5-(dimethylcarbamoyl)-[2,3'-bipyridin]-5'-yl)-1H-pyrrolo[2,3-b]pyridine-2-carboxylicacid

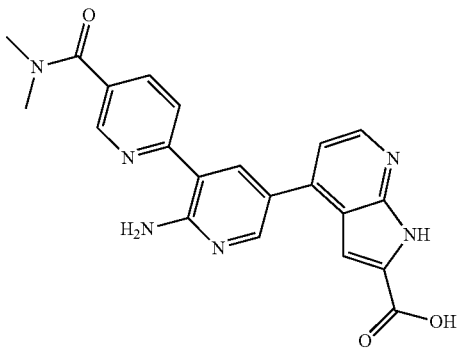 [SMILES: CN(C)C(=O)c1ccc(-c2cc(-c3ccnc4[nH]c(C(=O)O)cc34)cnc2N)nc1]

To a mixture of ethyl 4-(2'-amino-5-(dimethylcarbamoyl)-[2,3'-bipyridin]-5'-yl)-1H-pyrrolo[2,3-b]pyridine-2-carboxylate (0.650 g, 1.51 mmol) in THF (10 mL) was added KOH (169 mg, 3.02 mmol) in H$_2$O (10 mL). The mixture was stirred at 50° C. for 2 h. LCMS showed the purity of desired product (Rt=0.590 min; MS Calc'd: 402.4; MS Found: 403.1 [M+H]$^+$). The yellow suspension turned to brown solution. The mixture was added HCl (2 M) to adjust pH=3. A yellow solid was formed. Solvent was removed in high vacuum to give 4-(2'-amino-5-(dimethylcarbamoyl)-[2,3'-bipyridin]-5'-yl)-1H-pyrrolo[2,3-b]pyridine-2-carboxylic acid (0.600 g, crude) as a brown solid. $^1$H NMR (400 MHz, CDCl$_3$) δ 3.03 (3H, s), 3.04 (3H, s), 7.28 (1H, d, J=2.0 Hz), 7.41 (1H, d, J=4.8 Hz), 8.03 (1H, dd, J=8.8, 2.0 Hz), 8.22 (1H, d, J=8.0 Hz), 8.45 (1H, d, J=5.2 Hz), 8.51 (1H, s), 8.57 (1H, d, J=2.0 Hz), 8.76 (1H, d, J=2.0 Hz), 9.50 (1H, br s), 12.50 (1H, s).

Step 4: Preparation of 4-(2'-amino-5-(dimethylcarbamoyl)-[2,3'-bipyridin]-5'-yl)-N-(oxetan-3-yl)-1H-pyrrolo[2,3-b]pyridine-2-carboxamide

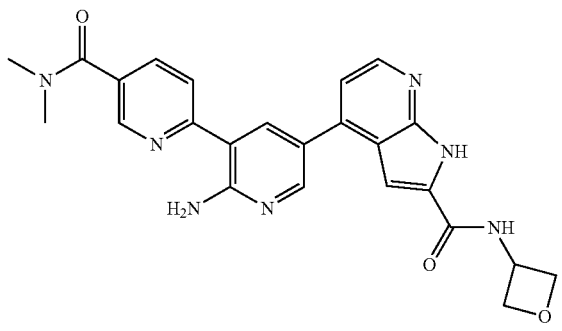 [SMILES: CN(C)C(=O)c1ccc(-c2cc(-c3ccnc4[nH]c(C(=O)NC5COC5)cc34)cnc2N)nc1]

To a solution of 4-(2'-amino-5-(dimethylcarbamoyl)-[2,3'-bipyridin]-5'-yl)-1H-pyrrolo[2,3-b]pyridine-2-carboxylic acid (50.0 mg, 0.124 mmol) and oxetan-3-amine (27.3 mg, 373 umol) in DMF (1 mL) was added hydroxybenzotriazole (HOBt) (33.6 mg, 0.248 mmol), EDC•HCl (47.6 mg, 0.248 mmol) and TEA (37.7 mg, 0.37 mmol). The mixture was stirred at 25° C. for 16 h. A yellow solution was formed. LCMS showed the purity of desired product (Rt=0.607 min; MS Calc'd: 457.5; MS Found: 458.1 [M+H]$^+$). The mixture was added H$_2$O (10 mL), extracted with EtOAc (10 mL×3). The combined organic layer was dried over Na$_2$SO$_4$ and concentrated. The residue was purified by preparative HPLC to give 4-(2'-amino-5-(dimethylcarbamoyl)-[2,3'-bipyridin]-5'-yl)-N-(oxetan-3-yl)-1H-pyrrolo[2,3-b]pyridine-2-carboxamide (12.0 mg, yield: 21%) as a yellow solid. $^1$H NMR (400 MHz, DMSO-d$_6$) δ 3.03 (3H, s), 3.05 (3H, s), 4.60 (2H, dd, J=6.4 Hz), 4.82 (2H, dd, J=6.8 Hz), 5.04-5.11 (1H, m), 7.38 (1H, d, J=2.0 Hz), 7.57 (1H, d, J=2.0 Hz), 7.82 (2H, br s), 8.02 (1H, dd, J=8.4, 2.4 Hz), 8.23 (1H, d, J=8.8 Hz), 8.38 (1H, d, J=6.4 Hz), 8.43 (1H, d, J=2.0 Hz), 8.61 (1H, d, J=2.8 Hz), 8.76 (1H, d, J=2.0 Hz), 9.20 (1H, d, J=7.2 Hz), 12.45 (1H, s).

Example 147: 5'-(2-(2-oxa-6-azaspiro[3.3]heptane-6-carbonyl)-1H-pyrrolo[2,3-b]pyridin-4-yl)-2'-amino-N,N-dimethyl-[2,3'-bipyridine]-5-carboxamide

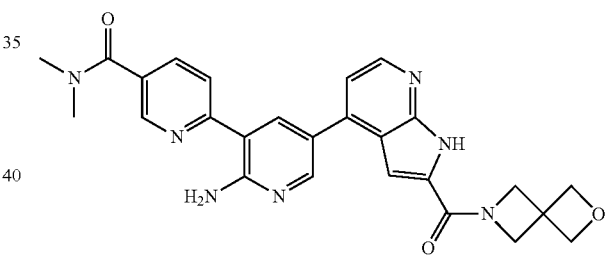

To a solution of 4-(2'-amino-5-(dimethylcarbamoyl)-[2,3'-bipyridin]-5'-yl)-1H-pyrrolo[2,3-b]pyridine-2-carboxylic acid (50.0 mg, 0.124 mmol) and 2-oxa-6-azaspiro[3.3]heptane (37.0 mg, 0.373 mmol) in DMF (1 mL) was added hydroxybenzotriazole (HOBt) (33.6 mg, 0.248 mmol), EDC·HCl (47.6 mg, 0.249 mmol,) and TEA (37.7 mg, 0.373 mmol). The mixture was stirred at 25° C. for 16 h. A yellow solution was formed. LCMS showed the purity of desired product (Rt=0.614 min; MS Calc'd: 483; MS Found: 484.1 [M+H]$^+$). The mixture was filtered purified by preparative HPLC and triturated with MeCN (2 mL) to give 5'-(2-(2-oxa-6-azaspiro[3.3]heptane-6-carbonyl)-1H-pyrrolo[2,3-b]pyridin-4-yl)-2'-amino-N,N-dimethyl-[2,3'-bipyridine]-5-carboxamide (10.0 mg, yield: 16.6%) as a yellow solid. $^1$H NMR (400 MHz, DMSO-d$_6$) δ 3.12 (3H, s), 3.18 (3H, s), 4.44 (2H, s), 4.68 (2H, s), 4.85 (4H, s), 6.85 (1H, d, J=1.6 Hz), 7.11 (2H, br s), 7.20 (1H, d, J=5.2 Hz), 7.87 (1H, d, J=8.8 Hz), 7.93 (1H, dd, J=8.8, 2.4 Hz), 8.20 (1H, d, J=2.0 Hz), 8.50 (1H, d, J=5.2 Hz), 8.60 (1H, d, J=2.0 Hz), 8.78 (1H, d, J=2.0 Hz), 10.30 (1H, s).

Example 148: 4-(2'-amino-5-(dimethylcarbamoyl)-[2,3'-bipyridin]-5'-yl)-N-((3S,4R)-4-aminotetrahydrofuran-3-yl)-1H-pyrrolo[2,3-b]pyridine-2-carboxamide

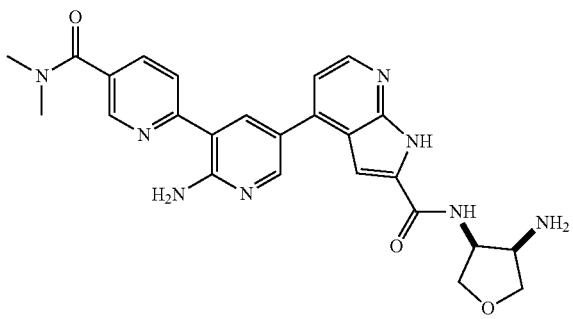

Step 1: Preparation of N-((3S,4R)-4-aminotetrahydrofuran-3-yl)-4-bromo-1H-pyrrolo[2,3-b]pyridine-2-carboxamide

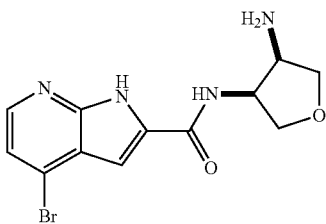

First Batch:

To a mixture of 4-bromo-H-pyrrolo[2,3-b]pyridine-2-carboxylic acid (100 mg, 0.415 mmol) in DMF (10 mL) was added cis-tetrahydrofuran-3,4-diamine (145 mg, 0.830 mmol, 2 HCl salt), TEA (210 mg, 2.07 mmol, 0.29 mL), EDC·HCl (159 mg, 0.83 mmol) and hydroxybenzotriazole (HOBt) (112 mg, 0.830 mmol), the reaction mixture was stirred at 50° C. for 4 h to give an off-white suspension. LCMS showed the reaction was completed. The mixture was diluted with water (15 mL), then extracted with EtOAc (20 mL×2), the combined extracts was washed with brine (25 mL×2), dried over Na$_2$SO$_4$, filtered and concentrated under reduced pressure to give N-(-4-aminotetrahydrofuran-3-yl)-4-bromo-1H-pyrrolo[2,3-b]pyridine-2-carboxamide (130 mg, crude) as a white solid.

Second Batch:

To a mixture of 4-bromo-1H-pyrrolo[2,3-b]pyridine-2-carboxylic acid (260 mg, 1.08 mmol) in DMF (20 mL) was added (3R,4S)-tetrahydrofuran-3,4-diamine (378 mg, 2.16 mmol, 2 HCl salt), TEA (655 mg, 6.47 mmol, 0.90 mL), EDC·HCl (414 mg, 2.16 mmol) and hydroxybenzotriazole (HOBt) (292 mg, 2.16 mmol), the reaction mixture was stirred at 50° C. for 4 h to give an off-white suspension. LCMS showed the reaction was completed. The mixture was diluted with water (15 mL), then extracted with DCM (20 mL×2), the combined extracts was washed with brine (30 mL×2), dried over Na$_2$SO$_4$, filtered and concentrated under reduced pressure to give a residue. The residue and the above batch were combined and purified by Combi Flash (DCM:MeOH=100:1 to 10:1) (TLC:DCM:MeOH=10:1) to give N-((3S,4R)-4-aminotetrahydrofuran-3-yl)-4-bromo-1H-pyrrolo[2,3-b]pyridine-2-carboxamide (120 mg, purity: 83%, average yield: 21%) as a white solid. $^1$H NMR (400 MHz, DMSO-d$_6$) δ 3.42-3.46 (1H, m), 3.51-3.54 (1H, m), 3.63-3.68 (1H, m), 3.90-3.98 (1H, m), 3.98-4.06 (1H, m), 4.36-4.44 (1H, m), 7.78 (1H, s), 7.43 (1H, d, J=5.2 Hz), 8.21 (1H, d, J=5.2 Hz).

Step 2: Preparation of N-((3S,4R)-4-aminotetrahydrofuran-3-yl)-4-(2'-(bis(4-methoxybenzyl)amino)-5-(dimethylcarbamoyl)-[2,3'-bipyridin]-5'-yl)-1H-pyrrolo[2,3-b]pyridine-2-carboxamide

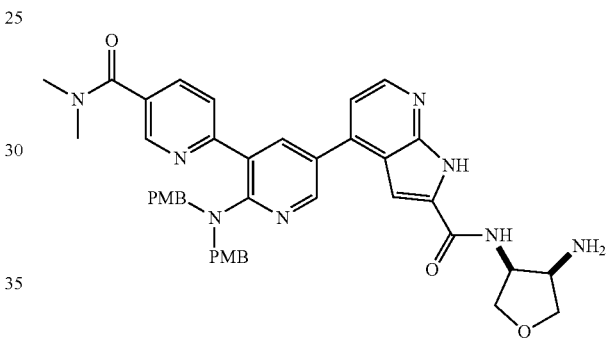

To a mixture of 2'-(bis(4-methoxybenzyl)amino)-N,N-dimethyl-5'-(4,4,5,5-tetramethyl-1,3,2-dioxaborolan-2-yl)-[2,3'-bipyridine]-5-carboxamide (271 mg, 0.446 mmol, crude) in dioxane (5 mL) was added N-((3S,4R)-4-aminotetrahydrofuran-3-yl)-4-bromo-1H-pyrrolo[2,3-b]pyridine-2-carboxamide (120 mg, 0.371 mmol), Na$_2$CO$_3$ (118 mg, 1.11 mmol) in H$_2$O (0.5 mL) and Pd(dppf)Cl$_2$ (27 mg, 0.037 mmol), the resulting mixture was stirred at 90° C. for 12 h to give a brown suspension. LCMS showed the purity of desired product (Rt=0.749 min; MS Calc'd: 726.3; MS Found: 727.2 [M+H]$^+$). The mixture was diluted with water (20 mL), then extracted with EtOAc (20 mL×2), the combined extracts was washed with brine (30 mL×2), dried over Na$_2$SO$_4$, filtered and concentrated under reduced pressure to give a residue. The residue was purified by combi flash (EtOAc:MeOH=100:0 to 95:5 to 10:1 to 8:1) (TLC:DCM:MeOH=10:1) to give N-((3S,4R)-4-aminotetrahydrofuran-3-yl)-4-(2'-(bis(4-methoxybenzyl)amino)-5-(dimethylcarbamoyl)-[2,3'-bipyridin]-5'-yl)-1H-pyrrolo[2,3-b]pyridine-2-carboxamide (40 mg, purity: 81%, yield: 12%) as a brown gum.

Step 3: Preparation of 4-(2'-amino-5-(dimethylcarbamoyl)-[2,3'-bipyridin]-5'-yl)-N-((3S,4R)-4-aminotetrahydrofuran-3-yl)-1H-pyrrolo[2,3-b]pyridine-2-carboxamide

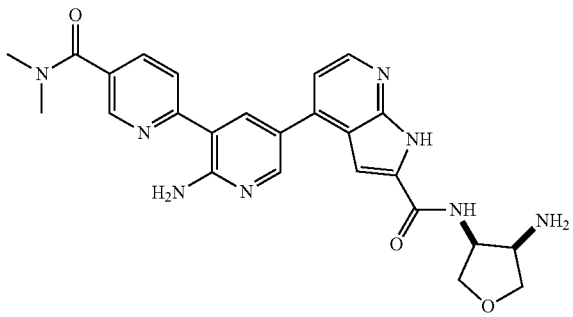

A mixture of N-((3S,4R)-4-aminotetrahydrofuran-3-yl)-4-(2'-(bis(4-methoxybenzyl)amino)-5-(dimethylcarbamoyl)-[2,3'-bipyridin]-5'-yl)-1H-pyrrolo[2,3-b]pyridine-2-carboxamide (40 mg, 0.055 mmol) in DCM (1 mL) was added TFA (2 mL), the reaction mixture was stirred at 50° C. for 6 h to give a brown solution. LCMS showed the purity of the desired product (Rt=0.572 min; MS Calc'd: 486.2; MS Found: 487.1 [M+H]$^+$). The mixture was concentrated under reduced pressure and then dissolved with MeOH (10 mL). The mixture was adjust to pH=8 with NaHCO$_3$ solid. DCM (15 mL) was added. The mixture was filtered. The filtrate was concentrated under reduced pressure to give a residue. The residue was purified by prep-HPLC (0.05% NH$_3$·H$_2$O as an additive) and lyophilized to give 4-(2'-amino-5-(dimethylcarbamoyl)-[2,3'-bipyridin]-5'-yl)-N-((3S,4R)-4-aminotetrahydrofuran-3-yl)-1H-pyrrolo[2,3-b]pyridine-2-carboxamide (2.41 mg, purity: 100%, yield: 9%) as a yellow solid. $^1$H NMR (400 MHz, DMSO-d$_6$) δ 2.98-3.02 (6H, m), 3.50-3.52 (1H, m), 3.52-5.56 (1H, m), 3.56-3.67 (1H, m), 3.86-4.02 (2H, m), 4.41-4.52 (1H, m), 7.36 (1H, d, J=4.4 Hz), 7.53 (1H, s), 7.78 (2H, br s), 7.99 (1H, dd, J=8.0, 2.0 Hz), 8.20 (1H, d, J=8.0 Hz), 8.37 (1H, d, J=5.6 Hz), 8.41 (1H, d, J=1.6 Hz), 8.60 (1H, d, J=2.0 Hz), 8.75 (1H, d, J=2.0 Hz), 12.23 (1H, br s).

Example 149: 4-(2'-amino-5-(dimethylcarbamoyl)-[2,3'-bipyridin]-5'-yl)-N-(2-oxopyrrolidin-3-yl)-1H-pyrrolo[2,3-b]pyridine-2-carboxamide

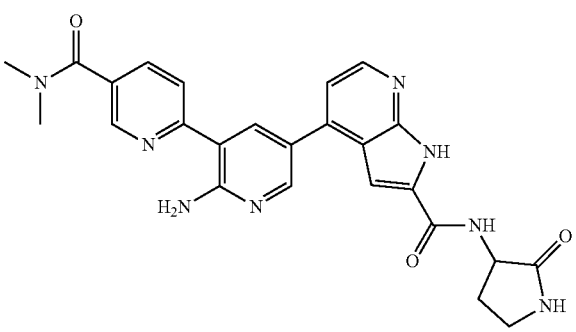 [SMILES: CN(C)C(=O)c1ccc(-c2cc(-c3ccnc4[nH]c(C(=O)NC5CCNC5=O)cc34)cnc2N)nc1]

Step 1: Preparation of 4-bromo-N-(2-oxopyrrolidin-3-yl)-1H-pyrrolo[2,3-b]pyridine-2-carboxamide

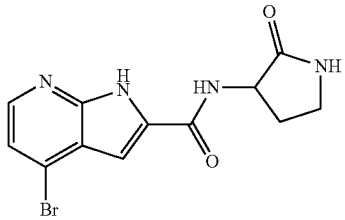 [SMILES: O=C(NC1CCNC1=O)c1cc2c(Br)ccnc2[nH]1]

To a mixture of 4-bromo-H-pyrrolo[2,3-b]pyridine-2-carboxylic acid (200 mg, 0.830 mmol) in DMF (10 mL) was added 3-aminopyrrolidin-2-one (208 mg, 2.07 mmol), TEA (252 mg, 2.49 mmol), EDC•HCl (318 mg, 1.66 mmol) and hydroxybenzotriazole (HOBt) (224 mg, 1.66 mmol), the reaction mixture was stirred at 50° C. for 4 h to give an off-white suspension. LCMS showed the reaction was completed. The mixture was diluted with water (20 mL). Some white solid was precipitate out. The white suspension was filtered. The filter cake was washed with MeCN (10 mL) to give 4-bromo-N-(2-oxopyrrolidin-3-yl)-1H-pyrrolo[2,3-b]pyridine-2-carboxamide (140 mg, yield: 52%) as a white solid. $^1$H NMR (400 MHz, DMSO-d$_6$) δ 1.91-2.04 (1H, m), 2.41-2.50 (1H, m), 3.21-3.38 (2H, m), 4.50-4.64 (1H, m), 7.24 (1H, s), 7.43 (1H, d, J=5.2 Hz), 7.93 (1H, br s), 8.21 (1H, d, J=5.2 Hz), 8.93 (1H, br s), 12.60 (1H, br s).

Step 2: Preparation of 4-(2'-(bis(4-methoxybenzyl)amino)-5-(dimethylcarbamoyl)-[2,3'-bipyridin]-5'-yl)-N-(2-oxopyrrolidin-3-yl)-1H-pyrrolo[2,3-b]pyridine-2-carboxamide

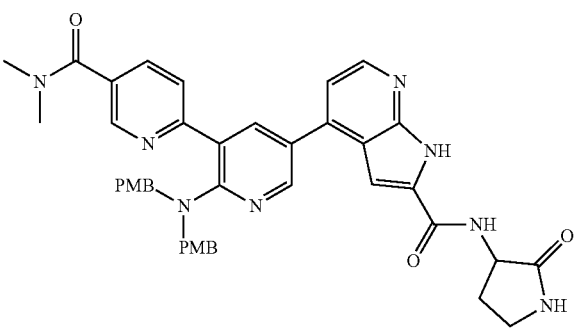

To a mixture of 2'-(bis(4-methoxybenzyl)amino)-N,N-dimethyl-5'-(4,4,5,5-tetramethyl-1,3,2-dioxaborolan-2-yl)-[2,3'-bipyridine]-5-carboxamide (271 mg, 0.446 mmol, crude) in dioxane (5 mL) and H$_2$O (0.5 mL) was added 4-bromo-N-(2-oxopyrrolidin-3-yl)-1H-pyrrolo[2,3-b]pyridine-2-carboxamide (120 mg, 0.371 mmol), Na$_2$CO$_3$ (118 mg, 1.11 mmol) and Pd(dppf)Cl$_2$ (27 mg, 0.037 mmol), the resulting mixture was stirred at 90° C. for 12 h to give a brown suspension. LCMS showed the purity of desired product (Rt=0.768 min; MS Calc'd: 724.3; MS Found: 725.4 [M+H]$^+$). The mixture was diluted with water (15 mL), then extracted with EtOAc (20 mL×2), the combined extracts was washed with brine (30 mL×2), dried over Na$_2$SO$_4$, filtered and concentrated under reduced pressure to give a residue. The residue was purified by Combi Flash (EtOAc:MeOH=100:0 to 95:5 to 10:1) (TLC:DCM: MeOH=10:1) to give 4-(2'-(bis(4-methoxybenzyl)amino)-5-(dimethylcarbamoyl)-[2,3'-bipyridin]-5'-yl)-N-(2-oxopyrrolidin-3-yl)-1H-pyrrolo[2,3-b]pyridine-2-carboxamide (180 mg, yield: 67%) as a brown solid. $^1$H NMR (400 MHz, DMSO-d$_6$) δ 2.45-2.47 (1H, m), 2.50-2.52 (1H, m), 2.93 (3H, s), 3.02 (3H, s), 3.35-3.38 (2H, m), 3.72 (6H, s), 4.26 (4H, s), 4.50-4.54 (1H, m), 6.86 (4H, d, J=8.8 Hz), 7.10 (4H, d, J=8.8 Hz), 7.35 (1H, d, J=5.2 Hz), 7.52 (1H, d, J=2.0 Hz), 7.85-7.89 (1H, m), 7.90-7.96 (2H, m), 8.17 (1H, d, J=2.4 Hz), 8.38 (1H, d, J=5.2 Hz), 8.72-8.77 (2H, m), 8.88 (1H, br s), 12.30 (1H, br s).

Step 3: Preparation of 4-(2'-amino-5-(dimethylcarbamoyl)-[2,3'-bipyridin]-5'-yl)-N-(2-oxopyrrolidin-3-yl)-1H-pyrrolo[2,3-b]pyridine-2-carboxamide

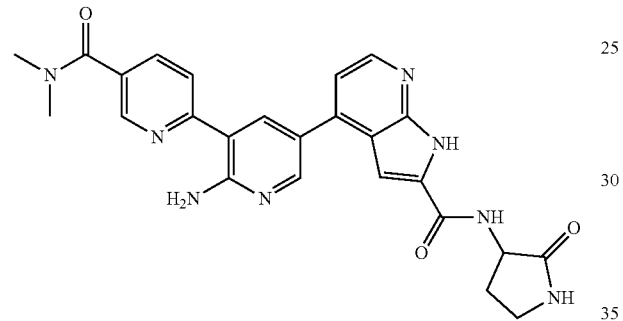

A mixture of 4-(2'-(bis(4-methoxybenzyl)amino)-5-(dimethylcarbamoyl)-[2,3'-bipyridin]-5'-yl)-N-(2-oxopyrrolidin-3-yl)-1H-pyrrolo[2,3-b]pyridine-2-carboxamide (100 mg, 0.138 mmol) in DCM (1 mL) was added TFA (2 mL), the reaction mixture was stirred at 50° C. for 3 h to give a brown solution. LCMS showed the purity of the desired product (Rt=0.591 min; MS Calc'd: 484.2; MS Found: 485.3 [M+H]$^+$). The mixture was concentrated under reduced pressure and then dissolved with MeOH (15 mL). The mixture was adjust to pH=8 with NaHCO$_3$ solid. DCM (20 mL) was added. The mixture was filtered. The filtrate was concentrated under reduced pressure to give a residue. The residue was purified by prep-HPLC (0.05% NH$_3$·H$_2$O as an additive) and lyophilized to give 4-(2'-amino-5-(dimethylcarbamoyl)-[2,3'-bipyridin]-5'-yl)-N-(2-oxopyrrolidin-3-yl)-1H-pyrrolo[2,3-b]pyridine-2-carboxamide (21.8 mg, purity: 98.59%, yield: 32%) as a yellow solid. $^1$H NMR (400 MHz, DMSO-d$_6$) δ 1.90-2.14 (1H, m), 2.31-2.43 (1H, m), 2.96-3.08 (6H, m), 3.19-3.27 (2H, m), 4.53-4.64 (1H, m), 7.36 (1H, d, J=5.2 Hz), 7.51 (1H, s), 7.79 (2H, br s), 7.90 (1H, br s), 8.00 (1H, dd, J=8.4, 2.4 Hz), 8.21 (1H, d, J=8.4 Hz), 8.37 (1H, d, J=4.8 Hz), 8.42 (1H, d, J=1.6 Hz), 8.58 (1H, d, J=2.0 Hz), 8.75 (1H, d, J=2.0 Hz), 8.80 (1H, br s), 12.24 (1H, br s).

Example 150: N-(2-(1H-imidazol-2-yl)ethyl)-4-(2'-amino-5-(dimethylcarbamoyl)-[2,3'-bipyridin]-5'-yl)-1H-pyrrolo[2,3-b]pyridine-2-carboxamide

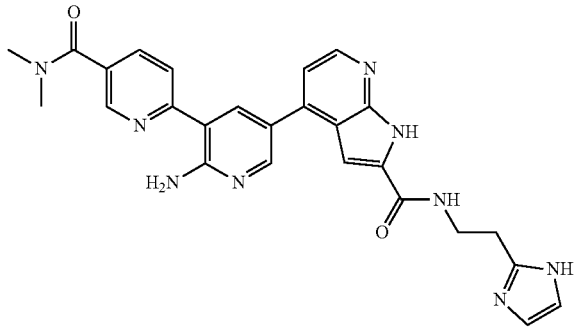 [SMILES: CN(C)C(=O)c1ccc(-c2cc(-c3ccnc4[nH]c(C(=O)NCCc5ncc[nH]5)cc34)cnc2N)nc1]

Step 1: Preparation of N-(2-(1H-imidazol-2-yl)ethyl-4-bromo-1H-pyrrolo[2,3-b]pyridine-2-carboxamide

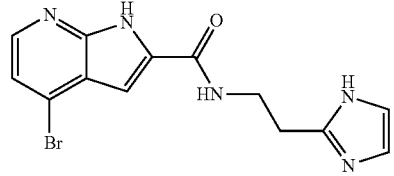 [SMILES: O=C(NCCc1ncc[nH]1)c1cc2c(Br)ccnc2[nH]1]

A mixture of 4-bromo-1H-pyrrolo[2,3-b]pyridine-2-carboxylic acid (200 mg, 0.830 mmol) in DMF (15 mL) was added hydroxybenzotriazole (HOBt) (224 mg, 1.66 mmol), EDC•HCl (318 mg, 1.66 mmol), TEA (420 mg, 4.15 mmol, 0.58 m), the reaction mixture was stirred at 50° C. for 0.5 hour, then added 2-(1H-imidazol-2-yl) ethanamine (305 mg, 1.66 mmol, 2 HCl salt) into it and continued stirred for another 2.5 h to give a pale yellow suspension. LCMS showed the purity of the desired product (Rt=0.600 min; MS Calc'd: 333.0; MS Found: 333.9 [M+H]$^+$). The mixture was diluted with water (15 mL), then extracted with EtOAc (20 mL×2), the combined extracts was washed with brine (25 mL×2), dried over Na$_2$SO$_4$, filtered and concentrated under reduced pressure to give N-(2-(1H-imidazol-2-yl)ethyl)-4-bromo-1H-pyrrolo[2,3-b]pyridine-2-carboxamide (250 mg, purity: 92%, yield: 83%) as an off-white solid $^1$H NMR (400 MHz, DMSO-d$_6$) δ 2.86-2.95 (2H, m), 3.52-3.65 (2H, m), 6.85-6.98 (2H, m), 7.15 (1H, s), 7.42 (1H, d, J=5.2 Hz), 8.19 (1H, d, J=4.8 Hz), 8.83 (1H, br s), 11.82 (1H, br s), 12.56 (1H, br s).

Step 2: Preparation of N-(2-(1H-imidazol-2-yl)ethyl)-4-(2'-(bis(4-methoxybenzyl)amino)-5-(dimethylcarbamoyl)-[2,3'-bipyridin]-5'-yl)-1H-pyrrolo[2,3-b]pyridine-2-carboxamide

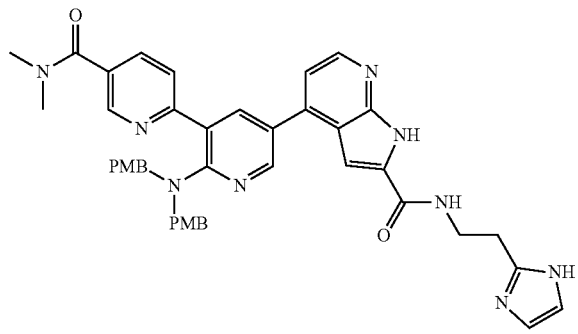

To a mixture of 2'-(bis(4-methoxybenzyl)amino)-N,N-dimethyl-5'-(4,4,5,5-tetramethyl-1,3,2-dioxaborolan-2-yl)-[2,3'-bipyridine]-5-carboxamide (262 mg, 0.431 mmol, crude) dioxane (5 mL) and in H$_2$O (0.5 mL) was added N-(2-(1H-imidazol-2-yl)ethyl)-4-bromo-1H-pyrrolo[2,3-b]pyridine-2-carboxamide (120 mg, 0.359 mmol), Na$_2$CO$_3$ (114 mg, 1.08 mmol) and Pd(dppf)Cl$_2$ (26 mg, 0.036 mmol), the resulting mixture was stirred at 90° C. for 12 h to give a brown suspension. LCMS showed the purity of desired product (Rt=0.637 min; MS Calc'd: 735.3; MS Found: 736.4 [M+H]$^+$). The mixture was diluted with water (15 mL), then extracted with EtOAc (20 mL×2), the combined extracts was washed with brine (30 mL×2), dried over Na$_2$SO$_4$, filtered and concentrated under reduced pressure to give a residue. The residue was purified by Combi Flash (EtOAc:MeOH=100:1 to 95:5 to 10:1) (TLC:DCM:MeOH=10:1) to give N-(2-(1H-imidazol-2-yl)ethyl)-4-(2'-(bis(4-methoxybenzyl)amino)-5-(dimethylcarbamoyl)-[2,3'-bipyridin]-5'-yl)-1H-pyrrolo[2,3-b]pyridine-2-carboxamide (80 mg, purity: 49%, yield: 15%) as a brown solid.

Step 3: Preparation of N-(2-(1H-imidazol-2-yl)ethyl)-4-(2'-amino-5-(dimethylcarbamoyl)-[2,3'-bipyridin]-5'-yl)-1H-pyrrolo[2,3-b]pyridine-2-carboxamide

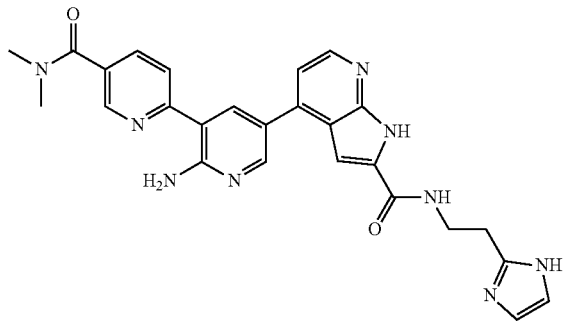 [SMILES: CN(C)C(=O)c1ccc(-c2cc(-c3ccnc4[nH]c(C(=O)NCCc5ncc[nH]5)cc34)cnc2N)nc1]

A mixture of N-(2-(1H-imidazol-2-yl)ethyl)-4-(2'-(bis(4-methoxybenzyl)amino)-5-(dimethylcarbamoyl)-[2,3'-bipyridin]-5'-yl)-1H-pyrrolo[2,3-b]pyridine-2-carboxamide (80 mg, 0.11 mmol) in DCM (1 mL) was added TFA (2 mL), the reaction mixture was stirred at 50° C. for 6 h to give a brown solution. LCMS showed the purity of the desired product (Rt=0.568 min; MS Calc'd: 495.2; MS Found: 496.1 [M+H]$^+$). The mixture was concentrated under reduced pressure and then dissolved with MeOH (10 mL). The mixture was adjust to pH=8 with NaHCO$_3$ solid. DCM (20 mL) was added. The mixture was filtered. The filtrate was concentrated under reduced pressure to give a residue. The residue was purified by prep-HPLC (0.05% NH$_3$·H$_2$O as an additive) and lyophilized to give N-(2-(1H-imidazol-2-yl)ethyl)-4-(2'-amino-5-(dimethylcarbamoyl)-[2,3'-bipyridin]-5'-yl)-1H-pyrrolo[2,3-b]pyridine-2-carboxamide (24.8 mg, purity: 100%, yield: 46%) as a yellow solid. $^1$H NMR (400 MHz, DMSO-d$_6$) δ 2.89 (2H, t, J=6.0 Hz), 3.01 (3H, s), 3.03 (3H, s), 3.59 (2H, dt, J=6.0 Hz), 6.70-7.08 (2H, m), 7.35 (1H, dd, J=4.8, 2.0 Hz), 7.43 (1H, s), 7.78 (2H, br s), 7.96-8.04 (1H, m), 8.19 (1H, d, J=8.4 Hz), 8.36 (1H, dd, J=6.0, 2.0 Hz), 8.41 (1H, s), 8.56 (1H, d, J=2.0 Hz), 8.66-8.79 (2H, m), 11.79 (1H, br s), 12.19 (1H, br s).

Example 151: 4-(5-(4-(6-ethyl-2-oxoindolin-1-yl)phenyl)pyridin-3-yl)-7-methyl-8,9-dihydropyrido[3',2':4,5]pyrrolo[1,2-a]pyrazin-6(7H)-one

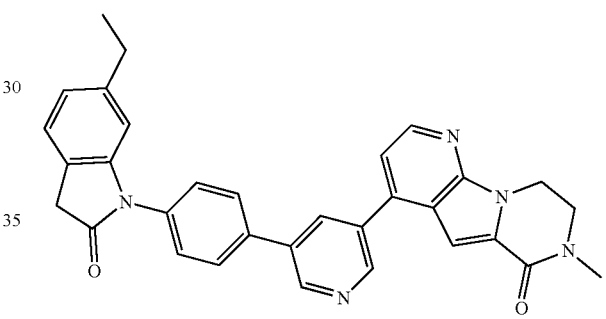

Step 1. Preparation of 6-ethylindolin-2-one

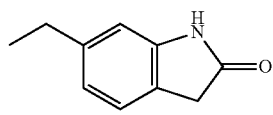

A mixture of 6-bromoindolin-2-one (1.50 g, 7.07 mmol), ethylboronic acid (1.50 g, 20.3 mmol), Pd(dppf)Cl$_2$ (1.04 g, 1.41 mmol), and K$_3$PO$_4$ (4.50 g, 21.2 mmol) in H$_2$O (10 mL) and dioxane (25 mL) was stirred at 90° C. for 24 hours under N$_2$ atmosphere. A black suspension was formed. LCMS showed the purity of the desired product is 27% (Rt=0.796 min; MS Calcd: 161.2; MS Found: 161.9 [M+H]$^+$). The reaction mixture was diluted with EtOAc (50 mL) and H$_2$O (30 mL) then separated. The aqueous was extracted with EtOAc (40 mL×2). The combined organic phase was dried over anhydrous Na$_2$SO$_4$ and concentrated. The residue was purified by Combi Flash (20% EtOAc in PE) to give 6-ethylindolin-2-one (300 mg, yield: 26% yield) as a white solid.

$^1$H NMR (400 MHz, CDCl$_3$) δ 1.23 (3H, t, J=7.6 Hz), 2.63 (2H, q, J=7.6 Hz), 3.50 (2H, s), 6.73 (1H, s), 6.86 (1H, d, J=7.2 Hz), 7.13 (1H, d, J=7.6 Hz), 7.80 (1H, brs).

Step 2. Preparation of 1-(4-bromophenyl)-6-ethylindolin-2-one

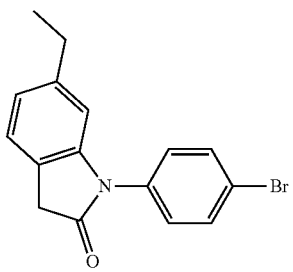 [SMILES: CCc1ccc2c(c1)N(c1ccc(Br)cc1)C(=O)C2]

A mixture of 6-ethylindolin-2-one (400 mg, 2.48 mmol), 1-bromo-4-iodobenzene (850 mg, 3.00 mmol), CuI (400 mg, 2.10 mmol), L-PROLINE (240 mg, 2.08 mmol) and CsF (750 mg, 4.94 mmol) in EtOAc (20 mL) was stirred at 50° C. for 36 hours under $N_2$ atmosphere. A black suspension was formed. TLC (PE/EtOAc=5/1, Rf=0.45) showed the starting material was consumed nearly. The reaction mixture was diluted with EtOAc/$H_2O$ (100 mL, 2/1) then separated. The aqueous was extracted with EtOAc (80 mL×3). The combined organic phase was concentrated. The residue was purified by Combi Flash (10% EtOAc in PE) to give 1-(4-bromophenyl)-6-ethylindolin-2-one (600 mg, yield: 76%) as an off-white solid.

$^1$H NMR (400 MHz, CDCl$_3$) δ 1.19 (3H, t, J=7.6 Hz), 2.60 (2H, q, J=7.6 Hz), 3.67 (2H, s), 6.62 (1H, d, J=2.8 Hz), 6.93 (1H, d, J=8.0 Hz), 7.18 (1H, m), 7.22 (1H, d, J=7.6 Hz), 7.31 (1H, d, J=8.4 Hz), 7.67 (1H, d, J=8.8 Hz), 7.86 (1H, d, J=8.8 Hz).

Step 3. Preparation of 6-ethyl-1-(4-(4,4,5,5-tetramethyl-1,3,2-dioxaborolan-2-yl)phenyl)indolin-2-one

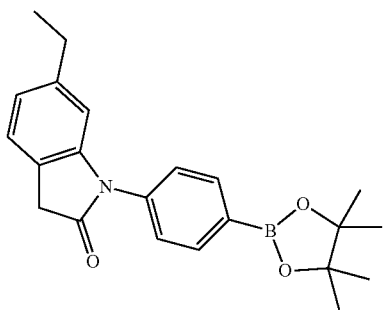 [SMILES: CCc1ccc2c(c1)N(c1ccc(B3OC(C)(C)C(C)(C)O3)cc1)C(=O)C2]

A mixture of 1-(4-bromophenyl)-6-ethylindolin-2-one (600 mg, 1.90 mmol), Bispin (580 mg, 2.28 mmol), Pd(dppf)Cl$_2$ (140 mg, 0.191 mmol) and KOAc (560 mg, 5.71 mmol) in dioxane (20 mL) was stirred at 100° C. for 16 hours under $N_2$ atmosphere. A black suspension was formed. LCMS showed the purity of the desired product is 54% (Rt=1.058 min; MS Calcd: 363.2; MS Found: 364.0 [M+H]$^+$). The reaction mixture was filtered and the filtrate was concentrated to give 6-ethyl-1-(4-(4,4,5,5-tetramethyl-1,3,2-dioxaborolan-2-yl)phenyl)indolin-2-one (700 mg, crude) as black brown oil, which was used for the next step without further purification.

Step 4. Preparation of 1-(4-(6-bromopyridin-3-yl)phenyl)-6-ethylindolin-2-one

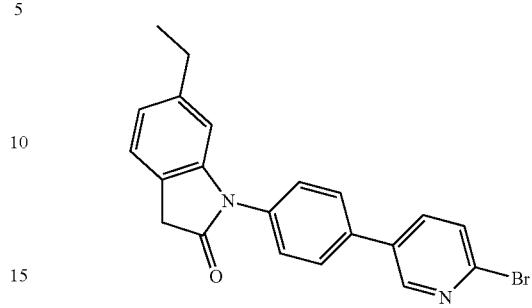

A mixture of 6-ethyl-1-(4-(4,4,5,5-tetramethyl-1,3,2-dioxaborolan-2-yl)phenyl)indolin-2-one (689 mg, 1.90 mmol), 3,5-dibromopyridine (730 mg, 3.08 mmol), Na$_2$CO$_3$ (600 mg, 5.66 mmol) and Pd(dppf)Cl$_2$ (150 mg, 0.205 mol) in dioxane (20 mL) and H$_2$O (5 mL) was stirred at 100° C. for 1 hours under N$_2$ atmosphere. A black suspension was formed. LCMS showed the purity of the desired product is 50% (Rt=0.997 min; MS Calcd: 393.2; MS Found: 393.8 [M+H]$^+$). The reaction mixture was diluted with EtOAc/H$_2$O (40 mL, 1/1) then extracted with EtOAc (30 mL×4). The combined organic phase was washed with brine (20 mL), dried over anhydrous Na$_2$SO$_4$ and concentrated. The residue was purified by Combi Flash (25% EtOAc in PE) to give 1-(4-(6-bromopyridin-3-yl)phenyl)-6-ethylindolin-2-one (190 mg, yield: 25% for two steps) as an off-white solid.

$^1$H NMR (400 MHz, CDCl$_3$) δ 1.21 (3H, t, J=7.2 Hz), 2.62 (2H, q, J=7.6 Hz), 3.61 (2H, s), 6.70 (1H, s), 6.95 (1H, d, J=7.6 Hz), 7.23 (1H, s), 7.57 (2H, d, J=8.8 Hz), 7.73 (2H, d, J=8.8 Hz), 8.07 (1H, t, J=2.0 Hz), 8.70 (1H, d, J=2.0 Hz), 8.81 (1H, d, J=2.0 Hz).

Step 5. Preparation of 6-ethyl-1-(4-(6-(4,4,5,5-tetramethyl-1,3,2-dioxaborolan-2-yl)pyridin-3-yl)phenyl)indolin-2-one

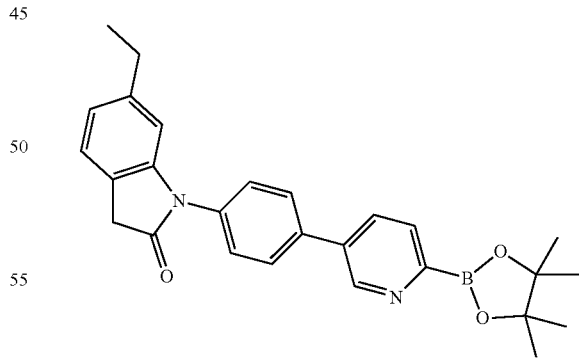

A mixture of 1-(4-(6-bromopyridin-3-yl)phenyl)-6-ethylindolin-2-one (90 mg, 0.23 mmol), Bispin (70 mg, 0.28 mmol), Pd(dppf)Cl$_2$ (20 mg, 0.027 mmol) and KOAc (70 mg, 0.71 mmol) in dioxane (3 mL) was stirred at 100° C. for 1.5 hours under N$_2$ atmosphere. A black suspension was formed. LCMS showed the purity of the desired product is 37% (Rt=0.809 min; MS Calcd: 358.1; MS Found: 358.9 [M+H]$^+$). The reaction mixture was filtered and the filtrate was concentrated to 6-ethyl-1-(4-(6-(4,4,5,5-tetramethyl-1,3,2-dioxaborolan-2-yl)pyridin-3-yl)phenyl)indolin-2-one (100 mg, crude) as black brown oil, which was used for the next step without further purification.

Step 6 Preparation of 4-(5-(4-(6-ethyl-2-oxoindolin-1-yl)phenyl)pyridin-3-yl)-7-methyl-8,9-dihydropyrido[3',2':4,5]pyrrolo[1,2-a]pyrazin-6(7H)-one

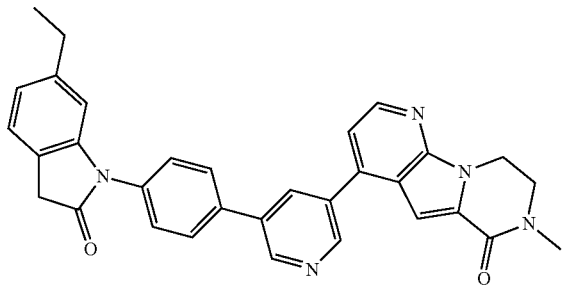 [SMILES: CCc1ccc2c(c1)N(c1ccc(-c3cncc(-c4ccnc5c4cc4n5CCN(C)C4=O)c3)cc1)C(=O)C2]

A mixture of 6-ethyl-1-(4-(6-(4,4,5,5-tetramethyl-1,3,2-dioxaborolan-2-yl)pyridin-3-yl)phenyl)indolin-2-one (100 mg, 0.227 mmol), 4-chloro-7-methyl-8,9-dihydropyrido[3',2':4,5]pyrrolo[1,2-a]pyrazin-6(7H)-one (67 mg, 0.28 mmol), $Cs_2CO_3$ (223 mg, 0.685 mmol) and $Pd(t-Bu_3P)_2$ (20 mg, 0.034 mmol) in dioxane (4 mL) and $H_2O$ (2 mL) was stirred at 100° C. for 1 hour under $N_2$ atmosphere. A black suspension was formed. LCMS showed the purity of the desired product is 23% (Rt=0.883 min; MS Calcd: 513.2; MS Found: 536.1 [M+Na]+). The reaction mixture was diluted with brine (10 mL) and DCM (20 mL) then extracted with DCM (20 mL×4). The resulting mixture was dried over anhydrous $Na_2SO_4$ and concentrated. The residue was prep-HPLC (0.04% $NH_3H_2O$+10 mM $NH_4HCO_3$ as additives) and lyophilized to 4-(5-(4-(6-ethyl-2-oxoindolin-1-yl)phenyl)pyridin-3-yl)-7-methyl-8,9-dihydropyrido[3',2':4,5]pyrrolo[1,2-a]pyrazin-6(7H)-one (2.21 mg, yield: 2% for two steps) as a white solid.

$^1$H NMR (400 MHz, DMSO-$d_6$) δ 1.13 (3H, t, J=7.6 Hz), 2.56-2.58 (2H, overlapped with DMSO signal), 3.710 (3H, s), 3.72 (2H, s), 3.87 (2H, t, J=5.6 Hz), 4.50 (2H, t, J=5.2 Hz), 6.68 (1H, s), 6.94 (1H, d, J=7.6 Hz), 7.20 (1H, s), 7.27 (1H, d, J=7.6 Hz), 7.57 (1H, d, J=4.8 Hz), 7.60 (2H, d, J=8.4 Hz), 8.07 (2H, d, J=7.6 Hz), 8.49 (1H, t, J=2.0 Hz), 8.57 (1H, d, J=4.8 Hz), 9.02 (1H, d, J=2.0 Hz), 9.11 (1H, d, J=2.4 Hz).

Example 152: 1-(4-(5-(5-((tetrahydro-2H-pyran-4-yl)oxy)-1H-pyrrolo[2,3-b]pyridin-4-yl)pyridin-3-yl)phenyl)pyrrolidin-2-one

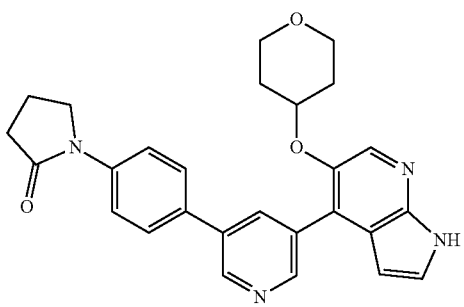 [SMILES: O=C1CCCN1c1ccc(-c2cncc(-c3c(OC4CCOCC4)cnc4[nH]ccc34)c2)cc1]

Step 1: Intermediate 59—(4-Chloro-5-tetrahydropyran-4-yloxy-pyrrolo[2,3-b]pyridin-1-yl)-triisopropylsilane

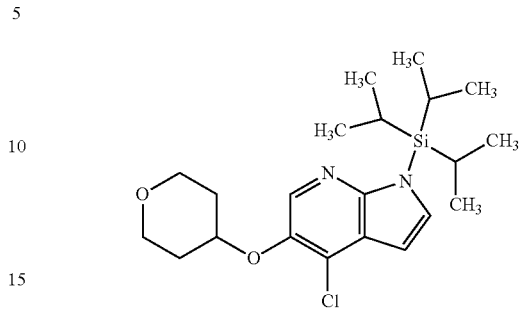

The title compound was prepared as described in Intermediate 57, replacing tert-butyl 3-hydroxypiperidine-1-carboxylate for tetrahydropyran-4-ol, to give the product as an oil (260 mg, 83%). MS ES+m/z 409 [M+H]+.

Step 2: Intermediate 60—1-[4-[5-(5-Tetrahydropyran-4-yloxy-1-triisopropylsilyl-pyrrolo[2,3-b]pyridin-4-yl)-3-pyridyl]phenyl]pyrrolidin-2-one

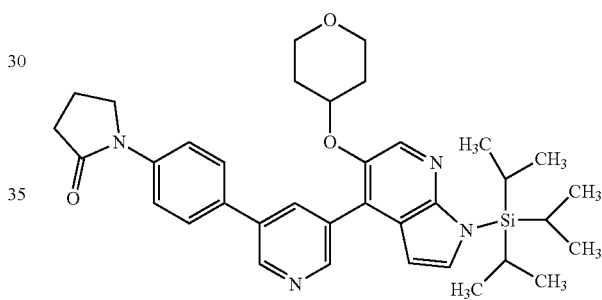

The title compound was prepared as described in Example 30, replacing 5-bromo-7H-pyrrolo[2,3-d]pyrimidine for (4-chloro-5-tetrahydropyran-4-yloxy-pyrrolo[2,3-b]pyridin-1-yl)-triisopropyl-silane. Extraction of the reaction mixture, using 1,2-dichloroethane and concentration of the organic layer gave a solid (117 mg), which was used in the next step. MS ES+m/z 611 [M+H]+.

Step 3: 1-(4-(5-(5-((tetrahydro-2H-pyran-4-yl)oxy)-1H-pyrrolo[2,3-b]pyridin-4-yl)pyridin-3-yl)phenyl)pyrrolidin-2-one

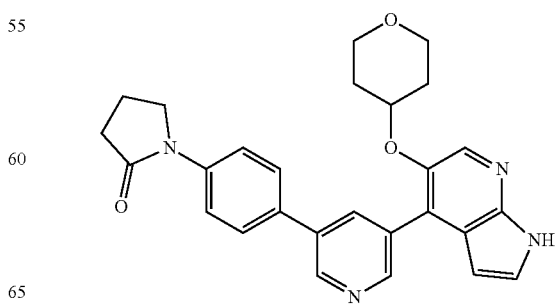

1-[4-[5-(5-Tetrahydropyran-4-yloxy-1-triisopropylsilyl-pyrrolo[2,3-b]pyridin-4-yl)-3-pyridyl]phenyl]pyrrolidin-2-one (117 mg, 0.19 mmol) was dissolved in MeOH (2 mL) at rt, a few drops of conc. HCl was added and the mixture was stirred at rt for 2 h. Sat. aq. NaHCO₃ was added and the mixture was extracted with DCM. The combined organics were washed with brine, dried over Na₂SO₄, filtered, concentrated and purified by preparative HPLC to give the product as a solid (14 mg, 16%). ¹H NMR (500 MHz, METHANOL-d₄) δ ppm 1.50-1.59 (m, 2H), 1.80-1.88 (m, 2H), 2.13-2.23 (m, 2H), 2.57-2.64 (m, 2H), 3.35-3.40 (m, 2H), 3.63-3.72 (m, 2H), 3.90-3.96 (m, 2H), 4.24-4.36 (m, 1H), 6.36-6.43 (m, 1H), 7.41-7.48 (m, 1H), 7.69-7.75 (m, 2H), 7.75-7.81 (m, 2H), 8.16-8.21 (m, 1H), 8.29-8.35 (m, 1H), 8.74-8.82 (m, 1H), 8.82-8.90 (m, 1H). MS ES+m/z 455 [M+H]⁺.

Example 153: 1-(4-(5-(7-methyl-7H-pyrrolo[2,3-d]pyrimidin-5-yl)pyridin-3-yl)phenyl)pyrrolidin-2-one

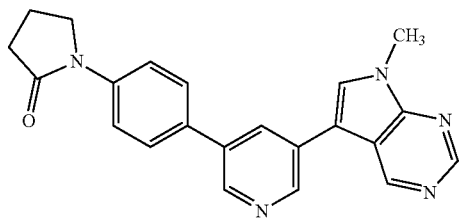 [SMILES: Cn1cc(-c2cncc(-c3ccc(N4CCCC4=O)cc3)c2)c2cncnc21]

Step 1 Intermediate 98—5-bromo-7-methyl-7H-pyrrolo[2,3-d]pyrimidine

Intermediate 98 was prepared in a similar manner as Intermediate 39 in Example 60, replacing methyl 3-bromo-1H-pyrrolo[2,3-b]pyridine-5-carboxylate for 5-bromo-7H-pyrrolo[2,3-d]pyrimidine, to give Intermediate 98 as a solid (120 mg, 28%). MS ES+m/z 212 [M+H]⁺.

Step 2: 1-(4-(5-(7-methyl-7H-pyrrolo[2,3-d]pyrimidin-5-yl)pyridin-3-yl)phenyl)pyrrolidin-2-one 1-[4-[5-(4,4,5,5-tetramethyl-1,3,2-dioxaborolan-2-yl)-3-pyridyl]phenyl]pyrrolidin-2-one was prepared according to Example 85, replacing 5-bromo-3-iodo-pyrin-2-amine with 3,5-dibromopyridine. 1-(4-(5-(7-methyl-7H-pyrrolo[2,3-d]pyrimidin-5-yl)pyridin-3-yl)phenyl)pyrrolidin-2-one was prepared according to Example 85, replacing 4-chloro-N-methyl-furo[2,3-b]pyridine-2-carboxamide for Intermediate 98, and replacing 1-[4-[2-amino-5-(4,4,5,5-tetramethyl-1,3,2-dioxaborolan-2-yl)-3-pyridyl]phenyl]pyrrolidin-2-one (Intermediate 90) with 1-[4-[5-(4,4,5,5-tetramethyl-1,3,2-dioxaborolan-2-yl)-3-pyridyl]phenyl]pyrrolidin-2-one, to give the 1-(4-(5-(7-methyl-7H-pyrrolo[2,3-d]pyrimidin-5-yl)pyridin-3-yl)phenyl)pyrrolidin-2-one as a solid (8 mg, 5%). ¹H NMR (500 MHz, DMSO-d₆) δ ppm 2.06-2.15 (m, 2H), 2.52-2.57 (m, 2H), 3.86-3.93 (m, 5H), 7.81-7.84 (m, 2H), 7.87-7.91 (m, 2H), 8.30 (s, 1H), 8.37 (t, J=2.21 Hz, 1H), 8.82 (d, J=2.21 Hz, 1H), 8.90 (s, 1H), 8.98 (d, J=2.21 Hz, 1H), 9.46 (s, 1H). MS ES+m/z 370 [M+H]⁺.

Example 154: 1-(4-(5-(5-(2-hydroxypropan-2-yl)-1-methyl-1H-pyrrolo[2,3-b]pyridin-3-yl)pyridin-3-yl)phenyl)pyrrolidin-2-one

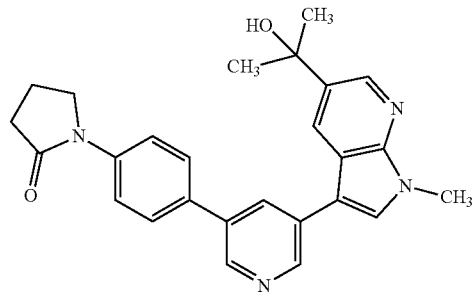 [SMILES: Cn1cc(-c2cncc(-c3ccc(N4CCCC4=O)cc3)c2)c2cc(C(C)(C)O)cnc21]

Step 1: Intermediate 99—2-(3-bromo-1-methyl-pyrrolo[2,3-b]pyridin-5-yl)propan-2-ol To a solution of 1-(3-bromo-1-methyl-pyrrolo[2,3-b]pyridin-5-yl)ethanone (178 mg, 0.7 mmol) in THF (3 mL) was added 3M MeMgCl in THF (0.47 ml, 1.41 mmol) dropwise. The resulting mixture was stirred at rt for 2 h. To the mixture was added sat. aq. NH₄Cl and the mixture was concentrated. The resulting aqueous residue was extracted with EtOAc and the combined organics were dried over Na₂SO₄, filtered, and concentrated to give Intermediate 99 as an oil (180 mg, 95%). MS ES+m/z 269 [M+H]⁺.

Step 2: 1-(4-(5-(5-(2-hydroxypropan-2-yl)-1-methyl-1H-pyrrolo[2,3-b]pyridin-3-yl)pyridin-3-yl)phenyl)pyrrolidin-2-one 1-[4-[5-(4,4,5,5-tetramethyl-1,3,2-dioxaborolan-2-yl)-3-pyridyl]phenyl]pyrrolidin-2-one was prepared according to Example 85, replacing 5-bromo-3-iodo-pyrin-2-amine with 3,5-dibromopyridine. 1-(4-(5-(5-(2-hydroxypropan-2-yl)-1-methyl-1H-pyrrolo[2,3-b]pyridin-3-yl)pyridin-3-yl)phenyl)pyrrolidin-2-one was prepared according to Example 85, replacing 4-chloro-N-methyl-furo[2,3-b]pyridine-2-carboxamide for Intermediate 99, and replacing 1-[4-[2-amino-5-(4,4,5,5-tetramethyl-1,3,2-dioxaborolan-2-yl)-3-pyridyl]phenyl]pyrrolidin-2-one (Intermediate 90) with 1-[4-[5-(4,4,5,5-tetramethyl-1,3,2-dioxaborolan-2-yl)-3-pyridyl]phenyl]pyrrolidin-2-one, to give 1-(4-(5-(5-(2-hydroxypropan-2-yl)-1-methyl-1H-pyrrolo[2,3-b]pyridin-3-yl)pyridin-3-yl)phenyl)pyrrolidin-2-one as a solid (51 mg, 36%). ¹H NMR (500 MHz, DMSO-d₆) δ ppm 1.55 (s, 6H), 2.06-2.13 (m, 2H), 2.51-2.56 (m, 2H), 3.87-3.92 (m, 5H), 5.16-5.38 (m, 1H), 7.81-7.87 (m, 4H), 8.16 (s, 1H), 8.27 (t, J=2.21 Hz, 1H), 8.40 (d, J=1.89 Hz, 1H), 8.49 (d, J=1.89 Hz, 1H), 8.78 (d, J=2.21 Hz, 1H), 8.93 (d, J=1.89 Hz, 1H). MS ES+m/z 427 [M+H]⁺.

217

Example 155: 1-(4-(5-(5-(2-methoxypropan-2-yl)-1-methyl-1H-pyrrolo[2,3-b]pyridin-3-yl)pyridin-3-yl)phenyl)pyrrolidin-2-one

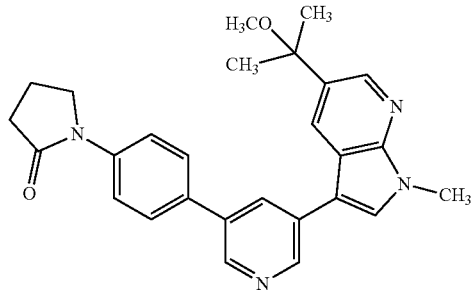 [SMILES: COC(C)(C)c1cnc2c(c1)c(-c1cncc(-c3ccc(N4CCCC4=O)cc3)c1)cn2C]

Step 1: Intermediate 100—3-bromo-5-(1-methoxy-1-methyl-ethyl)-1-methyl-pyrrolo[2,3-b]pyridine To a solution of NaH (60% dispersion in mineral oil, 33 mg, 0.87 mmol) in DMF (1 ml) at 0° C. was added a solution of 2-(3-bromo-1-methyl-pyrrolo[2,3-b]pyridin-5-yl)propan-2-ol (90 mg, 0.33 mmol) in DMF (1 ml). The resulting mixture was stirred at rt for 1 h, cooled to 0° C., and iodomethane (25 μl, 0.4 mmol) was added. The resulting mixture was stirred at rt overnight. Water was added and the mixture was extracted with EtOAc. The combined organics were dried over $Na_2SO_4$, filtered and concentrated to give the product as a solid (93 mg, 98%). MS ES+m/z 283 $[M+H]^+$.

Step 2: 1-(4-(5-(5-(2-methoxypropan-2-yl)-1-methyl-1H-pyrrolo[2,3-b]pyridin-3-yl)pyridin-3-yl)phenyl)pyrrolidin-2-one 1-[4-[5-(4,4,5,5-tetramethyl-1,3,2-dioxaborolan-2-yl)-3-pyridyl]phenyl]pyrrolidin-2-one was prepared according to Example 85, replacing 5-bromo-3-iodo-pyrin-2-amine with 3,5-dibromopyridine. 1-(4-(5-(5-(2-methoxypropan-2-yl)-1-methyl-1H-pyrrolo[2,3-b]pyridin-3-yl)pyridin-3-yl)phenyl)pyrrolidin-2-one was prepared according to Example 85, replacing 4-chloro-N-methyl-furo[2,3-b]pyridine-2-carboxamide for Intermediate 100, and replacing 1-[4-[2-amino-5-(4,4,5,5-tetramethyl-1,3,2-dioxaborolan-2-yl)-3-pyridyl]phenyl]pyrrolidin-2-one (Intermediate 90) with 1-[4-[5-(4,4,5,5-tetramethyl-1,3,2-dioxaborolan-2-yl)-3-pyridyl]phenyl]pyrrolidin-2-one, to give 1-(4-(5-(5-(2-methoxypropan-2-yl)-1-methyl-1H-pyrrolo[2,3-b]pyridin-3-yl)pyridin-3-yl)phenyl)pyrrolidin-2-one as a solid (46 mg, 32%). $^1$H NMR (500 MHz, DMSO-$d_6$) δ ppm 1.59 (s, 6H), 2.10 (quin, J=7.49 Hz, 2H), 2.52-2.56 (m, 2H), 3.02 (s, 3H), 3.88-3.94 (m, 5H), 7.82-7.88 (m, 4H), 8.18 (s, 1H), 8.23 (d, J=2.21 Hz, 1H), 8.28 (t, J=2.21 Hz, 1H), 8.43 (d, J=2.21 Hz, 1H), 8.78-8.80 (m, 1H), 8.90-8.94 (m, 1H). MS ES+m/z 441 $[M+H]^+$.

218

Example 156: 1-(4-(5-(7-methoxy-1-methyl-1H-pyrazolo[3,4-c]pyridin-4-yl)pyridin-3-yl)phenyl)pyrrolidin-2-one

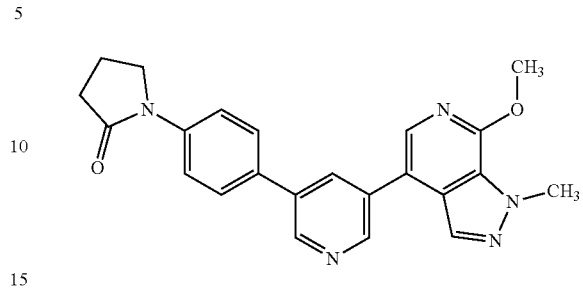

Step 1: Intermediate 101—4-bromo-7-methoxy-1-methyl-1H-pyrazolo[3,4-c]pyridine A mixture of 4-bromo-7-methoxy-1H-pyrazolo[3,4-c]pyridine (1.1 g, 4.82 mmol) and $Cs_2CO_3$ (3.14 g, 9.65 mmol) in DMF (25 ml) was stirred at rt for 30 min. Iodomethane (0.38 ml, 6.03 mmol) was added and the mixture was stirred at rt overnight. Aqueous 5% citric acid was added and the mixture was extracted with EtOAc. The combined organic layers were washed with brine, dried over $Na_2SO_4$, filtered, and concentrated. The resulting residue was purified on a silica gel column eluted with 0-100% EtOAc in heptane to give Intermediate 101 as a solid (770 mg, 66%), MS ES+m/z 242 $[M+H]^+$.

Step 2: 1-(4-(5-(7-methoxy-1-methyl-1H-pyrazolo[3,4-c]pyridin-4-yl)pyridin-3-yl)phenyl)pyrrolidin-2-one 1-[4-[5-(4,4,5,5-tetramethyl-1,3,2-dioxaborolan-2-yl)-3-pyridyl]phenyl]pyrrolidin-2-one was prepared according to Example 85, replacing 5-bromo-3-iodo-pyrin-2-amine with 3,5-dibromopyridine. 1-(4-(5-(7-methoxy-1-methyl-1H-pyrazolo[3,4-c]pyridin-4-yl)pyridin-3-yl)phenyl)pyrrolidin-2-one was prepared according to Example 85, replacing 4-chloro-N-methyl-furo[2,3-b]pyridine-2-carboxamide for Intermediate 101, and replacing 1-[4-[2-amino-5-(4,4,5,5-tetramethyl-1,3,2-dioxaborolan-2-yl)-3-pyridyl]phenyl]pyrrolidin-2-one (Intermediate 90) with 1-[4-[5-(4,4,5,5-tetramethyl-1,3,2-dioxaborolan-2-yl)-3-pyridyl]phenyl]pyrrolidin-2-one. Purification on a silica gel column, eluted with 0-10% MeOH in DCM gave 1-(4-(5-(7-methoxy-1-methyl-1H-pyrazolo[3,4-c]pyridin-4-yl)pyridin-3-yl)phenyl)pyrrolidin-2-one as a solid (360 mg, 90%). A portion (50 mg) of the isolated 1-(4-(5-(7-methoxy-1-methyl-1H-pyrazolo[3,4-c]pyridin-4-yl)pyridin-3-yl)phenyl)pyrrolidin-2-one was further purified by preparative HPLC to yield 18 mg of solid. $^1$H NMR (500 MHz, DMSO-$d_6$) δ ppm 2.11 (quin, J=7.57 Hz, 2H), 2.52-2.57 (m, 2H), 3.91 (t, J=7.09 Hz, 2H), 4.08-4.22 (m, 3H), 4.28-4.36 (m, 3H), 7.79-7.87 (m, 2H), 7.88-7.92 (m, 2H), 8.03 (s, 1H), 8.31 (s, 1H), 8.32 (s, 1H), 8.88 (d, J=2.21 Hz, 1H), 8.96 (d, J=2.21 Hz, 1H). MS ES+m/z 400 $[M+H]^+$.

Example 157: 1-[4-[5-(7-methoxy-2-methyl-pyrazolo[3,4-c]pyridin-4-yl)-3-pyridyl]phenyl]pyrrolidin-2-one

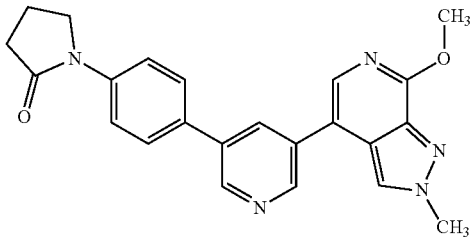 [SMILES: COc1ncc(-c2cncc(-c3ccc(N4CCCC4=O)cc3)c2)c2cn(C)nc12]

Step 1: Intermediate 102—4-bromo-7-methoxy-2-methyl-pyrazolo[3,4-c]pyridine A mixture of 4-bromo-7-methoxy-1H-pyrazolo[3,4-c]pyridine (1.1 g, 4.82 mmol) and $Cs_2CO_3$ (3.14 g, 9.65 mmol) in DMF (25 ml) was stirred at rt for 30 min. Iodomethane (0.38 ml, 6.03 mmol) was added and the mixture was stirred at rt overnight. Aqueous 5% citric acid was added and the mixture was extracted with EtOAc. The combined organic layers were washed with brine, dried over $Na_2SO_4$, filtered, and concentrated. The resulting residue was purified on a silica gel column eluted with 0-100% EtOAc in heptane to give Intermediate 102 as a solid (360 mg, 31%), MS ES+m/z 242 $[M+H]^+$.

Step 2: 1-[4-[5-(7-methoxy-2-methyl-pyrazolo[3,4-c]pyridin-4-yl)-3-pyridyl]phenyl]pyrrolidin-2-one 1-[4-[5-(4,4,5,5-tetramethyl-1,3,2-dioxaborolan-2-yl)-3-pyridyl]phenyl]pyrrolidin-2-one was prepared according to Example 85, replacing 5-bromo-3-iodo-pyrin-2-amine with 3,5-dibromopyridine. 1-[4-[5-(7-methoxy-2-methyl-pyrazolo[3,4-c]pyridin-4-yl)-3-pyridyl]phenyl]pyrrolidin-2-one was prepared according to Example 85, replacing 4-chloro-N-methyl-furo[2,3-b]pyridine-2-carboxamide for Intermediate 102, and replacing 1-[4-[2-amino-5-(4,4,5,5-tetramethyl-1,3,2-dioxaborolan-2-yl)-3-pyridyl]phenyl]pyrrolidin-2-one (Intermediate 90) with 1-[4-[5-(4,4,5,5-tetramethyl-1,3,2-dioxaborolan-2-yl)-3-pyridyl]phenyl]pyrrolidin-2-one. Purification on a silica gel column, eluted with 0-10% MeOH in DCM gave 1-[4-[5-(7-methoxy-2-methyl-pyrazolo[3,4-c]pyridin-4-yl)-3-pyridyl]phenyl]pyrrolidin-2-one as a solid (160 mg, 99%). A portion (40 mg) of the isolated 1-[4-[5-(7-methoxy-2-methyl-pyrazolo[3,4-c]pyridin-4-yl)-3-pyridyl]phenyl]pyrrolidin-2-one was further purified by preparative HPLC to yield 12 mg of solid. $^1$H NMR (500 MHz, DMSO-$d_6$) δ ppm 2.07-2.15 (m, 2H), 2.52-2.57 (m, 2H), 3.88-3.94 (m, 2H), 4.09 (s, 3H), 4.24 (s, 3H), 7.81-7.95 (m, 5H), 8.30 (t, J=2.21 Hz, 1H), 8.75 (s, 1H), 8.88 (d, J=1.89 Hz, 1H), 8.93 (d, J=2.21 Hz, 1H). MS ES+m/z 400 $[M+H]^+$.

Example 158: 1-methyl-4-(5-(4-(2-oxopyrrolidin-1-yl)phenyl)pyridin-3-yl)-1,6-dihydro-7H-pyrazolo[3,4-c]pyridin-7-one

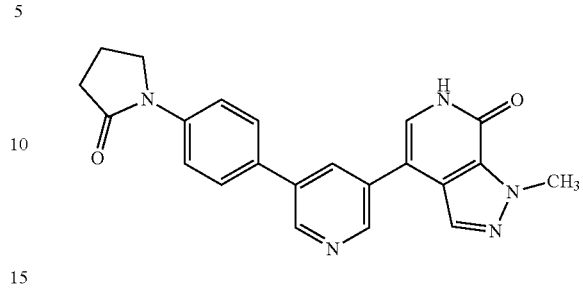

Step 1

1-(4-(5-(7-methoxy-1-methyl-1H-pyrazolo[3,4-c]pyridin-4-yl)pyridin-3-yl)phenyl)pyrrolidin-2-one was prepared according to Example 156.

Step 2

1-methyl-4-(5-(4-(2-oxopyrrolidin-1-yl)phenyl)pyridin-3-yl)-1,6-dihydro-7H-pyrazolo[3,4-c]pyridin-7-one was prepared in a similar manner as described in Example 74, replacing 1-(4-(5-(7-methoxy-1H-pyrazolo[3,4-c]pyridin-4-yl)pyridin-3-yl)phenyl)pyrrolidin-2-one with 1-(4-(5-(7-methoxy-1-methyl-1H-pyrazolo[3,4-c]pyridin-4-yl)pyridin-3-yl)phenyl)pyrrolidin-2-one. Purification on a silica gel column, eluted with 0-10% MeOH in DCM, gave 1-methyl-4-(5-(4-(2-oxopyrrolidin-1-yl)phenyl)pyridin-3-yl)-1,6-dihydro-7H-pyrazolo[3,4-c]pyridin-7-one as a solid (250 mg, 84%). $^1$H NMR (500 MHz, DMSO-$d_6$) δ ppm 2.06-2.14 (m, 2H), 2.52-2.56 (m, 2H), 3.91 (t, J=7.09 Hz, 2H), 4.33 (s, 3H), 7.36 (s, 1H), 7.80-7.90 (m, 4H), 8.09 (s, 1H), 8.20 (t, J=2.21 Hz, 1H), 8.79 (d, J=2.21 Hz, 1H), 8.87 (d, J=2.21 Hz, 1H), 11.68 (br s, 1H). MS ES+m/z 386 $[M+H]^+$.

Example 159: 2-methyl-4-(5-(4-(2-oxopyrrolidin-1-yl)phenyl)pyridin-3-yl)-2,6-dihydro-7H-pyrazolo[3,4-c]pyridin-7-one

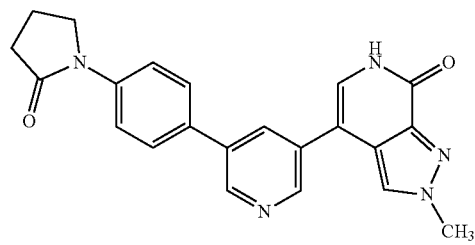 [SMILES: Cn1cc2c(-c3cncc(-c4ccc(N5CCCC5=O)cc4)c3)c[nH]c(=O)c2n1]

Step 1

1-(4-(5-(7-methoxy-2-methyl-2H-pyrazolo[3,4-c]pyridin-4-yl)pyridin-3-yl)phenyl)pyrrolidin-2-one was prepared according to Example 157.

Step 2

2-methyl-4-(5-(4-(2-oxopyrrolidin-1-yl)phenyl)pyridin-3-yl)-2,6-dihydro-7H-pyrazolo[3,4-c]pyridin-7-one was prepared in a similar manner as described in Example 74, replacing 1-(4-(5-(7-methoxy-1H-pyrazolo[3,4-c]pyridin-4-yl)pyridin-3-yl)phenyl)pyrrolidin-2-one with 1-(4-(5-(7-methoxy-2-methyl-2H-pyrazolo[3,4-c]pyridin-4-yl)pyridin-3-yl)phenyl)pyrrolidin-2-one. Purification on a silica gel column, eluted with 0-10% MeOH in DCM, gave 2-methyl-4-(5-(4-(2-oxopyrrolidin-1-yl)phenyl)pyridin-3-yl)-2,6-dihydro-7H-pyrazolo[3,4-c]pyridin-7-one as a solid (35 mg, 29%). $^1$H NMR (500 MHz, DMSO-$d_6$) δ ppm 2.07-2.14 (m, 2H), 2.52-2.57 (m, 2H), 3.91 (t, J=7.09 Hz, 2H), 4.13 (s, 3H), 7.26 (s, 1H), 7.81-7.90 (m, 4H), 8.20 (t, J=2.21 Hz, 1H), 8.48 (s, 1H), 8.78 (d, J=2.21 Hz, 1H), 8.86 (d, J=2.21 Hz, 1H), 11.25 (br s, 1H). MS ES+m/z 386 [M+H]$^+$.

Example 160: 2-(1-methyl-7-oxo-4-(5-(4-(2-oxopyrrolidin-1-yl)phenyl)pyridin-3-yl)-1,7-dihydro-6H-pyrazolo[3,4-c]pyridin-6-yl)acetonitrile

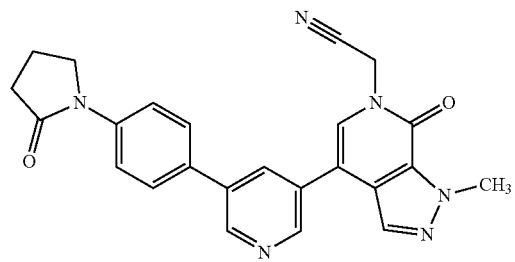 [SMILES: Cn1ncc2c(-c3cncc(-c4ccc(N5CCCC5=O)cc4)c3)cn(CC#N)c(=O)c21]

Step 1: 1-methyl-4-(5-(4-(2-oxopyrrolidin-1-yl)phenyl)pyridin-3-yl)-1,6-dihydro-7H-pyrazolo[3,4-c]pyridin-7-one 1-methyl-4-(5-(4-(2-oxopyrrolidin-1-yl)phenyl)pyridin-3-yl)-1,6-dihydro-7H-pyrazolo[3,4-c]pyridin-7-one was prepared according to Example 158.

Step 2: 2-(1-methyl-7-oxo-4-(5-(4-(2-oxopyrrolidin-1-yl)phenyl)pyridin-3-yl)-1,7-dihydro-6H-pyrazolo[3,4-c]pyridin-6-yl)acetonitrile A mixture of 1-methyl-4-(5-(4-(2-oxopyrrolidin-1-yl)phenyl)pyridin-3-yl)-1,6-dihydro-7H-pyrazolo[3,4-c]pyridin-7-one (300 mg, 0.78 mmol) and Cs$_2$CO$_3$ (507 mg, 1.56 mmol) in DMF (10 ml) was stirred at rt for 30 min. 2-Bromoacetonitrile (68 μl, 0.97 mmol) was added and the mixture was stirred at rt for 1 h. Water was added and the mixture was extracted with DCM (4×). The combined organics were dried over Na$_2$SO$_4$, filtered, concentrated and purified on a silica gel column eluted with 0-6% MeOH in DCM to give the product as a solid (170 mg, 52%). $^1$H NMR (500 MHz, DMSO-$d_6$) δ ppm 2.11 (quin, J=7.57 Hz, 2H), 2.52-2.57 (m, 2H), 3.91 (t, J=7.09 Hz, 2H), 4.33-4.37 (m, 3H), 5.17 (s, 2H), 7.81-7.90 (m, 5H), 8.19 (s, 1H), 8.25 (t, J=2.05 Hz, 1H), 8.82 (d, J=1.89 Hz, 1H), 8.94 (d, J=2.21 Hz, 1H). MS ES+m/z 425 [M+H]$^+$.

Example 161: isopropyl 4-(5-(4-(2-oxopyrrolidin-1-yl)phenyl)pyridin-3-yl)-1H-pyrrolo[2,3-b]pyridine-2-carboxylate

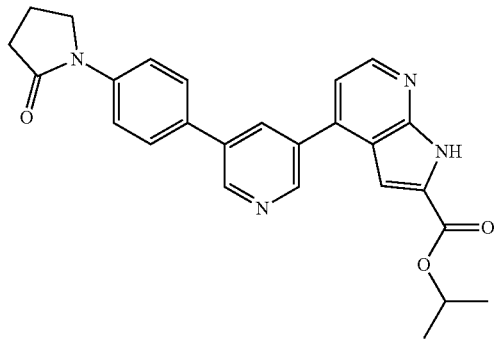 [SMILES: CC(C)OC(=O)c1cc2c(-c3cncc(-c4ccc(N5CCCC5=O)cc4)c3)ccnc2[nH]1]

Step 1: methyl 4-[5-[4-(2-oxopyrrolidin-1-yl)phenyl]-3-pyridyl]-1H-pyrrolo[2,3-b]pyridine-2-carboxylate

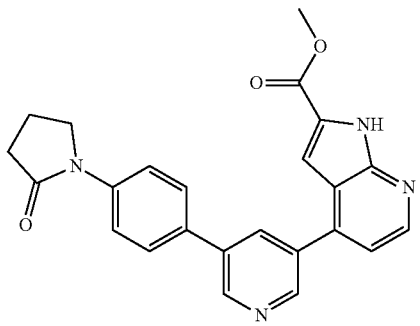 [SMILES: COC(=O)c1cc2c(-c3cncc(-c4ccc(N5CCCC5=O)cc4)c3)ccnc2[nH]1]

Methyl 4-[5-[4-(2-oxopyrrolidin-1-yl)phenyl]-3-pyridyl]-1H-pyrrolo[2,3-b]pyridine-2-carboxylate was prepared in a similar manner as compound methyl 4-(2'-amino-5-(dimethylcarbamoyl)-[2,3'-bipyridin]-5'-yl)-1H-pyrrolo[2,3-b]pyridine-2-carboxylate in Example 126, replacing 2'-amino-N,N-dimethyl-5'-(4,4,5,5-tetramethyl-1,3,2-dioxaborolan-2-yl)-[2,3'-bipyridine]-5-carboxamide for 1-[4-[5-(4,4,5,5-Tetramethyl-1,3,2-dioxaborolan-2-yl)-3-pyridyl]phenyl]pyrrolidin-2-one.

Step 2: isopropyl 4-(5-(4-(2-oxopyrrolidin-1-yl)phenyl)pyridin-3-yl)-1H-pyrrolo[2,3-b]pyridine-2-carboxylate To a solution of methyl 4-[5-[4-(2-oxopyrrolidin-1-yl)phenyl]-3-pyridyl]-1H-pyrrolo[2,3-b]pyridine-2-carboxylate (42 mg, 0.1 mmol) in 2-propanol (1 ml) was added NaH (60% in mineral oil, 5 mg, 0.12 mmol). The mixture was stirred at rt over the weekend. The reaction mixture was quenched by dropwise addition of water. The mixture filtered and purified by preparative HPLC to give isopropyl 4-(5-(4-(2-oxopyrrolidin-1-yl)phenyl)pyridin-3-yl)-1H-pyrrolo[2,3-b]pyridine-2-carboxylate as a solid (14 mg, 31%). $^1$H NMR (500 MHz, DMSO-$d_6$) δ ppm 1.33 (d, J=6.31 Hz, 6H), 2.06-2.13 (m, 2H), 2.52-2.56 (m, 2H), 3.91 (t, J=6.94 Hz, 2H), 5.12-5.19 (m, 1H), 7.19 (s, 1H), 7.40 (br d, J=4.41

Hz, 1H), 7.82-7.87 (m, 2H), 7.87-7.91 (m, 2H), 8.38 (t, J=2.21 Hz, 1H), 8.50 (d, J=4.73 Hz, 1H), 8.93 (d, J=2.21 Hz, 1H), 9.02 (d, J=2.21 Hz, 1H). MS ES+m/z 441 [M+H]+.

Example 162: ethyl 4-(5-(4-(2-oxopyrrolidin-1-yl)phenyl)pyridin-3-yl)-1H-pyrrolo[2,3-b]pyridine-2-carboxylate

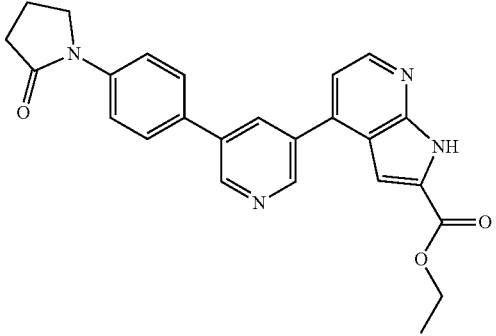 [SMILES: CCOC(=O)c1cc2c(-c3cncc(-c4ccc(N5CCCC5=O)cc4)c3)ccnc2[nH]1]

Step 1: methyl 4-[5-[4-(2-oxopyrrolidin-1-yl)phenyl]-3-pyridyl]-1H-pyrrolo[2,3-b]pyridine-2-carboxylate (not shown)

methyl 4-[5-[4-(2-oxopyrrolidin-1-yl)phenyl]-3-pyridyl]-1H-pyrrolo[2,3-b]pyridine-2-carboxylate was prepared according to Example 161.

Step 2: ethyl 4-(5-(4-(2-oxopyrrolidin-1-yl)phenyl)pyridin-3-yl)-1H-pyrrolo[2,3-b]pyridine-2-carboxylate ethyl 4-(5-(4-(2-oxopyrrolidin-1-yl)phenyl)pyridin-3-yl)-1H-pyrrolo[2,3-b]pyridine-2-carboxylate was prepared according to Example 161, replacing 2-propanol for ethanol to give ethyl 4-(5-(4-(2-oxopyrrolidin-1-yl)phenyl)pyridin-3-yl)-1H-pyrrolo[2,3-b]pyridine-2-carboxylate as a solid (4 mg, 7%). $^1$H NMR (500 MHz, DMSO-$d_6$) δ ppm 1.33 (t, J=7.09 Hz, 3H), 2.10 (t, J=7.57 Hz, 2H), 2.54 (t, J=8.04 Hz, 2H), 3.91 (t, J=7.09 Hz, 2H), 4.34 (d, J=6.94 Hz, 2H), 7.24 (s, 1H), 7.40-7.50 (m, 1H), 7.82-7.85 (m, 2H), 7.86-7.94 (m, 2H), 8.38 (t, J=2.21 Hz, 1H), 8.47-8.58 (m, 1H), 8.94 (d, J=2.21 Hz, 1H), 9.03 (d, J=2.21 Hz, 1H). MS ES+m/z 427 [M+H]+.

Example 163: 4-(5-(4-(2-oxopyrrolidin-1-yl)phenyl)pyridin-3-yl)-1H-pyrrolo[2,3-b]pyridine-2-carboxylic acid

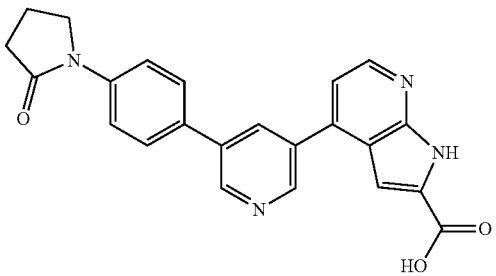 [SMILES: O=C(O)c1cc2c(-c3cncc(-c4ccc(N5CCCC5=O)cc4)c3)ccnc2[nH]1]

Step 1: methyl 4-[5-[4-(2-oxopyrrolidin-1-yl)phenyl]-3-pyridyl]-1H-pyrrolo[2,3-b]pyridine-2-carboxylate (not shown)

methyl 4-[5-[4-(2-oxopyrrolidin-1-yl)phenyl]-3-pyridyl]-1H-pyrrolo[2,3-b]pyridine-2-carboxylate was prepared according to Example 161.

Step 2: 4-(5-(4-(2-oxopyrrolidin-1-yl)phenyl)pyridin-3-yl)-1H-pyrrolo[2,3-b]pyridine-2-carboxylic acid To a solution of methyl 4-[5-[4-(2-oxopyrrolidin-1-yl)phenyl]-3-pyridyl]-1H-pyrrolo[2,3-b]pyridine-2-carboxylate (204 mg, 0.5 mmol) in MeOH:THF (1:1, 5 ml) was added a solution of LiOH H$_2$O (25 mg, 0.59 mmol) in H$_2$O (2 ml). The resulting mixture was refluxed for 3 h, cooled to rt, and concentrated. The crude product was purified by preparative HPLC to give 4-(5-(4-(2-oxopyrrolidin-1-yl)phenyl)pyridin-3-yl)-1H-pyrrolo[2,3-b]pyridine-2-carboxylic acid as a solid (51 mg, 26%). $^1$H NMR (500 MHz, DMSO-$d_6$) δ ppm 2.06-2.14 (m, 2H), 2.52-2.55 (m, 2H), 3.90 (t, J=7.09 Hz, 2H), 7.05 (s, 1H), 7.42 (d, J=4.73 Hz, 1H), 7.82-7.86 (m, 2H), 7.86-7.91 (m, 2H), 8.38 (t, J=2.21 Hz, 1H), 8.45 (d, J=4.73 Hz, 1H), 8.93 (d, J=1.89 Hz, 1H), 9.01 (d, J=2.21 Hz, 1H). MS ES+m/z 399 [M+H]+.

Example 164: 1-(4-(6-methyl-3,4'-bipyridin-5-yl)phenyl)pyrrolidin-2-one

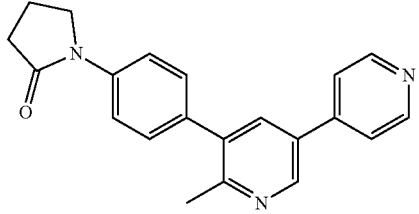 [SMILES: Cc1ncc(-c2ccncc2)cc1-c1ccc(N2CCCC2=O)cc1]

Step 1: Intermediate 93—1-(4-(4,4,5,5-tetramethyl-1,3,2-dioxaborolan-2-yl)phenyl)pyrrolidin-2-one Intermediate 93 was prepared according to Example 81, replacing 1-(4-bromo-3-methyl-phenyl)pyrrolidin-2-one with 1-(4-bromophenyl)pyrrolidin-2-one.

Step 2: 1-(4-(5-bromo-2-methylpyridin-3-yl)phenyl)pyrrolidin-2-one (not shown)

1-(4-(5-bromo-2-methylpyridin-3-yl)phenyl)pyrrolidin-2-one was prepared according to Example 81, replacing 1-[3-methyl-4-(4,4,5,5-tetramethyl-1,3,2-dioxaborolan-2-yl)phenyl]pyrrolidin-2-one with 1-(4-(4,4,5,5-tetramethyl-1,3,2-dioxaborolan-2-yl)phenyl)pyrrolidin-2-one, and replacing 3,5-dibromopyridine with 5-bromo-3-chloro-2-methylpyridine.

Step 3: 1-(4-(6-methyl-[3,4'-bipyridin]-5-yl)phenyl)pyrrolidin-2-one 1-(4-(6-methyl-[3,4'-bipyridin]-5-yl)phenyl)pyrrolidin-2-one was prepared according to Example 81, replacing 1-(4-(5-bromopyridin-3-yl)-3-methylphenyl)pyrrolidin-2-one for 1-(4-(5-bromo-2-methylpyridin-3-yl)phenyl)pyrrolidin-2- one, to give 1-(4-(6-methyl-[3,4'-bipyridin]-5-yl)phenyl) pyrrolidin-2-one as a solid (10 mg, 2%). ¹H NMR (500 MHz, METHANOL-d₄) δ ppm 2.16-2.23 (m, 2H), 2.31-2.35 (m, 3H), 2.59-2.65 (m, 2H), 3.93-3.99 (m, 2H), 7.28-7.34 (m, 1H), 7.55-7.60 (m, 1H), 7.61-7.65 (m, 1H), 7.80-7.86 (m, 2H), 8.17 (t, J=2.21 Hz, 1H), 8.60 (d, J=2.21 Hz, 1H), 8.63-8.69 (m, 2H), 8.92 (d, J=2.21 Hz, 1H). MS ES+m/z 330 [M+H]⁺.

Example 165: methyl 4-(5-(4-(2-oxopyrrolidin-1-yl) phenyl)pyridin-3-yl)furo[2,3-b]pyridine-2-carboxylate

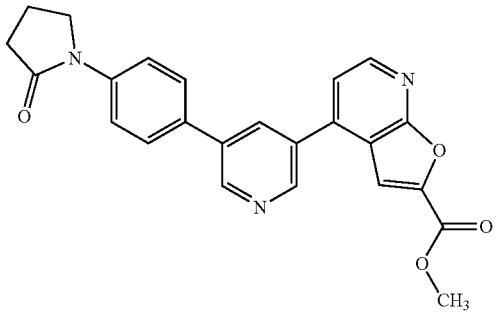 [SMILES: COC(=O)c1cc2c(-c3cncc(-c4ccc(N5CCCC5=O)cc4)c3)ccnc2o1]

Step 1: Intermediate 103—methyl 4-chlorofuro[2,3-b]pyridine-2-carboxylate

To a suspension of methyl 4-hydroxyfuro[2,3-b]pyridine-2-carboxylate (Intermediate 6; Example 14) (193 mg, 1 mmol) in CHCl₃ (10 ml) was added oxalyl chloride (0.42 ml, 5 mmol) and a few drops of DMF. The resulting mixture was stirred at 60° C. for 2 h. When cooled to rt the mixture was concentrated and chased with toluene. The resulting residue was dissolved in DCM, passed through a short plug of silica and concentrated to give Intermediate 103 as a solid (185 mg, 87%). MS ES+m/z 212 [M+H]⁺.

Step 2: methyl 4-(5-(4-(2-oxopyrrolidin-1-yl)phenyl)pyridin-3-yl)furo[2,3-b]pyridine-2-carboxylate 1-[4-[5-(4,4,5,5-tetramethyl-1,3,2-dioxaborolan-2-yl)-3-pyridyl]phenyl]pyrrolidin-2-one was prepared according to Example 85, replacing 5-bromo-3-iodo-pyrin-2-amine with 3,5-dibromopyridine. methyl 4-(5-(4-(2-oxopyrrolidin-1-yl) phenyl)pyridin-3-yl)furo[2,3-b]pyridine-2-carboxylate was prepared according to Example 85, replacing 1-[4-[2-amino-5-(4,4,5,5-tetramethyl-1,3,2-dioxaborolan-2-yl)-3-pyridyl] phenyl]pyrrolidin-2-one (Intermediate 90) with 1-[4-[5-(4, 4,5,5-tetramethyl-1,3,2-dioxaborolan-2-yl)-3-pyridyl] phenyl]pyrrolidin-2-one, and replacing K₂CO₃ for TEA, to give methyl 4-(5-(4-(2-oxopyrrolidin-1-yl)phenyl)pyridin-3-yl)furo[2,3-b]pyridine-2-carboxylate as a solid (12 mg, 17%). ¹H NMR (500 MHz, DMSO-d₆) δ ppm 2.11 (quin, J=7.57 Hz, 2H), 2.53-2.57 (m, 2H), 3.90-3.95 (m, 5H), 7.82-7.88 (m, 3H), 7.92 (d, J=7.69 Hz, 2H), 8.02 (s, 1H), 8.45 (t, J=2.21 Hz, 1H), 8.67 (d, J=5.04 Hz, 1H), 8.98 (d, J=1.89 Hz, 1H), 9.08 (d, J=2.21 Hz, 1H). MS ES+m/z 414 [M+H]⁺.

Example 166: N-(oxetan-3-yl)-4-(5-(4-(2-oxopyrrolidin-1-yl)phenyl)pyridin-3-yl)furo[2,3-b]pyridine-2-carboxamide

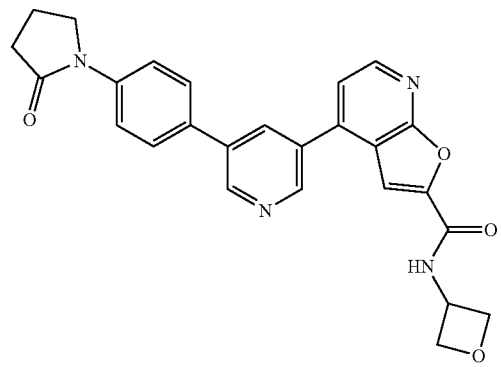 [SMILES: O=C(NC1COC1)c1cc2c(-c3cncc(-c4ccc(N5CCCC5=O)cc4)c3)ccnc2o1]

Step 1: Intermediate 104—4-chloro-N-(oxetan-3-yl) furo[2,3-b]pyridine-2-carboxamide Intermediate 104 was prepared according to Example 14, replacing methylamine for oxetan-3-amine to give Intermediate 104 as a solid (27 mg, 66%). MS ES+m/z 253 [M+H]⁺.

Step 2: N-(oxetan-3-yl)-4-(5-(4-(2-oxopyrrolidin-1-yl)phenyl)pyridin-3-yl)furo[2,3-b]pyridine-2-carboxamide 1-[4-[5-(4,4,5,5-tetramethyl-1,3,2-dioxaborolan-2-yl)-3-pyridyl]phenyl]pyrrolidin-2-one was prepared according to Example 85, replacing 5-bromo-3-iodo-pyrin-2-amine with 3,5-dibromopyridine. N-(oxetan-3-yl)-4-(5-(4-(2-oxopyrrolidin-1-yl)phenyl)pyridin-3-yl)furo[2,3-b]pyridine-2-carboxamide was prepared according to Example 85, replacing 1-[4-[2-amino-5-(4,4,5,5-tetramethyl-1,3,2-dioxaborolan-2-yl)-3-pyridyl]phenyl]pyrrolidin-2-one (Intermediate 90) with 1-[4-[5-(4,4,5,5-tetramethyl-1,3,2-dioxaborolan-2-yl)-3-pyridyl]phenyl]pyrrolidin-2-one, and replacing 4-chloro-N-methyl-furo[2,3-b]pyridine-2-carboxamide (Intermediate 7) with Intermediate 104, to give N-(oxetan-3-yl)-4-(5-(4-(2-oxopyrrolidin-1-yl)phenyl)pyridin-3-yl)furo[2,3-b]pyridine-2-carboxamide as a solid (16 mg, 35%). ¹H NMR (500 MHz, DMSO-d₆) δ ppm 2.05-2.17 (m, 2H), 2.52-2.57 (m, 2H), 3.91 (t, J=7.09 Hz, 2H), 4.64 (t, J=6.62 Hz, 2H), 4.78 (dd, J=7.57, 6.62 Hz, 2H), 5.01-5.09 (m, 1H), 7.82-7.84 (m, 2H), 7.85 (s, 1H), 7.92 (d, J=0.95 Hz, 2H), 7.93 (s, 1H), 8.46 (s, 1H), 8.60 (d, J=5.04 Hz, 1H), 8.97 (d, J=2.21 Hz, 1H), 9.08 (d, J=2.21 Hz, 1H), 9.56 (br s, 1H). MS ES+m/z 455 [M+H]⁺.

Example 167: isopropyl 4-(5-(4-(2-oxopyrrolidin-1-yl)phenyl)pyridin-3-yl)furo[2,3-b]pyridine-2-carboxylate

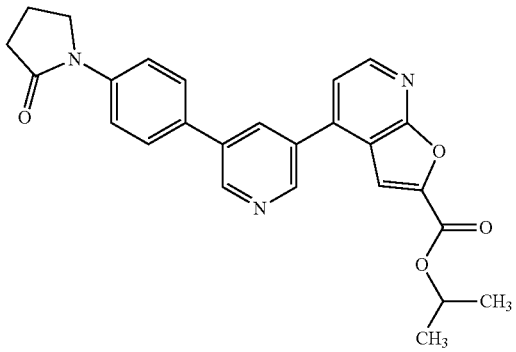 [SMILES: CC(C)OC(=O)c1cc2c(-c3cncc(-c4ccc(N5CCCC5=O)cc4)c3)ccnc2o1]

Step 1a: Intermediate 105—4-hydroxyfuro[2,3-b]pyridine-2-carboxylic acid

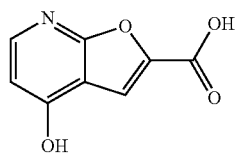 [SMILES: O=C(O)c1cc2c(O)ccnc2o1]

To a mixture of methyl 4-hydroxyfuro[2,3-b]pyridine-2-carboxylate (2 g, 10.4 mmol) in MeOH (40 ml) and THF (40 ml) was added a solution of LiOH H$_2$O (0.891 g, 21.2 mmol) in water (40 ml) and the resulting mixture was stirred at 60° C. overnight. The mixture was cooled to rt, concentrated, and the resulting aqueous residue was neutralized using 2M aq. HCl. The precipitate was filtered, washed with water, washed with pentane, and dried to give 4-hydroxyfuro[2,3-b]pyridine-2-carboxylic acid (Intermediate 105; not shown) as a solid (1.76 g, 95%). MS ES+m/z 180 [M+H]$^+$.

Step 1b: Intermediate 106—Isopropyl 4-hydroxyfuro[2,3-b]pyridine-2-carboxylate

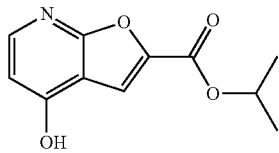 [SMILES: CC(C)OC(=O)c1cc2c(O)ccnc2o1]

To a solution of 4-hydroxyfuro[2,3-b]pyridine-2-carboxylic acid (Intermediate 105; not shown) (179 mg, 1 mmol) in CHCl$_3$ (10 ml) was added oxalyl chloride (0.846 ml, 10 mmol) and a few drops of DMF. The reaction was stirred at rt over the weekend, and then concentrated, and redissolved in DCM. The resulting solution was slowly added to a cooled solution of 2-propanol (10 ml) and TEA (2.5 ml). The ice bath was removed and the mixture was stirred at rt for 1 h. The reaction was quenched with sat. aq. NaHCO$_3$ and the resulting mixture was extracted with EtOAc (3×). The combined organics were washed with brine, dried over Na$_2$SO$_4$, filtered, concentrated and purified on a silica gel column eluted with 0-50% EtOAc in heptane to give Intermediate 106 as a solid (125 mg, 52%). MS ES+m/z 240 [M+H]$^+$.

Step 2: isopropyl 4-(5-(4-(2-oxopyrrolidin-1-yl)phenyl)pyridin-3-yl)furo[2,3-b]pyridine-2-carboxylate

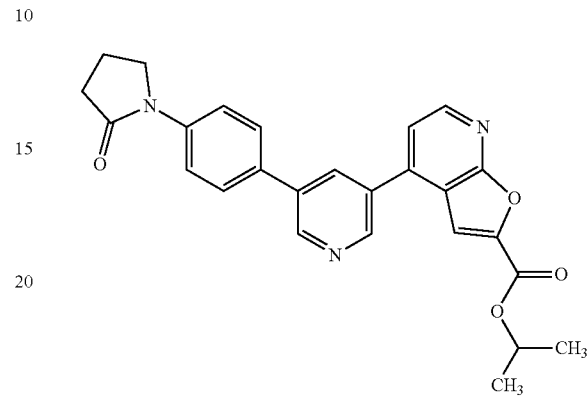

1-[4-[5-(4,4,5,5-tetramethyl-1,3,2-dioxaborolan-2-yl)-3-pyridyl]phenyl]pyrrolidin-2-one was prepared according to Example 85, replacing 5-bromo-3-iodo-pyrin-2-amine with 3,5-dibromopyridine. isopropyl 4-(5-(4-(2-oxopyrrolidin-1-yl)phenyl)pyridin-3-yl)furo[2,3-b]pyridine-2-carboxylate was prepared according to Example 85, replacing 1-[4-[2-amino-5-(4,4,5,5-tetramethyl-1,3,2-dioxaborolan-2-yl)-3-pyridyl]phenyl]pyrrolidin-2-one (Intermediate 90) with 1-[4-[5-(4,4,5,5-tetramethyl-1,3,2-dioxaborolan-2-yl)-3-pyridyl]phenyl]pyrrolidin-2-one, and replacing 4-chloro-N-methyl-furo[2,3-b]pyridine-2-carboxamide (Intermediate 7) with Intermediate 106, to give isopropyl 4-(5-(4-(2-oxopyrrolidin-1-yl)phenyl)pyridin-3-yl)furo[2,3-b]pyridine-2-carboxylate as a solid (58 mg, 53%). $^1$H NMR (500 MHz, DMSO-d$_6$) δ ppm 1.37 (d, J=6.31 Hz, 6H), 2.11 (quin, J=7.57 Hz, 2H), 2.53-2.57 (m, 2H), 3.91 (t, J=7.09 Hz, 2H), 5.22 (spt, J=6.25 Hz, 1H), 7.83-7.87 (m, 3H), 7.90-7.96 (m, 3H), 8.45 (t, J=2.21 Hz, 1H), 8.66 (d, J=5.04 Hz, 1H), 8.97 (d, J=2.21 Hz, 1H), 9.08 (d, J=2.21 Hz, 1H). MS ES+m/z 442 [M+H]$^+$.

Example 168: 1-(4-(5-(5-(2-hydroxypropan-2-yl)-1-methyl-1H-pyrrolo[2,3-b]pyridin-3-yl)pyridin-3-yl)-3-methylphenyl)pyrrolidin-2-one

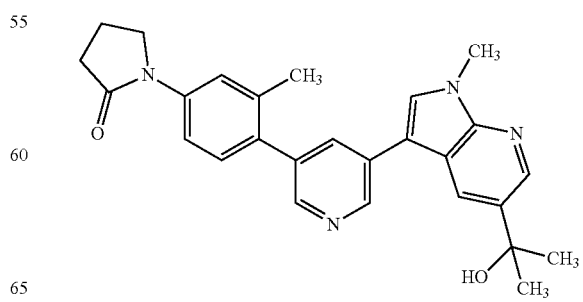

Step 1a: Intermediate 108—1-(3-methyl-4-(5-(4,4,5,5-tetramethyl-1,3,2-dioxaborolan-2-yl)pyridin-3-yl)phenyl)pyrrolidin-2-one 1-[4-(5-bromo-3-pyridyl)-3-methyl-phenyl]pyrrolidin-2-one (Intermediate 107; not shown) was prepared according to Example 85, replacing (4-(2-oxopyrrolidin-1-yl)phenyl) boronic acid with (2-methyl-4-(2-oxopyrrolidin-1-yl)phenyl)boronic acid, replacing 5-bromo-3-iodo-pyridin-2-amine with 3,5-dibromopyridine, and replacing n-BuOH for 1,4-dioxane. Intermediate 107 was obtained as a solid (662 mg, 38%). MS ES+m/z 331 [M+H]$^+$.

Step 1b: Intermediate 108—1-(3-methyl-4-(5-(4,4,5,5-tetramethyl-1,3,2-dioxaborolan-2-yl)pyridin-3-yl)phenyl)pyrrolidin-2-one Intermediate 108 was prepared according to Example 85, replacing 1-[4-(2-amino-5-bromo-3-pyridyl)phenyl]pyrrolidin-2-one with 1-[4-(5-bromo-3-pyridyl)-3-methyl-phenyl]pyrrolidin-2-one (Intermediate 107; not shown), and replacing DMSO for toluene. Intermediate 108 was obtained as a solid (297 mg, 39%). MS ES+m/z 379 [M+H]$^+$.

Step 2

Intermediate 99 was prepared in Example 156.

Step 3: 1-(4-(5-(5-(2-hydroxypropan-2-yl)-1-methyl-1H-pyrrolo[2,3-b]pyridin-3-yl)pyridin-3-yl)-3-methylphenyl)pyrrolidin-2-one 1-(4-(5-(5-(2-hydroxypropan-2-yl)-1-methyl-1H-pyrrolo[2,3-b]pyridin-3-yl)pyridin-3-yl)-3-methylphenyl)pyrrolidin-2-one was prepared according to Example 85, replacing 1-[3-methyl-4-[5-(4,4,5,5-tetramethyl-1,3,2-dioxaborolan-2-yl)-3-pyridyl]phenyl]pyrrolidin-2-one and 4-chloro-N-methyl-furo[2,3-b]pyridine-2-carboxamide for Intermediate 99, and replacing 1-[4-[2-amino-5-(4,4,5,5-tetramethyl-1,3,2-dioxaborolan-2-yl)-3-pyridyl]phenyl]pyrrolidin-2-one (Intermediate 90) with Intermediate 108. 1-(4-(5-(5-(2-hydroxypropan-2-yl)-1-methyl-1H-pyrrolo[2,3-b]pyridin-3-yl)pyridin-3-yl)-3-methylphenyl)pyrrolidin-2-one was obtained as a solid (5 mg, 13%). $^1$H NMR (500 MHz, DMSO-d$_6$) δ ppm 1.54 (s, 6H), 2.06-2.13 (m, 2H), 2.36 (s, 3H), 2.52-2.54 (m, 2H), 3.88 (s, 3H), 3.88-3.90 (m, 2H), 5.21 (s, 1H), 7.34-7.39 (m, 1H), 7.63-7.66 (m, 2H), 8.02 (t, J=2.21 Hz, 1H), 8.11 (s, 1H), 8.36 (d, J=2.21 Hz, 1H), 8.44 (d, J=2.21 Hz, 1H), 8.48 (d, J=1.89 Hz, 1H), 8.94 (d, J=2.21 Hz, 1H). MS ES+m/z 441 [M+H]$^+$.

Example 169: N,N-dimethyl-4-(5-(2-methyl-4-(2-oxopyrrolidin-1-yl)phenyl)pyridin-3-yl)-1H-pyrrolo[2,3-b]pyridine-2-carboxamide

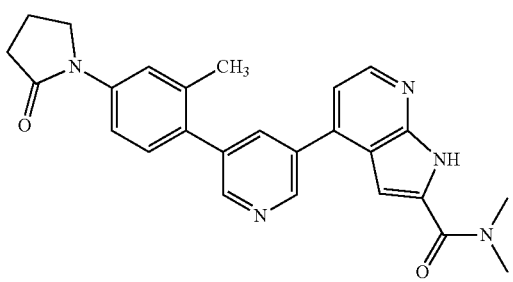 [SMILES: Cc1cc(N2CCCC2=O)ccc1-c1cncc(-c2ccnc3[nH]c(C(=O)N(C)C)cc23)c1]

Step 1: Intermediate 107—4-chloro-N,N-dimethyl-1H-pyrrolo[2,3-b]pyridine-2-carboxamide Intermediate 107 was prepared according to Example 13, replacing methylamine with dimethylamine, and replacing methyl 4-chloro-1H-pyrrolo[2,3-b]pyridine-2-carboxylate with methyl 4-chloro-1H-pyrrolo[2,3-b]pyridine-2-carboxylate.

Step 2: N,N-dimethyl-4-(5-(2-methyl-4-(2-oxopyrrolidin-1-yl)phenyl)pyridin-3-yl)-1H-pyrrolo[2,3-b]pyridine-2-carboxamide N,N-dimethyl-4-(5-(2-methyl-4-(2-oxopyrrolidin-1-yl)phenyl)pyridin-3-yl)-1H-pyrrolo[2,3-b]pyridine-2-carboxamide was prepared according to Example 85, replacing Intermediate 90 with Intermediate 108, and replacing 4-chloro-N-methyl-furo[2,3-b]pyridine-2-carboxamide (Intermediate 7) with Intermediate 106. N,N-dimethyl-4-(5-(2-methyl-4-(2-oxopyrrolidin-1-yl)phenyl)pyridin-3-yl)-1H-pyrrolo[2,3-b]pyridine-2-carboxamide was obtained as a solid (21 mg, 26%). $^1$H NMR (500 MHz, DMSO-d$_6$) δ ppm 2.09 (quin, J=7.57 Hz, 2H), 2.37 (s, 3H), 2.51-2.54 (m, 2H), 3.05-3.20 (m, 6H), 3.88 (t, J=7.09 Hz, 2H), 6.93 (s, 1H), 7.37 (d, J=4.73 Hz, 1H), 7.41 (d, J=8.51 Hz, 1H), 7.60-7.67 (m, 2H), 8.14 (t, J=2.21 Hz, 1H), 8.43 (d, J=4.73 Hz, 1H), 8.68 (d, J=1.89 Hz, 1H), 8.97 (d, J=2.21 Hz, 1H). MS ES+m/z 440 [M+H]$^+$.

Example 170: N-methyl-4-(5-(2-methyl-4-(2-oxopyrrolidin-1-yl)phenyl)pyridin-3-yl)furo[2,3-b]pyridine-2-carboxamide

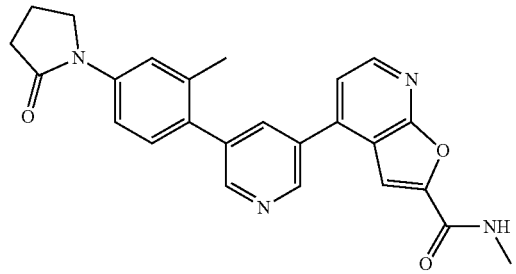 [SMILES: CNC(=O)c1cc2c(-c3cncc(-c4ccc(N5CCCC5=O)cc4C)c3)ccnc2o1]

Step 1

Intermediate 7 was prepared in Example 14.

Step 2: N-methyl-4-(5-(2-methyl-4-(2-oxopyrrolidin-1-yl)phenyl)pyridin-3-yl)furo[2,3-b]pyridine-2-carboxamide N-methyl-4-(5-(2-methyl-4-(2-oxopyrrolidin-1-yl)phenyl)pyridin-3-yl)furo[2,3-b]pyridine-2-carboxamide was prepared according to Example 85, replacing Intermediate 90 with Intermediate 108. N-methyl-4-(5-(2-methyl-4-(2-oxopyrrolidin-1-yl)phenyl)pyridin-3-yl)furo[2,3-b]pyridine-2-carboxamide was obtained as a solid (6 mg, 7%). $^1$H NMR (500 MHz, DMSO-d$_6$) δ ppm 2.09 (quin, J=7.57 Hz, 2H), 2.35 (s, 3H), 2.51-2.54 (m, 2H), 2.82 (d, J=4.41 Hz, 3H), 3.89 (t, J=7.09 Hz, 2H), 7.42 (d, J=7.88 Hz, 1H), 7.64-7.67 (m, 2H), 7.75 (s, 1H), 7.77 (d, J=5.04 Hz, 1H), 8.19 (t, J=2.21 Hz, 1H), 8.56 (d, J=5.04 Hz, 1H), 8.74 (d, J=2.21 Hz, 1H), 8.86 (br d, J=4.41 Hz, 1H), 9.00 (d, J=2.21 Hz, 1H). MS ES+m/z 427 [M+H]$^+$.

Example 171: methyl 4-(5-(2-methyl-4-(2-oxopyrrolidin-1-yl)phenyl)pyridin-3-yl)-1H-pyrrolo[2,3-b]pyridine-2-carboxylate

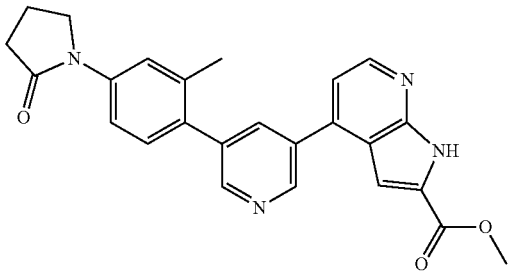 [SMILES: COC(=O)c1cc2c(-c3cncc(-c4ccc(N5CCCC5=O)cc4C)c3)ccnc2[nH]1]

Step 1

Intermediate 5 was prepared in Example 128.

Step 2: methyl 4-(5-(2-methyl-4-(2-oxopyrrolidin-1-yl)phenyl)pyridin-3-yl)-1H-pyrrolo[2,3-b]pyridine-2-carboxylate methyl 4-(5-(2-methyl-4-(2-oxopyrrolidin-1-yl)phenyl)pyridin-3-yl)-1H-pyrrolo[2,3-b]pyridine-2-carboxylate was prepared according to Example 85, replacing Intermediate 90 with Intermediate 108. methyl 4-(5-(2-methyl-4-(2-oxopyrrolidin-1-yl)phenyl)pyridin-3-yl)-1H-pyrrolo[2,3-b]pyridine-2-carboxylate was obtained as a solid (51 mg, 45%). $^1$H NMR (500 MHz, DMSO-$d_6$) δ ppm 2.09 (d, J=7.88 Hz, 2H), 2.36 (s, 3H), 2.52-2.55 (m, 2H), 3.85-3.92 (m, 5H), 7.27 (s, 1H), 7.40 (d, J=9.14 Hz, 1H), 7.45 (d, J=4.73 Hz, 1H), 7.65 (s, 2H), 8.13 (t, J=2.05 Hz, 1H), 8.54 (d, J=4.73 Hz, 1H), 8.71 (d, J=2.21 Hz, 1H), 8.97 (d, J=2.21 Hz, 1H), 12.68-12.91 (m, 1H). MS ES+m/z 427 [M+H]$^+$.

Example 172: 1-(4-(5-(5-(2-hydroxypropan-2-yl)-1-methyl-1H-pyrrolo[2,3-b]pyridin-3-yl)-4-methylpyridin-3-yl)phenyl)pyrrolidin-2-one

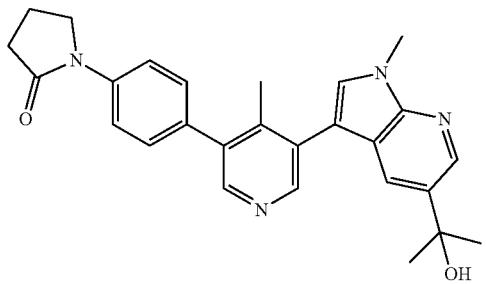 [SMILES: Cc1c(-c2ccc(N3CCCC3=O)cc2)cncc1-c1cn(C)c2ncc(C(C)(C)O)cc12]

Step 1

Intermediate 99 was prepared in Example 156.

Step 2: Intermediate 110—1-(4-(4-methyl-5-(4,4,5,5-tetramethyl-1,3,2-dioxaborolan-2-yl)pyridin-3-yl)phenyl)pyrrolidin-2-one Intermediate 110 was prepared according to Example 85. (4-(2-oxopyrrolidin-1-yl)phenyl)boronic acid was replaced with 1-[4-(4,4,5,5-tetramethyl-1,3,2-dioxaborolan-2-yl)phenyl]pyrrolidin-2-one to afford 1-[4-(5-Bromo-4-methyl-3-pyridyl)phenyl]pyrrolidin-2-one (Intermediate 109; not shown) as a solid (789 mg, quant.). MS ES+m/z 331 [M+H]$^+$. Further, 5-bromo-3-iodo-pyridin-2-amine was replaced with 3,5-dibromo-4-methyl-pyridine. Intermediate 110 was obtained as a solid (741 mg, 86%). MS ES+m/z 379 [M+H]$^+$.

Step 3: 1-(4-(5-(5-(2-hydroxypropan-2-yl)-1-methyl-1H-pyrrolo[2,3-b]pyridin-3-yl)-4-methylpyridin-3-yl)phenyl)pyrrolidin-2-one 1-(4-(5-(5-(2-hydroxypropan-2-yl)-1-methyl-1H-pyrrolo[2,3-b]pyridin-3-yl)-4-methylpyridin-3-yl)phenyl)pyrrolidin-2-one was prepared according to Example 85, replacing Intermediate 90 for Intermediate 110, and replacing 4-chloro-N-methyl-furo[2,3-b]pyridine-2-carboxamide (Intermediate 7) with Intermediate 99. 1-(4-(5-(5-(2-hydroxypropan-2-yl)-1-methyl-1H-pyrrolo[2,3-b]pyridin-3-yl)-4-methylpyridin-3-yl)phenyl)pyrrolidin-2-one was obtained as a solid (2 mg, 6%). $^1$H NMR (500 MHz, DMSO-$d_6$) δ ppm 1.51 (s, 6H), 2.05-2.14 (m, 2H), 2.22 (s, 3H), 2.53 (d, J=8.20 Hz, 2H), 3.89 (s, 3H), 3.90 (s, 2H), 5.11-5.16 (m, 1H), 7.50 (d, J=8.51 Hz, 2H), 7.73 (s, 1H), 7.80 (d, J=8.83 Hz, 2H), 7.95 (d, J=1.89 Hz, 1H), 8.35 (s, 1H), 8.48 (d, J=2.21 Hz, 1H), 8.51 (s, 1H). MS ES+m/z 441 [M+H]$^+$.

Example 173: N,N-dimethyl-4-(4-methyl-5-(4-(2-oxopyrrolidin-1-yl)phenyl)pyridin-3-yl)-1H-pyrrolo[2,3-b]pyridine-2-carboxamide

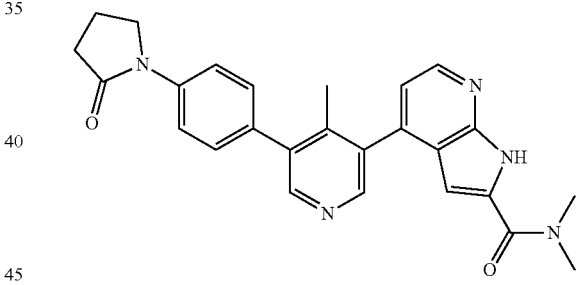

Step 1: Preparation of Intermediate 107

Intermediate 107 was prepared in Example 171.

Step 2: Preparation of Intermediate 110

Intermediate 110 was prepared in Example 174.

Step 3: N,N-dimethyl-4-(4-methyl-5-(4-(2-oxopyrrolidin-1-yl)phenyl)pyridin-3-yl)-1H-pyrrolo[2,3-b]pyridine-2-carboxamide N,N-dimethyl-4-(4-methyl-5-(4-(2-oxopyrrolidin-1-yl)phenyl)pyridin-3-yl)-1H-pyrrolo[2,3-b]pyridine-2-carboxamide was prepared according to Example 85, replacing Intermediate 90 for Intermediate 110, and replacing 4-chloro-N-methyl-furo[2,3-b]pyridine-2-carboxamide (Intermediate 7) with Intermediate 107. N,N-dimethyl-4-(4-methyl-5-(4-(2-oxopyrrolidin-1-yl)phenyl)pyridin-3-yl)-1H-pyrrolo[2,3-b]pyridine-2-carboxamide was obtained as a solid (5 mg, 7%). ¹H NMR (500 MHz, DMSO-d₆) δ ppm 2.09 (s, 5H), 2.52-2.55 (m, 2H), 2.94-3.11 (br s, 3H), 3.11-3.24 (br s, 3H), 3.87-3.93 (m, 2H), 6.61 (s, 1H), 7.15 (d, J=5.04 Hz, 1H), 7.52-7.56 (m, 2H), 7.79-7.84 (m, 2H), 8.43 (d, J=5.04 Hz, 1H), 8.48 (d, J=1.58 Hz, 2H), 12.19-12.39 (m, 1H). MS ES+m/z 440 [M+H]⁺.

Example 174: N-methyl-4-(4-methyl-5-(4-(2-oxopyrrolidin-1-yl)phenyl)pyridin-3-yl)furo[2,3-b]pyridine-2-carboxamide

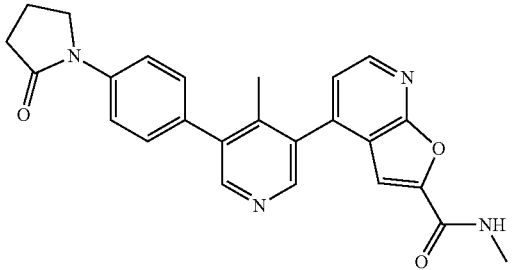 [SMILES: CNC(=O)c1cc2c(-c3cncc(-c4ccc(N5CCCC5=O)cc4)c3C)ccnc2o1]

Step 1: Preparation of Intermediate 7

Intermediate 7 was prepared in Example 14.

Step 2: Preparation of Intermediate 110

Intermediate 110 was prepared in Example 172.

Step 3: N-methyl-4-(4-methyl-5-(4-(2-oxopyrrolidin-1-yl)phenyl)pyridin-3-yl)furo[2,3-b]pyridine-2-carboxamide N-methyl-4-(4-methyl-5-(4-(2-oxopyrrolidin-1-yl)phenyl)pyridin-3-yl)furo[2,3-b]pyridine-2-carboxamide was prepared according to Example 85, replacing Intermediate 90 for Intermediate 110. N-methyl-4-(4-methyl-5-(4-(2-oxopyrrolidin-1-yl)phenyl)pyridin-3-yl)furo[2,3-b]pyridine-2-carboxamide was obtained as a solid (11 mg, 16%). ¹H NMR (500 MHz, DMSO-d₆) δ ppm 2.06-2.15 (m, 5H), 2.53 (t, J=8.04 Hz, 2H), 2.81 (d, J=4.73 Hz, 3H), 3.91 (t, J=7.09 Hz, 2H), 7.46 (s, 1H), 7.53 (d, J=5.04 Hz, 1H), 7.54 (d, J=8.51 Hz, 2H), 7.79-7.83 (m, 2H), 8.50 (s, 1H), 8.52 (s, 1H), 8.57 (d, J=5.04 Hz, 1H), 8.81 (q, J=4.62 Hz, 1H). MS ES+m/z 427 [M+H]⁺.

Example 175: methyl 4-(4-methyl-5-(4-(2-oxopyrrolidin-1-yl)phenyl)pyridin-3-yl)-1H-pyrrolo[2,3-b]pyridine-2-carboxylate

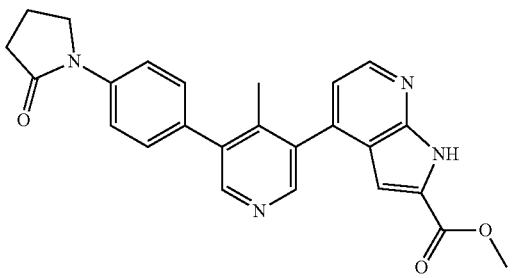 [SMILES: COC(=O)c1cc2c(-c3cncc(-c4ccc(N5CCCC5=O)cc4)c3C)ccnc2[nH]1]

Step 1: Preparation of Intermediate 5

Intermediate 5 was prepared in Example 128.

Step 2: Preparation of Intermediate 110

Intermediate 110 was prepared in Example 174.

Step 3: methyl 4-(4-methyl-5-(4-(2-oxopyrrolidin-1-yl)phenyl)pyridin-3-yl)-1H-pyrrolo[2,3-b]pyridine-2-carboxylate methyl 4-(4-methyl-5-(4-(2-oxopyrrolidin-1-yl)phenyl)pyridin-3-yl)-1H-pyrrolo[2,3-b]pyridine-2-carboxylate was prepared according to Example 85, replacing Intermediate 90 for Intermediate 110, and replacing Intermediate 7 for Intermediate 5. methyl 4-(4-methyl-5-(4-(2-oxopyrrolidin-1-yl)phenyl)pyridin-3-yl)-1H-pyrrolo[2,3-b]pyridine-2-carboxylate was obtained as a solid (64 mg, 37%). ¹H NMR (500 MHz, DMSO-d₆) δ ppm 2.08 (s, 3H), 2.08-2.13 (m, 2H), 2.51-2.55 (m, 2H), 3.86 (s, 3H), 3.88-3.92 (m, 2H), 6.95 (s, 1H), 7.22 (d, J=4.73 Hz, 1H), 7.54 (d, J=8.83 Hz, 2H), 7.80 (d, J=8.83 Hz, 2H), 8.46 (s, 1H), 8.47-8.50 (m, 1H), 8.50-8.56 (m, 1H), 12.75 (br s, 1H). MS ES+m/z 427 [M+H]⁺.

Example 176: 1-(4-(5-(1-methyl-3-(pyrimidin-5-yl)-1H-pyrrolo[2,3-b]pyridin-5-yl)pyridin-3-yl)phenyl)pyrrolidin-2-one

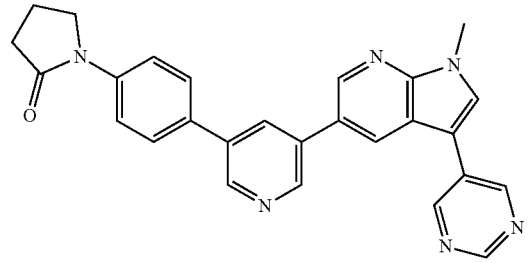 [SMILES: Cn1cc(-c2cncnc2)c2cc(-c3cncc(-c4ccc(N5CCCC5=O)cc4)c3)cnc21]

Step 1: Preparation of Intermediate 112

Step 1a: Intermediate 111—3-bromo-5-chloro-1-methyl-1H-pyrrolo[2,3-b]pyridine

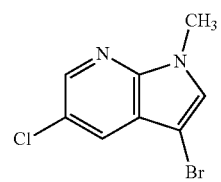

To a solution of 3-bromo-5-chloro-1H-pyrrolo[2,3-b]pyridine (463 mg, 2 mmol) in DMF (10 ml) was added Cs₂CO₃ (1.3 g, 4 mmol) and the suspension was stirred at rt for 1 h. Iodomethane (0.156 ml, 2.5 mmol) was added and the mixture was stirred at rt overnight. The reaction was added to water and extracted with EtOAc (3×). The combined organics were washed with brine (2×), dried over Na₂SO₄, filtered, and concentrated to give 3-bromo-5- chloro-1-methyl-pyrrolo[2,3-b]pyridine as a solid (480 mg, 98%). MS ES+m/z 245 [M+H]+.

Step 1b: Intermediate 112—5-chloro-1-methyl-3-pyrimidin-5-yl-pyrrolo[2,3-b]pyridine Intermediate 111 (246 mg, 1 mmol), pyrimidine-5-boronic acid (124 mg, 1 mmol), K₂CO₃ (276 mg, 2 mmol), PdCl₂(PPh₃)₂ (37 mg, 0.05 mmol) were taken up in 1,4-dioxane (4 ml) and water (1 ml) and the resulting mixture was stirred at 80° C. for 3 h. The mixture was cooled to rt, brine was added, and the mixture extracted with DCM (3×). The combined organics were washed with brine, dried over Na₂SO₄, filtered, concentrated, and purified on a silica gel column eluted with 0-6% MeOH in DCM to give Intermediate 112 as a solid (190 mg, 54%). MS ES+m/z 245 [M+H]+.

Step 2: 1-[4-[5-(4,4,5,5-tetramethyl-1,3,2-dioxaborolan-2-yl)-3-pyridyl]phenyl]pyrrolidin-2-one 1-[4-[5-(4,4,5,5-tetramethyl-1,3,2-dioxaborolan-2-yl)-3-pyridyl]phenyl]pyrrolidin-2-one was prepared according to Example 85, replacing 5-bromo-3-iodo-pyrin-2-amine with 3,5-dibromopyridine.

Step 3: 1-(4-(5-(1-methyl-3-(pyrimidin-5-yl)-1H-pyrrolo[2,3-b]pyridin-5-yl)pyridin-3-yl)phenyl)pyrrolidin-2-one 1-(4-(5-(1-methyl-3-(pyrimidin-5-yl)-1H-pyrrolo[2,3-b]pyridin-5-yl)pyridin-3-yl)phenyl)pyrrolidin-2-one was prepared according to Example 85, replacing Intermediate 90 for 1-[4-[5-(4,4,5,5-tetramethyl-1,3,2-dioxaborolan-2-yl)-3-pyridyl]phenyl]pyrrolidin-2-one, and replacing Intermediate 7 for Intermediate 112. 1-(4-(5-(1-methyl-3-(pyrimidin-5-yl)-1H-pyrrolo[2,3-b]pyridin-5-yl)pyridin-3-yl)phenyl)pyrrolidin-2-one was obtained as a solid (12 mg, 7%). ¹H NMR (500 MHz, DMSO-d₆) δ ppm 2.11 (quin, J=7.57 Hz, 2H), 2.53-2.57 (m, 2H), 3.89-3.94 (m, 2H), 3.97 (s, 3H), 7.82-7.86 (m, 2H), 7.90-7.94 (m, 2H), 8.31 (s, 1H), 8.50 (t, J=2.21 Hz, 1H), 8.83 (dd, J=8.99, 2.05 Hz, 2H), 8.92 (d, J=2.21 Hz, 1H), 9.03 (d, J=2.21 Hz, 1H), 9.10 (s, 1H), 9.32 (s, 2H). MS ES+m/z 447 [M+H]+.

Example 177: 1-(4-(5-(1H-benzo[d]imidazol-1-yl)pyridin-3-yl)phenyl)pyrrolidin-2-one

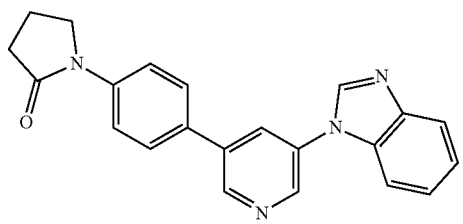 [SMILES: O=C1CCCN1c1ccc(-c2cncc(-n3cnc4ccccc43)c2)cc1]

Step 1: Preparation of Intermediate 115—1-(5-bromo-3-pyridyl)benzimidazole

Step 1a: Intermediate 113—5-bromo-N-(2-nitrophenyl)pyridin-3-amine

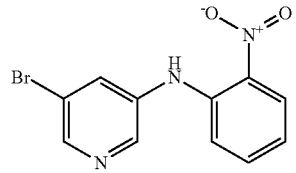

5-Bromopyridin-3-amine (500 mg, 2.89 mmol) was dissolved in 2-MeTHF (5 ml) and cooled to −10° C. LHMDS (1.06 M, 6.82 ml, 7.22 mol) was added and the mixture was stirred for 10 min. To the cooled mixture was added 1-fluoro-2-nitro-benzene (0.321 ml, 3.03 mmol) and the resulting mixture was allowed to stir for 10 min at −10° C. and then allowed to stir at rt for 3 h. The reaction was quenched with sat. aq. NH₄Cl. Water and EtOAc were added and the organic layer was separated, filtered, concentrated, and purified on a silica gel column eluted with 0-100% EtOAc in heptane to give Intermediate 113 as a solid (486 mg, 57%). MS ES+m/z 294 [M+H]+.

Step 1b: Intermediate 114—N¹-(5-bromo-3-pyridyl)benzene-12-diamine

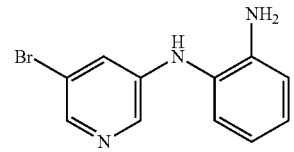 [SMILES: Nc1ccccc1Nc1cncc(Br)c1]

The nitro group in Intermediate 113 reduced under the conditions outlined in Example 54, step 1, to give Intermediate 114 as a solid (564 mg, quant.). MS ES+m/z 264 [M+H]+.

Step 1c: Intermediate 115—1-(5-bromopyridin-3-yl)-1H-benzo[d]imidazole

A mixture of diethoxymethoxyethane (0.549 ml, 3.30 mmol), Ni-(5-bromo-3-pyridyl)benzene-1,2-diamine (Intermediate 114) (436 mg, 1.65 mmol) and 4-methylbenzenesulfonic acid hydrate (63 mg, 0.33 mmol) in 1,4-dioxane (5 ml) was stirred at 100° C. for 1 h. Water and EtOAc were added, the organic layer was separated, dried over Na₂SO₄, filtered and concentrated to give Intermediate 115 as a solid (383 mg, 85%). MS ES+m/z 274 [M+H]+.

Step 2: 1-(4-(5-(1H-benzo[d]imidazol-1-yl)pyridin-3-yl)phenyl)pyrrolidin-2-one 1-(4-(5-(1H-benzo[d]imidazol-1-yl)pyridin-3-yl)phenyl)pyrrolidin-2-one was prepared according to Example 85, replacing Intermediate 90 for 1-[4-[5-(4,4,5,5-tetramethyl-1,3,2-dioxaborolan-2-yl)-3-pyridyl]phenyl]pyrrolidin-2-one, and replacing Intermediate 7 for Intermediate 115. 1-(4-(5-(1H-benzo[d]imidazol-1-yl)pyridin-3-yl)phenyl)

pyrrolidin-2-one was obtained as a solid (28 mg, 11%). $^1$H NMR (500 MHz, DMSO-$d_6$) δ ppm 2.05-2.14 (m, 2H), 2.52-2.57 (m, 2H), 3.87-3.93 (m, 2H), 7.32-7.41 (m, 2H), 7.71-7.76 (m, 1H), 7.80-7.86 (m, 3H), 7.90-7.96 (m, 2H), 8.39-8.44 (m, 1H), 8.70-8.74 (m, 1H), 8.89-8.93 (m, 1H), 9.02-9.07 (m, 1H). MS ES+m/z 355 [M+H]$^+$.

Example 178: 8-([3,4'-bipyridin]-5-yl)-2-methyl-2,8-diazaspiro[4.5]decan-1-one

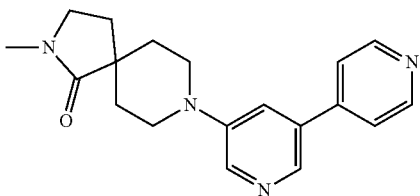 [SMILES: CN1CCC2(CCN(c3cncc(-c4ccncc4)c3)CC2)C1=O]

A mixture of 3-bromo-5-(4-pyridyl)pyridine (118 mg, 0.5 mmol) and 2-methyl-2,8-diazaspiro[4.5]decan-1-one•hydrochloride (102 mg, 0.5 mmol) in 1,4-dioxane (4 ml) was degassed with argon for 5 min. Cs$_2$CO$_3$ (489 mg, 1.5 mmol), XantPhos (28 mg, 0.05 mmol) and Pd(OAc)$_2$ (11 mg, 0.05 mmol) were added and the resulting mixture was stirred at 90° C. for 6 h. When cooled to rt water was added and the mixture extracted with DCM (3×10 ml). The combined organics were dried over Na$_2$SO$_4$, filtered, concentrated and purified by preparative HPLC to give 8-([3,4'-bipyridin]-5-yl)-2-methyl-2,8-diazaspiro[4.5]decan-1-one as a solid (20 mg, 12%). $^1$H NMR (500 MHz, DMSO-$d_6$) δ ppm 1.46 (br d, J=13.24 Hz, 2H), 1.75-1.86 (m, 2H), 1.99 (t, J=6.94 Hz, 2H), 2.75 (s, 3H), 2.99 (td, J=12.37, 2.68 Hz, 2H), 3 3.29-3.35 (m, 2H), 3.86 (dt, J=13.08, 3.55 Hz, 2H), 7.65 (s, 1H), 7.78-7.81 (m, 2H), 8.38 (d, J=1.89 Hz, 1H), 8.41 (d, J=2.84 Hz, 1H), 8.64-8.69 (m, 2H). MS ES+m/z 323 [M+H]$^+$.

Example 179: 4-([3,4'-bipyridin]-5-yl)-N-methyl-N-(piperidin-4-ylmethyl)benzamide

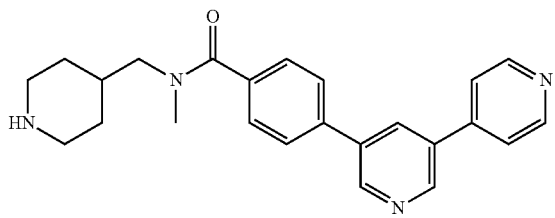 [SMILES: CN(CC1CCNCC1)C(=O)c1ccc(-c2cncc(-c3ccncc3)c2)cc1]

Step 1: Intermediate 116—(4-(((1-(tert-butoxycarbonyl)piperidin-4-yl)methyl)(methyl)carbamoyl)phenyl)boronic acid To a solution of 4-boronobenzoic acid (100 mg, 0.6 mmol) in MeCN (1 ml) was added N-methylmorpholine (0.13 ml, 1.2 mmol), followed by T3P (50% in EtOAc, 0.54 ml, 0.9 mmol) and tert-butyl 4-(methylaminomethyl)piperidine-1-carboxylate (0.15 ml, 0.66 mmol). The resulting mixture was heated and stirred at 90° C. for 2 h. The reaction was cooled to rt, water and EtOAc were added, and the organic layer separated. The aqueous layer was extracted with EtOAc and the combined organics were dried over MgSO$_4$, filtered, and concentrated to give Intermediate 116 as a solid (200 mg, 88%). MS ES+m/z 321 [M-tBu+H]$^+$.

Step 2: 4-([3,4'-bipyridin]-5-yl)-N-methyl-N-(piperidin-4-ylmethyl)benzamide

A mixture of 3-bromo-5-(4-pyridyl)pyridine (79 mg, 0.34 mmol) and [4-[(1-tert-butoxycarbonyl-4-piperidyl)methyl-methyl-carbamoyl]phenyl]boronic acid (Intermediate 116) (91 mg, 0.24 mmol) in 1,4-dioxane (5 ml) and water (0.3 ml) was degassed with nitrogen for 5 min. PdCl$_2$(Amphos) (9 mg, 0.01 mmol) and K$_2$CO$_3$ (67 mg, 0.48 mmol) were added and the resulting mixture was stirred at 100° C. for 2 h. When cooled to rt 1,2-dichloroethane and water were added. The organic layer was separated, concentrated and purified by preparative HPLC. The resulting material was dissolved in EtOH (2 ml) and a few drops of conc. HCl was added. The reaction was stirred at rt until all Boc protection group had been removed. The mixture was concentrated and the resulting residue was redissolved in aq. 0.5 M HCl (1 ml) and extracted with EtOAc. The aqueous layer was made alkaline using aq. 2M KOH and then extracted with EtOAc (2×). The combined organics were dried over dried over MgSO$_4$, filtered and concentrated to give 4-([3,4'-bipyridin]-5-yl)-N-methyl-N-(piperidin-4-ylmethyl)benzamide as a solid (17 mg, 18%). $^1$H NMR (500 MHz, MeOD) δ ppm 0.82-0.95 (m, 1H), 1.29-1.38 (m, 1H), 1.55-1.63 (m, 1H), 1.75-1.82 (m, 1H), 1.83-2.08 (m, 1H), 2.49-2.60 (m, 1H), 2.61-2.71 (m, 1H), 2.92-2.99 (m, 1H), 3.01-3.16 (m, 5H), 3.48-3.54 (m, 1H), 7.54-7.62 (m, 2H), 7.86-7.91 (m, 4H), 8.45-8.51 (m, 1H), 8.66-8.72 (m, 2H), 8.92-9.00 (m, 2H). MS ES+m/z 387 [M+H]$^+$.

Example 180: 4-([3,4'-bipyridin]-5-yl)-N-methyl-N-(piperidin-3-ylmethyl)benzamide

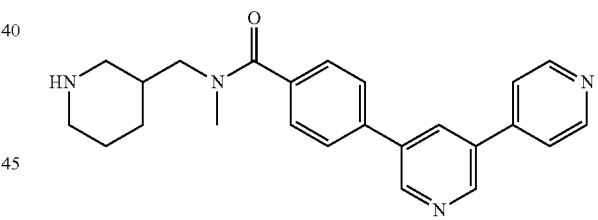

Step 1: Intermediate 117—N-methyl-N-(3-piperidylmethyl)-4-[5-(4-pyridyl)-3-pyridyl]benzamide Intermediate 117 was prepared according to Example 182, replacing tert-butyl 4-(methylaminomethyl)piperidine-1-carboxylate for tert-butyl 3-(methylaminomethyl)piperidine-1-carboxylate, to give Intermediate 117 as a solid (200 mg, 61%). MS ES+m/z 377 [M+H]$^+$.

Step 2: 4-([3,4'-bipyridin]-5-yl)-N-methyl-N-(piperidin-3-ylmethyl)benzamide 4-([3,4'-bipyridin]-5-yl)-N-methyl-N-(piperidin-3-ylmethyl)benzamide was prepared according to Example 181, replacing Intermediate 116 for Intermediate 117. Purification by preparative HPLC gave 4-([3,4'-bipyridin]-5-yl)-N-methyl-N-(piperidin-3-ylmethyl)benzamide as a solid (diacetic acid salt, 2 mg, 1%). $^1$H NMR (500 MHz, DMSO-$d_6$)

δ ppm 0.68 (s, 1H), 1.20-1.47 (m, 2H), 1.53-1.64 (m, 1H), 1.72-1.81 (m, 7H), 1.82-1.93 (m, 1H), 2.22-2.32 (m, 1H), 2.71-2.81 (m, 1H), 2.81-2.88 (m, 1H), 2.91-3.00 (m, 4H), 3.15-3.19 (m, 1H), 3.28-3.34 (m, 1H), 3.37-3.43 (m, 1H), 7.46-7.59 (m, 2H), 7.91-7.99 (m, 4H), 8.47-8.56 (m, 1H), 8.69-8.74 (m, 2H), 9.00-9.06 (m, 2H). MS ES+m/z 387 [M+H]⁺.

Example 181: 4-([3,4'-bipyridin]-5-yl)-N-(((1r,4r)-4-aminocyclohexyl)methyl)-N-methylbenzamide

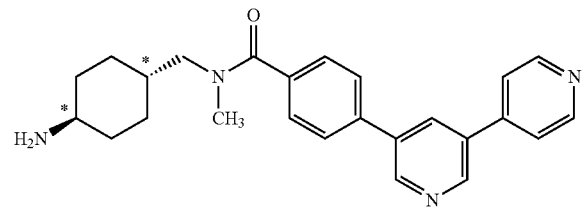

* relative sterochemistry

Step 1: Intermediate 118—trans-(4-(((4-((tert-butoxycarbonyl)amino)cyclohexyl)methyl)(methyl)carbamoyl)phenyl)boronic acid To a solution of trans-tert-butyl N-(4-formylcyclohexyl)carbamate (200 mg, 0.88 mmol) in 2-MeTHF (3 ml) was added titanium(IV) isopropoxide (586 μL, 1.97 mmol) and the mixture was stirred for 15 min at rt. To the reaction was added MeNH₂ (8.9 M in MeOH, 585 μL, 5.21 mmol) and the resulting mixture was stirred at rt overnight. MeOH (3 ml) was added and the mixture was cooled to 0° C. NaBH₄ (166 mg, 4.4 mmol) was added portionwise and after 10 min the cooling bath was removed and the mixture stirred at rt until the imine intermediate had been consumed. Water, sat. aq. NH₄Cl and EtOAc were added and the mixture stirred at rt for 30 min. The organic layer was separated and the aqueous layer extracted with EtOAc. The combined organics were washed with brine, dried over Na₂SO₄, filtered, and concentrated to give a residue (182 mg, 85%). The residue was taken up in MeCN (1 ml) and 4-boronobenzoic acid (120 mg, 0.72 mmol), N-methylmorpholine (0.16 ml, 1.4 mmol) and T3P (50% in EtOAc, 0.65 ml, 1.1 mmol) were added. The resulting mixture was stirred at 90° C. for 2 h. When cooled to rt water and EtOAc were added and the organic layer separated. The organic layer was extracted with EtOAc and the combined organics were dried over MgSO₄, filtered and concentrated to give the product as a solid (200 mg, 71%). MS ES+m/z 336 [M-tBu+H]⁺.

Step 2: 4-([3,4'-bipyridin]-5-yl)-N-(((1r,4r)-4-aminocyclohexyl)methyl)-N-methylbenzamide 4-([3,4'-bipyridin]-5-yl)-N-(((1r,4r)-4-aminocyclohexyl)methyl)-N-methylbenzamide was prepared according to Example 181, replacing Intermediate 116 for Intermediate 118. Purification by preparative HPLC gave 4-([3,4'-bipyridin]-5-yl)-N-(((1r,4r)-4-aminocyclohexyl)methyl)-N-methylbenzamide as a solid (acetic acid salt, 3 mg, 3%). ¹H NMR (500 MHz, DMSO-d₆) δ ppm 0.61-0.75 (m, 1H), 1.03-1.14 (m, 1H), 1.20-1.41 (m, 2H), 1.55-1.65 (m, 1H), 1.68-1.75 (m, 1H), 1.76-1.84 (m, 1H), 1.89-1.92 (m, 4H), 1.95-2.03 (m, 1H), 2.90-3.01 (m, 4H), 3.13-3.20 (m, 1H), 3.31-3.39 (m, 2H), 7.46-7.59 (m, 2H), 7.90-7.98 (m, 4H), 8.48-8.53 (m, 1H), 8.69-8.74 (m, 2H), 9.01-9.07 (m, 2H). MS ES+m/z 401 [M+H]⁺.

Example 182: 1-[4-[5-(7,8-Dihydro-6H-pyrido[3,2-b]pyrrolizin-5-yl)-3-pyridyl]phenyl]pyrrolidin-2-one

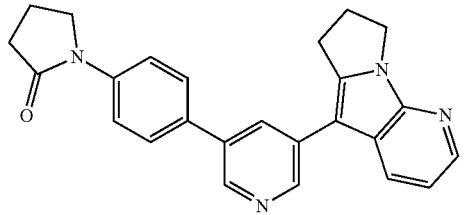 [SMILES: O=C1CCCN1c1ccc(-c2cncc(-c3c4n(c5ncccc35)CCC4)c2)cc1]

Step 1: Preparation of Intermediate 123

Step 1a: Intermediate 119—1-allylpyrrolo[2,3-b]pyridine-2-carbaldehyde

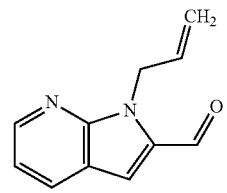

1H-Pyrrolo[2,3-b]pyridine-2-carbaldehyde (2 g, 13.7 mmol) and Cs₂CO₃ (6 g, 18.4 mmol) were taken up in DMF (20 ml) and the resulting mixture was stirred at rt for 15 min. Allyl bromide (1.5 ml, 17.4 mmol) was added and the resulting mixture was stirred at rt for 1 h. Water (60 ml) was added and the mixture was extracted with EtOAc (3×15 mL). The combined organics were washed with water (20 mL), brine, dried over MgSO₄, filtered, and concentrated to give Intermediate 119 as a brown oil (2.09 g, 82%). MS ES+m/z 187 [M+H]⁺.

Step 1b: Intermediate 120—1-allyl-2-vinyl-pyrrolo[2,3-b]pyridine

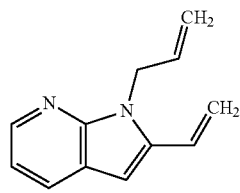

To a suspension of methyl(triphenyl)phosphonium bromide (4.5 g, 12.6 mmol) in THF (60 ml) at rt was added KHMDS (0.5 M in toluene, 30 ml, 15 mmol), and the resulting mixture was stirred at rt for 30 min. A solution of 1-allylpyrrolo[2,3-b]pyridine-2-carbaldehyde (Intermediate 119) (2.09 g, 11.2 mmol) in THF (10 ml) was added and the resulting mixture was stirred at rt for 1 h. The mixture was poured into water:Et₂O (1:1, 100 ml) and the organic layer was separated. The aqueous layer was extracted with Et₂O (2×30 ml) and the combined organics were dried over MgSO₄, filtered, and concentrated. The residue was suspended in Et₂O (20 ml) and stirred at rt for 15 min. Pentane (20 ml) was added slowly and after 10 min the resulting triphenylphosphine oxide precipitate was filtered, washed with Et₂O:pentane (1:1, 20 ml), and discarded. The filtrate was concentrated and purified on a silica gel column eluted with 0-20% EtOAc in heptane to give Intermediate 120 as an oil (1.5 g, 73%). MS ES+m/z 185 [M+H]⁺.

Step 1c: Intermediate 121—8H-pyrido[3,2-b]pyrrolizine

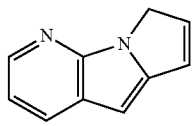 [SMILES: C1=Cc2cc3cccnc3n2C1]

To a solution of 1-allyl-2-vinyl-pyrrolo[2,3-b]pyridine (Intermediate 120) (1.45 g, 7.87 mmol) in DCM (150 ml) was added Hoveyda-Grubbs catalyst 2nd generation (700 mg, 1.12 mmol) and the reaction mixture was stirred at room temperature for 48 h. A second charge of Hoveyda-Grubbs catalyst 2nd generation (200 mg, 0.32 mmol) was added and the reaction was allowed to stir at rt for additional 2 days. The reaction was warmed to 40° C. an allowed to stir overnight. A third charge of Hoveyda-Grubbs catalyst 2nd generation (200 mg, 0.32 mmol) was added and the reaction was stirred at 40° C. overnight. The mixture was cooled to rt and filtered over silica. The filtrate was concentrated. The crude product was taken up in DCM/pentane (1:1, 10 ml) and filtered. The filtrate was purified on a silica gel column eluted with 10-70% DCM in heptane to give Intermediate 121 as an oil (400 mg, 33%). MS ES+m/z 157 [M+H]⁺.

Step 1d: Intermediate 122—7,8-dihydro-6H-pyrido[3,2-b]pyrrolizine

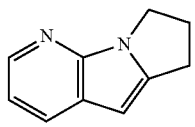

To a mixture of Pd/C (10%, 250 mg, 0.12 mmol) in EtOAc (5 ml) at rt was carefully added a solution of 8H-pyrido[3,2-b]pyrrolizine (300 mg, 1.92 mmol) in EtOH (10 ml) followed by ammonium formate (600 mg, 9.52 mmol). The resulting mixture was brought to 70° C. and stirred for 20 min. A second charge of ammonium formate (600 mg, 9.52 mmol) was added and the mixture was stirred for additional 30 min (repeated five times, i.e., a total of 3.6 g of ammonium formate was added). A second charge of Pd/C (10%, 100 mg), suspended in EtOAc, (2 ml) was added followed by an additional charge of ammonium formate (1 g, 15.87 mmol). The resulting mixture was stirred at 70° C. for 30 min. The reaction mixture was cooled to rt, filtered, and the filtrate was concentrated to give a solid. The solid was taken up in DCM (10 mL), filtered, and the filtrate was concentrated to give Intermediate 122 as a solid (280 mg, 92%). MS ES+m/z 159 [M+H]⁺.

Step 1e: Intermediate 123—5-Bromo-7,8-dihydro-6H-pyrido[3,2-b]pyrrolizine

To a solution of 7,8-dihydro-6H-pyrido[3,2-b]pyrrolizine (250 mg, 1.58 mmol) in DCM (10 ml) at 0° C. was added NBS (281 mg, 1.58 mmol) and the mixture was stirred at 0° C. for 15 min. Sat. aq. Na₂S₂O₃ (5 ml) and sat. aq. NaHCO₃ (5 mL) were added and the organic layer separated. The aqueous layer was extracted with DCM (3 mL). The combined organics were washed with sat. aq. NaHCO₃ (10 ml), concentrated, and purified on a silica gel column eluted with 0-40% EtOAc in heptane to give Intermediate 123 as a solid (150 mg. 40%). MS ES+m/z 237 [M+H]⁺.

Step 2: 1-[4-[5-(7,8-Dihydro-6H-pyrido[3,2-b]pyrrolizin-5-yl)-3-pyridyl]phenyl]pyrrolidin-2-one 1-[4-[5-(4,4,5,5-tetramethyl-1,3,2-dioxaborolan-2-yl)-3-pyridyl]phenyl]pyrrolidin-2-one (1-[4-[5-(4,4,5,5-tetramethyl-1,3,2-dioxaborolan-2-yl)-3-pyridyl]phenyl]pyrrolidin-2-one) (230 mg, 0.63 mmol) and 5-bromo-7,8-dihydro-6H-pyrido[3,2-b]pyrrolizine (Intermediate 123) (150 mg, 0.63 mmol) were dissolved in 1,4-dioxane (5 ml) and degassed with nitrogen for a few min. K₂CO₃ (175 mg, 1.27 mmol), PdCl₂(Amphos) (23 mg, 0.03 mmol) and water (1 ml) were added and the mixture was stirred at 90° C. for 30 min. A second charge of 1-[4-[5-(4,4,5,5-tetramethyl-1,3,2-dioxaborolan-2-yl)-3-pyridyl]phenyl]pyrrolidin-2-one (25 mg, 0.07 mmol) was added and the mixture was stirred for another 15 min. The reaction mixture was cooled to rt and EtOAc (2 ml) was added. The mixture was filtered through a syringe filter and the filter was rinsed with EtOAc (3 ml). To the filtrate was added half-saturated brine (5 ml) and the organic layer was separated. The aqueous layer was extracted with EtOAc (2×5 ml). The combined organics were washed with brine, stirred with MgSO₄ and active charcoal (100 mg) for 10 min, filtered through celite, and concentrated. Recrystallization from MeOH gave 1-[4-[5-(7,8-Dihydro-6H-pyrido[3,2-b]pyrrolizin-5-yl)-3-pyridyl]phenyl]pyrrolidin-2-one as a solid (70 mg, 28%). ¹H NMR (500 MHz, DMSO-d₆) δ ppm 2.10 (quin, J=7.57 Hz, 2H), 2.52-2.56 (m, 2H), 2.65 (quin, J=7.33 Hz, 2H), 3.33-3.38 (m, 2H), 3.87-3.93 (m, 2H), 4.23 (t, J=7.09 Hz, 2H), 7.16 (dd, J=7.88, 4.73 Hz, 1H), 7.80-7.87 (m, 4H), 8.15 (t, J=2.21 Hz, 1H), 8.23 (dd, J=4.57, 1.42 Hz, 1H), 8.27 (dd, J=7.88, 1.58 Hz, 1H), 8.75 (d, J=2.21 Hz, 1H), 8.83 (d, J=2.21 Hz, 1H). MS ES+m/z 395 [M+H]⁺.

Example 183: 1-[4-[5-(4-Methyl-2,4,5-triazatricyclo[7.3.0.0³,⁷]dodeca-1,3(7),5,8-tetraen-8-yl)-3-pyridyl]phenyl]pyrrolidin-2-one

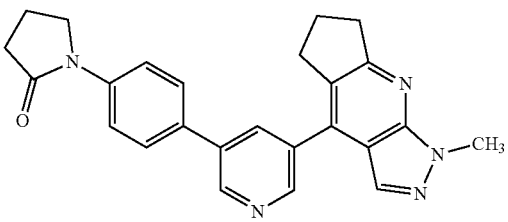 [SMILES: Cn1ncc2c(-c3cncc(-c4ccc(N5CCCC5=O)cc4)c3)c3c(nc21)CCC3]

Step 1: Preparation of Intermediate 125

Step 1a: Intermediate 124—4-methyl-2,4,5-triazatricyclo[7.3.0.0³,⁷]dodeca-1,3(7),5,8-tetraen-8-amine

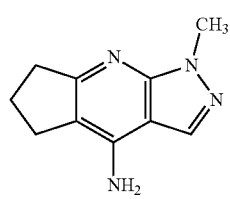

Cyclopentanone (0.51 ml, 5.7 mmol) and AlCl₃ (2.18 g, 16 mmol) were added to a solution of 5-amino-1-methylpyrazole-4-carbonitrile (500 mg, 4.1 mmol) in DCE (19 ml) and THF (5 ml) at rt. The resulting mixture was stirred at 85° C. for 2 h. The mixture was cooled to rt, concentrated, and the resulting residue was suspended in 10% aq. NaOH and stirred at rt for 30 min. The resulting precipitate was filtered, washed with H₂O and Et₂O and dried. The solid was suspended in MeOH, filtered through celite, and the filtrate was concentrated to give Intermediate 124 as a solid (400 mg, 52%). MS ES+m/z 189 [M+H]⁺.

Step 1b: Intermediate 125—8-bromo-4-methyl-2,4,5-triazatricyclo[7.3.0.0³,⁷]dodeca-1,3(7),5,8-tetraene To a mixture of CuBr₂ (549 mg, 2.5 mmol) in MeCN (5 ml) at 0° C. was added tert-butyl nitrite (0.49 ml, 4.2 mmol) dropwise and stirred for 5 min. 4-methyl-2,4,5-triazatricyclo[7.3.0.0³,⁷]dodeca-1,3(7),5,8-tetraen-8-amine (356 mg, 1.9 mmol) was added and the resulting mixture was stirred at rt overnight. EtOAc and 10% aq. NH₄C were added and the organic layer separated. The aqueous layer was extracted with EtOAc and the combined organic layers were dried over MgSO₄, filtered, concentrated, and purified on a silica gel column eluted with 0-100% EtOAc in heptane to give Intermediate 125 as a solid (180 mg, 38%). MS ES+m/z 252 [M+H]⁺.

Step 2: 1-[4-[5-(4-Methyl-2,4,5-triazatricyclo[7.3.0.0³,⁷]dodeca-1,3(7),5,8-tetraen-8-yl)-3-pyridyl]phenyl]pyrrolidin-2-one 1-[4-[5-(4-Methyl-2,4,5-triazatricyclo[7.3.0.0³,⁷]dodeca-1,3(7),5,8-tetraen-8-yl)-3-pyridyl]phenyl]pyrrolidin-2-one was prepared according to Example 184, replacing Intermediate 123 for Intermediate 125 to give 1-[4-[5-(4-Methyl-2,4,5-triazatricyclo[7.3.0.0³,⁷]dodeca-1,3(7),5,8-tetraen-8-yl)-3-pyridyl]phenyl]pyrrolidin-2-one a solid (6 mg, 22%). ¹H NMR (500 MHz, DMSO-d₆) δ ppm 2.05-2.19 (m, 4H), 2.51-2.55 (m, 2H), 3.06-3.12 (m, 4H), 3.87-3.92 (m, 2H), 4.05-4.08 (m, 3H), 7.80-7.84 (m, 2H), 7.85-7.90 (m, 2H), 8.03-8.05 (m, 1H), 8.30-8.32 (m, 1H), 8.82-8.84 (m, 1H), 9.02-9.04 (m, 1H). MS ES+m/z 410 [M+H]⁺.

Example 184: 1-[4-[5-(3-bromo-7,8-dihydro-6H-pyrido[3,2-b]pyrrolizin-5-yl)-3-pyridyl]phenyl]pyrrolidin-2-one

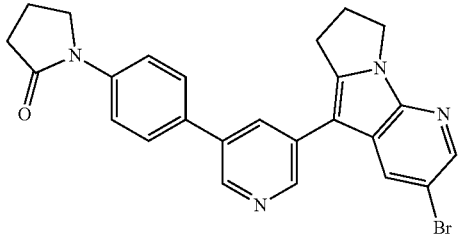 [SMILES: O=C1CCCN1c1ccc(-c2cncc(-c3c4n(c5ncc(Br)cc35)CCC4)c2)cc1]

Step 1: Preparation of Intermediate 129

Step 1a: Intermediate 126—5-bromo-3-(5-chloropent-1-ynyl)pyridin-2-amine

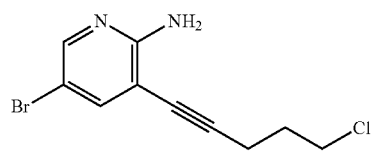 [SMILES: Nc1ncc(Br)cc1C#CCCCCl]

To a mixture of 5-bromo-3-iodo-pyridin-2-amine (6.5 g, 21.7 mmol), CuI (414 mg, 2.17 mmol) and PdCl₂(PPh₃)₂ (650 mg, 0.93 mmol) in TEA (75 ml) and THF (50 ml) was added 5-chloropent-1-yne (2.5 ml, 23.6 mmol) at rt. The resulting mixture was stirred at 50° C. for 5 h. The mixture was cooled to rt and filtered through celite, concentrated, and purified on a silica gel column eluted with 0-75% EtOAc in heptane to give Intermediate 126 as an oil (5.82 g, 98%). MS ES+m/z 273 [M+H]⁺.

Step 1b: Intermediate 127—5-bromo-2-(3-chloropropyl)-1H-pyrrolo[2,3-b]pyridine

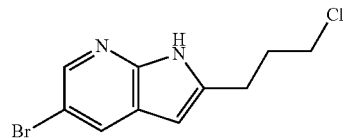 [SMILES: ClCCCc1cc2cc(Br)cnc2[nH]1]

A solution of TFAA (6 ml, 43.2 mmol) in MeCN (5 ml) was added slowly to a solution of 5-bromo-3-(5-chloropent-1-ynyl)pyridin-2-amine (Intermediate 126) (5.3 g, 19.4 mmol) in MeCN (50 ml) at 0° C. under a nitrogen atmosphere. The resulting mixture was stirred at 0° C. for 1.5 h. The mixture was concentrated and the resulting residue was taken up in MeCN (50 ml) under a nitrogen atmosphere. Bis(acetonitrile)dichloropalladium(II) (260 mg, 1.0 mmol) was added and the resulting mixture was stirred at 75° C. for 4 h. The mixture was cooled to rt, filtered, and concentrated. The resulting residue was dissolved in EtOAc (30 ml), washed with sat. aq. NaHCO₃ (2×10 ml) and brine, dried over MgSO₄, filtered, and concentrated to give a dark brown solid. The solid was dissolved in boiling EtOAc (10 ml) and EtOH (30 ml) was added slowly. The solution was re-heated to boiling after the addition of EtOH and was allowed to slowly cool to rt. The precipitate was filtered and discarded. The filtrate was concentrated to give Intermediate 127 as a solid (4.7 g, 89%). MS ES+m/z 273 [M+H]+.

Step 1c: Intermediate 128—3-bromo-7,8-dihydro-6H-pyrido[3,2-b]pyrrolizine

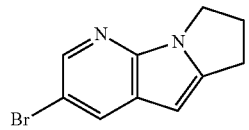 [SMILES: Brc1cnc2c(c1)cc1n2CCC1]

To a mixture of 5-bromo-2-(3-chloropropyl)-1H-pyrrolo[2,3-b]pyridine (Intermediate 127) (4.7 g, 17.2 mmol) and KI (2.85 g, 17.2 mmol) in DMF (20 ml) and MeCN (20 ml) was added NaH (60%, 1 g, 26.1 mmol) portion-wise at rt under a nitrogen atmosphere. The resulting mixture was stirred at rt for 2.5 h and then poured onto ice (200 ml) and sat. aq. NaHCO₃ (100 ml). EtOAc (50 ml) was added after the ice had melted and the organic layer separated. The aqueous layer was extracted with EtOAc (3×50 ml) and the combined organic layers were washed with brine, dried over MgSO₄, filtered, concentrated, and purified on a silica gel column eluted with 0-60% EtOAc in heptane to give Intermediate 128 as a solid (2.06 g, 51%). MS ES+m/z 237 [M+H]+.

Step 1d: Intermediate 129—3-bromo-5-iodo-7,8-dihydro-6H-pyrido[3,2-b]pyrrolizine To a cooled solution of 3-bromo-7,8-dihydro-6H-pyrido[3,2-b]pyrrolizine (Intermediate 128) (150 mg, 0.63 mmol) in DCM (10 ml) was added N-iodosuccinimide (142 mg, 0.63 mmol) and the resulting mixture was stirred at 0° C. for 15 min. The mixture was washed with water and sat. aq. NaHCO₃, dried over MgSO₄, filtered, and concentrated to give Intermediate 129 as a solid (200 mg, 87%). MS ES+m/z 363 [M+H]+.

Step 2: 1-[4-[5-(3-bromo-7,8-dihydro-6H-pyrido[3,2-b]pyrrolizin-5-yl)-3-pyridyl]phenyl]pyrrolidin-2-one 1-[4-[5-(3-bromo-7,8-dihydro-6H-pyrido[3,2-b]pyrrolizin-5-yl)-3-pyridyl]phenyl]pyrrolidin-2-one was prepared according to Example 85, replacing Intermediate 90 for 1-[4-[5-(4,4,5,5-tetramethyl-1,3,2-dioxaborolan-2-yl)-3-pyridyl]phenyl]pyrrolidin-2-one, and replacing Intermediate 7 for Intermediate 129. 1-[4-[5-(3-bromo-7,8-dihydro-6H-pyrido[3,2-b]pyrrolizin-5-yl)-3-pyridyl]phenyl]pyrrolidin-2-one was obtained as a solid (5 mg, 3%). ¹H NMR (500 MHz, DMSO-d₆) δ ppm 2.09 (quin, J=7.57 Hz, 2H), 2.53 (br t, J=8.04 Hz, 2H), 2.64 (quin, J=7.25 Hz, 2H), 3.01 (br t, J=7.41 Hz, 1H), 3.87-3.93 (m, 2H), 4.11 (t, J=6.94 Hz, 1H), 4.23 (t, J=7.09 Hz, 2H), 7.79-7.87 (m, 4H), 8.13-8.17 (m, 1H), 8.27-8.32 (m, 1H), 8.40 (d, J=2.21 Hz, 1H), 8.77 (d, J=2.21 Hz, 1H), 8.80 (d, J=1.89 Hz, 1H). MS ES+m/z 473 [M+H]+.

Example 185: 1-[4-[5-[3-(1-hydroxyethyl)-7,8-dihydro-6H-pyrido[3,2-b]pyrrolizin-5-yl]-3-pyridyl]phenyl]pyrrolidin-2-one

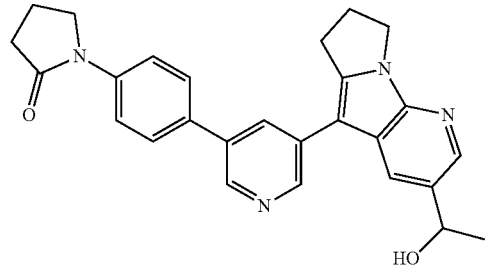 [SMILES: CC(O)c1cnc2c(c1)c(-c1cncc(-c3ccc(N4CCCC4=O)cc3)c1)c1n2CCC1]

Step 1: Preparation of Intermediate 131

Step 1a: Intermediate 130—1-(7,8-dihydro-6H-pyrido[3,2-b]pyrrolizin-3-yl)ethanol

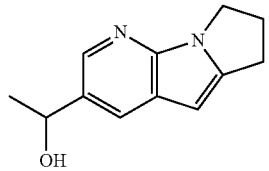

To a cooled solution of 3-bromo-7,8-dihydro-6H-pyrido[3,2-b]pyrrolizine (200 mg, 0.84 mmol) in 2-MeTHF (2 ml) at −10° C. was added n-BuLi (2.5 M, 0.68 ml, 1.69 mmol) dropwise. After 2 min acetaldehyde (66 μl, 1.69 mmol) was added and the reaction was allowed to warm to rt. The mixture was diluted with EtOAc and water was added. The organic layer was separated, dried over MgSO₄, filtered, concentrated, and purified on a silica gel column eluted with 0-10% MeOH in DCM to give Intermediate 130 as a solid (70 mg, 41%). MS ES+m/z 203 [M+H]+.

Step 1b: Intermediate 131—1-(5-iodo-7,8-dihydro-6H-pyrido[3,2-b]pyrrolizin-3-yl)ethanol Intermediate 131 was prepared according to Example 186, replacing 3-bromo-7,8-dihydro-6H-pyrido[3,2-b]pyrrolizine (Intermediate 128) for 1-(7,8-dihydro-6H-pyrido[3,2-b]pyrrolizin-3-yl)ethanol (Intermediate 130) to give Intermediate 131 as a solid (198 mg, 87%). MS ES+m/z 329 [M+H]+.

Step 2: 1-[4-[5-[3-(1-hydroxyethyl)-7,8-dihydro-6H-pyrido[3,2-b]pyrrolizin-5-yl]-3-pyridyl]phenyl]pyrrolidin-2-one 1-[4-[5-[3-(1-hydroxyethyl)-7,8-dihydro-6H-pyrido[3,2-b]pyrrolizin-5-yl]-3-pyridyl]phenyl]pyrrolidin-2-one was prepared according to Example 85, replacing Intermediate 90 for 1-[4-[5-(4,4,5,5-tetramethyl-1,3,2-dioxaborolan-2-yl)-3-pyridyl]phenyl]pyrrolidin-2-one, and replacing Intermediate 7 for Intermediate 131. 1-[4-[5-[3-(1-hydroxyethyl)-7,8-dihydro-6H-pyrido[3,2-b]pyrrolizin-5-yl]-3-pyridyl]phenyl]pyrrolidin-2-one was obtained as a solid (62 mg, 34%). ¹H NMR (500 MHz, DMSO-d₆) δ ppm 1.40-1.45

(m, 3H), 2.05-2.14 (m, 2H), 2.51-2.56 (m, 2H), 2.60-2.69 (m, 2H), 3.33-3.37 (m, 2H), 3.88-3.93 (m, 2H), 4.19-4.25 (m, 2H), 4.89-4.95 (m, 1H), 5.19-5.32 (m, 1H), 7.82-7.84 (m, 4H), 8.12-8.15 (m, 1H), 8.15-8.18 (m, 1H), 8.21-8.23 (m, 1H), 8.74-8.76 (m, 1H), 8.82-8.85 (m, 1H). MS ES+m/z 439 [M+H]⁺.

Example 186: 1-[4-[5-(7,8-dihydro-6H-pyrimido[5,4-b]pyrrolizin-5-yl)-3-pyridyl]phenyl]pyrrolidin-2-one

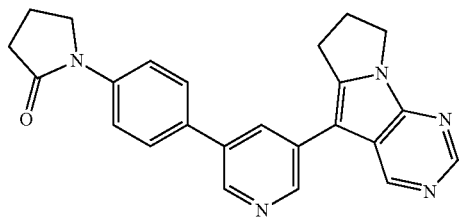 [SMILES: O=C1CCCN1c1ccc(-c2cncc(-c3c4n(c5ncncc35)CCC4)c2)cc1]

Step 1: Preparation of Intermediate 135

Step 1a: Intermediate 132—5-(5-chloropent-1-ynyl)pyrimidin-4-amine

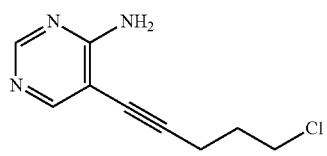 [SMILES: Nc1ncncc1C#CCCCCl]

Intermediate 132 was prepared according to Example 186, replacing 5-bromo-3-iodo-pyridin-2-amine for 5-iodopyrimidin-4-amine. Intermediate 132 was obtained as a solid (2.66 g, 99%). MS ES+m/z 196 [M+H]⁺.

Step 1b: Intermediate 133—6-(3-chloropropyl)-7H-pyrrolo[2,3-d]pyrimidine

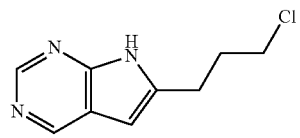

Intermediate 133 was prepared according to Example 186, replacing 5-bromo-3-(5-chloropent-1-ynyl)pyridin-2-amine (Intermediate 126) for 5-(5-chloropent-1-ynyl)pyrimidin-4-amine (Intermediate 132). Purification on a silica gel column eluted with 0-10% MeOH in DCM gave Intermediate 133 as a solid (1 g, 38%). MS ES+m/z 196 [M+H]⁺.

Step 1c: Intermediate 134—7,8-dihydro-6H-pyrimido[5,4-b]pyrrolizine

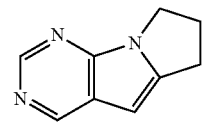

Intermediate 134 was prepared according to Example 186, replacing 5-bromo-2-(3-chloropropyl)-1H-pyrrolo[2,3-b]pyridine (Intermediate 127) for 6-(3-chloropropyl)-7H-pyrrolo[2,3-d]pyrimidine (Intermediate 133). Intermediate 134 was obtained as a solid (349 mg, 54%). MS ES+m/z 160 [M+H]⁺.

Step 1d: Intermediate 135—5-iodo-7,8-dihydro-6H-pyrimido[5,4-b]pyrrolizine

Intermediate 135 was prepared according to Example 186, replacing 3-bromo-7,8-dihydro-6H-pyrido[3,2-b]pyrrolizine (Intermediate 128) for 7,8-dihydro-6H-pyrimido[5,4-b]pyrrolizine (Intermediate 134). Intermediate 135 was obtained as a solid (551 mg, 88%). MS ES+m/z 286 [M+H]⁺.

Step 2: 1-[4-[5-(7,8-dihydro-6H-pyrimido[5,4-b]pyrrolizin-5-yl)-3-pyridyl]phenyl]pyrrolidin-2-one 1-[4-[5-(7,8-dihydro-6H-pyrimido[5,4-b]pyrrolizin-5-yl)-3-pyridyl]phenyl]pyrrolidin-2-one was prepared according to Example 85, replacing Intermediate 90 for 1-[4-[5-(4,4,5,5-tetramethyl-1,3,2-dioxaborolan-2-yl)-3-pyridyl]phenyl]pyrrolidin-2-one, and replacing Intermediate 7 for Intermediate 135. 1-[4-[5-(7,8-dihydro-6H-pyrimido[5,4-b]pyrrolizin-5-yl)-3-pyridyl]phenyl]pyrrolidin-2-one was obtained as a solid (54 mg, 33%). ¹H NMR (500 MHz, DMSO-d₆) δ ppm 2.06-2.14 (m, 2H), 2.52-2.56 (m, 2H), 2.62-2.70 (m, 2H), 3.35-3.39 (m, 2H), 3.87-3.93 (m, 2H), 4.22-4.28 (m, 2H), 7.79-7.84 (m, 2H), 7.84-7.90 (m, 2H), 8.20-8.24 (m, 1H), 8.78-8.81 (m, 2H), 8.87-8.89 (m, 1H), 9.27-9.30 (m, 1H). MS ES+m/z 396 [M+H]⁺.

Example 187: tert-butyl(4-(((2'-amino-5-(dimethylcarbamoyl)-[2,3':5',4"-terpyridin]-2"-yl)methyl)carbamoyl)phenyl)carbamate

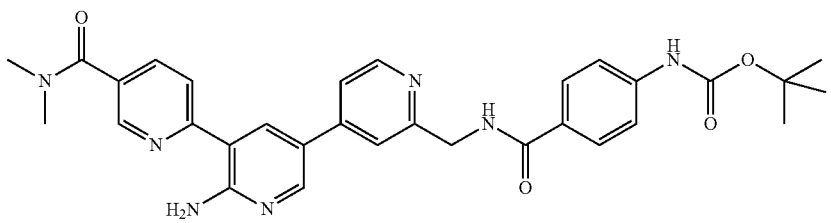 [SMILES: CN(C)C(=O)c1ccc(-c2cc(-c3ccnc(CNC(=O)c4ccc(NC(=O)OC(C)(C)C)cc4)c3)cnc2N)nc1]

Step 1: Preparation of tert-butyl ((4-bromopyridin-2-yl)methyl)carbamate

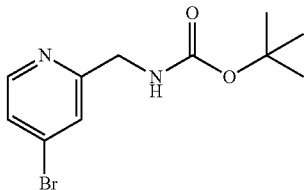 [SMILES: CC(C)(C)OC(=O)NCc1cc(Br)ccn1]

To a solution of 4-bromopicolinonitrile (5.00 g, 27.3 mmol), CoC$_2$·6H$_2$O (9.75 g, 41.0 mmol) in MeOH (5 mL) was added NaBH$_4$ (3.10 g, 82.0 mmol) at 0° C. portion wise, and the mixture was stirred at 0° C. for 30 min under N$_2$ atmosphere. TLC showed the reaction was completed. To the mixture was added H$_2$O (1 mL) and Boc$_2$O (11.9 g, 54.6 mmol). The mixture was reflux for 15.5 h. TLC indicated the reaction was completed. A black solution was formed. The resulting mixture was concentrated. The residue was diluted with H$_2$O (100 mL) and DCM (100 mL), then filtered. The aqueous layer was extracted with DCM (100 mL×3). The combined organic layer was washed with brine (100 mL), dried over anhydrous Na$_2$SO$_4$ and concentrated under reduced pressure. The residue was purified by Combi Flash (20% EtOAc in pentane) to give tert-butyl ((4-bromopyridin-2-yl)methyl)carbamate (2.50 g, yield: 32%) as a yellow solid. $^1$H NMR (400 MHz, CDCl$_3$) δ 1.47 (9H, s), 4.42 (2H, s), 5.46 (1H, br s), 7.41 (1H, d, J=40.0 Hz), 7.46 (1H, s), 8.34 (1H, d, J=4.8 Hz).

Step 2: Preparation of (4-bromopyridin-2-yl)methanamine

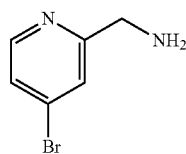

To a solution of tert-butyl ((4-bromopyridin-2-yl)methyl)carbamate (2.50 g, 8.71 mmol) in EtOAc (5 mL) was added HCl/EtOAc (4 M, 50 mL), and the mixture was stirred at 25° C. for 1 hour. TLC showed the starting material was consumed completely. A white suspension was formed. The mixture was concentrated to give (4-bromopyridin-2-yl)methanamine (2.00 g, yield: 88%) as a white solid. $^1$H NMR (400 MHz, DMSO-d$_6$) δ 4.17 (2H, dd, J=11.6, 6.0 Hz), 7.71 (1H, d, J=5.6 Hz), 7.89 (1H, s), 8.59 (1H, d, J=5.2 Hz), 8.72 (2H, br s).

Step 3: Preparation of 4-((tert-butoxycarbonyl)amino)benzoic acid

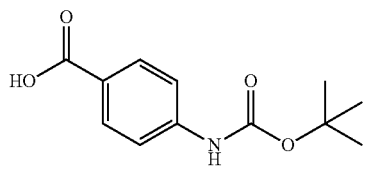 [SMILES: CC(C)(C)OC(=O)Nc1ccc(C(=O)O)cc1]

To a solution of 4-aminobenzoic acid (1.00 g, 7.29 mmol) in THF (10 mL) were added Boc$_2$O (3.18 g, 14.6 mmol) and TEA (3 mL, 21.9 mmol), and the mixture was stirred at 25° C. for 16 h. TLC showed the reaction was completed. A yellow solution was formed. The mixture was concentrated and poured into water (50 mL). The aqueous phase was acidified with HCl aq. (1N) to pH=6 and filtered. The residue was purified by crystallization from MTBE (30 mL) to afford 4-((tert-butoxycarbonyl)amino)benzoic acid (1.20 g, yield: 69%) as a white solid. $^1$H NMR (400 MHz, CDCl$_3$) δ 1.51 (9H, s), 6.76 (1H, br s), 7.45 (2H, d, J=8.8 Hz), 8.04 (2H, d, J=8.8 Hz).

Step 4: Preparation of tert-butyl (4-(((4-bromopyridin-2-yl)methyl)carbamoyl)phenyl)carbamate

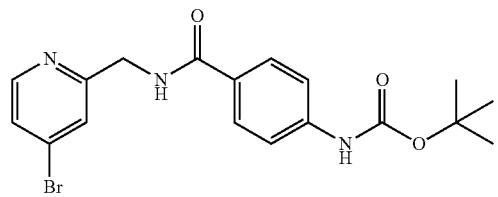 [SMILES: CC(C)(C)OC(=O)Nc1ccc(C(=O)NCc2cc(Br)ccn2)cc1]

A solution of 4-((tert-butoxycarbonyl)amino)benzoic acid (342 mg, 1.44 mmol) in pyridine (8 mL) was added (4-bromopyridin-2-yl)methanamine (250 mg, 0.962 mmol), EDCI (369 mg, 1.92 mmol) and the reaction was stirred at 20° C. for 15 h. The yellow solution turned to black. Crude LCMS (Rt=0.642 min; MS Calc'd: 405.1; MS Found: 405.7 [M+H]$^+$). The residue was purified by Combi Flash (8% MeOH in DCM) to give tert-butyl (4-(((4-bromopyridin-2-yl)methyl)carbamoyl)phenyl)carbamate (300 mg, yield: 77%) as a black solid. Crude LCMS is 85% (Rt=0.642 min; MS Calc'd: 405.1; MS Found: 405.7 [M+H]$^+$).

Step 5: Preparation of tert-butyl (4-(((2'-amino-5-(dimethylcarbamoyl)-[2,3':5',4"-terpyridin]-2"-yl)methyl)carbamoyl)phenyl)carbamate

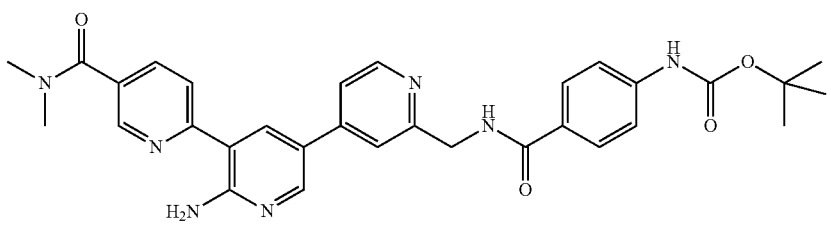 [SMILES: CN(C)C(=O)c1ccc(-c2cc(-c3ccnc(CNC(=O)c4ccc(NC(=O)OC(C)(C)C)cc4)c3)cnc2N)nc1]

A mixture of 2'-amino-N,N-dimethyl-5'-(4,4,5,5-tetramethyl-1,3,2-dioxaborolan-2-yl)-[2,3'-bipyridine]-5-carboxamide (300 mg, crude), tert-butyl (4-(((4-bromopyridin-2-yl)methyl)carbamoyl)phenyl)carbamate (188 mg, 0.463 mmol), $Cs_2CO_3$ (452 mg, 1.39 mmol) and $Pd(t-Bu_3P)_2$ (23 mg, 0.046 mmol, 10 mol %) in dioxane (1 mL) and $H_2O$ (0.1 mL) was stirred at 90-100° C. for 16 h under $N_2$ atmosphere. Crude LCMS (Rt=0.677 min; MS Calc'd: 567.3; MS Found: 568.3 [M+H]$^+$). A black solution was formed. The mixture was concentrated. The residue was purified by Combi Flash (8% MeOH in EtOAc) to give tert-butyl (4-(((2'-amino-5-(dimethylcarbamoyl)-[2,3':5',4"-terpyridin]-2"-yl)methyl)carbamoyl)phenyl)carbamate (90 mg, yield: 33%) as a yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 97.45%, Rt=1.249 min; MS Calc'd.: 567.3; MS Found: 568.1 [M+H]$^+$. $^1$H NMR (400 MHz, DMSO-$d_6$) δ 1.49 (9H, s), 3.01 (3H, s), 3.04 (3H, s), 4.62 (2H, d, J=6.0 Hz), 7.55 (2H, d, J=8.8 Hz), 7.69-7.75 (2H, m), 7.75-7.90 (4H, m), 8.01 (1H, d, J=2.4 Hz), 8.20 (1H, d, J=8.0 Hz), 8.42 (1H, d, J=2.4 Hz), 8.50-8.56 (2H, m), 8.73 (1H, d, J=1.6 Hz), 8.89 (1H, t, J=1.6 Hz), 9.63 (1H, br s).

Example 188: 2'-amino-2"-((4-aminobenzamido)methyl)-N,N-dimethyl-[2,3':5',4"-terpyridine]-5-carboxamide

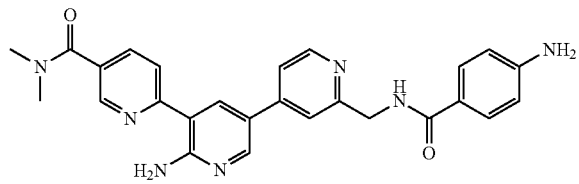 [SMILES: CN(C)C(=O)c1ccc(-c2cc(-c3ccnc(CNC(=O)c4ccc(N)cc4)c3)cnc2N)nc1]

To a solution of tert-butyl (4-(((2'-amino-5-(dimethylcarbamoyl)-[2,3':5',4"-terpyridin]-2"-yl)methyl)carbamoyl)phenyl)carbamate (88 mg, 0.155 mmol) in EtOAc (5 mL) was added HCl/EtOAc (4 M, 1 mL), and the mixture was stirred at 25° C. for 16 h. Crude LCMS (Rt=1.276 min; MS Calc'd: 467.2; MS Found: 468.1 [M+H]$^+$) and TLC showed the starting material was consumed completely. A white suspension was formed. The mixture was concentrated to give 2'-amino-2"-((4-aminobenzamido)methyl)-N,N-dimethyl-[2,3':5',4"-terpyridine]-5-carboxamide (92 mg, yield: 97%, 4HCl) as a yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 99.44%, Rt=1.276 min; MS Calc'd.: 467.3; MS Found: 468.1 [M+H]$^+$. $^1$H NMR (400 MHz, DMSO-$d_6$) δ 2.99 (3H, s), 3.04 (3H, s), 4.79 (2H, d, J=5.6 Hz), 6.84 (2H, d, J=8.0 Hz), 7.80 (2H, d, J=8.8 Hz), 8.08-8.15 (1H, m), 8.29-8.39 (1H, m), 8.40 (1H, d, J=8.4 Hz), 8.47 (1H, s), 8.72-8.85 (2H, m), 8.88 (2H, d, J=6.4 Hz), 9.13 (1H, br s). $^1$H NMR (400 MHz, DMSO-$d_6$+$D_{20}$) δ 2.99 (3H, s), 3.04 (3H, s), 4.78 (2H, s), 6.84 (2H, d, J=8.4 Hz), 7.78 (2H, d, J=8.4 Hz), 8.05-8.15 (1H, m), 8.29-8.39 (2H, m), 8.43 (1H, s), 8.70-8.89 (2H, m), 8.80-8.91 (2H, m).

Example 189: (E)-2'-amino-2"-((4-(4-(dimethylamino)but-2-enamido)benzamido)methyl)-N,N-dimethyl-[2,3':5',4"-terpyridine]-5-carboxamide

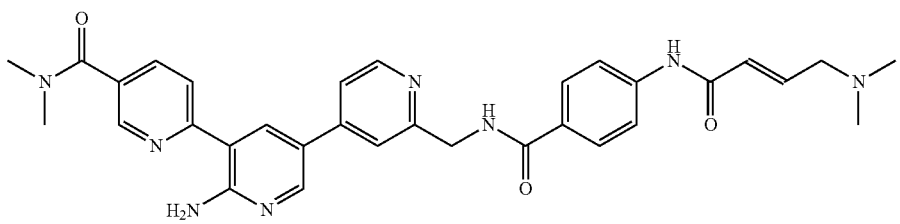

To a solution of (E)-4-(dimethylamino)but-2-enoic acid (29 mg, 0.18 mmol, HCl) and 2'-amino-2"-((4-aminobenzamido)methyl)-N,N-dimethyl-[2,3':5',4"-terpyridine]-5-carboxamide (90 mg, 0.15 mmol) in pyridine (5 mL) was added EDCI (56 mg, 0.29 mmol) under $N_2$ atmosphere. The mixture was stirred at 25° C. for 16 h under $N_2$ atmosphere. Crude LCMS (Rt=0.937 min; MS Calc'd: 578.3; MS Found: 579.2 [M+H]$^+$). A red solution was formed. The mixture was concentrated under reduced pressure. The residue was purified by prep-HPLC (0.05% $NH_3 \cdot H_2O$ as an additive) and lyophilized to give (E)-2'-amino-2"-((4-(4-(dimethylamino)but-2-enamido)benzamido)methyl)-N,N-dimethyl-[2,3':5',4"-terpyridine]-5-carboxamide (16 mg, yield: 19%) as a white solid. LCMS (Shimadzu LCMS 2010, mobile phase: from 100% [water+0.05% $NH_3 \cdot H_2O$] and 0% [MeCN] to 5% [water+0.05% $NH_3 \cdot H_2O$] and 95% [MeCN] in 5.8 min, then under this condition for 1.1 min, finally changed to 100% [water+0.05% $NH_3 \cdot H_2O$] and 0% [MeCN] and under this condition for 0.09 min.) purity is 99.01%, Rt=2.421 min; MS Calc'd.: 578.3, MS Found: 579.3 [M+H]$^+$.

$^1$H NMR (400 MHz, DMSO-$d_6$) δ 2.19 (6H, s), 2.95-3.10 (8H, m), 4.63 (2H, d, J=5.6 Hz), 6.30 (1H, d, J=15.2 Hz), 6.71-6.82 (1H, m), 7.65-7.85 (6H, m), 7.91 (2H, d, J=8.8 Hz), 7.94-8.03 (1H, m), 8.15-8.23 (1H, m), 8.20 (1H, d, J=2.4 Hz), 8.47-8.56 (2H, m), 8.73 (1H, d, J=1.6 Hz), 8.90-9.00 (1H, m), 10.30 (1H, br s).

Example 190: tert-butyl (3-(((2'-amino-5-(dimethylcarbamoyl)-[2,3':5',4"-terpyridin]-2"-yl)methyl)carbamoyl)phenyl)carbamate

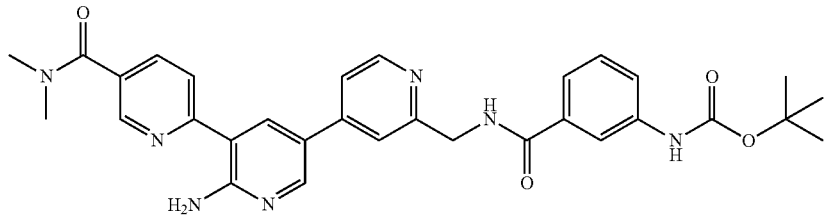 [SMILES: CN(C)C(=O)c1ccc(-c2cc(-c3ccnc(CNC(=O)c4cccc(NC(=O)OC(C)(C)C)c4)c3)cnc2N)nc1]

Step 1: Preparation of tert-butyl (3-(((4-bromopyridin-2-yl)methyl)carbamoyl)phenyl)carbamate

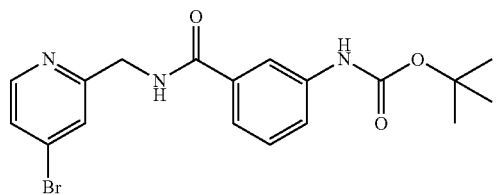 [SMILES: CC(C)(C)OC(=O)Nc1cccc(C(=O)NCc2cc(Br)ccn2)c1]

To a solution of (4-bromopyridin-2-yl)methanamine (300 mg, 1.15 mmol) and 3-((tert-butoxycarbonyl)amino)benzoic acid (273 mg, 1.15 mmol) in pyridine (3 mL) was added EDCI (441 mg, 2.30 mmol) under $N_2$ atmosphere. The mixture was stirred at 25° C. for 16 h under $N_2$ atmosphere. Crude LCMS (Rt=0.799 min; MS Calc'd: 405.1; MS Found: 406.0 [M+H]$^+$). A red solution was formed. The mixture was concentrated in reduced pressure. The residue was purified by Combi Flash (5% TEA in DCM) to afford tert-butyl (3-(((4-bromopyridin-2-yl)methyl)carbamoyl)phenyl)carbamate (200 mg, crude) as a yellow solid.

Step 2: Preparation of tert-butyl (3-(((2'-amino-5-(dimethylcarbamoyl)-[2,3':5',4"-terpyridin]-2"-yl)methyl)carbamoyl)phenyl)carbamate

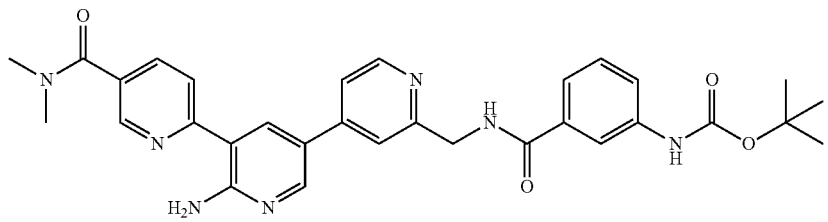 [SMILES: CN(C)C(=O)c1ccc(-c2cc(-c3ccnc(CNC(=O)c4cccc(NC(=O)OC(C)(C)C)c4)c3)cnc2N)nc1]

A mixture of 2'-amino-N,N-dimethyl-5'-(4,4,5,5-tetramethyl-1,3,2-dioxaborolan-2-yl)-[2,3'-bipyridine]-5-carboxamide (300 mg, Crude), tert-butyl (3-(((4-bromopyridin-2-yl)methyl)carbamoyl)phenyl)carbamate (200 mg, Crude), $CsCO_3$ (481 mg, 1.48 mmol) and Pd (t-Bu$_3$P)$_2$ (25 mg, 0.049 mmol, 10 mol %) in dioxane (1 mL) and $H_2O$ (0.1 mL) was stirred at 90-100° C. for 16 h under $N_2$ atmosphere. The color of the mixture was black still. Crude LCMS is 45% (Rt=0.704 min; MS Calc'd: 567.3; MS Found: 568.4 [M+H]$^+$). The mixture was concentrated under reduced pressure. The residue was purified by Combi Flash (10% MeOH in DCM) to give an impure product. Then the impure product was purified by re-crystallization from EtOAc (5 mL) to give tert-butyl (3-(((2'-amino-5-(dimethylcarbamoyl)-[2,3':5',4"-terpyridin]-2"-yl)methyl)carbamoyl)phenyl)carbamate (75 mg, yield: 27%) as a yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 98.02%, Rt=1.363 min; MS Calc'd: 567.3; MS Found: 568.1 [M+H]$^+$. $^1$H NMR (400 MHz, DMSO-d$_6$) δ 1.47 (9H, s), 3.00 (3H, s), 3.03 (3H, s), 4.61 (2H, d, J=5.2 Hz), 7.30-7.40 (1H, m), 7.45-7.59 (2H, m), 7.65-7.75 (2H, m), 7.90 (2H, br s), 7.95-8.05 (2H, m), 8.20 (1H, d, J=8.4 Hz), 8.42 (1H, d, J=2.4 Hz), 8.49-8.55 (2H, m), 8.72 (1H, d, J=2.4 Hz), 8.92-9.00 (1H, m), 9.51 (1H, br s).

Example 191: 2'-amino-2"-((3-aminobenzamido)methyl)-N,N-dimethyl-[2,3':5',4"-terpyridine]-5-carboxamide

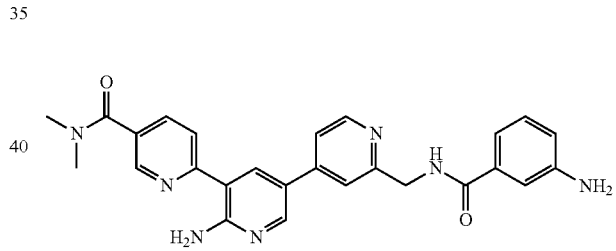

To a solution of tert-butyl (3-(((2'-amino-5-(dimethylcarbamoyl)-[2,3':5',4"-terpyridin]-2"-yl)methyl)carbamoyl)phenyl)carbamate (75 mg, 0.13 mmol) in EtOAc (5 mL) was added HCl/EtOAc (4 M, 50 mL), and the mixture was stirred at 25° C. for 1 hour. Crude LCMS is 86% (Rt=0.581 min; MS Calc'd: 467.2; MS Found: 468.3 [M+H]$^+$) and TLC showed the starting material was consumed completely. A white suspension was formed. The mixture was concentrated to give 2'-amino-2"-((3-aminobenzamido)methyl)-N,N-dimethyl-[2,3':5',4"-terpyridine]-5-carboxamide (80 mg, yield: 99%, 4HCl) as an off-white solid. LCMS (Shimadzu LCMS 2010, Mobile phase: from 100% [water+0.04% TFA] to 40% [water+0.04% TFA] and 60% [MeCN+0.02% TFA] in 1.35 min, then under this condition for 0.9 min, finally changed to 100% [water+0.04% TFA] and under this condition for 0.75 min.) purity is 98.16%, Rt=1.390 min; MS Calc'd.: 467.3; MS Found: 468.2 [M+H]$^+$. $^1$H NMR (400 MHz, DMSO-d$_6$) δ 2.99 (3H, s), 3.04 (3H, s), 4.85 (2H, d, J=5.6 Hz), 7.45-7.55 (1H, m), 7.55-7.65 (1H, m), 7.81 (1H, s), 7.95-8.06 (1H, m), 8.08-8.17 (1H, m), 8.30-8.40 (1H, m), 8.40-8.55 (2H, m), 8.80 (1H, s), 8.81-8.90 (1H, m), 8.94 (1H, s), 9.00 (1H, s), 9.58 (1H, br s). $^1$H NMR (400 MHz, DMSO-d$_6$+D$_2$O) δ 2.97 (3H, s), 3.02 (3H, s), 4.80 (2H, s), 7.32-7.40 (1H, m), 7.50-7.60 (1H, m), 7.68 (1H, s), 7.80 (1H, d, J=7.6 Hz), 8.05 (1H, dd, J=8.4, 1.6 Hz), 8.20 (1H, d, J=2.0 Hz), 8.27 (1H, s), 8.29 (1H, s), 8.68 (1H, d, J=6.0 Hz), 8.73 (2H, d, J=2.0 Hz), 8.81 (1H, s).

Example 192: (E)-2'-amino-2''-((3-(4-(dimethylamino)but-2-enamido)benzamido)methyl)-N,N-dimethyl-[2,3':5',4''-terpyridine]-5-carboxamide

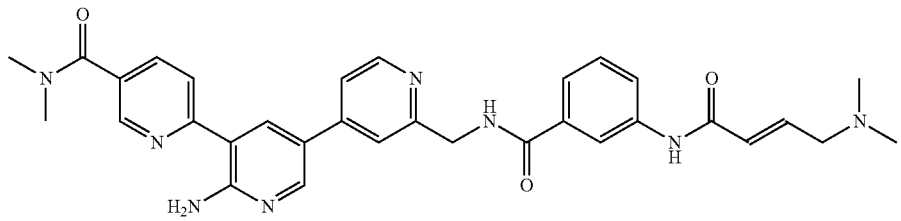

To a solution of 2'-amino-2''-((3-aminobenzamido)methyl)-N,N-dimethyl-[2,3':5',4''-terpyridine]-5-carboxamide (80 mg, 0.13 mmol, 4HCl) and (E)-4-(dimethylamino)but-2-enoic acid (26 mg, 0.16 mmol, HCl) in pyridine (5 mL) was added EDCI (50 mg, 0.26 mmol) under N$_2$ atmosphere. The mixture was stirred at 25° C. for 16 h under N$_2$ atmosphere. Crude LCMS (Rt=0.588 min; MS Calc'd: 578.3; MS Found: 579.1 [M+H]$^+$). A red solution was formed. The mixture was concentrated under reduced pressure. The residue was purified by prep-HPLC (0.05% NH$_3$·H$_2$O as an additive) and lyophilized to give (E)-2'-amino-2''-((3-(4-(dimethylamino)but-2-enamido)benzamido)methyl)-N,N-dimethyl-[2,3':5',4''-terpyridine]-5-carboxamide (23 mg, yield: 30%) as a white solid. LCMS (Shimadzu LCMS 2010, mobile phase: from 100% [water+0.05% NH$_3$·H$_2$O] and 0% [MeCN] to 5% [water+0.05% NH$_3$·H$_2$O] and 95% [MeCN] in 5.8 min, then under this condition for 1.1 min, finally changed to 100% [water+0.05% NH$_3$·H$_2$O] and 0% [MeCN] and under this condition for 0.09 min.) purity is 100.00%, Rt=2.641 min; MS Calc'd.: 578.3, MS Found: 579.3 [M+H]$^+$. $^1$H NMR (400 MHz, DMSO-d$_6$) δ 2.17 (6H, s), 2.95-3.10 (8H, m), 4.63 (2H, d, J=6.4 Hz), 6.27 (1H, d, J=16.0 Hz), 6.69-6.79 (1H, m), 7.42 (1H, t, J=8.0 Hz), 7.59-7.67 (1H, m), 7.70-7.89 (5H, m), 7.95-8.02 (1H, m), 8.15 (1H, s), 8.20 (1H, d, J=8.0 Hz), 8.40 (1H, d, J=2.0 Hz), 8.52 (1H, s), 8.53 (1H, s), 8.72 (1H, d, J=1.6 Hz), 8.95-9.05 (1H, m), 10.21 (1H, br s).

Example 193: tert-butyl (3-(3-(((2'-amino-5-(dimethylcarbamoyl)-[2,3':5',4''-terpyridin]-2''-yl)methyl)amino)-3-oxopropyl)phenyl)carbamate

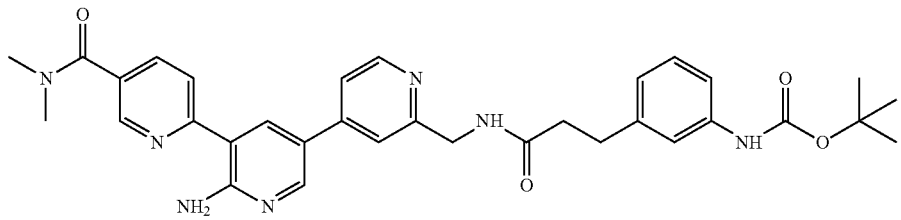 [SMILES: CN(C)C(=O)c1ccc(-c2cc(-c3ccnc(CNC(=O)CCc4cccc(NC(=O)OC(C)(C)C)c4)c3)cnc2N)nc1]

Step 1: Preparation of tert-butyl (3-(3-(((4-bromopyridin-2-yl)methyl)amino)-3-oxopropyl)phenyl)carbamate

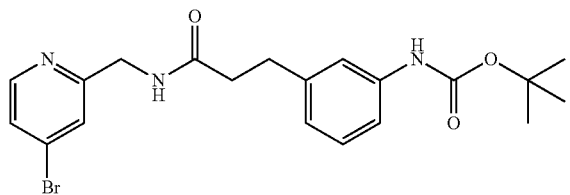 [SMILES: CC(C)(C)OC(=O)Nc1cccc(CCC(=O)NCc2cc(Br)ccn2)c1]

To a solution of 3-(3-((tert-butoxycarbonyl)amino)phenyl)propanoic acid (467 mg, 1.76 mmol) and (4-bromopyridin-2-yl)methanamine (300 mg, 1.60 mmol) in pyridine (5 mL) was added EDCI (613 mg, 3.20 mmol) under $N_2$ atmosphere. The mixture was stirred at 25° C. for 16 h under $N_2$ atmosphere. Crude LCMS (Rt=0.733 min; MS Calc'd: 433.1; MS Found: 435.8 [M+H]$^+$). The mixture was concentrated under reduced pressure. The residue was purified by Combi Flash (5% TEA in DCM) to give tert-butyl (3-(3-(((4-bromopyridin-2-yl)methyl)amino)-3-oxopropyl)phenyl)carbamate (200 mg, yield: 30%) as a yellow solid. LCMS is 70.54% (RT=0.766 min; MS Calc'd: 433.1; MS Found: 434.1[M+H]$^+$).

Step 2: Preparation of tert-butyl (3-(3-(((2'-amino-5-(dimethylcarbamoyl)-[2,3':5',4"-terpyridin]-2"-yl)methyl)amino)-3-oxopropyl)phenyl)carbamate

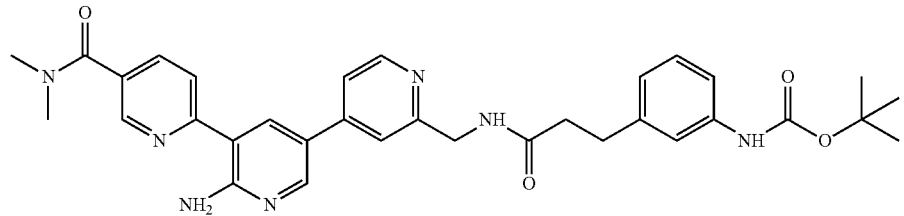 [SMILES: CN(C)C(=O)c1ccc(-c2cc(-c3ccnc(CNC(=O)CCc4cccc(NC(=O)OC(C)(C)C)c4)c3)cnc2N)nc1]

A mixture of 2'-amino-N,N-dimethyl-5'-(4,4,5,5-tetramethyl-1,3,2-dioxaborolan-2-yl)-[2,3'-bipyridine]-5-carboxamide (300 mg, Crude), tert-butyl (3-(3-(((4-bromopyridin-2-yl)methyl)amino)-3-oxopropyl)phenyl)carbamate (200 mg, 0.460 mmol), CsCO$_3$ (450 mg, 1.38 mmol) and Pd(t-Bu$_3$P)$_2$ (24 mg, 0.046 mmol, 10 mol %) in dioxane (1 mL) and H$_2$O (0.1 mL) was stirred at 90-100° C. for 16 h under N$_2$ atmosphere. Crude LCMS showed the starting material was consumed completely. A black solution was formed. The mixture was concentrated under reduced pressure. The residue was purified by Combi Flash (10% MeOH in DCM) to give an impure product. Then the impure product was purified by re-crystallization from EtOAc (5 mL) to give tert-butyl (3-(3-(((2'-amino-5-(dimethylcarbamoyl)-[2,3':5',4"-terpyridin]-2"-yl)methyl)amino)-3-oxopropyl)phenyl)carbamate (75 mg, yield: 27%) as an off-white solid. LCMS (Shimadzu LCMS 2010, Mobile phase: from 95% [water+0.04% TFA] and 5% [MeCN+0.02% TFA] to 5% [water+0.04% TFA] and 95% [MeCN+0.02% TFA] in 1.35 min, then under this condition for 0.9 min, finally changed to 5% [water+0.04% TFA] and 95% [MeCN+0.02% TFA] and under this condition for 0.75 min.) purity is 98.02%, Rt=1.363 min; MS Calc'd.: 595.3; MS Found: 596.1 [M+H]$^+$. $^1$HNMR (400 MHz, DMSO-d$_6$) δ 1.46 (9H, s), 2.42-2.50 (2H, m, overlapped with DMSO signal), 2.78 (2H, t, J=8.4 Hz), 3.00 (3H, s), 3.04 (3H, s), 4.42 (2H, d, J=6.0 Hz), 6.82 (1H, d, J=7.2 Hz), 7.12 (1H, t, J=7.2 Hz), 7.16-7.25 (1H, m), 7.38 (1H, s), 7.65-7.75 (2H, m), 7.85 (2H, br s), 7.94-8.01 (1H, m), 8.23 (1H, d, J=8.4 Hz), 8.40-8.50 (2H, m), 8.52 (1H, d, J=7.2 Hz), 8.73 (1H, d, J=2.0 Hz), 9.27 (1H, br s).

Example 194: 2'-amino-2"-((3-(3-aminophenyl)propanamido)methyl)-N,N-dimethyl-[2,3':5',4"-terpyridine]-5-carboxamide

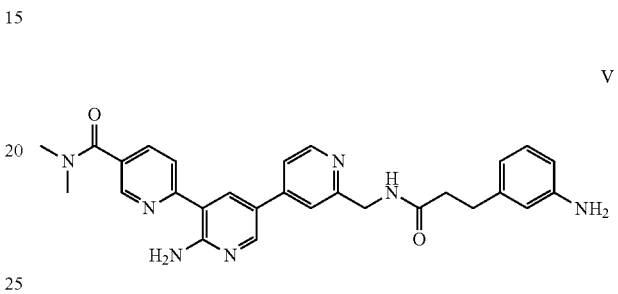

To a solution of tert-butyl (3-(3-(((2'-amino-5-(dimethylcarbamoyl)-[2,3':5',4"-terpyridin]-2"-yl)methyl)amino)-3-oxopropyl)phenyl)carbamate (75 mg, 0.12 mmol) in EtOAc (5 mL) was added HCl/EtOAc (4 M, 10 mL), and the mixture was stirred at 25° C. for 1 hour. Crude LCMS (Rt=0.586 min; MS Calc'd: 495.2; MS Found: 496.2 [M+H]$^+$) and TLC showed the starting material was consumed completely. A white suspension was formed. The mixture was concentrated to give 2'-amino-2"-((3-(3-aminophenyl)propanamido)methyl)-N,N-dimethyl-[2,3':5',4"-terpyridine]-5-carboxamide (80 mg, yield: 99%) as a white solid. LCMS (Shimadzu LCMS 2010, Mobile phase: from 100% [water+0.04% TFA] to 40% [water+0.04% TFA] and 60% [MeCN+0.02% TFA] in 1.35 min, then under this condition for 0.9 min, finally changed to 100% [water+0.04% TFA] and under this condition for 0.75 min.) purity is 96.66%, Rt=1.390 min; MS Calc'd.: 495.2; MS Found: 496.2 [M+H]$^+$. $^1$H NMR (400 MHz, DMSO-d$_6$) δ 2.50-2.80 (2H, m, overlapped with DMSO signal), 2.90-2.99 (2H, m), 3.00 (3H, s), 3.04 (3H, s), 4.59 (2H, d, J=7.2 Hz), 7.09-7.28 (3H, m), 7.29-7.41 (1H, m), 8.09 (1H, d, J=2.0 Hz), 8.20 (2H, br s), 8.38 (1H, d, J=8.4 Hz), 8.67-8.90 (5H, m). $^1$H NMR (400 MHz, DMSO-d$_6$+D$_2$O) δ 2.50-2.80 (2H, m, overlapped with DMSO signal), 2.90-2.97 (2H, m), 3.00 (3H, s), 3.04 (3H, s), 4.58 (2H, s), 7.08-7.22 (2H, m), 7.21-7.31 (1H, m), 7.31-7.42 (1H, m), 8.00-8.10 (1H, m), 8.10-8.27 (2H, m), 8.33 (1H, d, J=8.4 Hz), 8.63-8.82 (4H, m).

Example 195: (E)-2'-amino-2''-((3-(3-(4-(dimethylamino)but-2-enamido)phenyl)propanamido)methyl)-N,N-dimethyl-[2,3':5',4''-terpyridine]-5-carboxamide

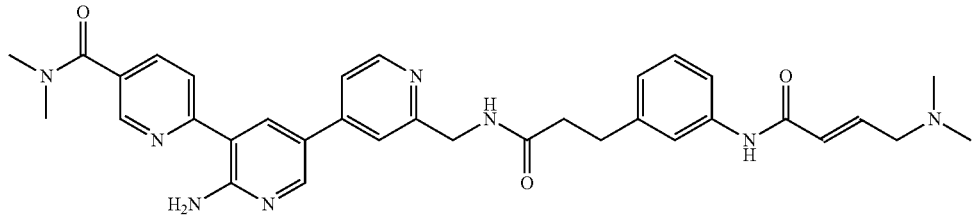

To a solution of 2'-amino-2''-((3-(3-aminophenyl)propanamido)methyl)-N,N-dimethyl-[2,3':5',4''-terpyridine]-5-carboxamide (78 mg, 0.12 mmol) and (E)-4-(dimethylamino)but-2-enoic acid (19 mg, 0.11 mmol, HCl) in pyridine (5 mL) was added EDCI (47 mg, 0.24 mmol) under $N_2$ atmosphere. The mixture was stirred at 25° C. for 16 h under $N_2$ atmosphere. Crude LCMS (Rt=0.588 min; MS Calc'd: 606.3; MS Found: 607.4 [M+H]$^+$). A solution was red. The mixture was concentrated under reduced pressure. The residue was purified by prep-HPLC (0.05% $NH_3 \cdot H_2O$ as an additive) and lyophilized to give (E)-2'-amino-2''-((3-(3-(4-(dimethylamino)but-2-enamido)phenyl)propanamido)methyl)-N,N-dimethyl-[2,3':5',4''-terpyridine]-5-carboxamide (16 mg, yield: 22%) as a yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 97.68%, Rt=1.205 min; MS Calc'd.: 606.3; MS Found: 607.1 [M+H]$^+$. $^1$H NMR (400 MHz, DMSO-d$_6$) δ 2.17 (6H, s), 2.84 (3H, t, J=7.2 Hz), 2.90-3.12 (9H, m), 4.42 (2H, d, J=5.6 Hz), 6.25 (1H, d, J=15.2 Hz), 6.65-7.77 (1H, m), 6.91 (1H, d, J=8.0 Hz), 7.10-7.21 (1H, m), 7.40-7.49 (1H, m), 7.53 (1H, s), 7.64-7.73 (2H, m), 7.80 (2H, br s), 7.95-8.01 (1H, m), 8.21 (1H, d, J=8.0 Hz), 8.36-8.45 (2H, m), 8.47-8.57 (2H, m), 8.72 (1H, d, J=1.6 Hz), 9.94 (1H, br s).

Example 196: 1-(4-(5-(5-(1-hydroxyethyl)-1-methyl-1H-pyrrolo[2,3-b]pyridin-3-yl)-4-methylpyridin-3-yl)phenyl)pyrrolidin-2-one

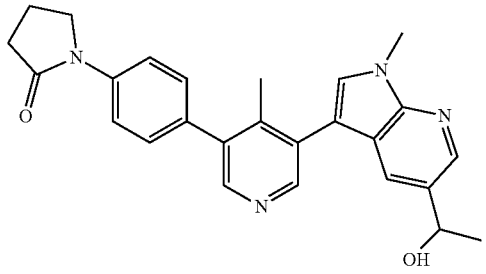 [SMILES: Cc1c(-c2ccc(N3CCCC3=O)cc2)cncc1-c1cn(C)c2ncc(C(C)O)cc12]

Step 1: Preparation of 1-(4-(5-bromo-4-methylpyridin-3-yl)phenyl)pyrrolidin-2-one

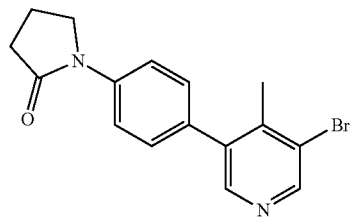 [SMILES: Cc1c(Br)cncc1-c1ccc(N2CCCC2=O)cc1]

First Batch

To a mixture of 1-(4-(4,4,5,5-tetramethyl-1,3,2-dioxaborolan-2-yl)phenyl)pyrrolidin-2-one (500 mg, 1.74 mmol), 3,5-dibromo-4-methyl-pyridine (524 mg, 2.09 mmol), Pd(dppf)Cl$_2$ (127 mg, 0.174 mmol) in dioxane (12 mL) was added Na$_2$CO$_3$ (461 mg, 4.35 mmol) and H$_2$O (2 mL), the resulting mixture was stirred at 85° C. under N$_2$ atmosphere for 3 hours to give a brown suspension. LCMS showed the purity of the desired product is 34% (Rt=0.789 min; MS Calcd: 332.0; MS Found: 332.9 [M+H]$^+$). The mixture was diluted with water (20 mL), then extracted with EtOAc (30 mL×2). The combined extracts were washed with brine (40 mL×2), dried over Na$_2$SO$_4$, filtered and concentrated under reduced pressure to give a residue (0.6 g, crude) as a brown gum. The residue was purified with next batch.

Second Batch: ES6958-486

To a mixture of 1-(4-(4,4,5,5-tetramethyl-1,3,2-dioxaborolan-2-yl)phenyl)pyrrolidin-2-one (1.30 g, 4.53 mmol), 3,5-dibromo-4-methyl-pyridine (1.48 g, 5.89 mmol), Pd(dppf)Cl$_2$ (166 mg, 0.226 mmol) in dioxane (50 mL) was added Na$_2$CO$_3$ (1.20 g, 11.3 mmol) and H$_2$O (8 mL), the resulting mixture was stirred at 85° C. under N$_2$ atmosphere for 3 hours to give a brown suspension. TLC (EtOAc) showed the reaction was completed. The mixture was diluted with water (40 mL), then extracted with EtOAc (60 mL×2). The combined extracts were washed with brine (50 mL×2), dried over Na$_2$SO$_4$, filtered and concentrated under reduced pressure to give a residue. The residue and the above batch were combined and purified by Combi Flash (PE/EtOAc=2/1 to ½ to 1/100), then washed with EtOAc (15 mL) to give 1-(4-(5-bromo-4-methylpyridin-3-yl)phenyl)pyrrolidin-2-one (1.3 g, average yield: 63%) as a white solid.

$^1$H NMR (400 MHz, DMSO-d$_6$) δ 2.02-2.12 (2H, m), 2.33 (3H, s), 2.48-2.51 (2H, m), 3.90 (2H, t, J=7.2 Hz), 7.43 (2H, d, J=8.8 Hz), 7.79 (2H, d, J=8.8 Hz), 8.35 (1H, s), 8.68 (1H, s).

Step 2: Preparation of 1-(4-(4-methyl-5-(4,4,5,5-tetramethyl-1,3,2-dioxaborolan-2-yl)pyridin-3-yl)phenyl)pyrrolidin-2-one

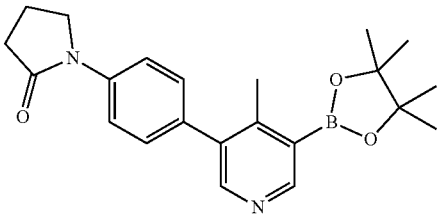 [SMILES: Cc1c(B2OC(C)(C)C(C)(C)O2)cncc1-c1ccc(N2CCCC2=O)cc1]

To a mixture of 1-(4-(5-bromo-4-methylpyridin-3-yl)phenyl)pyrrolidin-2-one (350 mg, 1.06 mmol), Bispin (349 mg, 1.37 mmol), Pd(dppf)Cl₂ (77 mg, 0.11 mmol) in dioxane (20 mL) was added KOAc (311 mg, 3.17 mmol), the resulting mixture was stirred at 100° C. under N₂ atmosphere for 16 hours to give a brown suspension. LCMS showed the reaction was completed. The mixture was filtered. The filtrate (a brown liquid) was used next step directly.

Step 3: Preparation of 1-(4-(5-(5-(1-hydroxyethyl)-1-methyl-1H-pyrrolo[2,3-b]pyridin-3-yl)-4-methylpyridin-3-yl)phenyl)pyrrolidin-2-one

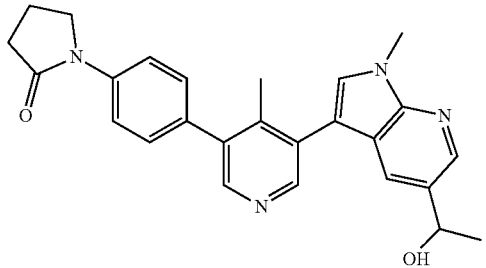 [SMILES: Cc1c(-c2ccc(N3CCCC3=O)cc2)cncc1-c1cn(C)c2ncc(C(C)O)cc12]

To a mixture of 1-(4-(4-methyl-5-(4,4,5,5-tetramethyl-1,3,2-dioxaborolan-2-yl)pyridin-3-yl)phenyl)pyrrolidin-2-one (0.4 g, 1.06 mmol, the brown liquid on the above) in dioxane (20 mL) was added 1-(3-bromo-1-methyl-H-pyrrolo[2,3-b]pyridin-5-yl)ethan-1-ol (270 mg, 1.06 mmol), Pd(dppf)Cl₂ (77 mg, 0.11 mmol) and Na₂CO₃ (280 mg, 2.64 mmol), H₂O (3 mL), the reaction mixture was stirred at 95° C. under N₂ atmosphere for 3 hours to give a brown suspension. LCMS showed the purity of product is 43% (Rt=0.709 min; MS Calcd: MS Found: 427.2 [M+H]⁺). The mixture was diluted with water (40 mL) and extracted with EtOAc (45 mL×2). The combined extracts were washed with brine (50 mL×2), dried over Na₂SO₄, filtered and concentrated under reduced pressure to give a residue. The residue was purified by Combi Flash (DCM/MeOH=100/1 to 95/5) (TLC:DCM/MeOH=20/1) to give an impure product (240 mg). Then further purified by prep-HPLC (0.225% FA as an additive) to give 1-(4-(5-(5-(1-hydroxyethyl)-1-methyl-1H-pyrrolo[2,3-b]pyridin-3-yl)-4-methylpyridin-3-yl)phenyl)pyrrolidin-2-one (100 mg, yield: 22%) as a white solid.

¹H NMR (400 MHz, DMSO-d₆) δ 1.40 (3H, d, J=6.4 Hz), 2.02-2.12 (2H, m), 2.24 (3H, s), 2.48-2.51 (2H, m), 3.85-3.93 (5H, m), 4.85-4.95 (1H, m), 7.52 (2H, d, J=8.4 Hz), 7.77 (1H, s), 7.81 (2H, d, J=8.4 Hz), 7.88 (1H, s), 8.35 (1H, d, J=1.6 Hz), 8.40 (1H, s), 8.54 (1H, s). Note: One active proton was not observed.

Step 4: Preparation of (R)-1-(4-(5-(5-(1-hydroxyethyl)-1-methyl-1H-pyrrolo[2,3-b]pyridin-3-yl)-4-methylpyridin-3-yl)phenyl)pyrrolidin-2-one; and

(S)-1-(4-(5-(5-(1-hydroxyethyl)-1-methyl-1H-pyrrolo[2,3-b]pyridin-3-yl)-4-methylpyridin-3-yl)phenyl)pyrrolidin-2-one

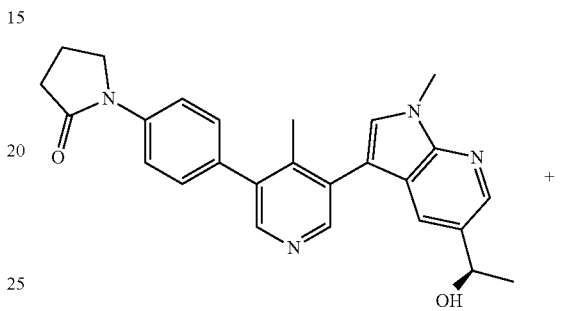

+

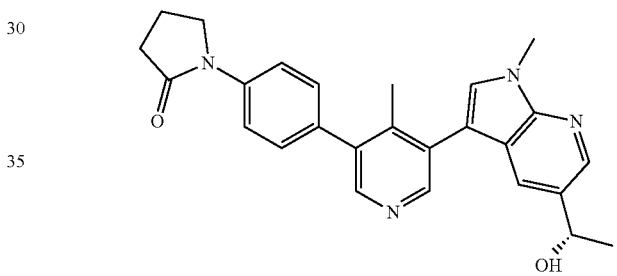

1-(4-(5-(5-(1-hydroxyethyl)-1-methyl-1H-pyrrolo[2,3-b]pyridin-3-yl)-4-methylpyridin-3-yl)phenyl)pyrrolidin-2-one (75 mg, 0.176 mmol) was further purified by SFC purification (column: YMC CHIRAL Amylose-C (250 mm*30 mm, 10 um; mobile phase: [0.1% NH₃H₂O ETOH]; B %: 40%-40%, min) to give (R)-1-(4-(5-(5-(1-hydroxyethyl)-1-methyl-1H-pyrrolo[2,3-b]pyridin-3-yl)-4-methylpyridin-3-yl)phenyl)pyrrolidin-2-one (peak 1, Rt: 2.839 min, 30.3 mg, yield: 40%, ee>99%) as a white solid and (S)-1-(4-(5-(5-(1-hydroxyethyl)-1-methyl-1H-pyrrolo[2,3-b]pyridin-3-yl)-4-methylpyridin-3-yl)phenyl)pyrrolidin-2-one (peak 2, Rt: 3.325 min, 32.8 mg, yield: 44%, ee: 98.77%) as a white solid.

¹H NMR (400 MHz, DMSO-d₆) δ 1.41 (3H, d, J=6.4 Hz), 2.02-2.12 (2H, m), 2.23 (3H, s), 2.48-2.51 (2H, m), 3.85-3.93 (5H, m), 4.85-4.95 (1H, m), 5.22 (1H, brs), 7.51 (2H, d, J=8.4 Hz), 7.76 (1H, s), 7.81 (2H, d, J=8.4 Hz), 7.88 (1H, d, J=1.2 Hz), 8.35 (1H, d, J=1.6 Hz), 8.37 (1H, s), 8.52 (1H, s).

¹H NMR (400 MHz, DMSO-d₆) δ 1.41 (3H, d, J=6.4 Hz), 2.02-2.12 (2H, m), 2.23 (3H, s), 2.48-2.51 (2H, m), 3.85-3.93 (5H, m), 4.85-4.95 (1H, m), 5.22 (1H, brs), 7.51 (2H, d, J=8.4 Hz), 7.76 (1H, s), 7.81 (2H, d, J=8.4 Hz), 7.88 (1H, d, J=2.0 Hz), 8.35 (1H, d, J=1.6 Hz), 8.36 (1H, s), 8.51 (1H, s).

Example 197: 1-(4-(5-(5-(1-hydroxyethyl)-1-methyl-1H-pyrrolo[2,3-b]pyridin-3-yl)pyridin-3-yl)-3-methylphenyl)pyrrolidin-2-one

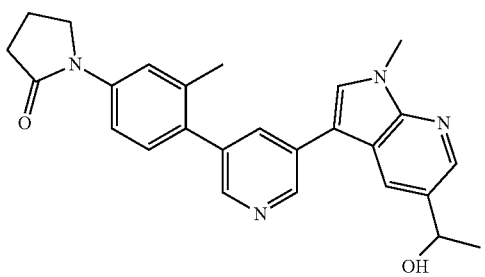 [SMILES: Cc1cc(N2CCCC2=O)ccc1-c1cncc(-c2cn(C)c3ncc(C(C)O)cc23)c1]

Step 1: Preparation of 1-(4-(5-bromopyridin-3-yl)-3-methylphenyl)pyrrolidin-2-one

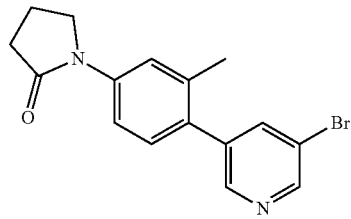 [SMILES: Cc1cc(N2CCCC2=O)ccc1-c1cncc(Br)c1]

To a mixture of 1-(3-methyl-4-(4,4,5,5-tetramethyl-1,3,2-dioxaborolan-2-yl)phenyl)pyrrolidin-2-one (2.70 g, 8.96 mmol), 3,5-dibromopyridine (2.76 g, 11.6 mmol), Pd(dppf)Cl$_2$ (328 mg, 0.448 mmol) in dioxane (50 mL) was added Na$_2$CO$_3$ (2.09 g, 19.7 mmol) and H$_2$O (8 mL), the resulting mixture was stirred at 90° C. under N$_2$ atmosphere for 3 hours to give a brown suspension. LCMS showed the purity of the desired product is 37% (Rt=0.815 min; MS Calcd: 332.0; MS Found: 332.8 [M+H]$^+$). The mixture was diluted with water (50 mL), then extracted with EtOAc (50 mL×2). The combined extracts were washed with brine (60 mL×2), dried over Na$_2$SO$_4$, filtered and concentrated under reduced pressure to give a residue. The residue was purified by Combi Flash (PE/EtOAc=4/1 to 2/1 to ⅔) to give 1-(4-(5-bromopyridin-3-yl)-3-methylphenyl)pyrrolidin-2-one (1.4 g, yield: 47%) as a brown gum.

$^1$H NMR (400 MHz, DMSO-d$_6$) δ 2.02-2.12 (2H, m), 2.28 (3H, s), 2.48-2.51 (2H, m), 3.87 (2H, t, J=6.8 Hz), 7.29 (1H, d, J=8.0 Hz), 7.60-7.65 (2H, m), 8.09 (1H, t, J=2.4 Hz), 8.57 (1H, d, J=1.6 Hz), 8.71 (1H, d, J=2.0 Hz).

Step 2: Preparation of 1-(3-methyl-4-(5-(4,4,5,5-tetramethyl-1,3,2-dioxaborolan-2-yl)pyridin-3-yl)phenyl)pyrrolidin-2-one

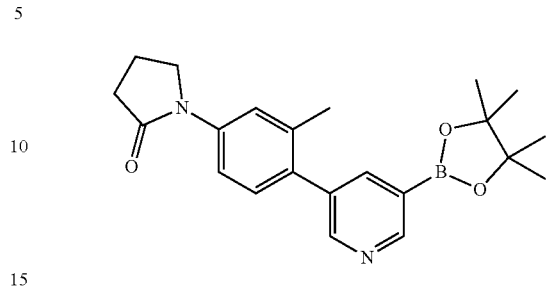

To a mixture of 1-(4-(5-bromopyridin-3-yl)-3-methylphenyl)pyrrolidin-2-one (400 mg, 1.21 mmol), Bispin (399 mg, 1.57 mmol), Pd(dppf)Cl$_2$ (88 mg, 0.12 mmol) in dioxane (20 mL) was added KOAc (355 mg, 3.62 mmol), the resulting mixture was stirred at 85° C. under N$_2$ atmosphere for 16 hours to give a brown suspension. LCMS showed the purity of desired product MS value is 69%. The mixture was cooled to room temperature and filtered. The filtrate was used next step directly (456 mg, crude) as a brown liquid.

Step 3: Preparation of 1-(4-(5-(5-(1-hydroxyethyl)-1-methyl-H-pyrrolo[2,3-b]pyridin-3-yl)pyridin-3-yl)-3-methylphenyl)pyrrolidin-2-one

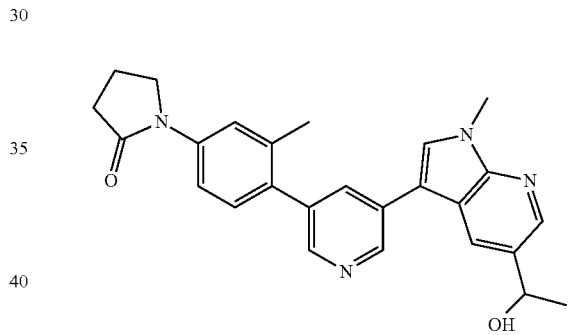

To a mixture of 1-(3-methyl-4-(5-(4,4,5,5-tetramethyl-1,3,2-dioxaborolan-2-yl)pyridin-3-yl)phenyl)pyrrolidin-2-one (456 mg, crude on page ES6958-506) in dioxane (12 mL) was added 1-(3-bromo-1-methyl-1H-pyrrolo[2,3-b]pyridin-5-yl)ethan-1-ol (307 mg, 1.21 mmol), Pd(dppf)Cl$_2$ (88 mg, 0.12 mmol) and Na$_2$CO$_3$ (319 mg, 3.01 mmol), H$_2$O (2 mL), the reaction mixture was stirred at 95° C. under N$_2$ atmosphere for 4 hours to give a brown suspension. LCMS showed the purity of product is 44% (Rt=0.735 min; MS Calcd: 426.2; MS Found: 449.1[M+Na]+). The mixture and another batch were combined and filtered. The filter cake as washed with EtOAc (10 mL×2). The filtrate was diluted with water (20 mL) and extracted with EtOAc (30 mL×2). The combined extracts were washed with brine (40 mL×2), dried over Na$_2$SO$_4$, filtered and concentrated under reduced pressure to give a residue. The residue was purified by Combi Flash (DCM/MeOH=100/1 to 95/1 to 10/1) to give an impure product. Then further purified by prep-HPLC (0.225% FA as an additive) to give 1-(4-(5-(5-(1-hydroxyethyl)-1-methyl-1H-pyrrolo[2,3-b]pyridin-3-yl)pyridin-3-yl)-3-methylphenyl)pyrrolidin-2-one (225 mg, average yield: 35%) as a white solid.

$^1$H NMR (400 MHz, DMSO-d$_6$) δ 1.43 (3H, d, J=6.4 Hz), 2.02-2.12 (2H, m), 2.36 (3H, s), 2.48-2.51 (2H, m), 3.85-

3.93 (5H, m), 4.92-4.96 (1H, m), 5.26 (1H, brs), 7.37 (1H, d, J=8.4 Hz), 7.63-7.68 (2H, m), 8.02 (1H, t, J=2.0 Hz), 8.14 (1H, s), 8.28 (1H, d, J=2.0 Hz), 8.35 (1H, d, J=1.6 Hz), 8.45 (1H, d, J=2.4 Hz), 8.95 (1H, d, J=2.4 Hz).

Step 4: Preparation of (R)-1-(4-(5-(5-(1-hydroxyethyl)-1-methyl-H-pyrrolo[2,3-b]pyridin-3-yl)pyridin-3-yl)-3-methylphenyl)pyrrolidin-2-one; and (S)-1-(4-(5-(5-(1-hydroxyethyl)-1-methyl-1H-pyrrolo[2,3-b]pyridin-3-yl)pyridin-3-yl)-3-methylphenyl)pyrrolidin-2-one

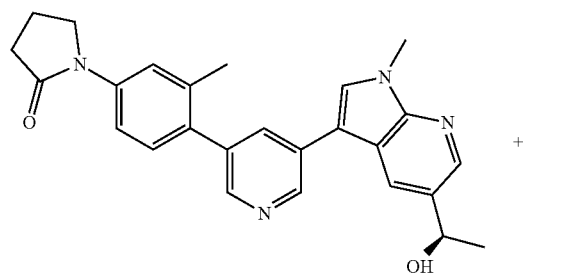

+

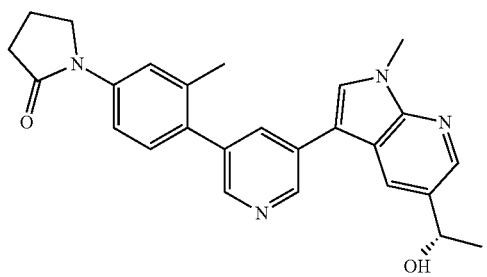 [SMILES: Cc1cc(N2CCCC2=O)ccc1-c1cncc(-c2cn(C)c3ncc(C(C)O)cc23)c1]

1-(4-(5-(5-(1-hydroxyethyl)-1-methyl-1H-pyrrolo[2,3-b]pyridin-3-yl)pyridin-3-yl)-3-methylphenyl)pyrrolidin-2-one (200 mg, 0.469 mmol) was further purified by SFC purification (column: YMC CHIRAL Amylose-C (250 mm*30 mm, 10 um; mobile phase: [0.1% NH₃H₂O ETOH];B %: 50%-50%, min) to give (R)-1-(4-(5-(5-(1-hydroxyethyl)-1-methyl-1H-pyrrolo[2,3-b]pyridin-3-yl)pyridin-3-yl)-3-methylphenyl)pyrrolidin-2-one (peak 1, Rt: 1.331 min, 58.2 mg, yield: 29%, ee: 100%) as a white solid and (S)-1-(4-(5-(5-(1-hydroxyethyl)-1-methyl-1H-pyrrolo[2,3-b]pyridin-3-yl)pyridin-3-yl)-3-methylphenyl)pyrrolidin-2-one (peak 2, Rt: 1.590 min, 69.2 mg, yield: 35%, ee: 97.87%) as a white solid.

¹H NMR (400 MHz, DMSO-d₆) δ 1.43 (3H, d, J=6.4 Hz), 2.02-2.12 (2H, m), 2.36 (3H, s), 2.48-2.51 (2H, m), 3.85-3.93 (5H, m), 4.92-4.96 (1H, m), 5.26 (1H, brs), 7.37 (1H, d, J=8.8 Hz), 7.63-7.68 (2H, m), 8.04 (1H, t, J=2.0 Hz), 8.15 (1H, s), 8.28 (1H, d, J=2.0 Hz), 8.35 (1H, d, J=2.0 Hz), 8.45 (1H, d, J=1.6 Hz), 8.95 (1H, d, J=1.6 Hz).

¹H NMR (400 MHz, DMSO-d₆) δ 1.43 (3H, d, J=6.4 Hz), 2.02-2.12 (2H, m), 2.36 (3H, s), 2.48-2.51 (2H, m), 3.85-3.93 (5H, m), 4.92-4.96 (1H, m), 5.27 (1H, brs), 7.37 (1H, d, J=8.8 Hz), 7.63-7.68 (2H, m), 8.02 (1H, t, J=2.0 Hz), 8.15 (1H, s), 8.28 (1H, d, J=2.0 Hz), 8.35 (1H, d, J=2.0 Hz), 8.45 (1H, d, J=2.0 Hz), 8.95 (1H, d, J=2.0 Hz).

Example 198: (R)-7-methyl-4-(5-(4-(4-methyl-2-oxopyrrolidin-1-yl)phenyl)pyridin-3-yl)-8,9-dihydropyrido[3',2':4,5]pyrrolo[1,2-a]pyrazin-6(7H)-one

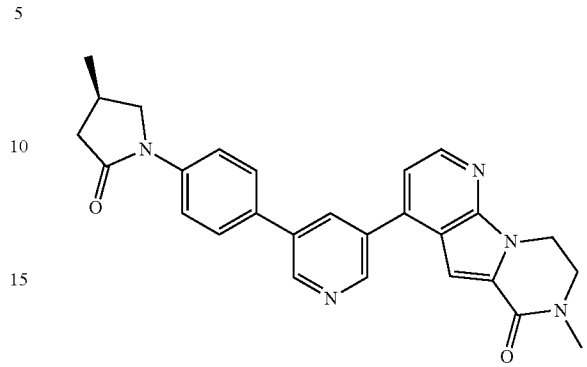

Step 1: Preparation of 4-chloro-7-methyl-8,9-dihydropyrido[3',2':4,5]pyrrolo[1,2-a]pyrazin-6(7H)-one

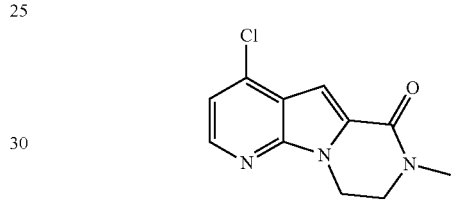

Step 1a. Preparation of methyl 1-(2-((tert-butoxycarbonyl)amino)ethyl)-4-chloro-1H-pyrrolo[2,3-b]pyridine-2-carboxylate

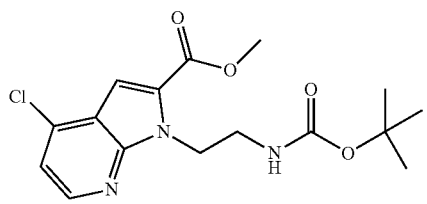 [SMILES: COC(=O)c1cc2c(Cl)ccnc2n1CCNC(=O)OC(C)(C)C]

methyl 4-chloro-1H-pyrrolo[2,3-b]pyridine-2-carboxylate (1.50 g, 7.12 mmol) was taken up in DMF (25 mL), cooled to 0° C. and KOtBu (825 mg, 7.35 mmol) was added. After 30 min, tert-butyl 1,2,3-oxathiazolidine-3-carboxylate 2,2-dioxide (1.72 g, 7.73 mmol) was added. The reaction mixture was warmed to 20° C., stirred at 20° C. for 1.5 hours under N₂ atmosphere. A yellow solution was formed gradually. LCMS showed the starting material was consumed completely, and the purity of the desired product is 62% (Rt=0.631 min; MS Calcd: 353.1; MS Found: 354.0 [M+H]⁺). Aq. 10% citric acid (30 mL) and EA (30 mL) were added and the organic layer separated. The aqueous layer was extracted with EtOAc (50 mL×3). The combined organics were washed with water (30 mL×3), brine (50 mL), dried over Na₂SO₄, filtered and concentrated to give methyl 1-(2-((tert-butoxycarbonyl)amino)ethyl)-4-chloro-1H-pyrrolo[2,3-b]pyridine-2-carboxylate (3.35 g, crude) as a yellow gum. Used for the next step without further purification.

Step 1b. Preparation of methyl 1-(2-aminoethyl)-4-chloro-1H-pyrrolo[2,3-b]pyridine-2-carboxylate

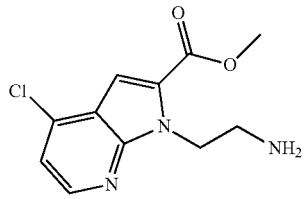 [SMILES: COC(=O)c1cc2c(Cl)ccnc2n1CCN]

TFA (5.3 mL, 71 mmol) was added to a solution of methyl 1-(2-((tert-butoxycarbonyl)amino)ethyl)-4-chloro-1H-pyrrolo[2,3-b]pyridine-2-carboxylate (2.52 g, 7.12 mmol) in DCM (15 mL) at 20° C. and the mixture was stirred at 20° C. for 14 hours. A red solution was formed. LCMS showed the starting material was consumed completely, the purity of the desired product is 87% (Rt=0.553 min; MS Calcd: 253.1; MS Found: 253.9 [M+H]$^+$). The mixture was concentrated to give methyl 1-(2-aminoethyl)-4-chloro-H-pyrrolo[2,3-b]pyridine-2-carboxylate (3 g, crude) as a red gum. Used for the next step without further purification.

Step 1c. Preparation of 4-chloro-8,9-dihydropyrido[3',2':4,5]pyrrolo[1,2-a]pyrazin-6(7H)-one

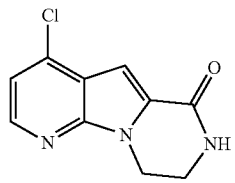 [SMILES: O=C1NCCn2c1cc1c(Cl)ccnc12]

methyl 1-(2-aminoethyl)-4-chloro-1H-pyrrolo[2,3-b]pyridine-2-carboxylate (2.62 g, 7.13 mmol) in MeOH (15 mL) was added K$_2$CO$_3$ (3.94 g, 28.5 mmol). And the mixture was stirred at 10° C. for 20 hours. A yellow mixture was formed. LCMS showed the starting material was remained. And the mixture was stirred at 30° C. for 5 hours. LCMS showed the purity of the desired product is 47% (Rt=0.566 min; MS Calcd: 221.0; MS Found: 221.8 [M+H]$^+$). Water (25 mL) and EtOAc (50 mL) were added and the organic layer separated. The aqueous layer was extracted with DCM (40 mL×2) and the combined organics were washed with brine (20 mL), dried over Na$_2$SO$_4$, filtered and concentrated. The residue was triturated with MeCN (30 mL) for 2 hours to give 4-chloro-8,9-dihydropyrido[3',2':4,5]pyrrolo[1,2-a]pyrazin-6(7H)-one (1.39 g, yield: 88% for three steps) as a yellow solid.

$^1$H NMR (400 MHz, CDCl$_3$) δ 3.82-3.88 (2H, m), 4.90 (2H, t, J=6.0 Hz), 6.41 (1H, brs), 7.18 (1H, d, J=5.2 Hz), 7.35 (1H, s), 8.34 (1H, d, J=5.2 Hz).

Step 1d. Preparation of 4-chloro-7-methyl-8,9-dihydropyrido[3',2':4,5]pyrrolo[1,2-a]pyrazin-6(7H)-one

To a solution of 4-chloro-8,9-dihydropyrido[3',2':4,5]pyrrolo[1,2-a]pyrazin-6(7H)-one (1.00 g, 4.51 mmol) in THF (25 mL) was added NaH (722 mg, 18.0 mmol, 60% in mineral oil) at 10° C. for 0.5 hour, and then added CH$_3$I (768 mg, 5.41 mmol) dropwise. The reaction mixture was stirred at 10° C. for 14 hours under N$_2$ atmosphere. A yellow mixture was formed gradually. LCMS showed the starting material was remained. The reaction mixture was stirred at 25° C. for 4 hours under N$_2$ atmosphere. LCMS showed the purity of the desired product is 95% (Rt=0.588 min; MS Calcd: 235.1; MS Found: 235.9 [M+H]$^+$). The solution was quenched with aq. NH$_4$Cl (25 mL) and the organic layer separated. The aqueous layer was extracted with EA (50 mL×2) and the combined organics were washed with brine (30 mL), dried over Na$_2$SO$_4$, filtered and concentrated to give 4-chloro-7-methyl-8,9-dihydropyrido[3',2':4,5]pyrrolo[1,2-a]pyrazin-6(7H)-one (1.06 g, yield: quantitative) as a yellow solid.

Step 2. Preparation of (R)-4-methyl-1-(4-(5-(4,4,5,5-tetramethyl-1,3,2-dioxaborolan-2-yl)pyridin-3-yl)phenyl)pyrrolidin-2-one

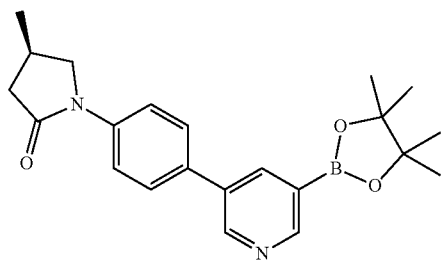 [SMILES: C[C@@H]1CC(=O)N(c2ccc(-c3cncc(B4OC(C)(C)C(C)(C)O4)c3)cc2)C1]

Step 2a. Preparation of (R)-1-(4-bromophenyl)-4-methylpyrrolidin-2-one

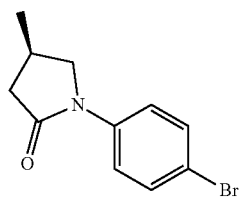

A mixture of (R)-4-methylpyrrolidin-2-one (50 mg, 0.50 mmol), 1-bromo-4-iodobenzene (171 mg, 0.605 mmol), CuI (29 mg, 0.15 mmol), CsF (192 mg, 1.26 mmol) in EtOAc (3 mL) was degassed and purged with N₂ for 3 times. Then N, N'-dimethylethylene diamine (27 mg, 0.30 mmol) was added into above mixture, the resulting reaction mixture was stirred at 50° C. for 16 hours. A blue suspension was formed. TLC showed (R)-4-methylpyrrolidin-2-one was consumed completely. The reaction mixture was diluted with water (20 mL). The aqueous layer was extracted with EtOAc/THF (30 mL×3, 1/1). The combined organic layer was washed with water (20 mL×2), brine (30 mL), dried over anhydrous Na₂SO₄, filtered and concentrated under reduced pressure. The residue was purified by Combi Flash (20% to 50% EtOAc in PE) to give (R)-1-(4-bromophenyl)-4-methylpyrrolidin-2-one (128 mg, yield: quantitative) as a light yellow solid.

¹H NMR (400 MHz, CDCl₃) δ 1.22 (3H, d, J=6.8 Hz), 2.22-2.31 (1H, m), 2.51-2.63 (1H, m), 2.70-2.80 (1H, m), 3.38-3.45 (1H, m), 3.67-3.95 (1H, m), 7.35-7.68 (4H, m).

Step 2b. Preparation of (R)-4-methyl-1-(4-(4,4,5,5-tetramethyl-1,3,2-dioxaborolan-2-yl)phenyl)pyrrolidin-2-one

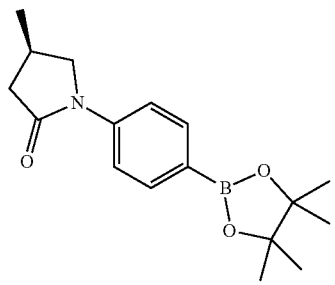 [SMILES: C[C@@H]1CC(=O)N(c2ccc(B3OC(C)(C)C(C)(C)O3)cc2)C1]

A mixture of (R)-1-(4-bromophenyl)-4-methylpyrrolidin-2-one (128 mg, 0.504 mmol), Bispin (153 mg, 0.604 mmol), Pd(dppf)Cl₂ (37 mg, 0.050 mmol) and KOAc (148 mg, 1.51 mmol) in anhydrous dioxane (5 mL) was degassed and purged with N₂ for 3 times. And the resulting mixture was stirred at 100° C. for 16 hours under N₂ atmosphere. A black suspension was formed. LCMS showed the purity of the desired product is 78% (Rt=0.867 min; MS Calcd: 301.2; MS Found: 301.9 [M+H]⁺). The reaction mixture was filtered through a pad of celite, washed with EtOAc (50 mL) and concentrated under reduced pressure to give (R)-4-methyl-1-(4-(4,4,5,5-tetramethyl-1,3,2-dioxaborolan-2-yl)phenyl)pyrrolidin-2-one (crude), which was used for the next step without further purification.

Step 2c. Preparation of (R)-1-(4-(5-bromopyridin-3-yl)phenyl)-4-methylpyrrolidin-2-one

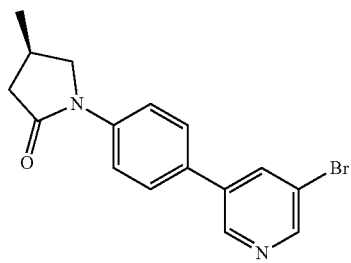 [SMILES: C[C@@H]1CC(=O)N(c2ccc(-c3cncc(Br)c3)cc2)C1]

A mixture of (R)-4-methyl-1-(4-(4,4,5,5-tetramethyl-1,3,2-dioxaborolan-2-yl)phenyl)pyrrolidin-2-one (crude), 3,5-dibromopyridine (178 mg, 0.752 mmol), Pd(dppf)Cl₂ (18 mg, 0.025 mmol) and Na₂CO₃ (159 mg, 1.50 mmol) in dioxane (4 mL) and water (1 mL) was degassed and purged with N₂ for 3 times. And the resulting reaction mixture was stirred at 100° C. for 4 hours under N₂ atmosphere. A black suspension was formed. LCMS showed the purity of the desired product is 39% (Rt=0.675 min; MS Calcd: 330.0; MS Found: 331.0 [M+H]⁺). The reaction mixture was diluted with water (20 mL). The aqueous layer was extracted with EtOAc (30 mL×2). The combined organic layer was washed with water (20 mL×2), brine (30 mL), dried over anhydrous Na₂SO₄, filtered and concentrated under reduced pressure. The residue was purified by Combi Flash (2% to 50% EtOAc in PE) to give (R)-1-(4-(5-bromopyridin-3-yl)phenyl)-4-methylpyrrolidin-2-one (100 mg, yield: 60% for two steps) as a light yellow solid.

Step 2d. Preparation of (R)-4-methyl-1-(4-(5-(4,4,5,5-tetramethyl-1,3,2-dioxaborolan-2-yl)pyridin-3-yl)phenyl)pyrrolidin-2-one

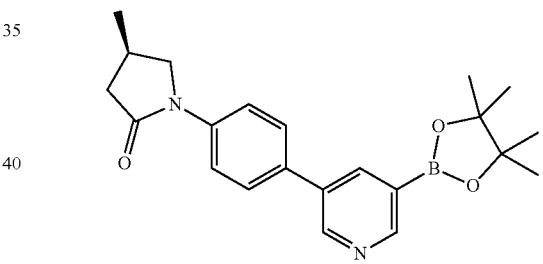

A mixture of (R)-1-(4-(5-bromopyridin-3-yl)phenyl)-4-methylpyrrolidin-2-one (100 mg, 0.302 mmol), Bispin (92 mg, 0.36 mmol), Pd(dppf)Cl₂ (22 mg, 0.030 mmol) and KOAc (89 mg, 0.51 mmol) in anhydrous dioxane (3 mL) was degassed and purged with N₂ for 3 times. And the resulting mixture was stirred at 100° C. for 16 hours under N₂ atmosphere. A black suspension was formed. LCMS showed the purity of the boronic acid of the desired product is 40% (Rt=0.721 min; MS Calcd: 296.1; MS Found: 297.0 [M+H]⁺). The reaction mixture was filtered through a pad of celite, washed with EtOAc (50 mL) and concentrated under reduced pressure to give (R)-4-methyl-1-(4-(5-(4,4,5,5-tetramethyl-1,3,2-dioxaborolan-2-yl)pyridin-3-yl)phenyl)pyrrolidin-2-one (crude), which was used for the next step without further purification.

Step 3. Preparation of (R)-7-methyl-4-(5-(4-(4-methyl-2-oxopyrrolidin-1-yl)phenyl)pyridin-3-yl)-8,9-dihydropyrido[3',2':4,5]pyrrolo[1,2-a]pyrazin-6(7H)-one

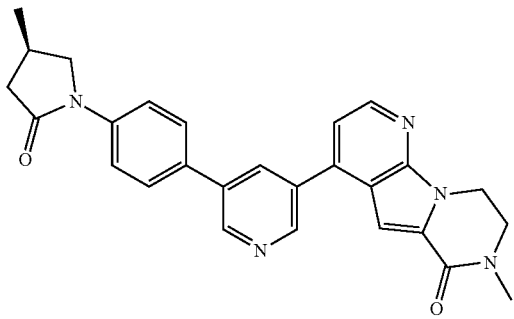 [SMILES: C[C@@H]1CC(=O)N(c2ccc(-c3cncc(-c4ccnc5c4cc4n5CCN(C)C4=O)c3)cc2)C1]

A mixture of (R)-4-methyl-1-(4-(5-(4,4,5,5-tetramethyl-1,3,2-dioxaborolan-2-yl)pyridin-3-yl)phenyl)pyrrolidin-2-one (crude), 4-chloro-7-methyl-8,9-dihydropyrido[3',2':4,5]pyrrolo[1,2-a]pyrazin-6(7H)-one (71 mg, 0.301 mmol), Pd(t-Bu$_3$P)$_2$ (15 mg, 0.030 mmol) and Cs$_2$CO$_3$ (196 mg, 0.602 mmol) in dioxane (3 mL) and water (0.8 mL) was degassed and purged with N$_2$ for 3 times. And the resulting reaction mixture was stirred at 100° C. for 16 hours under N$_2$ atmosphere. A black suspension was formed. LCMS showed the purity of the desired product is 52% (Rt=0.623 min; MS Calcd: 451.2; MS Found: 452.2 [M+H]$^+$). The reaction mixture was diluted with water (20 mL). The aqueous layer was extracted with EtOAc/THF (30 mL×3, 1/1). The combined organic layer was washed with water (20 mL×2), brine (30 mL), dried over anhydrous Na$_2$SO$_4$, filtered and concentrated under reduced pressure. The residue was purified by prep-HPLC (0.225% FA as an additive), prep-TLC (DCM/MeOH, 10/1) and further triturated with MeCN (3 mL) to give (R)-7-methyl-4-(5-(4-(4-methyl-2-oxopyrrolidin-1-yl)phenyl)pyridin-3-yl)-8,9-dihydropyrido[3',2':4,5]pyrrolo[1,2-a]pyrazin-6(7H)-one (14.8 mg, yield: 11% for two steps) as a white solid.

$^1$H NMR (400 MHz, DMSO-d$_6$) δ 1.15 (3H, d, J=6.8 Hz), 2.23 (1H, dd, J=16.4, 7.4 Hz), 2.53-2.59 (1H, m), 2.69 (1H, dd, J=16.8, 8.4 Hz), 3.10 (3H, s), 3.51 (1H, dd, J=9.6, 8.4 Hz), 3.88 (2H, t, J=5.8 Hz), 4.01 (1H, dd, J=9.6, 7.8 Hz), 4.49 (2H, t, J=5.8 Hz), 7.15 (1H, s), 7.54 (1H, d, J=4.8 Hz), 7.82 (2H, d, J=9.2 Hz), 7.90 (2H, d, J=8.8 Hz), 8.40 (1H, t, J=2.0 Hz), 8.56 (1H, d, J=5.0 Hz), 8.95 (1H, d, J=2.0 Hz), 9.04 (1H, d, J=2.0 Hz).

Example 199: (S)-7-methyl-4-(5-(4-(4-methyl-2-oxopyrrolidin-1-yl)phenyl)pyridin-3-yl)-8,9-dihydropyrido[3',2':4,5]pyrrolo[1,2-a]pyrazin-6(7H)-one

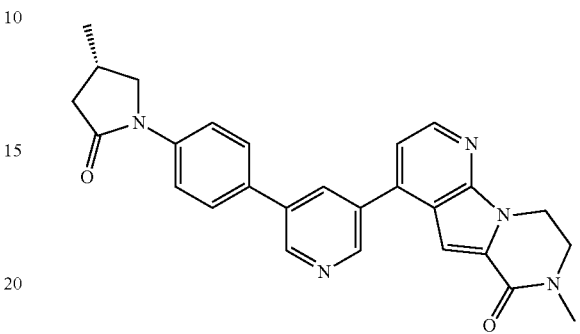

Step 1. Preparation of (S)-1-(4-bromophenyl)-4-methylpyrrolidin-2-one

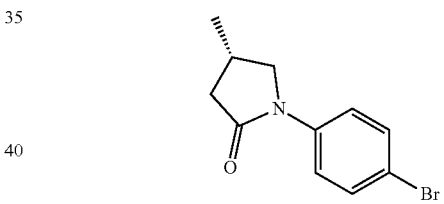

A mixture of (S)-4-methylpyrrolidin-2-one (50 mg, 0.50 mmol), 1-bromo-4-iodobenzene (171 mg, 0.605 mmol), CuI (29 mg, 0.15 mmol), CsF (192 mg, 1.26 mmol) in EtOAc (3 mL) was degassed and purged with N$_2$ for 3 times. Then N,N'-dimethylethylene diamine (27 mg, 0.30 mmol) was added into above mixture, the resulting reaction mixture was stirred at 50° C. for 16 hours. A blue suspension was formed. TLC showed (S)-4-methylpyrrolidin-2-one was consumed completely. The reaction mixture was concentrated under reduced pressure. The residue was purified by Combi Flash (20% to 50% EtOAc in PE) to give (S)-1-(4-bromophenyl)-4-methylpyrrolidin-2-one (128 mg, yield: quantitative) as a light yellow solid.

$^1$H NMR (400 MHz, CDCl$_3$) δ 1.22 (3H, d, J=6.8 Hz), 2.26 (1H, dd, J=16.8, 7.6 Hz), 2.51-2.60 (1H, m), 2.75 (1H, dd, J=16.8, 8.8 Hz), 3.38-3.44 (1H, m), 3.88-3.94 (1H, m), 7.38-7.68 (4H, m).

Step 2. Preparation of (S)-4-methyl-1-(4-(4,4,5,5-tetramethyl-1,3,2-dioxaborolan-2-yl)phenyl)pyrrolidin-2-one

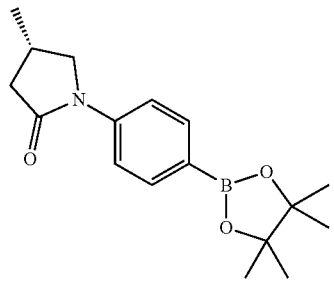 [SMILES: C[C@H]1CC(=O)N(c2ccc(B3OC(C)(C)C(C)(C)O3)cc2)C1]

A mixture of (S)-1-(4-bromophenyl)-4-methylpyrrolidin-2-one (125 mg, 0.492 mmol), Bispin (150 mg, 0.590 mmol), Pd(dppf)Cl$_2$ (36 mg, 0.049 mmol) and KOAc (145 mg, 1.45 mmol) in anhydrous dioxane (5 mL) was degassed and purged with N$_2$ for 3 times. And the resulting mixture was stirred at 100° C. for 16 hours under N$_2$ atmosphere. A black suspension was formed. LCMS showed the purity of the desired product is 78% (Rt=0.867 min; MS Calcd: 301.2; MS Found: 302.2 [M+H]$^+$). The reaction mixture was filtered through a pad of celite, washed with EtOAc (50 mL) and concentrated under reduced pressure to give (S)-4-methyl-1-(4-(4,4,5,5-tetramethyl-1,3,2-dioxaborolan-2-yl)phenyl)pyrrolidin-2-one (crude), which was used for the next step without further purification.

Step 3. Preparation of (S)-1-(4-(5-bromopyridin-3-yl)phenyl)-4-methylpyrrolidin-2-one

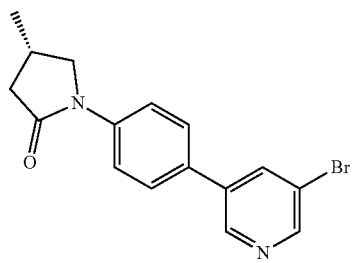 [SMILES: C[C@H]1CC(=O)N(c2ccc(-c3cncc(Br)c3)cc2)C1]

A mixture of (S)-4-methyl-1-(4-(4,4,5,5-tetramethyl-1,3,2-dioxaborolan-2-yl)phenyl)pyrrolidin-2-one (crude), 3,5-dibromopyridine (175 mg, 0.737 mmol), Pd(dppf)Cl$_2$ (18 mg, 0.025 mmol) and Na$_2$CO$_3$ (156 mg, 1.47 mmol) in dioxane (4 mL) and water (1 mL) was degassed and purged with N$_2$ for 3 times. And the resulting reaction mixture was stirred at 100° C. for 4 hours under N$_2$ atmosphere. A black suspension was formed. LCMS showed the purity of the desired product is 39% (Rt=0.675 min; MS Calcd: 330.0; MS Found: 330.6 [M+H]$^+$). The reaction mixture was diluted with water (20 mL). The aqueous layer was extracted with EtOAc (30 mL×2). The combined organic layer was washed with water (20 mL×2), brine (30 mL), dried over anhydrous Na$_2$SO$_4$, filtered and concentrated under reduced pressure. The residue was purified by Combi Flash (2% to 50% EtOAc in PE) to give (S)-1-(4-(5-bromopyridin-3-yl)phenyl)-4-methylpyrrolidin-2-one (92 mg, yield: 56% for two steps) as a light yellow solid.

Step 4. Preparation of (S)-4-methyl-1-(4-(5-(4,4,5,5-tetramethyl-1,3,2-dioxaborolan-2-yl)pyridin-3-yl)phenyl)pyrrolidin-2-one

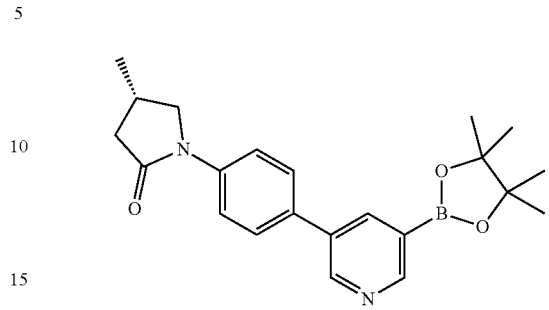

A mixture of (S)-1-(4-(5-bromopyridin-3-yl)phenyl)-4-methylpyrrolidin-2-one (50 mg, 0.15 mmol), Bispin (38 mg, 0.15 mmol), Pd(dppf)Cl$_2$ (11 mg, 0.015 mmol) and KOAc (44 mg, 0.45 mmol) in anhydrous dioxane (3 mL) was degassed and purged with N$_2$ for 3 times. And the resulting mixture was stirred at 100° C. for 12 hours under N$_2$ atmosphere. A black suspension was formed. LCMS showed the purity of the boronic acid of the desired product is 26% (Rt=0.716 min; MS Calcd: 296.1; MS Found: 297.0 [M+H]$^+$). The reaction mixture was filtered through a pad of celite, washed with EtOAc (50 mL) and concentrated under reduced pressure to give (S)-4-methyl-1-(4-(5-(4,4,5,5-tetramethyl-1,3,2-dioxaborolan-2-yl)pyridin-3-yl)phenyl)pyrrolidin-2-one (crude), which was used for the next step without further purification.

Step 5. Preparation of (S)-7-methyl-4-(5-(4-(4-methyl-2-oxopyrrolidin-1-yl)phenyl)pyridin-3-yl)-8,9-dihydropyrido[3',2':4,5]pyrrolo[1,2-a]pyrazin-6(7H)-one

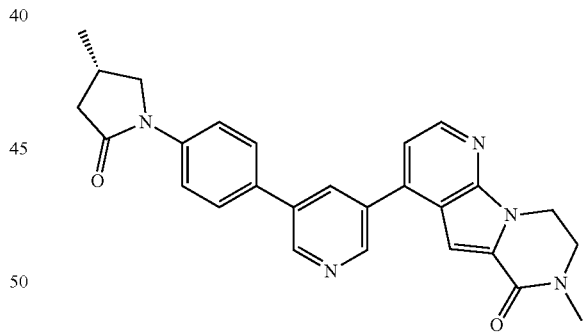

A mixture of (S)-4-methyl-1-(4-(5-(4,4,5,5-tetramethyl-1,3,2-dioxaborolan-2-yl)pyridin-3-yl)phenyl)pyrrolidin-2-one (crude), 4-chloro-7-methyl-8,9-dihydropyrido[3',2':4,5]pyrrolo[1,2-a]pyrazin-6(7H)-one (36 mg, 0.15 mmol) (see Example 212, Step 1), Pd(t-Bu$_3$P)$_2$ (8 mg, 0.015 mmol) and Cs$_2$CO$_3$ (98 mg, 0.30 mmol) in dioxane (3 mL) and water (0.8 mL) was degassed and purged with N$_2$ for 3 times. And the resulting reaction mixture was stirred at 100° C. for 16 hours under N$_2$ atmosphere. A black suspension was formed. LCMS showed the purity of the desired product is 52% (Rt=0.623 min; MS Calcd: 451.2; MS Found: 452.2 [M+H]$^+$). The reaction mixture was diluted with water (20 mL). The aqueous layer was extracted with EtOAc/THF (30 mL×3, 1/1). The combined organic layer was washed with water (20 mL×2), brine (30 mL), dried over anhydrous Na₂SO₄, filtered and concentrated under reduced pressure. The residue was purified by prep-HPLC (0.225% FA as an additive), prep-TLC (DCM/MeOH, 10/1) and further triturated with MeCN (3 mL) to give (S)-7-methyl-4-(5-(4-(4-methyl-2-oxopyrrolidin-1-yl)phenyl)pyridin-3-yl)-8,9-dihydropyrido[3',2':4,5]pyrrolo[1,2-a]pyrazin-6(7H)-one (4.7 mg, yield: 7% for two steps) as a white solid.

$^1$H NMR (400 MHz, DMSO-d₆) δ 1.15 (3H, d, J=6.8 Hz), 2.23 (1H, dd, J=16.4, 7.4 Hz), 2.53-2.59 (1H, m), 2.69 (1H, dd, J=16.8, 8.4 Hz), 3.10 (3H, s), 3.51 (1H, dd, J=9.4, 6.6 Hz), 3.88 (2H, t, J=5.8 Hz), 4.02 (1H, dd, J=9.2, 7.6 Hz), 4.50 (2H, t, J=5.8 Hz), 7.15 (1H, s), 7.55 (1H, d, J=5.0 Hz), 7.82 (2H, d, J=8.8 Hz), 7.90 (2H, d, J=8.8 Hz), 8.40 (1H, t, J=2.0 Hz), 8.56 (1H, d, J=4.8 Hz), 8.95 (1H, d, J=1.6 Hz), 9.04 (1H, d, J=2.0 Hz).

Example 200: 4-(5-(4-(4,4-dimethyl-2-oxopyrrolidin-1-yl)phenyl)pyridin-3-yl)-7-methyl-8,9-dihydropyrido[3',2':4,5]pyrrolo[1,2-a]pyrazin-6(7H)-one

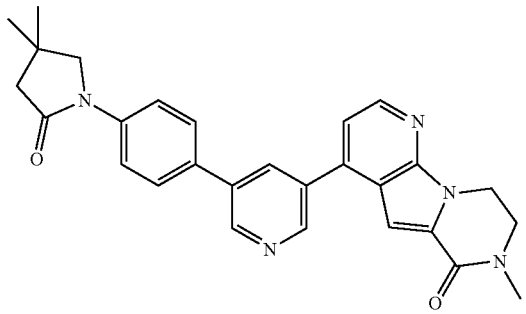

Step 1. Preparation of 1-(4-bromophenyl)-4,4-dimethylpyrrolidin-2-one

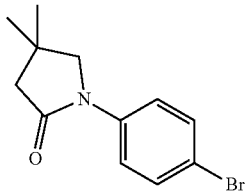

A mixture of 4,4-dimethylpyrrolidin-2-one (300 mg, 2.65 mmol), 1-bromo-4-iodobenzene (900 mg, 3.18 mmol), CuI (151 mg, 0.795 mmol), CsF (1.01 g, 6.63 mmol) in EtOAc (10 mL) was degassed and purged with N₂ for 3 times. Then N,N'-dimethylethylene diamine (140 mg, 1.59 mmol) was added into above mixture, the resulting reaction mixture was stirred at 50° C. for 16 hours. A blue suspension was formed. LCMS showed the purity of the desired product is 80% (Rt=0.736 min; MS Calcd: 267.0; MS Found: 267.8 [M+H]⁺). The reaction mixture was concentrated (combine with Batch ES7543-319) under reduced pressure. The residue was purified by Combi Flash (0% to 20% EtOAc in PE) to give 1-(4-bromophenyl)-4,4-dimethylpyrrolidin-2-one (820 mg, yield: quantitative) as a yellow solid.

$^1$H NMR (400 MHz, CDCl₃) δ 1.24 (6H, s), 2.44 (2H, s), 2.54 (2H, s), 7.38-7.68 (4H, m).

Step 2. Preparation of 4,4-dimethyl-1-(4-(4,4,5,5-tetramethyl-1,3,2-dioxaborolan-2-yl)phenyl)pyrrolidin-2-one

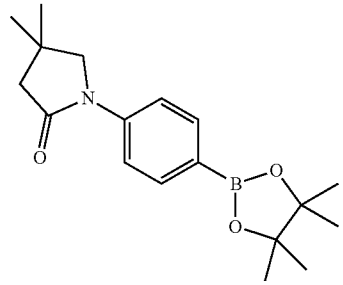

A mixture of 1-(4-bromophenyl)-4,4-dimethylpyrrolidin-2-one (620 mg, 2.31 mmol), Bispin (705 mg, 2.77 mmol), Pd(dppf)Cl₂ (169 mg, 0.231 mmol) and KOAc (681 mg, 6.94 mmol) in anhydrous dioxane (10 mL) was degassed and purged with N₂ for 3 times. And the resulting mixture was stirred at 100° C. for 16 hours under N₂ atmosphere. A black suspension was formed. LCMS showed the purity of the desired product is 59% (Rt=0.981 min; MS Calcd: 315.2; MS Found: 315.9 [M+H]⁺). The reaction mixture was filtered through a pad of celite, washed with EtOAc (50 mL) and concentrated under reduced pressure to give 4,4-dimethyl-1-(4-(4,4,5,5-tetramethyl-1,3,2-dioxaborolan-2-yl)phenyl)pyrrolidin-2-one (crude), which was used for the next step without further purification.

Step 3. Preparation of 1-(4-(5-bromopyridin-3-yl)phenyl)-4,4-dimethylpyrrolidin-2-one

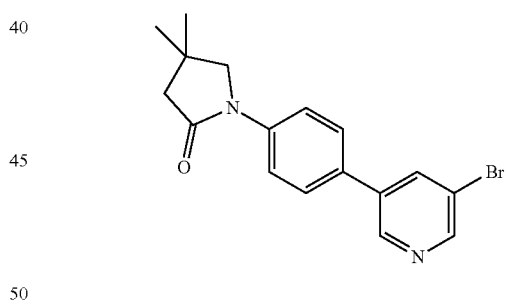

A mixture of 4,4-dimethyl-1-(4-(4,4,5,5-tetramethyl-1,3,2-dioxaborolan-2-yl)phenyl)pyrrolidin-2-one (crude), 3,5-dibromopyridine (1.09 g, 4.62 mmol), Pd(dppf)Cl₂ (169 mg, 0.231 mmol) and Na₂CO₃ (734 mg, 6.93 mmol) in dioxane (16 mL) and water (4 mL) was degassed and purged with N₂ for 3 times. And the resulting reaction mixture was stirred at 100° C. for 1 hour under N₂ atmosphere. A black suspension was formed. LCMS showed the purity of the desired product is 18% (Rt=0.557 min; MS Calcd: 438.2; MS Found: 439.1 [M+H]⁺). The reaction mixture was filtered through a pad of celite and the solid was washed with EtOAc (100 mL). The filtrate was diluted with water (50 mL). The aqueous layer was extracted with EtOAc (50 mL×2). The combined organic layer was washed with water (40 mL), brine (40 mL), dried over anhydrous Na₂SO₄, filtered and concentrated under reduced pressure. The residue was purified by Combi Flash (0% to 50% EtOAc in PE) to give 1-(4-(5- bromopyridin-3-yl)phenyl)-4,4-dimethylpyrrolidin-2-one (1.00 g, yield: quantitative for two steps) as a white solid.

$^1$H NMR (400 MHz, CDCl$_3$) δ 1.27 (6H, s), 2.48 (2H, s), 3.62 (2H, s), 7.57 (2H, d, J=8.8 Hz), 7.75 (2H, d, J=8.8 Hz), 7.80 (1H, t, J=2.0 Hz), 8.63 (1H, d, J=2.0 Hz), 8.74 (1H, d, J=1.6 Hz).

Step 4. Preparation of 4,4-dimethyl-1-(4-(5-(4,4,5, 5-tetramethyl-1,3,2-dioxaborolan-2-yl)pyridin-3-yl) phenyl)pyrrolidin-2-one

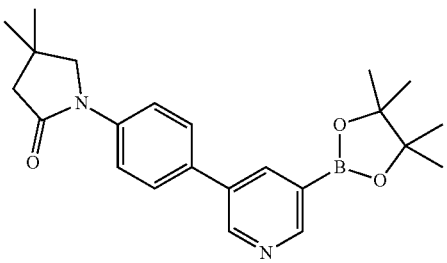

A mixture of 1-(4-(5-bromopyridin-3-yl)phenyl)-4,4-dimethylpyrrolidin-2-one (80 mg, 0.23 mmol), Bispin (71 mg, 0.28 mmol), Pd(dppf)Cl$_2$ (17 mg, 0.017 mmol) and KOAc (68 mg, 0.70 mmol) in anhydrous dioxane (5 mL) was degassed and purged with N$_2$ for 3 times. And the resulting mixture was stirred at 100° C. for 16 hours under N$_2$ atmosphere. A black suspension was formed. LCMS showed the purity of the boronic acid of the desired product is 57% (Rt=0.668 min; MS Calcd: 310.1; MS Found: 310.9 [M+H]$^+$). The reaction mixture was filtered through a pad of celite, washed with EtOAc (50 mL) and concentrated under reduced pressure to give 4,4-dimethyl-1-(4-(5-(4,4,5,5-tetramethyl-1,3,2-dioxaborolan-2-yl)pyridin-3-yl)phenyl)pyrrolidin-2-one (crude), which was used for the next step without further purification.

Step 5. Preparation of 4-(5-(4-(4,4-dimethyl-2-oxopyrrolidin-1-yl)phenyl)pyridin-3-yl)-7-methyl-8, 9-dihydropyrido[3',2':4,5]pyrrolo[1,2-a]pyrazin-6 (7H)-one

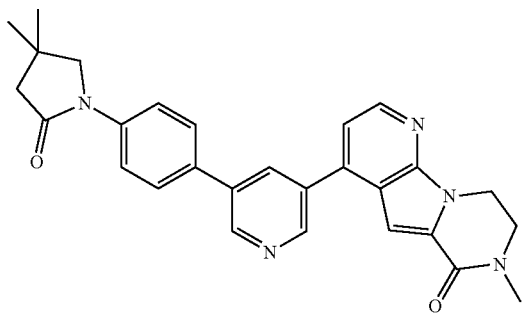

A mixture of 4,4-dimethyl-1-(4-(5-(4,4,5,5-tetramethyl-1, 3,2-dioxaborolan-2-yl)pyridin-3-yl)phenyl)pyrrolidin-2-one (crude), 4-chloro-7-methyl-8,9-dihydropyrido[3',2':4,5]pyrrolo[1,2-a]pyrazin-6(7H)-one (54 mg, 0.23 mmol) (see Example 212, Step 1), Pd(t-Bu$_3$P)$_2$ (12 mg, 0.015 mmol) and Cs$_2$CO$_3$ (150 mg, 0.459 mmol) in dioxane (3 mL) and water (0.8 mL) was degassed and purged with N$_2$ for 3 times. And the resulting reaction mixture was stirred at 100° C. for 16 hours under N$_2$ atmosphere. A black suspension was formed. LCMS showed the purity of the desired product is 47% (Rt=0.808 min; MS Calcd: 465.2; MS Found: 488.2 [M+H]$^+$). The reaction mixture was diluted with water (20 mL). The aqueous layer was extracted with EtOAc/THF (30 mL×3, 1/1). The combined organic layer was washed with water (20 mL×2), brine (30 mL), dried over anhydrous Na$_2$SO$_4$, filtered and concentrated under reduced pressure. The residue was purified by prep-HPLC (0.225% FA as an additive), prep-TLC (DCM/MeOH, 10/1) and lyophilized to give 4-(5-(4-(4,4-dimethyl-2-oxopyrrolidin-1-yl)phenyl)pyridin-3-yl)-7-methyl-8,9-dihydropyrido[3',2':4,5]pyrrolo [1,2-a]pyrazin-6(7H)-one (13.0 mg, yield: 12% for two steps) as a white solid.

$^1$H NMR (400 MHz, DMSO-d$_6$) δ 1.20 (6H, s), 2.41 (2H, s), 3.10 (3H, s), 3.66 (2H, s), 3.88 (2H, t, J=6.0 Hz), 4.49 (2H, t, J=6.0 Hz), 7.15 (1H, s), 7.54 (1H, d, J=5.2 Hz), 7.82 (2H, d, J=8.8 Hz), 7.89 (2H, d, J=8.4 Hz), 8.39 (1H, t, J=2.0 Hz), 8.56 (1H, d, J=4.8 Hz), 8.95 (1H, d, J=2.0 Hz), 9.04 (1H, d, J=2.0 Hz).

Example 201: 7-methyl-4-(5-(4-(6-oxo-5-azaspiro [2.4]heptan-5-yl)phenyl)pyridin-3-yl)-8,9-dihydropyrido[3',2':4,5]pyrrolo[1,2-a]pyrazin-6(7H)-one

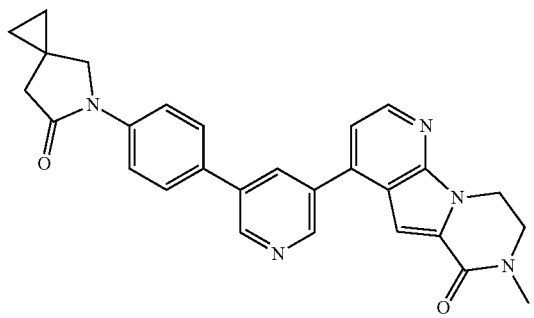 [SMILES: CN1CCn2c(cc3c(-c4cncc(-c5ccc(N6CC7(CC7)CC6=O)cc5)c4)ccnc32)C1=O]

Step 1. Preparation of 5-(4-bromophenyl)-5-azaspiro[2.4]heptan-6-one

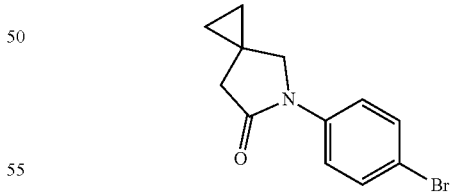

A mixture of 5-azaspiro[2.4]heptan-6-one (50 mg, 0.45 mmol), 1-bromo-4-iodobenzene (153 mg, 0.540 mmol), CuI (26 mg, 0.13 mmol), CsF (171 mg, 1.12 mmol) in EtOAc (3 mL) was degassed and purged with N$_2$ for 3 times. Then N, N'-dimethylethylene diamine (24 mg, 0.27 mmol) was added into above mixture, the resulting reaction mixture was stirred at 50° C. for 16 hours. A blue suspension was formed. TLC showed 5-azaspiro[2.4]heptan-6-one was consumed completely. The reaction mixture was concentrated under reduced pressure. The residue was purified by Combi Flash (20% to 50% EtOAc in PE) to give 5-(4-bromophenyl)-5-azaspiro[2.4]heptan-6-one (119 mg, yield: quantitative) as a white solid.
¹H NMR (400 MHz, CDCl₃) δ 0.69-0.80 (4H, m), 2.63 (2H, s), 3.70 (2H, s), 7.38-7.68 (4H, m).

Step 2. Preparation of 5-(4-(4,4,5,5-tetramethyl-1,3,2-dioxaborolan-2-yl)phenyl)-5-azaspiro[2.4]heptan-6-one

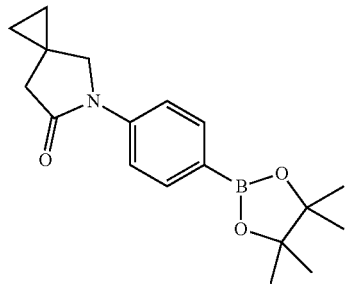 [SMILES: CC1(C)OB(c2ccc(N3CC4(CC4)CC3=O)cc2)OC1(C)C]

A mixture of 5-(4-bromophenyl)-5-azaspiro[2.4]heptan-6-one (119 mg, 0.447 mmol), Bispin (136 mg, 0.536 mmol), Pd(dppf)Cl₂ (33 mg, 0.045 mmol) and KOAc (132 mg, 1.34 mmol) in anhydrous dioxane (5 mL) was degassed and purged with N₂ for 3 times. And the resulting mixture was stirred at 100° C. for 14 hours under N₂ atmosphere. A black suspension was formed. LCMS showed the purity of the desired product is 35% (Rt=0.774 min; MS Calcd: 313.2; MS Found: 314.1 [M+H]⁺). The reaction mixture was filtered through a pad of silica gel, and the solid was washed with EtOAc (50 mL), the filtrate was concentrated under reduced pressure to give 5-(4-(4,4,5,5-tetramethyl-1,3,2-dioxaborolan-2-yl)phenyl)-5-azaspiro[2.4]heptan-6-one (crude), which was used for the next step without further purification.

Step 3. Preparation of 5-(4-(5-bromopyridin-3-yl)phenyl)-5-azaspiro[2.4]heptan-6-one

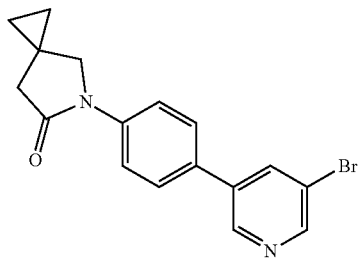 [SMILES: O=C1CC2(CC2)CN1c1ccc(-c2cncc(Br)c2)cc1]

A mixture of 5-(4-(4,4,5,5-tetramethyl-1,3,2-dioxaborolan-2-yl)phenyl)-5-azaspiro[2.4]heptan-6-one (crude), 3,5-dibromopyridine (159 mg, 0.670 mmol), Pd(dppf)Cl₂ (16 mg, 0.22 mmol) and Na₂CO₃ (142 mg, 1.34 mmol) in dioxane (4 mL) and water (1 mL) was degassed and purged with N₂ for 3 times. And the resulting reaction mixture was stirred at 100° C. for 4 hours under N₂ atmosphere. A black suspension was formed. LCMS showed the purity of the desired product is 32% (Rt=0.822 min; MS Calcd: 342.0; MS Found: 342.9 [M+H]⁺). The reaction mixture was diluted with water (20 mL). The aqueous layer was extracted with EtOAc (30 mL×2). The combined organic layer was washed with water (20 mL×2), brine (30 mL), dried over anhydrous Na₂SO₄, filtered and concentrated under reduced pressure. The residue was purified by Combi Flash (2% to 50% EtOAc in PE) to give 5-(4-(5-bromopyridin-3-yl)phenyl)-5-azaspiro[2.4]heptan-6-one (120 mg, yield: 78% for two steps) as a light yellow solid.
¹H NMR (400 MHz, CDCl₃) δ 0.72-0.82 (4H, m), 2.68 (2H, s), 3.79 (2H, s), 7.58 (2H, d, J=8.8 Hz), 7.77 (2H, d, J=8.8 Hz), 8.01 (1H, t, J=2.0 Hz), 8.64 (1H, d, J=1.2 Hz), 8.75 (1H, d, J=1.2 Hz).

Step 4. Preparation of 5-(4-(5-(4,4,5,5-tetramethyl-1,3,2-dioxaborolan-2-yl)pyridin-3-yl)phenyl)-5-azaspiro[2.4]heptan-6-one

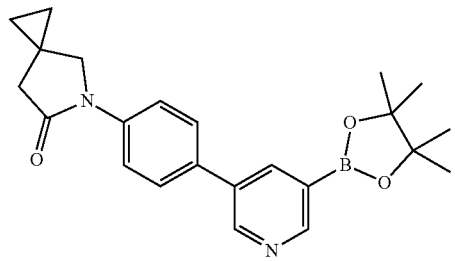 [SMILES: CC1(C)OB(c2cncc(-c3ccc(N4CC5(CC5)CC4=O)cc3)c2)OC1(C)C]

A mixture of 5-(4-(5-bromopyridin-3-yl)phenyl)-5-azaspiro[2.4]heptan-6-one (120 mg, 0.350 mmol), Bispin (89 mg, 0.35 mmol), Pd(dppf)Cl₂ (26 mg, 0.035 mmol) and KOAc (103 mg, 1.05 mmol) in anhydrous dioxane (5 mL) was degassed and purged with N₂ for 3 times. And the resulting mixture was stirred at 100° C. for 16 hours under N₂ atmosphere. A black suspension was formed. LCMS showed the purity of the boronic acid of the desired product is 31% (Rt=0.726 min; MS Calcd: 308.1; MS Found: 308.8 [M+H]⁺). The reaction mixture was filtered through a pad of celite, washed with EtOAc (50 mL) and concentrated under reduced pressure to give 5-(4-(5-(4,4,5,5-tetramethyl-1,3,2-dioxaborolan-2-yl)pyridin-3-yl)phenyl)-5-azaspiro[2.4]heptan-6-one (crude), which was used for the next step without further purification.

Step 5. Preparation of 7-methyl-4-(5-(4-(6-oxo-5-azaspiro[2.4]heptan-5-yl)phenyl)pyridin-3-yl)-8,9-dihydropyrido[3',2':4,5]pyrrolo[1,2-a]pyrazin-6(7H)-one

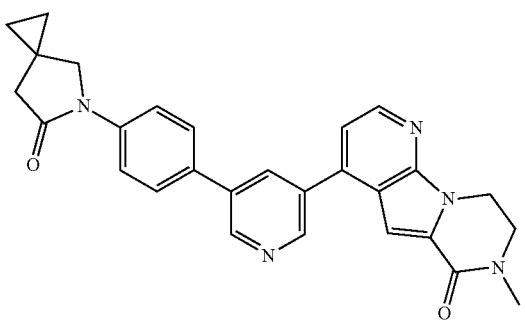 [SMILES: CN1CCn2c(cc3c(-c4cncc(-c5ccc(N6CC7(CC7)CC6=O)cc5)c4)ccnc32)C1=O]

A mixture of 5-(4-(5-(4,4,5,5-tetramethyl-1,3,2-dioxaborolan-2-yl)pyridin-3-yl)phenyl)-5-azaspiro[2.4]heptan-6-one (crude), 4-chloro-7-methyl-8,9-dihydropyrido[3',2':4,5]pyrrolo[1,2-a]pyrazin-6(7H)-one (82 mg, 0.35 mmol), Pd(t-Bu₃P)₂ (18 mg, 0.035 mmol) and Cs₂CO₃ (227 mg, 0.697 mmol) in dioxane (3 mL) and water (0.8 mL) was degassed and purged with N₂ for 3 times. And the resulting reaction mixture was stirred at 100° C. for 16 hours under N₂ atmosphere. A black suspension was formed. LCMS showed the purity of the desired product is 47% (Rt=0.789 min; MS Calcd: 463.2; MS Found: 486.1 [M+H]⁺). The reaction mixture was diluted with water (20 mL). The aqueous layer was extracted with EtOAc/THF (30 mL×3, 1/1). The combined organic layer was washed with water (20 mL×2), brine (30 mL), dried over anhydrous Na₂SO₄, filtered and concentrated under reduced pressure. The residue was purified by prep-HPLC (0.225% FA as an additive), and further tritrated with DMF/MeOH (1/1, 3 mL) to give 7-methyl-4-(5-(4-(6-oxo-5-azaspiro[2.4]heptan-5-yl)phenyl)pyridin-3-yl)-8,9-dihydropyrido[3',2':4,5]pyrrolo[1,2-a]pyrazin-6(7H)-one (12.6 mg, yield: 8% for two steps) as a white solid.

¹H NMR (400 MHz, DMSO-d₆) δ 0.69-0.76 (4H, m), 2.62 (2H, s), 3.10 (3H, s), 3.84 (2H, s), 3.88 (2H, t, J=6.0 Hz), 4.51 (2H, t, J=6.0 Hz), 7.34 (1H, s), 7.66 (1H, d, J=4.8 Hz), 7.88 (2H, d, J=8.8 Hz), 8.04 (2H, d, J=8.4 Hz), 8.62 (1H, d, J=4.8 Hz), 9.01 (1H, s), 9.21 (1H, s), 9.31 (1H, s).

Example 202: 7-methyl-4-(5-(4-(2-oxoindolin-1-yl)phenyl)pyridin-3-yl)-8,9-dihydropyrido[3',2':4,5]pyrrolo[1,2-a]pyrazin-6(7H)-one

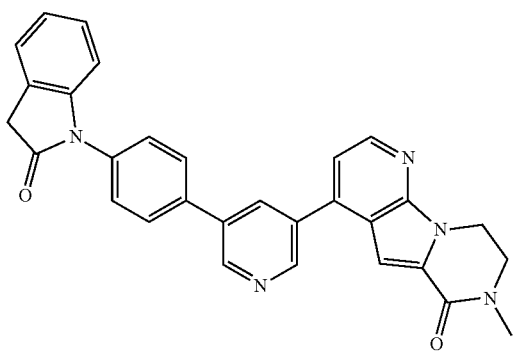 [SMILES: CN1CCn2c(cc3c(-c4cncc(-c5ccc(N6C(=O)Cc7ccccc76)cc5)c4)ccnc32)C1=O]

Step 1. Preparation of 1-(4-bromophenyl)indolin-2-one

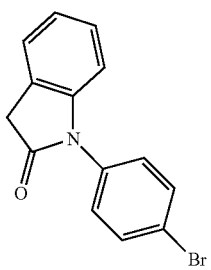 [SMILES: O=C1Cc2ccccc2N1c1ccc(Br)cc1]

A mixture of indolin-2-one (100 mg, 0.751 mmol), 1-bromo-4-iodobenzene (255 mg, 0.901 mmol), CuI (43 mg, 0.23 mmol), CsF (228 mg, 1.50 mmol) in EtOAc (5 mL) was degassed and purged with N₂ for 3 times. Then L-proline (52 mg, 0.45 mmol) was added into above mixture, the resulting reaction mixture was stirred at 50° C. for 48 hours. A gray suspension was formed. TLC showed most of indolin-2-one was consumed. The reaction mixture was filtered through a pad of celite (combined with Batch ES7543-341) and the solid was washed with EtOAc (50 mL). The filtrate was concentrated under reduced pressure. The residue was purified by Combi Flash (0% to 20% EtOAc in PE) to give 1-(4-bromophenyl)indolin-2-one (300 mg, yield: 49% for average) as a yellow solid.

Step 2. Preparation of 1-(4-(4,4,5,5-tetramethyl-1,3,2-dioxaborolan-2-yl)phenyl)indolin-2-one

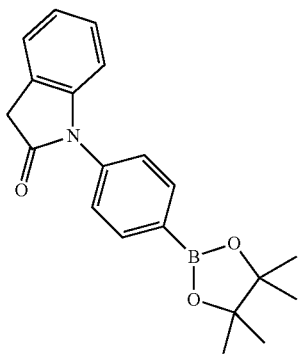 [SMILES: CC1(C)OB(c2ccc(N3C(=O)Cc4ccccc43)cc2)OC1(C)C]

A mixture of 1-(4-bromophenyl)indolin-2-one (300 mg, 1.04 mmol), Bispin (317 mg, 1.25 mmol), Pd(dppf)Cl₂ (76 mg, 0.10 mmol) and KOAc (306 mg, 3.12 mmol) in anhydrous dioxane (5 mL) was degassed and purged with N₂ for 3 times. And the resulting mixture was stirred at 100° C. for 14 hours under N₂ atmosphere. A black suspension was formed. LCMS showed the purity of the desired product is 49% (Rt=1.060 min; MS Calcd: 353.2; MS Found: 335.8 [M+H]⁺). The reaction mixture was filtered through a pad of silica gel, and the solid was washed with EtOAc (100 mL), the filtrate was concentrated under reduced pressure to give 1-(4-(4,4,5,5-tetramethyl-1,3,2-dioxaborolan-2-yl)phenyl)indolin-2-one (crude), which was used for the next step without further purification.

Step 3. Preparation of 1-(4-(5-bromopyridin-3-yl)phenyl)indolin-2-one

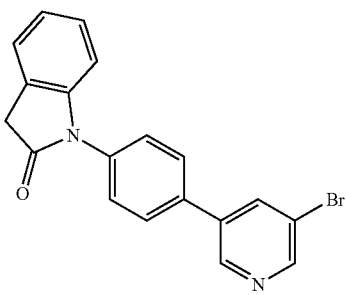 [SMILES: O=C1Cc2ccccc2N1c1ccc(-c2cncc(Br)c2)cc1]

A mixture of 1-(4-(4,4,5,5-tetramethyl-1,3,2-dioxaborolan-2-yl)phenyl)indolin-2-one (crude), 3,5-dibromopyridine (370 mg, 1.56 mmol), Pd(dppf)Cl$_2$ (76 mg, 0.10 mmol) and Na$_2$CO$_3$ (331 mg, 3.12 mmol) in dioxane (6 mL) and water (1.5 mL) was degassed and purged with N$_2$ for 3 times. And the resulting reaction mixture was stirred at 100° C. for 1 hour under N$_2$ atmosphere. A black suspension was formed. LCMS showed the purity of the desired product is 39% (Rt=0.950 min; MS Calcd: 364.0; MS Found: 364.9 [M+H]$^+$). The reaction mixture was diluted with water (20 mL). The aqueous layer was extracted with EtOAc/THF (30 mL×2, 1/1). The combined organic layer was washed with water (20 mL×2), brine (30 mL), dried over anhydrous Na$_2$SO$_4$, filtered and concentrated under reduced pressure. The residue was purified by Combi Flash (10% to 50% EtOAc in PE) to give 1-(4-(5-bromopyridin-3-yl)phenyl)indolin-2-one (110 mg, yield: 29% for two steps) as a yellow solid.

Step 4. Preparation of 1-(4-(5-(4,4,5,5-tetramethyl-1,3,2-dioxaborolan-2-yl)pyridin-3-yl)phenyl)indolin-2-one

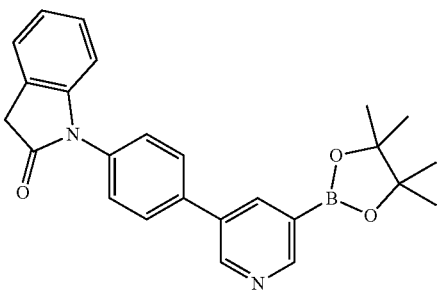 [SMILES: CC1(C)OB(c2cncc(-c3ccc(N4C(=O)Cc5ccccc54)cc3)c2)OC1(C)C]

A mixture of 1-(4-(5-bromopyridin-3-yl)phenyl)indolin-2-one (45 mg, 0.12 mmol), Bispin (38 mg, 0.15 mmol), Pd(dppf)Cl$_2$ (9 mg, 0.01 mmol) and KOAc (36 mg, 0.37 mmol) in anhydrous dioxane (3 mL) was degassed and purged with N$_2$ for 3 times. And the resulting mixture was stirred at 100° C. for 16 hours under N$_2$ atmosphere. A black suspension was formed. LCMS showed the purity of the boronic acid of the desired product is 60% (Rt=0.778 min; MS Calcd: 330.1; MS Found: 331.0 [M+H]$^+$). The reaction mixture was filtered through a pad of celite, washed with EtOAc (50 mL) and concentrated under reduced pressure to give 1-(4-(5-(4,4,5,5-tetramethyl-1,3,2-dioxaborolan-2-yl)pyridin-3-yl)phenyl)indolin-2-one (crude), which was used for the next step without further purification.

Step 5. Preparation of 7-methyl-4-(5-(4-(2-oxoindolin-1-yl)phenyl)pyridin-3-yl)-8,9-dihydropyrido[3',2':4,5]pyrrolo[1,2-a]pyrazin-6(7H)-one

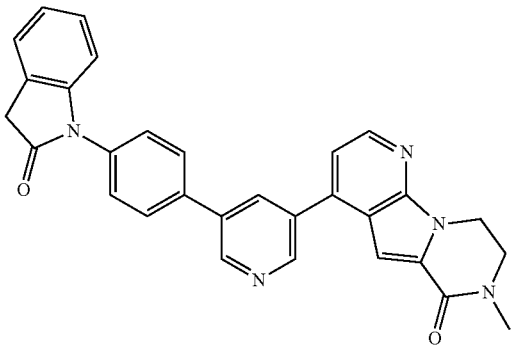 [SMILES: CN1CCn2c(cc3c(-c4cncc(-c5ccc(N6C(=O)Cc7ccccc76)cc5)c4)ccnc32)C1=O]

A mixture of 1-(4-(5-(4,4,5,5-tetramethyl-1,3,2-dioxaborolan-2-yl)pyridin-3-yl)phenyl)indolin-2-one (crude), 4-chloro-7-methyl-8,9-dihydropyrido[3',2':4,5]pyrrolo[1,2-a]pyrazin-6(7H)-one (29 mg, 0.12 mmol), Pd(t-Bu$_3$P)$_2$ (6 mg, 0.01 mmol) and Cs$_2$CO$_3$ (79 mg, 0.24 mmol) in dioxane (3 mL) and water (0.8 mL) was degassed and purged with N$_2$ for 3 times. And the resulting reaction mixture was stirred at 100° C. for 16 hours under N$_2$ atmosphere. A black suspension was formed. LCMS showed the purity of the desired product is 47% (Rt=0.844 min; MS Calcd: 485.2; MS Found: 486.1 [M+H]$^+$). The reaction mixture was diluted with water (20 mL). The aqueous layer was extracted with EtOAc/THF (30 mL×3, 1/1). The combined organic layer was washed with water (20 mL×2), brine (30 mL), dried over anhydrous Na$_2$SO$_4$, filtered and concentrated under reduced pressure. The residue was purified by Combi Flash (0% to 10% MeOH in DCM), prep-HPLC (0.225% FA as an additive), and further tritrated with MeCN (3 mL) to give 7-methyl-4-(5-(4-(2-oxoindolin-1-yl)phenyl)pyridin-3-yl)-8,9-dihydropyrido[3',2':4,5]pyrrolo[1,2-a]pyrazin-6(7H)-one (10.1 mg, yield: 17% for two steps) as a white solid.

$^1$H NMR (400 MHz, DMSO-d$_6$) δ 3.10 (3H, s), 3.80 (2H, s), 3.88 (2H, t, J=6.0 Hz), 4.50 (2H, t, J=6.0 Hz), 6.85 (1H, d, J=7.6 Hz), 7.10 (1H, t, J=7.6 Hz), 7.20 (1H, s), 7.26 (1H, t, J=7.6 Hz), 7.38 (1H, d, J=6.8 Hz), 7.58 (1H, d, J=4.4 Hz), 7.62 (2H, d, J=8.8 Hz), 8.07 (2H, d, J=8.4 Hz), 8.49 (1H, d, J=2.4 Hz), 8.58 (1H, d, J=5.2 Hz), 9.02 (1H, d, J=2.0 Hz), 9.11 (1H, d, J=2.0 Hz).

Example 203: N-(4-(5-(1H-pyrazolo[3,4-b]pyridin-4-yl)pyridin-3-yl)phenyl)-2-(2-azabicyclo[2.2.1]heptan-2-yl)-2-oxoacetamide

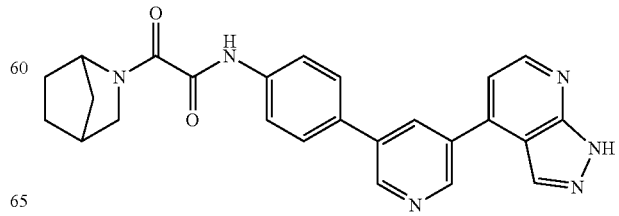

Step 1. Preparation of N-(4-(5-(1H-pyrazolo[3,4-b]pyridin-4-yl)pyridin-3-yl)phenyl)-2-(2-azabicyclo[2.2.1]heptan-2-yl)-2-oxoacetamide

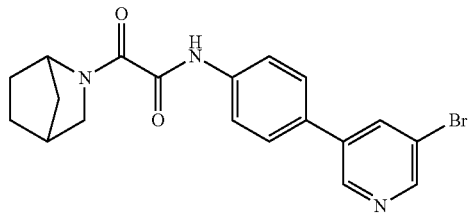 [SMILES: O=C(Nc1ccc(-c2cncc(Br)c2)cc1)C(=O)N1CC2CCC1C2]

Step 1a. Preparation of methyl 2-(2-azabicyclo[2.2.1]heptan-2-yl)-2-oxoacetate

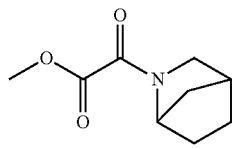

To a solution of 2-azabicyclo[2.2.1]heptane (300 mg, 2.25 mmol, HCl salt) and Et₃N (1 mL, 7 mmol) in DCM (5 mL), and methyl oxalyl chloride (0.3 mL, 2.7 mmol) was added dropwise at 0° C. Then the resulting reaction mixture was stirred at 20° C. for 1 hour. A yellow suspension was formed. LCMS showed the purity of the desired product is 98% (Rt=0.520 min; MS Calcd: 183.1; MS Found: 183.9 [M+H]⁺). The reaction mixture was quenched with water (20 mL). The aqueous layer was extracted with DCM (20 mL×2). The combined organic layer was washed with water (20 mL×2), brine (20 mL), dried over anhydrous Na₂SO₄, filtered and concentrated under reduced pressure. The residue was purified by Combi Flash (0% to 30% EtOAc in PE) to give methyl 2-(2-azabicyclo[2.2.1]heptan-2-yl)-2-oxoacetate (400 mg, yield: 96%) as colorless oil.

¹H NMR (400 MHz, CDCl₃) δ 1.41-1.52 (2H, m), 1.63-1.80 (4H, m), 2.64 (1H, s), 3.18 (0.68H, dd, J=11.6, 1.6 Hz), 3.50-3.44 (1H, m), 3.61 (0.36H, dt, J=10.4, 2.8 Hz), 3.83 (1H, s), 3.87 (2H, s), 4.48 (0.64H, s), 4.69 (0.35H, s).

Step 1b. Preparation of tert-butyl (4-(5-bromopyridin-3-yl)phenyl)carbamate

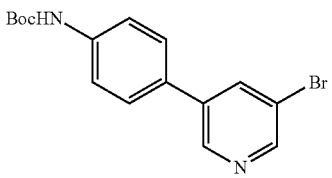 [SMILES: CC(C)(C)OC(=O)Nc1ccc(-c2cncc(Br)c2)cc1]

A mixture of (4-((tert-butoxycarbonyl)amino)phenyl)boronic acid (5.00 g, 21.1 mmol), 3,5-dibromopyridine (7.49 g, 31.6 mmol), Pd(dppf)Cl₂ (1.54 g, 2.11 mmol) and Na₂CO₃ (6.71 g, 63.3 mmol) in dioxane (40 mL) and water (10 mL) was degassed and purged with N₂ for 3 times. And the resulting reaction mixture was stirred at 100° C. for 1 hour under N₂ atmosphere. A black suspension was formed. LCMS showed the purity of the desired product is 52% (Rt=0.971 min; MS Calcd: 348.1; MS Found: 348.9 [M+H]⁺). The reaction mixture was filtered through a pad of celite and the solid was washed with EtOAc (200 mL) to give a filtrate, which was diluted with water (100 mL). The aqueous layer was extracted with EtOAc (50 mL×2). The combined organic layer was washed with water (60 mL×2), brine (60 mL), dried over anhydrous Na₂SO₄, filtered and concentrated under reduced pressure. The residue was purified by Combi Flash (0% to 30% EtOAc in PE) to give tert-butyl (4-(5-bromopyridin-3-yl)phenyl)carbamate (4.55 g, yield: 62%) as a white solid.

¹H NMR (400 MHz, CDCl₃) δ 1.54 (9H, s), 6.58 (1H, brs), 7.45-7.56 (4H, m), 7.99 (1H, t, J=2.0 Hz), 8.62 (1H, d, J=1.8 Hz), 8.73 (1H, d, J=1.8 Hz).

Step 1c. Preparation of 4-(5-bromopyridin-3-yl)aniline

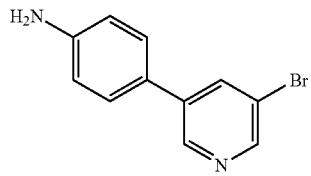

A solution of tert-butyl (4-(5-bromopyridin-3-yl)phenyl)carbamate (1.30 mg, 3.72 mmol) in TFA (5 mL) and DCM (5 mL) was stirred at 20° C. for 1 hour. An orange solution was formed. LCMS showed the purity of the desired product is 97% (Rt=0.536 min; MS Calcd: 248.0; MS Found: 248.8 [M+H]⁺). The reaction mixture was concentrated and diluted with water (20 mL), then basified with 1 N aqueous NaOH to pH=8. The aqueous layer was extracted with EtOAc (20 mL×3). The combined organic layer was washed with water (20 mL×2), brine (20 mL×2), dried over anhydrous Na₂SO₄, filtered and concentrated under reduced pressure to give 4-(5-bromopyridin-3-yl)aniline (920 mg, yield: 94%) as a brown solid.

¹H NMR (400 MHz, CDCl₃) δ 3.18 (2H, brs), 6.78 (2H, d, J=8.4 Hz), 7.38 (2H, d, J=8.8 Hz), 7.97 (1H, t, J=2.0 Hz), 8.56 (1H, s), 8.71 (1H, s).

Step 2. Preparation of 2-(2-azabicyclo[2.2.1]heptan-2-yl)-N-(4-(5-bromopyridin-3-yl)phenyl)-2-oxoacetamide

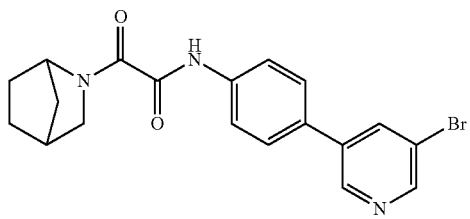 [SMILES: O=C(Nc1ccc(-c2cncc(Br)c2)cc1)C(=O)N1CC2CCC1C2]

To a mixture of 4-(5-bromopyridin-3-yl)aniline (100 mg, 0.401 mmol) and methyl 2-(2-azabicyclo[2.2.1]heptan-2-yl)-2-oxoacetate (81 mg, 0.44 mmol) in DCM (3 mL), AlMe₃ (0.6 mL, 1.2 mmol, 2M in toluene) was added dropwise at 0° C. Then the resulting reaction mixture was stirred at 20° C. for 16 hours. A yellow solution was formed. LCMS showed the purity of the desired product is 74% (Rt=0.924 min; MS Calcd: 399.1; MS Found: 400.0 [M+H]+). The reaction mixture was quenched with sat. aq. NaHCO₃ (20 mL), then filtered and the solid was washed with EtOAc (50 mL). The filtrate was washed with water (20 mL), brine (20 mL), dried over anhydrous Na₂SO₄, filtered and concentrated under reduced pressure. The residue was purified by Combi Flash (10% to 40% EtOAc in PE) and further tritrated with PE/EtOAc (50 mL, 5/1) to give 2-(2-azabicyclo[2.2.1]heptan-2-yl)-N-(4-(5-bromopyridin-3-yl)phenyl)-2-oxoacetamide (120 mg, yield: 75%) as a yellow solid.

¹H NMR (400 MHz, CDCl₃) δ 1.48-1.52 (2H, m), 1.67-1.87 (4H, m), 2.67 (1H, d, J=16.0 Hz), 3.25 (0.50H, dd, J=11.6, 2.0 Hz), 3.49 (0.50H, dt, J=11.6, 2.8 Hz), 3.79-3.85 (0.50H, m), 3.91-3.97 (0.50H, m), 4.75 (0.50H, s), 5.55 (0.50H, s), 7.57 (2H, dd, J=8.8, 2.4 Hz), 7.76 (2H, dd, J=8.8, 6.8 Hz), 7.97 (1H, t, J=2.0 Hz), 8.65 (1H, s), 8.75 (1H, s), 9.51-9.65 (1H, m).

Step 3. Preparation of 2-(2-azabicyclo[2.2.1]heptan-2-yl)-2-oxo-N-(4-(5-(4,4,5,5-tetramethyl-1,3,2-dioxaborolan-2-yl)pyridin-3-yl)phenyl)acetamide

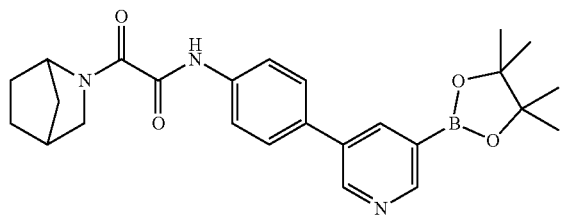 [SMILES: CC1(C)OB(c2cncc(-c3ccc(NC(=O)C(=O)N4CC5CCC4C5)cc3)c2)OC1(C)C]

A mixture of 2-(2-azabicyclo[2.2.1]heptan-2-yl)-N-(4-(5-bromopyridin-3-yl)phenyl)-2-oxoacetamide (60 mg, 0.15 mmol), Bispin (42 mg, 0.16 mmol), Pd(dppf)Cl₂ (11 mg, 0.015 mmol) and KOAc (44 mg, 0.45 mmol) in anhydrous dioxane (3 mL) was degassed and purged with N₂ for 3 times. And the resulting mixture was stirred at 100° C. for 16 hours under N₂ atmosphere. A black suspension was formed. LCMS showed the purity of the boronic acid of the desired product is 63% (Rt=0.574 min; MS Calcd: 365.2; MS Found: 366.1 [M+H]+). The reaction mixture was filtered through a pad of celite, the solid was washed with EtOAc (50 mL) and the filtrate was concentrated under reduced pressure to give 2-(2-azabicyclo[2.2.1]heptan-2-yl)-2-oxo-N-(4-(5-(4,4,5,5-tetramethyl-1,3,2-dioxaborolan-2-yl)pyridin-3-yl)phenyl)acetamide (crude), which was used for the next step without further purification.

Step 4. Preparation of N-(4-(5-(1H-pyrazolo[3,4-b]pyridin-4-yl)pyridin-3-yl)phenyl)-2-(2-azabicyclo[2.2.1]heptan-2-yl)-2-oxoacetamide

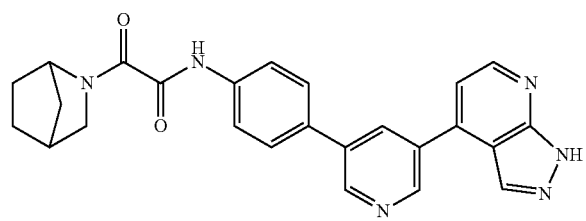 [SMILES: O=C(Nc1ccc(-c2cncc(-c3ccnc4[nH]ncc34)c2)cc1)C(=O)N1CC2CCC1C2]

A mixture of 2-(2-azabicyclo[2.2.1]heptan-2-yl)-2-oxo-N-(4-(5-(4,4,5,5-tetramethyl-1,3,2-dioxaborolan-2-yl)pyridin-3-yl)phenyl)acetamide (crude), 4-chloro-1H-pyrazolo[3,4-b]pyridine (23 mg, 0.15 mmol), Pd(dppf)Cl₂ (11 mg, 0.015 mmol) and Na₂CO₃ (48 mg, 0.45 mmol) in dioxane (3 mL) and water (0.8 mL) was degassed and purged with N₂ for 3 times. And the resulting reaction mixture was stirred at 100° C. for 16 hours under N₂ atmosphere. A black suspension was formed. LCMS showed the purity of the desired product is 17% (Rt=0.834 min; MS Calcd: 438.2; MS Found: 339.0 [M+H]+). The reaction mixture was diluted with water (20 mL). The aqueous layer was extracted with EtOAc/THF (30 mL×3, 1/1). The combined organic layer was washed with water (20 mL×2), brine (30 mL), dried over anhydrous Na₂SO₄, filtered and concentrated under reduced pressure. The residue was purified by Combi Flash (0% to 10% MeOH in DCM) and further purified by prep-HPLC (0.225% FA as an additive), and then lyophilizated to give N-(4-(5-(1H-pyrazolo[3,4-b]pyridin-4-yl)pyridin-3-yl)phenyl)-2-(2-azabicyclo[2.2.1]heptan-2-yl)-2-oxoacetamide (5.1 mg, yield: 8% for two steps) as an off-white solid.

¹H NMR (400 MHz, DMSO-d₆) δ 1.37-1.51 (2H, m), 1.58-1.76 (4H, m), 2.61 (1H, s), 3.09 (0.5H, d, J=11.6 Hz), 3.42-3.46 (0.5H, m), 3.51 (0.5H, d, J=11.2 Hz), 3.69 (0.5H, d, J=8.0 Hz), 4.55 (0.5H, s), 4.72 (0.5H, s), 7.58 (1H, d, J=4.4 Hz), 7.86-7.96 (4H, m), 8.44 (1H, s), 8.48 (1H, s), 8.66 (1H, d, J=4.8 Hz), 8.98-9.11 (2H, m), 10.74-10.82 (1H, m), 13.89 (1H, brs).

Example 204: N-(4-(5-(1H-pyrazolo[3,4-b]pyridin-4-yl)pyridin-3-yl)phenyl)-2-(7-azabicyclo[2.2.1]heptan-7-yl)-2-oxoacetamide

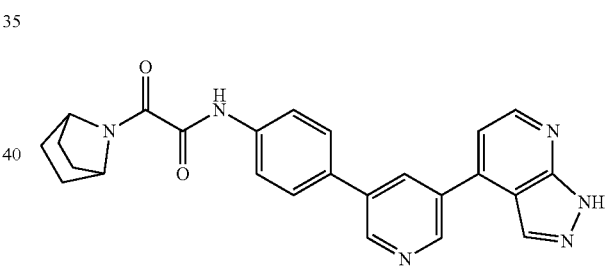

Step 1. Preparation of methyl 2-(7-azabicyclo[2.2.1]heptan-7-yl)-2-oxoacetate

To a solution of 7-azabicyclo[2.2.1]heptane (100 mg, 0.748 mmol, HCl salt) and Et₃N (0.3 mL, 2 mmol) in DCM (3 mL), and methyl oxalyl chloride (0.1 mL, 0.9 mmol) was added dropwise at 0° C. Then the resulting reaction mixture was stirred at 20° C. for 1 hour. A yellow suspension was formed. LCMS showed the purity of the desired product is 99% (Rt=0.519 min; MS Calcd: 183.1; MS Found: 183.9 [M+H]+). The reaction mixture was quenched by water (10 mL). The aqueous layer was extracted with DCM (20 mL×3). The combined organic layer was washed with water (20 mL), brine (20 mL), dried over anhydrous $Na_2SO_4$, filtered and concentrated under reduced pressure. The residue was purified by Combi Flash (0% to 30% EtOAc in PE) to give methyl 2-(7-azabicyclo[2.2.1]heptan-7-yl)-2-oxoacetate (137 mg, yield: quantitative) as colorless oil.

$^1$H NMR (400 MHz, $CDCl_3$) δ 1.46-1.57 (4H, m), 1.77-1.93 (4H, m), 3.86 (3H, s), 4.60 (1H, t, J=4.0 Hz), 4.73 1H, t, J=4.0 Hz).

Step 2. Preparation of 2-(7-azabicyclo[2.2.1]heptan-7-yl)-N-(4-(5-bromopyridin-3-yl)phenyl)-2-oxoacetamide

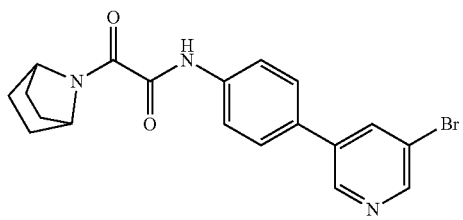 [SMILES: O=C(Nc1ccc(-c2cncc(Br)c2)cc1)C(=O)N1C2CCC1CC2]

To a mixture of 4-(5-bromopyridin-3-yl)aniline (66 mg, 0.26 mmol) (see Example 217, Step 1c) and methyl 2-(7-azabicyclo[2.2.1]heptan-7-yl)-2-oxoacetate (53 mg, 0.29 mmol) in DCM (3 mL), $AlMe_3$ (0.4 mL, 0.8 mmol, 2M in toluene) was added dropwise at 0° C. Then the resulting reaction mixture was stirred at 20° C. for 20 hours. A yellow solution was formed. LCMS showed the purity of the desired product is 51% (Rt=0.936 min; MS Calcd: 399.1; MS Found: 400.0 [M+H]$^+$). The reaction mixture was quenched with sat. aq. $NaHCO_3$ (20 mL), then filtered and the solid was washed with EtOAc (50 mL). The filtrate was washed with water (20 mL), brine (20 mL), dried over anhydrous $Na_2SO_4$, filtered and concentrated under reduced pressure. The residue was purified by Combi Flash (50% to 100% EtOAc in PE) to give 2-(7-azabicyclo[2.2.1]heptan-7-yl)-N-(4-(5-bromopyridin-3-yl)phenyl)-2-oxoacetamide (90 mg, yield: 85%) as a white solid.

$^1$H NMR (400 MHz, $CDCl_3$) δ 1.55-1.64 (4H, m), 1.80-1.88 (2H, m), 1.91-1.99 (2H, m), 4.80 (1H, t, J=4.8 Hz), 5.72 (1H, t, J=4.8 Hz), 7.57 (2H, d, J=8.4 Hz), 7.76 (2H, d, J=8.4 Hz), 8.02 (1H, t, J=2.0 Hz), 8.65 (1H, s), 8.75 (1H, s), 9.55 (1H, s).

Step 3. Preparation of 2-(7-azabicyclo[2.2.1]heptan-7-yl)-2-oxo-N-(4-(5-(4,4,5,5-tetramethyl-1,3,2-dioxaborolan-2-yl)pyridin-3-yl)phenyl)acetamide

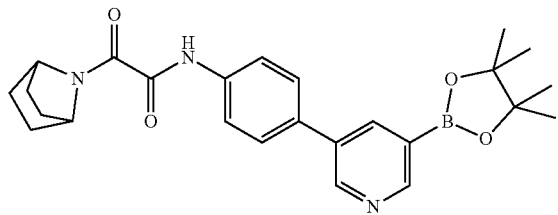 [SMILES: CC1(C)OB(c2cncc(-c3ccc(NC(=O)C(=O)N4C5CCC4CC5)cc3)c2)OC1(C)C]

A mixture of 2-(7-azabicyclo[2.2.1]heptan-7-yl)-N-(4-(5-bromopyridin-3-yl)phenyl)-2-oxoacetamide (50 mg, 0.12 mmol), Bispin (38 mg, 0.15 mmol), $Pd(dppf)Cl_2$ (9 mg, 0.01 mmol) and KOAc (37 mg, 0.37 mmol) in anhydrous dioxane (3 mL) was degassed and purged with $N_2$ for 3 times. And the resulting mixture was stirred at 100° C. for 16 hours under $N_2$ atmosphere. A black suspension was formed. LCMS showed the purity of the boronic acid of the desired product is 55% (Rt=0.677 min; MS Calcd: 365.2; MS Found: 365.8 [M+H]$^+$). The reaction mixture was filtered through a pad of celite, the solid was washed with EtOAc (50 mL) and the filtrate was concentrated under reduced pressure to give 2-(7-azabicyclo[2.2.1]heptan-7-yl)-2-oxo-N-(4-(5-(4,4,5,5-tetramethyl-1,3,2-dioxaborolan-2-yl)pyridin-3-yl)phenyl)acetamide (crude), which was used for the next step without further purification.

Step 4. Preparation of N-(4-(5-(1H-pyrazolo[3,4-b]pyridin-4-yl)pyridin-3-yl)phenyl)-2-(7-azabicyclo[2.2.1]heptan-7-yl)-2-oxoacetamide

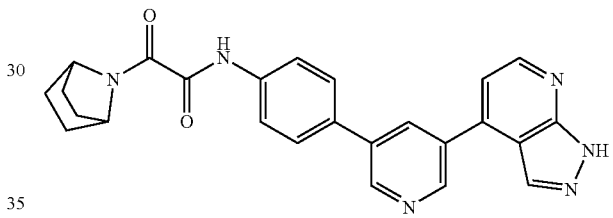

A mixture of 2-(7-azabicyclo[2.2.1]heptan-7-yl)-2-oxo-N-(4-(5-(4,4,5,5-tetramethyl-1,3,2-dioxaborolan-2-yl)pyridin-3-yl)phenyl)acetamide (crude), 4-chloro-1H-pyrazolo[3,4-b]pyridine (19 mg, 0.12 mmol), $Pd(dppf)Cl_2$ (9 mg, 0.01 mmol) and $Na_2CO_3$ (39 mg, 0.369 mmol) in dioxane (3 mL) and water (1 mL) was degassed and purged with $N_2$ for 3 times. And the resulting reaction mixture was stirred at 100° C. for 16 hours under $N_2$ atmosphere. A black suspension was formed. LCMS showed the purity of the desired product is 27% (Rt=0.826 min; MS Calcd: 438.2; MS Found: 439.2 [M+H]$^+$). The reaction mixture was diluted with water (20 mL). The aqueous layer was extracted with EtOAc/THF (30 mL×3, 1/1). The combined organic layer was washed with water (20 mL×2), brine (30 mL), dried over anhydrous $Na_2SO_4$, filtered and concentrated under reduced pressure. The residue was purified by prep-HPLC (0.225% FA as an additive) to give N-(4-(5-(1H-pyrazolo[3,4-b]pyridin-4-yl)pyridin-3-yl)phenyl)-2-(7-azabicyclo[2.2.1]heptan-7-yl)-2-oxoacetamide (9.1 mg, yield: 16% for two steps) as an off-white solid.

$^1$H NMR (400 MHz, DMSO-$d_6$) δ 1.49-1.61 (4H, m), 1.65-1.74 (2H, m), 1.78-1.86 (2H, m), 4.60 (1H, t, J=4.8 Hz), 4.89 (1H, t, J=4.8 Hz), 7.59 (1H, d, J=4.8 Hz), 7.90-7.94 (4H, m), 8.45 (1H, s), 8.50 (1H, t, J=2.0 Hz), 8.66 (1H, d, J=4.8 Hz), 9.04-9.09 (2H, m), 10.82 (1H, brs), 13.90 (1H, brs).

Example 205: N-(4-(5-(1H-pyrazolo[3,4-b]pyridin-4-yl)pyridin-3-yl)phenyl)-5-cyclobutylisoxazole-3-carboxamide

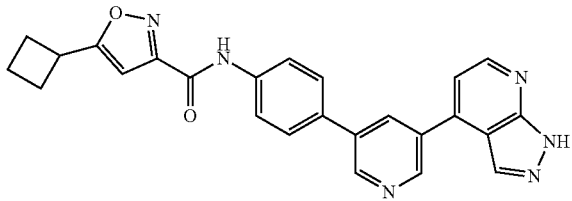 [SMILES: O=C(Nc1ccc(-c2cncc(-c3ccnc4[nH]ncc34)c2)cc1)c1cc(C2CCC2)on1]

Step 1. Preparation of 5-cyclobutlisoxazole-3-carboxylic acid

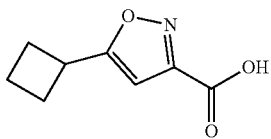 [SMILES: O=C(O)c1cc(C2CCC2)on1]

Step 1a. Preparation of methyl 4-cyclobutyl-2,4-dioxobutanoate

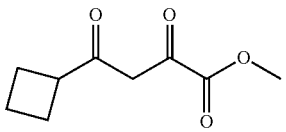

To a solution of 1-cyclobutylethan-1-one (1.00 g, 10.2 mmol) and dimethyl oxalate (1.32 g, 11.2 mmol) in toluene (20 mL), a solution of KOtBu (1.37 g, 12.2 mmol) in THF (10 mL) was added dropwise at 0° C. Then the resulting reaction mixture was stirred at 20° C. for 16 hours. A yellow suspension was formed. LCMS showed the purity of the desired product is 85% (Rt=0.813 min; MS Calcd: 184.1; MS Found: 184.8 [M+H]$^+$). The reaction mixture was quenched by 1 N aqueous HCl (30 mL). The aqueous layer was extracted with EtOAc (30 mL×3). The combined organic layer was washed with water (20 mL×2), brine (20 mL), dried over anhydrous Na$_2$SO$_4$, filtered and concentrated to give methyl 4-cyclobutyl-2,4-dioxobutanoate (crude) as colorless oil, which was used for the next step directly without further purification. $^1$H NMR (400 MHz, CDCl$_3$) δ 1.84-1.91 (1H, m), 1.97-2.06 (1H, m), 2.19-2.35 (4H, m), 3.27-3.36 (1H, m), 3.89 (3H, s), 6.32 (1H, s), 14.52 (1H, brs).

Step 1b. Preparation of methyl 5-cyclobutylisoxazole-3-carboxylate

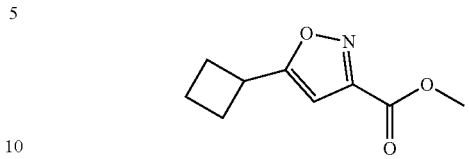

To a mixture of methyl 4-cyclobutyl-2,4-dioxobutanoate (1.80 g, crude) in DCM (3 mL), NH$_2$OH·HCl (1.02 g, 14.7 mmol) was added. Then the resulting reaction mixture was stirred at 50° C. for 6 hours. A yellow solution was formed. LCMS showed the purity of the desired product is 59% (Rt=0.771 min; MS Calcd: 181.1; MS Found: 181.9 [M+H]$^+$). The reaction mixture was concentrated under reduced pressure. The residue was purified by Combi Flash (0% to 20% EtOAc in PE) to give methyl 5-cyclobutyl-isoxazole-3-carboxylate (950 mg, yield: 54%) as colorless oil.

$^1$H NMR (400 MHz, CDCl$_3$) δ 1.93-2.02 (1H, m), 2.04-2.12 (1H, m), 2.24-2.34 (2H, m), 2.38-2.47 (2H, m), 3.63-3.72 (1H, m), 3.96 (3H, s), 6.43 (1H, s).

Step 1c. Preparation of 5-cyclobutylisoxazole-3-carboxylic acid

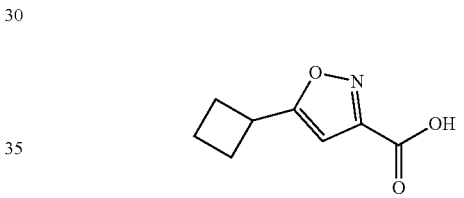

The methyl 5-cyclobutylisoxazole-3-carboxylate (950 mg, 5.24 mmol) was dissolved in THF (5 mL) and water (5 mL), and was treated with LiOH·H$_2$O (880 mg, 21.0 mmol) at 50° C. for 16 hours. A light yellow suspension was formed. TLC showed the starting material was consumed up. The reaction mixture was diluted with water (5 mL). Then the pH of the mixture was adjust to 4 with aqueous HCl (1 M). The aqueous layer was extracted with EtOAc (30 mL×3). The combined organic layer was washed with brine (20 mL), dried over anhydrous Na$_2$SO$_4$, filtered and concentrated to give 5-cyclobutylisoxazole-3-carboxylic acid (850 mg, yield: 97%) as a light yellow solid.

$^1$H NMR (400 MHz, CDCl$_3$) δ 1.95-2.02 (1H, m), 2.07-2.14 (1H, m), 2.26-2.35 (2H, m), 2.41-2.49 (2H, m), 3.66-3.75 (1H, m), 6.49 (1H, s), 7.91 (1H, brs).

Step 2. Preparation of 4-(5-(1H-pyrazolo[3,4-b]pyridin-4-yl)pyridin-3-yl)aniline

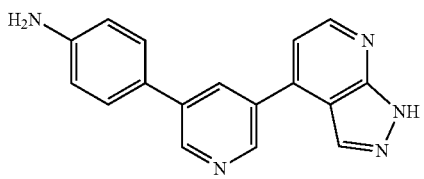 [SMILES: Nc1ccc(-c2cncc(-c3ccnc4[nH]ncc34)c2)cc1]

Step 2a. Preparation of tert-butyl (4-(5-bromopyridin-3-yl)phenyl)carbamate

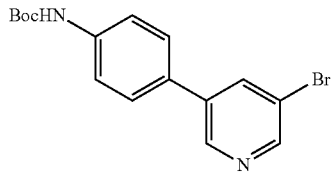

A mixture of (4-((tert-butoxycarbonyl)amino)phenyl)boronic acid (5.00 g, 21.1 mmol), 3,5-dibromopyridine (7.49 g, 31.6 mmol), Pd(dppf)Cl$_2$ (1.54 g, 2.11 mmol) and Na$_2$CO$_3$ (6.71 g, 63.3 mmol) in dioxane (40 mL) and water (10 mL) was degassed and purged with N$_2$ for 3 times. And the resulting reaction mixture was stirred at 100° C. for 1 hour under N$_2$ atmosphere. A black suspension was formed. LCMS showed the purity of the desired product is 52% (Rt=0.971 min; MS Calcd: 348.1; MS Found: 348.9 [M+H]$^+$). The reaction mixture was filtered through a pad of celite and the solid was washed with EtOAc (200 mL) to give a filtrate, which was diluted with water (100 mL). The aqueous layer was extracted with EtOAc (50 mL×2). The combined organic layer was washed with water (60 mL×2), brine (60 mL), dried over anhydrous Na$_2$SO$_4$, filtered and concentrated under reduced pressure. The residue was purified by Combi Flash (0% to 30% EtOAc in PE) to give tert-butyl (4-(5-bromopyridin-3-yl)phenyl)carbamate (4.55 g, yield: 62%) as a white solid.

$^1$H NMR (400 MHz, CDCl$_3$) δ 1.54 (9H, s), 6.58 (1H, brs), 7.45-7.56 (4H, m), 7.99 (1H, t, J=2.0 Hz), 8.62 (1H, d, J=1.8 Hz), 8.73 (1H, d, J=1.8 Hz).

Step 2b. Preparation of tert-butyl (4-(5-(4,4,5,5-tetramethyl-1,3,2-dioxaborolan-2-yl)pyridin-3-yl)phenyl)carbamate

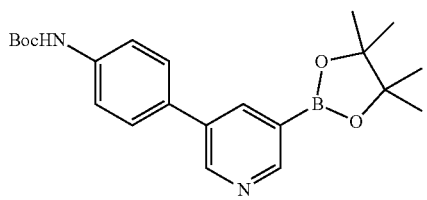 [SMILES: CC(C)(C)OC(=O)Nc1ccc(-c2cncc(B3OC(C)(C)C(C)(C)O3)c2)cc1]

A mixture of tert-butyl (4-(5-bromopyridin-3-yl)phenyl)carbamate (200 mg, 0.573 mmol), Bispin (174 mg, 0.687 mmol), Pd(dppf)Cl$_2$ (42 mg, 0.057 mmol) and KOAc (169 mg, 1.72 mmol) in anhydrous dioxane (5 mL) was degassed and purged with N$_2$ for 3 times. And the resulting mixture was stirred at 100° C. for 16 hours under N$_2$ atmosphere. A black suspension was formed. LCMS showed the purity of the boronic acid of the desired product is 78% (Rt=0.593 min; MS Calcd: 314.1; MS Found: 315.0 [M+H]$^+$). The reaction mixture was filtered through a pad of celite, washed with EtOAc (50 mL) and concentrated under reduced pressure to give tert-butyl (4-(5-(4,4,5,5-tetramethyl-1,3,2-dioxaborolan-2-yl)pyridin-3-yl)phenyl)carbamate (crude), which was used for the next step without further purification.

Step 2c. Preparation of tert-butyl (4-(5-(1H-pyrazolo[3,4-b]pyridin-4-yl)pyridin-3-yl)phenyl)carbamate

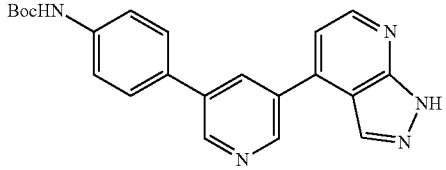 [SMILES: CC(C)(C)OC(=O)Nc1ccc(-c2cncc(-c3ccnc4[nH]ncc34)c2)cc1]

A mixture of tert-butyl (4-(5-(4,4,5,5-tetramethyl-1,3,2-dioxaborolan-2-yl)pyridin-3-yl)phenyl)carbamate (crude), 4-chloro-1H-pyrazolo[3,4-b]pyridine (88 mg, 0.570 mmol), Pd(dppf)Cl$_2$ (42 mg, 0.057 mmol) and Na$_2$CO$_3$ (181 mg, 1.71 mmol) in dioxane (4 mL) and water (1 mL) was degassed and purged with N$_2$ for 3 times. And the resulting reaction mixture was stirred at 100° C. for 16 hours under N$_2$ atmosphere. A black suspension was formed. LCMS showed the purity of the desired product is 47% (Rt=0.832 min; MS Calcd: 387.2; MS Found: 388.0 [M+H]$^+$). The reaction mixture was diluted with water (20 mL). The aqueous layer was extracted with EtOAc (30 mL×3). The combined organic layer was washed with water (20 mL), brine (40 mL), dried over anhydrous Na$_2$SO$_4$, filtered and concentrated under reduced pressure. The residue was purified by Combi Flash (20% to 100% EtOAc in PE) to give tert-butyl (4-(5-(1H-pyrazolo[3,4-b]pyridin-4-yl)pyridin-3-yl)phenyl)carbamate (200 mg, yield: 91% for two steps) as a yellow solid.

Step 2d Preparation of 4-(5-(1H-pyrazolo[3,4-b]pyridin-4-yl)pyridin-3-yl)aniline

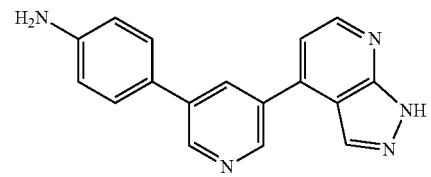 [SMILES: Nc1ccc(-c2cncc(-c3ccnc4[nH]ncc34)c2)cc1]

A solution of tert-butyl (4-(5-(1H-pyrazolo[3,4-b]pyridin-4-yl)pyridin-3-yl)phenyl)carbamate (200 mg, 0.516 mmol) in TFA (2.5 mL) and DCM (2.5 mL) was stirred at 20° C. for 2 hours. An orange solution was formed. LCMS showed the purity of the desired product is 83% (Rt=0.664 min; MS Calcd: 287.1; MS Found: 300.0 [M+H]$^+$). The reaction mixture was concentrated and the residue was dissolved in DCM/MeOH (20 mL, 1/1), then basified with 1 N aqueous NaOH to PH=8. The precipitate was filtrated and washed with water (10 mL), MeCN (10 mL) and dried under reduced pressure to give 4-(5-(1H-pyrazolo[3,4-b]pyridin-4-yl)pyridin-3-yl)aniline (142 mg, yield: 96%) as a white solid.

Step 3. Preparation of N-(4-(5-(1H-pyrazolo[3,4-b]pyridin-4-yl)pyridin-3-yl)phenyl)-5-cyclobutylisoxazole-3-carboxamide

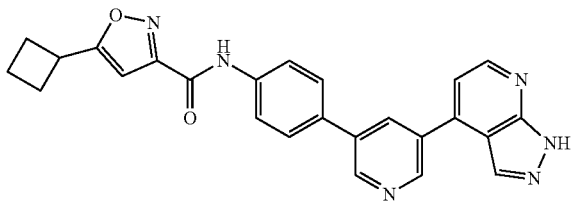 [SMILES: O=C(Nc1ccc(-c2cncc(-c3ccnc4[nH]ncc34)c2)cc1)c1cc(C2CCC2)on1]

A mixture of 5-cyclobutylisoxazole-3-carboxylic acid (49 mg, 0.29 mmol), 4-(5-(1H-pyrazolo[3,4-b]pyridin-4-yl)pyridin-3-yl)aniline (70 mg, 0.24 mmol) and EDC·HCl (70 mg, 0.36 mmol) in pyridine (2 mL) was heated at 50° C. for 2 hours. A yellow solution was formed. LCMS showed the purity of the desired product is 49% (Rt=0.802 min; MS Calcd: 436.2; MS Found: 436.9 [M+H]$^+$). The mixture was concentrated to remove the residual pyridine. The residue was purified by prep-HPLC (0.225% FA as an additive) to give N-(4-(5-(1H-pyrazolo[3,4-b]pyridin-4-yl)pyridin-3-yl)phenyl)-5-cyclobutylisoxazole-3-carboxamide (15.9 mg, yield: 15%) as a white solid.

$^1$H NMR (400 MHz DMSO-d$_6$) δ 1.90-1.97 (1H, m), 2.02-2.10 (1H, m), 2.23-2.31 (2H, m), 2.36-2.45 (2H, m), 3.74-3.83 (1H, m), 6.83 (1H, s), 7.59 (1H, d, J=4.8 Hz), 7.90-8.01 (4H, m), 8.46 (1H, s), 8.49 (1H, t, J=2.0 Hz), 8.66 (1H, d, J=4.8 Hz), 9.07 (1H, d, J=10.0 Hz, 2.0 Hz), 10.85 (1H, brs), 13.91 (1H, brs).

Example 206: N-(3-(1H-1,2,3-triazol-1-yl)phenyl)-4-(5-(1H-pyrazolo[3,4-b]pyridin-4-yl)pyridin-3-yl)-N-methylbenzamide

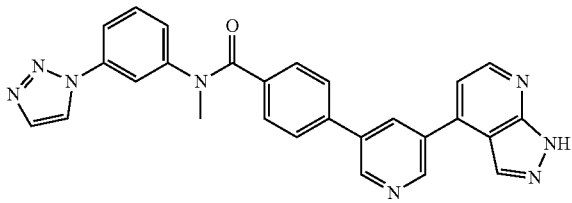 [SMILES: CN(C(=O)c1ccc(-c2cncc(-c3ccnc4[nH]ncc34)c2)cc1)c1cccc(-n2ccnn2)c1]

Step 1: Preparation of methyl 4-(5-bromopyridin-3-yl)benzoate

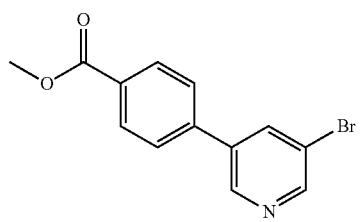 [SMILES: COC(=O)c1ccc(-c2cncc(Br)c2)cc1]

Step 1a: Preparation of methyl 4-(4,4,5,5-tetramethyl-1,3,2-dioxaborolan-2-yl)benzoate

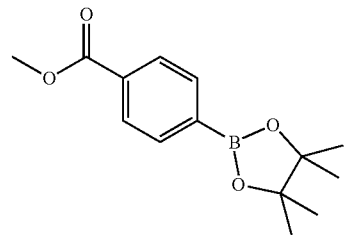

A mixture of methyl 4-bromobenzoate (2.00 g, 9.30 mmol), Bispin (2.83 g, 11.2 mmol), Pd(dppf)Cl$_2$ (680 mg, 0.930 mmol) and KOAc (2.74 g, 27.9 mmol) in anhydrous dioxane (20 mL) was degassed and purged with N$_2$ for 3 times. And the resulting mixture was stirred at 100° C. for 16 hours under N$_2$ atmosphere. A black suspension was formed. LCMS showed the purity of the desired product is 58% (Rt=0.993 min; MS Calcd: 262.1; MS Found: 262.9 [M+H]$^+$). The reaction mixture was filtered through a pad of celite, and the solid was washed with EtOAc (100 mL), the filtrate was concentrated under reduced pressure to give methyl 4-(4,4,5,5-tetramethyl-1,3,2-dioxaborolan-2-yl)benzoate (crude), which was used for the next step without further purification.

Step 1b. Preparation of methyl 4-(5-bromopyridin-3-yl)benzoate

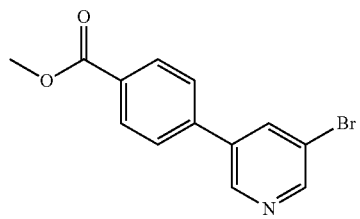 [SMILES: COC(=O)c1ccc(-c2cncc(Br)c2)cc1]

A mixture of methyl 4-(4,4,5,5-tetramethyl-1,3,2-dioxaborolan-2-yl)benzoate (crude), 3,5-dibromopyridine (3.31 g, 14.0 mmol), Pd(dppf)Cl$_2$ (340 mg, 0.465 mmol) and Na$_2$CO$_3$ (2.96 g, 27.9 mmol) in dioxane (30 mL) and water (6 mL) was degassed and purged with N$_2$ for 3 times. And the resulting reaction mixture was stirred at 100° C. for 4 hours under N$_2$ atmosphere. A black suspension was formed. LCMS showed the purity of the desired product is 27% (Rt=0.839 min; MS Calcd: 291.0; MS Found: 291.7 [M+H]$^+$). The reaction mixture was diluted with water (50 mL). The aqueous layer was extracted with EtOAc/THF (50 mL×2, 1/1). The combined organic layer was washed with water (50 mL×2), brine (50 mL), dried over anhydrous Na$_2$SO$_4$, filtered and concentrated under reduced pressure. The residue was purified by Combi Flash (2% to 50% EtOAc in PE) to give methyl 4-(5-bromopyridin-3-yl)benzoate (4.00 g, purity: 61%, yield: 90% for two steps) as a yellow solid.

Step 2. Preparation of 3-(1H-1,2,3-triazol-1-yl)aniline

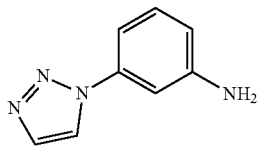 [SMILES: Nc1cccc(-n2ccnn2)c1]

Step 2a. Preparation of tert-butyl (3-(1H-1,2,3-triazol-1-yl)phenyl)carbamate

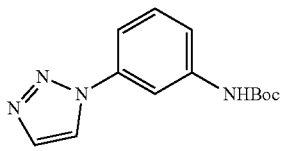 [SMILES: CC(C)(C)OC(=O)Nc1cccc(-n2ccnn2)c1]

A mixture of (3-((tert-butoxycarbonyl)amino)phenyl)boronic acid (200 mg, 0.843 mmol), NaN₃ (60 mg, 0.093 mmol) and CuI (32 mg, 0.17 mmol) in DMF (4.8 mL) and H₂O (0.8 mL) was stirred at 80° C. for 0.5 hour under $N_2$ atmosphere. A blue mixture was formed. TLC showed (3-((tert-butoxycarbonyl)amino)phenyl)boronic acid was consumed completely. After cooling to 20° C., DBU (64 mg, 0.42 mmol), sodium L-ascorbate (66 mg, 0.34 mmol) and propiolic acid (88 mg, 1.3 mmol) were added, and the reaction was stirred at 80° C. for 15 hours under $N_2$ atmosphere. The blue mixture turned to black. TLC showed tert-butyl (3-azidophenyl)carbamate was consumed nearly. Five batches were allowed to cool to rt and combined, then quenched with H₂O (35 mL), and extracted with EA (50 mL×3). The combined organic layer was dried over anhydrous Na₂SO₄ and concentrated. The residue was purified by Combi Flash (35% EA in PE) to give tert-butyl (3-(1H-1,2,3-triazol-1-yl)phenyl)carbamate (400 mg, yield: 36% for two steps) as a white solid.

Step 2b. Preparation of 3-(1H-1,2,3-triazol-1-yl)aniline

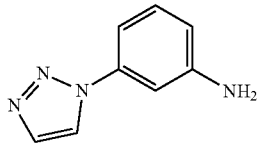 [SMILES: Nc1cccc(-n2ccnn2)c1]

TFA (1.3 mL, 17 mmol) was added to a solution of tert-butyl (3-(1H-1,2,3-triazol-1-yl)phenyl)carbamate (160 mg, 0.614 mmol) in DCM (3 mL) at 15° C. and the mixture was stirred at 15° C. for 12 hours. A yellow solution was formed. LCMS showed the starting material was consumed completely. The mixture was concentrated. Sat. aq. NaHCO₃ (10 mL) was added followed by DCM (15 mL). The organic layer was separated and the aqueous layer extracted with DCM (10 mL×2). The combined organics were dried over Na₂SO₄, filtered and concentrated to give 3-(1H-1,2,3-triazol-1-yl)aniline (98 mg, yield: quantitative) as a white solid. Used for the next step without further purification.

¹H NMR (400 MHz, DMSO-d₆) δ 5.53 (2H, brs), 6.63-6.66 (1H, m), 6.91-6.95 (1H, m), 7.08 (1H, t, J=2.0 Hz), 7.19 (1H, t, J=8.0 Hz), 7.92 (1H, d, J=1.2 Hz), 8.63 (1H, d, J=1.2 Hz).

Step 3. Preparation of N-(3-(1H-1,2,3-triazol-1-yl)phenyl)-4-(5-bromopyridin-3-yl)benzamide

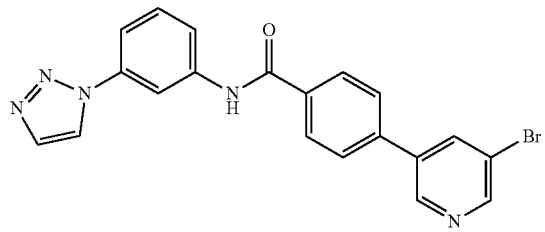 [SMILES: O=C(Nc1cccc(-n2ccnn2)c1)c1ccc(-c2cncc(Br)c2)cc1]

To a mixture of 3-(1H-1,2,3-triazol-1-yl)aniline (95 mg, 0.59 mmol) and methyl 4-(5-bromopyridin-3-yl)benzoate (248 mg, 0.59 mmol) in DCM (5 mL), AlMe₃ (0.9 mL, 1.8 mmol, 2M in toluene) was added dropwise at 0° C. Then the resulting reaction mixture was stirred at 20° C. for 16 hours. A yellow solution was formed. LCMS showed the purity of the desired product is 62% (Rt=0.909 min; MS Calcd: 419.0; MS Found: 419.9 [M+H]⁺). The reaction mixture was quenched with sat. aq. NaHCO₃ (5 mL), then filtered through a pad of celite and the solid was washed with DCM (50 mL). The filtrate was washed with brine (30 mL), dried over anhydrous Na₂SO₄, filtered and concentrated under reduced pressure. The residue was purified by Combi Flash (50% to 100% EtOAc in PE) to give N-(3-(1H-1,2,3-triazol-1-yl)phenyl)-4-(5-bromopyridin-3-yl)benzamide (200 mg, yield: 80%) as a yellow solid.

Step 4. Preparation of N-(3-(1H-1,2,3-triazol-1-yl)phenyl)-4-(5-bromopyridin-3-yl)-N-methylbenzamide

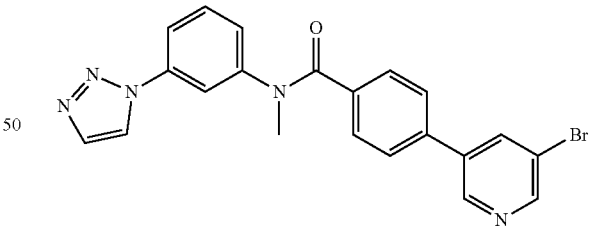

To a solution of N-(3-(1H-1,2,3-triazol-1-yl)phenyl)-4-(5-bromopyridin-3-yl)benzamide (200 mg, 0.476 mmol) in anhydrous DMF (3 mL), NaH (28 mg, 0.714 mmol) was added firstly. Then the reaction mixture was stirred at 0° C. for 30 minutes. After that, CH₃I (203 mg, 1.43 mmol, 0.090 mL) was added dropwise at 0° C. Then the resulting reaction mixture was stirred at 0° C. for 2.5 hours. A yellow suspension was formed. LCMS showed the purity of the desired product is 78% (Rt=0.771 min; MS Calcd: 433.0; MS Found: 434.0 [M+H]⁺). The reaction mixture was quenched by saturate aqueous NH₄Cl (20 mL). The aqueous layer was extracted with DCM/MeOH (20 mL×3, 10/1). The combined organic layer was washed with water (20 mL×2), brine (20 mL×2), dried over anhydrous Na$_2$SO$_4$, filtered and concentrated to give N-(3-(1H-1,2,3-triazol-1-yl)phenyl)-4-(5-bromopyridin-3-yl)-N-methylbenzamide (crude) as black gum, which was used for the next step directly without further purification.

Step 5. Preparation of N-(3-(1H-1,2,3-triazol-1-yl) phenyl)-N-methyl-4-(5-(4,4,5,5-tetramethyl-1,3,2-dioxaborolan-2-yl)pyridin-3-yl)benzamide

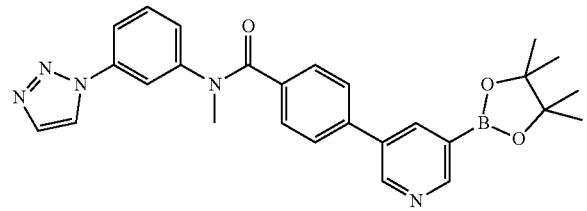 [SMILES: CN(C(=O)c1ccc(-c2cncc(B3OC(C)(C)C(C)(C)O3)c2)cc1)c1cccc(-n2ccnn2)c1]

A mixture of N-(3-(1H-1,2,3-triazol-1-yl)phenyl)-4-(5-bromopyridin-3-yl)-N-methylbenzamide (200 mg, 0.460 mmol), Bispin (152 mg, 0.599 mmol), Pd(dppf)Cl$_2$ (34 mg, 0.046 mmol) and KOAc 135 mg, 1.38 mmol) in anhydrous dioxane (5 mL) was degassed and purged with N$_2$ for 3 times. And the resulting mixture was stirred at 100° C. for 16 hours under N$_2$ atmosphere. A black suspension was formed. LCMS showed the purity of the boronic acid of the desired product is 54% (Rt=0.634 min; MS Calcd: 399.2; MS Found: 400.1 [M+H]$^+$). The reaction mixture was filtered through a pad of celite, the solid was washed with EtOAc (50 mL) and the filtrate was concentrated under reduced pressure to give N-(3-(1H-1,2,3-triazol-1-yl)phenyl)-N-methyl-4-(5-(4,4,5,5-tetramethyl-1,3,2-dioxaborolan-2-yl)pyridin-3-yl)benzamide (crude), which was used for the next step without further purification.

Step 6. Preparation of N-(3-(1H-1,2,3-triazol-1-yl) phenyl)-4-(5-(1H-pyrazolo[3,4-b]pyridin-4-yl)pyridin-3-yl)-N-methylbenzamide

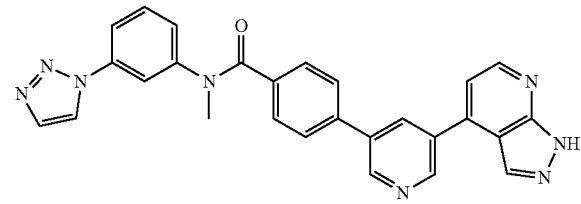 [SMILES: CN(C(=O)c1ccc(-c2cncc(-c3ccnc4[nH]ncc34)c2)cc1)c1cccc(-n2ccnn2)c1]

A mixture of N-(3-(1H-1,2,3-triazol-1-yl)phenyl)-N-methyl-4-(5-(4,4,5,5-tetramethyl-1,3,2-dioxaborolan-2-yl) pyridin-3-yl)benzamide (crude), 4-chloro-1H-pyrazolo[3,4-b]pyridine (70 mg, 0.50 mmol), Pd(dppf)Cl$_2$ (34 mg, 0.046 mmol) and Na$_2$CO$_3$ (146 mg, 1.38 mmol) in dioxane (4 mL) and water (1 mL) was degassed and purged with N$_2$ for 3 times. And the resulting reaction mixture was stirred at 100° C. for 16 hours under N$_2$ atmosphere. A black suspension was formed. LCMS showed the purity of the desired product is 33% (Rt=0.690 min; MS Calcd: 472.2; MS Found: 495.2 [M+Na]+). The reaction mixture was diluted with water (20 mL). The aqueous layer was extracted with EtOAc/THF (30 mL×3, 1/1). The combined organic layer was washed with water (20 mL×2), brine (30 mL), dried over anhydrous Na$_2$SO$_4$, filtered and concentrated under reduced pressure. The residue was purified by Combi Flash (0% to 10% MeOH in DCM), and further purified by prep-HPLC (0.225% FA as an additive) to give N-(3-(1H-1,2,3-triazol-1-yl)phenyl)-4-(5-(1H-pyrazolo[3,4-b]pyridin-4-yl)pyridin-3-yl)-N-methylbenzamide (20.1 mg, yield: 9% for two steps) as an off-white solid.
$^1$H NMR (400 MHz, DMSO-d$_6$) δ 3.49 (3H, s), 7.30 (1H, d, J=8.0 Hz), 7.47-7.56 (4H, m), 7.78 (1H, d, J=8.0 Hz), 7.85 (2H, d, J=8.0 Hz), 7.97-8.00 (2H, m), 8.42 (1H, s), 8.45 (1H, t, J=2.0 Hz), 8.63 (1H, d, J=4.8 Hz), 8.81 (1H, s), 9.02 (1H, s), 9.06 (1H, s), 13.89 (1H, brs).

Example 207: 4-(5-(4-(2-oxopyrrolidin-1-yl)phenyl)pyridin-3-yl)-7-(pyridin-2-yl)-8,9-dihydropyrido[3',2':4,5]pyrrolo[1,2-a]pyrazin-6(7H)-one

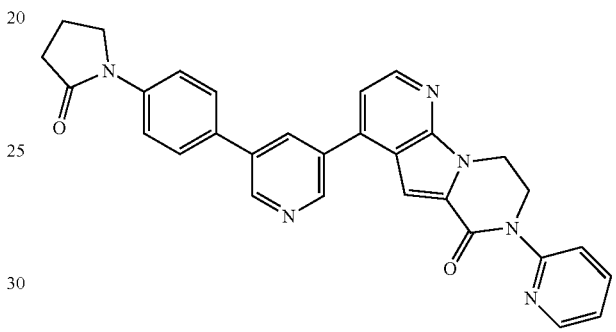

Step 1. Preparation of 4-(5-(4-(2-oxopyrrolidin-1-yl)phenyl)pyridin-3-yl)-8,9-dihydropyrido[3',2':4,5] pyrrolo[1,2-a]pyrazin-6(7H)-one

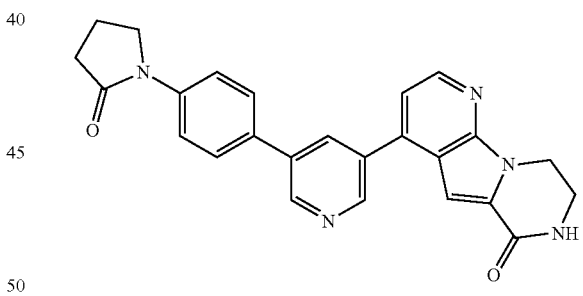

A mixture of 4-chloro-8,9-dihydropyrido[3',2':4,5]pyrrolo[1,2-a]pyrazin-6(7H)-one (50 mg, 0.23 mmol), 1-(4-(5-(4,4,5,5-tetramethyl-1,3,2-dioxaborolan-2-yl)pyridin-3-yl)phenyl)pyrrolidin-2-one (100 mg, 0.27 mmol), Pd(t-Bu$_3$P)$_2$ (12 mg, 0.023 mmol) and Cs$_2$CO$_3$ (221 mg, 0.677 mmol) in dioxane (3 mL) and H$_2$O (0.5 mL) was stirred at 100° C. for 1 hour. A black suspension was formed. LCMS showed the purity of the desired product is 67% (Rt=0.668 min; MS Calcd: 423.1; MS Found: 423.8 [M+Na]+). The reaction mixture was diluted with DCM/H$_2$O (30 mL, 1/1) and extracted with DCM (20 mL×3). The combined organic phase was concentrated. The residue was purified by prep-TLC (7% MeOH in DCM, Rf=0.46) to give 4-(5-(4-(2-oxopyrrolidin-1-yl)phenyl)pyridin-3-yl)-8,9-dihydropyrido[3',2':4,5]pyrrolo[1,2-a]pyrazin-6(7H)-one (32 mg, yield: 31% yield) as a gray solid.

Step 2. Preparation of 4-(5-(4-(2-oxopyrrolidin-1-yl)phenyl)pyridin-3-yl)-7-(pyridin-2-yl)-8,9-dihydropyrido[3',2':4,5]pyrrolo[1,2-a]pyrazin-6(7H)-one

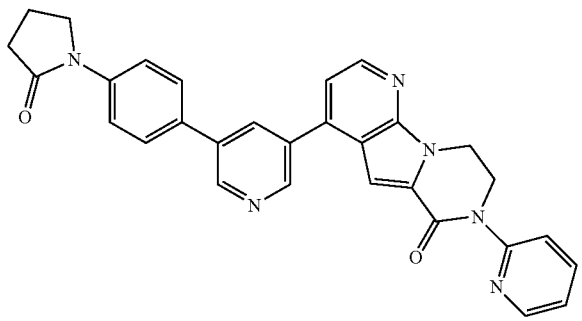 [SMILES: O=C1CCCN1c1ccc(-c2cncc(-c3ccnc4c3cc3n4CCN(c4ccccn4)C3=O)c2)cc1]

A mixture of 4-(5-(4-(2-oxopyrrolidin-1-yl)phenyl)pyridin-3-yl)-8,9-dihydropyrido[3',2':4,5]pyrrolo[1,2-a]pyrazin-6(7H)-one (30 mg, 0.071 mmol), 2-bromopyridine (20 mg, 0.13 mmol), Xantphos (16 mg, 0.028 mmol), $Pd_2(dba)_3$ (10 mg, 0.011 mmol) and $Cs_2CO_3$ (70 mg, 0.21 mmol) in dioxane (1 mL) was stirred at 90° C. for 16 hours under $N_2$ atmosphere. A black suspension was formed. LCMS showed the purity of the desired product is 14% (Rt=0.819 min; MS Calcd: 500.1; MS Found: 523.1 [M+Na]+). The reaction mixture was filtered and the filtrate was concentrated. The residue was purified by prep-HPLC (0.04% $NH_3H_2O$+10 mM $NH_4HCO_3$ as additives) and lyophilized to give 4-(5-(4-(2-oxopyrrolidin-1-yl)phenyl)pyridin-3-yl)-7-(pyridin-2-yl)-8,9-dihydropyrido[3',2':4,5]pyrrolo[1,2-a]pyrazin-6(7H)-one (7.8 mg, yield: 22% yield) as a white solid.

$^1$H NMR (400 MHz, DMSO-$d_6$) δ 2.01-2.16 (2H, m), 2.53-2.57 (2H, m, overlapped with DMSO signal), 3.90 (2H, t, J=6.8 Hz), 4.52-4.58 (2H, m), 4.59-4.66 (2H, m), 7.24-7.29 (1H, m), 7.38 (1H, s), 7.85 (1H, d, J=5.2 Hz), 7.80-7.95 (5H, m), 7.99 (1H, d, J=8.0 Hz), 8.40-8.44 (1H, m), 8.51 (1H, d, J=4.0 Hz), 8.62 (1H, d, J=4.8 Hz), 8.97 (1H, d, J=2.0 Hz), 9.05 (1H, d, J=2.0 Hz).

Example 208: 7-methyl-4-(5-(4-(4-methyl-2-oxoindolin-1-yl)phenyl)pyridin-3-yl)-8,9-dihydropyrido[3',2':4,5]pyrrolo[1,2-a]pyrazin-6(7H)-one

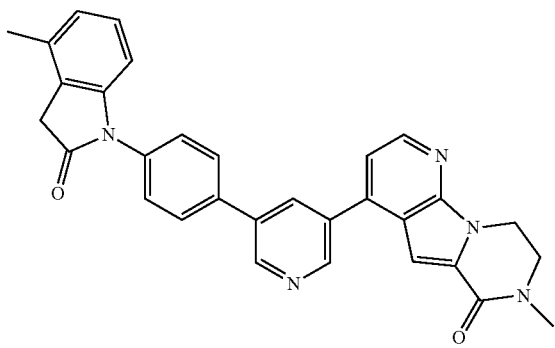

Step 1. Preparation of 1-(4-bromophenyl)-4-methylindolin-2-one

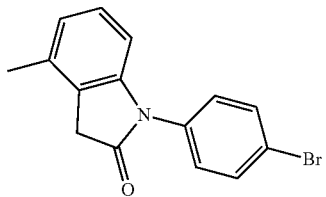 [SMILES: Cc1cccc2c1CC(=O)N2c1ccc(Br)cc1]

A mixture of 4-methylindolin-2-one (500 mg, 3.40 mmol), 1-bromo-4-iodobenzene (1.15 g, 4.06 mmol), CuI (500 mg, 2.63 mmol), L-PROLINE (310 mg, 2.69 mmol) and CsF (1.03 g, 6.78 mmol) in EtOAc (20 mL) was stirred at 50° C. for 36 hours under $N_2$ atmosphere. A black suspension was formed. TLC (PE/EtOAc=3/1, Rf=0.67) showed the starting material was consumed nearly. The reaction mixture was diluted with EtOAc/$H_2O$ (2/1, 100 mL) then separated. The aqueous was extracted with EtOAc (800 mL×3). The combined organic phase was concentrated. The residue was purified by Combi Flash (15% EtOAc in PE) to give 1-(4-bromophenyl)-4-methylindolin-2-one (235 mg, yield: 23%) as a light yellow solid. $^1$H NMR (400 MHz, $CDCl_3$) δ 2.32 (3H, s), 3.60 (2H, s), 6.62 (1H, d, J=8.0 Hz), 6.92 (1H, d, J=7.6 Hz), 7.13 (1H, t, J=8.0 Hz), 7.30 (2H, d, J=8.4 Hz), 7.65 (2H, d, J=8.2 Hz).

Step 2. Preparation of 4-methyl-1-(4-(4,4,5,5-tetramethyl-1,3,2-dioxaborolan-2-yl)phenyl)indolin-2-one

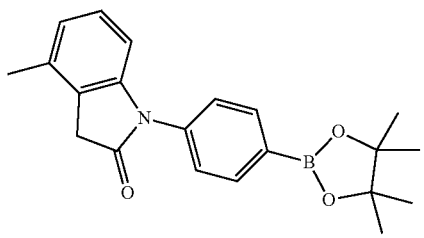

A mixture of 1-(4-bromophenyl)-4-methylindolin-2-one (230 mg, 0.761 mmol), Bispin (230 mg, 0.906 mmol), KOAc (230 mg, 2.34 mmol) and Pd(dppf)$Cl_2$ (50 mg, 0.068 mmol) in dioxane (4 mL) was stirred at 100° C. for 16 hours under $N_2$ atmosphere. A black suspension was formed. LCMS showed the purity of the desired product is 60% (Rt=1.038 min; MS Calcd: 349.2; MS Found: 350.2 [M+H]$^+$). The reaction mixture was filtered and the filtrate was concentrated to give 4-methyl-1-(4-(4,4,5,5-tetramethyl-1,3,2-dioxaborolan-2-yl)phenyl)indolin-2-one (270 mg, crude) as black-brown oil, which was used for the next step directly without further purification.

Step 3. Preparation of 1-(4-(5-bromopyridin-3-yl)phenyl)-4-methylindolin-2-one

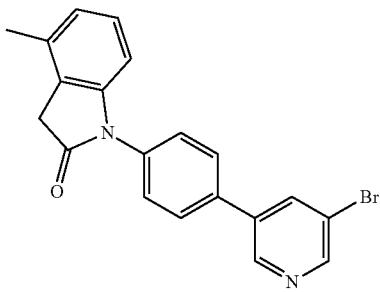 [SMILES: Cc1cccc2c1CC(=O)N2c1ccc(-c2cncc(Br)c2)cc1]

A mixture of 4-methyl-1-(4-(4,4,5,5-tetramethyl-1,3,2-dioxaborolan-2-yl)phenyl)indolin-2-one (265 mg, 0.759 mmol), 3,5-dibromopyridine (270 mg, 1.14 mmol) Na$_2$CO$_3$ (241 mg, 2.28 mmol) and Pd(dppf)Cl$_2$ (100 mg, 0.137 mmol) in dioxane (5 mL) and H$_2$O (2 mL) was stirred at 100° C. for 2 hours under N$_2$ atmosphere. A black suspension was formed. LCMS showed the purity of the desired product is 53% (Rt=0.975 min; MS Calcd: 378.0; MS Found: 379.3 [M+H]$^+$). The reaction mixture was diluted with DCM/H$_2$O (30 mL, 1/1) then extracted with DCM (30 mL×3). The combined organic phase was dried over anhydrous Na$_2$SO$_4$ and concentrated. The residue was purified by Combi Flash (10% EtOAc in PE) and triturated with PE/EtOAc (20 mL, 20/1) to give 1-(4-(5-bromopyridin-3-yl)phenyl)-4-methylindolin-2-one (50 mg, yield: 16% for two steps) as an off white solid.

$^1$H NMR (400 MHz, CDCl$_3$) δ 2.34 (3H, s), 3.64 (2H, s), 6.71 (1H, d, J=7.6 Hz), 6.94 (1H, d, J=7.6 Hz), 7.16 (1H, t, J=7.6 Hz), 7.53-7.74 (4H, m), 8.05 (1H, t, J=2.0 Hz), 8.69 (1H, d, J=2.4 Hz), 8.79 (1H, d, J=2.0 Hz).

Step 4. Preparation of 4-methyl-1-(4-(5-(4,4,5,5-tetramethyl-1,3,2-dioxaborolan-2-yl)pyridin-3-yl)phenyl)indolin-2-one

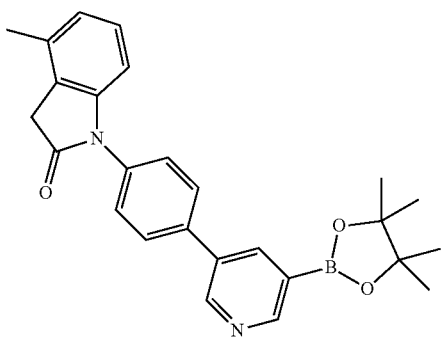

A mixture of 1-(4-(5-bromopyridin-3-yl)phenyl)-4-methylindolin-2-one (50 mg, 0.13 mmol), Bispin (41 mg, 0.16 mmol), Pd(dppf)Cl$_2$ (10 mg, 0.013 mmol) and KOAc (40 mg, 0.41 mmol) in dioxane (3 mL) was stirred at 100° C. for 16 hours under N$_2$ atmosphere. A black suspension was formed. LCMS showed the purity of the desired product is 49% (Rt=0.772 min; MS Calcd: 344.1; MS Found: 345.2 [M+H]$^+$). The reaction mixture was filtered and the filtrate was concentrated to give 4-methyl-1-(4-(5-(4,4,5,5-tetramethyl-1,3,2-dioxaborolan-2-yl)pyridin-3-yl)phenyl)indolin-2-one (60 mg, crude) as a black brown oil, which was used for the next step directly without purification.

Step 5. Preparation of 7-methyl-4-(5-(4-(4-methyl-2-oxoindolin-1-yl)phenyl)pyridin-3-yl)-8,9-dihydropyrido[3',2':4,5]pyrrolo[1,2-a]pyrazin-6(7H)-one

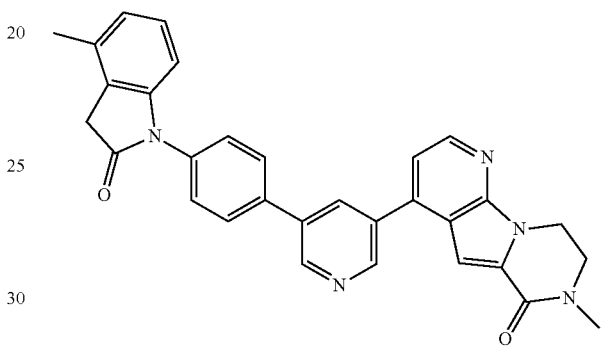

A mixture of 4-methyl-1-(4-(5-(4,4,5,5-tetramethyl-1,3,2-dioxaborolan-2-yl)pyridin-3-yl)phenyl)indolin-2-one (56 mg, 0.13 mmol), 4-chloro-7-methyl-8,9-dihydropyrido[3',2':4,5]pyrrolo[1,2-a]pyrazin-6(7H)-one (40 mg, 0.16 mmol), Pd(t-Bu$_3$P)$_2$ (7 mg, 0.01 mmol) and Cs$_2$CO$_3$ (130 mg, 0.399 mmol) in dioxane (3 mL) and H$_2$O (1 mL) was stirred at 100° C. for 1 hour under N$_2$ atmosphere. A black suspension was formed. LCMS showed the purity of the desired product is 58% (Rt=0.847 min; MS Calcd: 499.2; MS Found: 500.1 [M+H]$^+$). The reaction mixture was diluted with brine (10 mL) and DCM (20 mL) then extracted with DCM (20 mL×4). The resulting mixture was dried over anhydrous Na$_2$SO$_4$ and concentrated. The residue was purified by Combi Flash (5% MeOH in DCM) and triturated with DMF/MeCN (4 mL, 1/1). The mother liquid was purified by prep-HPLC (0.04% NH$_3$H$_2$O+10 mM NH$_4$HCO$_3$ as additives) and lyophilized to give 7-methyl-4-(5-(4-(4-methyl-2-oxoindolin-1-yl)phenyl)pyridin-3-yl)-8,9-dihydropyrido[3',2':4,5]pyrrolo[1,2-a]pyrazin-6(7H)-one (5.8 mg, yield: 9% for two steps) as a white solid.

$^1$H NMR (400 MHz, DMSO-d$_6$) δ 2.28 (3H, s), 3.10 (3H, s), 3.72 (2H, s), 3.87 (2H, t, J=5.6 Hz), 4.49 (2H, t, J=5.2 Hz), 6.66 (1H, d, J=8.0 Hz), 6.92 (1H, d, J=7.2 Hz), 7.15 (1H, t, J=9.2 Hz), 7.19 (1H, s), 7.54-7.62 (3H, m), 8.06 (2H, d, J=8.4 Hz), 8.48 (1H, d, J=2.0 Hz), 8.57 (1H, d, J=4.8 Hz), 9.01 (1H, d, J=2.0 Hz), 9.10 (1H, d, J=2.4 Hz).

Example 209: 4-(5-(4-(4-ethyl-2-oxoindolin-1-yl)phenyl)pyridin-3-yl)-7-methyl-8,9-dihydropyrido[3',2':4,5]pyrrolo[1,2-a]pyrazin-6(7H)-one

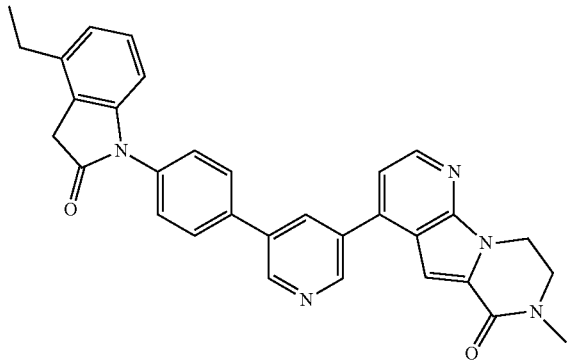 [SMILES: CCc1cccc2c1CC(=O)N2c1ccc(-c2cncc(-c3ccnc4c3cc3n4CCN(C)C3=O)c2)cc1]

Step 1. Preparation of 4-ethylindolin-2-one

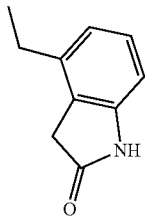

A mixture of 4-bromoindolin-2-one (500 mg, 2.36 mmol), ethylboronic acid (523 mg, 7.07 mmol), Pd(dppf)Cl$_2$ (345 mg, 0.472 mmol) and Na$_2$CO$_3$ (750 mg, 7.07 mmol) in dioxane (10 mL) and water (2 mL) was degassed and purged with N$_2$ for 3 times. And the resulting reaction mixture was stirred at 100° C. for 6 hours under N$_2$ atmosphere. A black suspension was formed. LCMS showed the purity of the desired product is 43% (Rt=0.603 min; MS Calcd: 161.1; MS Found: 161.9 [M+H]). The reaction mixture was filtered through a pad of celite and the solid was washed with EtOAc (100 mL). The aqueous layer was extracted with EtOAc (30 mL×2). The filtrate was washed with water (40 mL×2), brine (40 mL), dried over anhydrous Na$_2$SO$_4$, filtered and concentrated under reduced pressure. The residue was purified by Combi Flash (20% to 50% EtOAc in PE) to give 4-ethylindolin-2-one (220 mg, yield: 48%) as a yellow solid.

$^1$H NMR (400 MHz, CDCl$_3$) δ 1.22 (3H, t, J=7.6 Hz), 2.59 (2H, q, J=7.6 Hz), 3.47 (2H, s), 6.73 (1H, d, J=7.8 Hz), 6.88 (1H, d, J=7.8 Hz), 7.13-7.19 (1H, m), 8.31 (1H, brs).

Step 2. Preparation of 1-(4-bromophenyl)-4-ethylindolin-2-one

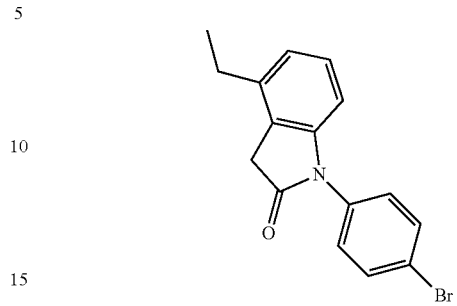

A mixture of 4-ethylindolin-2-one (80 mg, 0.50 mmol), 1-bromo-4-iodobenzene (168 mg, 0.605 mmol), CuI (28 mg, 0.15 mmol), CsF (188 mg, 1.24 mmol) in EtOAc (3 mL) was degassed and purged with N$_2$ for 3 times. Then N,N'-dimethylethylene diamine (26 mg, 0.30 mmol) was added into above mixture, the resulting reaction mixture was stirred at 50° C. for 16 hours. A blue suspension was formed. TLC showed 4-ethylindolin-2-one was consumed completely. The reaction mixture was concentrated under reduced pressure combined with batch ES7543-378 and batch ES7543-379. The residue was purified by Combi Flash (5% to 30% EtOAc in PE) to give 1-(4-bromophenyl)-4-ethylindolin-2-one (200 mg, yield: 42% for average) as a yellow solid.

Step 3. Preparation of 4-ethyl-1-(4-(4,4,5,5-tetramethyl-1,3,2-dioxaborolan-2-yl)phenyl)indolin-2-one

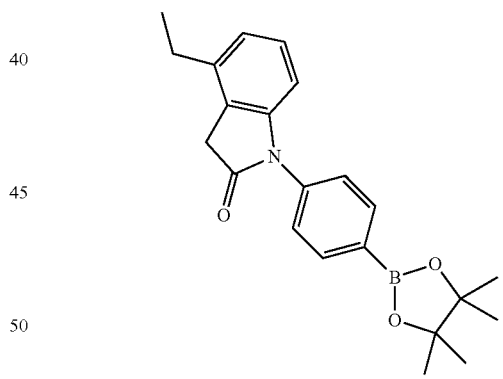

A mixture of 1-(4-bromophenyl)-4-ethylindolin-2-one (200 mg, 0.632 mmol), Bispin (193 mg, 0.759 mmol), Pd(dppf)Cl$_2$ (46 mg, 0.063 mmol) and KOAc (186 mg, 1.90 mmol) in anhydrous dioxane (5 mL) was degassed and purged with N$_2$ for 3 times. And the resulting mixture was stirred at 100° C. for 16 hours under N$_2$ atmosphere. A black suspension was formed. LCMS showed the purity of the desired product is 21% (Rt=1.062 min; MS Calcd: 363.2; MS Found: 364.0 [M+H]$^+$). The reaction mixture was filtered through a pad of silica gel, washed with EtOAc (50 mL) and concentrated under reduced pressure to give 4-ethyl-1-(4-(4,4,5,5-tetramethyl-1,3,2-dioxaborolan-2-yl)phenyl)indolin-2-one (crude) as black brown gum, which was used for the next step without further purification.

Step 4. Preparation of 1-(4-(5-bromopyridin-3-yl)phenyl)-4-ethylindolin-2-one

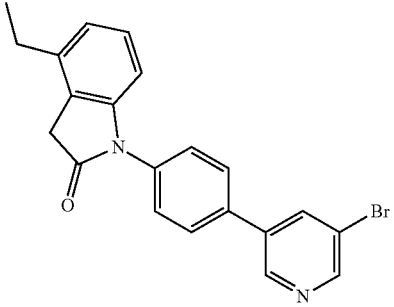 [SMILES: CCc1cccc2c1CC(=O)N2c1ccc(-c2cncc(Br)c2)cc1]

A mixture of 4-ethyl-1-(4-(4,4,5,5-tetramethyl-1,3,2-dioxaborolan-2-yl)phenyl)indolin-2-one (crude), 3,5-dibromopyridine (224 mg, 0.946 mmol), Pd(dppf)Cl$_2$ (23 mg, 0.032 mmol) and Na$_2$CO$_3$ (200 mg, 1.89 mmol) in dioxane (4 mL) and water (1 mL) was degassed and purged with N$_2$ for 3 times. And the resulting reaction mixture was stirred at 100° C. for 4 hours under N$_2$ atmosphere. A black suspension was formed. LCMS showed the purity of the desired product is 34% (Rt=0.991 min; MS Calcd: 392.1; MS Found: 392.9 [M+H]$^+$). The reaction mixture was diluted with water (20 mL). The aqueous layer was extracted with EtOAc (30 mL×2). The combined organic layer was washed with water (20 mL×2), brine (30 mL), dried over anhydrous Na$_2$SO$_4$, filtered and concentrated under reduced pressure. The residue was purified by Combi Flash (10% to 50% EtOAc in PE) to give 1-(4-(5-bromopyridin-3-yl)phenyl)-4-ethylindolin-2-one (130 mg, yield: 34% for two steps) as a yellow solid.

Step 5. Preparation of 4-ethyl-1-(4-(5-(4,4,5,5-tetramethyl-1,3,2-dioxaborolan-2-yl)pyridin-3-yl)phenyl)indolin-2-one

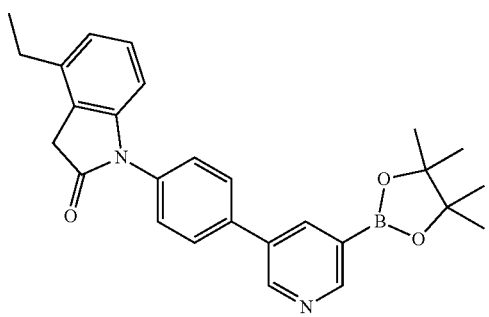 [SMILES: CCc1cccc2c1CC(=O)N2c1ccc(-c2cncc(B3OC(C)(C)C(C)(C)O3)c2)cc1]

Step 6 Preparation of 4-(5-(4-(4-ethyl-2-oxoindolin-1-yl)phenyl)pyridin-3-yl)-7-methyl-8,9-dihydropyrido[3',2':4,5]pyrrolo[1,2-a]pyrazin-6(7H)-one

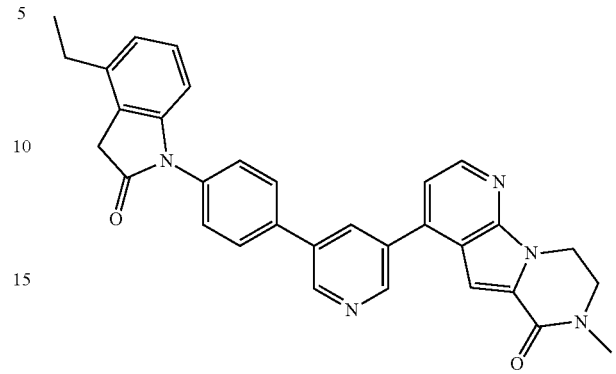

A mixture of 1-(4-(5-bromopyridin-3-yl)phenyl)-4-ethylindolin-2-one (130 mg, 0.330 mmol), Bispin (101 mg, 0.397 mmol), Pd(dppf)Cl$_2$ (24 mg, 0.033 mmol) and KOAc (97 mg, 0.99 mmol) in anhydrous dioxane (5 mL) was degassed and purged with N$_2$ for 3 times. And the resulting mixture was stirred at 100° C. for 12 hours under N$_2$ atmosphere. A black suspension was formed. LCMS showed the purity of the boronic acid of the desired product is 30% (Rt=0.798 min; MS Calcd: 358.2; MS Found: 359.1 [M+H]$^+$). The reaction mixture was filtered through a pad of celite, washed with EtOAc (50 mL) and concentrated under reduced pressure to give 4-ethyl-1-(4-(5-(4,4,5,5-tetramethyl-1,3,2-dioxaborolan-2-yl)pyridin-3-yl)phenyl)indolin-2-one (crude) as black brown gum, which was used for the next step without further purification.

A mixture of 4-ethyl-1-(4-(5-(4,4,5,5-tetramethyl-1,3,2-dioxaborolan-2-yl)pyridin-3-yl)phenyl)indolin-2-one (crude), 4-chloro-7-methyl-8,9-dihydropyrido[3',2':4,5]pyrrolo[1,2-a]pyrazin-6(7H)-one (78 mg, 0.329 mmol), Pd(t-Bu$_3$P)$_2$ (17 mg, 0.033 mmol) and Cs$_2$CO$_3$ (215 mg, 0.658 mmol) in dioxane (3 mL) and water (0.8 mL) was degassed and purged with N$_2$ for 3 times. And the resulting reaction mixture was stirred at 100° C. for 4 hours under N$_2$ atmosphere. A black suspension was formed. LCMS showed the purity of the desired product is 32% (Rt=0.873 min; MS Calcd: 513.2; MS Found: 514.1 [M+H]$^+$). The reaction mixture was diluted with water (20 mL). The aqueous layer was extracted with EtOAc/THF (30 mL×3, 1/1). The combined organic layer was washed with water (20 mL×2), brine (30 mL), dried over anhydrous Na$_2$SO$_4$, filtered and concentrated under reduced pressure. The residue was purified by prep-HPLC (0.225% FA as an additive), and lyophilized to give 4-(5-(4-(4-ethyl-2-oxoindolin-1-yl)phenyl)pyridin-3-yl)-7-methyl-8,9-dihydropyrido[3',2':4,5]pyrrolo[1,2-a]pyrazin-6(7H)-one (12.1 mg, yield: 7% for two steps) as an off-white solid.

1H NMR (400 MHz, DMSO-d$_6$) δ 1.22 (3H, t, J=7.6 Hz), 2.62 (2H, q, J=7.6 Hz), 3.10 (3H, s), 3.77 (2H, s), 3.88 (2H, t, J=5.8 Hz), 4.50 (2H, t, J=5.8 Hz), 6.67 (1H, d, J=7.8 Hz), 6.96 (1H, d, J=7.8 Hz), 7.16-7.22 (2H, m), 7.55-7.62 (3H, m), 8.03-8.10 (2H, m), 8.46-8.50 (1H, m), 8.57 (1H, d, J=4.8 Hz), 9.02 (1H, s), 9.11 (1H, s).

The following compounds were prepared according to the general procedure described herein, as well as the individual procedure for any structurally related compounds. The procedure utilized the appropriate reagents, solvents, and starting materials according to the final products. All reactions were carried out under suitable conditions, including but not limited to temperature, pressure, and time.

Table 1 illustrates compounds of the invention that were prepared in accordance with any of the synthetic method described above using suitable starting materials, reagents and appropriate and necessary conditions to these compounds.

| Example | Compound Name | Structure |
|---|---|---|
| 210 | 1-(4-(5-(2-(3-cyclopropyl-3-hydroxypiperidine-1-carbonyl)-1H-pyrrolo[2,3-b]pyridin-4-yl)pyridin-3-yl)phenyl)pyrrolidin-2-one | 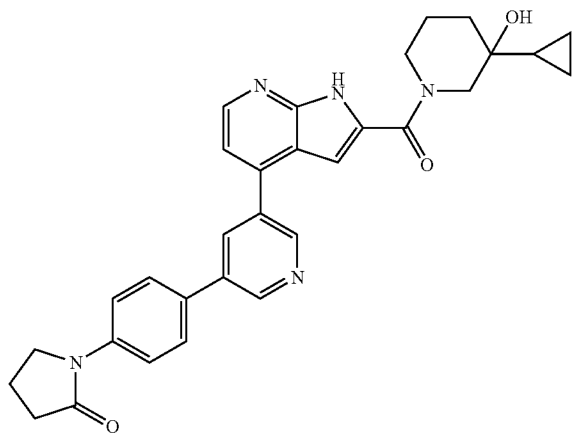 [SMILES: O=C(c1cc2c(-c3cncc(-c4ccc(N5CCCC5=O)cc4)c3)ccnc2[nH]1)N1CCCC(O)(C2CC2)C1] |
| 211 | methyl 4-(5-(4-(4-isopropyl-4H-1,2,4-triazol-3-yl)phenyl)pyridin-3-yl)-1H-pyrrolo[2,3-b]pyridine-2-carboxylate | 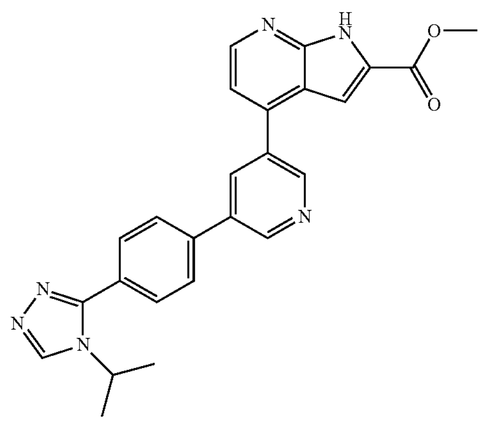 [SMILES: COC(=O)c1cc2c(-c3cncc(-c4ccc(-c5nncn5C(C)C)cc4)c3)ccnc2[nH]1] |
| 212 | 2'-amino-N,N-dimethyl-5'-(2H-pyrazolo[3,4-b]pyridin-4-yl)-[2,3'-bipyridine]-5-carboxamide | 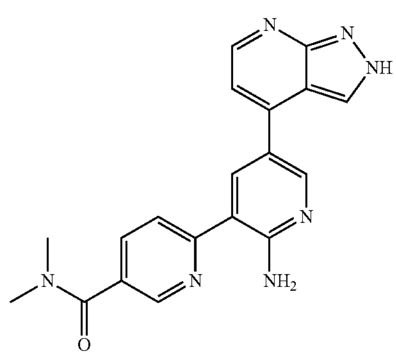 [SMILES: CN(C)C(=O)c1ccc(-c2cc(-c3ccnc4n[nH]cc34)cnc2N)nc1] |
| 213 | 2'-amino-5'-(1H-imidazo[4,5-b]pyridin-7-yl)-N,N-dimethyl-[2,3'-bipyridine]-5-carboxamide | 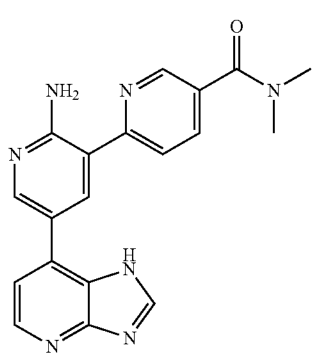 [SMILES: CN(C)C(=O)c1ccc(-c2cc(-c3ccnc4nc[nH]c34)cnc2N)nc1] |

-continued

| Example | Compound Name | Structure |
|---|---|---|
| 214 | 2'-amino-N,N-dimethyl-5'-(2H-pyrazolo[3,4-d]pyrimidin-3-yl)-[2,3'-bipyridine]-5-carboxamide | 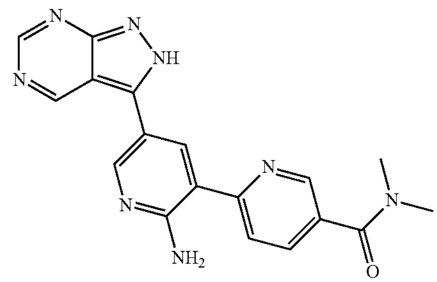 [SMILES: CN(C)C(=O)c1ccc(-c2cc(-c3[nH]nc4ncncc34)cnc2N)nc1] |
| 215 | 1-(4-(5-(2H-pyrazolo[3,4-b]pyridin-4-yl)pyridin-3-yl)phenyl)pyrrolidin-2-one | 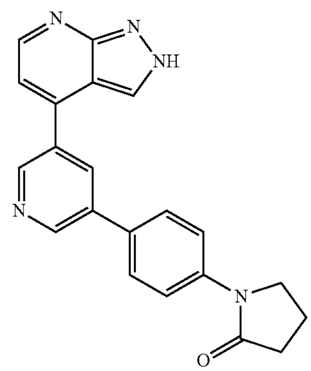 |
| 216 | 2'-amino-5'-(6-((3-aminophenyl)amino)pyrimidin-4-yl)-N,N-dimethyl-[2,3'-bipyridine]-5-carboxamide | 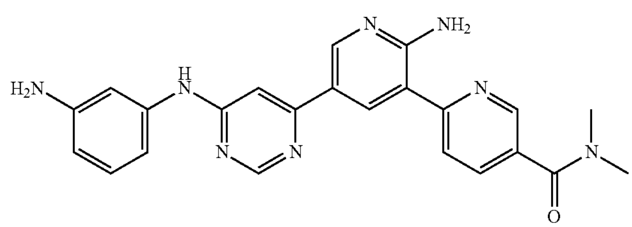 [SMILES: CN(C)C(=O)c1ccc(-c2cc(-c3cc(Nc4cccc(N)c4)ncn3)cnc2N)nc1] |
| 217 | 2'-amino-5'-(6-aminopyrimidin-4-yl)-N,N-dimethyl-[2,3'-bipyridine]-5-carboxamide | 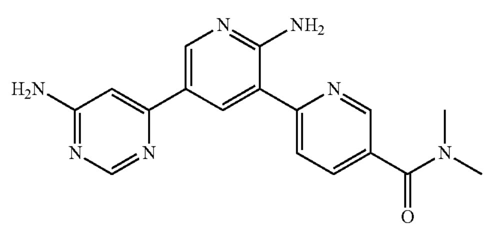 [SMILES: CN(C)C(=O)c1ccc(-c2cc(-c3cc(N)ncn3)cnc2N)nc1] |
| 218 | 1-(4-(5-(1-methyl-1H-pyrazolo[3,4-b]pyridin-4-yl)pyridin-3-yl)phenyl)pyrrolidin-2-one | 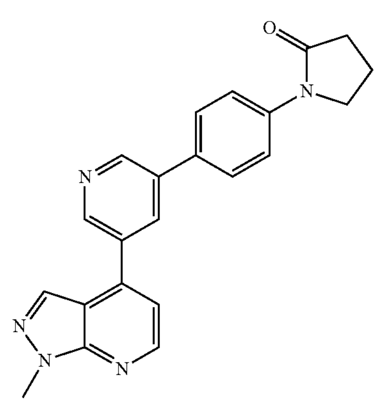 [SMILES: Cn1ncc2c(-c3cncc(-c4ccc(N5CCCC5=O)cc4)c3)ccnc21] |

-continued

| Example | Compound Name | Structure |
|---|---|---|
| 219 | 2'-amino-5'-(6-((3-(3-aminobenzamido)phenyl)amino)pyrimidin-4-yl)-N,N-dimethyl-[2,3'-bipyridine]-5-carboxamide | 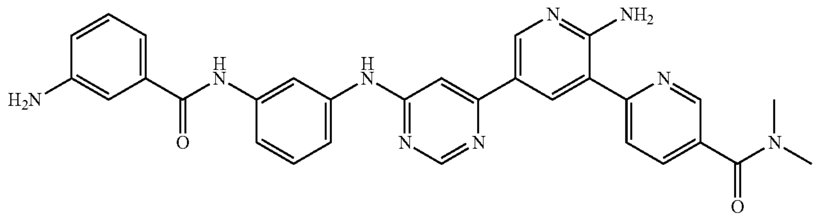 [SMILES: CN(C)C(=O)c1ccc(-c2cc(-c3cc(Nc4cccc(NC(=O)c5cccc(N)c5)c4)ncn3)cnc2N)nc1] |
| 220 | 1-(4-(5-(2H-pyrazolo[4,3-b]pyridin-7-yl)pyridin-3-yl)phenyl)pyrrolidin-2-one | 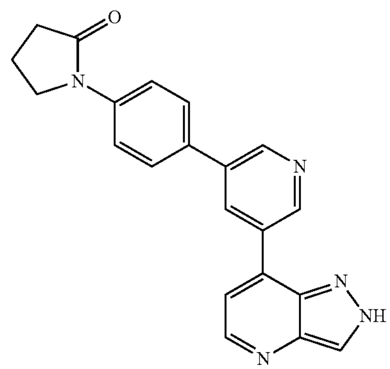 [SMILES: O=C1CCCN1c1ccc(-c2cncc(-c3ccnc4c[nH]nc34)c2)cc1] |
| 221 | 4-(2'-amino-5-(benzylcarbamoyl)-[2,3'-bipyridin]-5'-yl)-N-benzyl-1H-pyrrolo[2,3-b]pyridine-2-carboxamide | 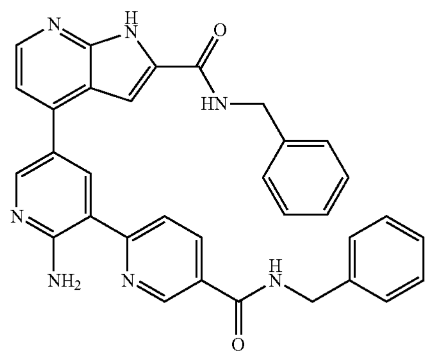 [SMILES: Nc1ncc(-c2ccnc3[nH]c(C(=O)NCc4ccccc4)cc23)cc1-c1ccc(C(=O)NCc2ccccc2)cn1] |
| 222 | 2'-amino-5'-(6-((4-aminopyridin-2-yl)amino)pyrimidin-4-yl)-N,N-dimethyl-[2,3'-bipyridine]-5-carboxamide | 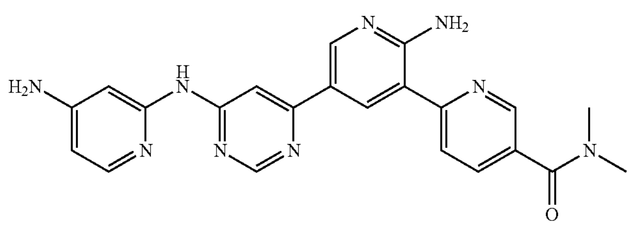 [SMILES: CN(C)C(=O)c1ccc(-c2cc(-c3cc(Nc4cc(N)ccn4)ncn3)cnc2N)nc1] |
| 223 | 1-(4-(5-(2H-pyrazolo[3,4-d]pyrimidin-4-yl)pyridin-3-yl)phenyl)pyrrolidin-2-one | 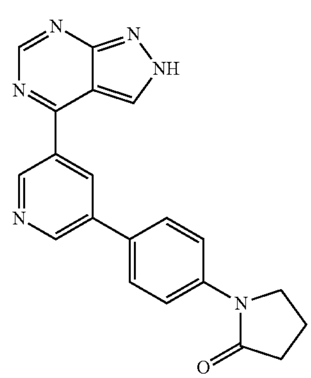 [SMILES: O=C1CCCN1c1ccc(-c2cncc(-c3ncnc4n[nH]cc34)c2)cc1] |

| Example | Compound Name | Structure |
|---|---|---|
| 224 | 1-(4-(5-(6-chloro-2H-pyrazolo[3,4-b]pyridin-4-yl)pyridin-3-yl)phenyl)pyrrolidin-2-one | 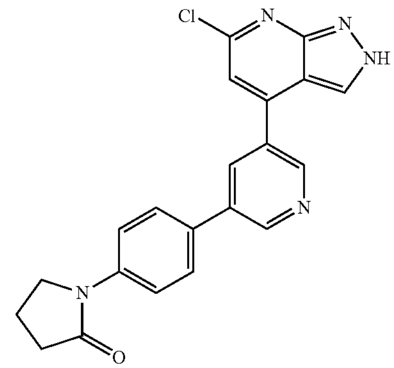 [SMILES: O=C1CCCN1c1ccc(-c2cncc(-c3cc(Cl)nc4n[nH]cc34)c2)cc1] |
| 225 | 1-(4-(5-(6-methyl-2H-pyrazolo[3,4-d]pyrimidin-4-yl)pyridin-3-yl)phenyl)pyrrolidin-2-one | 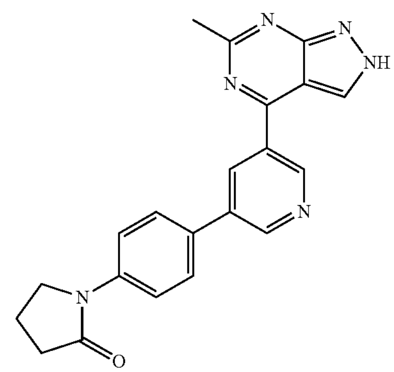 [SMILES: Cc1nc(-c2cncc(-c3ccc(N4CCCC4=O)cc3)c2)c2c[nH]nc2n1] |
| 226 | 4-(2'-amino-5-(dimethylcarbamoyl)-[2,3'-bipyridin]-5'-yl)-N-((3R,4S)-4-aminotetrahydrofuran-3-yl)-1H-pyrrolo[2,3-b]pyridine-2-carboxamide | 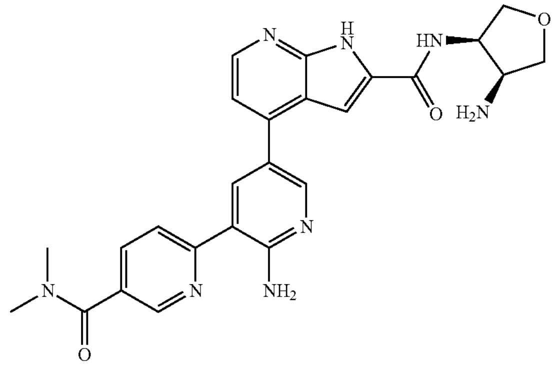 [SMILES: CN(C)C(=O)c1ccc(-c2cc(-c3ccnc4[nH]c(C(=O)N[C@H]5COC[C@H]5N)cc34)cnc2N)nc1] |
| 227 | N,N-dimethyl-3-(5-(4-(2-oxopyrrolidin-1-yl)phenyl)pyridin-3-yl)-2H-pyrazolo[3,4-b]pyridine-5-carboxamide | 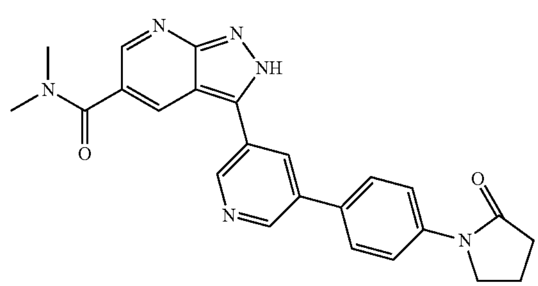 [SMILES: CN(C)C(=O)c1cnc2n[nH]c(-c3cncc(-c4ccc(N5CCCC5=O)cc4)c3)c2c1] |

-continued

| Example | Compound Name | Structure |
|---|---|---|
| 228 | N-(2-methoxyethyl)-4-(5-(4-(2-oxopyrrolidin-1-yl)phenyl)pyridin-3-yl)-1H-pyrrolo[2,3-b]pyridine-2-carboxamide | 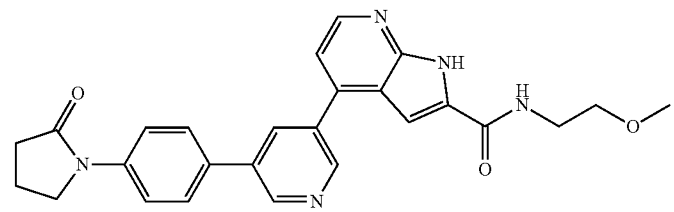 [SMILES: COCCNC(=O)c1cc2c(-c3cncc(-c4ccc(N5CCCC5=O)cc4)c3)ccnc2[nH]1] |
| 229 | 1-(4-(5-(2-(morpholine-4-carbonyl)-1H-pyrrolo[2,3-b]pyridin-4-yl)pyridin-3-yl)phenyl)pyrrolidin-2-one | 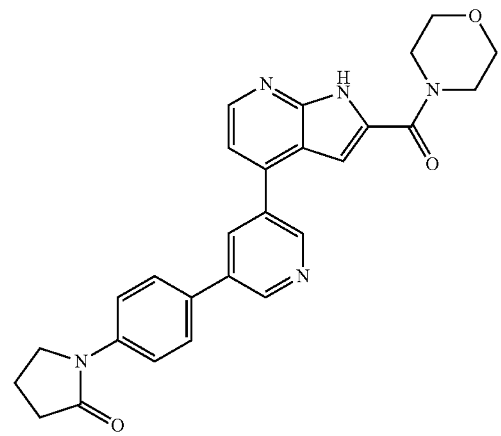 [SMILES: O=C(c1cc2c(-c3cncc(-c4ccc(N5CCCC5=O)cc4)c3)ccnc2[nH]1)N1CCOCC1] |
| 230 | 4-(5-(4-(5-azaspiro[2.4]heptane-5-carbonyl)phenyl)pyridin-3-yl)-7-methyl-8,9-dihydropyrido[3',2':4,5]pyrrolo[1,2-a]pyrazin-6(7H)-one | 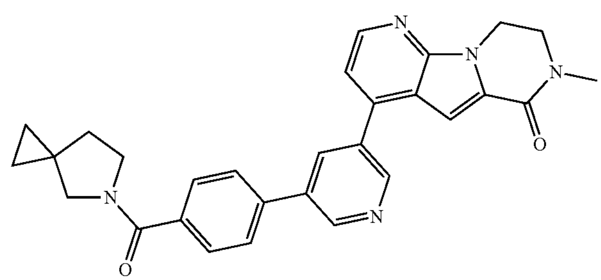 [SMILES: CN1CCn2c(cc3c(-c4cncc(-c5ccc(C(=O)N6CCC7(CC7)C6)cc5)c4)ccnc32)C1=O] |
| 231 | N,N,1-trimethyl-3-(5-(4-(2-oxopyrrolidin-1-yl)phenyl)pyridin-3-yl)-1H-pyrazolo[3,4-b]pyridine-5-carboxamide | 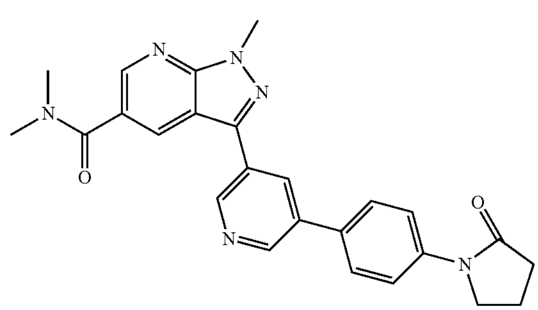 [SMILES: CN(C)C(=O)c1cnc2c(c1)c(-c1cncc(-c3ccc(N4CCCC4=O)cc3)c1)nn2C] |

| Example | Compound Name | Structure |
|---|---|---|
| 232 | N-benzyl-4-(5-(4-(2-oxopyrrolidin-1-yl)phenyl)pyridin-3-yl)-1H-pyrrolo[2,3-b]pyridine-2-carboxamide | 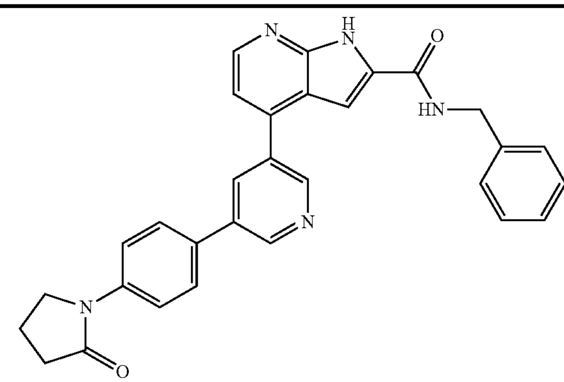 |
| 233 | 4-(5-(4-(2-oxopyrrolidin-1-yl)phenyl)pyridin-3-yl)-N-(pyridin-4-ylmethyl)-1H-pyrrolo[2,3-b]pyridine-2-carboxamide | 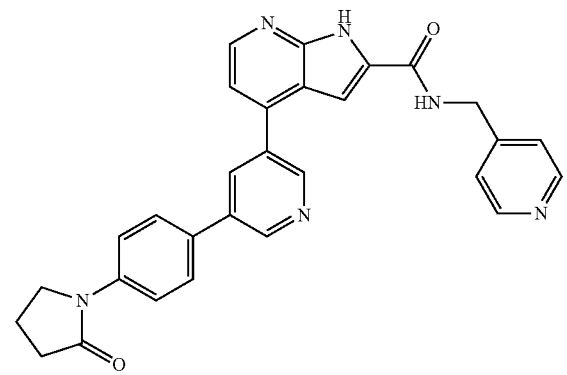 [SMILES: O=C(NCc1ccncc1)c1cc2c(-c3cncc(-c4ccc(N5CCCC5=O)cc4)c3)ccnc2[nH]1] |
| 234 | N-isobutyl-4-(5-(4-(2-oxopyrrolidin-1-yl)phenyl)pyridin-3-yl)-1H-pyrrolo[2,3-b]pyridine-2-carboxamide | 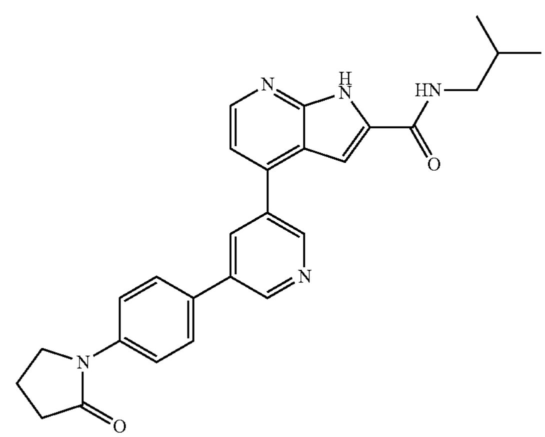 [SMILES: CC(C)CNC(=O)c1cc2c(-c3cncc(-c4ccc(N5CCCC5=O)cc4)c3)ccnc2[nH]1] |
| 235 | 1-(4-(5-(2-(pyrrolidine-1-carbonyl)-1H-pyrrolo[2,3-b]pyridin-4-yl)pyridin-3-yl)phenyl)pyrrolidin-2-one | 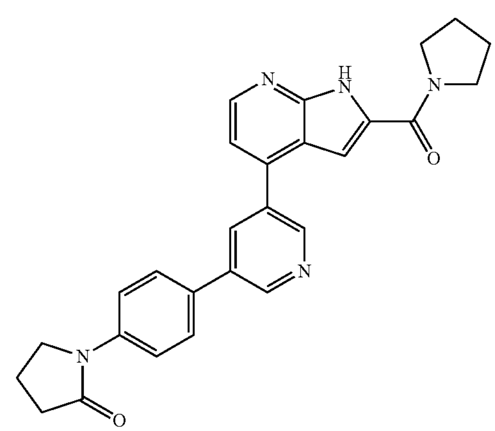 [SMILES: O=C(c1cc2c(-c3cncc(-c4ccc(N5CCCC5=O)cc4)c3)ccnc2[nH]1)N1CCCC1] |

-continued

| Example | Compound Name | Structure |
|---------|---------------|-----------|
| 236 | 4-(5-(4-(2-oxopyrrolidin-1-yl)phenyl)pyridin-3-yl)-N-phenethyl-1H-pyrrolo[2,3-b]pyridine-2-carboxamide | 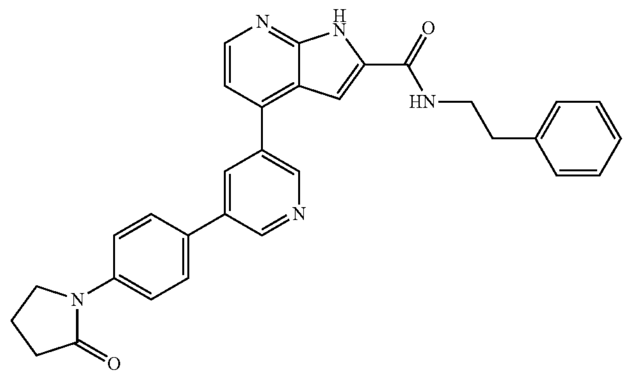 [SMILES: O=C(NCCc1ccccc1)c1cc2c(-c3cncc(-c4ccc(N5CCCC5=O)cc4)c3)ccnc2[nH]1] |
| 237 | 4-(5-(4-(2-oxopyrrolidin-1-yl)phenyl)pyridin-3-yl)-N-(2-(pyridin-3-yl)ethyl)-1H-pyrrolo[2,3-b]pyridine-2-carboxamide | 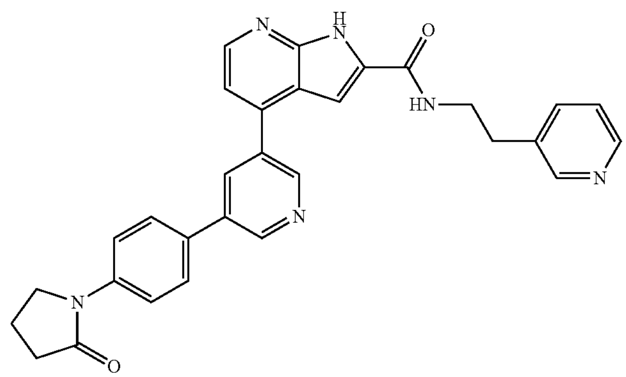 [SMILES: O=C(NCCc1cccnc1)c1cc2c(-c3cncc(-c4ccc(N5CCCC5=O)cc4)c3)ccnc2[nH]1] |
| 238 | 4-(5-(4-(2-oxopyrrolidin-1-yl)phenyl)pyridin-3-yl)-N-(pyridin-3-ylmethyl)-1H-pyrrolo[2,3-b]pyridine-2-carboxamide | 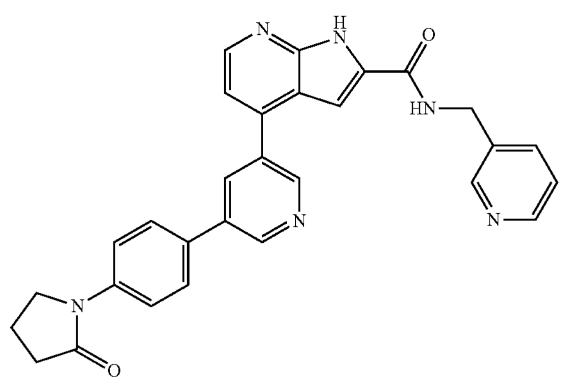 [SMILES: O=C(NCc1cccnc1)c1cc2c(-c3cncc(-c4ccc(N5CCCC5=O)cc4)c3)ccnc2[nH]1] |
| 239 | 4-(5-(4-(2-oxopyrrolidin-1-yl)phenyl)pyridin-3-yl)-N-(pyridin-2-ylmethyl)-1H-pyrrolo[2,3-b]pyridine-2-carboxamide | 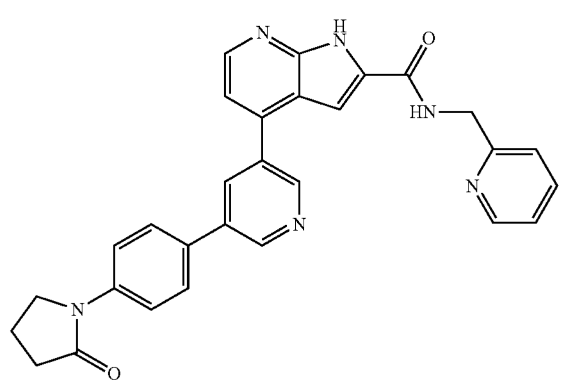 |

|  |  |  |
|---|---|---|
| Example | Compound Name | Structure |
| 240 | N-methyl-4-(5-(4-(2-oxopyrrolidin-1-yl)phenyl)pyridin-3-yl)-1H-pyrrolo[2,3-b]pyridine-2-carboxamide | |
| 241 | N,N-dimethyl-4-(5-(4-(2-oxopyrrolidin-1-yl)phenyl)pyridin-3-yl)-1H-pyrrolo[2,3-b]pyridine-2-carboxamide | |
| 242 | N-cyclopropyl-4-(5-(4-(2-oxopyrrolidin-1-yl)phenyl)pyridin-3-yl)-1H-pyrrolo[2,3-b]pyridine-2-carboxamide | |
| 243 | 1,6-dimethyl-3-(5-(4-(2-oxopyrrolidin-1-yl)phenyl)pyridin-3-yl)-1,6-dihydro-7H-pyrrolo[2,3-c]pyridin-7-one | |

-continued

| Example | Compound Name | Structure |
|---|---|---|
| 244 | N-(2-(1H-imidazol-2-yl)ethyl)-4-(5-(4-(pyrrolidin-1-yl)phenyl)pyridin-3-yl)-1H-pyrrolo[2,3-b]pyridine-2-carboxamide | 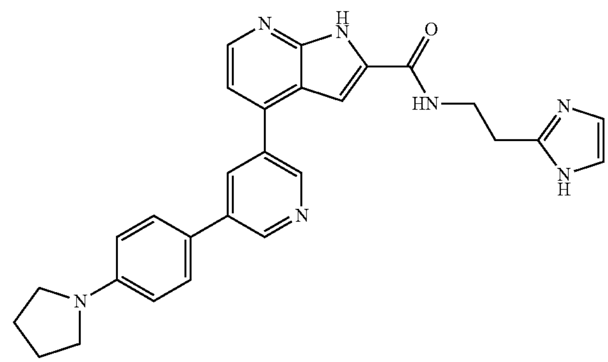 [SMILES: O=C(NCCc1ncc[nH]1)c1cc2c(-c3cncc(-c4ccc(N5CCCC5)cc4)c3)ccnc2[nH]1] |
| 245 | N-(benzo[d]oxazol-2-ylmethyl)-4-(5-(4-(2-oxopyrrolidin-1-yl)phenyl)pyridin-3-yl)-1H-pyrrolo[2,3-b]pyridine-2-carboxamide | 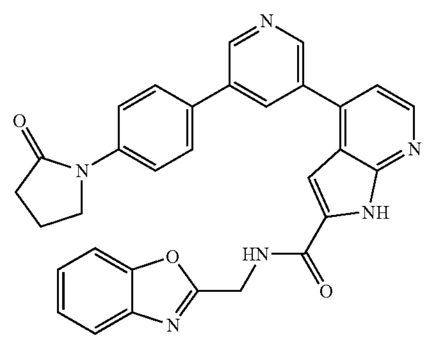 |
| 246 | 4-(5-(4-(2-oxopyrrolidin-1-yl)phenyl)pyridin-3-yl)-N-(2-(pyridin-2-yl)ethyl)-1H-pyrrolo[2,3-b]pyridine-2-carboxamide | 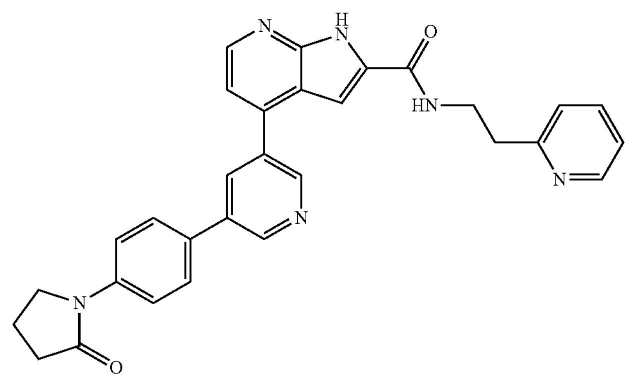 |
| 247 | 4-(5-(4-(2-oxopyrrolidin-1-yl)phenyl)pyridin-3-yl)-N-(2-(pyridin-4-yl)ethyl)-1H-pyrrolo[2,3-b]pyridine-2-carboxamide | 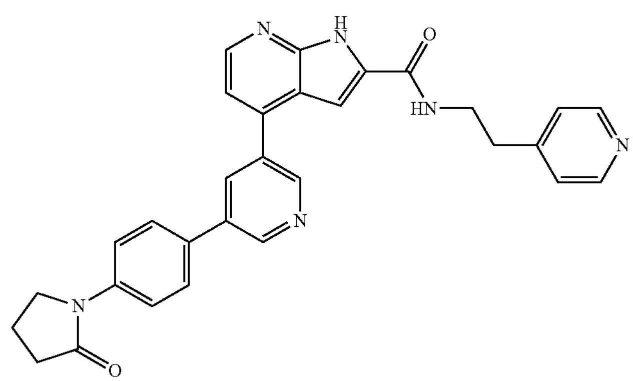 [SMILES: O=C(NCCc1ccncc1)c1cc2c(-c3cncc(-c4ccc(N5CCCC5=O)cc4)c3)ccnc2[nH]1] |

| Example | Compound Name | Structure |
|---|---|---|
| 248 | methyl 4-(5-(2-oxopyrrolidin-1-yl)-[2,3'-bipyridin]-5'-yl)-1H-pyrrolo[2,3-b]pyridine-2-carboxylate | 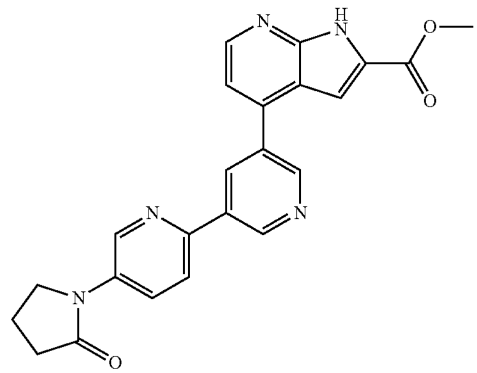 [SMILES: COC(=O)c1cc2c(-c3cncc(-c4ccc(N5CCCC5=O)cn4)c3)ccnc2[nH]1] |
| 249 | N,N,1,2-tetramethyl-3-(5-(4-(2-oxopyrrolidin-1-yl)phenyl)pyridin-3-yl)-1H-pyrrolo[2,3-b]pyridine-5-carboxamide | 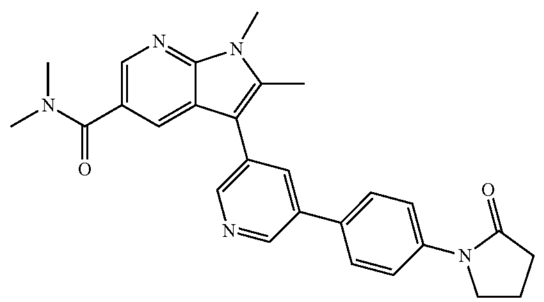 [SMILES: Cc1c(-c2cncc(-c3ccc(N4CCCC4=O)cc3)c2)c2cc(C(=O)N(C)C)cnc2n1C] |
| 250 | N,N,2-trimethyl-3-(5-(4-(2-oxopyrrolidin-1-yl)phenyl)pyridin-3-yl)-1H-pyrrolo[2,3-b]pyridine-5-carboxamide | 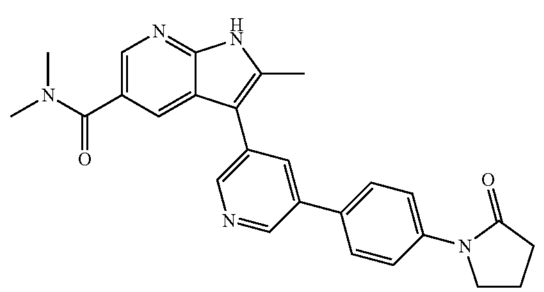 [SMILES: Cc1[nH]c2ncc(C(=O)N(C)C)cc2c1-c1cncc(-c2ccc(N3CCCC3=O)cc2)c1] |
| 251 | N-(2-(2H-tetrazol-5-yl)ethyl)-4-(5-(4-(2-oxopyrrolidin-1-yl)phenyl)pyridin-3-yl)-1H-pyrrolo[2,3-b]pyridine-2-carboxamide | 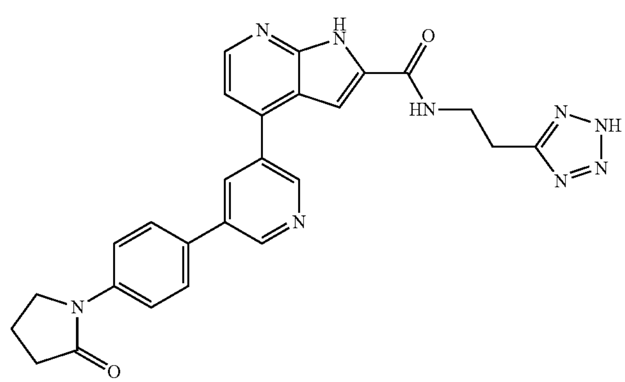 [SMILES: O=C(NCCc1nn[nH]n1)c1cc2c(-c3cncc(-c4ccc(N5CCCC5=O)cc4)c3)ccnc2[nH]1] |

| Example | Compound Name | Structure |
|---|---|---|
| 252 | 2-cyclopropyl-N,N-dimethyl-3-(5-(4-(2-oxopyrrolidin-1-yl)phenyl)pyridin-3-yl)-1H-pyrrolo[2,3-b]pyridine-5-carboxamide | 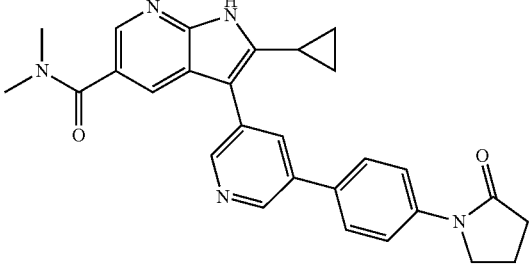 |
| 253 | 1-(4-(5-(1H-pyrrolo[3,2-b]pyridin-1-yl)pyridin-3-yl)phenyl)pyrrolidin-2-one | 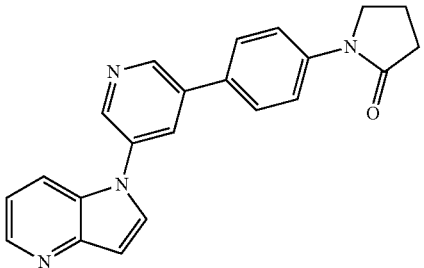 [SMILES: O=C1CCCN1c1ccc(-c2cncc(-n3ccc4ncccc43)c2)cc1] |
| 254 | N,N-dimethyl-1-(5-(4-(2-oxopyrrolidin-1-yl)phenyl)pyridin-3-yl)-1H-pyrrolo[3,2-b]pyridine-6-carboxamide | 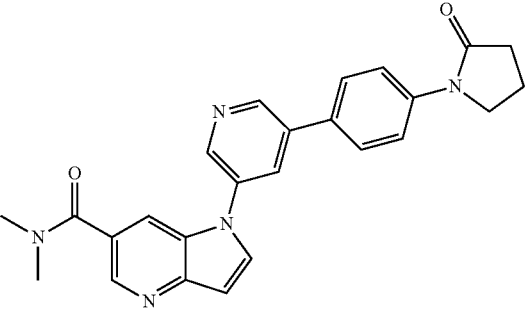 [SMILES: CN(C)C(=O)c1cnc2ccn(-c3cncc(-c4ccc(N5CCCC5=O)cc4)c3)c2c1] |
| 255 | 4-(5-(4-(2-oxopyrrolidin-1-yl)phenyl)pyridin-3-yl)-N-(2-(pyrazin-2-yl)ethyl)-1H-pyrrolo[2,3-b]pyridine-2-carboxamide | 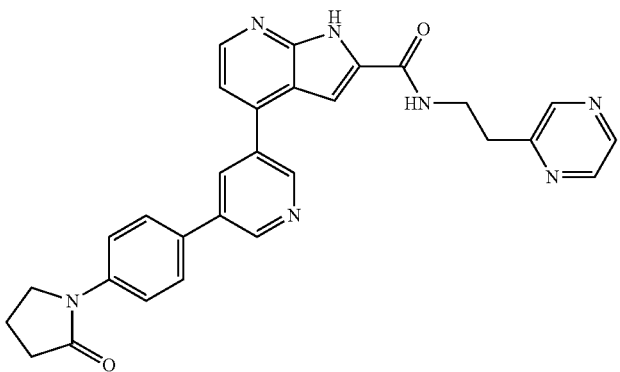 |

-continued

| Example | Compound Name | Structure |
|---|---|---|
| 256 | 4-(5-(4-(2-oxopyrrolidin-1-yl)phenyl)pyridin-3-yl)-N-(2-(thiazol-2-yl)ethyl)-1H-pyrrolo[2,3-b]pyridine-2-carboxamide | 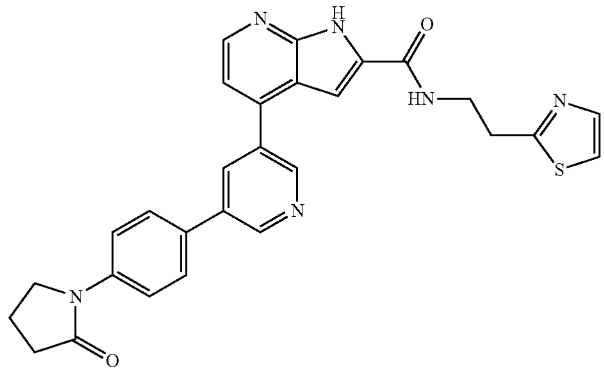 [SMILES: O=C(NCCc1nccs1)c1cc2c(-c3cncc(-c4ccc(N5CCCC5=O)cc4)c3)ccnc2[nH]1] |
| 257 | 1-(4-(5-(6-methoxy-2H-pyrazolo[3,4-b]pyridin-4-yl)pyridin-3-yl)phenyl)pyrrolidin-2-one | 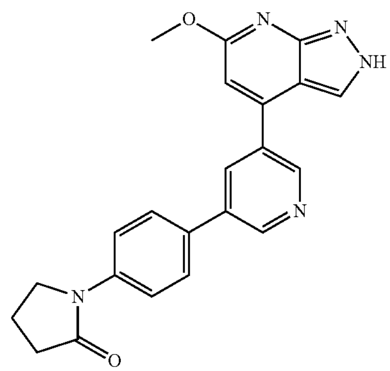 [SMILES: COc1cc(-c2cncc(-c3ccc(N4CCCC4=O)cc3)c2)c2c[nH]nc2n1] |
| 258 | 1-(4-(2-amino-5-(7-methoxy-2H-pyrazolo[3,4-c]pyridin-4-yl)pyridin-3-yl)phenyl)pyrrolidin-2-one | 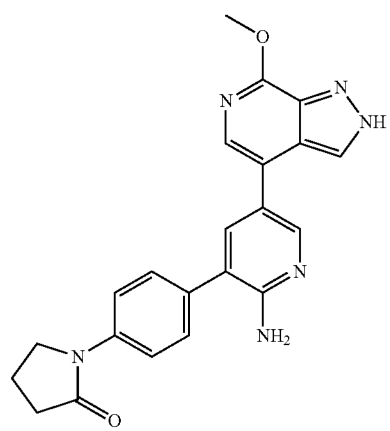 [SMILES: COc1ncc(-c2cnc(N)c(-c3ccc(N4CCCC4=O)cc3)c2)c2c[nH]nc12] |
| 259 | N,1,6-trimethyl-7-oxo-3-(5-(4-(2-oxopyrrolidin-1-yl)phenyl)pyridin-3-yl)-6,7-dihydro-1H-pyrrolo[2,3-c]pyridine-5-carboxamide | 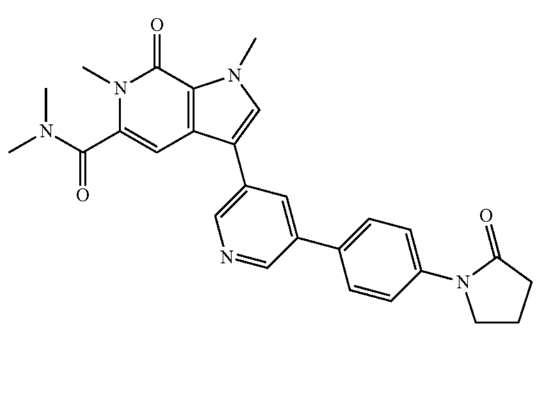 [SMILES: CN(C)C(=O)c1cc2c(-c3cncc(-c4ccc(N5CCCC5=O)cc4)c3)cn(C)c2c(=O)n1C] |

-continued

| Example | Compound Name |
|---|---|
| 260 | N,N,1,6-tetramethyl-7-oxo-3-(5-(4-(2-oxopyrrolidin-1-yl)phenyl)pyridin-3-yl)-6,7-dihydro-1H-pyrrolo[2,3-c]pyridine-5-carboxamide |
| 261 | N-(2-(1H-pyrrol-2-yl)ethyl)-4-(5-(4-(2-oxopyrrolidin-1-yl)phenyl)pyridin-3-yl)-1H-pyrrolo[2,3-b]pyridine-2-carboxamide |
| 262 | 2-cyclopropyl-N,N,1-trimethyl-3-(5-(4-(2-oxopyrrolidin-1-yl)phenyl)pyridin-3-yl)-1H-pyrrolo[2,3-b]pyridine-5-carboxamide |
| 263 | 1,6-dimethyl-7-oxo-3-(5-(4-(2-oxopyrrolidin-1-yl)phenyl)pyridin-3-yl)-6,7-dihydro-1H-pyrrolo[2,3-c]pyridine-5-carboxamide |

-continued

| Example | Compound Name | Structure |
|---|---|---|
| 264 | 4-(5-(4-(2-oxopyrrolidin-1-yl)phenyl)pyridin-3-yl)-N-(2-phenylcyclopropyl)-1H-pyrrolo[2,3-b]pyridine-2-carboxamide | 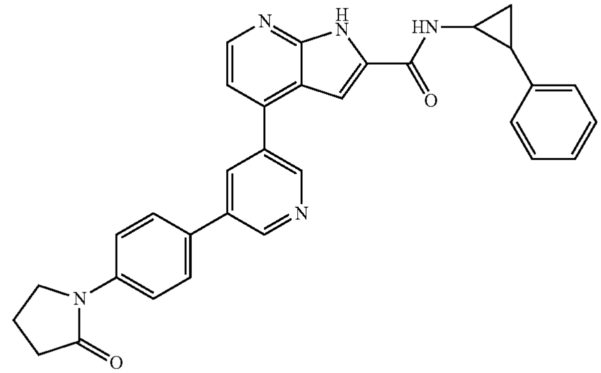 [SMILES: O=C(NC1CC1c1ccccc1)c1cc2c(-c3cncc(-c4ccc(N5CCCC5=O)cc4)c3)ccnc2[nH]1] |
| 265 | N,N,1-trimethyl-3-(5-(4-(2-oxopyrrolidin-1-yl)phenyl)pyridin-3-yl)-1H-b]pyridine-5-sulfonamide | 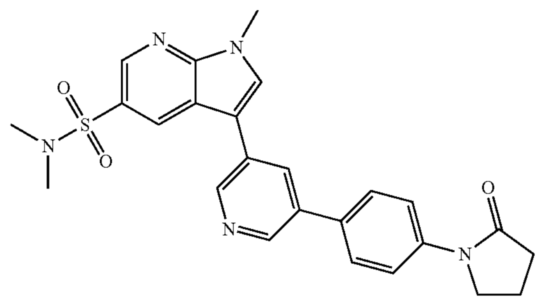 [SMILES: CN(C)S(=O)(=O)c1cnc2c(c1)c(-c1cncc(-c3ccc(N4CCCC4=O)cc3)c1)cn2C] |
| 266 | 2-isopropyl-N,N,1-trimethyl-3-(5-(4-(2-oxopyrrolidin-1-yl)phenyl)pyridin-3-yl)-1H-pyrrolo[2,3-b]pyridine-5-carboxamide | 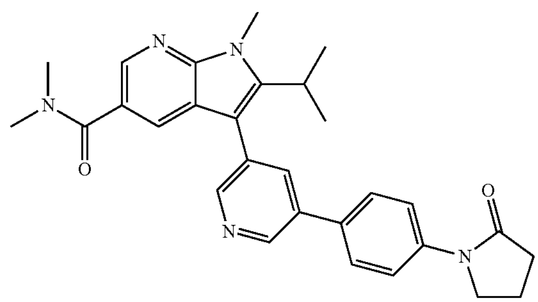 [SMILES: CC(C)c1c(-c2cncc(-c3ccc(N4CCCC4=O)cc3)c2)c2cc(C(=O)N(C)C)cnc2n1C] |
| 267 | 1-(4-(5-(6-cyclopropyl-2H-pyrazolo[3,4-b]pyridin-4-yl)pyridin-3-yl)phenyl)pyrrolidin-2-one | 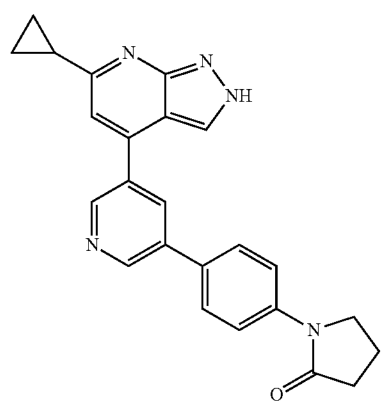 [SMILES: O=C1CCCN1c1ccc(-c2cncc(-c3cc(C4CC4)nc4n[nH]cc34)c2)cc1] |

-continued

| Example | Compound Name | Structure |
|---|---|---|
| 268 | 1-(4-(5-(5-((tetrahydro-2H-pyran-4-yl)oxy)-1H-pyrrolo[2,3-b]pyridin-4-yl)pyridin-3-yl)phenyl)pyrrolidin-2-one | 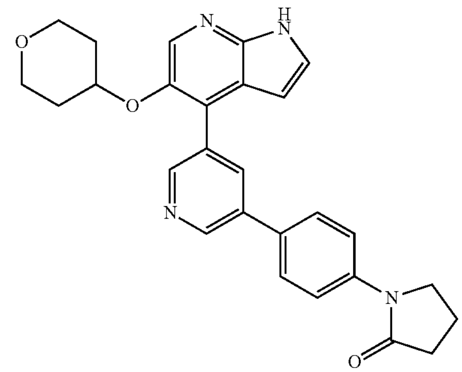 [SMILES: O=C1CCCN1c1ccc(-c2cncc(-c3c(OC4CCOCC4)cnc4[nH]ccc34)c2)cc1] |
| 269 | 2-isopropyl-N,N-dimethyl-3-(5-(4-(2-oxopyrrolidin-1-yl)phenyl)pyridin-3-yl)-1H-pyrrolo[2,3-b]pyridine-5-carboxamide | 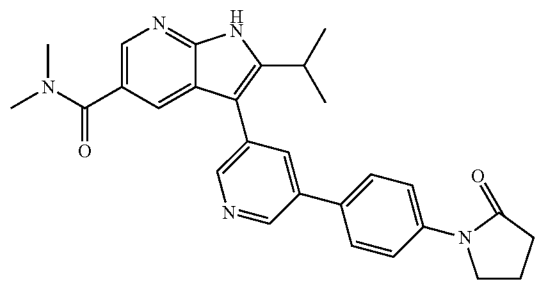 [SMILES: CC(C)c1[nH]c2ncc(C(=O)N(C)C)cc2c1-c1cncc(-c2ccc(N3CCCC3=O)cc2)c1] |
| 270 | 1-(4-(5-(7-methoxy-2H-pyrazolo[3,4-c]pyridin-4-yl)pyridin-3-yl)phenyl)pyrrolidin-2-one | 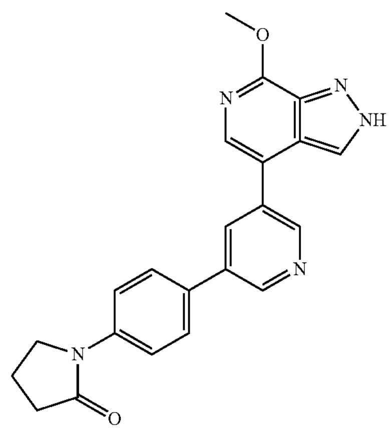 |
| 271 | 1-[4-[5-(7-Methylpyrrolo[2,3-d]pyrimidin-5-yl)-3-pyridyl]phenyl]pyrrolidin-2-one | 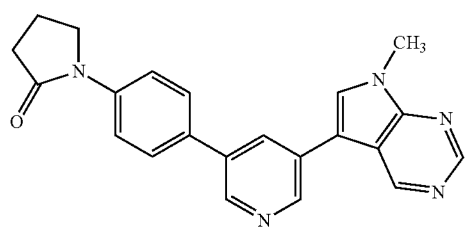 [SMILES: Cn1cc(-c2cncc(-c3ccc(N4CCCC4=O)cc3)c2)c2cncnc21] |
| 272 | 2-Methyl-8-[5-(4-pyridyl)-3-pyridyl]-2,8-diazaspiro[4.5]decan-1-one | 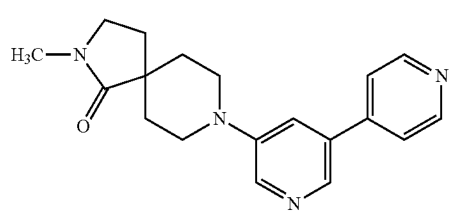 [SMILES: CN1CCC2(CCN(c3cncc(-c4ccncc4)c3)CC2)C1=O] |

-continued

| Example | Compound Name |
|---|---|
| 273 | trans-N-[(4-aminocyclohexyl)methyl]-N-methyl-4-[5-(4-pyridyl)-3-pyridyl]benzamide |
| 274 | 1-(4-(5-(1-methyl-3-(2-methylpyrimidin-5-yl)-1H-pyrrolo[2,3-b]pyridin-5-yl)pyridin-3-yl)phenyl)pyrrolidin-2-one |
| 275 | 1-(4-(5-(imidazo[1,2-a]pyrimidin-6-yl)pyridin-3-yl)phenyl)pyrrolidin-2-one |
| 276 | N-((1-hydroxy-1,3-dihydrobenzo[c][1,2]oxaborol-5-yl)methyl)-4-(5-(4-(2-oxopyrrolidin-1-yl)phenyl)pyridin-3-yl)-1H-pyrrolo[2,3-b]pyridine-2-carboxamide |
| 277 | 5-ethyl-6-methyl-3-(5-(4-(2-oxopyrrolidin-1-yl)phenyl)pyridin-3-yl)pyrazolo[1,5-a]pyrimidin-7(4H)-one |

-continued

| Example | Compound Name | Structure |
|---|---|---|
| 278 | 1-(4-(5-(5-(2-oxopyrrolidin-1-yl)furo[2,3-b]pyridin-3-yl)pyridin-3-yl)phenyl)pyrrolidin-2-one | 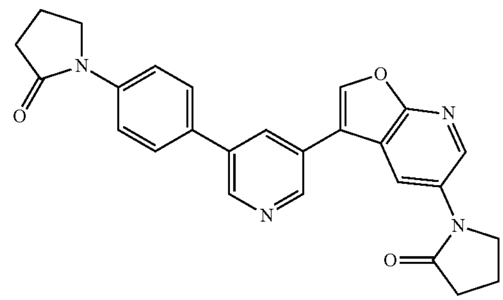 [SMILES: O=C1CCCN1c1ccc(-c2cncc(-c3coc4ncc(N5CCCC5=O)cc34)c2)cc1] |
| 279 | 1-(4-(5-(5-(1-hydroxyethyl)furo[2,3-b]pyridin-3-yl)pyridin-3-yl)phenyl)pyrrolidin-2-one | 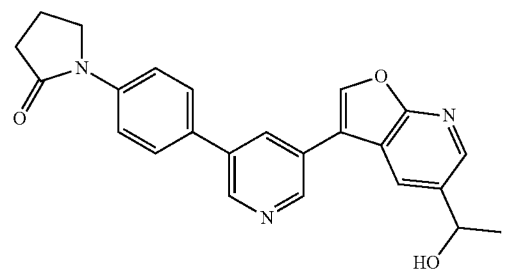 [SMILES: CC(O)c1cnc2occ(-c3cncc(-c4ccc(N5CCCC5=O)cc4)c3)c2c1] |
| 280 | N-((1-hydroxy-1,3-dihydrobenzo[c][1,2]oxaborol-6-yl)methyl)-4-(5-(4-(2-oxopyrrolidin-1-yl)phenyl)pyridin-3-yl)-1H-pyrrolo[2,3-b]pyridine-2-carboxamide | 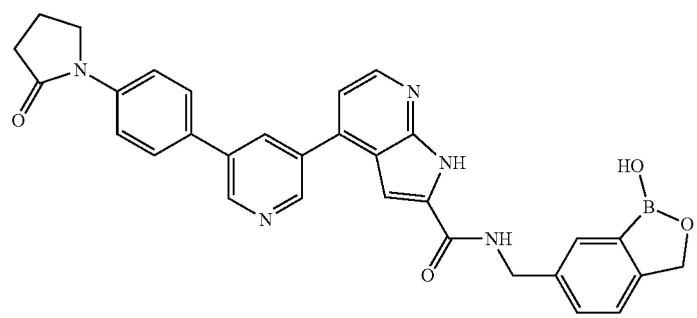 [SMILES: O=C(NCc1ccc2c(c1)B(O)OC2)c1cc2c(-c3cncc(-c4ccc(N5CCCC5=O)cc4)c3)ccnc2[nH]1] |
| 281 | 5-isopropyl-3-(5-(4-(2-oxopyrrolidin-1-yl)phenyl)pyridin-3-yl)pyrazolo[1,5-a]pyrimidin-7(4H)-one | 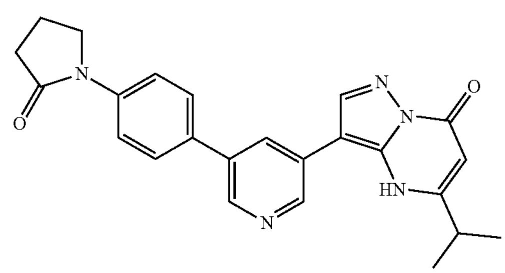 [SMILES: CC(C)c1cc(=O)n2ncc(-c3cncc(-c4ccc(N5CCCC5=O)cc4)c3)c2[nH]1] |
| 282 | N,N-dimethyl-3-(5-(4-(2-oxopyrrolidin-1-yl)phenyl)pyridin-3-yl)furo[2,3-b]pyridine-5-carboxamide | 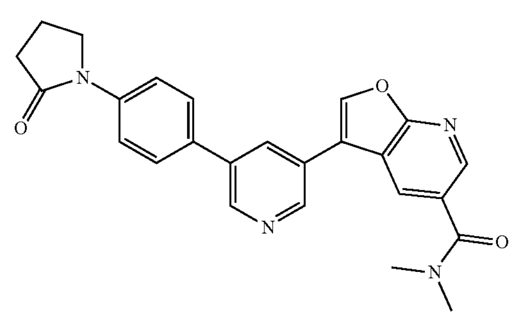 [SMILES: CN(C)C(=O)c1cnc2occ(-c3cncc(-c4ccc(N5CCCC5=O)cc4)c3)c2c1] |

-continued

| Example | Compound Name | Structure |
|---|---|---|
| 283 | 1-(4-(5-(5-cyclopropyl-1H-pyrazolo[3,4-b]pyridin-3-yl)pyridin-3-yl)phenyl)pyrrolidin-2-one | 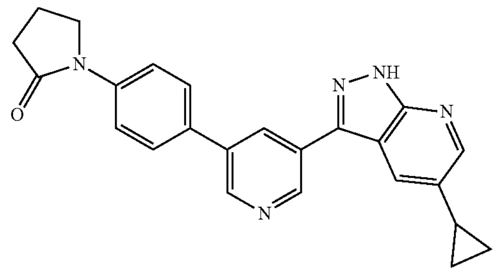 [SMILES: O=C1CCCN1c1ccc(-c2cncc(-c3n[nH]c4ncc(C5CC5)cc34)c2)cc1] |
| 284 | 6-(2-hydroxyethyl)-2,5-dimethyl-3-(5-(4-(2-oxopyrrolidin-1-yl)phenyl)pyridin-3-yl)pyrazolo[1,5-a]pyrimidin-7(4H)-one | 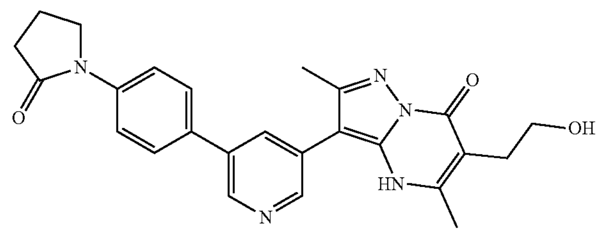 [SMILES: Cc1nn2c(=O)c(CCO)c(C)[nH]c2c1-c1cncc(-c2ccc(N3CCCC3=O)cc2)c1] |
| 285 | 1-(4-(5-(5-(methoxymethyl)-2-methylpyrazolo[1,5-a]pyrimidin-7-yl)pyridin-3-yl)phenyl)pyrrolidin-2-one | 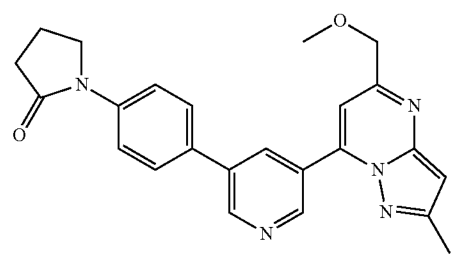 [SMILES: COCc1cc(-c2cncc(-c3ccc(N4CCCC4=O)cc3)c2)n2nc(C)cc2n1] |
| 286 | 1-(4-(5-(5-methyl-2-(piperidin-1-yl)thiazolo[4,5-d]pyrimidin-7-yl)pyridin-3-yl)phenyl)pyrrolidin-2-one | 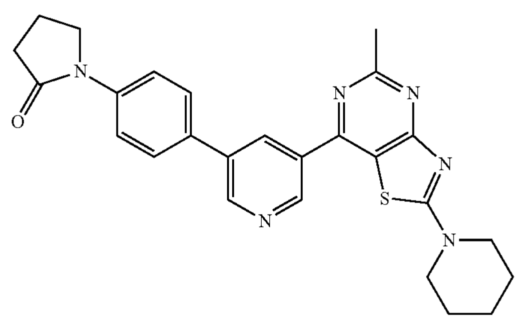 [SMILES: Cc1nc(-c2cncc(-c3ccc(N4CCCC4=O)cc3)c2)c2sc(N3CCCCC3)nc2n1] |
| 287 | N-(4-(5-(4-(2-oxopyrrolidin-1-yl)phenyl)pyridin-3-yl)pyrimidin-2-yl)cyclobutanecarboxamide | 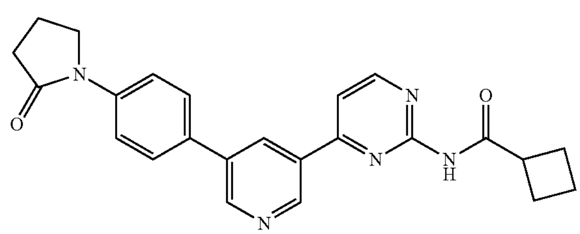 [SMILES: O=C(Nc1nccc(-c2cncc(-c3ccc(N4CCCC4=O)cc3)c2)n1)C1CCC1] |
| 288 | 6-ethyl-5-methyl-3-(5-(4-(2-oxopyrrolidin-1-yl)phenyl)pyridin-3-yl)pyrazolo[1,5-a]pyrimidin-7(4H)-one | 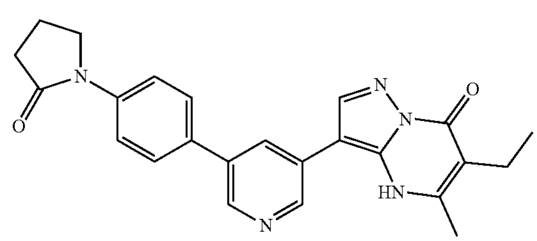 [SMILES: CCc1c(C)[nH]c2c(-c3cncc(-c4ccc(N5CCCC5=O)cc4)c3)cnn2c1=O] |

-continued

| Example | Compound Name | Structure |
|---|---|---|
| 289 | 1-(4-(5-(8-cyclobutyl-7H-purin-6-yl)pyridin-3-yl)phenyl)pyrrolidin-2-one | 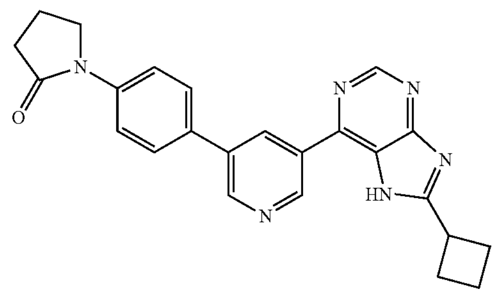 [SMILES: O=C1CCCN1c1ccc(-c2cncc(-c3ncnc4nc(C5CCC5)[nH]c34)c2)cc1] |
| 290 | methyl 5-methyl-4-(5-(4-(2-oxopyrrolidin-1-yl)phenyl)pyridin-3-yl)-1H-pyrrolo[2,3-b]pyridine-2-carboxylate | 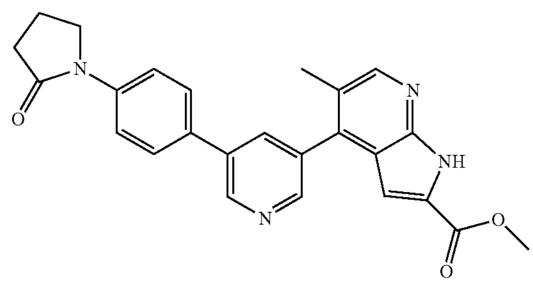 [SMILES: COC(=O)c1cc2c(-c3cncc(-c4ccc(N5CCCC5=O)cc4)c3)c(C)cnc2[nH]1] |
| 291 | 1-(4-(5-(2-cyclopropyl-5-(1-hydroxyethyl)-1H-pyrrolo[2,3-b]pyridin-3-yl)pyridin-3-yl)phenyl)pyrrolidin-2-one | 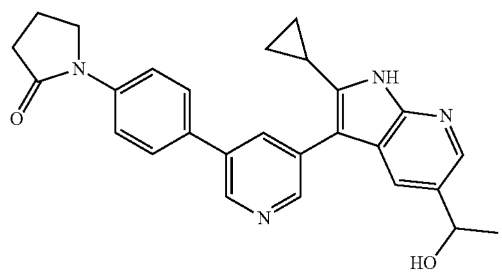 [SMILES: CC(O)c1cnc2[nH]c(C3CC3)c(-c3cncc(-c4ccc(N5CCCC5=O)cc4)c3)c2c1] |
| 292 | 1-(4-(5-(thieno[2,3-b]pyridin-3-yl)pyridin-3-yl)phenyl)pyrrolidin-2-one | 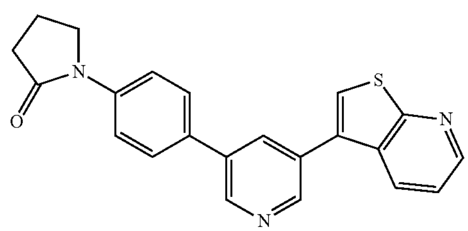 [SMILES: O=C1CCCN1c1ccc(-c2cncc(-c3csc4ncccc34)c2)cc1] |
| 293 | (R)-1-(4-(5-(5-(1-hydroxyethyl)-1-methyl-1H-pyrrolo[2,3-b]pyridin-3-yl)pyridin-3-yl)phenyl)pyrrolidin-2-one | 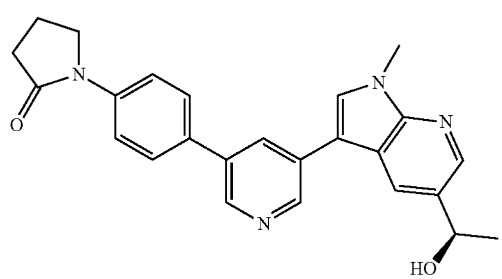 [SMILES: C[C@@H](O)c1cnc2c(c1)c(-c1cncc(-c3ccc(N4CCCC4=O)cc3)c1)cn2C] |

| Example | Compound Name | Structure |
|---|---|---|
| 294 | (S)-1-(4-(5-(5-(1-hydroxyethyl)-1-methyl-1H-pyrrolo[2,3-b]pyridin-3-yl)pyridin-3-yl)phenyl)pyrrolidin-2-one | 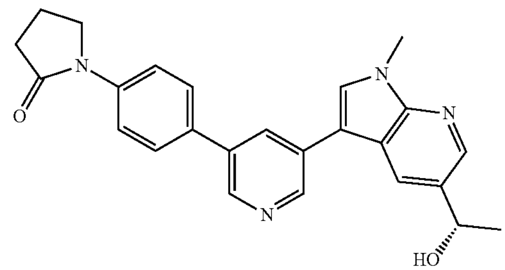 [SMILES: C[C@H](O)c1cnc2c(c1)c(-c1cncc(-c3ccc(N4CCCC4=O)cc3)c1)cn2C] |
| 295 | N,N-dimethyl-3-(5-(4-(2-oxopyrrolidin-1-yl)phenyl)pyridin-3-yl)-1H-pyrrolo[2,3-b]pyridine-5-sulfonamide | 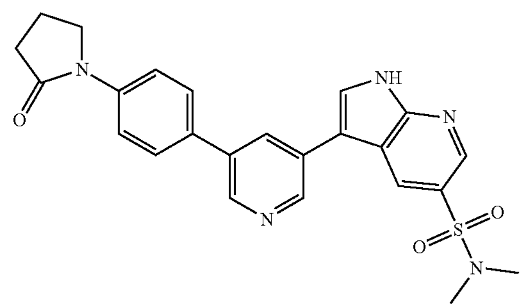 [SMILES: CN(C)S(=O)(=O)c1cnc2[nH]cc(-c3cncc(-c4ccc(N5CCCC5=O)cc4)c3)c2c1] |
| 296 | methyl 5-chloro-4-(5-(4-(2-oxopyrrolidin-1-yl)phenyl)pyridin-3-yl)-1H-pyrrolo[2,3-b]pyridine-2-carboxylate | 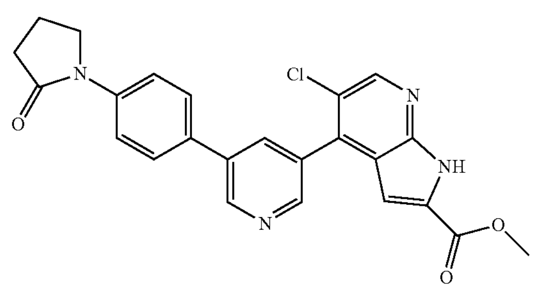 [SMILES: COC(=O)c1cc2c(-c3cncc(-c4ccc(N5CCCC5=O)cc4)c3)c(Cl)cnc2[nH]1] |
| 297 | 4-(5-(4-(2-oxopyrrolidin-1-yl)phenyl)pyridin-3-yl)-N-((1r,3r)-3-phenylcyclobutyl)-1H-pyrrolo[2,3-b]pyridine-2-carboxamide | 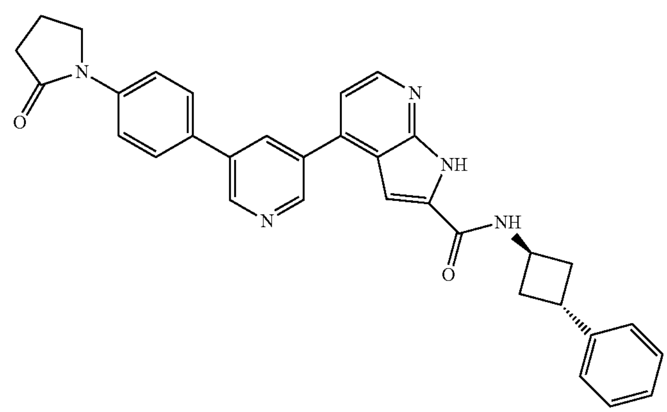 [SMILES: O=C(N[C@H]1C[C@H](c2ccccc2)C1)c1cc2c(-c3cncc(-c4ccc(N5CCCC5=O)cc4)c3)ccnc2[nH]1] |

-continued

| Example | Compound Name | Structure |
|---|---|---|
| 298 | 4-(5-(4-(2-oxopyrrolidin-1-yl)phenyl)pyridin-3-yl)-N-(2-(thiazol-5-yl)ethyl)-1H-pyrrolo[2,3-b]pyridine-2-carboxamide | 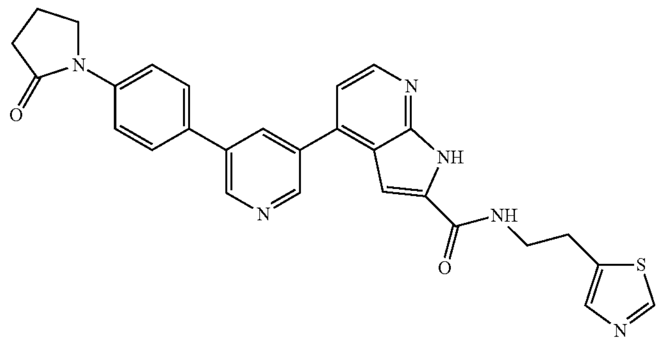 [SMILES: O=C(NCCc1cncs1)c1cc2c(-c3cncc(-c4ccc(N5CCCC5=O)cc4)c3)ccnc2[nH]1] |
| 299 | 1-(4-(5-(7,8-dihydro-6H-pyrido[3,2-b]pyrrolizin-5-yl)pyridin-3-yl)phenyl)pyrrolidin-2-one | 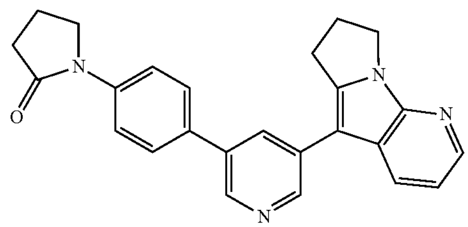 [SMILES: O=C1CCCN1c1ccc(-c2cncc(-c3c4n(c5ncccc35)CCC4)c2)cc1] |
| 300 | 1-(4-(5-(1-methyl-1,5,6,7-tetrahydrocyclopenta[b]pyrazolo[4,3-e]pyridin-4-yl)pyridin-3-yl)phenyl)pyrrolidin-2-one | 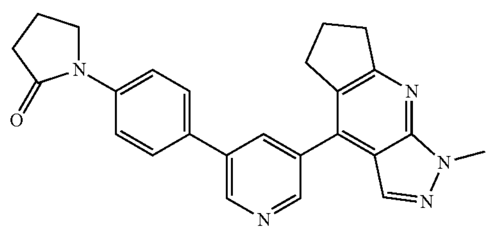 [SMILES: Cn1ncc2c(-c3cncc(-c4ccc(N5CCCC5=O)cc4)c3)c3c(nc21)CCC3] |
| 301 | N-((1-hydroxy-1,3-dihydrobenzo[c][1,2]oxaborol-4-yl)methyl)-4-(5-(4-(2-oxopyrrolidin-1-yl)phenyl)pyridin-3-yl)-1H-pyrrolo[2,3-b]pyridine-2-carboxamide | 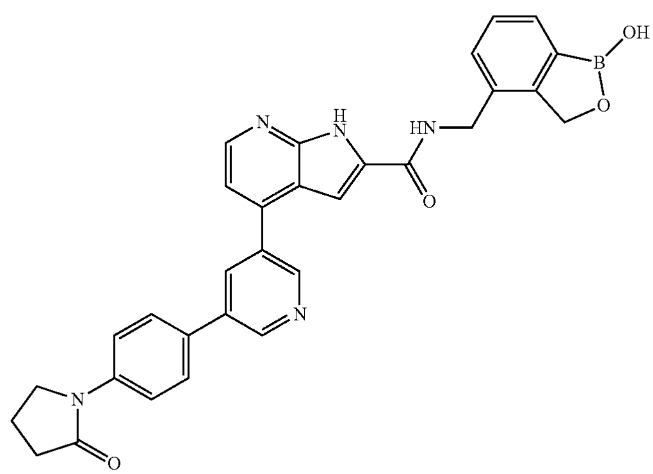 [SMILES: O=C(NCc1cccc2c1COB2O)c1cc2c(-c3cncc(-c4ccc(N5CCCC5=O)cc4)c3)ccnc2[nH]1] |

-continued

| Example | Compound Name | Structure |
|---|---|---|
| 302 | methyl 4-(5-(4-(2-oxopyrrolidin-1-yl)phenyl)pyridin-3-yl)-1H-pyrrolo[2,3-b]pyridine-2-carboxylate | 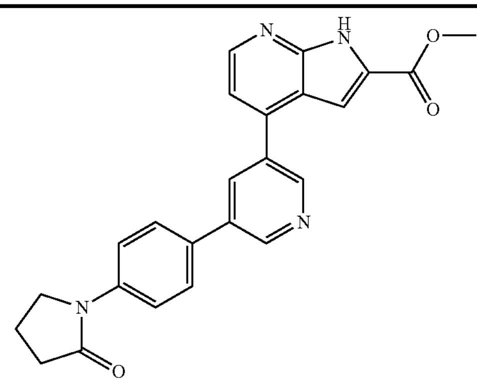 |
| 303 | 1-(4-([3,4'-bipyridin]-5-yl)phenyl)pyrrolidin-2-one | 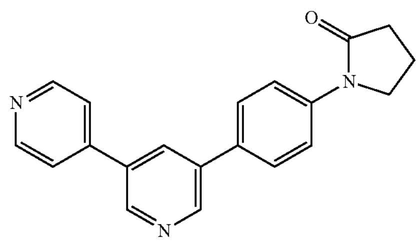 [SMILES: O=C1CCCN1c1ccc(-c2cncc(-c3ccncc3)c2)cc1] |
| 304 | 4-(5-(4-(2-oxopyrrolidin-1-yl)phenyl)pyridin-3-yl)-5,6-dihydro-7H-pyrrolo[3,4-b]pyridin-7-one | 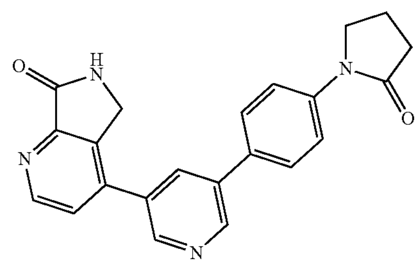 [SMILES: O=C1NCc2c(-c3cncc(-c4ccc(N5CCCC5=O)cc4)c3)ccnc21] |
| 305 | 1-(4-(5-(2,3-dihydro-[1,4]dioxino[2,3-b]pyridin-8-yl)pyridin-3-yl)phenyl)pyrrolidin-2-one | 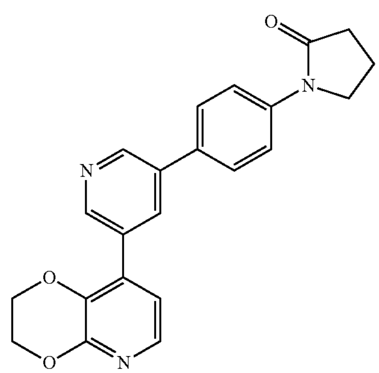 [SMILES: O=C1CCCN1c1ccc(-c2cncc(-c3ccnc4c3OCCO4)c2)cc1] |
| 306 | (R)-7-methyl-4-(5-(4-(2-methyl-5-oxopyrrolidin-1-yl)phenyl)pyridin-3-yl)-8,9-dihydropyrido[3',2':4,5]pyrrolo[1,2-a]pyrazin-6(7H)-one | 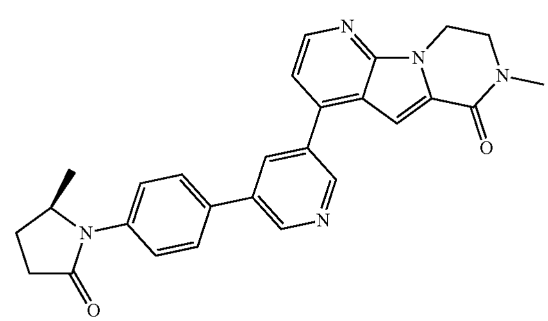 [SMILES: C[C@@H]1CCC(=O)N1c1ccc(-c2cncc(-c3ccnc4c3cc3n4CCN(C)C3=O)c2)cc1] |

| Example | Compound Name | Structure |
|---|---|---|
| 307 | 1-(4-(5-(3-methylisoxazolo[5,4-b]pyridin-4-yl)pyridin-3-yl)phenyl)pyrrolidin-2-one | 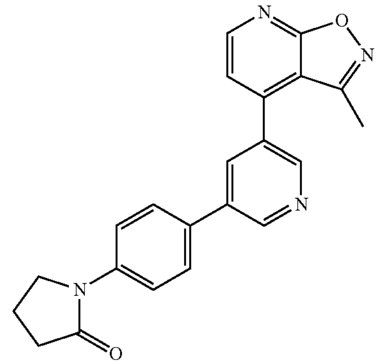 [SMILES: Cc1noc2nccc(-c3cncc(-c4ccc(N5CCCC5=O)cc4)c3)c12] |
| 308 | 7-(2,3-dihydro-[1,4]dioxino[2,3-b]pyridin-6-yl)-4-(5-(4-(2-oxopyrrolidin-1-yl)phenyl)pyridin-3-yl)-8,9-dihydropyrido[3′,2′:4,5]pyrrolo[1,2-a]pyrazin-6(7H)-one | 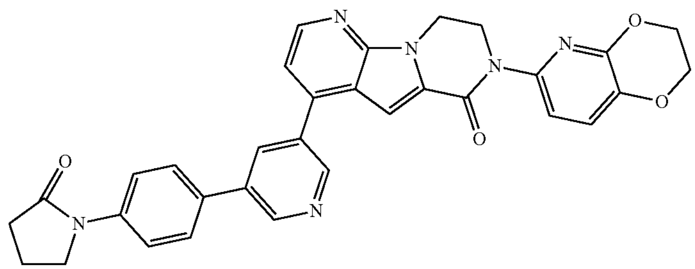 [SMILES: O=C1CCCN1c1ccc(-c2cncc(-c3ccnc4c3cc3n4CCN(c4ccc5c(n4)OCCO5)C3=O)c2)cc1] |
| 309 | 1-(4-(2-amino-5-(3-methyl-1H-pyrrolo[2,3-b]pyridin-4-yl)pyridin-3-yl)phenyl)pyrrolidin-2-one | 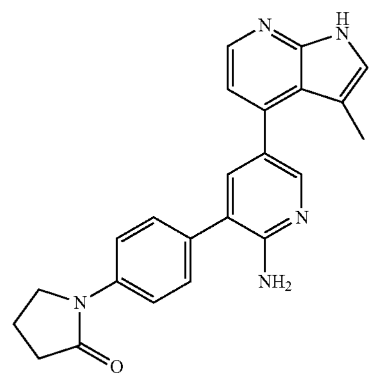 [SMILES: Cc1c[nH]c2nccc(-c3cnc(N)c(-c4ccc(N5CCCC5=O)cc4)c3)c12] |
| 310 | N-methyl-4-(5-(4-(2-oxopyrrolidin-1-yl)phenyl)pyridin-3-yl)-N-(pyridin-3-yl)-1H-pyrrolo[2,3-b]pyridine-2-carboxamide | 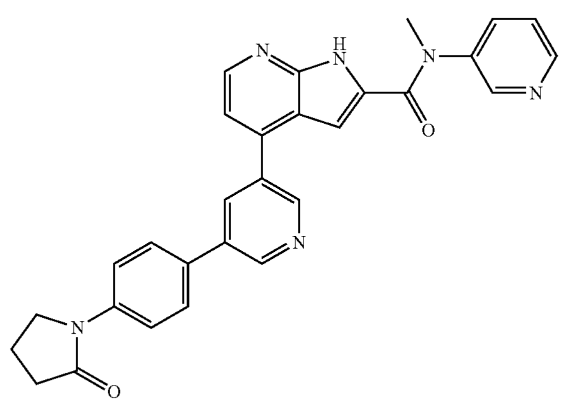 [SMILES: CN(C(=O)c1cc2c(-c3cncc(-c4ccc(N5CCCC5=O)cc4)c3)ccnc2[nH]1)c1cccnc1] |

-continued

| Example | Compound Name | Structure |
|---|---|---|
| 311 | N-methyl-4-(5-(4-(2-oxopyrrolidin-1-yl)phenyl)pyridin-3-yl)-N-phenyl-1H-pyrrolo[2,3-b]pyridine-2-carboxamide | 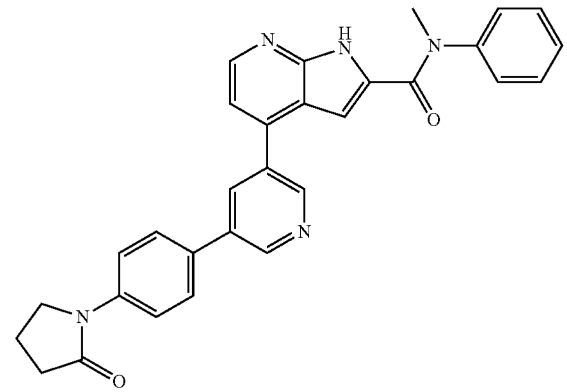 |
| 312 | 4-(5-(4-(2-oxopyrrolidin-1-yl)phenyl)pyridin-3-yl)-N-(pyridin-2-yl)-1H-pyrrolo[2,3-b]pyridine-2-carboxamide | 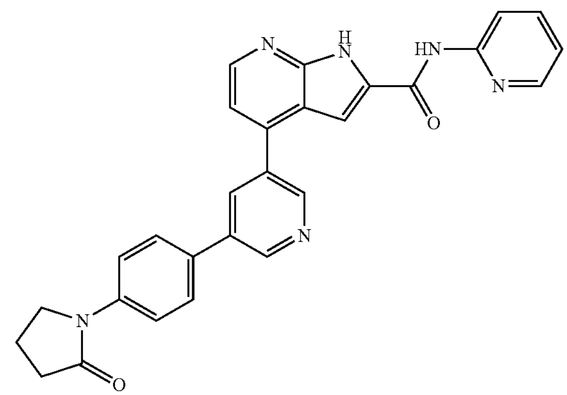 [SMILES: O=C(Nc1ccccn1)c1cc2c(-c3cncc(-c4ccc(N5CCCC5=O)cc4)c3)ccnc2[nH]1] |
| 313 | N,3-dimethyl-4-(5-(4-(2-oxopyrrolidin-1-yl)phenyl)pyridin-3-yl)-1H-pyrrolo[2,3-b]pyridine-2-carboxamide | 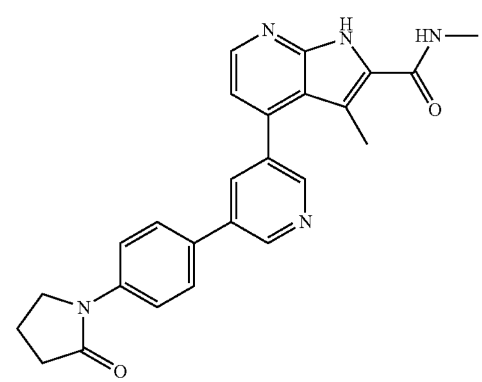 [SMILES: CNC(=O)c1[nH]c2nccc(-c3cncc(-c4ccc(N5CCCC5=O)cc4)c3)c2c1C] |
| 314 | 4-(5-(4-(2-oxopyrrolidin-1-yl)phenyl)pyridin-3-yl)-N-(pyridin-4-yl)-1H-pyrrolo[2,3-b]pyridine-2-carboxamide | 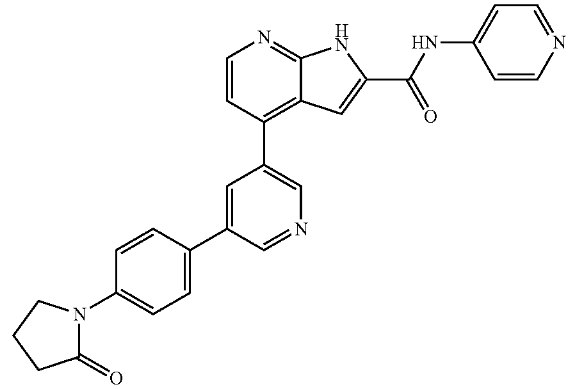 [SMILES: O=C(Nc1ccncc1)c1cc2c(-c3cncc(-c4ccc(N5CCCC5=O)cc4)c3)ccnc2[nH]1] |

| Example | Compound Name | Structure |
|---|---|---|
| 315 | N-((5,6-dimethyl-1H-benzo[d]imidazol-2-yl)methyl)-4-(5-(4-(2-oxopyrrolidin-1-yl)phenyl)pyridin-3-yl)-1H-pyrrolo[2,3-b]pyridine-2-carboxamide | 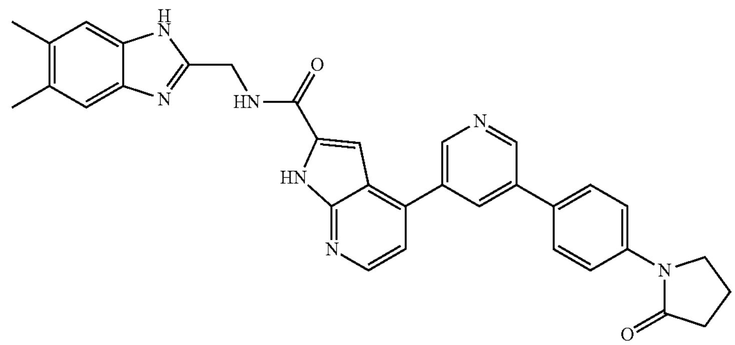 [SMILES: Cc1cc2nc(CNC(=O)c3cc4c(-c5cncc(-c6ccc(N7CCCC7=O)cc6)c5)ccnc4[nH]3)[nH]c2cc1C] |
| 316 | 1-(4-(6-amino-5-(3-methyl-1H-pyrrolo[2,3-b]pyridin-4-yl)pyridin-3-yl)phenyl)pyrrolidin-2-one | 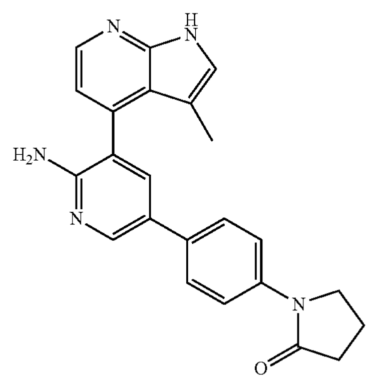 [SMILES: Cc1c[nH]c2nccc(-c3cc(-c4ccc(N5CCCC5=O)cc4)cnc3N)c12] |
| 317 | N-((4-methyl-1H-benzo[d]imidazol-2-yl)methyl)-4-(5-(4-(2-oxopyrrolidin-1-yl)phenyl)pyridin-3-yl)-1H-pyrrolo[2,3-b]pyridine-2-carboxamide | 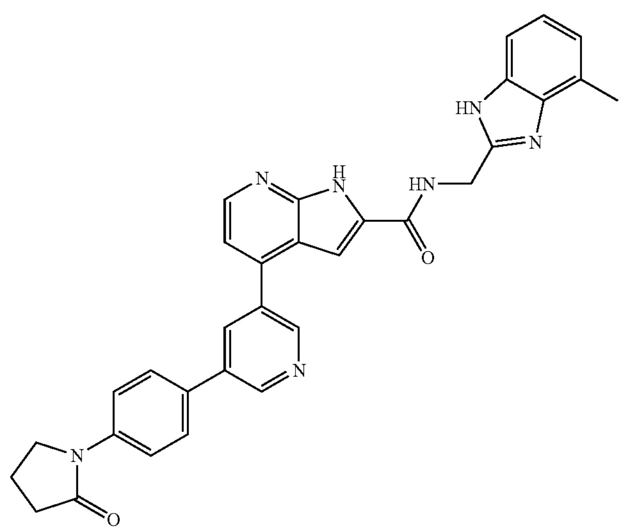 [SMILES: Cc1cccc2[nH]c(CNC(=O)c3cc4c(-c5cncc(-c6ccc(N7CCCC7=O)cc6)c5)ccnc4[nH]3)nc12] |

-continued

| Example | Compound Name | Structure |
|---|---|---|
| 318 | 1-(4-(5-(3-methyl-2H-pyrazolo[3,4-b]pyridin-4-yl)pyridin-3-yl)phenyl)pyrrolidin-2-one | 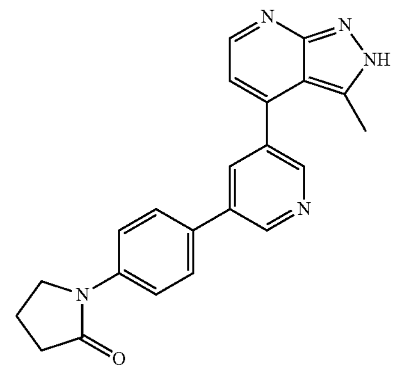 [SMILES: Cc1[nH]nc2nccc(-c3cncc(-c4ccc(N5CCCC5=O)cc4)c3)c12] |
| 319 | N-(benzo[d]thiazol-2-ylmethyl)-4-(5-(4-(2-oxopyrrolidin-1-yl)phenyl)pyridin-3-yl)-1H-pyrrolo[2,3-b]pyridine-2-carboxamide | 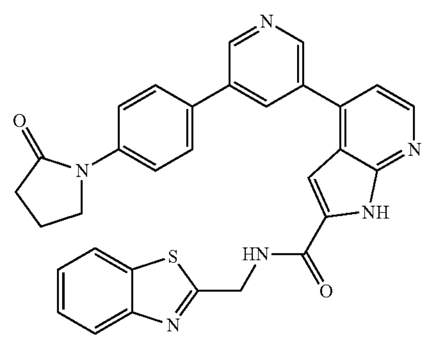 |
| 320 | N-((6-methyl-1H-benzo[d]imidazol-2-yl)methyl)-4-(5-(4-(2-oxopyrrolidin-1-yl)phenyl)pyridin-3-yl)-1H-pyrrolo[2,3-b]pyridine-2-carboxamide | 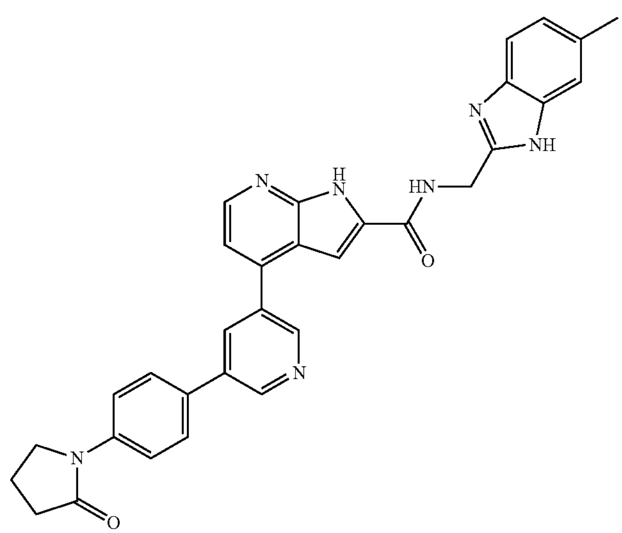 [SMILES: Cc1ccc2nc(CNC(=O)c3cc4c(-c5cncc(-c6ccc(N7CCCC7=O)cc6)c5)ccnc4[nH]3)[nH]c2c1] |

-continued

| Example | Compound Name | Structure |
|---|---|---|
| 321 | N-((1-methyl-1H-benzo[d]imidazol-2-yl)methyl)-4-(5-(4-(2-oxopyrrolidin-1-yl)phenyl)pyridin-3-yl)-1H-pyrrolo[2,3-b]pyridine-2-carboxamide | 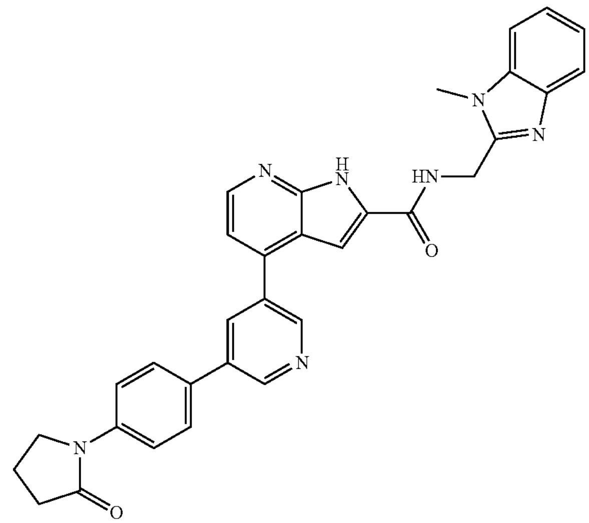 [SMILES: Cn1c(CNC(=O)c2cc3c(-c4cncc(-c5ccc(N6CCCC6=O)cc5)c4)ccnc3[nH]2)nc2ccccc21] |
| 322 | N-((1H-benzo[d]imidazol-2-yl)methyl)-4-(5-(4-(2-oxopyrrolidin-1-yl)phenyl)pyridin-3-yl)-1H-pyrrolo[2,3-b]pyridine-2-carboxamide | 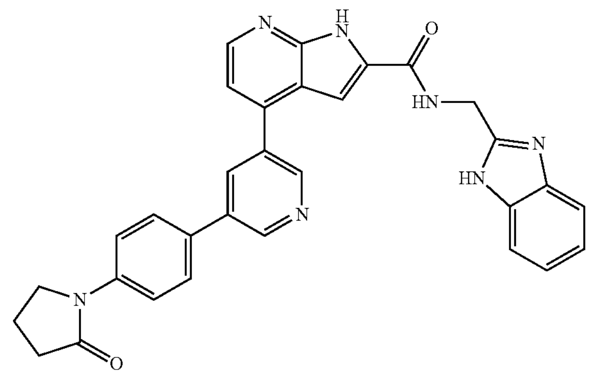 [SMILES: O=C(NCc1nc2ccccc2[nH]1)c1cc2c(-c3cncc(-c4ccc(N5CCCC5=O)cc4)c3)ccnc2[nH]1] |
| 323 | 1-(4-(5-(3-methyl-1H-pyrrolo[2,3-b]pyridin-4-yl)pyridin-3-yl)phenyl)pyrrolidin-2-one | 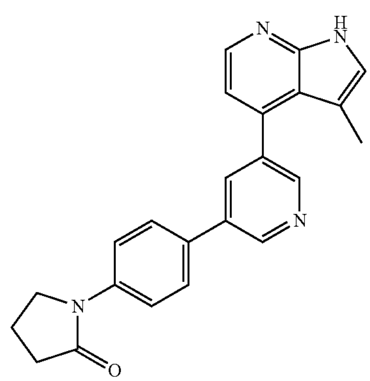 [SMILES: Cc1c[nH]c2nccc(-c3cncc(-c4ccc(N5CCCC5=O)cc4)c3)c12] |
| 324 | N-ethyl-N-methyl-4-(5-(7-methyl-6-oxo-6,7,8,9-tetrahydropyrido[3',2':4,5]pyrrolo[1,2-a]pyrazin-4-yl)pyridin-3-yl)benzamide | 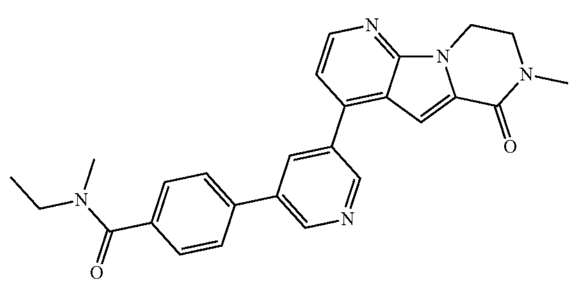 [SMILES: CCN(C)C(=O)c1ccc(-c2cncc(-c3ccnc4c3cc3n4CCN(C)C3=O)c2)cc1] |

-continued

| Example | Compound Name | Structure |
|---------|---------------|-----------|
| 325 | 1-(4-(5-(2-(6-methyl-3,4-dihydro-2H-benzo[b][1,4]oxazine-4-carbonyl)-1H-pyrrolo[2,3-b]pyridin-4-yl)pyridin-3-yl)phenyl)pyrrolidin-2-one | 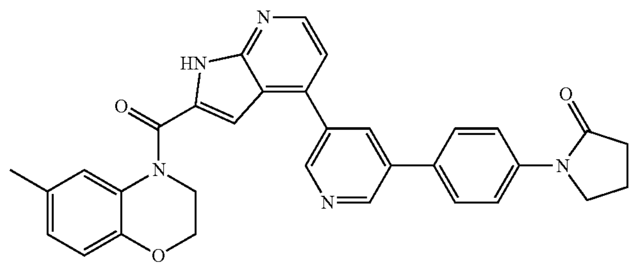 [SMILES: Cc1ccc2c(c1)N(C(=O)c1cc3c(-c4cncc(-c5ccc(N6CCCC6=O)cc5)c4)ccnc3[nH]1)CCO2] |
| 326 | 4-(5-(4-(5,5-dimethyl-2-oxopiperidin-1-yl)phenyl)pyridin-3-yl)-7-methyl-8,9-dihydropyrido[3',2':4,5]pyrrolo[1,2-a]pyrazin-6(7H)-one | 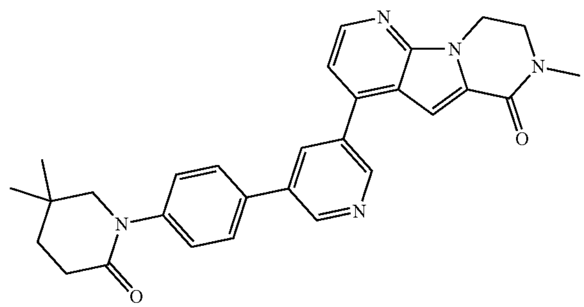 |
| 327 | 7-methyl-4-(5-(4-(morpholine-4-carbonyl)phenyl)pyridin-3-yl)-8,9-dihydropyrido[3',2':4,5]pyrrolo[1,2-a]pyrazin-6(7H)-one | 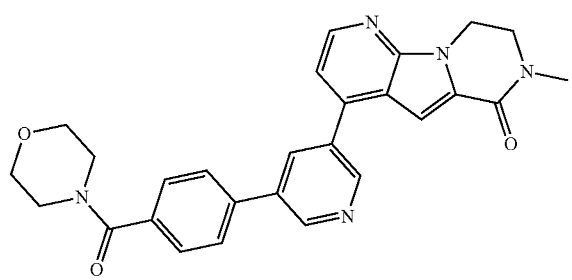 |
| 328 | 4-(5-(4-(2-oxopyrrolidin-1-yl)phenyl)pyridin-3-yl)-N-(pyridin-3-yl)-1H-pyrrolo[2,3-b]pyridine-2-carboxamide | 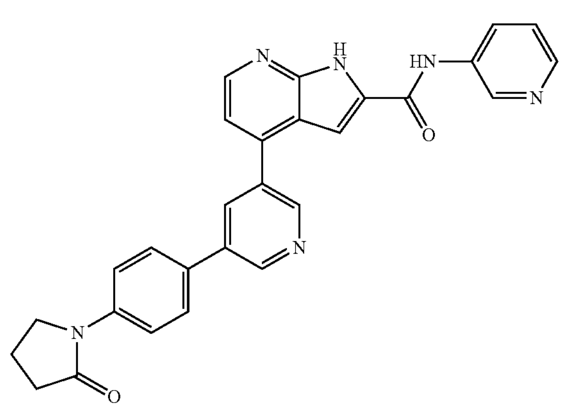 [SMILES: O=C(Nc1cccnc1)c1cc2c(-c3cncc(-c4ccc(N5CCCC5=O)cc4)c3)ccnc2[nH]1] |

| Example | Compound Name | Structure |
|---|---|---|
| 329 | 4-(5-(4-(2-oxopyrrolidin-1-yl)phenyl)pyridin-3-yl)-N-phenyl-1H-pyrrolo[2,3-b]pyridine-2-carboxamide | 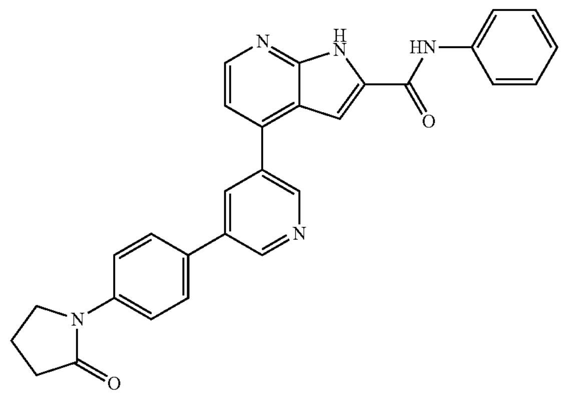 |
| 330 | N-(oxazol-2-ylmethyl)-4-(5-(4-(2-oxopyrrolidin-1-yl)phenyl)pyridin-3-yl)-1H-pyrrolo[2,3-b]pyridine-2-carboxamide | 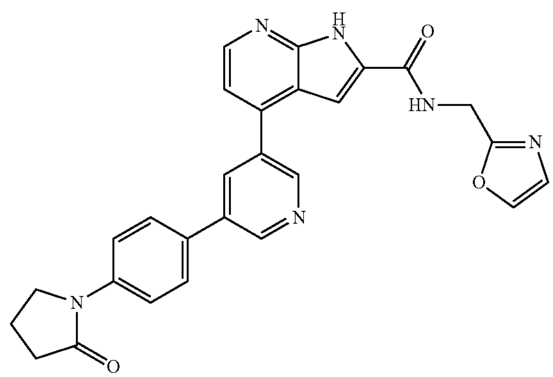 [SMILES: O=C(NCc1ncco1)c1cc2c(-c3cncc(-c4ccc(N5CCCC5=O)cc4)c3)ccnc2[nH]1] |
| 331 | 7-(1,5-dimethyl-1H-pyrazol-3-yl)-4-(5-(4-(2-oxopyrrolidin-1-yl)phenyl)pyridin-3-yl)-8,9-dihydropyrido[3',2':4,5]pyrrolo[1,2-a]pyrazin-6(7H)-one | 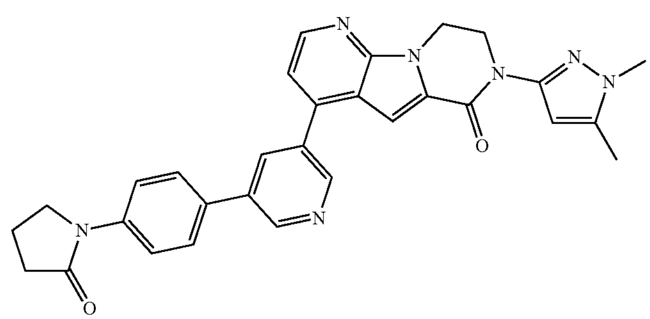 [SMILES: Cc1cc(N2CCn3c(cc4c(-c5cncc(-c6ccc(N7CCCC7=O)cc6)c5)ccnc43)C2=O)nn1C] |
| 332 | 1-(4-(5-(2-(1-oxa-7-azaspiro[4.5]decane-7-carbonyl)-1H-pyrrolo[2,3-b]pyridin-4-yl)pyridin-3-yl)phenyl)pyrrolidin-2-one | 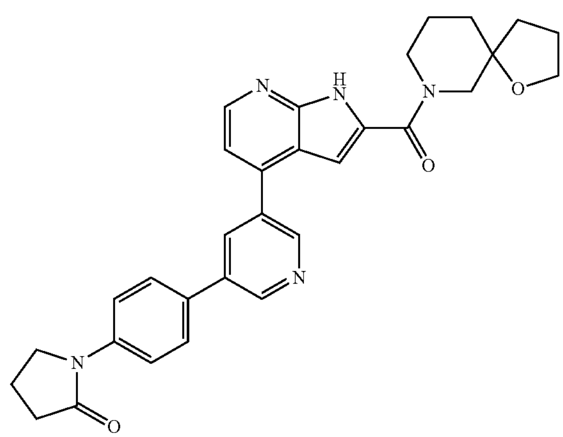 [SMILES: O=C(c1cc2c(-c3cncc(-c4ccc(N5CCCC5=O)cc4)c3)ccnc2[nH]1)N1CCCC2(CCCO2)C1] |

-continued

| Example | Compound Name | Structure |
|---|---|---|
| 333 | 1-(4-(5-(7-cyclopropyl-[1,2,4]triazolo[4,3-a]pyrimidin-5-yl)pyridin-3-yl)phenyl)pyrrolidin-2-one | 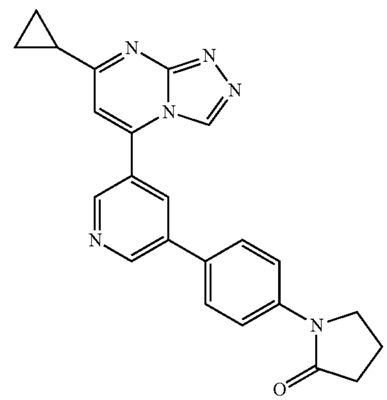 [SMILES: O=C1CCCN1c1ccc(-c2cncc(-c3cc(C4CC4)nc4nncn34)c2)cc1] |
| 334 | 1-(4-(5-(3-(2-aminopyrimidin-5-yl)imidazo[1,2-a]pyrimidin-6-yl)pyridin-3-yl)phenyl)pyrrolidin-2-one | 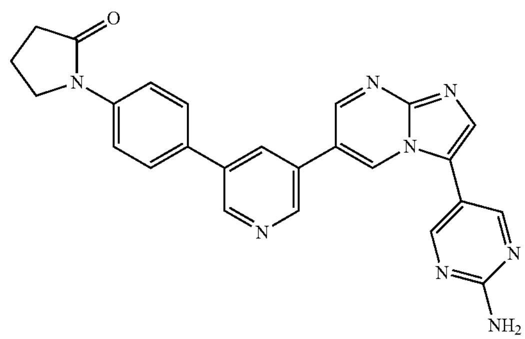 |
| 335 | 4-(5-(4-(4,4-dimethylpiperidine-1-carbonyl)phenyl)pyridin-3-yl)-7-methyl-8,9-dihydropyrido[3',2':4,5]pyrrolo[1,2-a]pyrazin-6(7H)-one | 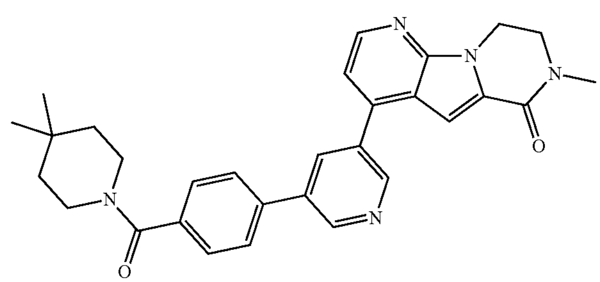 |
| 336 | 1-(4-(5-(7-methyl-[1,2,4]triazolo[4,3-a]pyrimidin-5-yl)pyridin-3-yl)phenyl)pyrrolidin-2-one | 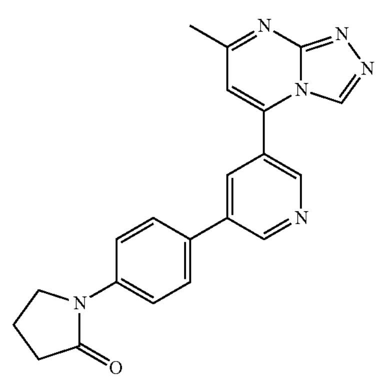 [SMILES: Cc1cc(-c2cncc(-c3ccc(N4CCCC4=O)cc3)c2)n2cnnc2n1] |

-continued

| Example | Compound Name | Structure |
|---|---|---|
| 337 | 1-(4-(5-(3-(6-aminopyridin-3-yl)imidazo[1,2-a]pyrimidin-6-yl)pyridin-3-yl)phenyl)pyrrolidin-2-one | 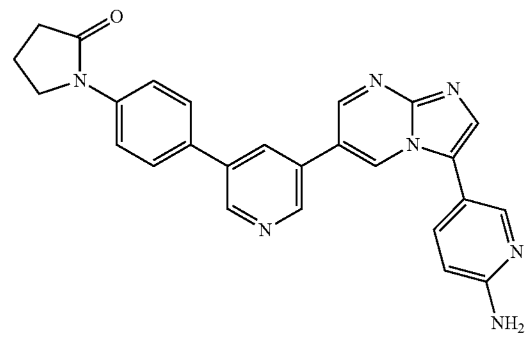 [SMILES: Nc1ccc(-c2cnc3ncc(-c4cncc(-c5ccc(N6CCCC6=O)cc5)c4)cn23)cn1] |
| 338 | 1-(4-(5-(2-cyclopropyl-5-(2-hydroxypropan-2-yl)-1H-pyrrolo[2,3-b]pyridin-3-yl)pyridin-3-yl)phenyl)pyrrolidin-2-one | 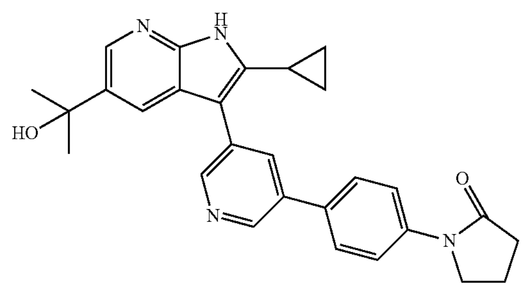 [SMILES: CC(C)(O)c1cnc2[nH]c(C3CC3)c(-c3cncc(-c4ccc(N5CCCC5=O)cc4)c3)c2c1] |
| 339 | 1-(4-(5-(2-(7-methyl-3,4-dihydro-2H-benzo[b][1,4]oxazine-4-carbonyl)-1H-pyrrolo[2,3-b]pyridin-4-yl)pyridin-3-yl)phenyl)pyrrolidin-2-one | 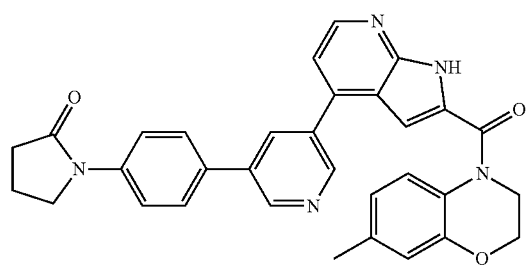 [SMILES: Cc1ccc2c(c1)OCCN2C(=O)c1cc2c(-c3cncc(-c4ccc(N5CCCC5=O)cc4)c3)ccnc2[nH]1] |
| 340 | 1-(4-(5-([1,2,4]triazolo[4,3-a]pyrimidin-5-yl)pyridin-3-yl)phenyl)pyrrolidin-2-one | 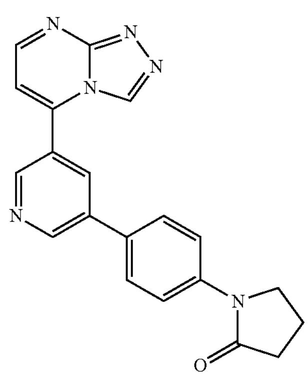 [SMILES: O=C1CCCN1c1ccc(-c2cncc(-c3ccnc4nncn34)c2)cc1] |
| 341 | 1-(4-(5-(3-(pyrimidin-5-yl)imidazo[1,2-a]pyrimidin-6-yl)pyridin-3-yl)phenyl)pyrrolidin-2-one | 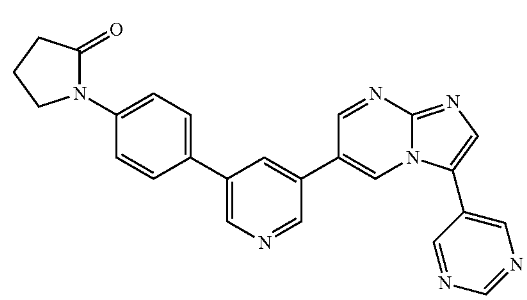 [SMILES: O=C1CCCN1c1ccc(-c2cncc(-c3cnc4ncc(-c5cncnc5)n4c3)c2)cc1] |

-continued

| Example | Compound Name |
|---|---|
| 342 | 4-(5-(4-(4,4-dimethyl-2-oxopiperidin-1-yl)phenyl)pyridin-3-yl)-7-methyl-8,9-dihydropyrido[3',2':4,5]pyrrolo[1,2-a]pyrazin-6(7H)-one |
| 343 | N-(5-(1-methyl-5-(5-(4-(2-oxopyrrolidin-1-yl)phenyl)pyridin-3-yl)-1H-pyrrolo[2,3-b]pyridin-3-yl)pyridin-2-yl)acetamide |
| 344 | 1-(4-(5-(3-(pyridin-3-yl)imidazo[1,2-a]pyrimidin-6-yl)pyridin-3-yl)phenyl)pyrrolidin-2-one |
| 345 | 7-methyl-4-(5-(4-(2-oxoazepan-1-yl)phenyl)pyridin-3-yl)-8,9-dihydropyrido[3',2':4,5]pyrrolo[1,2-a]pyrazin-6(7H)-one |
| 346 | 7-methyl-4-(5-(4-(2-oxopiperidin-1-yl)phenyl)pyridin-3-yl)-8,9-dihydropyrido[3',2':4,5]pyrrolo[1,2-a]pyrazin-6(7H)-one |

-continued

| Example | Compound Name | Structure |
|---|---|---|
| 347 | 1-(4-(5-(3-(6-aminopyridin-3-yl)-1-methyl-1H-pyrrolo[2,3-b]pyridin-5-yl)pyridin-3-yl)phenyl)pyrrolidin-2-one | 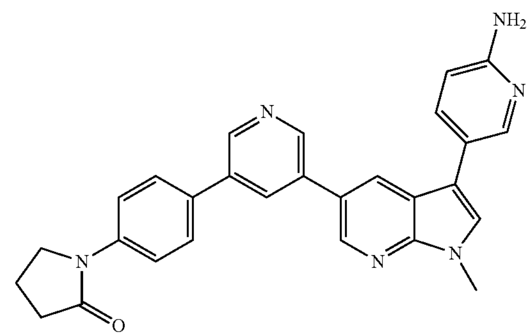 [SMILES: Cn1cc(-c2ccc(N)nc2)c2cc(-c3cncc(-c4ccc(N5CCCC5=O)cc4)c3)cnc21] |
| 348 | 4-(5-(4-(6,7-dihydro-5H-pyrrolo[2,1-c][1,2,4]triazol-3-yl)phenyl)pyridin-3-yl)-7-methyl-8,9-dihydropyrido[3',2':4,5]pyrrolo[1,2-a]pyrazin-6(7H)-one | 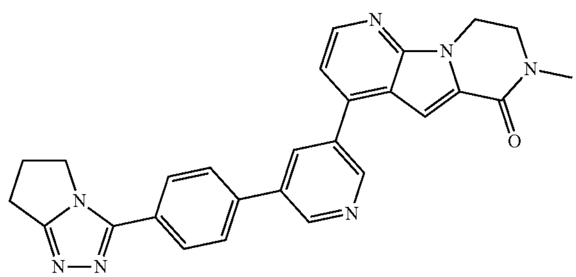 [SMILES: CN1CCn2c(cc3c(-c4cncc(-c5ccc(-c6nnc7n6CCC7)cc5)c4)ccnc32)C1=O] |
| 349 | 7-methyl-4-(5-(4-(pyrrolidine-1-carbonyl)phenyl)pyridin-3-yl)-8,9-dihydropyrido[3',2':4,5]pyrrolo[1,2-a]pyrazin-6(7H)-one | 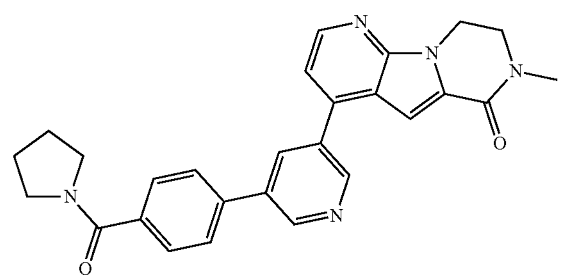 [SMILES: CN1CCn2c(cc3c(-c4cncc(-c5ccc(C(=O)N6CCCC6)cc5)c4)ccnc32)C1=O] |
| 350 | N-(5-(1-methyl-5-(5-(4-(2-oxopyrrolidin-1-yl)phenyl)pyridin-3-yl)-1H-pyrrolo[2,3-b]pyridin-3-yl)pyrimidin-2-yl)acetamide | 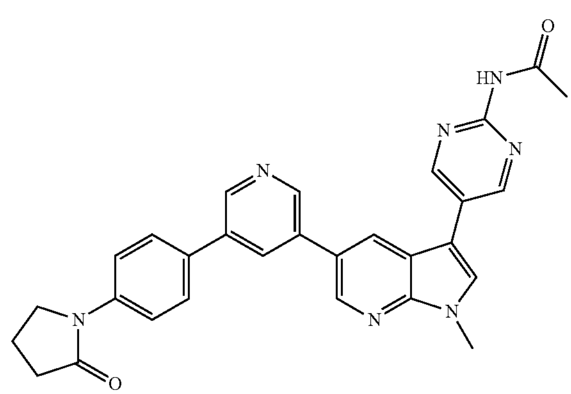 [SMILES: CC(=O)Nc1ncc(-c2cn(C)c3ncc(-c4cncc(-c5ccc(N6CCCC6=O)cc5)c4)cc23)cn1] |

-continued

| Example | Compound Name | Structure |
|---|---|---|
| 351 | 1-(4-(5-(3-(1-hydroxyethyl)-7,8-dihydro-6H-pyrido[3,2-b]pyrrolizin-5-yl)pyridin-3-yl)phenyl)pyrrolidin-2-one | 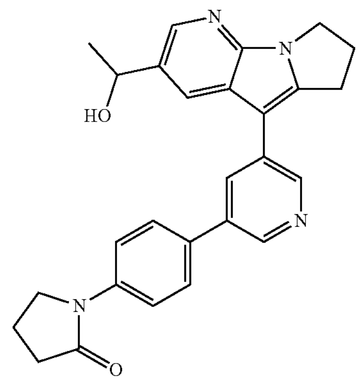 [SMILES: CC(O)c1cnc2c(c1)c(-c1cncc(-c3ccc(N4CCCC4=O)cc3)c1)c1n2CCC1] |
| 352 | 1-(4-(5-(7,8-dihydro-6H-pyrimido[5,4-b]pyrrolizin-5-yl)pyridin-3-yl)phenyl)pyrrolidin-2-one | 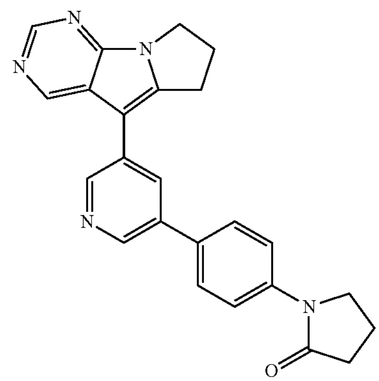 [SMILES: O=C1CCCN1c1ccc(-c2cncc(-c3c4n(c5ncncc35)CCC4)c2)cc1] |
| 353 | 1-(4-(5-(3-bromo-7,8-dihydro-6H-pyrido[3,2-b]pyrrolizin-5-yl)pyridin-3-yl)phenyl)pyrrolidin-2-one | 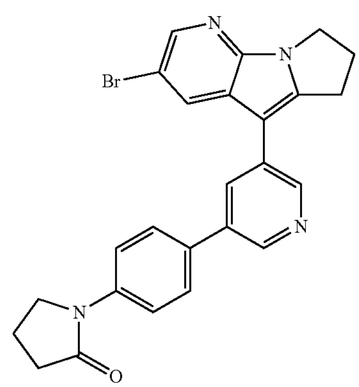 [SMILES: O=C1CCCN1c1ccc(-c2cncc(-c3c4n(c5ncc(Br)cc35)CCC4)c2)cc1] |
| 354 | 7-methyl-4-(5-(4-(piperidine-1-carbonyl)phenyl)pyridin-3-yl)-8,9-dihydropyrido[3',2':4,5]pyrrolo[1,2-a]pyrazin-6(7H)-one | 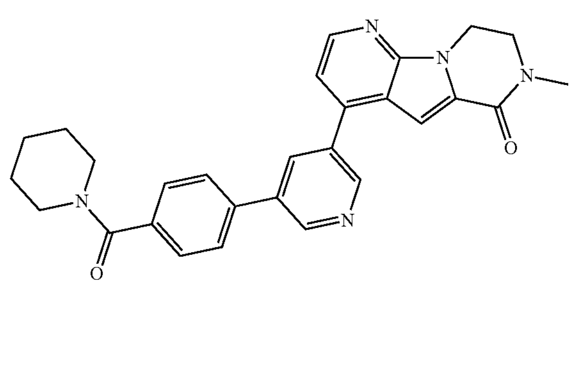 [SMILES: CN1CCn2c(cc3c(-c4cncc(-c5ccc(C(=O)N6CCCCC6)cc5)c4)ccnc32)C1=O] |

-continued

| Example | Compound Name | Structure |
|---|---|---|
| 355 | 1-(4-(5-(3-(2-aminopyrimidin-5-yl)-1-methyl-1H-pyrrolo[2,3-b]pyridin-5-yl)pyridin-3-yl)phenyl)pyrrolidin-2-one | 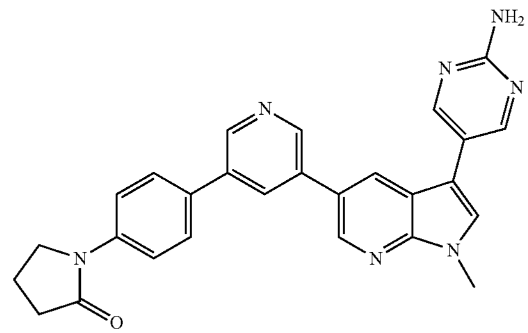 |
| 356 | 4-(5-(4-(4-cyclobutyl-4H-1,2,4-triazol-3-yl)phenyl)pyridin-3-yl)-5-methyl-7-(pyridin-2-yl)-8,9-dihydropyrido[3',2':4,5]pyrrolo[1,2-a]pyrazin-6(7H)-one | 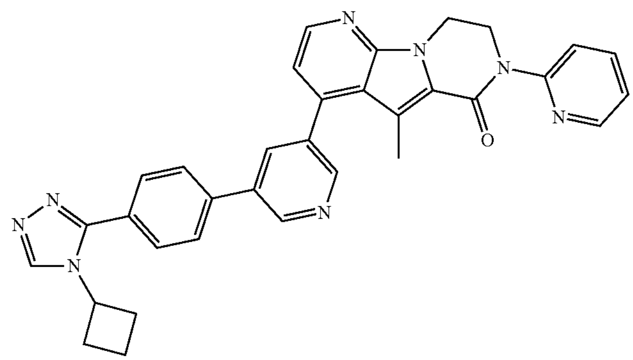 [SMILES: Cc1c2n(c3nccc(-c4cncc(-c5ccc(-c6nncn6C6CCC6)cc5)c4)c13)CCN(c1ccccn1)C2=O] |
| 357 | 4-(5-(4-(5-isopropyl-1H-1,2,3-triazol-1-yl)phenyl)pyridin-3-yl)-7-(pyridin-2-yl)-8,9-dihydropyrido[3',2':4,5]pyrrolo[1,2-a]pyrazin-6(7H)-one | 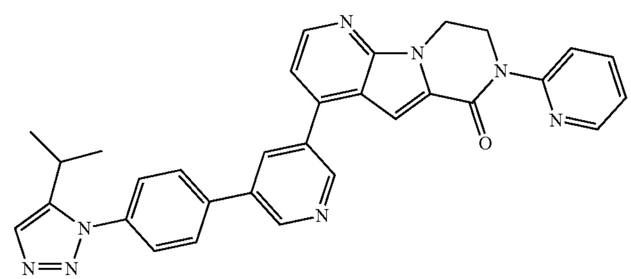 [SMILES: CC(C)c1cnnn1-c1ccc(-c2cncc(-c3ccnc4c3cc3n4CCN(c4ccccn4)C3=O)c2)cc1] |
| 358 | 4-(5-(4-(4-ethyl-4H-1,2,4-triazol-3-yl)phenyl)pyridin-3-yl)-7-methyl-8,9-dihydropyrido[3',2':4,5]pyrrolo[1,2-a]pyrazin-6(7H)-one | 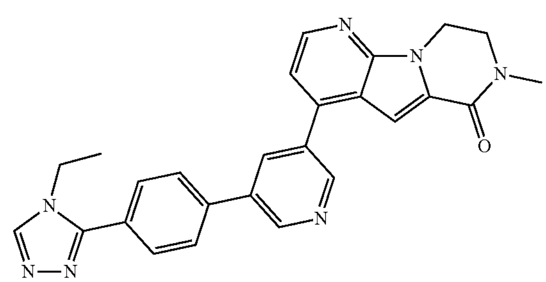 [SMILES: CCn1cnnc1-c1ccc(-c2cncc(-c3ccnc4c3cc3n4CCN(C)C3=O)c2)cc1] |
| 359 | 4-(5-(4-(1-isopropyl-1H-imidazol-5-yl)phenyl)pyridin-3-yl)-7-methyl-8,9-dihydropyrido[3',2':4,5]pyrrolo[1,2-a]pyrazin-6(7H)-one | 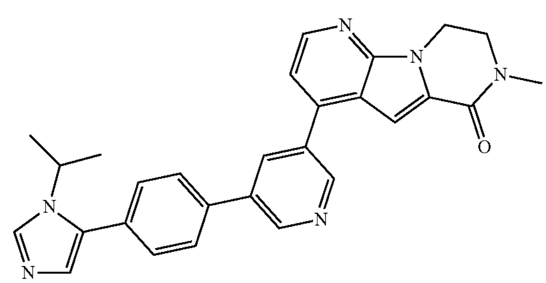 [SMILES: CC(C)n1cncc1-c1ccc(-c2cncc(-c3ccnc4c3cc3n4CCN(C)C3=O)c2)cc1] |

-continued

| Example | Compound Name |
|---|---|
| 360 | (S)-4-(5-(4-(4-(sec-butyl)-4H-1,2,4-triazol-3-yl)phenyl)pyridin-3-yl)-7-methyl-8,9-dihydropyrido[3',2':4,5]pyrrolo[1,2-a]pyrazin-6(7H)-one |
| 361 | (R)-4-(5-(4-(4-(sec-butyl)-4H-1,2,4-triazol-3-yl)phenyl)pyridin-3-yl)-7-methyl-8,9-dihydropyrido[3',2':4,5]pyrrolo[1,2-a]pyrazin-6(7H)-one |
| 362 | 4-(6-amino-5-(4-(4-isopropyl-4H-1,2,4-triazol-3-yl)phenyl)pyridin-3-yl)-N-methylfuro[2,3-b]pyridine-2-carboxamide |
| 363 | 4-(5-(4-(4-isopropylisoxazol-5-yl)phenyl)pyridin-3-yl)-7-methyl-8,9-dihydropyrido[3',2':4,5]pyrrolo[1,2-a]pyrazin-6(7H)-one |
| 364 | 4-(5-(4-(1-isopropyl-1H-imidazol-2-yl)phenyl)pyridin-3-yl)-7-methyl-8,9-dihydropyrido[3',2':4,5]pyrrolo[1,2-a]pyrazin-6(7H)-one |

| Example | Compound Name |
|---|---|
| 365 | 4-(5-(4-(4-cyclobutyl-4H-1,2,4-triazol-3-yl)phenyl)pyridin-3-yl)-7-methyl-8,9-dihydropyrido[3',2':4,5]pyrrolo[1,2-a]pyrazin-6(7H)-one |
| 366 | 4-(6-amino-5-(4-(4-isobutyl-4H-1,2,4-triazol-3-yl)phenyl)pyridin-3-yl)-N-methylfuro[2,3-b]pyridine-2-carboxamide |
| 367 | 4-(5-(4-(4-isobutyl-4H-1,2,4-triazol-3-yl)phenyl)pyridin-3-yl)-7-(pyridin-2-yl)-8,9-dihydropyrido[3',2':4,5]pyrrolo[1,2-a]pyrazin-6(7H)-one |
| 368 | 4-(5-(4-(5-isopropyl-1H-1,2,3-triazol-1-yl)phenyl)pyridin-3-yl)-7-methyl-8,9-dihydropyrido[3',2':4,5]pyrrolo[1,2-a]pyrazin-6(7H)-one |

| Example | Compound Name | Structure |
|---|---|---|
| 369 | 4-(5-(4-(4-(2-cyclopropylethyl-4H-1,2,4-triazol-3-yl)phenyl)pyridin-3-yl)-7-methyl-8,9-dihydropyrido[3',2':4,5]pyrrolo[1,2-a]pyrazin-6(7H)-one | 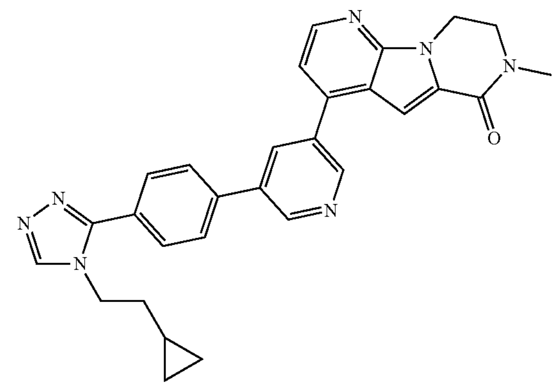 [SMILES: CN1CCn2c(cc3c(-c4cncc(-c5ccc(-c6nncn6CCC6CC6)cc5)c4)ccnc32)C1=O] |
| 370 | 7-methyl-4-(5-(4-(4-methylpyridazin-3-yl)phenyl)pyridin-3-yl)-8,9-dihydropyrido[3',2':4,5]pyrrolo[1,2-a]pyrazin-6(7H)-one | 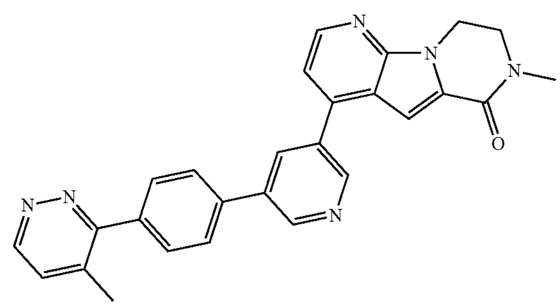 [SMILES: Cc1ccnnc1-c1ccc(-c2cncc(-c3ccnc4c3cc3n4CCN(C)C3=O)c2)cc1] |
| 371 | 4-(5-(4-(4-isopropyl-4H-1,2,4-triazol-3-yl)phenyl)pyridin-3-yl)-N-(2-(pyridin-4-yl)ethyl)-1H-pyrrolo[2,3-b]pyridine-2-carboxamide | 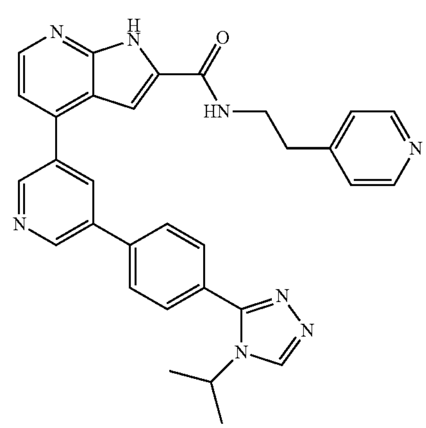 [SMILES: CC(C)n1cnnc1-c1ccc(-c2cncc(-c3ccnc4[nH]c(C(=O)NCCc5ccncc5)cc34)c2)cc1] |
| 372 | N-benzyl-4-(5-(4-(4-isobutyl-4H-1,2,4-triazol-3-yl)phenyl)pyridin-3-yl)-1H-pyrrolo[2,3-b]pyridine-2-carboxamide | 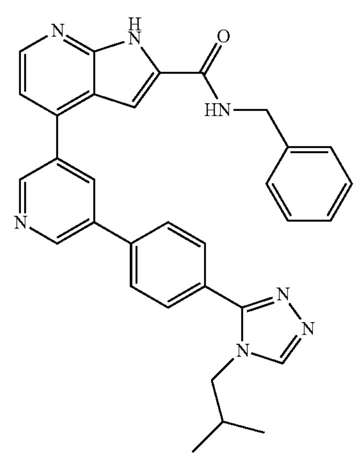 [SMILES: CC(C)Cn1cnnc1-c1ccc(-c2cncc(-c3ccnc4[nH]c(C(=O)NCc5ccccc5)cc34)c2)cc1] |

| Example | Compound Name | Structure |
| --- | --- | --- |
| 373 | N-benzyl-4-(5-(4-(4-isopropyl-4H-1,2,4-triazol-3-yl)phenyl)pyridin-3-yl)-1H-pyrrolo[2,3-b]pyridine-2-carboxamide | 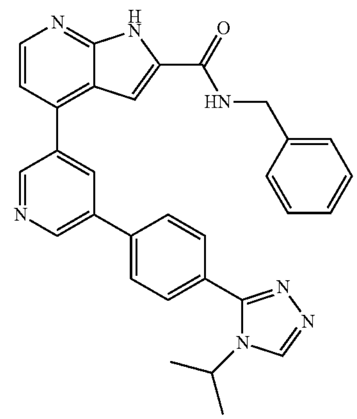 [SMILES: CC(C)n1cnnc1-c1ccc(-c2cncc(-c3ccnc4[nH]c(C(=O)NCc5ccccc5)cc34)c2)cc1] |
| 374 | 4-(6-amino-5-(4-(4-isopropyl-4H-1,2,4-triazol-3-yl)phenyl)pyridin-3-yl)-7-(cyclopropylmethyl)-8,9-dihydropyrido[3',2':4,5]pyrrolo[1,2-a]pyrazin-6(7H)-one | 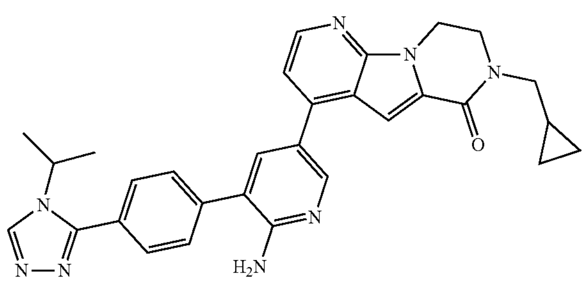 [SMILES: CC(C)n1cnnc1-c1ccc(-c2cc(-c3ccnc4c3cc3n4CCN(CC4CC4)C3=O)cnc2N)cc1] |
| 375 | 4-(5-(4-(4-isopropylisoxazol-3-yl)phenyl)pyridin-3-yl)-7-methyl-8,9-dihydropyrido[3',2':4,5]pyrrolo[1,2-a]pyrazin-6(7H)-one | 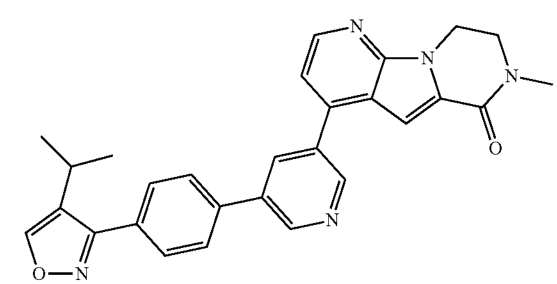 [SMILES: CC(C)c1conc1-c1ccc(-c2cncc(-c3ccnc4c3cc3n4CCN(C)C3=O)c2)cc1] |
| 376 | 4-(5-(4-(4-(cyclopropylmethyl)-4H-1,2,4-triazol-3-yl)phenyl)pyridin-3-yl)-7-methyl-8,9-dihydropyrido[3',2':4,5]pyrrolo[1,2-a]pyrazin-6(7H)-one | 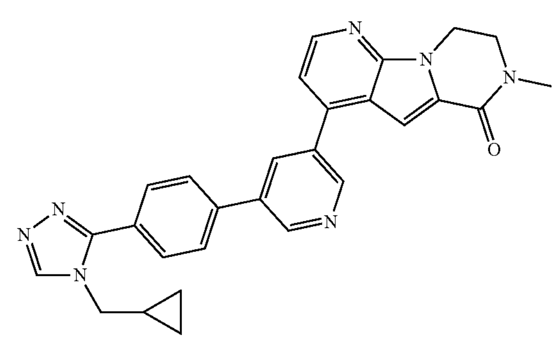 [SMILES: CN1CCn2c(cc3c(-c4cncc(-c5ccc(-c6nncn6CC6CC6)cc5)c4)ccnc32)C1=O] |

-continued

| Example | Compound Name | Structure |
|---|---|---|
| 377 | 4-(5-(4-(4-(tert-butyl)-4H-1,2,4-triazol-3-yl)phenyl)pyridin-3-yl)-7-methyl-8,9-dihydropyrido[3',2':4,5]pyrrolo[1,2-a]pyrazin-6(7H)-one | 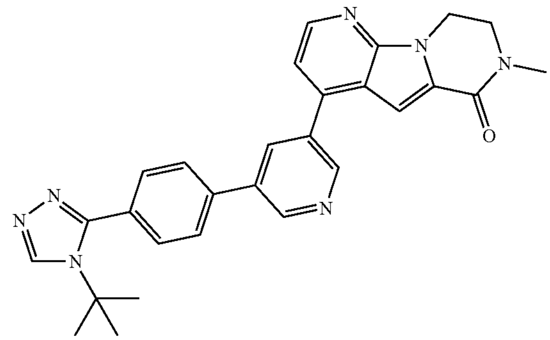 [SMILES: CN1CCn2c(cc3c(-c4cncc(-c5ccc(-c6nncn6C(C)(C)C)cc5)c4)ccnc32)C1=O] |
| 378 | 4-(5-(4-(4-isopropyl-4H-1,2,4-triazol-3-yl)phenyl)pyridin-3-yl)-N-(pyridin-3-ylmethyl)-1H-pyrrolo[2,3-b]pyridine-2-carboxamide | 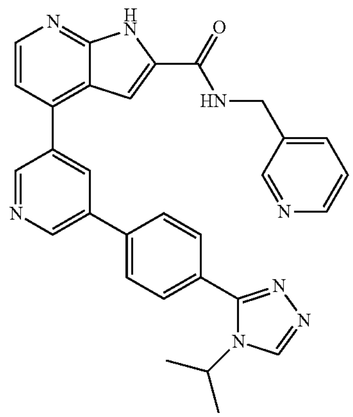 |
| 379 | N-((1-hydroxy-1,3-dihydrobenzo[c][1,2]oxaborol-7-yl)methyl)-4-(5-(4-(2-oxopyrrolidin-1-yl)phenyl)pyridin-3-yl)-1H-pyrrolo[2,3-b]pyridine-2-carboxamide | 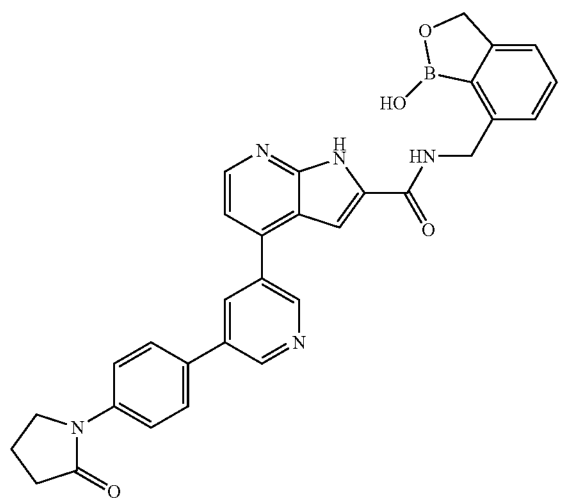 [SMILES: O=C(NCc1cccc2c1B(O)OC2)c1cc2c(-c3cncc(-c4ccc(N5CCCC5=O)cc4)c3)ccnc2[nH]1] |
| 380 | 4-(5-(4-(5-isopropylpyridin-3-yl)phenyl)pyridin-3-yl)-7-methyl-8,9-dihydropyrido[3',2':4,5]pyrrolo[1,2-a]pyrazin-6(7H)-one | 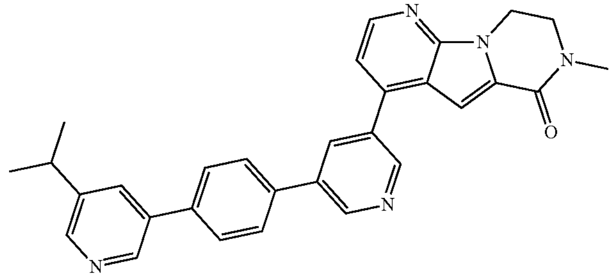 [SMILES: CC(C)c1cncc(-c2ccc(-c3cncc(-c4ccnc5c4cc4n5CCN(C)C4=O)c3)cc2)c1] |

| Example | Compound Name | Structure |
|---|---|---|
| 381 | 4-(5-(4-(3,3-dimethylazetidine-1-carbonyl)phenyl)pyridin-3-yl)-7-methyl-8,9-dihydropyrido[3',2':4,5]pyrrolo[1,2-a]pyrazin-6(7H)-one | 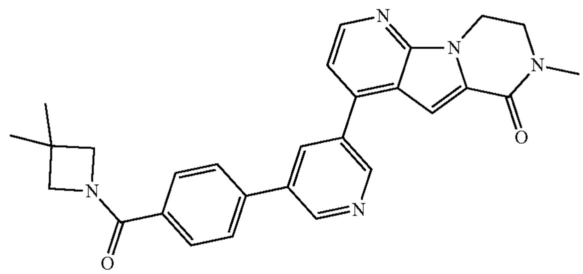 |
| 382 | 4-(5-(4-(7-azabicyclo[2.2.1]heptane-7-carbonyl)phenyl)pyridin-3-yl)-7-methyl-8,9-dihydropyrido[3',2':4,5]pyrrolo[1,2-a]pyrazin-6(7H)-one | 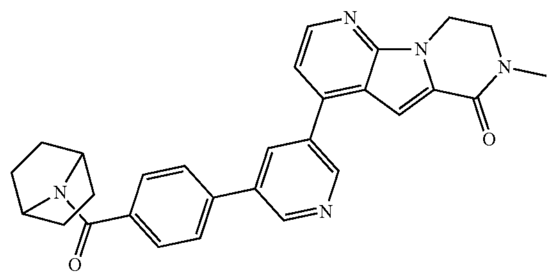 [SMILES: CN1CCn2c(cc3c(-c4cncc(-c5ccc(C(=O)N6C7CCC6CC7)cc5)c4)ccnc32)C1=O] |
| 383 | 4-(5-(4-(4-isobutyl-4H-1,2,4-triazol-3-yl)phenyl)pyridin-3-yl)-7-methyl-8,9-dihydropyrido[3',2':4,5]pyrrolo[1,2-a]pyrazin-6(7H)-one | 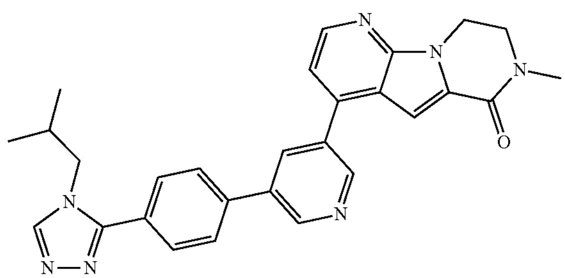 [SMILES: CC(C)Cn1cnnc1-c1ccc(-c2cncc(-c3ccnc4c3cc3n4CCN(C)C3=O)c2)cc1] |
| 384 | 4-(5-(4-(4-isopropyl-4H-1,2,4-triazol-3-yl)phenyl)pyridin-3-yl)-7-methyl-8,9-dihydropyrido[3',2':4,5]pyrrolo[1,2-a]pyrazin-6(7H)-one | 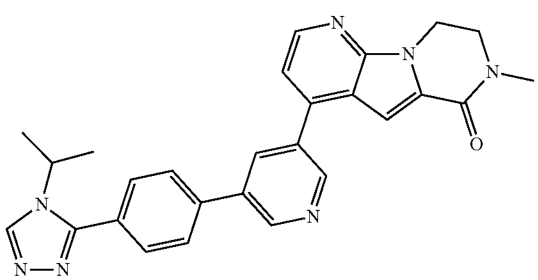 [SMILES: CC(C)n1cnnc1-c1ccc(-c2cncc(-c3ccnc4c3cc3n4CCN(C)C3=O)c2)cc1] |
| 385 | 4-(5-(4-(4-isopropyl-4H-1,2,4-triazol-3-yl)phenyl)pyridin-3-yl)-7-(pyridin-4-ylmethyl)-8,9-dihydropyrido[3',2':4,5]pyrrolo[1,2-a]pyrazin-6(7H)-one | 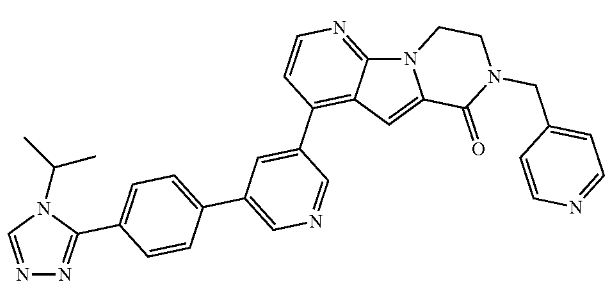 [SMILES: CC(C)n1cnnc1-c1ccc(-c2cncc(-c3ccnc4c3cc3n4CCN(Cc4ccncc4)C3=O)c2)cc1] |

| Example | Compound Name |
|---|---|
| 386 | 4-(5-(4-(1,1-dioxidoisothiazolidin-2-yl)phenyl)pyridin-3-yl)-7-methyl-8,9-dihydropyrido[3′,2′:4,5]pyrrolo[1,2-a]pyrazin-6(7H)-one |
| 387 | 4-(5-(4-(1-isopropyl-1H-tetrazol-5-yl)phenyl)pyridin-3-yl)-7-methyl-8,9-dihydropyrido[3′,2′:4,5]pyrrolo[1,2-a]pyrazin-6(7H)-one |
| 388 | N-(8-(2-((2-(2,6-dioxopiperidin-3-yl)-1,3-dioxoisoindolin-4-yl)oxy)acetamido)octyl)-4-(5-(4-(4-isopropyl-4H-1,2,4-triazol-3-yl)phenyl)pyridin-3-yl)-1H-pyrrolo[2,3-b]pyridine-2-carboxamide |
| 389 | N-(1-((2-(2,6-dioxopiperidin-3-yl)-1,3-dioxoisoindolin-4-yl)oxy)-2-oxo-6,9,12-trioxa-3-azatetradecan-14-yl)-4-(5-(4-(4-isopropyl-4H-1,2,4-triazol-3-yl)phenyl)pyridin-3-yl)-1H-pyrrolo[2,3-b]pyridine-2-carboxamide |

-continued

| Example | Compound Name | Structure |
|---|---|---|
| 390 | N-((4,5-dimethyloxazol-2-yl)methyl)-4-oxopyrrolidin-1-yl)phenyl)pyridin-3-yl)-1H-pyrrolo[2,3-b]pyridine-2-carboxamide | 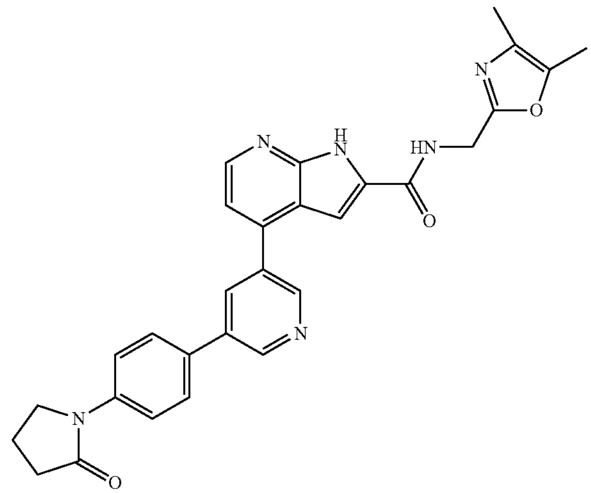 [SMILES: Cc1nc(CNC(=O)c2cc3c(-c4cncc(-c5ccc(N6CCCC6=O)cc5)c4)ccnc3[nH]2)oc1C] |
| 391 | 4-(6-amino-5-(4-(4-isobutyl-4H-1,2,4-triazol-3-yl)phenyl)pyridin-3-yl)-7-(cyclopropylmethyl)-8,9-dihydropyrido[3',2':4,5]pyrrolo[1,2-a]pyrazin-6(7H)-one | 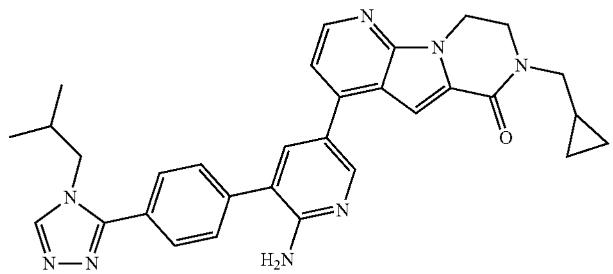 [SMILES: CC(C)Cn1cnnc1-c1ccc(-c2cc(-c3ccnc4c3cc3n4CCN(CC4CC4)C3=O)cnc2N)cc1] |
| 392 | 4-(6-amino-5-(4-(4-isopropyl-4H-1,2,4-triazol-3-yl)phenyl)pyridin-3-yl)-N-(cyclopropylmethyl)furo[2,3-b]pyridine-2-carboxamide | 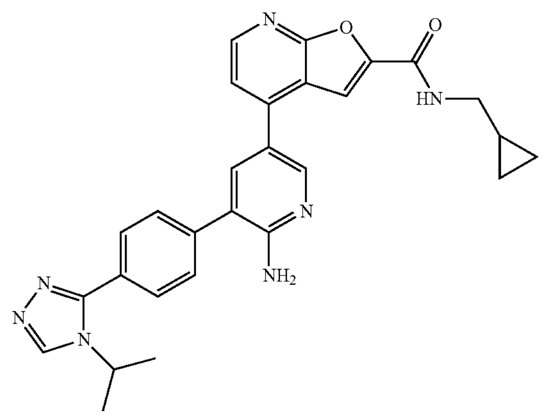 [SMILES: CC(C)n1cnnc1-c1ccc(-c2cc(-c3ccnc4oc(C(=O)NCC5CC5)cc34)cnc2N)cc1] |
| 393 | N-(1-((2-(2,6-dioxopiperidin-3-yl)-1,3-dioxoisoindolin-4-yl)oxy)-2-oxo-6,9,12-trioxa-3-azatetradecan-14-yl)-4-(5-(4-(2-oxopyrrolidin-1-yl)phenyl)pyridin-3-yl)-1H-pyrrolo[2,3-b]pyridine-2-carboxamide | 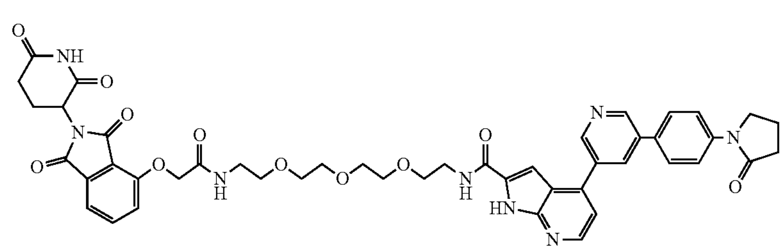 [SMILES: O=C(COc1cccc2c1C(=O)N(C1CCC(=O)NC1=O)C2=O)NCCOCCOCCOCCNC(=O)c1cc2c(-c3cncc(-c4ccc(N5CCCC5=O)cc4)c3)ccnc2[nH]1] |

-continued

| Example | Compound Name | Structure |
|---|---|---|
| 394 | 4-(5-(4-(4-(3,3-difluorocyclobutyl)-4H-1,2,4-triazol-3-yl)phenyl)pyridin-3-yl)-7-methyl-8,9-dihydropyrido[3',2':4,5]pyrrolo[1,2-a]pyrazin-6(7H)-one | 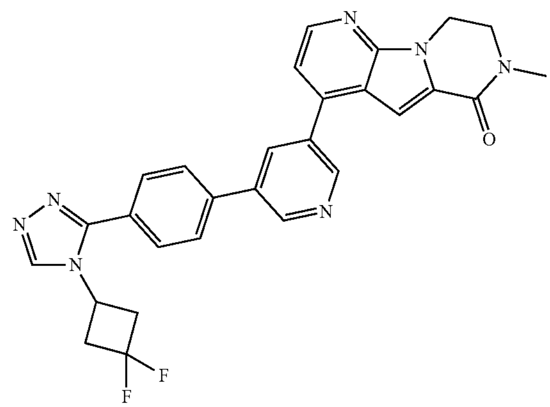 [SMILES: CN1CCn2c(cc3c(-c4cncc(-c5ccc(-c6nncn6C6CC(F)(F)C6)cc5)c4)ccnc32)C1=O] |
| 395 | N-(8-(2-((2-(2,6-dioxopiperidin-3-yl)-1,3-dioxoisoindolin-4-yl)oxy)acetamido)octyl)-4-(5-(4-(2-oxopyrrolidin-1-yl)phenyl)pyridin-3-yl)-1H-pyrrolo[2,3-b]pyridine-2-carboxamide | 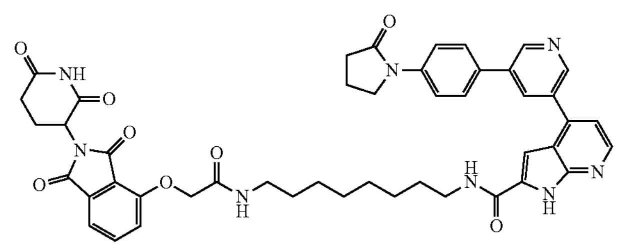 [SMILES: O=C(COc1cccc2c1C(=O)N(C1CCC(=O)NC1=O)C2=O)NCCCCCCCCNC(=O)c1cc2c(-c3cncc(-c4ccc(N5CCCC5=O)cc4)c3)ccnc2[nH]1] |
| 396 | 4-(5-(4-(4-isobutyl-4H-1,2,4-triazol-3-yl)phenyl)pyridin-3-yl)-N-(2-(pyridin-4-yl)ethyl)-1H-pyrrolo[2,3-b]pyridine-2-carboxamide | 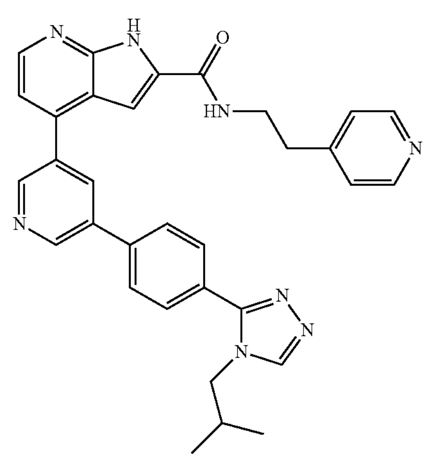 [SMILES: CC(C)Cn1cnnc1-c1ccc(-c2cncc(-c3ccnc4[nH]c(C(=O)NCCc5ccncc5)cc34)c2)cc1] |

| Example | Compound Name | Structure |
|---|---|---|
| 397 | 1-(4-(5-(2-((2S,4R)-2-(2-hydroxypropan-methylpyrrolidine-1-carbonyl)-1H-pyrrolo[2,3-b]pyridin-4-yl)pyridin-3-yl)phenyl)pyrrolidin-2-one | 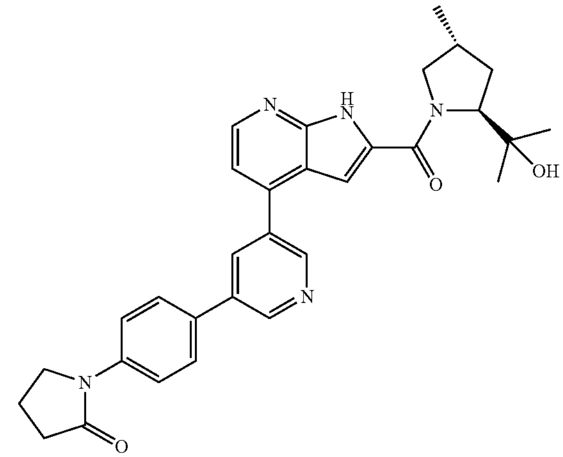 [SMILES: C[C@@H]1C[C@@H](C(C)(C)O)N(C(=O)c2cc3c(-c4cncc(-c5ccc(N6CCCC6=O)cc5)c4)ccnc3[nH]2)C1] |

Biochemical Assays

Example 398: ADP-Glo Biochemical Assay

Dilution series of the compounds were prepared in DMSO at 100 times the final assay concentration ($n_1=n_0/3$ in 10 points). The compounds were further diluted to three times the assay concentration in assay buffer (20 mM MOPS pH 7.2, 25 mM magnesium chloride, 0.005% Tween 20). 6 μL of the diluted compounds were added to a 384 well assay plate followed by 9 μL of a mix consisting of 4 nM PIP4K$_2$A (full length protein, SignalChem) and 100 μM PI(5)P diC8 (Tebu-Bio). Enzyme and compounds were pre-incubated at room temperature for 15 min.

Then 3 μL of a solution containing 60 μM ATP (Promega) in assay buffer was added to the wells containing compound and enzyme and mixing was performed by pipetting several times. The reaction was incubated at room temperature for 1 h. Then 18 μL of ADP-Glo™ Reagent (Promega) was added to stop the kinase reaction and deplete the unconsumed ATP, mixing was performed by pipetting several times. The plate was incubated at room temperature for 40 min before addition of 36 μL of Kinase Detection Reagent (Promega) to convert ADP to ATP and introduce luciferase and luciferin to detect ATP. The reaction was incubated at room temperature for 40 min before the luminescence was measured in a in a Victor 3V 1420 multilabel counter (Perkin Elmer).

Percent inhibition of the compounds as compared to dimethyl sulfoxide treated control samples was calculated. Compound concentration versus percent inhibition were fitted to generate $IC_{50}$ values. Results obtained with this assay are disclosed in Table 1 below.

Example 399: Assay Protocol—PIP4KtypeTA

GST tagged PIP4KtypeIIA and B enzymes were overexpressed in *E. Coli* and purified to >80% homogeneity. Phosphatidyl inositol-5-phosphate (PI5P, Cat. #850152, Avanti Polar Lipids Inc.) was used as the lipid substrate and phosphatidyl ethanolamine (DOPE 18:1, Cat. #850725, Avanti Polar Lipids Inc.) was used as the carrier lipid for assays. Ultrapure ATP and GTP was purchased from Bellbrooke Labs. ADP Glo reagents were obtained from Promega. Transcreener FI reagent was obtained from Bellbrooke labs.

Buffers:
1. HEPES buffer mix: 200 mM HEPES pH 7.4, 50 mM MgCl2, 0.05% v/v triton×100
2. HNE buffer: 20 mM HEPES, pH 7.4, 100 mM NaCl, 0.5 mM EGTA
3. H:E buffer: 30 mM HEPES, pH 7.4, 1 mM EGTA Enzyme preparation: GST-tagged PIP4KtypeIIA (5 uL, 1.43 mg/mL) was diluted (1:10) to 50 uL using HNE buffer. From the 1:10 diluted stock, a 6.4 uL aliquot was diluted further to 5 mL using HNE buffer to yield 5× enzyme stock (2.5 nM).

GST-tagged PIP4KtypeIIB (3.4 uL, 2.77 mg/mL) was diluted to 5 mL using HNE buffer to yield 5× enzyme stock (25 nM)

Lipid Preparation: In a 10 mL pyrex glass vial, 1ug of PI5P and 1ug of DOPE were suspended in 2.5 mL of HEPES buffer mix and 2.5 mL of H:E buffer. The contents were mixed and sonicated for 3 min to yield a translucent lipid stock.

Compound Preparation: Compounds were stored as 5 mM stocks in neat DMSO as room temperature in glass vials. 5 mM stocks were diluted to 2 mM and then serially diluted (3×) in neat DMSO in 96 well polypropylene plates. From the serially diluted stocks, 3 uL was delivered into 250 uL of 25% DMSO (in water) to generate 5× compound stocks. Typically, the highest compound conc. was 24 uM.

Example 400: PIP4KtypeIIA Inhibition Assay

The assay volume was kept at 25 uL. To each well of the reaction plate, 10 uL of lipid stock (1:1 ratio PI5P:DOPE) was delivered. This was followed by the addition of 5 uL of compound in 25% DMSO. Then, to each well, 5 uL of 2.5 nM (5×) typeIIA enzyme was delivered. The contents were mixed well and incubated for 1 h at 27 C. After 1 h, reaction was initiated by adding 5 uL of 50 uM ATP and the contents were mixed well with a multi-channel pipetteman. The final concentration of the reagents are as follows: 50 mM HEPES, pH 7.3, 10 mM MgCl$_2$, 20 mM NaCl, 0.01% v/v triton-X100, 5% DMSO, 10 uM ATP, 80 uM (2 ug) PI5P, 2 ug DOPE, and 0.5 nM PIP4KIIA. Typically, the highest conc. of compounds was 4.8 uM and the lowest conc. was 0.

After 1 hr, the reaction was quenched by adding 25 uL of ADP Glo reagent. The contents were incubated for 1 hr. Afterwards, 50 uL of kinase detection reagent was delivered. The contents were incubated for another hour. The luminescence was read using Molecular Devices Paradigm plate reader. Each plate had a "No inhibitor" control (max. activity, 4 wells) and a blank (background noise, 4 wells). The blanks were averaged and subtracted from all other wells. Using a calibration curve, RLU was converted to uM ADP (product). IC50 was calculated by plotting the residual activity (expressed as % No inhibitor control) vs. log [Inh. conc.]

Example 401: PIP4KtypeIIB Inhibition Assay

The assay volume was kept at 25 uL. To each well of the reaction plate, 10 uL of lipid stock (1:1 ratio PI5P:DOPE) was delivered. This was followed by the addition of 5 uL of compound in 25% DMSO. Then, to each well, 5 uL of 25 nM (5×) typeIIB enzyme was delivered. The contents were mixed well and incubated for 1 h at 27 C. After 1 h, reaction was initiated by adding 5 uL of 500 uM GTP and the contents were mixed well with a multi-channel pipetteman. The final concentration of the reagents are as follows: 50 mM HEPES, pH 7.3, 10 mM $MgCl_2$, 20 mM NaCl, 0.01% v/v triton-$X_{100}$, 5% DMSO, 100 uM GTP, 80 uM (2 ug) PI5P, 2 ug DOPE, and 5 nM PIP4KIIB Typically, the highest conc. of compounds was 4.8 uM and the lowest conc. was 0.

After 2 h, the reaction was quenched by adding 25 uL of transcreener FI reagent. The contents were incubated at RT for 1 h and the Fluorescence (Ex: 584 Em: 623) was read using Molecular Devices Paradigm plate reader. Each plate had a "No inhibitor" control (max. activity, 4 wells) and a blank (background noise, 4 wells). The blanks were averaged and subtracted from all other wells. Using a calibration curve, RFU was converted to uM GDP (product). IC50 was calculated by plotting the residual activity (expressed as % No inhibitor control) vs. log [Inh. conc.] Table 2 represents PI5P4K activity of compounds (Example No.) of the invention arranged in accordance with the inhibition of $PIP4K_2$ A kinase assay.

| Kinase Assay- PIP4K2 A $1 < IC_{50} \leq 5$ nM |
|---|
| 85 |
| 89 |
| 95 |

| Kinase Assay- PIP4K2 A $5 < IC_{50} \leq 100$ nM |
|---|
| 212 |
| 126 |
| 113 |
| 23 |
| 27 |
| 12 |
| 28 |
| 26 |
| 215 |
| 127 |
| 45 |
| 218 |
| 31 |
| 30 |
| 15 |
| 48 |
| 49 |
| 50 |
| 34 |
| 46 |
| 47 |
| 134 |
| 135 |
| 136 |
| 51 |
| 224 |
| 54 |
| 302 |
| 227 |
| 241 |
| 249 |
| 250 |
| 79 |
| 88 |
| 77 |
| 87 |
| 69 |
| 90 |
| 68 |
| 78 |
| 80 |
| 91 |
| 258 |
| 70 |
| 92 |
| 39 |
| 58 |
| 55 |
| 61 |
| 71 |
| 267 |
| 62 |
| 60 |
| 67 |
| 270 |
| 74 |
| 93 |
| 174 |
| 166 |
| 173 |
| 165 |
| 299 |
| 175 |
| 171 |
| 167 |
| 176 |
| 170 |
| 162 |
| 159 |
| 163 |
| 161 |
| 158 |
| 72 |
| 306 |
| 325 |
| 337 |
| 343 |
| 350 |
| 355 |
| 357 |
| 366 |
| 368 |
| 370 |
| 377 |
| 379 |
| 390 |
| 211 |
| 301 |
| 276 |

| Kinase Assay- PIP4K2 A $100 < IC_{50} \leq 1000$ nM |
|---|
| 19 |
| 20 |
| 21 |

| 401 -continued |
|---|
| 103 |
| 105 |
| 100 |
| 104 |
| 110 |
| 5 |
| 3 |
| 4 |
| 2 |
| 111 |
| 213 |
| 214 |
| 121 |
| 122 |
| 123 |
| 125 |
| 24 |
| 14 |
| 10 |
| 216 |
| 217 |
| 44 |
| 11 |
| 129 |
| 130 |
| 219 |
| 220 |
| 35 |
| 128 |
| 131 |
| 132 |
| 138 |
| 140 |
| 223 |
| 225 |
| 42 |
| 56 |
| 231 |
| 243 |
| 84 |
| 76 |
| 257 |
| 40 |
| 65 |
| 64 |
| 59 |
| 94 |
| 82 |
| 172 |
| 169 |
| 168 |
| 160 |
| 177 |
| 157 |
| 308 |
| 309 |
| 310 |
| 319 |
| 324 |
| 330 |
| 331 |
| 332 |
| 333 |
| 334 |
| 335 |
| 338 |
| 339 |
| 345 |
| 346 |
| 347 |
| 348 |
| 349 |
| 354 |
| 275 |
| 358 |
| 359 |
| 360 |
| 361 |
| 362 |

| 402 -continued |
|---|
| 363 |
| 369 |
| 371 |
| 373 |
| 374 |
| 375 |
| 378 |
| 381 |
| 382 |
| 383 |
| 384 |
| 385 |
| 387 |
| 388 |
| 392 |
| 397 |
| 210 |
| 230 |
| 386 |
| Kinase Assay- PIP4K2 A $1000 < IC_{50} \leq 2500$ nM |
| 13 |
| 8 |
| 102 |
| 106 |
| 107 |
| 112 |
| 101 |
| 6 |
| 109 |
| 193 |
| 194 |
| 191 |
| 192 |
| 188 |
| 189 |
| 124 |
| 25 |
| 36 |
| 41 |
| 268 |
| 83 |
| 307 |
| 311 |
| 312 |
| 313 |
| 314 |
| 315 |
| 316 |
| 318 |
| 320 |
| 322 |
| 323 |
| 326 |
| 341 |
| 342 |
| 365 |
| 372 |
| 376 |
| 380 |
| 391 |
| 393 |
| 395 |
| 396 |
| Kinase Assay- PIP4K2 A $2500 < IC_{50} \leq 5000$ nM |
| 7 |
| 108 |
| 190 |
| 187 |
| 37 |
| 164 |
| 327 |
| 328 |
| 329 |
| 344 |
| 367 |

| 394 Kinase Assay- PIP4K2 A (Sprint) IC$_{50}$ < 5000 nM |
| --- |
| 1 |
| 16 |
| 17 |
| 18 |
| 119 |
| 118 |
| 114 |
| 195 |
| 120 |
| 22 |
| 9 |
| 33 |
| 221 |
| 139 |
| 57 |
| 66 |
| 156 |
| 81 |
| 155 |
| 154 |
| 153 |
| 179 |
| 181 |
| 180 |
| 317 |
| 321 |
| 336 |
| 340 |
| 356 |
| 364 |
| 389 |

Table 3 represents PI5P4K activity of compounds (Example No.) of the invention arranged in accordance with the inhibition of ADP-glo kinase assay PIP4K 2A.

| ADP-glo kinase assay PIP4K 2A 1 < IC$_{50}$ ≤ 10 nM |
| --- |
| 125 |
| 89 |

| ADP-glo kinase assay PIP4K 2A 10 < IC$_{50}$ ≤ 100 nM |
| --- |
| 126 |
| 26 |
| 31 |
| 49 |
| 224 |
| 302 |
| 241 |
| 252 |
| 79 |
| 88 |
| 90 |
| 68 |
| 85 |
| 92 |
| 153 |
| 282 |
| 283 |
| 286 |
| 207 |
| 291 |
| 166 |
| 165 |
| 175 |
| 171 |
| 167 |
| 351 |
| 352 |
| 353 |
| 355 |

| ADP-glo kinase assay PIP4K 2A 100 < IC$_{50}$ ≤ 1000 nM |
| --- |
| 21 |
| 110 |
| 2 |
| 111 |
| 214 |
| 113 |
| 23 |
| 14 |
| 27 |
| 12 |
| 28 |
| 215 |
| 10 |
| 127 |
| 216 |
| 217 |
| 45 |
| 218 |
| 44 |
| 30 |
| 15 |
| 11 |
| 129 |
| 130 |
| 220 |
| 48 |
| 50 |
| 34 |
| 46 |
| 47 |
| 134 |
| 131 |
| 132 |
| 135 |
| 136 |
| 138 |
| 140 |
| 137 |
| 141 |
| 142 |
| 51 |
| 223 |
| 225 |
| 54 |
| 144 |
| 145 |
| 143 |
| 150 |
| 146 |
| 147 |
| 227 |
| 228 |
| 229 |
| 231 |
| 232 |
| 233 |
| 234 |
| 235 |
| 236 |
| 237 |
| 238 |
| 239 |
| 240 |
| 242 |
| 243 |
| 244 |
| 72 |
| 246 |
| 247 |
| 249 |
| 250 |
| 251 |
| 253 |
| 254 |
| 255 |
| 256 |

| |
|---|
| 84 |
| 77 |
| 87 |
| 257 |
| 78 |
| 80 |
| 91 |
| 258 |
| 70 |
| 260 |
| 261 |
| 264 |
| 39 |
| 55 |
| 61 |
| 71 |
| 267 |
| 62 |
| 60 |
| 269 |
| 67 |
| 270 |
| 74 |
| 284 |
| 199 |
| 198 |
| 287 |
| 288 |
| 203 |
| 201 |
| 204 |
| 200 |
| 290 |
| 197(S) |
| 197(R) |
| 197 |
| 196(S) |
| 196(R) |
| 196 |
| 292 |
| 293 |
| 294 |
| 174 |
| 295 |
| 296 |
| 173 |
| 298 |
| 160 |
| 176 |
| 177 |
| 170 |
| 157 |
| 162 |
| 159 |
| 163 |
| 161 |
| 158 |
| 345 |
| 346 |
| 354 |
| 275 |
| 384 |
| 276 |
| ADP-glo kinase assay PIP4K 2A 1000 < IC$_{50}$ ≤ 2500 nM |
| 20 |
| 123 |
| 24 |
| 219 |
| 35 |
| 128 |
| 133 |
| 56 |
| 149 |
| 226 |
| 248 |
| 69 |
| 259 |
| 263 |
| 65 |
| 59 |
| 81 |
| 281 |
| 297 |
| 172 |
| 169 |
| ADP-glo kinase assay PIP4K 2A 2500 < IC$_{50}$ ≤ 5000 nM |
| 13 |
| 5 |
| 4 |
| 109 |
| 213 |
| 25 |
| 42 |
| 266 |
| 76 |
| 262 |
| 58 |
| 40 |
| 285 |
| 289 |
| 168 |
| ADP-glo kinase assay PIP4K 2A IC$_{50}$ > 5000 nM |
| 1 |
| 7 |
| 6 |
| 118 |
| 114 |
| 193 |
| 194 |
| 195 |
| 120 |
| 190 |
| 191 |
| 187 |
| 188 |
| 124 |
| 22 |
| 9 |
| 33 |
| 36 |
| 37 |
| 221 |
| 139 |
| 222 |
| 41 |
| 57 |
| 245 |
| 268 |
| 83 |
| 66 |
| 64 |
| 206 |
| 202 |
| 151 |
| 209 |
| 208 |
| 205 |
| 179 |
| 181 |
| 180 |
| 164 |

Table 4 represents PI5P4K activity of compounds (Example No.) of the invention arranged in accordance with the inhibition of Trans-FI P kinase assays: PIP4K$_2$B.

Trans-FI P kinase assays:
PIP4K2B 1 < IC$_{50}$ ≤ 10 nM 88
90
85
89
306
308
357
358
367
368
370
374
377
385
387
392
211

Trans-FI P kinase assays:
PIP4K2B 10 < IC$_{50}$ ≤ 100 nM 126
127
45
48
49
50
46
47
134
131
132
135
136
138
137
141
51
224
144
149
143
226
150
146
147
302
228
232
233
234
236
237
238
239
240
241
242
244
245
246
247
251
252
255
256
79
68
80
91
92
261
264
71
283
199
198
201
207
200
291
165
298
175
171
167
162
163
161
309
312
314
316
317
319
322
324
328
329
330
331
338
345
351
352
353
354
360
361
362
363
365
366
369
371
372
373
375
376
378
379
383
384
390
391
396
301
276

Trans-FI P kinase assays:
PIP4K2B 100 < IC$_{50}$ ≤ 1000 nM 20
21
110
2
111
214
121
113
23
14
27
12
28
26
215
10
216
217
218
44
31
30
15
11
129
130
219

| 409 -continued |
|---|
| 220 |
| 34 |
| 35 |
| 128 |
| 140 |
| 133 |
| 142 |
| 223 |
| 225 |
| 54 |
| 145 |
| 227 |
| 229 |
| 235 |
| 243 |
| 72 |
| 248 |
| 249 |
| 250 |
| 253 |
| 254 |
| 84 |
| 77 |
| 87 |
| 69 |
| 257 |
| 78 |
| 258 |
| 70 |
| 260 |
| 262 |
| 39 |
| 58 |
| 55 |
| 61 |
| 267 |
| 60 |
| 269 |
| 59 |
| 67 |
| 270 |
| 74 |
| 282 |
| 284 |
| 286 |
| 287 |
| 288 |
| 290 |
| 197 |
| 196(S) |
| 196(R) |
| 205 |
| 292 |
| 293 |
| 294 |
| 174 |
| 296 |
| 166 |
| 173 |
| 169 |
| 160 |
| 177 |
| 170 |
| 157 |
| 159 |
| 158 |
| 307 |
| 310 |
| 311 |
| 313 |
| 315 |
| 318 |
| 320 |
| 321 |
| 323 |
| 325 |
| 326 |
| 327 |
| 332 |

| 410 -continued |
|---|
| 333 |
| 334 |
| 335 |
| 337 |
| 339 |
| 342 |
| 343 |
| 346 |
| 347 |
| 348 |
| 349 |
| 350 |
| 355 |
| 356 |
| 359 |
| 381 |
| 382 |
| 388 |
| 389 |
| 393 |
| 394 |
| 395 |
| 397 |
| 210 |
| 230 |
| 386 |
| Trans-FI P kinase assays: PIP4K2B 1000 < IC$_{50}$ ≤ 2500 nM |
| 13 |
| 5 |
| 109 |
| 213 |
| 191 |
| 188 |
| 122 |
| 24 |
| 221 |
| 42 |
| 231 |
| 266 |
| 76 |
| 259 |
| 263 |
| 40 |
| 65 |
| 268 |
| 62 |
| 281 |
| 209 |
| 289 |
| 197(S) |
| 197(R) |
| 295 |
| 172 |
| 176 |
| 341 |
| 364 |
| Trans-FI P kinase assays: PIP4K2B 2500 < IC$_{50}$ ≤ 5000 nM |
| 4 |
| 193 |
| 194 |
| 195 |
| 125 |
| 36 |
| 139 |
| 222 |
| 56 |
| 285 |
| 203 |
| 168 |
| 164 |
| 275 |
| 380 |

-continued

Trans-FI P kinase assays:
PIP4K2B IC$_{50}$ > 5000 nM 1
7
6
118
120
190
187
123
124
22
25
9
33
37
41
57
66
64
206
202
151
208
205
204
179
181
180
297
336
340
344

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A compound of Formula (I):

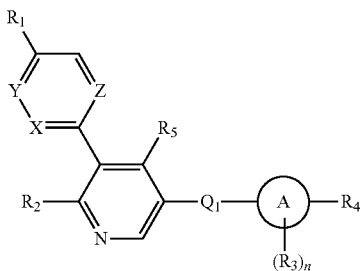

or a pharmaceutically acceptable salt, stereoisomer, or tautomer thereof,
wherein:
X, Y, and Z are independently CH, C(C$_{1-6}$ alkyl) or N, wherein at least one of X, Y, and Z is CH;
Ring A is heteroaryl;
R$_1$ is pyrrolidinyl optionally substituted with one or more R$_5$;
R$_2$ is —H, —NH$_2$, or C$_{1-6}$ alkyl;
Q$_1$ is a bond;
each R$_3$ is independently, at each occurrence, —H, halogen, oxo, C$_{1-6}$ alkyl, C$_{3-6}$ cycloalkyl, heterocyclyl, —OR$_6$, —NR$_6$R$_7$, —CN, —C(O)NR$_6$R$_7$, —N(R$_6$)C(O)R$_7$, —C(O)OR$_6$, —S(O)$_2$R$_6$, or —S(O)$_2$N(R$_6$)(R$_7$), wherein the C$_{1-6}$ alkyl or C$_{3-6}$ cycloalkyl is optionally substituted with one or more R$_8$, or
two R$_3$, when on adjacent atoms, with the atoms to which they are attached, form a C$_{4-8}$ cycloalkyl, C$_5$-C$_8$ spirocycloalkyl, spiroheterocycloalkyl, or heterocyclyl, wherein the heterocyclyl, C$_5$-C$_8$ spirocycloalkyl, spiroheterocycloalkyl, or C$_{4-8}$ cycloalkyl is optionally substituted with one or more R$_8$;
R$_4$ is —H, C$_3$-C$_8$ cycloalkyl, C$_5$-C$_8$ spirocycloalkyl, spiroheterocycloalkyl, aryl, heterocyclyl, heteroaryl, —C(O)N(R$_{10}$)—(C$_0$-C$_6$ alkylene)-R$_9$, —C(O)N(R$_{10}$)—R$_9$, —C(O)—R$_9$,—N(R$_{10}$)—(C$_0$-C$_6$ alkylene)-R$_9$, —(C$_0$-C$_6$ alkylene)-N(R$_{10}$)C(O)—(C$_0$-C$_6$ alkylene)-R$_9$,—N(R$_{10}$)C(O)—(C$_0$-C$_6$ alkylene)-R$_9$—N(R$_{10}$)C(O)—(C$_0$-C$_6$ alkylene)-, —N(R$_{10}$)C(O)—R$_9$, —(CH$_2$)$_q$—R$_9$, or —(CH$_2$)$_r$—N(R$_{10}$)C(O)—(CH$_2$)$_s$—R$_9$, wherein the C$_3$-C$_8$ cycloalkyl, C$_5$-C$_8$ spirocycloalkyl, spiroheterocycloalkyl, heterocyclyl, aryl, or heteroaryl is optionally substituted with one or more R$_9$;
R$_5$ is —H, halogen, —OH, C$_{1-6}$ alkyl, or C$_{1-6}$ alkoxy, wherein the C$_{1-6}$ alkyl or C$_{1-6}$ alkoxy is optionally substituted with R$_{10}$;
R$_6$ is independently, at each occurrence, —H or C$_{1-6}$ alkyl;
R$_7$ is independently, at each occurrence, C$_{1-6}$ alkyl, aryl, or heteroaryl, wherein the C$_{1-6}$ alkyl, aryl, or heteroaryl is optionally substituted with one or more R$_5$, or
R$_6$ and R$_7$ when taken together with the atoms to which they are each attached form a heterocycle, wherein the heterocycle is optionally substituted with one or more R$_5$;
R$_8$ is independently, at each occurrence, —CN, halogen, —OH, —NH$_2$, —NO$_2$, —C(O)NH$_2$,—C(O)OH, oxo, C$_{1-6}$ alkyl, C$_{1-6}$ alkoxy, aryl, C$_{3-6}$cycloalkyl, C$_5$-C$_8$ spirocycloalkyl, spiroheterocycloalkyl, heterocyclyl, or heteroaryl, wherein the C$_{1-6}$ alkyl, C$_{1-6}$ alkoxy, C$_{3-6}$ cycloalkyl, C$_5$-C$_8$ spirocycloalkyl, spiroheterocycloalkyl, aryl, heterocyclyl, or heteroaryl is optionally substituted with one or more R$_9$;
R$_9$ is independently, at each occurrence, —H, halogen, C$_{1-6}$ alkyl, C$_{2-6}$ alkenyl, C$_{2-6}$ alkynyl, C$_{3-8}$ cycloalkyl, heterocyclyl, aryl, heteroaryl, —OR$_{11}$, —C(O)O(R$_{11}$), —C(O)N(R$_{11}$)(R$_{12}$), —N(R$_{11}$)(R$_{12}$), —CN, —N(R$_{11}$)C(O)OR$_{12}$, —N(R$_{11}$)C(O)R$_{12}$, —C(O)—V—N(R$_{11}$)—F, —N(R$_{11}$)C(O)—V—N(R$_{12}$)—F, —C(O)—Ar, or —N(R$_{11}$)C(O)—Ar, wherein the C$_{1-6}$ alkyl, C$_{2-6}$ alkenyl, C$_{2-6}$ alkynyl, C$_{3-8}$ cycloalkyl, heterocyclyl, heteroaryl, or aryl is optionally substituted with one or more —OR$_{11}$,—C(O)N(R$_{11}$)(R$_{12}$), —N(R$_1$ 1)(R$_{12}$), —CN, —N(R$_1$ 1)C(O)OR$_{12}$, —N(R$_1$ 1)C(O)R$_{12}$, —C(O)—V—N(R$_1$ 1)—F, —N(R$_1$ 1)C(O)—V—N(R$_{12}$)—F, —C(O)—Ar, —N(R$_1$ 1)C(O)—V—O(R$_{12}$), —O-Q$_2$-N(R$_{11}$)C(O)—V—O(R$_{12}$), or —N(R$_{11}$)C(O)—Ar;
each Ar is independently aryl substituted with —NR$_{11}$R$_{12}$, —C(O)-Q$_2$-N(R$_{11}$)—F or —N(R$_{11}$)C(O)-Q$_2$-N(R$_{12}$)—F;
each Q$_2$ is independently —CH═CH(CH$_2$)$_m$—, —(CH$_2$)$_m$—, or —(CH$_2$CH$_2$O)$_o$—CH$_2$CH$_2$—;
each V is independently —CH═CH(CH$_2$)$_m$—, —(CH$_2$)$_m$—, or —(CH$_2$CH$_2$O)$_o$—CH$_2$CH$_2$—;
each F is independently —H, C$_{1-6}$ alkyl, or —C(O)-Q$_2$-N(R$_{11}$)(R$_{12}$);

R₁₀ is independently, at each occurrence, —H, halogen, —CN, —OH, —NO₂, oxo, C₁₋₆ alkyl, C₁₋₆ alkoxy, C₃₋₈ cycloalkyl, heterocyclyl, heteroaryl, or aryl;

R₁₁ and R₁₂ are independently, at each occurrence, —H, C₁₋₆ alkyl, C₂₋₆ alkenyl, C₂₋₆ alkynyl, C₃₋₈ cycloalkyl, heterocyclyl, aryl, or heteroaryl, wherein the C₁₋₆ alkyl, C₂₋₆ alkenyl, C₂₋₆ alkynyl, C₃₋₈ cycloalkyl, heterocyclyl, heteroaryl, or aryl is optionally substituted with one or more —H, halogen, —CN, —OH, —NO₂, oxo, C₁₋₆ alkyl, C₁₋₆ alkoxy, C₃₋₈ cycloalkyl, heterocyclyl, heteroaryl, aryl, —N(R₁₃)(R₁₄), —C(O)R₁₃, —N(R₁₃)C(O)R₁₄, —C(O)N(R₁₃)(R₁₄), or —C(O)OR₁₃;

R₁₃ and R₁₄ are independently, at each occurrence, —H, C₁₋₆ alkyl, C₁₋₆ alkoxy, C₂₋₆ alkenyl, C₂₋₆ alkynyl, C₃₋₈ cycloalkyl, heterocyclyl, aryl, or heteroaryl, wherein the C₁₋₆ alkyl, C₂₋₆ alkenyl, C₂₋₆ alkynyl, C₃₋₈ cycloalkyl, heterocyclyl, heteroaryl, or aryl is optionally substituted with one or more H, halogen, —CN, —OH, —NH₂, —NO₂, oxo, C₁₋₆ alkyl, C₁₋₆ alkoxy, C₃₋₈ cycloalkyl, heterocyclyl, heteroaryl, or aryl;

each m is independently 1-4;
o is 1-3;
n is 1, 2, or 3;
q is 1-4;
r is 0-4; and
s is 0-4;
provided that:
(1) A is not oxadiazolyl,
(2) when A is thiophenyl, or 1,3,4-oxadiazolyl, both R₃ and R₄ are not simultaneously H; and
(3) when R₃ is —N(R₆)(R₇) and R₆ is H, R₇ is not methyl.

2. The compound of claim 1 selected from the group consisting of:

1-(2'-amino-5'-(imidazo[1,2-a]pyridin-5-yl)[2,3'-bipyridin]-5-yl)pyrrolidin-2-one,
1-(2'-amino-5'-(benzo[d]thiazol-7-yl)[2,3'-bipyridin]-5-yl)pyrrolidin-2-one,
1-(2'-amino-5'-(thieno[2,3-b]pyridin-3-yl)-[2,3'-bipyridin]-5-yl)pyrrolidin-2-one,
1-(4-(5-(5-chloro-1H-pyrrolo[2,3-b]pyridin-3-yl)pyridin-3-yl)phenyl)pyrrolidin-2-one,
1-(4-(5-(1H-pyrrolo[2,3-b]pyridin-3-yl)pyridin-3-yl)phenyl)pyrrolidin-2-one,
1-(2'-amino-5'-(5-chloro-1H-pyrrolo[2,3-b]pyridin-3-yl)-[2,3'-bipyridin]-5-yl)pyrrolidin-2-one,
1-(4-(5-(2H-pyrazolo[3,4-b]pyridin-4-yl)pyridin-3-yl)phenyl)pyrrolidin-2-one,
4-(5-(4-(2-oxopyrrolidin-1-yl)phenyl)pyridin-3-yl)-8,9-dihydropyrido[3',2':4,5]pyrrolo[1,2-a]pyrazin-6(7H)-one,
1-(4-(5-(1-methyl-1H-pyrazolo[3,4-b]pyridin-4-yl)pyridin-3-yl)phenyl)pyrrolidin-2-one,
1-(4-(5-(1-(2-hydroxyethyl)-1H-pyrazolo[3,4-b]pyridin-4-yl)pyridin-3-yl)phenyl)pyrrolidin-2-one,
1-(4-(5-(5-methyl-1H-pyrrolo[2,3-b]pyridin-3-yl)pyridin-3-yl)phenyl)pyrrolidin-2-one,
1-(4-(5-(7H-pyrrolo[2,3-d]pyrimidin-5-yl)pyridin-3-yl)phenyl)pyrrolidin-2-one,
1-(4-(5-(2H-pyrazolo[4,3-b]pyridin-7-yl)pyridin-3-yl)phenyl)pyrrolidin-2-one,
1-(4-(5-(5-(1-hydroxyethyl)-1H-pyrrolo[2,3-b]pyridin-3-yl)pyridin-3-yl)phenyl)pyrrolidin-2-one,
N-methyl-4-(5-(4-(2-oxopyrrolidin-1-yl)phenyl)pyridin-3-yl)furo[2,3-b]pyridine-2-carboxamide,
N,N-dimethyl-4-(5-(4-(2-oxopyrrolidin-1-yl)phenyl)pyridin-3-yl)furo[2,3-b]pyridine-2-carboxamide,
1-(4-(5-(5-methoxy-1H-pyrrolo[2,3-b]pyridin-4-yl)pyridin-3-yl)phenyl)pyrrolidin-2-one,
1-(4-(5-(5-methyl-1H-pyrrolo[2,3-b]pyridin-4-yl)pyridin-3-yl)phenyl)pyrrolidin-2-one,
7-methyl-4-(5-(4-(2-oxopyrrolidin-1-yl)phenyl)pyridin-3-yl)-8,9-dihydropyrido[3',2':4,5]pyrrolo[1,2-a]pyrazin-6(7H)-one,
7-(cyclopropylmethyl)-4-(5-(4-(2-oxopyrrolidin-1-yl)phenyl)pyridin-3-yl)-8,9-dihydropyrido[3',2':4,5]pyrrolo[1,2-a]pyrazin-6(7H)-one,
3-(5-(4-(2-oxopyrrolidin-1-yl)phenyl)pyridin-3-yl)-1H-pyrrolo[2,3-b]pyridine-2-carbonitrile,
1-(4-(5-(2H-pyrazolo[3,4-d]pyrimidin-4-yl)pyridin-3-yl)phenyl)pyrrolidin-2-one,
1-(4-([3,4'-bipyridin]-5-yl)phenyl)pyrrolidin-2-one,
1-(4-(5-(6-chloro-2H-pyrazolo[3,4-b]pyridin-4-yl)pyridin-3-yl)phenyl)pyrrolidin-2-one,
1-(4-(5-(6-methyl-2H-pyrazolo[3,4-d]pyrimidin-4-yl)pyridin-3-yl)phenyl)pyrrolidin-2-one,
N-methyl-N-(5-(4-(2-oxopyrrolidin-1-yl)phenyl)-[3,4'-bipyridin]-2'-yl)acetamide,
4-(5-(4-(2-oxopyrrolidin-1-yl)phenyl)pyridin-3-yl)-1,3-dihydro-2H-pyrrolo[2,3-b]pyridin-2-one,
1-(4-(5-(1-methyl-5-(piperazin-1-yl)-1H-pyrrolo[2,3-b]pyridin-3-yl)pyridin-3-yl)phenyl)pyrrolidin-2-one,
methyl 4-(5-(4-(2-oxopyrrolidin-1-yl)phenyl)pyridin-3-yl)-1H-pyrrolo[2,3-b]pyridine-2-carboxylate,
N,N-dimethyl-3-(5-(4-(2-oxopyrrolidin-1-yl)phenyl)pyridin-3-yl)-2H-pyrazolo[3,4-b]pyridine-5-carboxamide,
N-(2-methoxyethyl)-4-(5-(4-(2-oxopyrrolidin-1-yl)phenyl)pyridin-3-yl)-1H-pyrrolo[2,3-b]pyridine-2-carboxamide,
1-(4-(5-(2-(morpholine-4-carbonyl)-1H-pyrrolo[2,3-b]pyridin-4-yl)pyridin-3-yl)phenyl)pyrrolidin-2-one,
N,N,1-trimethyl-3-(5-(4-(2-oxopyrrolidin-1-yl)phenyl)pyridin-3-yl)-1H-pyrazolo[3,4-b]pyridine-5-carboxamide,
N-benzyl-4-(5-(4-(2-oxopyrrolidin-1-yl)phenyl)pyridin-3-yl)-1H-pyrrolo[2,3-b]pyridine-2-carboxamide,
4-(5-(4-(2-oxopyrrolidin-1-yl)phenyl)pyridin-3-yl)-N-(pyridin-4-ylmethyl)-1H-pyrrolo[2,3-b]pyridine-2-carboxamide,
N-isobutyl-4-(5-(4-(2-oxopyrrolidin-1-yl)phenyl)pyridin-3-yl)-1H-pyrrolo[2,3-b]pyridine-2-carboxamide,
1-(4-(5-(2-(pyrrolidine-1-carbonyl)-1H-pyrrolo[2,3-b]pyridin-4-yl)pyridin-3-yl)phenyl)pyrrolidin-2-one,
4-(5-(4-(2-oxopyrrolidin-1-yl)phenyl)pyridin-3-yl)-N-phenethyl-1H-pyrrolo[2,3-b]pyridine-2-carboxamide,
4-(5-(4-(2-oxopyrrolidin-1-yl)phenyl)pyridin-3-yl)-N-(2-(pyridin-3-phenyl)-1H-pyrrolo[2,3-b]pyridine-2-carboxamide,
4-(5-(4-(2-oxopyrrolidin-1-yl)phenyl)pyridin-3-yl)-N-(pyridin-3-ylmethyl)-1H-pyrrolo[2,3-b]pyridine-2-carboxamide,
4-(5-(4-(2-oxopyrrolidin-1-yl)phenyl)pyridin-3-yl)-N-(pyridin-2-ylmethyl)-1H-pyrrolo[2,3-b]pyridine-2-carboxamide,
N-methyl-4-(5-(4-(2-oxopyrrolidin-1-yl)phenyl)pyridin-3-yl)-1H-pyrrolo[2,3-b]pyridine-2-carboxamide,
N,N-dimethyl-4-(5-(4-(2-oxopyrrolidin-1-yl)phenyl)pyridin-3-yl)-1H-pyrrolo[2,3-b]pyridine-2-carboxamide,
N-cyclopropyl-4-(5-(4-(2-oxopyrrolidin-1-yl)phenyl)pyridin-3-yl)-1H-pyrrolo[2,3-b]pyridine-2-carboxamide, 1,6-dimethyl-3-(5-(4-(2-oxopyrrolidin-1-yl)phenyl)pyridin-3-yl)-1,6-dihydro-7H-pyrrolo[2,3-c]pyridin-7-one,
N-(2-(1H-imidazol-2-yl)ethyl)-4-(5-(4-(pyrrolidin-1-yl)phenyl)pyridin-3-yl)-1H-pyrrolo[2,3-b]pyridine-2-carboxamide,
N-(benzo[d]oxazol-2-ylmethyl)-4-(5-(4-(2-oxopyrrolidin-1-yl)phenyl)pyridin-3-yl)-1H-pyrrolo[2,3-b]pyridine-2-carboxamide,
2-isopropyl-N,N-dimethyl-3-(5-(4-(2-oxopyrrolidin-1-yl)phenyl)pyridin-3-yl)-1H-pyrrolo[2,3-b]pyridine-5-carboxamide,
2-isopropyl-N,N,1-trimethyl-3-(5-(4-(2-oxopyrrolidin-1-yl)phenyl)pyridin-3-yl)-1H-pyrrolo[2,3-b]pyridine-5-carboxamide,
4-(5-(4-(2-oxopyrrolidin-1-yl)phenyl)pyridin-3-yl)-N-(2-(pyridin-2-yl)ethyl)-1H-pyrrolo[2,3-b]pyridine-2-carboxamide,
4-(5-(4-(2-oxopyrrolidin-1-yl)phenyl)pyridin-3-yl)-N-(2-(pyridin-4-yl)ethyl)-1H-pyrrolo[2,3-b]pyridine-2-carboxamide,
methyl 4-(5-(2-oxopyrrolidin-1-yl)[2,3-b]pyridinyl-5'-yl)-1H-pyrrolo[2,3-b]pyridine-2-carboxylate,
N,N,1,2-tetramethyl-3-(5-(4-(2-oxopyrrolidin-1-yl)phenyl)pyridin-3-yl)-1H-pyrrolo[2,3-b]pyridine-5-carboxamide,
N,N,2-trimethyl-3-(5-(4-(2-oxopyrrolidin-1-yl)phenyl)pyridin-3-yl)-1H-pyrrolo[2,3-b]pyridine-5-carboxamide,
N-(2-(2H-tetrazol-5-yl)ethyl)-4-(5-(4-(2-oxopyrrolidin-1-yl)phenyl)pyridin-3-yl)-1H-pyrrolo[2,3-b]pyridine-2-carboxamide,
2-cyclopropyl-N,N-dimethyl-3-(5-(4-(2-oxopyrrolidin-1-yl)phenyl)pyridin-3-yl)-1H-pyrrolo[2,3-b]pyridine-5-carboxamide,
1-(4-(5-(1H-pyrrolo[3,2-b]pyridin-1-yl)pyridin-3-yl)phenyl)pyrrolidin-2-one,
N,N-dimethyl-1-(5-(4-(2-oxopyrrolidin-1-yl)phenyl)pyridin-3-yl)-1H-pyrrolo[3,2-b]pyridine-6-carboxamide,
4-(5-(4-(2-oxopyrrolidin-1-yl)phenyl)pyridin-3-yl)-N-(2-(pyrazin-2-yl)ethyl)-1H-pyrrolo[2,3-b]pyridine-2-carboxamide,
4-(5-(4-(2-oxopyrrolidin-1-yl)phenyl)pyridin-3-yl)-N-(2-(thiazol-2-yl)ethyl)-1H-pyrrolo[2,3-b]pyridine-2-carboxamide,
1-(4-(6-amino-[3,4'-bipyridin]-5-yl)phenyl)pyrrolidin-2-one,
N-(cyclopropylmethyl)-4-(5-(4-(2-oxopyrrolidin-1-yl)phenyl)pyridin-3-yl)furo[2,3-b]pyridine-2-carboxamide,
4-(6-amino-5-(4-(2-oxopyrrolidin-1-yl)phenyl)pyridin-3-yl)-7-(cyclopropylmethyl)-8,9-dihydropyrido[3',2':4,5]pyrrolo[1,2-a]pyrazin-6(7H)-one,
1-methyl-4-(5-(4-(2-oxopyrrolidin-1-yl)phenyl)pyridin-3-yl)-1,3-dihydro-2H-pyrrolo[2,3-b]pyridin-2-one,
1-(1-methyl-3-(5-(4-(2-oxopyrrolidin-1-yl)phenyl)pyridin-3-yl)-1H-pyrrolo[2,3-b]pyridin-5-yl)pyrrolidin-2-one,
1-(4-(2-amino-5-(1-methyl-1H-pyrrolo[2,3-b]pyridin-3-yl)pyridin-3-yl)phenyl)pyrrolidin-2-one,
4-(6-amino-5-(4-(2-oxopyrrolidin-1-yl)phenyl)pyridin-3-yl)-N-(2-methoxyethyl)furo[2,3-b]pyridine-2-carboxamide,
1-(4-(5-(6-methoxy-2H-pyrazolo[3,4-b]pyridin-4-yl)pyridin-3-yl)phenyl)pyrrolidin-2-one,
4-(6-amino-5-(4-(2-oxopyrrolidin-1-yl)phenyl)pyridin-3-yl)-N-methylfuro[2,3-b]pyridine-2-carboxamide,
4-(6-amino-5-(4-(2-oxopyrrolidin-1-yl)phenyl)pyridin-3-yl)-N-(cyclopropylmethyl)furo[2,3-b]pyridine-2-carboxamide,
4-(5-(4-(2-oxopyrrolidin-1-yl)phenyl)pyridin-3-yl)-5,6-dihydro-7H-pyrrolo[3,4-b]pyridin-7-one,
N-(2-methoxyethyl)-4-(5-(4-(2-oxopyrrolidin-1-yl)phenyl)pyridin-3-yl)furo[2,3-b]pyridine-2-carboxamide,
1-(4-(2-amino-5-(1-methyl-5-(2-oxopyrrolidin-1-yl)-1H-pyrrolo[2,3-b]pyridin-3-yl)pyridin-3-yl)phenyl)pyrrolidin-2-one,
1-(4-(2-amino-5-(7-methoxy-2H-pyrazolo[3,4-c]pyridin-4-yl)pyridin-3-yl)phenyl)pyrrolidin-2-one,
N,1,6-trimethyl-7-oxo-3-(5-(4-(2-oxopyrrolidin-1-yl)phenyl)pyridin-3-yl)-6,7-dihydro-1H-pyrrolo[2,3-c]pyridine-5-carboxamide,
N,N,1,6-tetramethyl-7-oxo-3-(5-(4-(2-oxopyrrolidin-1-yl)phenyl)pyridin-3-yl)-6,7-dihydro-1H-pyrrolo[2,3-c]pyridine-5-carboxamide,
N-(2-(1H-pyrrol-2-yl)ethyl)-4-(5-(4-(2-oxopyrrolidin-1-yl)phenyl)pyridin-3-yl)-1H-pyrrolo[2,3-b]pyridine-2-carboxamide,
2-cyclopropyl-N,N,1-trimethyl-3-(5-(4-(2-oxopyrrolidin-1-yl)phenyl)pyridin-3-yl)-1H-pyrrolo[2,3-b]pyridine-5-carboxamide,
1,6-dimethyl-7-oxo-3-(5-(4-(2-oxopyrrolidin-1-yl)phenyl)pyridin-3-yl)-6,7-dihydro-1H-pyrrolo[2,3-c]pyridine-5-carboxamide,
N,N,1-trimethyl-3-(5-(4-(2-oxopyrrolidin-1-yl)phenyl)pyridin-3-yl)-1H-pyrrolo[2,3-b]pyridine-5-sulfonamide,
1-(4-(5-(1-methyl-1H-pyrrolo[2,3-b]pyridin-3-yl)pyridin-3-yl)phenyl)pyrrolidin-2-one,
1-(4-(5-(1H-pyrrolo[2,3-b]pyridin-4-yl)pyridin-3-yl)phenyl)pyrrolidin-2-one,
1-(4-(5-(2,3-dihydro-[1,4]dioxino[2,3-b]pyridin-8-yl)pyridin-3-yl)phenyl)pyrrolidin-2-one,
N,N,1-trimethyl-3-(5-(4-(2-oxopyrrolidin-1-yl)phenyl)pyridin-3-yl)-1H-pyrrolo[2,3-b]pyridine-5-carboxamide,
N-methyl-3-(5-(4-(2-oxopyrrolidin-1-yl)phenyl)pyridin-3-yl)-1H-pyrrolo[2,3-b]pyridine-5-carboxamide,
1-(4-(5-(6-cyclopropyl-2H-pyrazolo[3,4-b]pyridin-4-yl)pyridin-3-yl)phenyl)pyrrolidin-2-one,
1-(4-(4-(methoxymethyl)[3,4-b]pyridinyl-5-yl)phenyl)pyrrolidin-2-one,
1-(4-(5-(5-(1-hydroxyethyl)-1-methyl-1H-pyrrolo[2,3-b]pyridin-3-yl)pyridin-3-yl)phenyl)pyrrolidin-2-one,
N,1-dimethyl-3-(5-(4-(2-oxopyrrolidin-1-yl)phenyl)pyridin-3-yl)-1H-pyrrolo[2,3-b]pyridine-5-carboxamide,
N,N-dimethyl-3-(5-(4-(2-oxopyrrolidin-1-yl)phenyl)pyridin-3-yl)-1H-pyrrolo[2,3-b]pyridine-5-carboxamide,
1-(4-(5-(5-ethoxy-1H-pyrrolo[2,3-b]pyridin-4-yl)pyridin-3-yl)phenyl)pyrrolidin-2-one,
1-(4-(5-(7-methoxy-2H-pyrazolo[3,4-c]pyridin-4-yl)pyridin-3-yl)phenyl)pyrrolidin-2-one,
4-(6-amino-5-(4-(2-oxopyrrolidin-1-yl)phenyl)pyridin-3-yl)-5,6-dihydro-7H-pyrrolo[3,4-b]pyridin-7-one,
methyl 4-(6-amino-5-(4-(2-oxopyrrolidin-1-yl)phenyl)pyridin-3-yl)-1H-pyrrolo[2,3-b]pyridine-2-carboxylate,
1-(4-(4-methyl-[3,4'-bipyridin]-5-yl)phenyl)pyrrolidin-2-one,
1-(4-(2-amino-5-(5-(1-hydroxyethyl)-1-methyl-1H-pyrrolo[2,3-b]pyridin-3-yl)pyridin-3-yl)phenyl)pyrrolidin-2-one, 4-(6-amino-5-(4-(2-oxopyrrolidin-1-yl)phenyl)pyridin-3-yl)-N-(oxetan-3-yl)furo[2,3-b]pyridine-2-carboxamide,
1-(4-([3,4'-bipyridin]-5-yl)-3-methylphenyl)pyrrolidin-2-one,
1-(4-(5-(7-methyl-7H-pyrrolo[2,3-d]pyrimidin-5-yl)pyridin-3-yl)phenyl)pyrrolidin-2-one,
1-(4-(6-methyl-[3,4'-bipyridin]-5-yl)phenyl)pyrrolidin-2-one,
1-[4-[5-(7-methylpyrrolo[2,3-d]pyrimidin-5-yl)-3-pyridyl]phenyl]pyrrolidin-2-one,
1-(4-(5-(5-(2-hydroxypropan-2-yl)-1-methyl-1H-pyrrolo[2,3-b]pyridin-3-yl)pyridin-3-yl)phenyl)pyrrolidin-2-one,
1-(4-(5-(5-(2-methoxypropan-2-yl)-1-methyl-1H-pyrrolo[2,3-b]pyridin-3-yl)pyridin-3-yl)phenyl)pyrrolidin-2-one,
1-(4-(5-(7-methoxy-1-methyl-1H-pyrazolo[3,4-c]pyridin-4-yl)pyridin-3-yl)phenyl)pyrrolidin-2-one,
1-[4-[5-(3-bromo-7,8-dihydro-6H-pyrido[3,2-b]pyrrolizin-5-yl)-3-pyridyl]phenyl]pyrrolidin-2-one,
1-[4-[5-[3-(1-Hydroxyethyl)-7,8-dihydro-6H-pyrido[3,2-b]pyrrolizin-5-yl]-3-pyridyl]phenyl]pyrrolidin-2-one,
1-[4-[5-(7,8-dihydro-6H-pyrimido[5,4-b]pyrrolizin-5-yl)-3-pyridyl]phenyl]pyrrolidin-2-one,
1-(4-(5-(imidazo[1,2-a]pyrimidin-6-yl)pyridin-3-yl)phenyl)pyrrolidin-2-one,
N-((1-hydroxy-1,3-dihydrobenzo[c][1,2]oxaborol-5-yl)methyl)-4-(5-(4-(2-oxopyrrolidin-1-yl)phenyl)pyridin-3-yl)-1H-pyrrolo[2,3-b]pyridine-2-carboxamide,
5-ethyl-6-methyl-3-(5-(4-(2-oxopyrrolidin-1-yl)phenyl)pyridin-3-yl)pyrazolo[1,5-a]pyrimidin-7(4H)-one,
1-(4-(5-(5-(2-oxopyrrolidin-1-yl)furo[2,3-b]pyridin-3-yl)pyridin-3-yl)phenyl)pyrrolidin-2-one,
1-(4-(5-(5-(1-hydroxyethyl)furo[2,3-b]pyridin-3-yl)pyridin-3-yl)phenyl)pyrrolidin-2-one,
N-((1-hydroxy-1,3-dihydrobenzo[c][1,2]oxaborol-6-yl)methyl)-4-(5-(4-(2-oxopyrrolidin-1-yl)phenyl)pyridin-3-yl)-1H-pyrrolo[2,3-b]pyridine-2-carboxamide,
5-isopropyl-3-(5-(4-(2-oxopyrrolidin-1-yl)phenyl)pyridin-3-yl)pyrazolo[1,5-a]pyrimidin-7(4H)-one,
N,N-dimethyl-3-(5-(4-(2-oxopyrrolidin-1-yl)phenyl)pyridin-3-yl)furo[2,3-b]pyridine-5-carboxamide,
1-(4-(5-(5-cyclopropyl-1H-pyrazolo[3,4-b]pyridin-3-yl)pyridin-3-yl)phenyl)pyrrolidin-2-one,
6-(2-hydroxyethyl-2,5-dimethyl-3-(5-(4-(2-oxopyrrolidin-1-yl)phenyl)pyridin-3-yl)pyrazolo[1,5-a]pyrimidin-7(4H)-one,
(S)-7-methyl-4-(5-(4-(4-methyl-2-oxopyrrolidin-1-yl)phenyl)pyridin-3-yl)-8,9-dihydropyrido[3',2':4,5]pyrrolo[1,2-a]pyrazin-6(7H)-one,
(R)-7-methyl-4-(5-(4-(4-methyl-2-oxopyrrolidin-1-yl)phenyl)pyridin-3-yl)-8,9-dihydropyrido[3',2':4,5]pyrrolo[1,2-a]pyrazin-6(7H)-one,
1-(4-(5-(5-(methoxymethyl)-2-methylpyrazolo[1,5-a]pyrimidin-7-yl)pyridin-3-yl)phenyl)pyrrolidin-2-one,
N-(4-(5-(4-(2-oxopyrrolidin-1-yl)phenyl)pyridin-3-yl)pyrimidin-2-yl-cyclobutanecarboxamide, 6-ethyl-5-methyl-3-(5-(4-(2-oxopyrrolidin-1-yl)phenyl)pyridin-3-yl)pyrazolo[1,5-a]pyrimidin-7 (4H)-one,
1-(4-(5-(8-cyclobutyl-7H-purin-6-yl)pyridin-3-yl)phenyl)pyrrolidin-2-one,
4-(5-(4-(2-oxopyrrolidin-1-yl)phenyl)pyridin-3-yl)-7-(pyridin-2-yl)-8,9-dihydropyrido[3',2':4,5]pyrrolo[1,2-a]pyrazin-6(7H)-one,
4-(5-(4-(4,4-dimethyl-2-oxopyrrolidin-1-yl)phenyl)pyridin-3-yl)-7-methyl-8,9-dihydropyrido[3',2':4,5]pyrrolo[1,2-a]pyrazin-6(7H)-one,
methyl 5-methyl-4-(5-(4-(2-oxopyrrolidin-1-yl)phenyl)pyridin-3-yl)-1H-pyrrolo[2,3-b]pyridine-2-carboxylate,
(S)-1-(4-(5-(5-(1-hydroxyethyl)-1-methyl-1H-pyrrolo[2,3-b]pyridin-3-yl)pyridin-3-yl)-3-methylphenyl)pyrrolidin-2-one,
(R)-1-(4-(5-(5-(1-hydroxyethyl)-1-methyl-1H-pyrrolo[2,3-b]pyridin-3-yl)pyridin-3-yl)-3-methylphenyl)pyrrolidin-2-one,
1-(4-(5-(5-(1-hydroxyethyl)-1-methy 1-1H-pyrrolo[2,3-b]pyridin-3-yl)pyridin-3-yl)-3-methylphenyl)pyrrolidin-2-one,
1-(4-(5-(2-cyclopropyl-5-(1-hydroxyethyl)-1H-pyrrolo[2,3-b]pyridin-3-yl)pyridin-3-yl)phenyl)pyrrolidin-2-one,
(S)-1-(4-(5-(5-(1-hydroxyethyl)-1-methyl-1H-pyrrolo[2,3-b]pyridin-3-yl)-4-methylpyridin-3-yl)phenyl)pyrrolidin-2-one,
(R)-1-(4-(5-(5-(1-hydroxyethyl)-1-methyl-1H-pyrrolo[2,3-b]pyridin-3-yl)-4-methylpyridin-3-yl)phenyl)pyrrolidin-2-one,
1-(4-(5-(5-(1-hydroxy ethyl)-1-methy 1-1H-pyrrolo[2,3-b]pyridin-3-yl)-4-methylpyridin-3-yl)phenyl)pyrrolidin-2-one,
1-(4-(5-(thieno[2,3-b]pyridin-3-yl)pyridin-3-yl)phenyl)pyrrolidin-2-one,
(R)-1-(4-(5-(5-(1-hydroxyethyl)-1-methyl-1H-pyrrolo[2,3-b]pyridin-3-yl)pyridin-3-yl)phenyl)pyrrolidin-2-one,
(S)-1-(4-(5-(5-(1-hydroxyethyl)-1-methyl-1H-pyrrolo[2,3-b]pyridin-3-yl)pyridin-3-yl)phenyl)pyrrolidin-2-one,
N-methyl-4-(4-methyl-5-(4-(2-oxopyrrolidin-1-yl)phenyl)pyridin-3-yl)furo[2,3-b]pyridine-2-carboxamide,
N,N-dimethyl-3-(5-(4-(2-oxopyrrolidin-1-yl)phenyl)pyridin-3-yl)-1H-pyrrolo[2,3-b]pyridine-5-sulfonamide,
methyl 5-chloro-4-(5-(4-(2-oxopyrrolidin-1-yl)phenyl)pyridin-3-yl)-1H-pyrrolo[2,3-b]pyridine-2-carboxylate,
N-(oxetan-3-yl)-4-(5-(4-(2-oxopyrrolidin-1-yl)phenyl)pyridin-3-yl)furo[2,3-b]pyridine-2-carboxamide,
N,N-dimethyl-4-(4-methyl-5-(4-(2-oxopyrrolidin-1-yl)phenyl)pyridin-3-yl)-1H-pyrrolo[2,3-b]pyridine-2-carboxamide,
1-(4-(5-(5-(2-hydroxypropan-2-yl)-1-methyl-1H-pyrrolo[2,3-b]pyridin-3-yl)-4-methylpyridin-3-yl)phenyl)pyrrolidin-2-one,
N,N-dimethyl-4-(5-(2-methyl-4-(2-oxopyrrolidin-1-yl)phenyl)pyridin-3-yl)-1H-pyrrolo[2,3-b]pyridine-2-carboxamide,
1-(4-(5-(5-(2-hydroxypropan-2-yl)-1-methyl-1H-pyrrolo[2,3-b]pyridin-3-yl)pyridin-3-yl)-3-methylphenyl)pyrrolidin-2-one,
methyl 4-(5-(4-(2-oxopyrrolidin-1-yl)phenyl)pyridin-3-yl)furo[2,3-b]pyridine-2-carboxylate,
4-(5-(4-(2-oxopyrrolidin-1-yl)phenyl)pyridin-3-yl)-N-(2-(thiazol-5-yl)ethyl)-1H-pyrrolo[2,3-b]pyridine-2-carboxamide,
1-(4-(5-(7,8-dihydro-6H-pyrido[3,2-b]pyrrolizin-5-yl)pyridin-3-yl)phenyl)pyrrolidin-2-one,
1-(4-(5-(1-methyl-1,5,6,7-tetrahydrocyclopenta[b]pyrazolo[4,3-e]pyridin-4-yl)pyridin-3-yl)phenyl)pyrrolidin-2-one, methyl 4-(4-methyl-5-(4-(2-oxopyrrolidin-1-yl)phenyl)pyridin-3-yl)-1H-pyrrolo[2,3-b]pyridine-2-carboxylate,
2-(1-methyl-7-oxo-4-(5-(4-(2-oxopyrrolidin-1-yl)phenyl)pyridin-3-yl)-1,7-dihydro-6H-pyrazolo[3,4-c]pyridin-6-yl)acetonitrile,
methyl 4-(5-(2-methyl-4-(2-oxopyrrolidin-1-yl)phenyl)pyridin-3-yl)-1H-pyrrolo[2,3-b]pyridine-2-carboxylate,
isopropyl 4-(5-(4-(2-oxopyrrolidin-1-yl)phenyl)pyridin-3-yl)furo[2,3-b]pyridine-2-carboxylate,
1-(4-(5-(1-methyl-3-(pyrimidin-5-yl)-1H-pyrrolo[2,3-b]pyridin-5-yl)pyridin-3-yl)phenyl)pyrrolidin-2-one,
1-(4-(5-(1H-benzo[d]imidazol-1-yl)pyridin-3-yl)phenyl)pyrrolidin-2-one,
N-methyl-4-(5-(2-methyl-4-(2-oxopyrrolidin-1-yl)phenyl)pyridin-3-yl)furo[2,3-b]pyridine-2-carboxamide,
1-(4-(5-(7-methoxy-2-methyl-2H-pyrazolo[3,4-c]pyridin-4-yl)pyridin-3-yl)phenyl)pyrrolidin-2-one,
ethyl 4-(5-(4-(2-oxopyrrolidin-1-yl)phenyl)pyridin-3-yl)-1H-pyrrolo[2,3-b]pyridine-2-carboxylate,
4-(5-(4-(2-oxopyrrolidin-1-yl)phenyl)pyridin-3-yl)-1H-pyrrolo[2,3-b]pyridine-2-carboxylic acid, isopropyl 4-(5-(4-(2-oxopyrrolidin-1-yl)phenyl)pyridin-3-yl)-1H-pyrrolo[2,3-b]pyridine-2-carboxylate,
1-(4-(5-(1H-pyrazolo[3,4-b]pyridin-4-yl)pyridin-3-yl)phenyl)pyrrolidin-2-one,
1-(4-(5-(1H-pyrazolo[4,3-b]pyridin-7-yl)pyridin-3-yl)phenyl)pyrrolidin-2-one,
1-(4-(5-(6-methyl-1H-pyrazolo[3,4-d]pyrimidin-4-yl)pyridin-3-yl)phenyl)pyrrolidin-2-one,
1-(4-(5-(2,3-Dihydro-[1,4]dioxino[2,3-b]pyridin-8-yl)-3-pyridyl)phenyl)pyrrolidin-2-one,
1-(4-(5-(4-Pyridyl)-3-pyridyl)phenyl)pyrrolidin-2-one,
1-(4-(5-(2-methyl-2H-pyrazolo[3,4-b]pyridin-4-yl)pyridin-3-yl)phenyl)pyrrolidin-2-one,
1-(4-(5-(1H-pyrazolo[3,4-d]pyrimidin-4-yl)pyridin-3-yl)phenyl)pyrrolidin-2-one,
1-(4-(5-(6-chloro-1H-pyrazolo[3,4-b]pyridin-4-yl)pyridin-3-yl)phenyl)pyrrolidin-2-one,
1-(4-(5-(6-cyclopropyl-1H-pyrazolo[3,4-b]pyridin-4-yl)pyridin-3-yl)phenyl)pyrrolidin-2-one,
1-(4-(5-(7-methoxy-1H-pyrazolo[3,4-c]pyridin-4-yl)pyridin-3-yl)phenyl)pyrrolidin-2-one,
1-(4-(5-(1-methyl-3-(2-methylpyrimidin-5-yl)-1H-pyrrolo[2,3-b]pyridin-5-yl)pyridin-3-yl)phenyl)pyrrolidin-2-one,
1-(4-(5-(6-methoxy-1H-pyrazolo[3,4-b]pyridin-4-yl)pyridin-3-yl)phenyl)pyrrolidin-2-one,
4-(4-(5-(4-(2-Oxopyrrolidin-1-yl)phenyl[-3-pyridyl]-5,6-dihydropyrrolo[3,4-b]pyridin-7-one,
1-(4-(2-amino-5-(7-methoxy-1H-pyrazolo[3,4-c]pyridin-4-yl)pyridin-3-yl)phenyl)pyrrolidin-2-one,
1-(4-(5-(7-methoxy-2-methyl-pyrazolo[3,4-c]pyridin-4-yl)-3-pyridyl)phenyl)pyrrolidin-2-one,
1-(4-(5-(7,8-Dihydro-6H-pyrido[3,2-b]pyrrolizin-5-yl)-3-pyridyl)phenyl)pyrrolidin-2-one,
1-(4-(5-(4-Methyl-2,4,5-triazatricyclo[7.3.0.03,7]dodeca-1,3(7),5,8-tetraen-8-yl)-3-pyridyl)phenyl)pyrrolidin-2-one,
1-(4-(5-(5-methyl-2-(piperidin-1-yl)thiazolo[4,5-d]pyrimidin-7-yl)pyridin-3-yl)phenyl)pyrrolidin-2-one,
(R)-7-methyl-4-(5-(4-(2-methyl-5-oxopyrrolidin-1-yl)phenyl)pyridin-3-yl)-8,9-dihydropyrido[3',2':4,5]pyrrolo[1,2-a]pyrazin-6(7H)-one,
1-(4-(5-(3-methylisoxazolo[5,4-b]pyridin-4-yl)phenyl)pyrrolidin-2-one,
7-(2,3-dihydro-[1,4]dioxino[2,3-b]pyridin-6-yl)-4-(5-(4-(2-oxopyrrolidin-1-yl)phenyl)pyridin-3-yl)-8,9-dihydropyrido[3',2':4,5]pyrrolo[1,2-a]pyrazin-6(7H)-one,
1-(4-(2-amino-5-(3-methyl-1H-pyrrolo[2,3-b]pyridin-4-yl)pyridin-3-yl)phenyl)pyrrolidin-2-one,
N-methyl-4-(5-(4-(2-oxopyrrolidin-1-yl)phenyl)pyridin-3-yl)-N-(pyridin-3-yl)-1H-pyrrolo[2,3-b]pyridine-2-carboxamide,
N-methyl-4-(5-(4-(2-oxopyrrolidin-1-yl)phenyl)pyridin-3-yl)-N-phenyl-1H-pyrrolo[2,3-b]pyridine-2-carboxamide,
4-(5-(4-(2-oxopyrrolidin-1-yl)phenyl)pyridin-3-yl)-N-(pyridin-2-yl)-1H-pyrrolo[2,3-b]pyridine-2-carboxamide,
N,3-dimethyl-4-(5-(4-(2-oxopyrrolidin-1-yl)phenyl)pyridin-3-yl)-1H-pyrrolo[2,3-b]pyridine-2-carboxamide,
4-(5-(4-(2-oxopyrrolidin-1-yl)phenyl)pyridin-3-yl)-N-(pyridin-4-yl)-1H-pyrrolo[2,3-b]pyridine-2-carboxamide,
N-((5,6-dimethyl-1H-benzo[d]imidazol-2-yl)methyl)-4-(5-(4-(2-oxopyrrolidin-1-yl)phenyl)pyridin-3-yl)-1H-pyrrolo[2,3-b]pyridine-2-carboxamide,
1-(4-(6-amino-5-(3-methyl-1H-pyrrolo[2,3-b]pyridin-4-yl)pyridin-3-yl)phenyl)pyrrolidin-2-one,
N-((4-methyl-1H-benzo[d]imidazol-2-yl)methyl)-4-(5-(4-(2-oxopyrrolidin-1-yl)phenyl)pyridin-3-yl)-1H-pyrrolo[2,3-b]pyridine-2-carboxamide,
1-(4-(5-(3-methyl-2H-pyrazolo[3,4-b]pyridin-4-yl)pyridin-3-yl)phenyl)pyrrolidin-2-one,
N-(benzo[d]thiazol-2-ylmethyl)-4-(5-(4-(2-oxopyrrolidin-1-yl)phenyl)pyridin-3-yl)-1H-pyrrolo[2,3-b]pyridine-2-carboxamide,
N-((6-methyl-1H-benzo[d]imidazol-2-yl)methyl)-4-(5-(4-(2-oxopyrrolidin-1-yl)phenyl)pyridin-3-yl)-1H-pyrrolo[2,3-b]pyridine-2-carboxamide,
N-((1-methyl-1H-benzo[d]imidazol-2-yl)methyl)-4-(5-(4-(2-oxopyrrolidin-1-yl)phenyl)pyridin-3-yl)-1H-pyrrolo[2,3-b]pyridine-2-carboxamide,
N-((1H-benzo[d]imidazol-2-yl)methyl)-4-(5-(4-(2-oxopyrrolidin-1-yl)phenyl)pyridin-3-yl)-1H-pyrrolo[2,3-b]pyridine-2-carboxamide,
1-(4-(5-(3-methyl-1H-pyrrolo[2,3-b]pyridin-4-yl)pyridin-3-yl)phenyl)pyrrolidin-2-one,
1-(4-(5-(2-(6-methyl-3,4-dihydro-2H-benzo[b][1,4]oxazine-4-carbonyl)-1H-pyrrolo[2,3-b]pyridin-4-yl)pyridin-3-yl)phenyl)pyrrolidin-2-one,
4-(5-(4-(2-oxopyrrolidin-1-yl)phenyl)pyridin-3-yl)-N-(pyridin-3-yl)-1H-pyrrolo[2,3-b]pyridine-2-carboxamide,
4-(5-(4-(2-oxopyrrolidin-1-yl)phenyl)pyridin-3-yl)-N-phenyl-1H-pyrrolo[2,3-b]pyridine-2-carboxamide,
N-(oxazol-2-ylmethyl)-4-(5-(4-(2-oxopyrrolidin-1-yl)phenyl)pyridin-3-yl)-1H-pyrrolo[2,3-b]pyridine-2-carboxamide,
7-(1,5-dimethyl-1H-pyrazol-3-yl)-4-(5-(4-(2-oxopyrrolidin-1-yl)phenyl)pyridin-3-yl)-8,9-dihydropyrido[3',2':4,5]pyrrolo[1,2-a]pyrazin-6(7H)-one,
1-(4-(5-(7-cyclopropyl-[1,2,4]triazolo[4,3-a]pyrimidin-5-yl)pyridin-3-yl)phenyl)pyrrolidin-2-one,
1-(4-(5-(3-(2-aminopyrimidin-5-yl)imidazo[1,2-a]pyrimidin-6-yl)pyridin-3-yl)phenyl)pyrrolidin-2-one,
1-(4-(5-(7-methyl-[1,2,4]triazolo[4,3-a]pyrimidin-5-yl)pyridin-3-yl)phenyl)pyrrolidin-2-one,
1-(4-(5-(3-(6-aminopyridin-3-yl)imidazo[1,2-yl]pyrimidin-6-yl)pyridin-3-yl)phenyl)pyrrolidin-2-one, 1-(4-(5-(2-cyclopropyl-5-(2-hydroxypropan-2-yl)-1H-pyrrolo[2,3-b]pyridin-3-yl)pyridin-3-yl)phenyl)pyrrolidin-2-one, 1-(4-(5-(2-(7-methyl-3,4-dihydro-2H-benzo[b][1,4]oxazine-4-carbonyl)-1H-pyrrolo[2,3-b]pyridin-4-yl)pyridin-3-yl)phenyl)pyrrolidin-2-one, 1-(4-(5-([1,2,4]triazolo[4,3-a]pyrimidin-5-yl)pyridin-3-yl)phenyl)pyrrolidin-2-one, 1-(4-(5-(3-(pyrimidin-5-yl)imidazo[1,2-a]pyrimidin-6-yl)pyridin-3-yl)phenyl)pyrrolidin-2-one, N-(5-(1-methyl-5-(5-(4-(2-oxopyrrolidin-1-yl)phenyl)pyridin-3-yl)-1H-pyrrolo[2,3-b]pyridin-3-yl)pyridin-2-yl)acetamide, 1-(4-(5-(3-(pyridin-3-yl)imidazo[1,2-a]pyrimidin-6-yl)pyridin-3-yl)phenyl)pyrrolidin-2-one, 1-(4-(5-(3-(6-aminopyridin-3-yl)-1-methyl-1H-pyrrolo[2,3-b]pyridin-5-yl)pyridin-3-yl)phenyl)pyrrolidin-2-one, N-(5-(1-methyl-5-(5-(4-(2-oxopyrrolidin-1-yl)phenyl)pyridin-3-yl)-1H-pyrrolo[2,3-b]pyridin-3-yl)pyrimidin-2-yl)acetamide, 1-(4-(5-(3-(1-hydroxyethyl)-7,8-dihydro-6H-pyrido[3,2-b]pyrrolizin-5-yl)pyridin-3-yl)phenyl)pyrrolidin-2-one, 1-(4-(5-(7,8-dihydro-6H-pyrimido[5,4-b]pyrrolizin-5-yl)pyridin-3-yl)phenyl)pyrrolidin-2-one, 1-(4-(5-(3-bromo-7,8-dihydro-6H-pyrido[3,2-b]pyrrolizin-5-yl)pyridin-3-yl)phenyl)pyrrolidin-2-one, 1-(4-(5-(3-(2-aminopyrimidin-5-yl)-1-methyl-1H-pyrrolo[2,3-b]pyridin-5-yl)pyridin-3-yl)phenyl)pyrrolidin-2-one, N-((1-hydroxy-1,3-dihydrobenzo[c][1,2]oxaborol-7-yl)methyl)-4-(5-(4-(2-oxopyrrolidin-1-yl)phenyl)pyridin-3-yl)-1H-pyrrolo[2,3-b]pyridine-2-carboxamide, N-((4,5-dimethyloxazol-2-yl)methyl)-4-(5-(4-(2-oxopyrrolidin-1-yl)phenyl)pyridin-3-yl)-1H-pyrrolo[2,3-b]pyridine-2-carboxamide, 1-(4-(5-(2-((2S,4R)-2-(2-hydroxypropan-2-yl)-4-methylpyrrolidine-1-carbonyl)-1H-pyrrolo[2,3-b]pyridin-4-yl)pyridin-3-yl)phenyl)pyrrolidin-2-one, 1-(4-(5-(2-(3-cyclopropyl-3-hydroxypiperidine-1-carbonyl)-1H-pyrrolo[2,3-b]pyridin-4-yl)pyridin-3-yl)phenyl)pyrrolidin-2-one, and N-((1-hydroxy-1,3-dihydrobenzo[c][1,2]oxaborol-4-yl)methyl)-4-(5-(4-(2-oxopyrrolidin-1-yl)phenyl)pyridin-3-yl)-1H-pyrrolo[2,3-b]pyridine-2-carboxamide; or a pharmaceutically acceptable salt, stereoisomer, or tautomer thereof.

3. A pharmaceutical composition comprising a compound of claim 1, and a pharmaceutically acceptable carrier.

4. A method of inhibiting PI5P4K comprising administering to a patient in need thereof an effective amount of a compound of claim 1.

5. The compound of claim 1, wherein $R_1$ is optionally substituted with oxo.

6. The compound of claim 1, wherein X, Y, and Z are independently CH.

7. The compound of claim 1, wherein $R_2$ is —$NH_2$.

8. The compound of claim 1, wherein $R_5$ is —H.

9. The compound of claim 1, wherein $R_4$ is —H.

10. The compound of claim 1, wherein $R_3$ is —C(O)$NR_6R_7$.

11. The compound of claim 10, wherein $R_6$ is —H.

12. The compound of claim 10, wherein $R_7$ is $C_{1-6}$ alkyl optionally substituted with one or more $R_8$.

13. The compound of claim 12, wherein $R_5$ is $C_{3-8}$ cycloalkyl.

* * * * *